US012503464B2

(12) United States Patent
Li et al.

(10) Patent No.: US 12,503,464 B2
(45) Date of Patent: Dec. 23, 2025

(54) 1,2,5-THIADIAZOLIDIN-3-ONE 1,1-DIOXIDE CONTAINING COMPOUNDS AND USES THEREOF

(71) Applicant: Kumquat Biosciences Inc., San Diego, CA (US)

(72) Inventors: Liansheng Li, San Diego, CA (US); Pingda Ren, San Diego, CA (US)

(73) Assignee: Kumquat Biosciences Inc., San Diego, CA (US)

( * ) Notice: Subject to any disclaimer, the term of this patent is extended or adjusted under 35 U.S.C. 154(b) by 0 days.

(21) Appl. No.: 19/229,649

(22) Filed: Jun. 5, 2025

(65) Prior Publication Data

US 2025/0296927 A1 Sep. 25, 2025

Related U.S. Application Data

(63) Continuation of application No. PCT/US2024/030846, filed on May 23, 2024.
(Continued)

(51) Int. Cl.
*C07D 417/10* (2006.01)
*A61K 31/433* (2006.01)
(Continued)

(52) U.S. Cl.
CPC .......... *C07D 417/10* (2013.01); *A61K 31/433* (2013.01); *A61K 31/4439* (2013.01); *A61K 31/454* (2013.01); *C07D 285/10* (2013.01); *C07D 417/12* (2013.01); *C07D 487/04* (2013.01)

(58) Field of Classification Search
CPC .. C07D 417/10; C07D 417/12; C07D 285/10; C07D 487/04; A61K 31/433; A61K 31/4439; A61K 31/454
See application file for complete search history.

(56) References Cited

U.S. PATENT DOCUMENTS 4,760,057 A 7/1988 Alexander
2016/0304533 A1 10/2016 Kirkpatrick et al.
(Continued)

FOREIGN PATENT DOCUMENTS

CN 117658947 A 3/2024
CN 118359557 A 7/2024
(Continued)

OTHER PUBLICATIONS

Bibi, Shabana. et al. Lead identification and optimization of plant insulin-based antidiabetic drugs through molecular docking analyses. International Journal of Pharmacy and Pharmaceutical Sciences 7(3):337-343 (2015).
(Continued)

*Primary Examiner* — Sarah Pihonak
*Assistant Examiner* — Padmaja S Rao
(74) *Attorney, Agent, or Firm* — Wilson Sonsini Goodrich & Rosati

(57) ABSTRACT

The present disclosure provides compounds and pharmaceutical compositions comprising the same. The compounds, pharmaceutical compositions thereof, and methods of using the same have a range of utilities as therapeutics, diagnostics, and research tools. The subject compositions and methods are particularly useful for potentiating immune response and/or for treating cancer and other diseases.

30 Claims, 2 Drawing Sheets

Related U.S. Application Data

(60) Provisional application No. 63/517,046, filed on Aug. 1, 2023, provisional application No. 63/504,147, filed on May 24, 2023.

(51) Int. Cl.

| | |
|---|---|
| ***A61K 31/4439*** | (2006.01) |
| ***A61K 31/454*** | (2006.01) |
| ***C07D 285/10*** | (2006.01) |
| ***C07D 417/12*** | (2006.01) |
| ***C07D 487/04*** | (2006.01) |

(56) References Cited

U.S. PATENT DOCUMENTS

| | | | |
|---|---|---|---|
| 2017/0015690 A1 | 1/2017 | Tremblay et al. |
| 2017/0224731 A1 | 8/2017 | Tiganis et al. |
| 2024/0166641 A1 | 5/2024 | Li et al. |
| 2024/0398828 A1 | 12/2024 | Li et al. |

FOREIGN PATENT DOCUMENTS

| | | | |
|---|---|---|---|
| CN | 118480013 | A | 8/2024 |
| CN | 119330909 | A | 1/2025 |
| CN | 119707952 | A | 3/2025 |
| CN | 119707953 | A | 3/2025 |
| CN | 120004876 | A | 5/2025 |
| CN | 120004877 | A | 5/2025 |
| WO | WO-03082841 | A1 | 10/2003 |
| WO | WO-2004041799 | A1 | 5/2004 |
| WO | WO-2007067612 | A1 | 6/2007 |
| WO | WO-2007067613 | A1 | 6/2007 |
| WO | WO-2007067614 | A1 | 6/2007 |
| WO | WO-2007067615 | A2 | 6/2007 |
| WO | WO-2007115058 | A2 | 10/2007 |
| WO | WO-2008148744 | A1 | 12/2008 |
| WO | WO-2009049098 | A2 | 4/2009 |
| WO | WO-2010118241 | A2 | 10/2010 |
| WO | WO-2012149048 | A1 | 11/2012 |
| WO | WO-2014089546 | A1 | 6/2014 |
| WO | WO-2017205765 | A1 | 11/2017 |
| WO | WO-2019036815 | A1 | 2/2019 |
| WO | WO-2019178422 | A1 | 9/2019 |
| WO | WO-2019246513 | A1 | 12/2019 |
| WO | WO-2020163365 | A2 | 8/2020 |
| WO | WO-2020186199 | A1 | 9/2020 |
| WO | WO-2021108867 | A1 | 6/2021 |
| WO | WO-2021127499 | A1 | 6/2021 |
| WO | WO-2021127586 | A1 | 6/2021 |
| WO | WO-2021259173 | A1 | 12/2021 |
| WO | WO-2022056281 | A1 | 3/2022 |
| WO | WO-2022192598 | A1 | 9/2022 |
| WO | WO-2022261145 | A1 | 12/2022 |
| WO | WO-2023086495 | A1 | 5/2023 |
| WO | WO-2023086498 | A1 | 5/2023 |
| WO | WO-2023096928 | A1 | 6/2023 |
| WO | WO-2023147531 | A1 | 8/2023 |
| WO | WO-2023150150 | A1 | 8/2023 |
| WO | WO-2023150523 | A1 | 8/2023 |
| WO | WO-2023150535 | A1 | 8/2023 |
| WO | WO-2023200964 | A1 | 10/2023 |
| WO | WO-2023220572 | A1 | 11/2023 |
| WO | WO-2024059041 | A1 | 3/2024 |
| WO | WO-2024067802 | A1 | 4/2024 |
| WO | WO-2024102791 | A1 | 5/2024 |
| WO | WO-2024102794 | A1 | 5/2024 |
| WO | WO-2024137724 | A1 | 6/2024 |
| WO | WO-2024137727 | A1 | 6/2024 |
| WO | WO-2024141015 | A1 | 7/2024 |
| WO | WO-2024222506 | A1 | 10/2024 |
| WO | WO-2024243441 | A1 | 11/2024 |
| WO | WO-2025026158 | A1 | 2/2025 |
| WO | WO-2025030006 | A2 | 2/2025 |
| WO | WO-2025030008 | A1 | 2/2025 |
| WO | WO-2025055985 | A1 | 3/2025 |

OTHER PUBLICATIONS

Cerulli, Robert A., and Joshua A. Kritzer. Phosphotyrosine isosteres: past, present and future. Organic and Biomolecular Chemistry 18(4):583-605 (2020).

Co-pending U.S. Appl. No. 19/075,486, filed Mar. 10, 2025.

Lafleur, Martin W. et al. PTPN2 regulates the generation of exhausted CD8+ T cell subpopulations and restrains tumor immunity. Nature Immunology 20(10):1335-1347 (2019).

Luo, Na. et al. Melanoma response to anti-PD-L1 immunotherapy requires JAK1 signaling, but not JAK2. Oncoimmunology 7(6):e1438106, 1-12 (2018).

Manguso, Robert T. et al. In vivo CRISPR screening identifies Ptpn2 as a cancer immunotherapy target. Nature 547(7664):413-418 (2017).

PCT/US2024/030846 International Search Report and Written Opinion dated Nov. 14, 2024.

Punthasee, Puminan. et al. Covalent allosteric inactivation of protein tyrosine phosphatase 1B (PTP1B) by an inhibitor-electrophile conjugate. Biochemistry 56(14):2051-2060 (2017).

Wiede, Florian. et al. PTPN2 deletion in T cells promotes anti-tumour immunity and CAR T cell efficacy in solid tumours. bioRxiv preprint :757419, 1-87 (2019).

1,2,5-THIADIAZOLIDIN-3-ONE 1,1-DIOXIDE CONTAINING COMPOUNDS AND USES THEREOF

CROSS-REFERENCE

This application is a continuation of International Application No. PCT/US2024/030846, filed May 23, 2024, which claims the benefit of U.S. Provisional Application No. 63/504,147, filed May 24, 2023, and U.S. Provisional Application No. 63/517,046, filed Aug. 1, 2023, each incorporated herein by reference in its entirety.

BACKGROUND

PTPN2 encodes a protein tyrosine phosphatase that has been implicated in a number of intracellular signaling pathways of immune cells. PTPN2 can negatively regulate αβ TCR T cell receptor (TCR) signaling by dephosphorylating and inactivating, e.g., the Src family kinase including LCK. In addition, PTPN2 can antagonize growth factor or cytokine-mediated signaling required for T cell function, homeostasis, and/or differentiation by dephosphorylating and inactivating JAK family kinases, e.g., JAK-1 and JAK-3, and/or target substrates of the JAK family kinases, e.g., STAT-1, STAT-3, and STAT-5.

Based on genome-wide association studies, PTPN2 single nucleotide polymorphisms (SNPs) have been linked with the development of several human autoimmune diseases including, but not limited to, type 1 diabetes, rheumatoid arthritis, Crohn's disease, and celiac disease. For example, a PTPN2 variant, rs1893217 (C), has been associated with about a 40% decrease in PTPN2 mRNA expression in CD4+ T cells, as well as the development of type 1 diabetes. In addition, PTPN2 mRNA expression levels in lung cancer tissues have been shown to be higher than those in normal lung tissues or adjacent normal tissues, such overexpression of PTPN2 promoting proliferation of lung cancer cells. Furthermore, two PTPN2 SNPs, rs2847297 and rs2847282, have been associated with a decrease in both PTPN2 mRNA expression and lung cancer risk, especially squamous cell lung carcinoma risk.

Cancer is the second leading cause of human death. There were close to 10 million deaths from cancer worldwide in 2020 and over 18 million new cases were diagnosed. In the United States alone, cancer causes the death of over a half-million people annually, with some 1.9 million new cases diagnosed per year (excluding basal cell and squamous cell skin cancers). Lung, liver, stomach, and bowel cancers account for more than four in ten of all cancer deaths worldwide.

Adoptive transfer of gene modified lymphoid cells, particularly T cells (i.e., ACT), is an emerging treatment for cancer. While efficacy has been demonstrated in a range of hematological cancers, including ALL, CLL, DLBCL, FL, and multiple myeloma, its efficacy in treating solid tumors is still yet to be established. Current immune cell therapy (e.g., CAR-T therapy) suffers from a number of profound deficiencies. T cell manufacturing and clonal expansion are highly inefficient and costly. When introduced in to a patient, T cell's anti-tumor activity and numbers can be reduced in the immunosuppressive microenvironment often found in a tumor. In addition, CAR-T therapy has been limited by life threatening toxicities in over 30% of patients. Toxicities primarily manifest as cytokine release syndrome (CRS) characterized by an early phase with fever, hypotension and elevations of various cytokines, and a later phase associated with life-ending neurologic events.

SUMMARY

In view of the foregoing, there exists a considerable need for alternative compositions and methods to treat cancer, and/or carry out immunotherapy. The compositions and methods of the present disclosure address this need and provide additional advantages as well. The ability of PTPN2 to act as a negative regulator of immunoreceptor-related pathways (e.g., TCR signaling) and promote cancer cell proliferation can be exploited for cancer and tumor treatment. The various aspects of the disclosure provide compositions and methods for inducing activity of lymphoid cells.

In certain aspects, the present disclosure provides a compound of Formula (I):

(I)

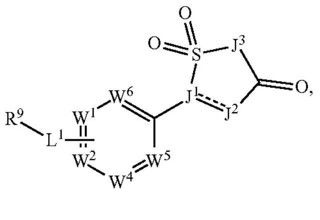

or a pharmaceutically acceptable salt or solvate thereof, wherein:

- $W^1$ is selected from C, C($R^8$), and N;
- $W^2$ is selected from C, C($R^8$), and N;
- $W^4$ is selected from N and C($R^4$);
- $W^5$ is selected from N and C($R^5$);
- $W^6$ is selected from N and C($R^6$);
- $J^1$ is selected from N, C, and C($R^8$);
- $J^2$ is selected from N, N($R^7$), C($R^8$), C($R^8$)$_2$, and C(O);
- $J^3$ is selected from N($R^7$) and C($R^8$)$_2$;
- $L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —N($R^{12}$)—, —C(N$R^{12}$)—, —N($R^{12}$)C(N$R^{12}$)—, —C(N$R^{12}$)N($R^{12}$)—, —N($R^{12}$)C(N$R^{12}$)N($R^{12}$)—, —C(O)O—, —OC(O)O—, —OC(O)N($R^{12}$)—, —N($R^{12}$)C(O)N($R^{12}$)—, —N($R^{12}$)C(O)O—, —C(O)N($R^{12}$)C(O)—, —C(O)N($R^{12}$)C(O)N($R^{12}$)—, —N($R^{12}$)S(O)$_2$—, —C(O)—, —S(O)—, —OC(O)—, —C(O)N($R^{12}$)—, —C(O)C(O)N($R^{12}$)—, —N($R^{12}$)C(O)—, —S(O)$_2$—, —OS(O)—, —S(O)O—, —OS(O)$_2$—, —S(O)$_2$O—, —S(O)(N$R^{12}$)—, —S(O)$_2$N($R^{12}$)—, —S(O)(N$R^{12}$)N($R^{12}$)—, —N($R^{12}$)S(O)—, —S(O)N($R^{12}$)—, —N($R^{12}$)S(O)$_2$N($R^{12}$)—, —N($R^{12}$) S(O)N($R^{12}$)—, —P(O)(O$R^{12}$)—, and —P(O)($R^{12}$)—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^9$ is selected from $C_{3-12}$ carbocycle and 3- to 12-membered heterocycle, each of which is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$;

$R^4$, $R^5$, $R^6$, and $R^8$ are independently selected at each occurrence from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —C(O)$OR^{12}$, —OC(O)$N(R^{12})(R^{13})$, —$N(R^{12})C(O)N(R^{12})(R^{13})$, —$N(R^{12})C(O)$ $OR^{12}$, —$N(R^{12})S(O)_2R^{12}$, —C(O)$R^{12}$, —S(O)$R^{12}$, —OC(O)$R^{12}$, —C(O)$N(R^{12})(R^{13})$, —C(O)C(O)$N(R^{12})(R^{13})$, —$N(R^{12})C(O)R^{12}$, —$S(O)_2R^{12}$, —S(O)$(NR^{12})R^{12}$, —$S(O)_2N(R^{12})(R^{13})$, and —S(O)$(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^7$ is independently selected at each occurrence from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O) $OR^{12}$, —C(O)O—($C_{1-6}$ alkyl)-$OR^{15}$, —($C_{1-6}$ alkyl)-$OR^{15}$, —C(O)$R^{12}$, —C(O)$N(R^{12})(R^{13})$, —C(O)C(O)$N(R^{12})(R^{13})$, —$S(O)_2R^{12}$, —S(O)$(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{15}$ is independently selected at each occurrence from (5-methyl-2-oxo-1,3-dioxol-4-yl)methyl, —C(O)$OR^{12}$, —C(O)$R^{12}$, —P(O)(X—$R^{16}$)(Y—$R^{17}$), and —$CH_2P(O)$(X—$R^{16}$)(Y—$R^{17}$);

X and Y are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —C(O)$OR^{12}$, —OC(O)$N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—C(O)$R^{12}$, —C(O)$R^{12}$, —S(O)$R^{12}$, —OC(O)$R^{12}$, —OC(O)$OR^{12}$, —C(O)$N(R^{12})(R^{13})$, —C(O)C(O)$N(R^{12})(R^{13})$, —$N(R^{12})C(O)R^{12}$, —$S(O)_2R^{12}$, —S(O)$(NR^{12})R^{12}$, —$S(O)_2N(R^{12})(R^{13})$, —S(O)$(NR^{12})N(R^{12})(R^{13})$, —P(O)$(OR^{12})_2$, —P(O)$(R^{12})_2$, —OP(O)$(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —C(O)$R^{22}$, —S(O)$R^{22}$, —OC(O)$R^{22}$, —C(O)$N(R^{22})(R^{23})$, —C(O)C(O)$N(R^{22})(R^{23})$, —$N(R^{22})C(O)R^{22}$, —$S(O)_2R^{22}$, —S(O)$(NR^{22})R^{22}$, —$S(O)_2N(R^{22})(R^{23})$—, —S(=O)(=$NR^{22}$)$N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)OR^{22}$, —$N(R^{22})S(O)_2R^{22}$, —C(O)$R^{22}$, —S(O)$R^{22}$, —OC(O)$R^{22}$, —C(O)$N(R^{22})(R^{23})$, —C(O)C(O)$N(R^{22})(R^{23})$, —$N(R^{22})C(O)R^{22}$, —$S(O)_2R^{22}$, —S(O)$(NR^{22})R^{22}$, —$S(O)_2N(R^{22})(R^{23})$, and —S(=O)(=$NR^{22}$)$N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ------ indicates a single or double bond such that all valences are satisfied;

wherein at least one of $R^9$, $W^1$, $W^2$, $W^4$, $W^5$, $W^6$, $J^2$, or $J^3$ is substituted with (5-methyl-2-oxo-1,3-dioxol-4-yl)methyl, —$OR^{15}$, —O—($C_{1-6}$ alkyl)-$OR^{15}$, —OC(O)N($R^{12}$)($R^{13}$), —($C_{1-6}$ alkyl)-$OR^{15}$, or —C(O)O—($C_{1-6}$ alkyl)-$OR^{15}$.

In some embodiments, for a compound of Formula (I), $W^4$ is C($R^4$), $W^5$ is C($R^5$), and $W^6$ is C($R^6$). In some embodiments, $W^1$ is C and $W^2$ is C($R^8$). In some embodiments, $J^3$ is N($R^7$). In some embodiments, $R^9$ is 4- to 7-membered heterocycle, wherein the 4- to 7-membered heterocycle is (i) optionally substituted with one, two, or three $R^{20}$ and (ii) optionally substituted with —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is 4- to 7-membered heterocycle comprising a ring nitrogen atom substituted by (5-methyl-2-oxo-1,3-dioxol-4-yl)methyl, —($C_{1-6}$ alkyl)-$OR^{15}$ or —C(O)O—($C_{1-6}$ alkyl)-$OR^{15}$. In some embodiments, $R^9$ comprises a ring carbon atom substituted by —$OR^{15}$ or O—($C_{1-6}$ alkyl)-$OR^{15}$.

In some embodiments, for a compound of Formula (I), $R^9$ is

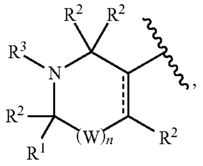

wherein:

W is C($R^2$)$_2$;

n is 0, 1, or 2;

$R^1$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), and —S(O)($NR^{12}$)N($R^{12}$)($R^{13}$), or (1) $R^1$ and $R^2$ attached to the same carbon atom are taken together to form oxo, =$NR^{12}$, or =C($R^{14}$)$_2$, (2) $R^1$ and $R^2$, together with the atom(s) to which they are attached, form $C_{3-12}$ carbocycle or 3- to 12-membered heterocycle, or (3) $R^1$ and $R^3$, together with the atoms to which they are attached, form 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), and —S(O)($NR^{12}$)N($R^{12}$)($R^{13}$), optionally wherein one or both of (1) two $R^2$ attached to the same carbon atom are taken together to form oxo, =$NR^{12}$, or =C($R^{14}$)$_2$ and (2) two $R^2$, together with the atom(s) to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O)$OR^{12}$, —C(O)O—($C_{1-6}$ alkyl)-$OR^{15}$, —($C_{1-6}$ alkyl)-$OR^{15}$, —C(O)$R^{12}$, —C(O)N($R^{12}$)($R^{13}$), —C(O)C(O)N($R^{12}$)($R^{13}$), —S(O)$_2R^{12}$, —S(O)($NR^{12}$)$R^{12}$, —S(O)$_2$N($R^{12}$)($R^{13}$), and —S(=O)(=$NR^{12}$)N($R^{12}$)($R^{13}$), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$; and $R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$.

In certain aspects, the present disclosure provides a compound of Formula (II):

(II)

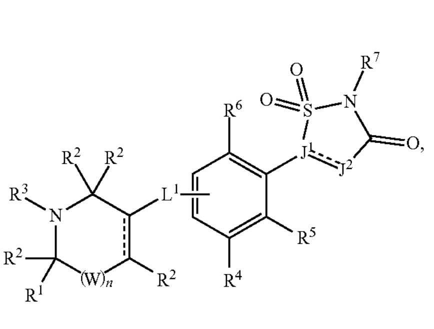

or a pharmaceutically acceptable salt or solvate thereof, wherein:

W is $C(R^2)_2$;

n is 0, 1, or 2;

$J^1$ is N and $J^2$ is $CH_2$; or $J^1$ is C and $J^2$ is CH;

$R^1$ is selected from halogen, —$C_{0-6}$ alkyl-CN, —$C_{0-6}$ alkyl-($C_3$ carbocycle), —$C_{0-6}$ alkyl-($C_{4-5}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, or (1) $R^1$ and $R^2$ attached to the same carbon atom are taken together to form oxo, =$NR^{12}$, or =$C(R^{14})_2$, (2) $R^1$ and $R^2$ attached to the same carbon atom, together with the carbon atom to which they are attached, form $C_{3-12}$ carbocycle or 3- to 12-membered heterocycle, (3) $R^1$ and a vicinal $R^2$, together with the carbon atoms to which they are attached, form $C_{3-12}$ carbocycle or 3- to 12-membered heterocycle, or (4) $R^1$ and $R^3$, together with the atoms to which they are attached, form 3- to 12-membered heterocycle; wherein —$C_{0-6}$ alkyl-($C_3$ carbocycle) is substituted with one, two, or three $R^{20}$; and wherein —$C_{0-6}$ alkyl-CN, —$C_{0-6}$ alkyl-($C_{4-5}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, optionally wherein one or more of (1) two $R^2$ attached to the same carbon atom are taken together to form oxo, =$NR^{12}$, or =$C(R^{14})_2$, (2) two $R^2$ attached to the same carbon atom, together with the carbon atom to which they are attached, form $C_{3-12}$ carbocycle or 3- to 12-membered heterocycle, and (3) two vicinal $R^2$, together with the carbon atoms to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —$C(O)OR^{12}$, —$C(O)O$—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —$C(O)N(R^{12})C(O)$—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})C(O)$—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})S(O)$—, —$S(O)N(R^{12})$—, —$N(R^{12})S(O)_2N(R^{12})$—, —$N(R^{12})$ $S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —C(O)$R^{12}$, —C(O)O$R^{12}$, —P(O)(X—$R^{16}$)(Y—$R^{17}$), and —$CH_2$P(O)(X—$R^{16}$)(Y—$R^{17}$);

X and Y are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —O$R^{12}$, —S$R^{12}$, —N($R^{12}$)($R^{13}$), —C(O)O$R^{12}$, —OC(O)N($R^{12}$)($R^{13}$), —N($R^{12}$)C(O)N($R^{12}$)($R^{13}$), N($R^{12}$)C(O)O$R^{12}$, —N($R^{12}$)S(O)$_2R^{12}$, —N($R^{12}$)S(O)$_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)O$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)(N$R^{12}$)$R^{12}$, —S(O)$_2$N($R^{12}$)($R^{13}$), —S(O)(N$R^{12}$)N($R^{12}$)($R^{13}$), —P(O)(O$R^{12}$)$_2$, —P(O)($R^{12}$)$_2$, —OP(O)(O$R^{12}$)$_2$, =O, =S, and =N$R^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$)—, —S(=O)(=N$R^{22}$)N($R^{22}$)($R^{23}$), and —OC$H_2$C(O)O$R^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ----- independently indicates a single or double bond such that all valences are satisfied.

In certain aspects, the present disclosure provides a compound of Formula (III) or (IV):

(II)

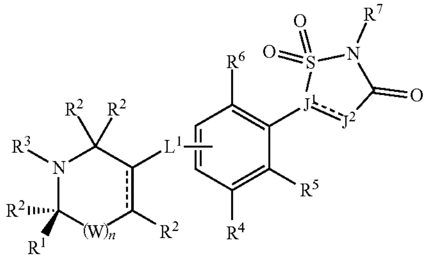

or (II)

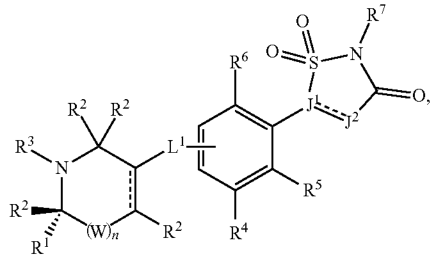

or a pharmaceutically acceptable salt or solvate thereof, wherein:

W is C($R^2$)$_2$;

n is 0, 1, or 2;

$J^1$ is N and $J^2$ is $CH_2$; or $J^1$ is C and $J^2$ is CH;

$R^1$ is selected from halogen, —CN, $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, or (1) $R^1$ and $R^2$ attached to the same carbon atom are taken together to form oxo, =$NR^{12}$, or =$C(R^{14})_2$, (2) $R^1$ and $R^2$, together with the atom(s) to which they are attached, form $C_{3-12}$ carbocycle or 3- to 12-membered heterocycle, or (3) $R^1$ and $R^3$, together with the atoms to which they are attached, form 3- to 12-membered heterocycle, wherein $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$.

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, optionally wherein one or both of (1) two $R^2$ attached to the same carbon atom are taken together to form oxo, =$NR^{12}$, or =$C(R^{14})_2$ and (2) two $R^2$, together with the atom(s) to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —$C(O)OR^{12}$, —$C(O)O$—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —$C(O)N(R^{12})C(O)$—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})C(O)$—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})S(O)$—, —$S(O)N(R^{12})$—, —$N(R^{12})S(O)_2N(R^{12})$—, —$N(R^{12})S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)R^{12}$, —$C(O)OR^{12}$, —$P(O)(X—R^{16})(Y—R^{17})$, and —$CH_2P(O)(X—R^{16})(Y—R^{17})$;

X and Y are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S$(O)_2R^{12}$, —N($R^{12}$)$S(O)_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)$OR^{12}$, —C(O)N($R^{12}$)($R^{13}$), —C(O)C(O)N($R^{12}$)($R^{13}$), —N($R^{12}$)C(O)$R^{12}$, —$S(O)_2R^{12}$, —S(O)($NR^{12}$)$R^{12}$, —$S(O)_2$N($R^{12}$)($R^{13}$), —S(O)($NR^{12}$)N($R^{12}$)($R^{13}$), —P(O)$(OR^{12})_2$, —P(O)$(R^{12})_2$, —OP(O)$(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), =$NR^{22}$, =C$(R^{21})_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)$S(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —$S(O)_2R^{22}$, —S(O)($NR^{22}$)$R^{22}$, —$S(O)_2$N($R^{22}$)($R^{23}$)—, —S(=O)(=$NR^{22}$)N($R^{22}$)($R^{23}$), and —$OCH_2$C(O)$OR^{22}$, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —N($R^{22}$)($R^{23}$), =$NR^{22}$, =C$(R^{21})_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)$S(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —$S(O)_2R^{22}$, —S(O)($NR^{22}$)$R^{22}$, —$S(O)_2$N($R^{22}$)($R^{23}$), and —S(=O)(=$NR^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ------ independently indicates a single or double bond such that all valences are satisfied.

In some embodiments, the compound is a compound of Formula (III) provided in at least 98% enantiomeric excess. In some embodiments, the compound is a compound of Formula (IV) provided in at least 98% enantiomeric excess.

In some embodiments, for a compound of Formula (I), (II), (III), or (IV), $R^4$ is selected from hydrogen, halogen, $C_{1-6}$ alkyl, $C_{3-6}$ carbocycle, 3- to 6-membered heterocycle, —$OR^{12}$, and —N($R^{12}$)($R^{13}$), wherein $C_{1-6}$ alkyl, $C_{3-6}$ carbocycle, and 3- to 6-membered heterocycle are optionally substituted with one, two, or three $R^{20}$. In some embodiments, $R^4$ is selected from hydrogen, halogen, and —OH. In some embodiments, $R^4$ is hydrogen. In some embodiments, $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$. In some embodiments, $R^5$ is —OH. In some embodiments, $R^5$ is selected from —$OR^{15}$ and —O—($C_{1-6}$ alkyl)-$OR^{15}$. In some embodiments, $R^6$ is selected from halogen, —$OR^{12}$, and $C_{1-6}$ alkyl, wherein $C_{1-6}$ alkyl is optionally substituted with one, two, or three $R^{20}$. In some embodiments, $R^6$ is halogen. In some embodiments, $R^6$ is selected from fluorine and chlorine. In some embodiments, $R^4$ is hydrogen, $R^5$ is —OH, and $R^6$ is fluorine.

In some embodiments, for a compound of Formula (I), (II), (III), or (IV), $J^1$ is N and $J^2$ is $CH_2$. In some embodiments, $R^7$ is selected from hydrogen and —($C_{1-6}$ alkyl)-$OR^{15}$. In some embodiments, $R^7$ is hydrogen. In some embodiments, $R^7$ is —($C_{1-6}$ alkyl)-$OR^{15}$.

In some embodiments, for a compound of Formula (I), (II), (III), or (IV), $L^1$ is absent or selected from $C_{1-6}$ alkylene, —O—, —S—, —N($R^{12}$)—, —C($NR^{12}$)—, —N($R^{12}$)$S(O)_2$—, —C(O)—, —C(O)N($R^{12}$)—, —N($R^{12}$)C(O)—, —S(O)—, —$S(O)_2$—, and —$S(O)_2$N($R^{12}$)—. In some embodiments, $L^1$ is absent or selected from $C_{1-3}$ alkylene, —O—, and —C(O)N($R^{12}$)—. In some embodiments, $L^1$ is absent.

In some embodiments, for a compound of Formula (II), (III), or (IV), W is $CH_2$. In some embodiments, n is 0 or 1, such as n is 0. In some embodiments, $R^1$ is selected from halogen, $C_{2-6}$ alkyl, $C_{2-6}$ alkenyl, 2- to 6-membered heteroalkyl, —$C_{0-6}$ alkyl-($C_{3-12}$ carbocycle), and —$C_{0-6}$ alkyl-(3- to 12-membered heterocycle), or $R^1$ and $R^2$ attached to the same carbon atom are taken together to form oxo, =$NR^{12}$, or =C$(R^{14})_2$, or $R^1$ and $R^3$, together with the atoms to which they are attached, form 3- to 12-membered heterocycle, wherein $C_{2-6}$ alkyl, $C_{2-6}$ alkenyl, 2- to 6-membered heteroalkyl, —$C_{0-6}$ alkyl-($C_{3-12}$ carbocycle), —$C_{0-6}$ alkyl-(3- to 12-membered heterocycle), and 3- to 12-membered heterocycle are optionally substituted with one, two, or three $R^{20}$. In some embodiments, $R^1$ is selected from $C_{2-6}$ alkyl and —$C_{0-6}$ alkyl-($C_{3-8}$ carbocycle), each of which is optionally substituted with one, two, or three $R^{20}$. In some embodiments, $R^1$ is selected from $C_{2-6}$ alkyl and —$C_{0-3}$ alkyl-($C_{3-6}$ carbocycle). In some embodiments, $R^1$ is selected from

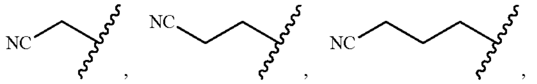,
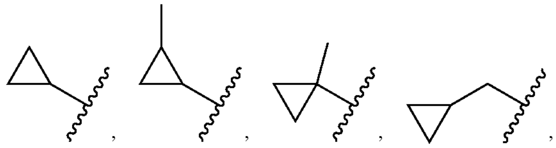,
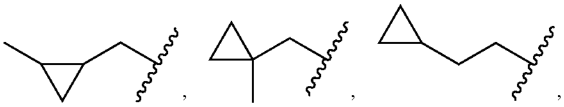,
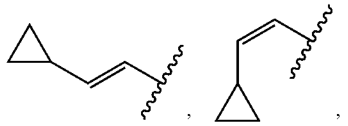,
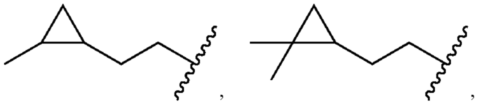,
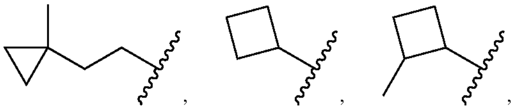,
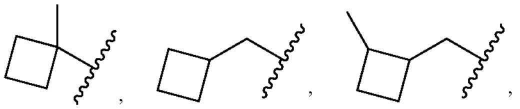,
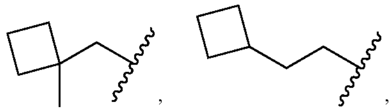,
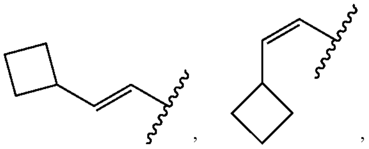,
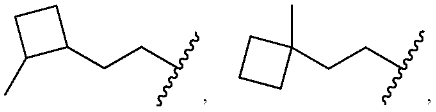,
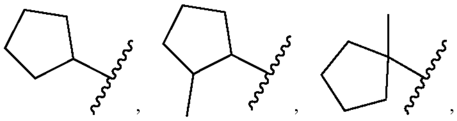,
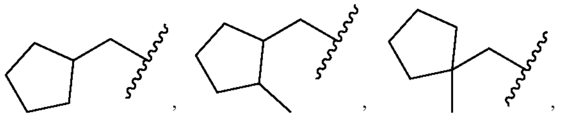,
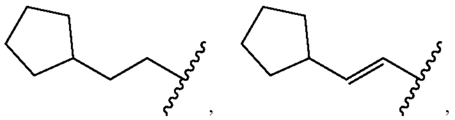,
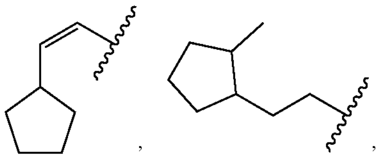 and
-continued
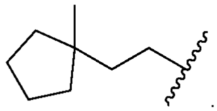.
In some embodiments, $R^1$ is selected from
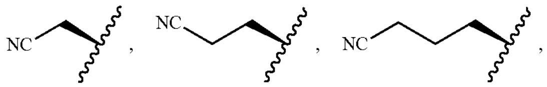,
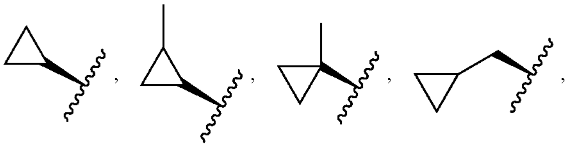,
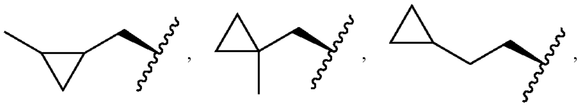,
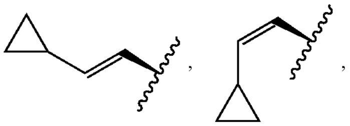,
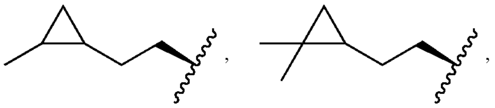,
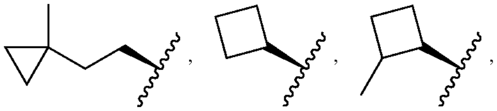,
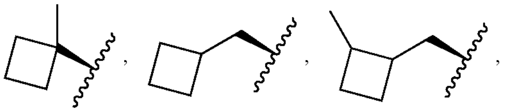,
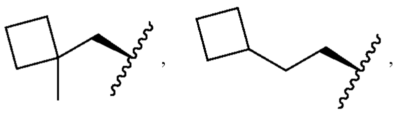,
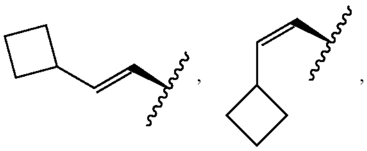,
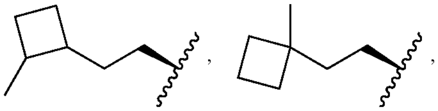,
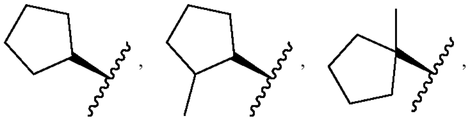,
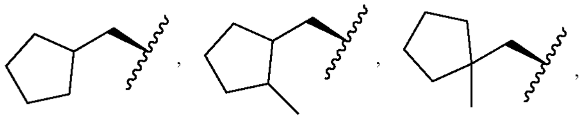, -continued

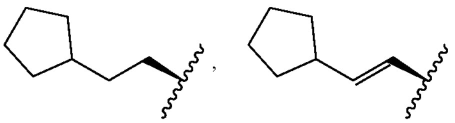
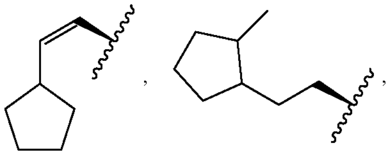
, and
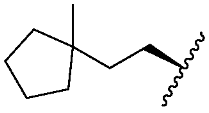
.

In some embodiments, $R^1$ is selected from

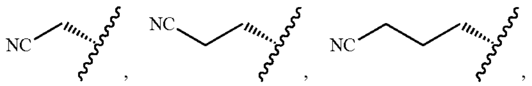
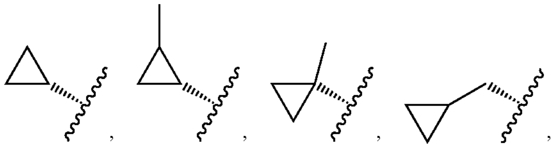
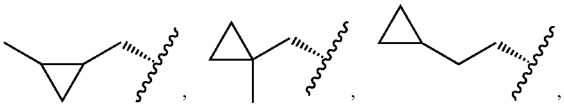
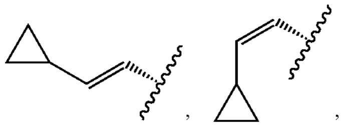
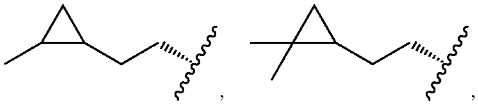
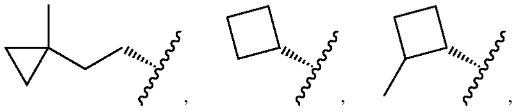
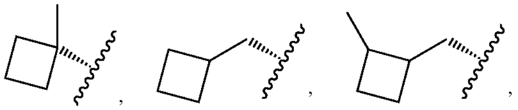
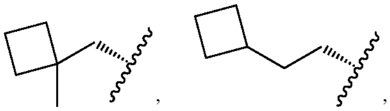
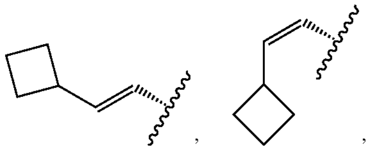
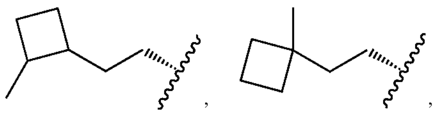

-continued

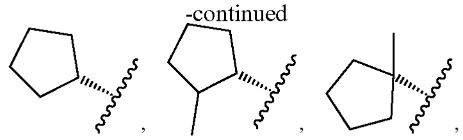
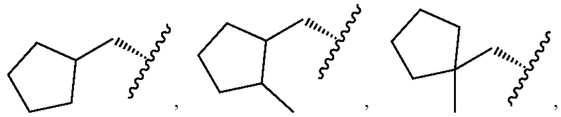
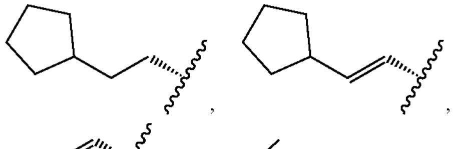
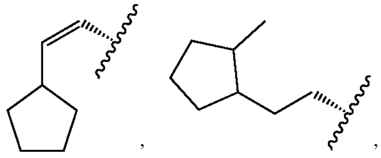
, and
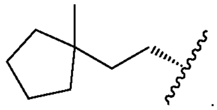
.

In some embodiments, for a compound of Formula (II), (III), or (IV), $R^2$ is independently selected at each occurrence from hydrogen, halogen, $C_{1-6}$ alkyl, —$OR^{12}$, and —$N(R^{12})(R^{13})$, or two $R^2$ attached to the same carbon atom are taken together to form oxo, =$NR^{12}$, or =$C(R^{14})_2$, wherein $C_{1-6}$ alkyl is optionally substituted with one, two, or three $R^{20}$. In some embodiments, each $R^2$ is hydrogen. In some embodiments, $R^3$ is selected from hydrogen, $C_{1-6}$ alkyl, —$C_{0-6}$ alkyl-(3- to 12-membered heterocycle), —$C(O)OR^{12}$, and —C(O)O—($C_{1-6}$ alkyl)-$OR^{15}$, wherein $C_{1-6}$ alkyl and —$C_{0-6}$ alkyl-(3- to 12-membered heterocycle) are optionally substituted with one, two, or three $R^{20}$. In some embodiments, $R^3$ is hydrogen. In some embodiments, $R^3$ is selected from —$C_2$ alkyl-(5- to 6-membered heterocycle) and —C(O)O—($C_{1-6}$ alkyl)-$OR^{15}$, wherein-$C_2$ alkyl-(5- to 6-membered heterocycle) is substituted with one, two, or three substituents independently selected from $C_{1-3}$ alkyl and oxo.

In some embodiments, for a compound of Formula (I), (II), (III), or (IV), $R^{15}$ is selected from —$C(O)R^{12}$ and —P(O)(X—$R^{16}$)(Y—$R^{17}$). In some embodiments, $R^{12}$ is $C_{1-6}$ alkyl optionally substituted with —$NH_2$. In some embodiments, X and Y are each —O—. In some embodiments, at least one of $R^{16}$ and $R^{17}$ is $C_{1-6}$ alkyl optionally substituted at each occurrence with one or more substituents independently selected from halogen, —$OR^{12}$, —S—S—$R^{12}$, —S—$C(O)R^{12}$, —$OC(O)R^{12}$, —$OC(O)OR^{12}$, and —$P(O)(OR^{12})_2$. In some embodiments, $R^{16}$ and $R^{17}$ are independently $C_{1-6}$ alkyl optionally substituted at each occurrence with one or more substituents independently selected from halogen, —$OR^{12}$, —S—S—$R^{12}$, —S—C(O)$R^{12}$, —$OC(O)R^{12}$, —$OC(O)OR^{12}$, and —$P(O)(OR^{12})_2$. In some embodiments, $R^{16}$ and $R^{17}$ are independently selected from hydrogen and $C_{1-6}$ alkyl optionally substituted at each occurrence with one or more substituents independently selected from halogen, —$OR^{12}$, —S—S—$R^{12}$, —S—C(O)$R^{12}$, —$OC(O)R^{12}$, —$OC(O)OR^{12}$, and —$P(O)(OR^{12})_2$. In some embodiments, $R^{16}$ and $R^{17}$ are independently selected from hydrogen, —$CH_2OC(O)R^{12}$, and —$CH_2OC(O)OR^{12}$. In some embodiments, $R^{16}$ and $R^{17}$ are independently selected from $-CH_2OC(O)C(CH_3)$ 3, $-CH_2OC(O)OCH(CH_3)_2$, $-CH_2OC(O)CH_3$, $-CH_2CH_2-S-S-(CH_2)_2OH$, and $-CH_2CH_2-S-C(O)CH_3$. In some embodiments, $R^{15}$ is $-P(O)(OH)_2$.

In certain aspects, the present disclosure provides a compound of formula:

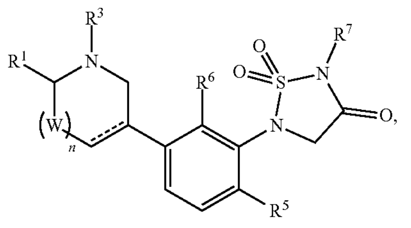

or a pharmaceutically acceptable salt or solvate thereof, wherein: W is $CH_2$; n is 0; $R^1$ is

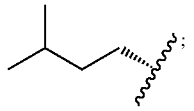

$R^3$ is selected from hydrogen and $-C(O)OCH(CH_3)OC(O)R^{12}$; $R^5$ is —OH; $R^6$ is fluorine; $R^7$ is hydrogen; $R^{12}$ is selected from $C_{1-6}$ alkyl and $C_{3-6}$ carbocycle; and ----- indicates a double bond. In certain aspects, the present disclosure provides a compound selected from

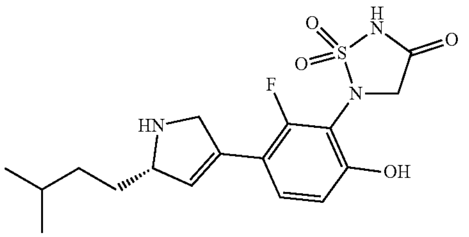

and

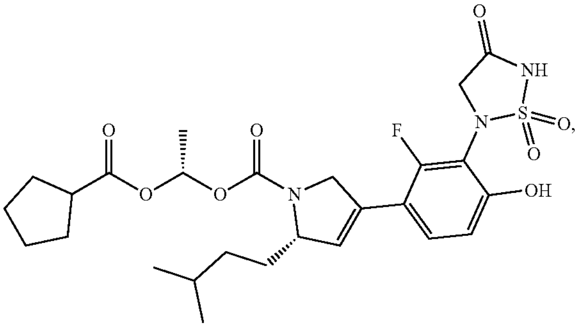

or a pharmaceutically acceptable salt or solvate thereof.

In certain aspects, the present disclosure provides a compound selected from Table 1, or a pharmaceutically acceptable salt or solvate thereof.

In certain aspects, the present disclosure provides a compound having the formula D-$L^{DE}$-E wherein D is a monovalent form of a compound described herein; $L^{DE}$ is a covalent linker bonded to D and E; and E is a monovalent form of a degradation enhancer. In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN ($CRL4^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE20, UBE2Q1, UBE2Q2, UBE2R1, UBE2R2, UBE2S, UBE2T, UBE2U, UBE2V1, UBE2V2, UBE2 W, UBE2Z, ATG3, BIRC6, and UFC1. In some embodiments, $L^{DE}$ is $-L^{DE1}-L^{DE2}-L^{DE3}-L^{DE4}-L^{DE5}-$; $L^{DE1}$, $L^{DE2}$, $L^{DE3}$, $L^{DE4}$, and $L^{DE5}$ are independently a bond, —O—, $-N(R^{12})-$, —C(O)—, $-N(R^{12})C(O)-$, $-C(O)N(R^{12})-$, —S—, $-S(O)_2-$, —S(O)—, $-S(O)_2N(R^{12})-$, $-S(O)N(R^{12})-$, $-N(R^{12})S(O)-$, $-N(R^{12})S(O)_2-$, $C_{1-6}$ alkylene, $(-O-C_{1-6}\ alkyl)_z$-, $(-C_{1-6}\ alkyl-O)_z-$, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene, wherein $C_{1-6}$ alkylene, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene are optionally substituted with one, two, or three $R^{20}$, and wherein each $C_{1-6}$ alkyl of $(-O-C_{1-6}\ alkyl)_z$- and $(-C_{1-6}\ alkyl-O)_z-$ is optionally substituted with one, two, or three $R^{20}$, and z is independently an integer from 0 to 10. In some embodiments, $L^{DE}$ is $-(O-C_2\ alkyl)_z$- and z is an integer from 1 to 10. In some embodiments, $L^{DE}$ is $-(C_2\ alkyl-O-)_z-$ and z is an integer from 1 to 10. In some embodiments, $L^{DE}$ is $-(CH_2)_{zz1}L^{DE2}(CH_2O)_{zz2}-$, wherein $L^{DE2}$ is a bond, a 5 or 6 membered heterocycloalkylene or heteroarylene, phenylene, $-C_{2-4}$alkynylene, $-SO_2-$ or —NH—; and zz1 and zz2 are independently an integer from 0 to 10. In some embodiments, $L^{DE}$ is $-(CH_2)_{zz1}(CH_2O)_{zz2}-$, wherein zz1 and zz2 are each independently an integer from 0 to 10. In some embodiments, $L^{DE}$ is a PEG linker. In some embodiments, E is a monovalent form of a compound selected from

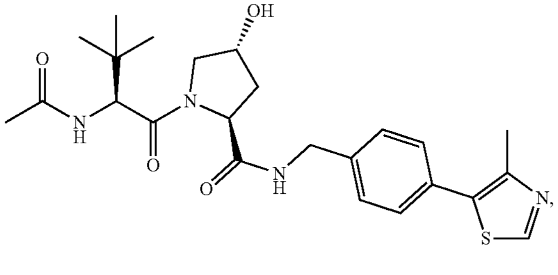

-continued

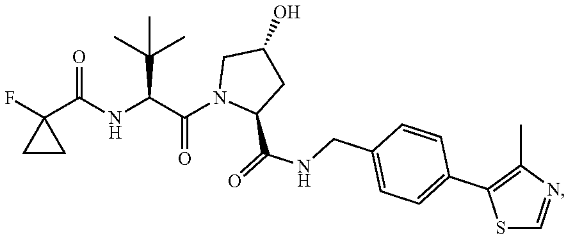

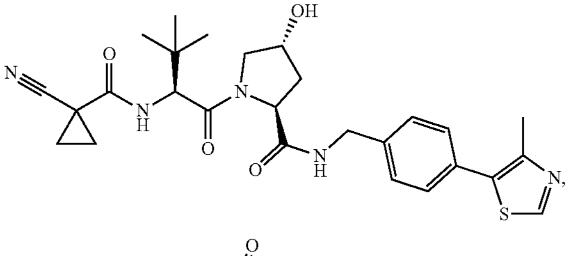

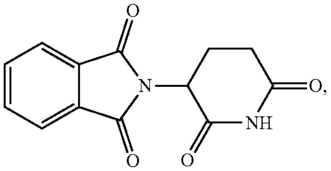

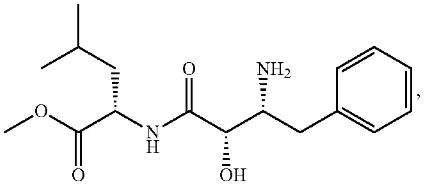

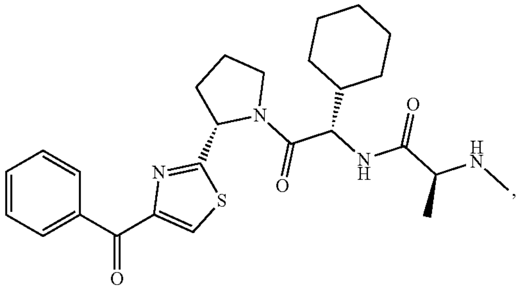

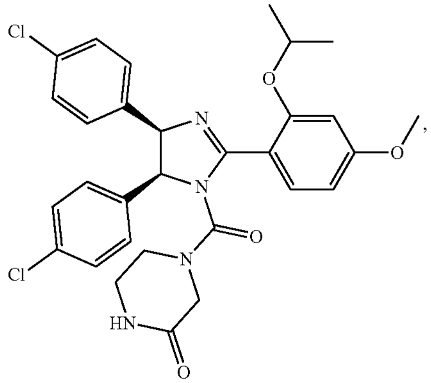

-continued

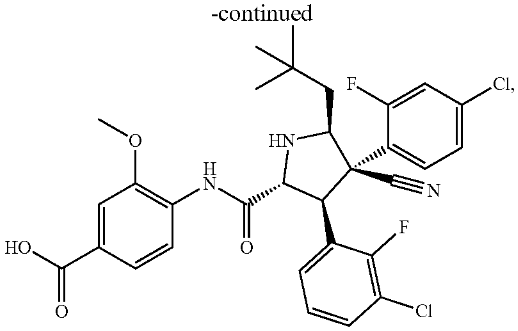

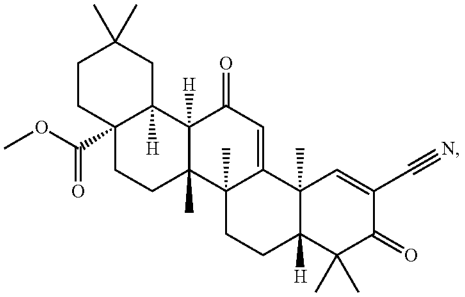

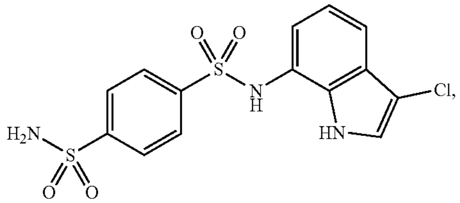

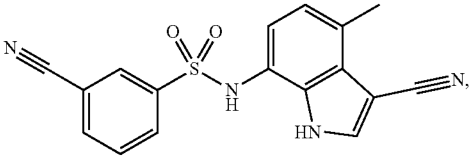

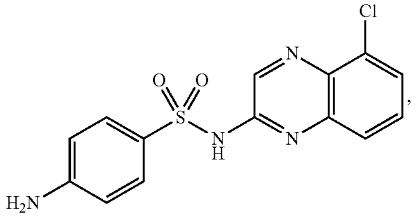

and

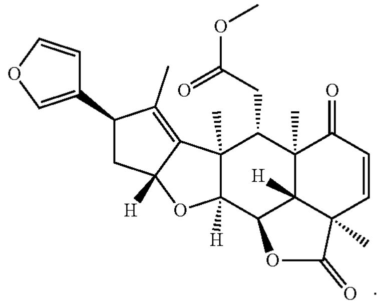

In some embodiments, a compound described herein is provided in at least 99% enantiomeric excess. In certain aspects, the present disclosure provides a pharmaceutical composition comprising a compound described herein, or a pharmaceutically acceptable salt or solvate thereof, and a pharmaceutically acceptable excipient.

In certain aspects, the present disclosure provides a method of treating cancer in a subject in need thereof, comprising administering to the subject a therapeutically effective amount of a compound described herein, or a pharmaceutically acceptable salt or solvate thereof. In certain aspects, the present disclosure provides a method of potentiating immunity of a cell, comprising: (a) contacting the cell with a compound described herein, thereby potentiating immunity of the cell, wherein the cell comprises (i) a chimeric T-cell receptor sequence encoding a T-cell receptor fusion protein (TFP) and/or (ii) a chimeric antigen receptor (CAR) sequence encoding a CAR, wherein each of TFP and CAR exhibits specific binding to an antigen.

In certain aspects, the present disclosure provides a method of potentiating immunity of a cell, comprising: (a) contacting the cell with a compound described herein; and (b) introducing to the cell (i) a chimeric T-cell receptor sequence encoding a T-cell receptor fusion protein (TFP) and/or (ii) a chimeric antigen receptor (CAR) sequence encoding a CAR, wherein each of TFP and CAR exhibits specific binding to an antigen, thereby potentiating immunity of the cell. In some embodiments, (a) is performed prior to, concurrent with, or subsequent to (b). In some embodiments, the cell retains expression or activity of PTPN2 prior to (a). In some embodiments, the cell is a lymphoid cell. In some embodiments, a method described herein further comprises administering the cell to a subject in need thereof. In some embodiments, a method described herein further comprises administering a compound described herein to the subject prior to, concurrent with, or subsequent to the administering the cell. In some embodiments, prior to the administering the compound described herein, a cell of the subject exhibits expression or activity of PTPN2.

In certain aspects, the present disclosure provides a method of treating cancer in a subject in need thereof, comprising: (a) administering a compound described herein; and (b) administering a second agent or a second therapy concurrently, before, or after step (a), wherein the second agent or the second therapy comprises a lymphoid cell that (1) retains expression or activity of PTPN2 prior to being exposed to the compound, and (2) expresses (i) a chimeric T-cell receptor (TCR) sequence encoding a T-cell receptor fusion protein (TFP) and/or (ii) a chimeric antigen receptor (CAR) sequence encoding a CAR, wherein each of TFP and CAR exhibits specific binding to a tumor antigen. In some embodiments, the compound is administered systemically and/or transiently to the subject in need thereof, and wherein the second agent or the second therapy comprises a lymphoid cell that (1) retains expression or activity of PTPN2 prior to being exposed to the compound, and (2) a chimeric antigen receptor (CAR) sequence encoding a CAR that exhibits specific binding to a tumor antigen. In some embodiments, a compound described herein is systemically and transiently administered to the subject in need thereof. In some embodiments, prior to being exposed to the compound, the lymphoid cell retains at least about 90% of the expression or activity of PTPN2 as compared to a control. In some embodiments, the second agent or the second therapy comprises a sub-therapeutic amount of the lymphoid cells. In some embodiments, the compound (i) does not regulate site-specific recombination of a gene encoding PTPN2, and (ii) does not affect editing of the gene encoding PTPN2. In some embodiments, the lymphoid cell is an immune effector cell. In some embodiments, the lymphoid cell is selected from the group consisting of: T cell, B cell, NK cell, KHYG cell, T helper cell, regulatory T cell, memory T cell, tumor infiltration T cell (TIL), antigen presenting cell, and dendritic cell. In some embodiments, the lymphoid cell is selected from the group consisting of a CD4+ T cell, a CD8+ T cell, and a CD4+ and CD8+ T cell. In some embodiments, the subject suffers from a cancer selected from cancer of bladder, bone, brain, breast, cervix, colon, lung, esophagus, head and neck, ovary, prostate, uterus, stomach, skin, and renal tissue. In some embodiments, the compound exhibits an $IC_{50}$ of less than or equal to 500 nM for PTPN2 as ascertained in a phosphatase assay utilizing DiFMUP as a substrate. In some embodiments, the compound exhibits (i) an $IC_{50}$ less than 5 nM as ascertained in a phosphatase assay utilizing DiFMUP as the substrate, and (ii) an $EC_{50}$ less than 10 μM in a pSTAT1 assay. In some embodiments, the compound exhibits (i) an $IC_{50}$ less than 5 nM as ascertained in a phosphatase assay utilizing DiFMUP as the substrate, (ii) an $EC_{50}$ less than 5 μM in a pSTAT1 assay, and (iii) an $EC_{50}$ less than 1 μM when tested in a CD25 assay. In some embodiments, the compound exhibits an $IC_{50}$ of less than or equal to 500 nM for PTP1B as ascertained in a phosphatase assay utilizing DiFMUP as a substrate. In some embodiments, expression or activity of PTPN2 is transiently downregulated by intermittent administration of the compound to the lymphoid cell. In some embodiments, the method further comprises monitoring, concurrent with or subsequent to the administration of the compound and/or the lymphoid cell, one or more inflammatory biomarkers present in the subject selected from the group consisting of: antibodies, cytokines, radicals, and coagulation factors. In some embodiments, the cytokines comprise IL-1, IL-6, TNF-α, IL-10, or IL-1RR.

In some embodiments, a method of the present disclosure further comprises administering to the subject another agent selected from the group consisting of a chemotherapeutic agent, a radioactive agent, an anti-tumor marker inhibitor, and a checkpoint inhibitor. In some embodiments, a method of the present disclosure further comprises administering an additional therapeutic agent in conjunction with the compound.

In certain aspects, the present disclosure provides a method of potentiating immunity of a subject in need thereof, comprising administering (e.g., systemically or locally administering) a PTPN2 inhibitor, such as a compound of Formula (I), (II), (II-a), (III), or (IV), to the subject, thereby potentiating immunity of the subject. In another aspect, the present disclosure provides a method of potentiating immunity of a subject in need thereof, comprising (e.g., transiently) downregulating expression or activity of PTPN2 in vivo in a cell of the subject with one or more compounds described herein, such as a compound of Formula (I), (II), (II-a), (III), or (IV), thereby potentiating immunity of the subject. In yet another aspect, the present disclosure provides a method of potentiating immunity of a subject in need thereof, comprising systemically and transiently downregulating expression or activity of PTPN2 in vivo in a cell of the subject with one or more compounds described herein, such as a compound of Formula (I), (II), (II-a), (III), or (IV), thereby potentiating immunity of the subject.

In certain aspects, the present disclosure provides a modified lymphoid cell comprising (i) a chimeric T-cell receptor (TCR) sequence encoding a T-cell receptor fusion protein (TFP) and/or (ii) a chimeric antigen receptor (CAR) sequence encoding a CAR, wherein each of TFP and CAR exhibits specific binding to an antigen, wherein the lymphoid cell comprises a compound described herein. In some embodiments, the compound exhibits (i) an $IC_{50}$ less than 5 nM as ascertained in a phosphatase assay utilizing DiFMUP as the substrate, (ii) an $EC_{50}$ less than 10 μM in a pSTAT1 assay, and/or (iii) an $EC_{50}$ less than 1 μM when tested in a CD25 assay.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

DETAILED DESCRIPTION

Figure 1:
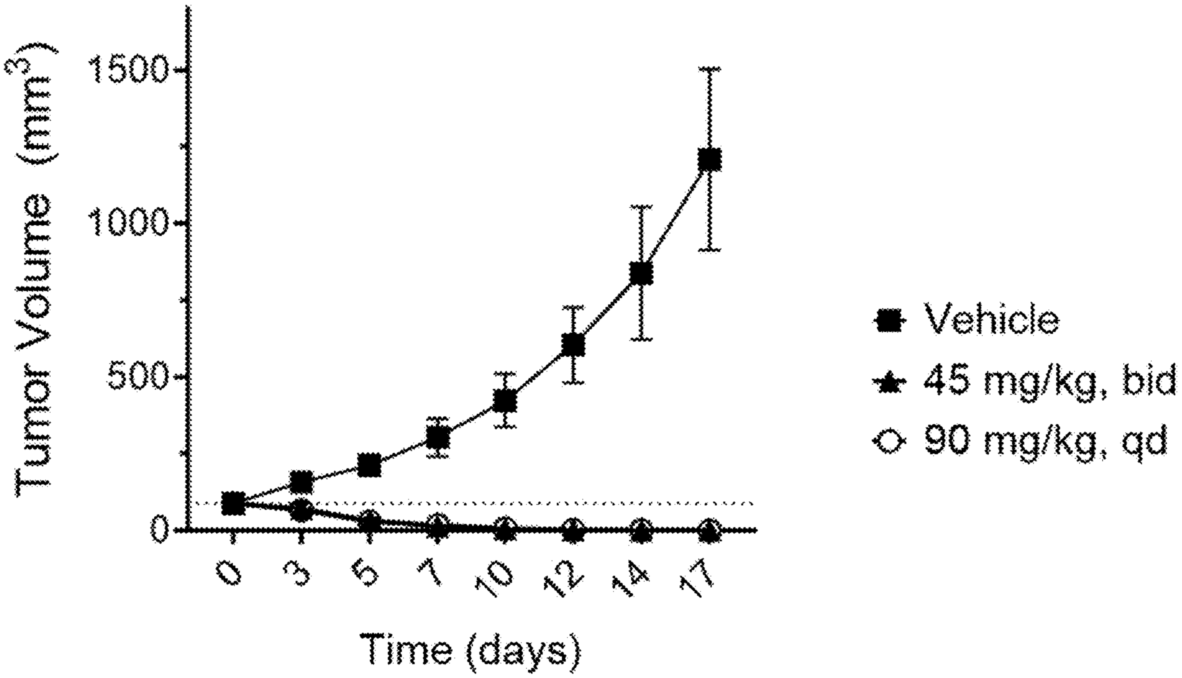
FIG. 1 shows results of a study in which MC38 tumor-bearing mice were treated with (i) a PTPN2 inhibitor of the present disclosure (e.g., Compound A, at various concentrations) or (ii) vehicle.

Unless defined otherwise, all technical and scientific terms used herein have the same meaning as is commonly understood by one of skill in the art to which this disclosure belongs. In the event that there are a plurality of definitions for terms herein, those in this section prevail. All patents, patent applications, publications and published nucleotide and amino acid sequences (e.g., sequences available in GenBank or other databases) referred to herein are incorporated by reference. Chemical structures are named herein according to IUPAC conventions as implemented in ChemDraw® software (Perkin Elmer, Inc., Cambridge, MA). The section headings used herein are for organizational purposes only and are not to be construed as limiting the subject matter described. As used in the specification and claims, the singular forms "a", "an" and "the" include plural references unless the context clearly dictates otherwise. Furthermore, use of the term "including" as well as other forms, such as "include", "includes", and "included", is not limiting. The section headings used herein are for organizational purposes only and are not to be construed as limiting the subject matter described.

The term "$C_{x-y}$" or "$C_x$-$C_y$" when used in conjunction with a chemical moiety, such as alkyl, alkenyl, or alkynyl, is meant to include groups that contain from x to y carbons in the chain. For example, the term "$C_{x-y}$ alkyl" refers to substituted or unsubstituted saturated hydrocarbon groups, including straight-chain alkyl and branched-chain alkyl groups, that contain from x to y carbons in the chain.

"Alkyl" refers to substituted or unsubstituted saturated hydrocarbon groups, including linear and branched alkyl groups. An alkyl group may contain from one to twelve carbon atoms (e.g., $C_{1-12}$ alkyl), such as one to eight carbon atoms ($C_{1-8}$ alkyl) or one to six carbon atoms ($C_{1-6}$ alkyl). Exemplary alkyl groups include methyl, ethyl, n-propyl, isopropyl, n-butyl, isobutyl, sec-butyl, tert-butyl, pentyl, isopentyl, neopentyl, hexyl, septyl, octyl, nonyl, and decyl. An alkyl group is attached to the rest of the molecule by a single bond. Unless stated otherwise specifically in the specification, an alkyl group is optionally substituted by one or more substituents such as those substituents described herein.

"Haloalkyl" refers to an alkyl group that is substituted by one or more halogens. Exemplary haloalkyl groups include trifluoromethyl, difluoromethyl, trichloromethyl, 2,2,2-trifluoroethyl, 1,2-difluoroethyl, 3-bromo-2-fluoropropyl, and 1,2-dibromoethyl.

"Alkenyl" refers to substituted or unsubstituted hydrocarbon groups, including linear and branched alkenyl groups, containing at least one double bond. An alkenyl group may contain from two to twelve carbon atoms (e.g., $C_{2-12}$ alkenyl), such as two to eight carbon atoms ($C_{2-8}$ alkenyl) or two to six carbon atoms ($C_{2-6}$ alkenyl). Exemplary alkenyl groups include ethenyl (i.e., vinyl), prop-1-enyl, but-1-enyl, pent-1-enyl, penta-1,4-dienyl, and the like. Unless stated otherwise specifically in the specification, an alkenyl group is optionally substituted by one or more substituents such as those substituents described herein.

"Alkynyl" refers to substituted or unsubstituted hydrocarbon groups, including linear and branched alkynyl groups, containing at least one triple bond. An alkynyl group may contain from two to twelve carbon atoms (e.g., $C_{2-12}$ alkynyl), such as two to eight carbon atoms ($C_{2-8}$ alkynyl) or two to six carbon atoms ($C_{2-6}$ alkynyl). Exemplary alkynyl groups include ethynyl, propynyl, butynyl, pentynyl, hexynyl, and the like. Unless stated otherwise specifically in the specification, an alkynyl group is optionally substituted by one or more substituents such as those substituents described herein.

"Alkylene" or "alkylene chain" refers to substituted or unsubstituted divalent saturated hydrocarbon groups, including linear alkylene and branched alkylene groups, that contain from one to twelve carbon atoms (e.g., $C_{1-12}$ alkylene), such as one to eight carbon atoms ($C_{1-8}$ alkylene) or one to six carbon atoms ($C_{1-6}$ alkylene). Exemplary alkylene groups include methylene, ethylene, propylene, and n-butylene. Similarly, "alkenylene" and "alkynylene" refer to alkylene groups, as defined above, which comprise one or more carbon-carbon double or triple bonds, respectively. The points of attachment of the alkylene, alkenylene or alkynylene chain to the rest of the molecule can be through one carbon or any two carbons of the chain. Unless stated otherwise specifically in the specification, an alkylene, alkenylene, or alkynylene group is optionally substituted by one or more substituents such as those substituents described herein.

"Heteroalkyl", "heteroalkenyl" and "heteroalkynyl" refer to substituted or unsubstituted alkyl, alkenyl and alkynyl groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkyl group has a chain length of 3 to 8 atoms. Connection to the rest of the molecule may be through either a heteroatom or a carbon in the heteroalkyl, heteroalkenyl, or heteroalkynyl chain. Unless stated otherwise specifically in the specification, a heteroalkyl, heteroalkenyl, or heteroalkynyl group is optionally substituted by one or more substituents such as those substituents described herein.

"Heteroalkylene", "heteroalkenylene" and "heteroalkynylene" refer to substituted or unsubstituted alkylene, alkenylene and alkynylene groups, respectively, in which one or more, such as 1, 2 or 3, of the carbon atoms are replaced with a heteroatom, such as O, N, P, Si, S, or combinations thereof. Any nitrogen, phosphorus, and sulfur heteroatoms present in the chain may optionally be oxidized, and any nitrogen heteroatoms may optionally be quaternized. If given, a numerical range refers to the chain length in total. For example, a 3- to 8-membered heteroalkylene group has a chain length of 3 to 8 atoms. The points of attachment of the heteroalkylene, heteroalkenylene or heteroalkynylene chain to the rest of the molecule can be through either one heteroatom or one carbon, or any two heteroatoms, any two carbons, or any one heteroatom and any one carbon in the heteroalkylene, heteroalkenylene or heteroalkynylene chain. Unless stated otherwise specifically in the specification, a heteroalkylene, heteroalkenylene, or heteroalkynylene group is optionally substituted by one or more substituents such as those substituents described herein.

"Carbocycle" refers to a saturated, unsaturated or aromatic ring in which each atom of the ring is a carbon atom. Carbocycle may include $C_{3-10}$ monocyclic rings, $C_{5-12}$ bicyclic rings, $C_{5-18}$ polycyclic rings, $C_{5-12}$ spirocyclic rings, and $C_{5-12}$ bridged rings. Each ring of a bicyclic or polycyclic carbocycle may be selected from saturated, unsaturated, and aromatic rings. A polycyclic carbocycle contains a number or rings equal to the minimum number of scissions required to convert the carbocycle into an acyclic skeleton (e.g., bicyclic, tricyclic, tetracyclic, etc.). In some embodiments, the carbocycle is a $C_{6-12}$ aryl group, such as $C_{6-10}$ aryl. In some embodiments, the carbocycle is a $C_{3-12}$ cycloalkyl group. In some embodiments, the carbocycle is a $C_{5-12}$ cycloalkenyl group. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic rings, as valence permits, are included in the definition of carbocycle. A carbocycle may comprise a fused ring, a bridged ring, a spirocyclic ring, a saturated ring, an un saturated ring, an aromatic ring, or any combination thereof. Exemplary carbocycles include cyclopentyl, cyclohexyl, cyclohexenyl, adamantly, phenyl, indanyl, and naphthyl. Unless state otherwise specifically in the specification, a carbocycle is optionally substituted by one or more substituents such as those substituents described herein.

"Heterocycle" refers to a saturated, unsaturated or aromatic ring comprising one or more heteroatoms, for example 1, 2, 3, or 4 heteroatoms selected from O, S, P, and N. Heterocycle may include 3- to 10-membered monocyclic rings, 5- to 12-membered bicyclic rings, 5- to 18-membered polycyclic rings, 5- to 12-membered spirocyclic rings, and 5- to 12-membered bridged rings. Each ring of a bicyclic or polycyclic heterocycle may be selected from saturated, unsaturated, and aromatic rings. A polycyclic heterocycle contains a number or rings equal to the minimum number of scissions required to convert the heterocycle into an acyclic skeleton (e.g., bicyclic, tricyclic, tetracyclic, etc.). The heterocycle may be attached to the rest of the molecule through any atom of the heterocycle, valence permitting, such as a carbon or nitrogen atom of the heterocycle. In some embodiments, the heterocycle is a 5- to 10-membered heteroaryl group, such as 5- or 6-membered heteroaryl. In some embodiments, the heterocycle is a 3- to 12-membered heterocycloalkyl group. A heterocycle may comprise a fused ring, a bridged ring, a spirocyclic ring, a saturated ring, an unsaturated ring, an aromatic ring, or any combination thereof. In an exemplary embodiment, a heterocycle, e.g., pyridyl, may be fused to a saturated or unsaturated ring, e.g., cyclohexane, cyclopentane, or cyclohexene. Exemplary heterocycles include pyrrolidinyl, pyrrolyl, imidazolyl, pyrazolyl, triazolyl, piperidinyl, pyridinyl, pyrimidinyl, pyridazinyl, pyrazinyl, thiophenyl, oxazolyl, thiazolyl, morpholinyl, indazolyl, indolyl, benzothienyl, benzoxazolyl, and quinolinyl. Unless stated otherwise specifically in the specification, a heterocycle is optionally substituted by one or more substituents such as those substituents described herein.

"Heteroaryl" refers to an aromatic ring that comprises at least one heteroatom, for example 1, 2, 3, or 4 heteroatoms selected from O, S and N. Heteroaryl may include 5- to 10-membered monocyclic rings, 6- to 12-membered bicyclic rings, 6- to 18-membered polycyclic rings, 5- to 12-membered spirocyclic rings, and 6- to 12-membered bridged rings. As used herein, the heteroaryl ring may be selected from monocyclic, bicyclic, or polycyclic—including fused, spirocyclic and bridged ring systems—wherein at least one of the rings in the ring system is aromatic and comprises at least one heteroatom. A polycyclic heteroaryl contains a number or rings equal to the minimum number of scissions required to convert the heteroaryl into an acyclic skeleton (e.g., bicyclic, tricyclic, tetracyclic, etc.). The heteroatom(s) in the heteroaryl may optionally be oxidized. One or more nitrogen atoms, if present, are optionally quaternized. The heteroaryl may be attached to the rest of the molecule through any atom of the heteroaryl, valence permitting, such as a carbon or nitrogen atom of the heteroaryl. Examples of heteroaryl groups include, but are not limited to, azepinyl, benzimidazolyl, benzisothiazolyl, benzisoxazolyl, benzofuranyl, benzothiazolyl, benzothiophenyl, benzoxazolyl, furanyl, imidazolyl, indazolyl, indolyl, isoquinolinyl, isothiazolyl, isoxazolyl, oxadiazolyl, oxazolyl, purinyl, pyrazinyl, pyrazolidinyl, pyrazolyl, pyridazinyl, pyridazolyl, pyridyl, pyrimidinyl, pyrrolyl, quinazolinyl, quinolinyl, quinoxalinyl, tetrahydroquinolinyl, thiadiazolyl, thiazolyl, and thienyl groups. Unless stated otherwise specifically in the specification, a heteroaryl is optionally substituted by one or more substituents such as those substituents described herein.

Unless stated otherwise, hydrogen atoms are implied in structures depicted herein as necessary to satisfy the valence requirement.

A waved line "" drawn across or at the end of a bond or a dashed bond "" are used interchangeably herein to denote where a bond disconnection or attachment occurs. For example, in the structure

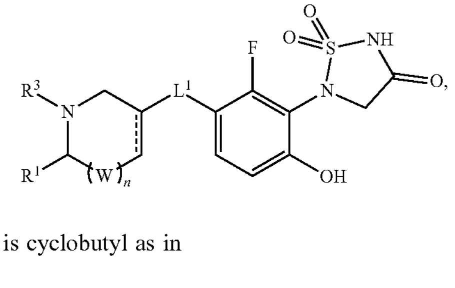

if $R^1$ is cyclobutyl as in

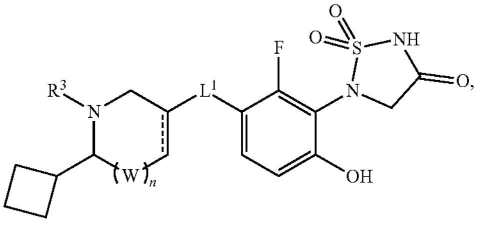

in then $R^1$ may be depicted as

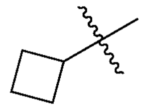,

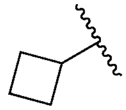, or

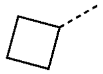.

The term "substituted" refers to moieties having substituents replacing a hydrogen on one or more carbons or heteroatoms of the structure. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, heteroatoms such as nitrogen may have any permissible substituents of organic compounds described herein which satisfy the valences of the heteroatoms.

A compound disclosed herein, such as a compound of Formula (I), (I-1), (II), (II-1), (II-a), (II-a1), (III), (III-1), (IV), or (IV-1), is optionally substituted by one or more—such as 1, 2 or 3—substituents selected from:

halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, and —S(=O)(=$NR^{22}$)$N(R^{22})(R^{23})$; wherein two substituents attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —S(=O)(=$NR^{22}$)$N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein —$C_{0-6}$ alkyl-($C_{3-12}$ carbocycle) and —$C_{0-6}$ alkyl-(3- to 12-membered heterocycle) are optionally substituted with one, two, or three groups independently selected from halogen and $C_{1-6}$ alkyl; and $R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula (I), (I-1), (II), (II-1), (II-a), (II-a1), (III), (III-1), (IV), or (IV-1), is optionally substituted by one or more—such as 1, 2 or 3—substituents selected from:

halogen, oxo, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, and —$S(O)_2N(R^{22})(R^{23})$—, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, and =$C(R^{21})_2$;

$R^{21}$ is independently selected at each occurrence from hydrogen, halogen, $C_{1-6}$ alkyl, and $C_{1-6}$ haloalkyl;

$R^{22}$ is independently selected at each occurrence from hydrogen, $C_{1-6}$ alkyl, $C_{1-6}$ haloalkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein —$C_{0-6}$ alkyl-($C_{3-12}$ carbocycle) and —$C_{0-6}$ alkyl-(3- to 12-membered heterocycle) are optionally substituted with one, two, or three groups independently selected from halogen and $C_{1-6}$ alkyl;

$R^{23}$ is independently selected at each occurrence from hydrogen and $C_{1-6}$ alkyl; or $R^{22}$ and $R^{23}$ attached to the same nitrogen atom form 3- to 10 membered heterocycle.

In some embodiments, a compound disclosed herein, such as a compound of Formula (I), (I-1), (II), (II-1), (II-a), (II-a1), (III), (III-1), (IV), or (IV-1), is optionally substituted by one or more—such as 1, 2 or 3—substituents selected from halogen, oxo, =NH, —CN, —$NO_2$, $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, —$CH_2$-(3- to 10-membered heterocycle), —OH, —$OCH_3$, —$OCH_2CH_3$, —$NH_2$, —$NHCH_3$, and —$NHCH_2CH_3$, wherein $C_{1-6}$ alkyl, $C_{2-6}$ alkenyl, $C_{2-6}$ alkynyl, $C_{3-10}$ carbocycle, —$CH_2$—($C_{3-10}$ carbocycle), 3- to 10-membered heterocycle, and —$CH_2$-(3- to 10-membered heterocycle) are optionally substituted with one, two, or three groups independently selected from halogen, oxo, =NH, —CN, —$NO_2$, —$CH_3$, —$CH_2CH_3$, —$CH(CH_3)_2$, —$C(CH_3)$ 3, —OH, —$OCH_3$, —$OCH_2CH_3$, —$NH_2$, —$NHCH_3$, and —$NHCH_2CH_3$.

It will be understood by those skilled in the art that substituents can themselves be substituted, if appropriate. Unless specifically stated as "unsubstituted", references to chemical moieties herein are understood to include substituted variants. For example, reference to a "heteroaryl" group or moiety implicitly includes both substituted and unsubstituted variants.

Where bivalent substituent groups are specified herein by their conventional chemical formulae, written from left to right, they are intended to encompass the isomer that would result from writing the structure from right to left, e.g., —$CH_2O$— is also intended to encompass —$OCH_2$—.

"Optional" or "optionally" means that the subsequently described event or circumstances may or may not occur, and that the description includes instances where the event or circumstance occurs and instances in which it does not. For example, an "optionally substituted" group may be either unsubstituted or substituted.

Compounds of the present disclosure also include crystalline and amorphous forms of those compounds, pharmaceutically acceptable salts, and active metabolites having the same type of activity, including, for example, polymorphs, pseudopolymorphs, solvates, hydrates, unsolvated polymorphs (including anhydrates), conformational polymorphs, amorphous forms of the compounds, and mixtures thereof.

The compounds described herein may exhibit their natural isotopic abundance, or one or more of the atoms may be artificially enriched in a particular isotope having the same atomic number, but an atomic mass or mass number different from the atomic mass or mass number predominantly found in nature. All isotopic variations of the compounds of the present disclosure, whether radioactive or not, are encompassed within the scope of the present disclosure. For example, hydrogen has three naturally occurring isotopes, denoted $^{1}H$ (protium), $^{2}H$ (deuterium), and $^{3}H$ (tritium). Protium is the most abundant isotope of hydrogen in nature. Enriching for deuterium may afford certain therapeutic advantages, such as increased in vivo half-life and/or exposure, or may provide a compound useful for investigating in vivo routes of drug elimination and metabolism. Examples of isotopes that may be incorporated into compounds of the present disclosure include, but are not limited to, $^{2}H$, $^{3}H$, $^{13}C$, $^{14}C$, $^{15}N$, $^{18}O$, $^{17}O$, $^{35}S$, $^{36}Cl$, and $^{18}F$. Of particular interest are compounds of Formula (I), (I-1), (II), (II-1), (II-a), (II-a1), (III), (III-1), (IV), or (IV-1) enriched in tritium or carbon-14, which can be used, for example, in tissue distribution studies; compounds of the disclosure enriched in deuterium—especially at a site of metabolism-resulting, for example, in compounds having greater metabolic stability; and compounds of Formula (I), (I-1), (II), (II-1), (II-a), (II-a1), (III), (III-1), (IV), or (IV-1) enriched in a positron emitting isotope, such as $^{11}C$, $^{18}F$, $^{15}O$ and $^{13}N$, which can be used, for example, in Positron Emission Topography (PET) studies. Isotopically-enriched compounds may be prepared by conventional techniques well known to those skilled in the art.

As used herein, the phrase "of the formula", "having the formula" or "having the structure" is not intended to be limiting and is used in the same way that the term "comprising" is commonly used. For example, if one structure is depicted, it is understood that all stereoisomer and tautomer forms are encompassed, unless stated otherwise.

Certain compounds described herein contain one or more asymmetric centers and can thus give rise to enantiomers, diastereomers, and other stereoisomeric forms, the asymmetric centers of which can be defined, in terms of absolute stereochemistry, as (R)- or (S)-. In some embodiments, in order to optimize the therapeutic activity of the compounds of the disclosure, e.g., to treat cancer, it may be desirable that the carbon atoms have a particular configuration (e.g., (R,R), (S,S), (S,R), or (R,S)) or are enriched in a stereoisomeric form having such configuration. The compounds of the disclosure may be provided as racemic mixtures. Accordingly, the disclosure relates to racemic mixtures, pure stereoisomers (e.g., enantiomers and diastereomers), stereoisomer-enriched mixtures, and the like, unless otherwise indicated. When a chemical structure is depicted herein without any stereochemistry, it is understood that all possible stereoisomers are encompassed by such structure. Similarly, when a particular stereoisomer is shown or named herein, it will be understood by those skilled in the art that minor amounts of other stereoisomers may be present in the compositions of the disclosure unless otherwise indicated, provided that the utility of the composition as a whole is not eliminated by the presence of such other isomers. Individual stereoisomers may be obtained by numerous methods that are known in the art, including preparation using chiral synthons or chiral reagents, resolution using chiral chromatography using a suitable chiral stationary phase or support, or by chemically converting them into diastereomers, separating the diastereoisomers by conventional means such as chromatography or recrystallization, then regenerating the original stereoisomer.

Additionally, where applicable, all cis-trans or E/Z isomers (geometric isomers), tautomeric forms and topoisomeric forms of the compounds described herein are included with the scope of the disclosure unless otherwise specified.

The term "tautomer", as used herein, refers to each of two or more isomers of a compound that exist in equilibrium and which readily interconvert. For example, one skilled in the art would understand that 1,2,3-triazole exists in two tautomeric forms:

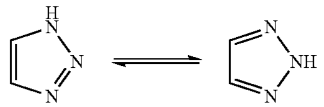 [SMILES: c1c[nH]nn1 ; c1cn[nH]n1]

Unless otherwise specified, chemical entities described herein are intended to encompass all possible tautomers, even when a structure depicts only one of them. For example, even though a single tautomer of the compound below may be depicted herein for clarity, the disclosure is intended to encompass all possible tautomers, including:

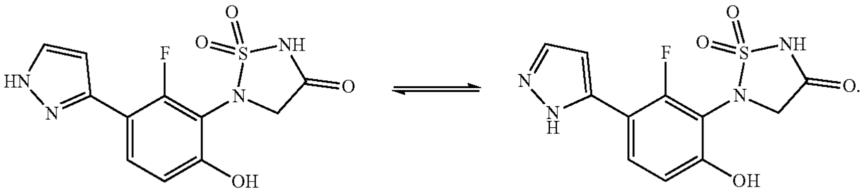 [SMILES: O=C1CN(c2c(O)ccc(-c3cc[nH]n3)c2F)S(=O)(=O)N1 ; O=C1CN(c2c(O)ccc(-c3ccn[nH]3)c2F)S(=O)(=O)N1]

The term "pharmaceutically acceptable" refers to a material that is not biologically or otherwise unacceptable when used in the subject compositions and methods. For example, the term "pharmaceutically acceptable carrier" refers to a material—such as an adjuvant, excipient, glidant, sweetening agent, diluent, preservative, dye, colorant, flavor enhancer, surfactant, wetting agent, dispersing agent, suspending agent, stabilizer, isotonic agent, solvent or emulsifier—that can be incorporated into a composition and administered to a patient without causing unacceptable biological effects or interacting in an unacceptable manner with other components of the composition. Such pharmaceutically acceptable materials typically have met the required standards of toxicological and manufacturing testing, and include those materials identified as suitable inactive ingredients by the U.S. Food and Drug Administration.

The terms "salt" and "pharmaceutically acceptable salt" refer to a salt prepared from a base or an acid. Pharmaceutically acceptable salts are suitable for administration to a patient, such as a mammal (for example, salts having acceptable mammalian safety for a given dosage regime). Salts can be formed from inorganic bases, organic bases, inorganic acids and organic acids. In addition, when a compound contains both a basic moiety, such as an amine, pyridine or imidazole, and an acidic moiety, such as a carboxylic acid or tetrazole, zwitterions may be formed and are included within the term "salt" as used herein. Preferred pharmaceutically acceptable salts of the compounds described herein are pharmaceutically acceptable acid addition salts and pharmaceutically acceptable base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid, hydroiodic acid, hydrofluoric acid, phosphorous acid, and the like. Also included are salts that are formed with organic acids such as aliphatic mono- and dicarboxylic acids, phenyl-substituted alkanoic acids, hydroxy alkanoic acids, alkanedioic acids, aromatic acids, aliphatic and aromatic sulfonic acids, etc., and include, for example, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Exemplary salts thus include sulfates, pyrosulfates, bisulfates, sulfites, bisulfites, nitrates, phosphates, monohydrogenphosphates, dihydrogenphosphates, metaphosphates, pyrophosphates, chlorides, bromides, iodides, acetates, trifluoroacetates, propionates, caprylates, isobutyrates, oxalates, malonates, succinate suberates, sebacates, fumarates, maleates, mandelates, benzoates, chlorobenzoates, methylbenzoates, dinitrobenzoates, phthalates, benzenesulfonates, toluenesulfonates, phenylacetates, citrates, lactates, malates, tartrates, methanesulfonates, and the like. Also contemplated are salts of amino acids, such as arginates, gluconates, and galacturonates (see, for example, Berge S. M. et al., "Pharmaceutical Salts," Journal of Pharmaceutical Science, 66:1-19 (1997)). Acid addition salts of basic compounds are, in some embodiments, prepared by contacting the free base forms with a sufficient amount of the desired acid to produce the salt according to methods and techniques with which a skilled artisan is familiar.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Pharmaceutically acceptable base addition salts are, in some embodiments, formed with metals or amines, such as alkali and alkaline earth metals or organic amines. Salts derived from inorganic bases include, but are not limited to, sodium, potassium, lithium, ammonium, calcium, magnesium, iron, zinc, copper, manganese, aluminum salts and the like. Salts derived from organic bases include, but are not limited to, salts of primary, secondary, and tertiary amines, substituted amines including naturally occurring substituted amines, cyclic amines and basic ion exchange resins, for example, isopropylamine, trimethylamine, diethylamine, triethylamine, tripropylamine, ethanolamine, diethanolamine, 2-dimethylaminoethanol, 2-diethylaminoethanol, dicyclohexylamine, lysine, arginine, histidine, caffeine, procaine, N,N-dibenzylethylenediamine, chloroprocaine, hydrabamine, choline, betaine, ethylenediamine, ethylenedianiline, N-methylglucamine, glucosamine, methylglucamine, theobromine, purines, piperazine, piperidine, N-ethylpiperidine, polyamine resins and the like. See Berge et al., supra.

"Prodrug" is meant to indicate a compound that may be converted under physiological conditions or by solvolysis to a biologically active compound described herein. Thus, the term "prodrug" refers to a precursor of a biologically active compound that is pharmaceutically acceptable. In some aspects, a prodrug is inactive when administered to a subject but is converted in vivo to an active compound, for example, by hydrolysis. The prodrug compound often offers advantages of solubility, tissue compatibility or delayed release in a mammalian organism (see, e.g., Bundgard, H., Design of Prodrugs (1985), pp. 7-9, 21-24 (Elsevier, Amsterdam); Higuchi, T., et al., "Pro-drugs as Novel Delivery Systems," (1987) A.C.S. Symposium Series, Vol. 14; and Bioreversible Carriers in Drug Design, ed. Edward B. Roche, American Pharmaceutical Association and Pergamon Press each of which is incorporated in full by reference herein). The term "prodrug" is also meant to include any covalently bonded carriers, which release the active compound in vivo when such prodrug is administered to a mammalian subject. Prodrugs of an active compound, as described herein, are typically prepared by modifying functional groups present in the active compound in such a way that the modifications are cleaved, either in routine manipulation or in vivo, to the parent active compound. Prodrugs include compounds wherein a hydroxy, amino or mercapto group is bonded to any group that, when the prodrug of the active compound is administered to a mammalian subject, cleaves to form a free hydroxy, free amino or free mercapto group, respectively. Examples of prodrugs include, but are not limited to, acetate, formate and benzoate derivatives of a hydroxy functional group, or acetamide, formamide and benzamide derivatives of an amine functional group in the active compound, and the like.

The term "in vivo" refers to an event that takes place in a subject's body. The term "ex vivo" refers to an event that first takes place outside of the subject's body for a subsequent in vivo application into a subject's body. For example, an ex vivo preparation may involve preparation of cells outside of a subject's body for the purpose of introduction of the prepared cells into the same or a different subject's body. The term "in vitro" refers to an event that takes place outside of a subject's body. For example, an in vitro assay encompasses any assay run outside of a subject's body. In vitro assays encompass cell-based assays in which cells alive or dead are employed. In vitro assays also encompass a cell-free assay in which no intact cells are employed.

The disclosure is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the disclosure includes compounds produced by a process comprising administering a compound disclosed herein to a mammal for a period of time sufficient to yield a metabolic product thereof. Such products are typically identified by administering a radiolabeled compound of the disclosure in a detectable dose to an animal, such as rat, mouse, guinea pig, monkey, or to a human, allowing sufficient time for metabolism to occur, and isolating its conversion products from the urine, blood or other biological samples.

The terms "administer," "administering," "administration," and derivatives thereof refer to methods that may be used to enable delivery of agents or compositions to the desired site of biological action. These methods include, but are not limited to parenteral administration (e.g., intravenous, subcutaneous, intraperitoneal, intramuscular, intravascular, intrathecal, intranasal, intravitreal, infusion and local injection), transmucosal injection, oral administration, administration as a suppository, and topical administration. Administration is by any route, including parenteral. Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transplantation, etc. One skilled in the art will know of additional methods for administering a therapeutically effective amount of a composition of the present disclosure for preventing or relieving one or more symptoms associated with a disease.

The term "systemic administration" refers to administration of agents or compositions such that the agents or compositions become distributed in a subject's body. The distribution of the agents or compositions throughout the subject's body may be an even distribution. Alternatively, the distribution may be preferential, resulting in a higher localization of the agents or compositions in one or more desired sites. A desired site may be the blood or another site that is reachable by the vascular system. Non-limiting examples of systemic routes of administration include administration by (1) introducing the agent directly into the vascular system or (2) oral, pulmonary, or intramuscular administration wherein the agent is adsorbed, enters the vascular system, and is carried to one or more desired site(s) of action via the blood. By contrast, "non-systemic administration" refers to administration of agents or compositions such that the agents or compositions are administered locally to the target site of interest of a subject's body to affect primarily a local effect.

The terms "co-administration," "administered in combination with," and their grammatical equivalents, encompass administration of two or more agents to a subject so that both agents and/or their metabolites can assert their respective functions. Co-administration includes simultaneous administration in separate compositions, administration at different times in separate compositions, or administration in a composition in which both agents are present.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. An effective amount of an active agent may be administered in a single dose or in multiple doses. A component may be described herein as having at least an effective amount, or at least an amount effective, such as that associated with a particular goal or purpose, such as any described herein. The term "effective amount" also applies to a dose that will provide an image for detection by an appropriate imaging method. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, "treating" or "treatment" refers to an approach for obtaining beneficial or desired results with respect to a disease, disorder, or medical condition (such as cancer) in a subject, including but not limited to the following: (a) preventing the disease or medical condition from occurring, e.g., preventing the reoccurrence of the disease or medical condition or prophylactic treatment of a subject that is pre-disposed to the disease or medical condition; (b) ameliorating the disease or medical condition, e.g., eliminating or causing regression of the disease or medical condition in a subject; (c) suppressing the disease or medical condition, e.g., slowing or arresting the development of the disease or medical condition in a subject; or (d) alleviating symptoms of the disease or medical condition in a subject. For example, "treating cancer" would include preventing cancer from occurring, ameliorating cancer, suppressing cancer, and alleviating the symptoms of cancer. Also, a therapeutic benefit is achieved with the eradication or amelioration of one or more of the physiological symptoms associated with the underlying disorder such that an improvement is observed in the subject, notwithstanding that the subject may still be afflicted with the underlying disorder.

A "therapeutic effect", as that term is used herein, encompasses a therapeutic benefit and/or prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The terms "antagonist" and "inhibitor" are used interchangeably, and they refer to a compound having the ability to inhibit a biological function (e.g., activity, expression, binding, protein-protein interaction) of a target protein (e.g., PTPN2). Accordingly, the terms "antagonist" and "inhibitor" are defined in the context of the biological role of the target protein. While preferred antagonists herein specifically interact with (e.g., bind to) the target, compounds that inhibit a biological activity of the target protein by interacting with other members of the signal transduction pathway of which the target protein is a member are also specifically included within this definition.

The term "selective inhibition" or "selectively inhibit" refers to the ability of a biologically active agent to preferentially reduce the target signaling activity as compared to off-target signaling activity, via direct or indirect interaction with the target.

The terms "subject" and "patient" refer to an animal, such as a mammal, for example a human. The methods described herein can be useful in both human therapeutics and veterinary applications. In some embodiments, the subject is a mammal, such as a human. "Mammal" includes humans and both domestic animals such as laboratory animals and household pets (e.g., cats, dogs, swine, cattle, sheep, goats, horses, rabbits), and non-domestic animals such as wildlife and the like.

The terms "therapeutic agent", "therapeutic capable agent" or "treatment agent" are used interchangeably and refer to a molecule or compound that confers some beneficial effect upon administration to a subject. The beneficial effect includes enablement of diagnostic determinations; amelioration of a disease, symptom, disorder, or pathological condition; reducing or preventing the onset of a disease, symptom, disorder or condition; and generally counteracting a disease, symptom, disorder or pathological condition.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" refers to either natural and/or unnatural or synthetic amino acids, including glycine and both the D or L optical isomers, and amino acid analogs and peptidomimetics.

The terms "polynucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs, such as peptide nucleic acid (PNA), morpholino and locked nucleic acid (LNA), glycol nucleic acid (GNA), threose nucleic acid (TNA), 2'-fluoro, 2'-OMe, and phosphorothiolated DNA. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component or other conjugation target.

As used herein, "expression" refers to the process by which a polynucleotide is transcribed from a DNA template (such as into an mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

"Aberrantly expressed" or "aberrant expression" as applied to a nucleotide sequence (e.g., a gene) or polypeptide sequence in a subject, refers to the aberrant production of the mRNA transcribed and/or translated from the nucleotide sequence or the protein product encoded by the nucleotide sequence. A differentially expressed sequence may be overexpressed (or aberrantly high expression) or underexpressed (or aberrantly low expression) as compared to the expression level of a reference sample (i.e., a reference level). As used herein, overexpression is an increase in expression—such as by at least 1.25 fold, or alternatively, at least 1 fold, at least 2 fold, at least 3 fold, at least 4 fold, or at least 10 fold—over that detected in a reference sample. As used herein, underexpression is a reduction in expression—such as by at least 1.25 fold, or alternatively, at least 1 fold, at least 2 fold, at least 3 fold, at least 4 fold, or at least 10 fold—under that detected in a reference sample. Underexpression also encompasses absence of expression of a particular sequence as evidenced by the absence of detectable expression in a test subject when compared to a reference sample.

The term "reference level" refers to a control level used to evaluate a test level. In some examples, a reference level may be a control. For example, a biomarker may be considered to be underexpressed when the expression level of that biomarker is lower than a reference level. The reference level can be determined by a plurality of methods, provided that the resulting reference level accurately provides a level of a biomarker above which exists a first group of subjects having a different probability of exhibiting a clinically beneficial response to treatment with a PTPN2 inhibitor than that of a second group of patients having levels of the biomarker below the reference level. The reference level may be determined, for example, by measuring the level of expression of a biomarker in tumorous or non-tumorous cancer cells from the same tissue as the tissue of the cancer cells to be tested. In some examples, the reference level may be a level of a biomarker determined in vitro. A reference level may be determined by comparison of the level of a biomarker in populations of subjects having the same cancer. Two or more separate groups of subjects may be determined by identification of subsets of populations of the cohort that have the same or similar levels of a biomarker. Determination of a reference level can then be made based on a level that distinguishes these separate groups. A reference level may be a single number, equally applicable to every subject, or a reference level can vary according to specific subpopulations of subjects. For example, older men may have a different reference level than younger men for the same cancer, and women may have a different reference level than men for the same cancer. Furthermore, the reference level may be some level determined for each subject individually. For example, the reference level may be a ratio of a biomarker level in a cancer cell of a subject relative to the biomarker level in a normal cell within the same subject. In some embodiments, a reference level is a numerical range of gene expression that is obtained from a statistical sampling from a population of individuals having cancer. The sensitivity of the individuals having cancer to treatment with a PTPN2 inhibitor may be known. In certain embodiments, the reference level is derived by comparing gene expression to a control gene that is expressed in the same cellular environment at relatively stable levels (e.g. a housekeeping gene such as an actin). Comparison to a reference level may be a qualitative assessment or a quantitative determination.

The terms "determining," "measuring," "evaluating," "assessing," "assaying," "testing," and "analyzing" are used interchangeably herein to refer to any form of measurement and include determining if an analyte is present or not (e.g., detection). These terms can include both quantitative and/or qualitative determinations. Assessing may be relative or absolute. A relative amount could be, for example, high, medium, or low. An absolute amount could reflect the measured strength of a signal or the translation of this signal strength into another quantitative format, such as micrograms/mL. "Detecting the presence of" can include determining the amount of something present, as well as determining whether it is present or absent.

"Signal transduction" is a process during which stimulatory or inhibitory signals are transmitted into and within a cell to elicit an intracellular response. A molecule can mediate its signaling effect via direct or indirect interaction with downstream molecules of the same pathway or related pathway(s). For instance, PTPN2 signaling can involve a host of downstream molecules including but not limited PI3-kinase and AKT.

The term "downregulating PTPN2 activity", as used herein, refers to slowing, reducing, altering, inhibiting, as well as completely eliminating and/or preventing PTPN2 activity.

The term "effector function" refers to a specialized function of a cell. Effector function of a T-cell, for example, may be cytolytic activity or helper activity including the secretion of cytokines. Thus, the term "intracellular signaling domain" refers to the portion of a protein which transduces the effector function signal and directs the cell to perform a specialized function.

The term "autologous" refers to any material derived from the same individual to whom it is later to be re-introduced into the individual. The term "allogeneic" refers to any material derived from a different animal of the same species as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that are contribute to an efficient immune response. Costimulatory molecules include but are not limited to an MHC class I molecule, BTLA and a Toll ligand receptor, as well as OX40, CD27, CD28, CDS, ICAM-1, LFA-1 (CD11a/CD18), ICOS (CD278), and 4-1BB (CD137). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAMI (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand that specifically binds with CD83. A costimulatory intracellular signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors. Examples of such molecules include CD27, CD28, 4-1BB (CD137), OX40, GITR, CD30, CD40, ICOS, BAFFR, HVEM, ICAM-1, lymphocyte function-associated antigen-1 (LFA-1), CD2, CDS, CD7, CD287, LIGHT, NKG2C, NKG2D, SLAMF7, NKp80, NKp30, NKp44, NKp46, CD160, B7-H3, and a ligand that specifically binds with CD83, and the like. The intracellular signaling domain can comprise the entire intracellular portion, or the entire native intracellular signaling domain, of the molecule from which it is derived, or a functional fragment or derivative thereof.

The terms "immune effector cell" and "effector cell" are used interchangeably here. They refer to a cell that is involved in an immune response, e.g., in the promotion of an immune effector response. Examples of immune effector cells include T cells, e.g., alpha/beta T cells and gamma/delta T cells, B cells, natural killer (NK) cells, natural killer T (NKT) cells, mast cells, and myeloic-derived phagocytes.

The terms "immunity" and "immune response" are used herein interchangeably. As applied to a subject, they refer to the ability of the subject to elicit an immune response via their immune cells against an antigen, including without limitation tumor antigen, viral antigen, bacterial antigen, or neoantigen. As applied to a cell, the terms refer to the ability of the cell to generate a cellular response directly or indirectly against an antigen, including without limitation tumor antigen, viral antigen, bacterial antigen, or neoantigen.

The term "lymphoid cell" or "lymphoid cells" refers to any of the cells responsible for the production of immunity (or immune response) mediated by cells or antibodies and including lymphocytes, lymphoblasts, and plasma cells. Lymphoid cells include granulocytes such as asophils, eosinophils, and neutrophils; mast cells; monocytes which can develop into macrophages; antigen-presenting cells such as dendritic cells; and lymphocytes such as natural killer cells (NK cells), B cells, and T cells (including activated T cells). In some examples, T cells include both naive and memory cells (e.g. central memory or TCM, effector memory or $T_{EM}$ and effector memory RA or $T_{EMRA}$), effector cells (e.g. cytotoxic T cells or CTLs or Tc cells), helper cells (e.g. Th1, Th2, Th3, Th9, Th7, TFH), regulatory cells (e.g. Treg, and Trl cells), natural killer T cells (NKT cells), tumor infiltrating lymphocytes (TILs), lymphocyte-activated killer cells (LAKs), αβ T cells, γδ T cells, and similar unique classes of the T cell lineage.

The terms "tumor marker, "tumor antigen", and "tumor-associated antigen" are used herein interchangeably, each referring to a molecule or fragment thereof expressed on the surface or inside of a cancer cell, or secreted or otherwise a molecule or fragment thereof derived from a cancer cell (e.g., circulating tumor DNA or circulating tumor RNA), and which is useful for the detecting a cancer cell or preferential targeting an agent to the cancer cell. A tumor antigen can be a marker expressed by both normal cells and cancer cells, e.g., a lineage marker, e.g., CD19 on B cells. A tumor antigen can be a cell surface molecule that is over-expressed or underexpressed in a cancer cell in comparison to a normal cell. A tumor antigen can also be a cell surface molecule that is inappropriately synthesized in the cancer cell, for instance, a molecule that contains deletions, additions or mutations in comparison to the molecule expressed on a normal cell. A tumor antigen can be expressed exclusively on the cell surface of a cancer cell, entirely or as a fragment (e.g., MHC/peptide), and not synthesized or expressed on the surface of a normal cell. A tumor antigen includes neoantigens encoded by tumor-specific mutated genes.

The term "transiently downregulated" as used herein generally means that a downregulation of expression or activity of a target molecule (e.g., PTPN2) is not permanent. A transient downregulation may not be a permanent down-regulation. In some cases, a transient downregulation may involve downregulating (e.g., reducing) expression or activity of a target molecule for a period of time, followed by regaining at least a portion of expression or activity level of the target molecule that was previously downregulated. A transient downregulation can involve an intermittent down-regulation of a target molecule (e.g., PTPN2).

The term "intermittent" is used herein to describe a process that is not continuous. An intermittent process may be followed by a break or stop. A plurality of intermittent processes may involve alternatively starting and stopping a same process or different processes. In some embodiments, the term "intermittent dosing regimen" as used here refers to a dosing regimen that comprises administering a pharmaceutical composition, followed by a rest period.

The term "side effect" as used herein refers to any complication, unwanted, or pathological outcome of a therapy (e.g., a cell therapy, an immunotherapy, etc.) that occurs in addition to or in place of a desired treatment outcome of the therapy. Examples of a side effect may include, but are not limited to, (i) off-target cell toxicity, (ii) on-target off-tumor toxicity, and/or (iii) autoimmunity (e.g., chronic autoimmunity). In an example, a side effect of a cell therapy involving a T-cell receptor fusion protein (TFP) and/or a chimeric antigen receptor (CAR) may include a graft-versus-host disease. In another example, a side effect of a cell therapy involving a TFP and/or a CAR may include death of a cell configured to express the TFP and/or the CAR.

Other examples of a side effect of a cell therapy may include, but are not limited to, disorders mediated by phagocytic cells, which includes macrophages and neutrophil granulocytes (Polymorphonuclear leukocytes, PMNs) and/or T cells. Examples include inflammatory skin diseases including psoriasis; responses associated with inflammatory bowel disease (such as Crohn's disease and ulcerative colitis); adult respiratory distress syndrome; dermatitis; CNS inflammatory disorders such as multiple sclerosis; uveitic disorders; allergic conditions such as eczema and asthma and other conditions involving infiltration of T cells and chronic inflammatory responses; skin hypersensitivity reactions (including poison ivy and poison oak); autoimmune diseases such as rheumatoid arthritis, systemic lupus erythematosus (SLE), diabetes mellitus, multiple sclerosis, Raynaud's syndrome, autoimmune thyroiditis, Sjogren's syndrome, juvenile onset diabetes, and immune responses associated with delayed hypersensitivity mediated by cytokines and T-lymphocytes typically found in tuberculosis, sarcoidosis, polymyositis, granulomatosis and vasculitis; pernicious anemia; multiple organ injury syndrome secondary to septicaemia or trauma; autoimmune haemolytic anemia; myethemia gravis; antigen-antibody complex mediated diseases; and/or all types of transplantation rejection, including graft vs. host or host vs. graft disease.

The term "efficacy" of a treatment or method, as used herein, can be measured based on changes in the course of disease or condition in response to such treatment or method. For example, the efficacy of a treatment or method of the present disclosure may be measured by its impact on signs or symptoms of a disease or condition of a subject, e.g., a tumor or cancer of the subject. A response may be achieved when a subject having the disease or condition experiences partial or total alleviation of the disease or condition, or reduction of one or more symptoms of the disease or condition. In an example, a response is achieved when a subject suffering from a tumor exhibits a reduction in the tumor size after the treatment or method, as provided in the present disclosure. In some examples, the efficacy may be measured by assessing cancer cell death, reduction of tumor (e.g., as evidenced by tumor size reduction), and/or inhibition of tumor growth, progression, and dissemination.

An "antigen" is a moiety or molecule that contains an epitope, and, as such, also specifically binds to an antibody. An "antigen binding unit" may be whole or a fragment (or fragments) of a full-length antibody, a structural variant thereof, a functional variant thereof, or a combination thereof. A full-length antibody may be, for example, a monoclonal, recombinant, chimeric, deimmunized, humanized and human antibody. Examples of a fragment of a full-length antibody may include, but are not limited to, variable heavy (VH), variable light (VL), a heavy chain found in camelids, such as camels, llamas, and alpacas (VHH or $V_HH$), a heavy chain found in sharks (V-NAR domain), a single domain antibody (sdAb, e.g., "nanobody") that comprises a single antigen-binding domain, Fv, Fd, Fab, Fab', F(ab')2, and "r IgG" (or half antibody). Examples of modified fragments of antibodies may include, but are not limited to scFv, di-scFv or bi(s)-scFv, scFv-Fc, scFv-zipper, scFab, Fab2, Fab3, diabodies, single chain diabodies, tandem diabodies (Tandab's), tandem di-scFv, tandem tri-scFv, minibodies (e.g., $(VH\text{-}VL\text{-}CH3)_2$, $(scFv\text{-}CH3)_2$, ((scFv) 2-CH3+CH3), ((scFv) 2-CH3) or (scFv-CH3-scFv)2), and multibodies (e.g., triabodies or tetrabodies).

The term "antibody" and "antibodies" encompass any antigen binding units, including without limitation: monoclonal antibodies, human antibodies, humanized antibodies, camelised antibodies, chimeric antibodies, and any other epitope-binding fragments.

The practice of some embodiments disclosed herein employ, unless otherwise indicated, conventional techniques of immunology, biochemistry, chemistry, molecular biology, microbiology, cell biology, genomics and recombinant DNA, which are within the skill of the art. See for example Sambrook and Green, Molecular Cloning: A Laboratory Manual, 4th Edition (2012); the series Current Protocols in Molecular Biology (F. M. Ausubel, et al. eds.); the series Methods In Enzymology (Academic Press, Inc.), PCR 2: A Practical Approach (M. J. MacPherson, B. D. Hames and G. R. Taylor eds. (1995)), Harlow and Lane, eds. (1988) Antibodies, A Laboratory Manual, and Culture of Animal Cells: A Manual of Basic Technique and Specialized Applications, 6th Edition (R. I. Freshney, ed. (2010)).

Compounds

Compounds disclosed herein, including the compounds of Formula (I), (I-1), (II), (II-1), (II-a), (II-a1), (III), (III-1), (IV), and (IV-1) or pharmaceutically acceptable salts or solvates thereof, are PTPN2 inhibitors and have a wide range of applications in therapeutics, diagnostics, and other biomedical research.

In certain aspects, the present disclosure provides a compound of Formula (I):

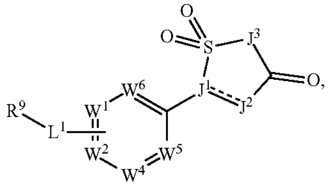

(I)

or a pharmaceutically acceptable salt or solvate thereof, wherein:

$W^1$ is selected from C, $C(R^8)$, and N;

$W^2$ is selected from C, $C(R^8)$, and N;

$W^4$ is selected from N and $C(R^4)$;

$W^5$ is selected from N and $C(R^5)$;

$W^6$ is selected from N and $C(R^6)$;

$J^1$ is selected from N, C, and $C(R^8)$;

$J^2$ is selected from N, $N(R^7)$, $C(R^8)$, $C(R^8)_2$, and C(O);

$J^3$ is selected from $N(R^7)$ and $C(R^8)_2$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —$C(O)N(R^{12})C(O)$—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})C(O)$—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})S(O)$—, —$S(O)N(R^{12})$—, —$N(R^{12})S(O)_2N(R^{12})$—, —$N(R^{12})$ $S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^9$ is selected from $C_{3-12}$ carbocycle and 3- to 12-membered heterocycle, each of which is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$, $R^4$, $R^5$, $R^6$, and $R^8$ are independently selected at each occurrence from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^7$ is independently selected at each occurrence from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —$C(O)OR^{12}$, —C(O)O—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(═O)(═$NR^{12}$)$N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{15}$ is independently selected at each occurrence from (5-methyl-2-oxo-1,3-dioxol-4-yl)methyl, —$C(O)R^{12}$, —$C(O)OR^{12}$, —P(O)(X—$R^{16}$)(Y—$R^{17}$), and —$CH_2P(O)$(X—$R^{16}$)(Y—$R^{17}$);

X and Y are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —OC(O)OR$^{12}$, —C(O)N(R$^{12}$)(R$^{13}$), —C(O)C(O)N(R$^{12}$)(R$^{13}$), —N(R$^{12}$)C(O)R$^{12}$, —S(O)$_2$R$^{12}$, —S(O)(NR$^{12}$)R$^{12}$, —S(O)$_2$N(R$^{12}$)(R$^{13}$), —S(O)(NR$^{12}$)N(R$^{12}$)(R$^{13}$), —P(O)(OR$^{12}$)$_2$, —P(O)(R$^{12}$)$_2$, —OP(O)(OR$^{12}$)$_2$, =O, =S, and =NR$^{12}$; or R$^{16}$ and R$^{17}$ are taken together with the atoms to which they are attached to form 3- to 12-membered heterocycle optionally substituted with one, two, or three R$^{20}$;

R$^{20}$ is independently selected at each occurrence from halogen, oxo, —CN, C$_{1-6}$ alkyl, C$_{2-6}$ alkenyl, C$_{2-6}$ alkynyl, 2- to 6-membered heteroalkyl, 2- to 6-membered heteroalkenyl, 2- to 6-membered heteroalkynyl, —C$_{0-6}$ alkyl-(C$_{3-12}$ carbocycle), -(2- to 6-membered heteroalkyl)-(C$_{3-12}$ carbocycle), —C$_{0-6}$ alkyl-(3- to 12-membered heterocycle), -(2- to 6-membered heteroalkyl)-(3- to 12-membered heterocycle), —OR$^{22}$, —SR$^{22}$, —N(R$^{22}$)(R$^{23}$), =NR$^{22}$, =C(R$^{21}$)$_2$, —C(O)OR$^{22}$, —OC(O)N(R$^{22}$)(R$^{23}$), —N(R$^{22}$)C(O)N(R$^{22}$)(R$^{23}$), —N(R$^{22}$)C(O)OR$^{22}$, —N(R$^{22}$)S(O)$_2$R$^{22}$, —C(O)R$^{22}$, —S(O)R$^{22}$, —OC(O)R$^{22}$, —C(O)N(R$^{22}$)(R$^{23}$), —C(O)C(O)N(R$^{22}$)(R$^{23}$), —N(R$^{22}$)C(O)R$^{22}$, —S(O)$_2$R$^{22}$, —S(O)(NR$^{22}$)R$^{22}$, —S(O)$_2$N(R$^{22}$)(R$^{23}$)—, —S(=O)(=NR$^{22}$)N(R$^{22}$)(R$^{23}$), and —OCH$_2$C(O)OR$^{22}$, wherein two R$^{20}$ attached to the same or adjacent atoms optionally join to form C$_{3-12}$ carbocycle or 3- to 12-membered heterocycle; wherein C$_{1-6}$ alkyl, C$_{2-6}$ alkenyl, C$_{2-6}$ alkynyl, 2- to 6-membered heteroalkyl, 2- to 6-membered heteroalkenyl, 2- to 6-membered heteroalkynyl, —C$_{0-6}$ alkyl-(C$_{3-12}$ carbocycle), -(2- to 6-membered heteroalkyl)-(C$_{3-12}$ carbocycle), —C$_{0-6}$ alkyl-(3- to 12-membered heterocycle), -(2- to 6-membered heteroalkyl)-(3- to 12-membered heterocycle), C$_{3-12}$ carbocycle, and 3- to 12-membered heterocycle are optionally substituted with one or more substituents independently selected from halogen, oxo, —CN, C$_{1-6}$ alkyl, C$_{1-6}$ haloalkyl, C$_{1-6}$ alkoxy, C$_{1-6}$ haloalkoxy, —OR$^{22}$, —SR$^{22}$, —N(R$^{22}$)(R$^{23}$), =NR$^{22}$, =C(R$^{21}$)$_2$, —C(O)OR$^{22}$, —OC(O)N(R$^{22}$)(R$^{23}$), —N(R$^{22}$)C(O)N(R$^{22}$)(R$^{23}$), —N(R$^{22}$)C(O)OR$^{22}$, —N(R$^{22}$)S(O)$_2$R$^{22}$, —C(O)R$^{22}$, —S(O)R$^{22}$, —OC(O)R$^{22}$, —C(O)N(R$^{22}$)(R$^{23}$), —C(O)C(O)N(R$^{22}$)(R$^{23}$), —N(R$^{22}$)C(O)R$^{22}$, —S(O)$_2$R$^{22}$, —S(O)(NR$^{22}$)R$^{22}$, —S(O)$_2$N(R$^{22}$)(R$^{23}$), and —S(=O)(=NR$^{22}$)N(R$^{22}$)(R$^{23}$);

R$^{21}$ is independently selected at each occurrence from hydrogen, halogen, C$_{1-6}$ alkyl, C$_{1-6}$ haloalkyl, —C$_{0-6}$ alkyl-(C$_{3-12}$ carbocycle), and —C$_{0-6}$ alkyl-(3- to 12-membered heterocycle), or two R$^{21}$ are taken together with the carbon atom to which they are attached to form C$_{3-12}$ carbocycle or 3- to 12-membered heterocycle, each of which is optionally substituted with one, two, or three substituents independently selected from halogen, C$_{1-3}$ alkyl, C$_{1-3}$ haloalkyl, and —OH;

R$^{22}$ is independently selected at each occurrence from hydrogen, C$_{1-6}$ alkyl, C$_{1-6}$ haloalkyl, —C$_{0-6}$ alkyl-(C$_{3-12}$ carbocycle), and —C$_{0-6}$ alkyl-(3- to 12-membered heterocycle);

R$^{23}$ is independently selected at each occurrence from hydrogen and C$_{1-6}$ alkyl; or R$^{22}$ and R$^{23}$ attached to the same nitrogen atom form 3- to 10 membered heterocycle; and ------ indicates a single or double bond such that all valences are satisfied;

wherein at least one of R$^9$, W$^1$, W$^2$, W$^4$, W$^5$, W$^6$, J$^2$, or J$^3$ is substituted with (5-methyl-2-oxo-1,3-dioxol-4-yl)methyl, —OR$^{15}$, —O—(C$_{1-6}$ alkyl)-OR$^{15}$, —OC(O)N(R$^{12}$)(R$^{13}$), —(C$_{1-6}$ alkyl)-OR$^{15}$, or —C(O)O—(C$_{1-6}$ alkyl)-OR$^{15}$.

In certain aspects, the present disclosure provides a compound of Formula (I-1):

(I-1)

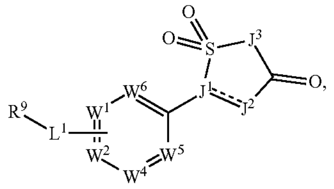

or a pharmaceutically acceptable salt or solvate thereof, wherein:

W$^1$ is selected from C, C(R$^8$), and N;

W$^2$ is selected from C, C(R$^8$), and N;

W$^4$ is selected from N and C(R$^4$);

W$^5$ is selected from N and C(R$^5$);

W$^6$ is selected from N and C(R$^6$);

J$^1$ is selected from N, C, and C(R$^8$);

J$^2$ is selected from N, N(R$^7$), C(R$^8$), C(R$^8$)$_2$, and C(O);

J$^3$ is selected from N(R$^7$) and C(R$^8$)$_2$;

L$^1$ is absent or selected from C$_{1-6}$ alkylene, C$_{2-6}$ alkenylene, C$_{2-6}$ alkynylene, 2- to 6-membered heteroalkylene, 3- to 6-membered heteroalkenylene, 3- to 6-membered heteroalkynylene, —C$_{0-6}$ alkyl-(C$_{3-12}$ carbocycle)-, -(2- to 6-membered heteroalkyl)-(C$_{3-12}$ carbocycle)-, —C$_{0-6}$ alkyl-(3- to 12-membered heterocycle)-, -(2- to 6-membered heteroalkyl)-(3- to 12-membered heterocycle)-, —O—, —S—, —N(R$^{12}$)—, —C(NR$^{12}$)—, —N(R$^{12}$)C(NR$^{12}$)—, —C(NR$^{12}$)N(R$^{12}$)—, —N(R$^{12}$)C(NR$^{12}$)N(R$^{12}$)—, —C(O)O—, —OC(O)O—, —OC(O)N(R$^{12}$)—, —N(R$^{12}$)C(O)N(R$^{12}$)—, —N(R$^{12}$)C(O)O—, —C(O)N(R$^{12}$)C(O)—, —C(O)N(R$^{12}$)C(O)N(R$^{12}$)—, —N(R$^{12}$)S(O)$_2$—, —C(O)—, —S(O)—, —OC(O)—, —C(O)N(R$^{12}$)—, —C(O)C(O)N(R$^{12}$)—, —N(R$^{12}$)C(O)—, —S(O)$_2$—, —OS(O)—, —S(O)O—, —OS(O)$_2$—, —S(O)$_2$O—, —S(O)(NR$^{12}$)—, —S(O)$_2$N(R$^{12}$)—, —S(O)(NR$^{12}$)N(R$^{12}$)—, —N(R$^{12}$)S(O)—, —S(O)N(R$^{12}$)—, —N(R$^{12}$)S(O)$_2$N(R$^{12}$)—, —N(R$^{12}$) S(O)N(R$^{12}$)—, —P(O)(OR$^{12}$)—, and —P(O)(R$^{12}$)—, wherein C$_{1-6}$ alkylene, C$_{2-6}$ alkenylene, C$_{2-6}$ alkynylene, 2- to 6-membered heteroalkylene, 3- to 6-membered heteroalkenylene, 3- to 6-membered heteroalkynylene, —C$_{0-6}$ alkyl-(C$_{3-12}$ carbocycle)-, -(2- to 6-membered heteroalkyl)-(C$_{3-12}$ carbocycle)-, —C$_{0-6}$ alkyl-(3- to 12-membered heterocycle)-, and -(2- to 6-membered heteroalkyl)-(3- to 12-membered heterocycle)- are optionally substituted with one, two, or three R$^{20}$.

R$^9$ is selected from C$_{3-12}$ carbocycle and 3- to 12-membered heterocycle, each of which is (i) optionally substituted with one, two, or three R$^{20}$ and (ii) optionally substituted with (5-methyl-2-oxo-1,3-dioxol-4-yl)methyl, —OR$^{15}$, —O—(C$_{1-6}$ alkyl)-OR$^{15}$, —(C$_{1-6}$ alkyl)-OR$^{15}$, or —C(O)O—(C$_{1-6}$ alkyl)-OR$^{15}$, wherein each C$_{1-6}$ alkyl is optionally substituted with one, two, or three R$^{20}$;

R$^4$, R$^5$, R$^6$, and R$^8$ are independently selected at each occurrence from hydrogen, halogen, —CN, C$_{1-6}$ alkyl, C$_{2-6}$ alkenyl, C$_{2-6}$ alkynyl, C$_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —C(O)$OR^{12}$, —OC(O)$N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$R^7$ is independently selected at each occurrence from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —$C(O)OR^{12}$, —C(O)O—($C_{1-6}$ alkyl)-$OR^{15}$, —($C_{1-6}$ alkyl)-$OR^{15}$, —$C(O)R^{12}$, —C(O)$N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three substituents independently selected from —$N(R^{22})C(O)CH(R^{20})N(R^{22})_2$, —$C(O)CH(R^{20})N(R^{22})_2$, and $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{15}$ is independently selected at each occurrence from (5-methyl-2-oxo-1,3-dioxol-4-yl)methyl, —$C(O)R^{12}$, —$C(O)OR^{12}$, —P(O)(X—$R^{16}$)(Y—$R^{17}$), and —$CH_2$P(O)(X—$R^{16}$)(Y—$R^{17}$);

X and Y are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —S(O)$R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —P(O)$(R^{12})_2$, —$OP(O)(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O)$OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —S(=O)(=$NR^{22}$)$N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —OC(O)$R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —S(=O)(=$NR^{22}$)$N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ------ indicates a single or double bond such that all valences are satisfied;

wherein at least one of $R^9$, $W^1$, $W^2$, $W^4$, $W^5$, $W^6$, $J^2$, or $J^3$ is substituted with (5-methyl-2-oxo-1,3-dioxol-4-yl)methyl, —$OR^{15}$, —O—($C_{1-6}$ alkyl)-$OR^{15}$, —OC(O)N$(R^{12})(R^{13})$, —($C_{1-6}$ alkyl)-$OR^{15}$, or —C(O)O—($C_{1-6}$ alkyl)-$OR^{15}$.

In some embodiments, for a compound of Formula (I) or (I-1), $W^4$ is $C(R^4)$, $W^5$ is $C(R^5)$, and $W^6$ is $C(R^6)$. In some embodiments, $W^4$ is $C(R^4)$. In some embodiments, $W^4$ is N. In some embodiments, $W^5$ is $C(R^5)$. In some embodiments, $W^6$ is $C(R^6)$. In some embodiments, $W^4$ is N, $W^5$ is $C(R^5)$, and $W^6$ is $C(R^6)$. In some embodiments, $W^1$ is C and $W^2$ is $C(R^8)$. In some embodiments, $W^1$ is $C(R^8)$ and $W^2$ is C. In some embodiments, $W^1$ is C, $W^2$ is $C(R^8)$, $W^4$ is $C(R^4)$, $W^5$ is $C(R^5)$, and $W^6$ is $C(R^6)$. In some embodiments, $W^1$ is $C(R^8)$, $W^2$ is C, $W^4$ is $C(R^4)$, $W^5$ is $C(R^5)$, and $W^6$ is $C(R^6)$. In some embodiments, $W^1$ is C, $W^2$ is CH, $W^4$ is CH, $W^5$ is $C(R^5)$, and $W^6$ is $C(R^6)$. In some embodiments, $W^1$ is CH, $W^2$ is C, $W^4$ is CH, $W^5$ is $C(R^5)$, and $W^6$ is $C(R^6)$. In some embodiments, $W^1$ is C, $W^2$ is CH, $W^4$ is CH, $W^5$ is $C(R^5)$, and $W^6$ is CF. In some embodiments, $W^1$ is CH, $W^2$ is C, $W^4$ is CH, $W^5$ is $C(R^5)$, and $W^6$ is CF. In some embodiments, $W^1$ is C, $W^2$ is CH, $W^4$ is CH, $W^5$ is C(OH), and $W^6$ is CF. In some embodiments, $W^1$ is CH, $W^2$ is C, $W^4$ is CH, $W^5$ is C(OH), and $W^6$ is CF.

In some embodiments, for a compound of Formula (I) or (I-1), $J^1$ is selected from N and C; $J^2$ is selected from $C(R^8)$ and $C(R^8)_2$; and $J^3$ is $N(R^7)$. In some embodiments, $J^1$ is selected from N and C and $J^2$ is selected from $C(R^8)$ and $C(R^8)_2$. In some embodiments, $J^1$ is N. In some embodiments, $J^2$ is $C(R^8)_2$. In some embodiments, $J^3$ is $N(R^7)$. In some embodiments, $J^1$ is N and $J^2$ is $C(R^8)_2$. In some embodiments, $J^1$ is N; $J^2$ is $C(R^8)_2$; and $J^3$ is $N(R^7)$. In some embodiments, $J^1$ is C. In some embodiments, $J^2$ is $C(R^8)$. In some embodiments, $J^1$ is C and $J^2$ is $C(R^8)$. In some embodiments, $J^1$ is C; $J^2$ is $C(R^8)$; and $J^3$ is $N(R^7)$. In some embodiments, $J^1$ is selected from N and C; $J^2$ is selected from CH and $CH_2$; and $J^3$ is $N(R^7)$. In some embodiments, $J^1$ is selected from N and C; $J^2$ is selected from CH and $CH_2$; and $J^3$ is NH. In some embodiments, $J^1$ is selected from N and C and $J^2$ is selected from CH and $CH_2$. In some embodiments, $J^2$ is $CH_2$. In some embodiments, $J^3$ is $N(R^7)$. In some embodiments, $J^3$ is NH. In some embodiments, $J^1$ is N and $J^2$ is $CH_2$. In some embodiments, $J^1$ is N; $J^2$ is $CH_2$; and $J^3$ is $N(R^7)$. In some embodiments, $J^1$ is N; $J^2$ is $CH_2$; and $J^3$ is NH. In some embodiments, $J^2$ is CH. In some embodiments, $J^1$ is C and $J^2$ is CH. In some embodiments, $J^1$ is C; $J^2$ is CH; and $J^3$ is $N(R^7)$. In some embodiments, $J^1$ is C; $J^2$ is CH; and $J^3$ is NH.

In some embodiments, for a compound of Formula (I) or (I-1), $R^9$ is selected from $C_{3-8}$ carbocycle and 3- to 8-membered heterocycle, each of which is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is 4- to 7-membered heterocycle, wherein the 4- to 7-membered heterocycle is (i) optionally substituted with one, two, or three $R^{20}$ and (ii) optionally substituted with —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is 4- to 7-membered heterocycle, wherein the 4- to 7-membered heterocycle is (i) substituted with one, two, or three $R^{20}$, (ii) substituted with —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$, and (iii) contains one carbon-carbon double bond. In some embodiments, $R^9$ is selected from $C_{3-8}$ carbocycle and 3- to 8-membered heterocycle, each of which is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$, wherein the $C_{3-8}$ carbocycle and 3- to 8-membered heterocycle are saturated or partially unsaturated. In some embodiments, the $C_{3-8}$ carbocycle and 3- to 8-membered heterocycle are saturated. In some embodiments, the $C_{3-8}$ carbocycle and 3- to 8-membered heterocycle are partially unsaturated. In some embodiments, the $C_{3-8}$ carbocycle and 3- to 8-membered heterocycle contain one carbon-carbon double bond. In some embodiments, $R^9$ is selected from pyrrolidine, 2,5-dihydro-1H-pyrrole, piperidine, and 1,2,3,6-tetrahydropyridine, each of which is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is selected from pyrrolidine-3-yl, 2,5-dihydro-1H-pyrrol-3-yl, piperidin-3-yl, and 1,2,3,6-tetrahydropyridin-3-yl, each of which is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is pyrrolidine-3-yl, wherein the pyrrolidine-3-yl is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is 2,5-dihydro-1H-pyrrol-3-yl, wherein the 2,5-dihydro-1H-pyrrol-3-yl is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is piperidin-3-yl, wherein the piperidin-3-yl is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is 1,2,3,6-tetrahydropyridin-3-yl, wherein the 1,2,3,6-tetrahydropyridin-3-yl is (i) optionally substituted with one, two, or three $R^{20}$ and (ii) optionally substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is substituted with (5-methyl-2-oxo-1,3-dioxol-4-yl)methyl, —$OR^{15}$, —O—($C_{1-6}$ alkyl)-$OR^{15}$, —($C_{1-6}$ alkyl)-$OR^{15}$, or —C(O)O—($C_{1-6}$ alkyl)-$OR^{15}$. In some embodiments, $R^9$ is 4- to 7-membered heterocycle comprising a ring nitrogen atom substituted by (5-methyl-2-oxo-1,3-dioxol-4-yl) methyl, —($C_{1-6}$ alkyl)-$OR^{15}$ or —C(O)O—($C_{1-6}$ alkyl)-$OR^{15}$. In some embodiments, $R^9$ comprises a ring carbon atom substituted by —$OR^{15}$ or O—($C_{1-6}$ alkyl)-$OR^{15}$.

In some embodiments, for a compound of Formula (I) or (I-1), $R^9$ is

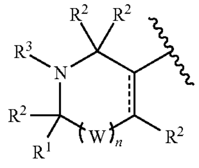, wherein:

W is $C(R^2)_2$;

n is 0, 1, or 2;

$R^1$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —OC (O)N($R^{12}$)($R^{13}$), —N($R^{12}$)C(O)N($R^{12}$)($R^{13}$), —N($R^{12}$)C(O)O$R^{12}$, —N($R^{12}$)S$(O)_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S$(O)_2R^{12}$, —S(O)(N$R^{12}$)$R^{12}$, —S$(O)_2$N($R^{12}$)($R^{13}$), and —S(O)(N$R^{12}$)N($R^{12}$)($R^{13}$), or (1) $R^1$ and $R^2$ attached to the same carbon atom are taken together to form oxo, =N$R^{12}$, or =C$(R^{14})_2$, (2) $R^1$ and $R^2$, together with the atom(s) to which they are attached, form $C_{3-12}$ carbocycle or 3- to 12-membered heterocycle, or (3) $R^1$ and $R^3$, together with the atoms to which they are attached, form 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{12}$, —S$R^{12}$, —N($R^{12}$)($R^{13}$), —C(O)O$R^{12}$, —OC(O)N($R^{12}$)($R^{13}$), —N($R^{12}$)C(O)N($R^{12}$)($R^{13}$), —N($R^{12}$)C(O)O$R^{12}$, —N($R^{12}$)S$(O)_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S$(O)_2R^{12}$, —S(O)(N$R^{12}$)$R^{12}$, —S$(O)_2$N($R^{12}$)($R^{13}$), and —S(O)(N$R^{12}$)N($R^{12}$)($R^{13}$), optionally wherein one or both of (1) two $R^2$ attached to the same carbon atom are taken together to form oxo, =N$R^{12}$, or =C$(R^{14})_2$ and (2) two $R^2$, together with the atom(s) to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ is selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O)O$R^{12}$, —C(O)O—($C_{1-6}$ alkyl)-O$R^{15}$, —($C_{1-6}$ alkyl)-O$R^{15}$, —C(O)$R^{12}$, —C(O)N($R^{12}$)($R^{13}$), —C(O)C(O)N($R^{12}$)($R^{13}$), —S$(O)_2R^{12}$, —S(O)(N$R^{12}$)$R^{12}$, —S$(O)_2$N($R^{12}$)($R^{13}$), and —S(=O)(=N$R^{12}$)N($R^{12}$)($R^{13}$), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$; and $R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$.

In some embodiments, for a compound of Formula (I) or (I-1), $R^9$ is selected from

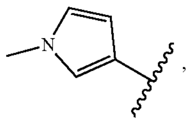
,
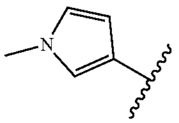
,
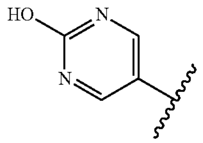
,
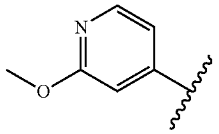
,
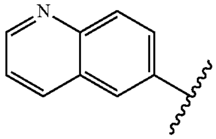
,
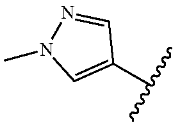
,
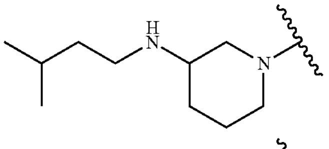
,
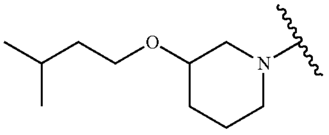
,
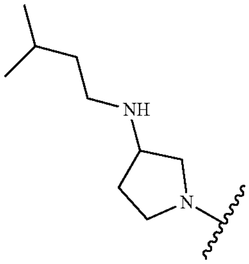
,
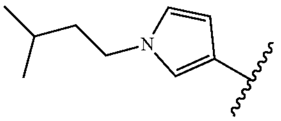
,
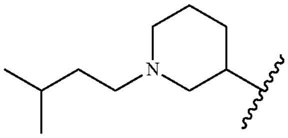
,
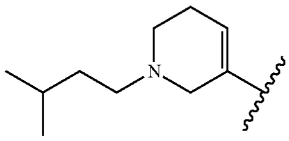
,
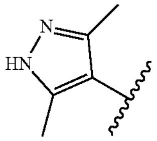
,
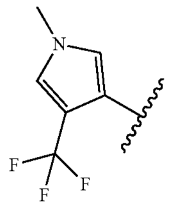
,
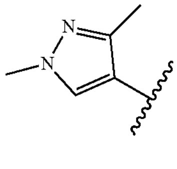
, -continued
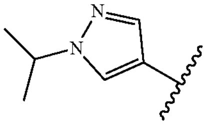,
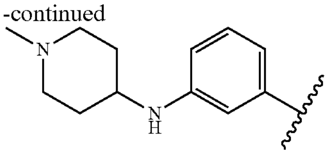,
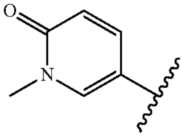,
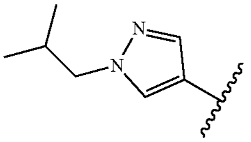,
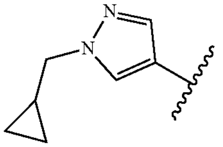,
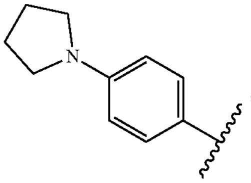,
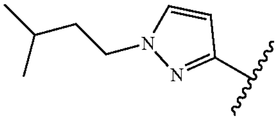,
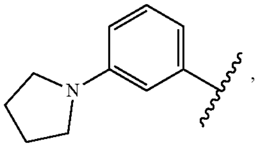,
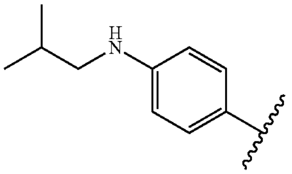,
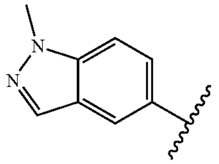,
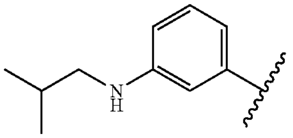,
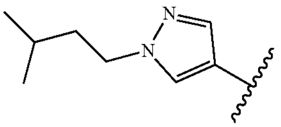,
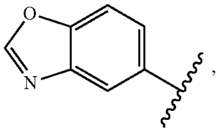,
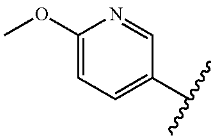,
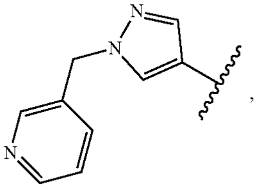,
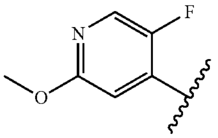,
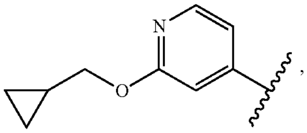,
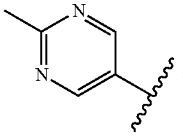,
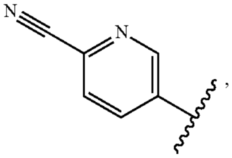,
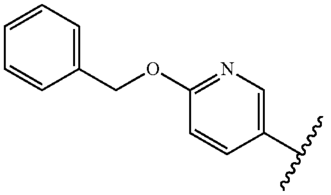,
-continued
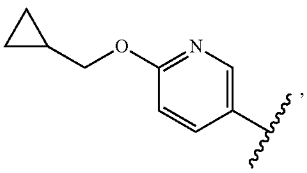,
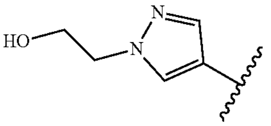,
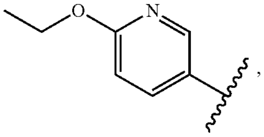,
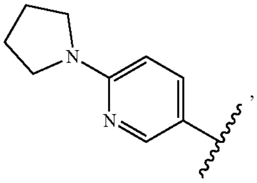,
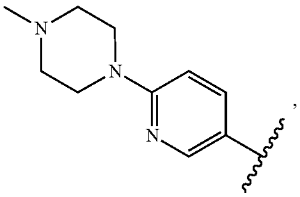,
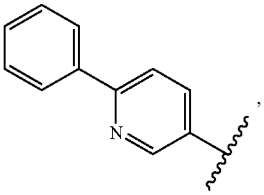,
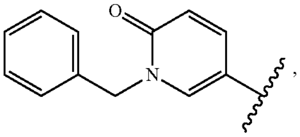,
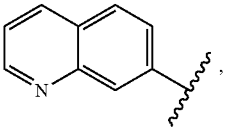,
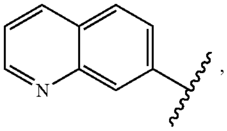,
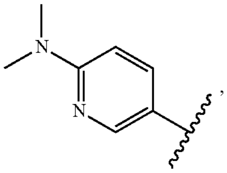,
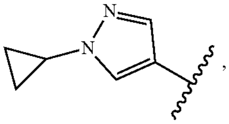,
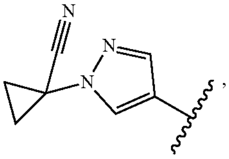,
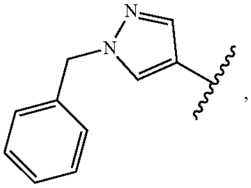,
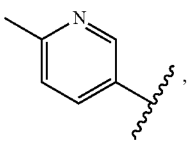,
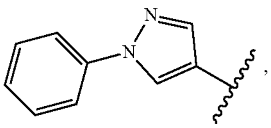,
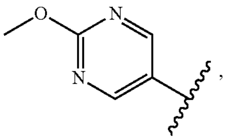,
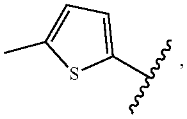, -continued
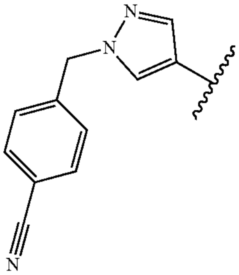,
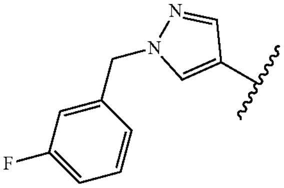,
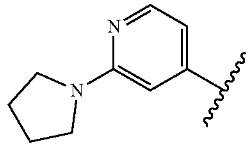,
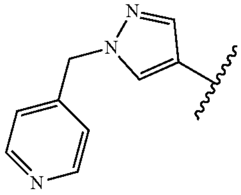,
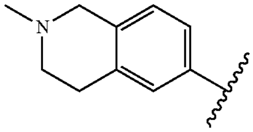,
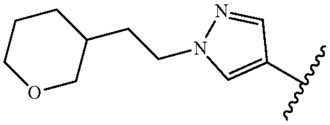,
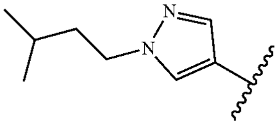,
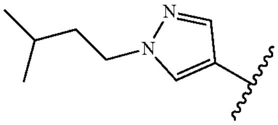,
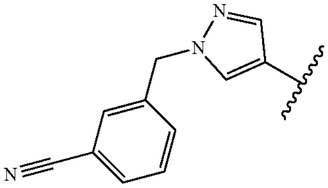,
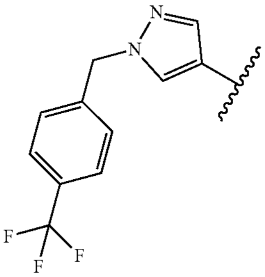,
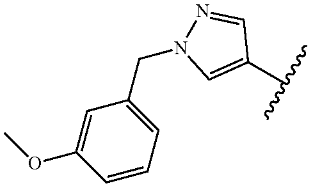,
-continued
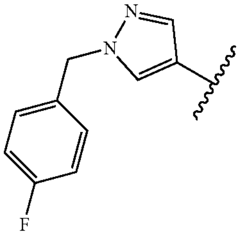,
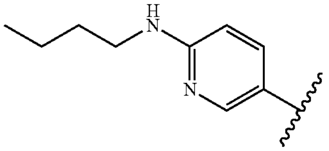,
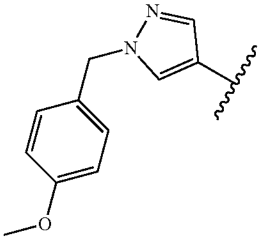,
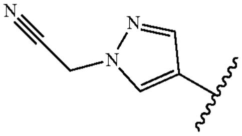,
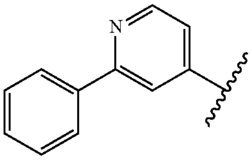,
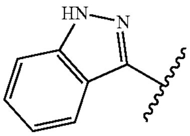,
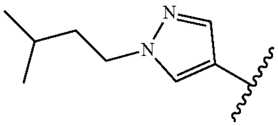,
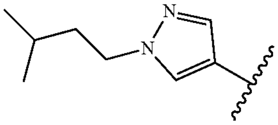,
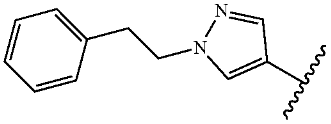,
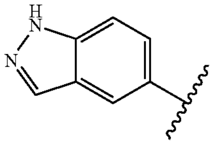,
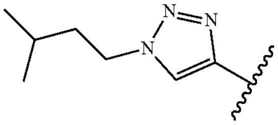,
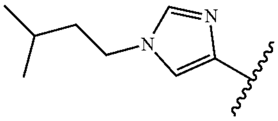,
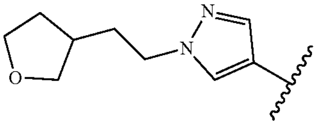,
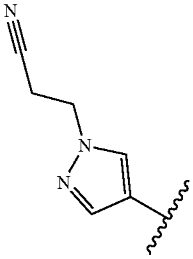, -continued
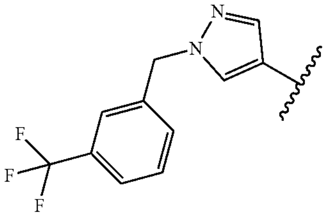,
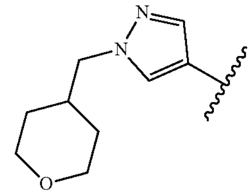, 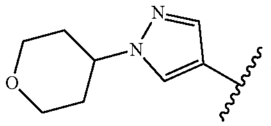,
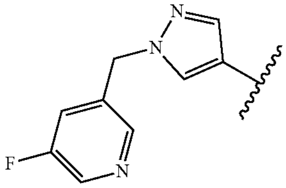, 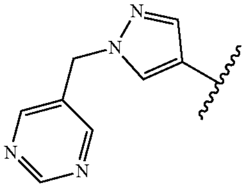,
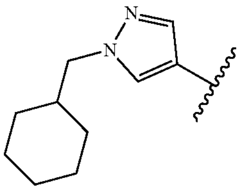,
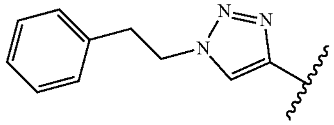,
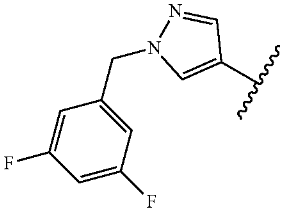, 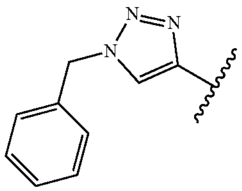,
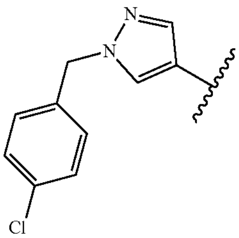, 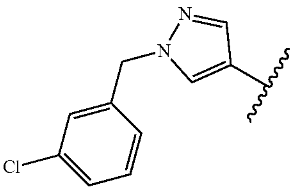,
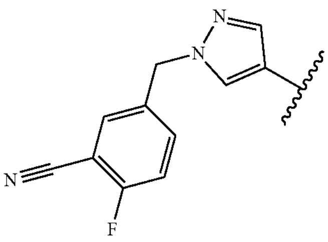,
-continued
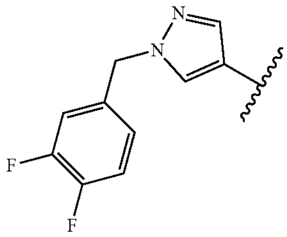, 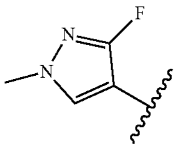,
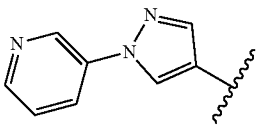, 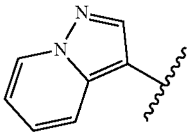,
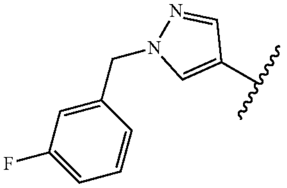, 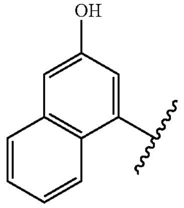,
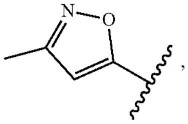, 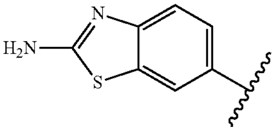,
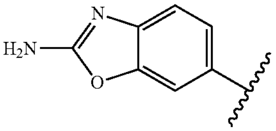, 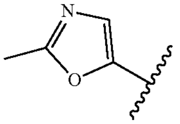,
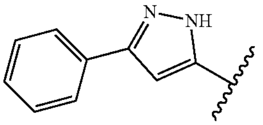, 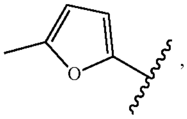,
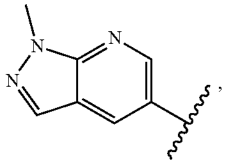, 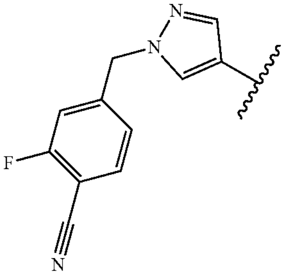,
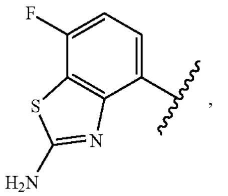, 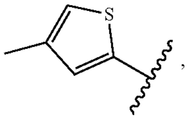,
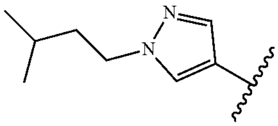, 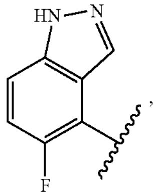, -continued
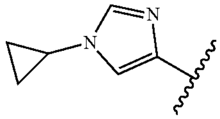, 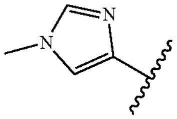,
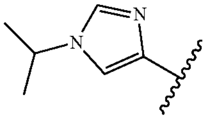, 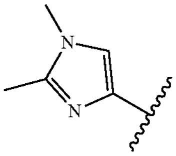,
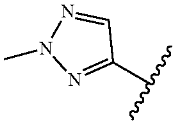, 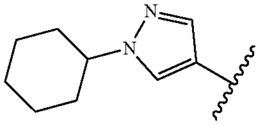,
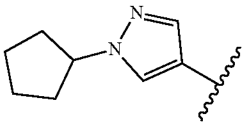, 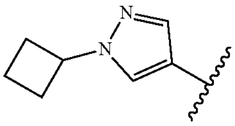,
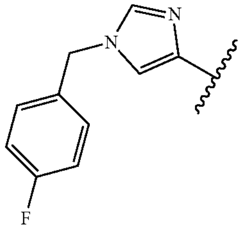, 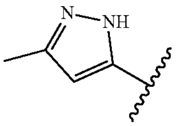,
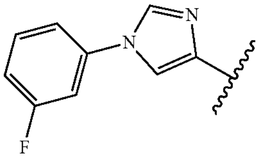,
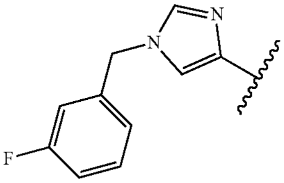,
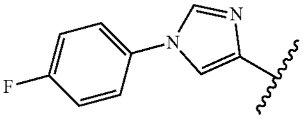,
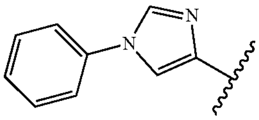,
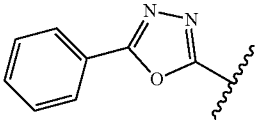, and
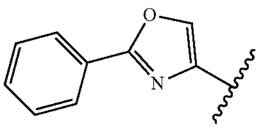.
In some embodiments, $R^9$ is
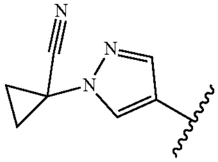.
In some embodiments, for a compound of Formula (I) or (I-1), $R^9$ is selected from
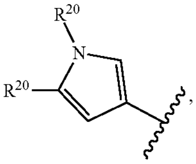, 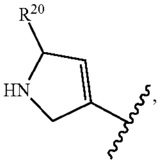, 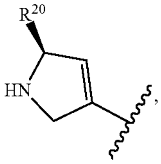,
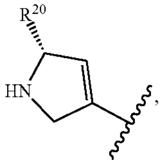, 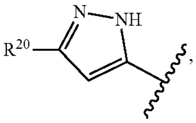,
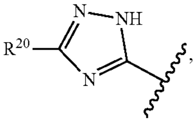, 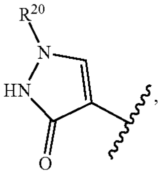,
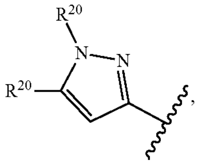, 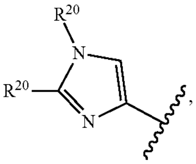,
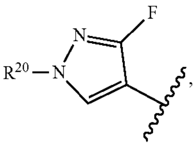, 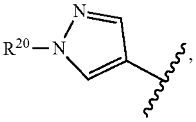,
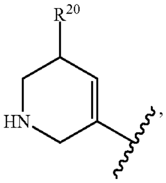, 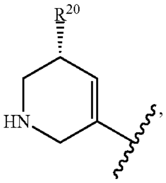, 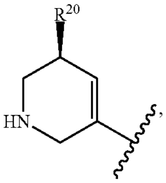,
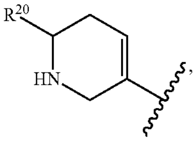, 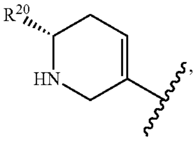, and
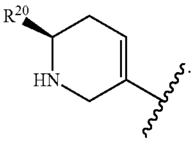.

In some embodiments, $R^9$ is selected from
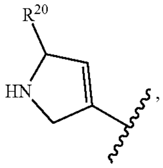,
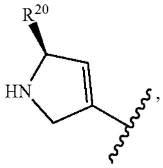, and
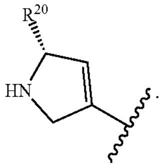.
In some embodiments, $R^9$ is
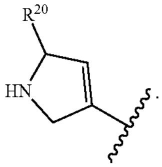.
In some embodiments, $R^9$ is
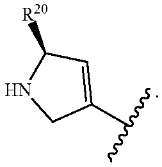.
In some embodiments, $R^9$ is
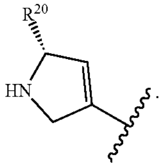.
In some embodiments, for a compound of Formula (I) or (I-1), $R^9$ is substituted with a substituent selected from $C_{1-6}$ alkyl,
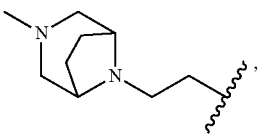,
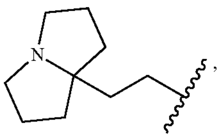,
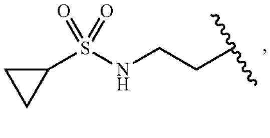,
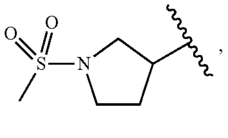,
-continued
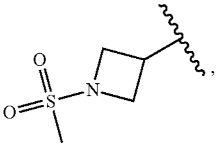,
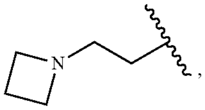,
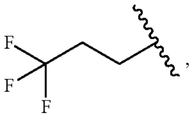,
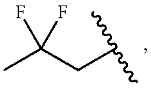,
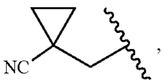,
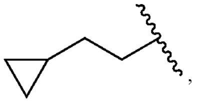,
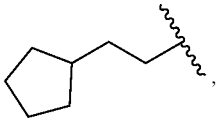,
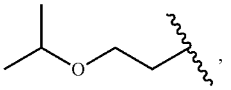,
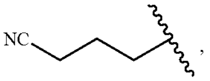,
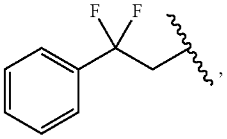,
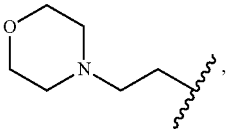,
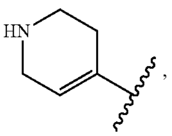,
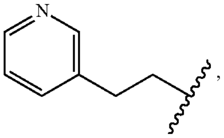,
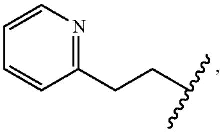,
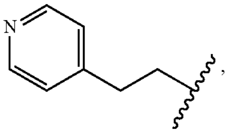,
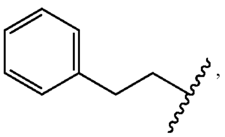,
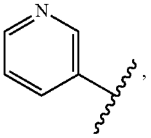,
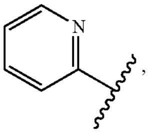,
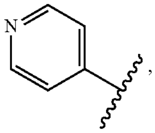,
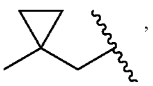,
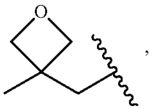,
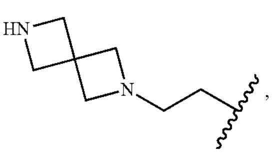,
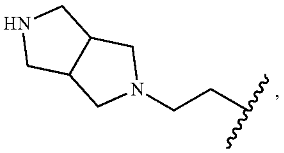,
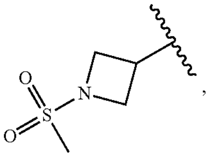,
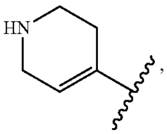, and
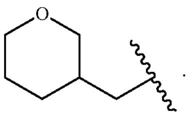.

In some embodiments, $R^9$ is substituted with

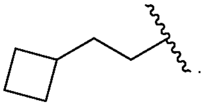 [SMILES: *CCC1CCC1]

In some embodiments, $R^9$ is substituted with

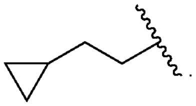 [SMILES: *CCC1CC1]

In some embodiments, $R^9$ is substituted with

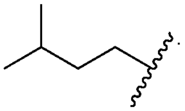 [SMILES: *CCC(C)C]

In some embodiments, $R^9$ is substituted with —CN.

In some embodiments, for a compound of Formula (I) or (I-1), $R^9$ is substituted with a substituent selected from

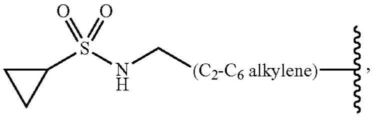

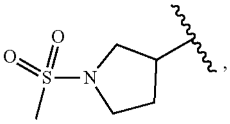 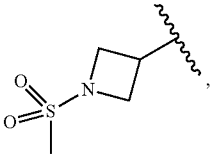

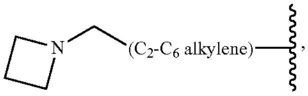

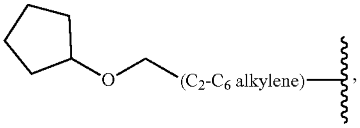

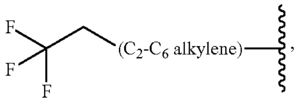

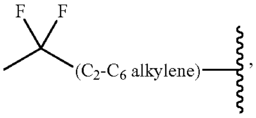 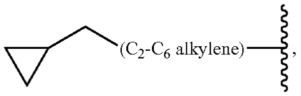

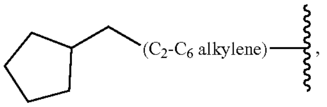

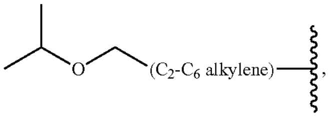

-continued

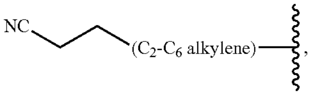

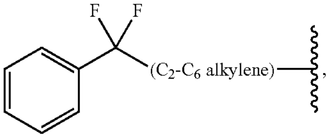

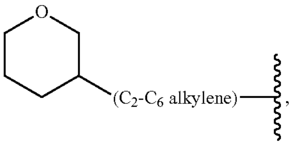

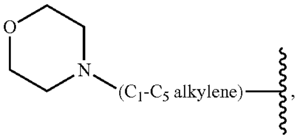

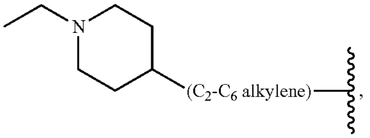 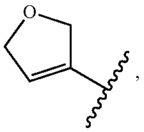

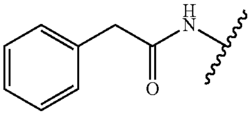 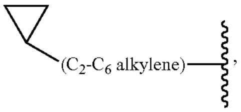

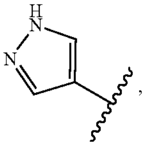 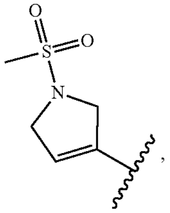 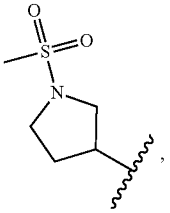 and

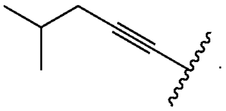

In some embodiments, $R^9$ is substituted with

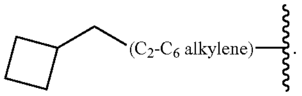

In some embodiments, for a compound of Formula (I) or (I-1), $R^9$ is substituted with a substituent selected from

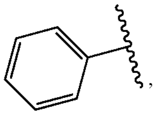 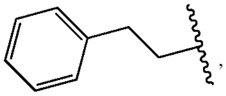 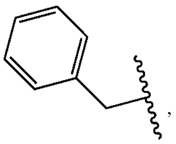

-continued
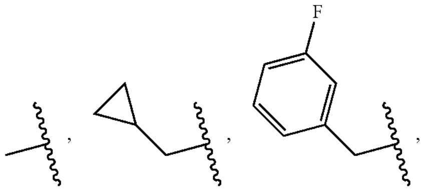
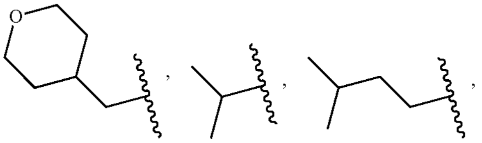
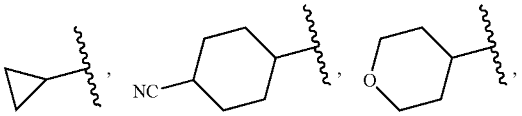
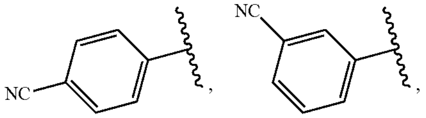
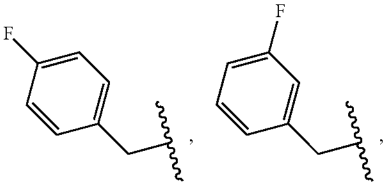
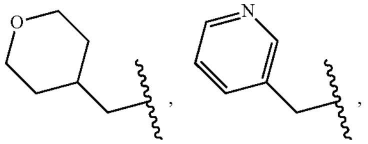
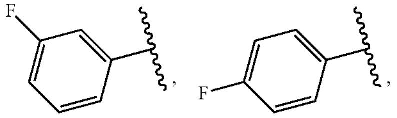
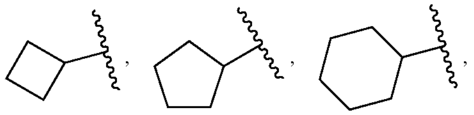
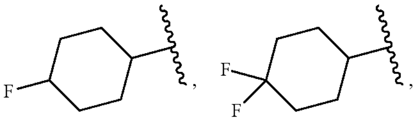
and
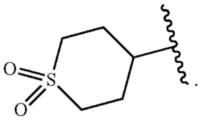
In some embodiments, for a compound of Formula (I) or (I-1), $R^9$ is substituted with a substituent selected from
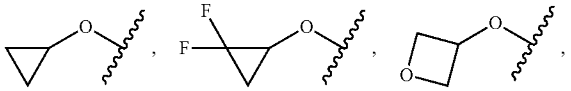
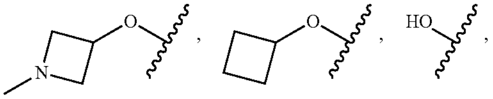
-continued
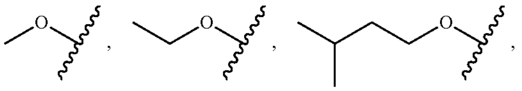
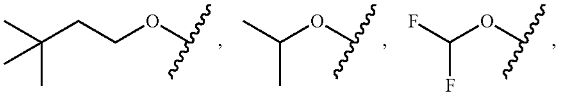
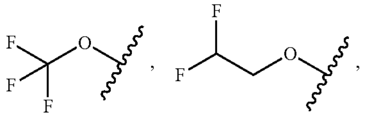
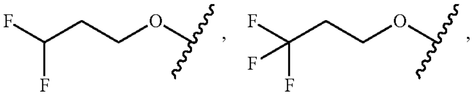
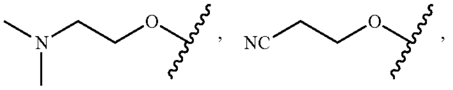
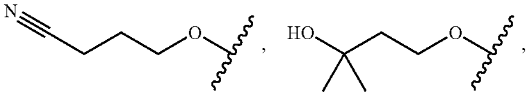
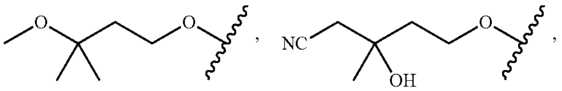
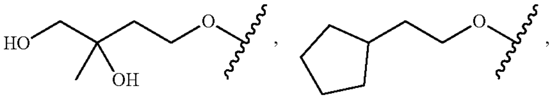
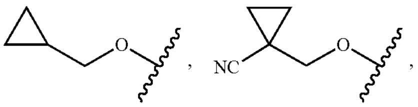
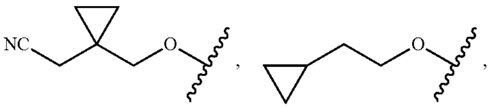
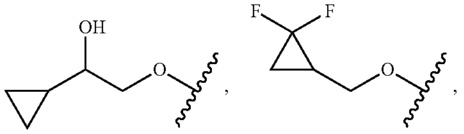
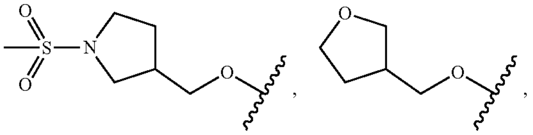
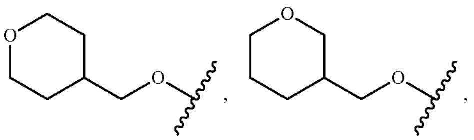
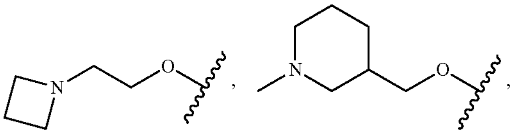
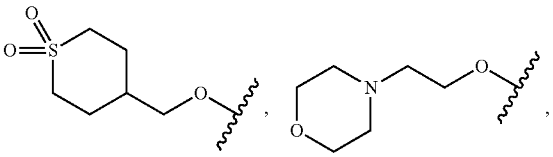

-continued
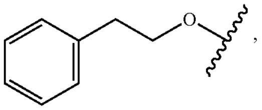,
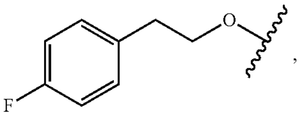, and
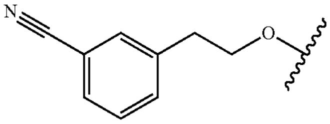.
In some embodiments, for a compound of Formula (I) or (I-1), $R^9$ is substituted with a substituent selected from
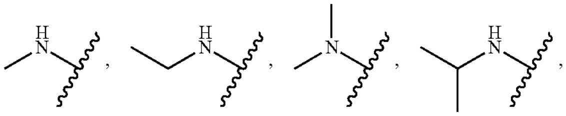
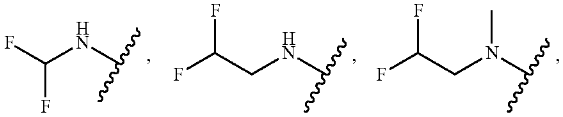
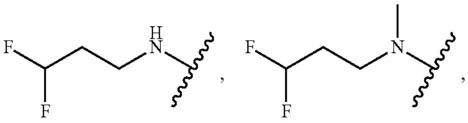
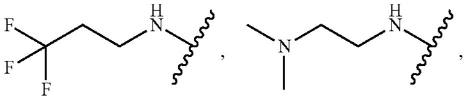
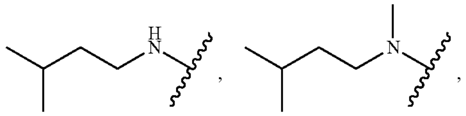
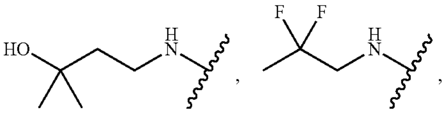
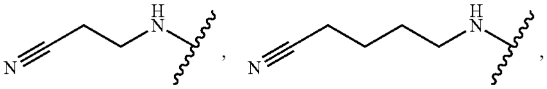
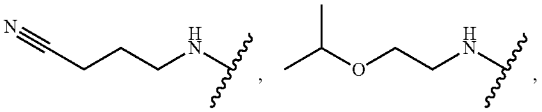
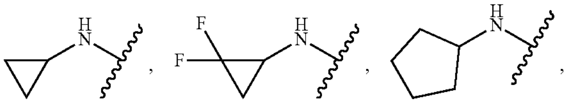
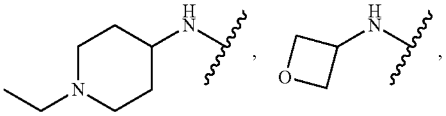
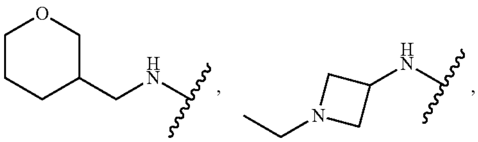
-continued
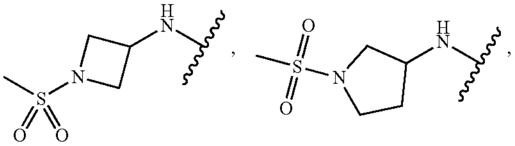
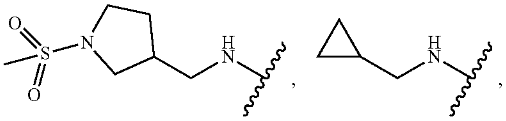
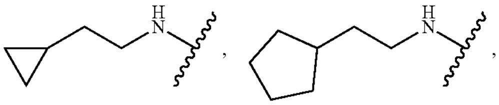
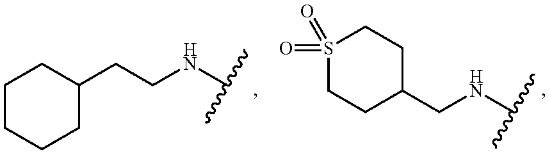
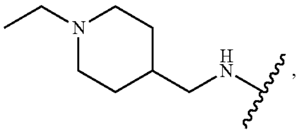
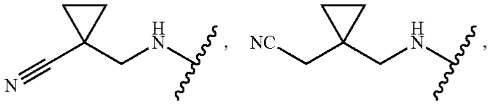
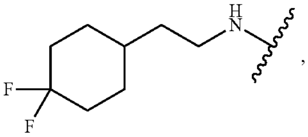
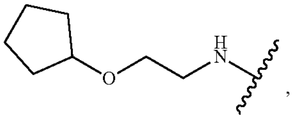
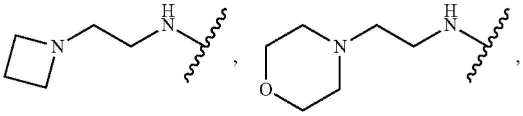
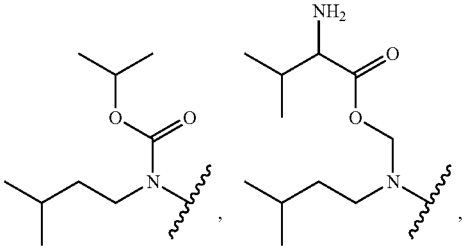
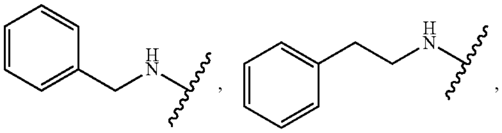
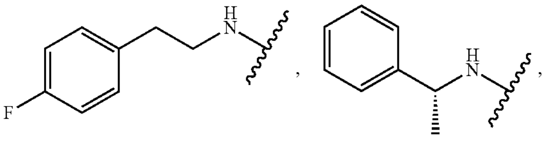

-continued
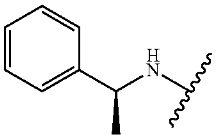
, and
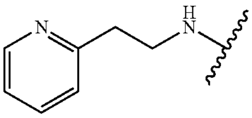
.
In some embodiments, for a compound of Formula (I) or (I-1), $R^9$ is substituted with a substituent selected from
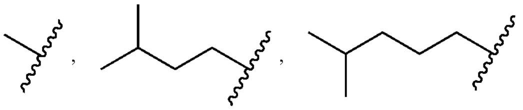
, , ,
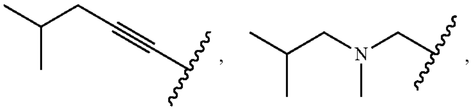
, ,
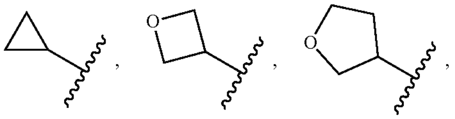
, , ,
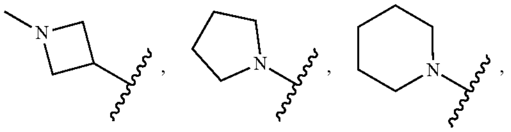
, , ,
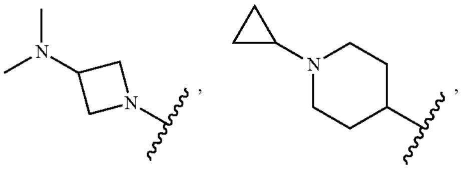
, ,
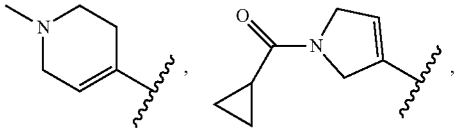
, ,
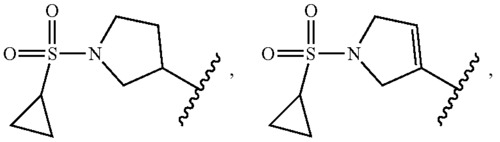
, ,
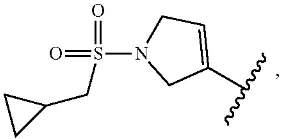
,
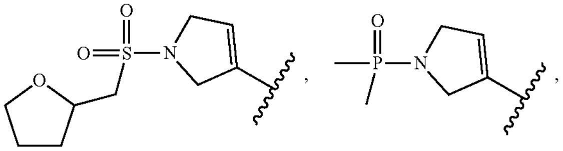
, ,
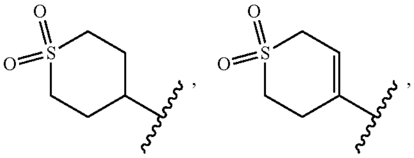
, ,
-continued
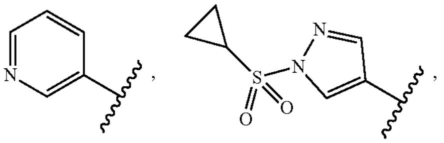
, ,
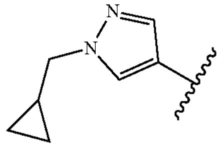
, and
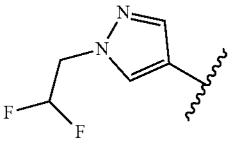
.
In some embodiments, for a compound of Formula (I) or (I-1), $R^9$ is substituted with a substituent selected from
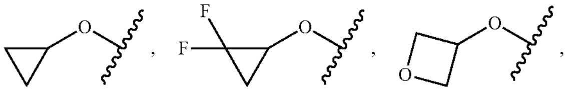
, , ,
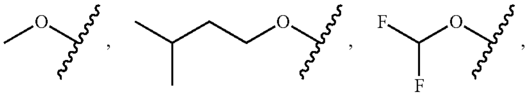
, , ,
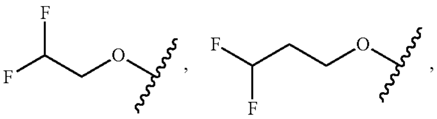
, ,
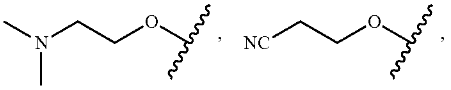
, ,
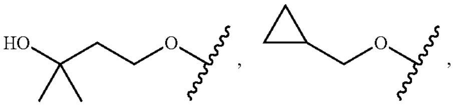
, ,
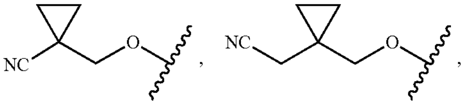
, ,
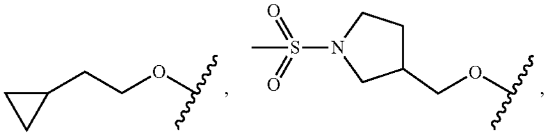
, ,
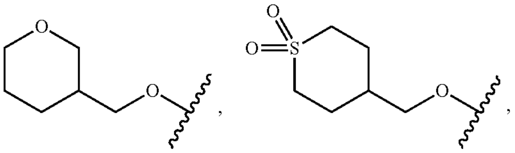
, ,
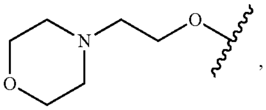
,
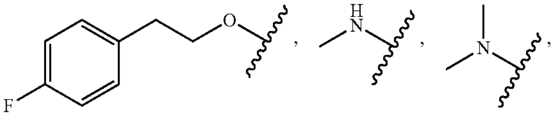
, , ,
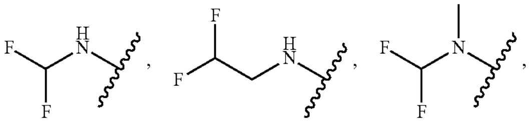
, , , -continued

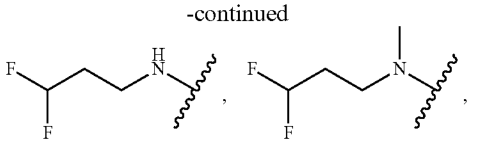
,
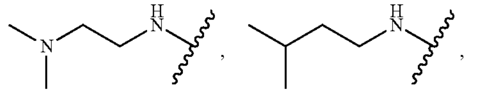
,
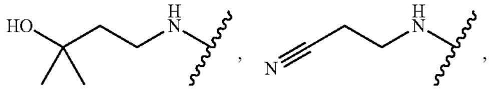
,
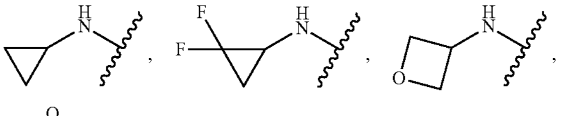
,
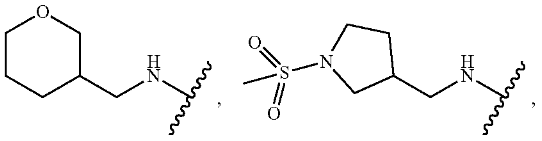
,
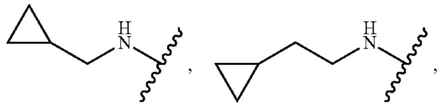
,
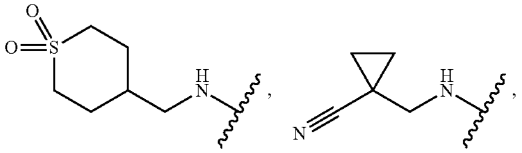
,
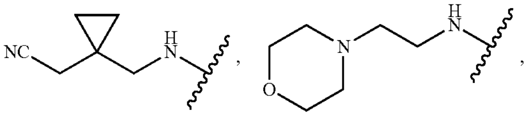
,
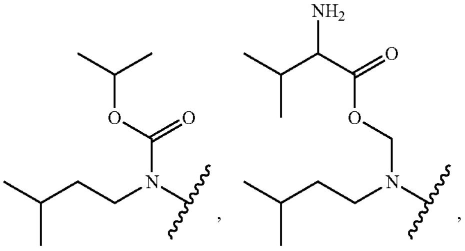
,
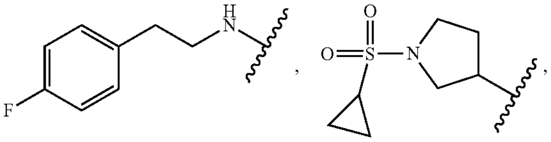
,
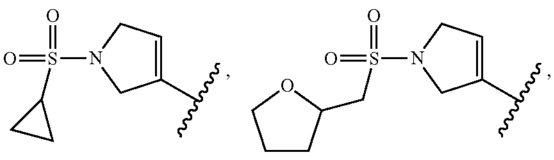
,
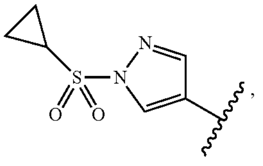
and
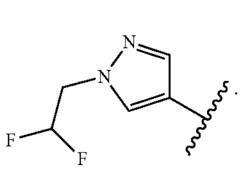
.

In some embodiments, for a compound of Formula (I) or (I-1), $R^9$ is substituted with a substituent selected from

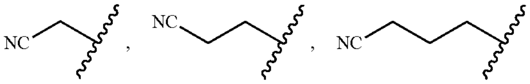
,
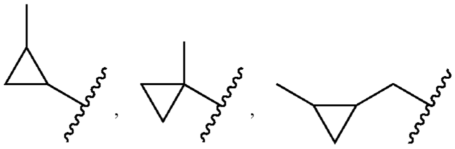
,
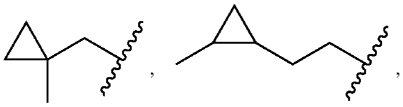
,
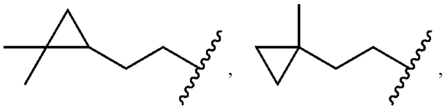
,
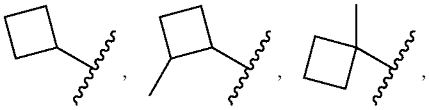
,
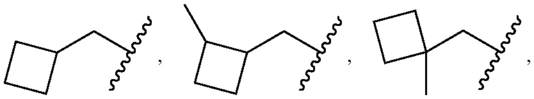
,
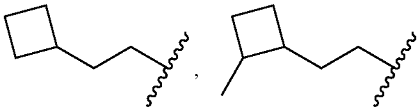
,
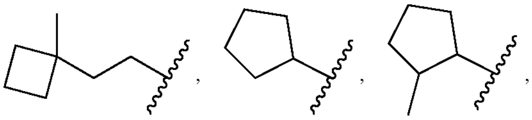
,
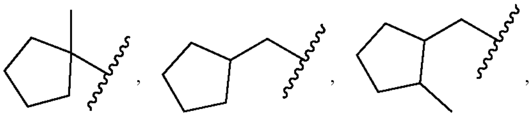
,
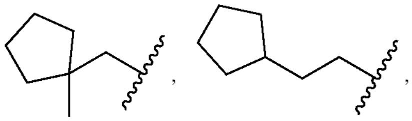
,
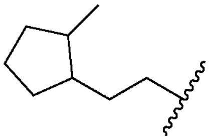
and
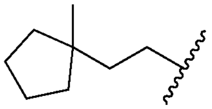
.

In some embodiments, for a compound of Formula (I) or (I-1), either (i) $R^9$ is substituted with (5-methyl-2-oxo-1,3-dioxol-4-yl)methyl, $—OR^{15}$, $—O—(C_{1-6}$ alkyl)-$OR^{15}$, $—(C_{1-6}$ alkyl)-$OR^{15}$, or $—C(O)O—(C_{1-6}$ alkyl)-$OR^{15}$; (ii) $W^1$, $W^2$, $W^4$, $W^5$ or $W^6$ is substituted with $—OR^{15}$, $—O—(C_{1-6}$ alkyl)-$OR^{15}$, or $—OC(O)N(R^{12})(R^{13})$; or (iii) $J^2$ or $J^3$ is substituted with (5-methyl-2-oxo-1,3-dioxol-4-yl)methyl, $—C(O)O—(C_{1-6}$ alkyl)-$OR^{15}$, or $—(C_{1-6}$ alkyl)-$OR^{15}$. In some embodiments, at least one of $R^9$, $W^1$, $W^2$, $W^4$, $W^5$, $W^6$, $J^2$, or $J^3$ is substituted with $—OR^{15}$, $—O—(C_{1-6}$ alkyl)-$OR^{15}$, $—OC(O)N(R^{12})(R^{13})$, $—C(O)OR^{12}$, $—C(O)O—(C_{1-6}$ alkyl)-$OR^{15}$, $—(C_{1-6}$ alkyl)-$OR^{15}$, $—P(O)(X—R^{16})(Y—R^{17})$, or $—CH_2P(O)(X—R^{16})(Y—R^{17})$. In some embodiments, at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, $—OC(O)N(R^{12})(R^{13})$, $—OCH(R^{20})OC(O)OR^{12}$, $—OC(O)CH(R^{20})$ $NH_2$, —OCH $(R^{20})OC(O)R^{12}$, $—OC(O)R^{12}$, $—OC(O)OR^{12}$, $—C(O)OR^{12}$, $—C(O)OCH(R^{20})OC(O)R^{12}$, $—CH(R^{20})OC(O)R^{12}$, $—P(O)(X—R^{16})(Y—R^{17})$, or $—CH_2P(O)(X—R^{16})(Y—R^{17})$. In some embodiments, at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, $—OC(O)N(R^{12})(R^{13})$, $—OCH(R^{20})OC(O)OR^{12}$, $—OC(O)CH(R^{20})$ $NH_2$, $—OCH(R^{20})OC(O)R^{12}$, $—OC(O)R^{12}$, $—OC(O)OR^{12}$, $—C(O)OR^{12}$, $—C(O)OCH(R^{20})OC(O)R^{12}$, $—CH(R^{20})OC(O)R^{12}$, $—P(O)(X—R^{16})(Y—R^{17})$, or $—CH_2P(O)(X—R^{16})(Y—R^{17})$; and $R^{12}$ is $C_{1-6}$ alkyl optionally substituted with one, two, or three $R^{20}$. In some embodiments, at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, $—OC(O)N(R^{12})(R^{13})$, $—OCH(R^{20})OC(O)OR^{12}$, $—OC(O)CH(R^{20})$ $NH_2$, $—OCH(R^{20})OC(O)R^{12}$, $—OC(O)R^{12}$, $—OC(O)OR^{12}$, $—C(O)OR^{12}$, $—C(O)OCH(R^{20})OC(O)R^{12}$, $—CH(R^{20})OC(O)R^{12}$, $—P(O)(X—R^{16})(Y—R^{17})$, or $—CH_2P(O)(X—R^{16})(Y—R^{17})$; and $R^{12}$ is $C_{1-6}$ alkyl. In some embodiments, at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, $—OC(O)N(R^{12})(R^{13})$, $—OCH_2OC(O)OR^{12}$, $—OCH(CH_3)OC(O)OR^{12}$, $—OC(O)CH_2NH_2$, $—OC(O)CH(CH_3)$ $NH_2$, $—OCH_2OC(O)R^{12}$, $—OCH(CH_3)OC(O)R^{12}$, $—OC(O)R^{12}$, $—OC(O)OR^{12}$, $—C(O)OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(X—R^{16})(Y—R^{17})$, or $—CH_2P(O)(X—R^{16})(Y—R^{17})$. In some embodiments, $R^9$ is substituted with $—C(O)OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(X—R^{16})(Y—R^{17})$, or $—CH_2P(O)(X—R^{16})(Y—R^{17})$. In some embodiments, $R^9$ is substituted with $—C(O)OCH_2OC(O)R^{12}$ or $—C(O)OCH(CH_3)OC(O)R^{12}$. In some embodiments, at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, $—OC(O)N(R^{12})(R^{13})$, $—OCH_2OC(O)OR^{12}$, $—OCH(CH_3)OC(O)OR^{12}$, $—OC(O)CH_2NH_2$, $—OC(O)CH(CH_3)$ $NH_2$, $—OCH_2OC(O)R^{12}$, $—OCH(CH_3)OC(O)R^{12}$, $—OC(O)R^{12}$, $—OC(O)OR^{12}$, $—C(O)OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(X—R^{16})(Y—R^{17})$, or $—CH_2P(O)(X—R^{16})(Y—R^{17})$; and $R^{12}$ is $C_{1-6}$ alkyl optionally substituted with one, two, or three $R^{20}$. In some embodiments, at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, $—OC(O)N(R^{12})(R^{13})$, $—OCH_2OC(O)OR^{12}$, $—OCH(CH_3)OC(O)OR^{12}$, $—OC(O)CH_2NH_2$, $—OC(O)CH(CH_3)$ $NH_2$, $—OCH_2OC(O)R^{12}$, $—OCH(CH_3)OC(O)R^{12}$, $—OC(O)R^{12}$, $—OC(O)OR^{12}$, $—C(O)OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(X—R^{16})(Y—R^{17})$, or $—CH_2P(O)(X—R^{16})(Y—R^{17})$; and $R^{12}$ is $C_{1-6}$ alkyl. In some embodiments, at least one of $R^9$, $W^1$, $W^2$, $W^4$, $W^5$, $W^6$, $J^2$, or $J^3$ is substituted with $—OP(O)(OH)_2$, $—OCH_2OP(O)(OH)_2$, $—OC(O)N(R^{12})(R^{13})$, $—OCH_2OC(O)OR^{12}$, $—OCH(CH_3)OC(O)OR^{12}$, $—OC(O)CH_2NH_2$, $—OC(O)CH(CH_3)$ $NH_2$, $—OCH_2OC(O)R^{12}$, $—OCH(CH_3)OC(O)R^{12}$, $—OC(O)R^{12}$, $—OC(O)OR^{12}$, $—C(O)OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(OH)_2$, or $—CH_2P(O)(OH)_2$. In some embodiments, at least one of $R^9$, $W^1$, $W^2$, $W^4$, $W^5$, $W^6$, $J^2$, or $J^3$ is substituted with $—OP(O)(OH)_2$, $—OCH_2OP(O)(OH)_2$, $—OC(O)N(R^{12})(R^{13})$, $—OCH_2OC(O)OR^{12}$, $—OCH(CH_3)OC(O)OR^{12}$, $—OC(O)CH_2NH_2$, $—OC(O)CH(CH_3)$ $NH_2$, $—OCH_2OC(O)R^{12}$, $—OCH(CH_3)OC(O)R^{12}$, $—OC(O)R^{12}$, $—OC(O)OR^{12}$, $—C(O)OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(OH)_2$, or $—CH_2P(O)(OH)_2$; and $R^{12}$ is $C_{1-6}$ alkyl optionally substituted with one, two, or three $R^{20}$. In some embodiments, at least one of $R^9$, $W^1$, $W^2$, $W^4$, $W^5$, $W^6$, $J^2$, or $J^3$ is substituted with $—OP(O)(OH)_2$, $—OCH_2OP(O)(OH)_2$, $—OC(O)N(R^{12})(R^{13})$, $—OCH_2OC(O)OR^{12}$, $—OCH(CH_3)OC(O)OR^{12}$, $—OC(O)CH_2NH_2$, $—OC(O)CH(CH_3)$ $NH_2$, $—OCH_2OC(O)R^{12}$, $—OCH(CH_3)OC(O)R^{12}$, $—OC(O)R^{12}$, $—OC(O)OR^{12}$, $—C(O)OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(OH)_2$, or $—CH_2P(O)(OH)_2$; and $R^{12}$ is $C_{1-6}$ alkyl. In some embodiments, at least one of $R^9$, $W^1$, $W^2$, $W^4$, $W^5$, $W^6$, $J^2$, or $J^3$ is substituted with $—OC(O)N(CH_3)_2$, $—OC(O)N(CH_3)(CH_2CH_2OCH_3)$, $—OC(O)$ $NHCH_2CH_3$, —OC(O)(pyrrolidine-1-yl), $—OC(O)CH(CH_3)OC(O)CH_3$, $—OC(O)CH(CH_3)OC(O)CH(CH_3)_2$, $—OC(O)CH(CH_3)_2$, methyleneoxy (4-methyl-1,3-dioxol-2-one), $—OCH_2OC(O)CH_2CH_2CH_3$, $—OCH_2OP(O)(OCH_2OC(O)OCH(CH_3)_2)_2$, $—OC(O)CH(NH_2)CH(CH_3)_2$, $—OCH_2OP(O)(OH)_2$, $—C(O)OCH(CH_3)OC(O)CH(CH_3)_2$, $—C(O)OCH(CH_3)OC(O)CH_3$, $—C(O)OCH(CH_3)OC(O)CH_2CH_2CH_3$, $—C(O)OCH(CH_3)_2$, $—C(O)OCH_2CH(CH_3)_2$, $—C(O)O(CH_2)_3CH_3$, ((5-methyl-2-oxo-1,3-dioxol-4-yl) methoxy)(oxo)methyl, (5-methyl-2-oxo-1,3-dioxol-4-yl)methyl, $—C(O)OCH(CH_3)OC(O)CH(NH_2)(CH(CH_3)_2)$, $—C(O)OCH_2OC(O)$(4-(phosphonooxy)phenyl)methyl, $—CH_2OP(O)(OH)(OCH_2OC(O)OCH(CH_3)_2)$, $—C(O)OCH(CH_3)OP(O)(OH)_2$, or $—CH_2OP(O)(OH_2)$. In some embodiments, at least one of $R^9$, $W^1$, $W^2$, $W^4$, $W^5$, $W^6$, $J^2$, or $J^3$ is substituted with $—OC(O)N(CH_3)_2$, $—OC(O)N(CH_3)(CH_2CH_2OCH_3)$, $—OC(O)$ $NHCH_2CH_3$, —OC(O)(pyrrolidine-1-yl), $—OC(O)CH(CH_3)OC(O)CH_3$, $—OC(O)CH(CH_3)OC(O)CH(CH_3)_2$, $—OC(O)CH(CH_3)_2$, methyleneoxy (4-methyl-1,3-dioxol-2-one), $—OCH_2OC(O)CH_2CH_2CH_3$, $—OCH_2OP(O)(OCH_2OC(O)OCH(CH_3)_2)_2$, $—OC(O)CH(NH_2)CH(CH_3)_2$, $—OCH_2OP(O)(OH)_2$, $—CH_2OP(O)(OH)_2$, $—CH(CH_3)OP(O)(OH)_2$, $—CH_2OP(O)(OCH_2OC(O)OCH(CH_3)_2)_2$, $—CH_2OC(O)CH(NH_2)(CH(CH_3)_2)$, $—CH(CH_3)OC(O)CH(NH_2)(CH(CH_3)_2)$, or $—CH_2OC(O)CH(CH_3)_2$.

In some embodiments, for a compound of Formula (I) or (I-1), at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, $—OC(O)N(R^{12})(R^{13})$, $—OCH(R^{20})OC(O)OR^{12}$, $—OC(O)CH(R^{20})$ $NH_2$, $—OCH(R^{20})OC(O)R^{12}$, $—OC(O)R^{12}$, $—OC(O)OR^{12}$, $—C(O)OR^{12}$, $—C(O)OCH(R^{20})OC(O)R^{12}$, $—CH(R^{20})OC(O)R^{12}$, $—P(O)(X—R^{16})(Y—R^{17})$, or $—CH_2P(O)(X—R^{16})(Y—R^{17})$, wherein $R^{12}$ is selected from $C_{1-6}$ alkyl, $—C_{0-6}$ alkyl-($C_{3-12}$ carbocycle), and $—C_{0-6}$ alkyl-(3- to 12-membered heterocycle), each of which is optionally substituted with one, two, or three substituents independently selected from $—N(R^{22})C(O)CH(R^{20})N(R^{22})_2$, $—C(O)CH(R^{20})N(R^{22})_2$, and $R^{20}$. In some embodiments, at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, $—OC(O)N(R^{12})(R^{13})$, $—OCH(R^{20})OC(O)OR^{12}$, $—OC(O)CH(R^{20})$ $NH_2$, $—OCH(R^{20})OC(O)R^{12}$, $—OC(O)R^{12}$, $—OC(O)OR^{12}$, $—C(O)OR^{12}$, $—C(O)OCH(R^{20})OC(O)R^{12}$, $—CH(R^{20})OC(O)R^{12}$, $—P(O)(X—R^{16})(Y—R^{17})$, or $—CH_2P(O)(X—R^{16})(Y—R^{17})$; and $R^{12}$ is $C_{1-6}$ alkyl optionally substituted with one, two, or three substituents independently selected from $—N(R^{22})C(O)CH(R^{20})N(R^{22})_2$, $—C(O)CH(R^{20})N(R^{22})_2$, and $R^{20}$. In some embodiments, at least one of $R^9$, $W^1$, $W^2$, $W^4$, $W^5$, $W^6$, $J^2$, or $J^3$ is substituted with $—OP(O)(X—R^{16})(Y—R^{17})$, $—OCH_2OP(O)(X—R^{16})(Y—R^{17})$, —OC(O)N $(R^{12})(R^{13})$, —$OCH(R^{20})OC(O)OR^{12}$, —$OC(O)CH(R^{20})NH_2$, —$OCH(R^{20})OC(O)R^{12}$, —$OC(O)R^{12}$, —$OC(O)OR^{12}$, —$C(O)OR^{12}$, —$C(O)OCH(R^{20})OC(O)R^{12}$, —$CH(R^{20})OC(O)R^{12}$, —$P(O)(X—R^{16})(Y—R^{17})$, or —$CH_2P(O)(X—R^{16})(Y—R^{17})$; and $R^{12}$ is $C_{1-6}$ alkyl substituted with —$N(R^{22})C(O)CH(R^{20})N(R^{22})_2$. In some embodiments, at least one of $R^9$, $W^1$, $W^2$, $W^4$, $W^5$, $W^6$, $J^2$, or $J^3$ is substituted with —$OP(O)(X—R^{16})(Y—R^{17})$, —$OCH_2OP(O)(X—R^{16})(Y—R^{17})$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)NH_2$, —$OCH_2OC(O)R^{12}$, —$OCH(CH_3)OC(O)R^{12}$, —$OC(O)R^{12}$, —$OC(O)OR^{12}$, —$C(O)OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(X—R^{16})(Y—R^{17})$, or —$CH_2P(O)(X—R^{16})(Y—R^{17})$; and $R^{12}$ is $C_{1-6}$ alkyl substituted with —$N(R^{22})C(O)CH(R^{20})N(R^{22})_2$. In some embodiments, at least one of $R^9$, $W^1$, $W^2$, $W^4$, $W^5$, $W^6$, $J^2$, or $J^3$ is substituted with —$OP(O)(X—R^{16})(Y—R^{17})$, —$OCH_2OP(O)(X—R^{16})(Y—R^{17})$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)NH_2$, —$OCH_2OC(O)R^{12}$, —$OCH(CH_3)OC(O)R^{12}$, —$OC(O)R^{12}$, —$OC(O)OR^{12}$, —$C(O)OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(X—R^{16})(Y—R^{17})$, or —$CH_2P(O)(X—R^{16})(Y—R^{17})$; and $R^{12}$ is $C_{1-6}$ alkyl optionally substituted with —$NHC(O)CH(CH_3)NH_2$, —$NHC(O)CH(CH_3)N(CH_3)_2$, —$NHC(O)CH(CH(CH_3)_2)NH_2$, or —$NHC(O)CH(CH(CH_3)_2)N(CH_3)_2$. In some embodiments, at least one of $R^9$, $W^1$, $W^2$, $W^4$, $W^5$, $W^6$, $J^2$, or $J^3$ is substituted with —$OP(O)(OH)_2$, —$OCH_2OP(O)(OH)_2$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)NH_2$, —$OCH_2OC(O)R^{12}$, —$OCH(CH_3)OC(O)R^{12}$, —$OC(O)R^{12}$, —$OC(O)OR^{12}$, —$C(O)OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, or —$CH_2P(O)(OH)_2$; and $R^{12}$ is $C_{1-6}$ alkyl substituted with —$N(R^{22})C(O)CH(R^{20})N(R^{22})_2$. In some embodiments, at least one of $R^9$, $W^1$, $W^2$, $W^4$, $W^5$, $W^6$, $J^2$, or $J^3$ is substituted with —$OP(O)(OH)_2$, —$OCH_2OP(O)(OH)_2$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)NH_2$, —$OCH_2OC(O)R^{12}$, —$OCH(CH_3)OC(O)R^{12}$, —$OC(O)R^{12}$, —$OC(O)OR^{12}$, —$C(O)OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, or —$CH_2P(O)(OH)_2$; and $R^{12}$ is $C_{1-6}$ alkyl optionally substituted with —$NHC(O)CH(CH_3)NH_2$, —$NHC(O)CH(CH_3)N(CH_3)_2$, —$NHC(O)CH(CH(CH_3)_2)NH_2$, or —$NHC(O)CH(CH(CH_3)_2)N(CH_3)_2$. In some embodiments, at least one of $R^9$, $W^1$, $W^2$, $W^4$, $W^5$, $W^6$, $J^2$, or $J^3$ is substituted with —$OC(O)N(CH_3)_2$, —$OC(O)N(CH_3)(CH_2CH_2OCH_3)$, —$OC(O)NHCH_2CH_3$, —OC(O)(pyrrolidine-1-yl), —$OC(O)CH(CH_3)OC(O)CH_3$, —$OC(O)CH(CH_3)OC(O)CH(CH_3)_2$, —$OC(O)CH(CH_3)_2$, methyleneoxy (4-methyl-1,3-dioxol-2-one), —$OCH_2OC(O)CH_2CH_2CH_3$, —$OCH_2OP(O)(OCH_2OC(O)OCH(CH_3)_2)_2$, —$OC(O)CH(NH_2)CH(CH_3)_2$, —$OCH_2OP(O)(OH)_2$, —$C(O)OCH(CH_3)OC(O)CH(CH_3)_2$, —$C(O)OCH(CH_3)OC(O)CH_3$, —$C(O)OCH(CH_3)OC(O)CH_2CH_2CH_3$, —$C(O)OCH(CH_3)_2$, —$C(O)OCH_2CH(CH_3)_2$, —$C(O)O(CH_2)_3CH_3$, ((5-methyl-2-oxo-1,3-dioxol-4-yl) methoxy)(oxo)methyl, (5-methyl-2-oxo-1,3-dioxol-4-yl)methyl, —$C(O)OCH(CH_3)OC(O)CH(NH_2)(CH(CH_3)_2)$, —$C(O)OCH(CH_3)OC(O)CH(CH(CH_3)_2)NHC(O)CH(CH_3)NH_2$, —$C(O)OCH(CH(CH_3)_2)OC(O)CH(CH(CH_3)_2)NHC(O)CH(CH_3)NH_2$, —$C(O)OCH(CH_3)OC(O)CH(CH(CH_3)_2)NHC(O)CH(CH(CH_3)_2)NH_2$, —$C(O)OCH(CH(CH_3)_2)OC(O)CH(CH(CH_3)_2)NHC(O)CH(CH(CH_3)_2)NH_2$, —$C(O)OCH(CH_3)OC(O)CH(CH(CH_3)_2)NHC(O)CH(CH_3)N(CH_3)_2$, —$C(O)OCH(CH(CH_3)_2)OC(O)CH(CH(CH_3)_2)NHC(O)CH(CH_3)N(CH_3)_2$, —$C(O)OCH(CH_3)OC(O)CH(CH(CH_3)_2)NHC(O)CH(CH(CH_3)_2)N(CH_3)_2$, —$C(O)OCH(CH(CH_3)_2)OC(O)CH(CH(CH_3)_2)NHC(O)CH(CH(CH_3)_2)N(CH_3)_2$, —$C(O)OCH_2OC(O)$(4-(phosphonooxy)phenyl)methyl, —$CH_2OP(O)(OH)(OCH_2OC(O)OCH(CH_3)_2)$, —$C(O)OCH(CH_3)OP(O)(OH)_2$, or —$CH_2OP(O)(OH_2)$.

In some embodiments, the compound of Formula (I) or (I-1) is a compound selected from:

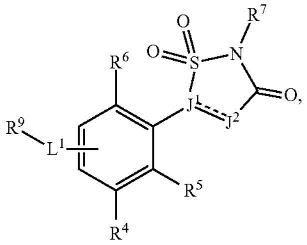

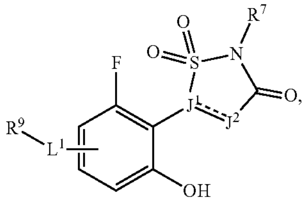

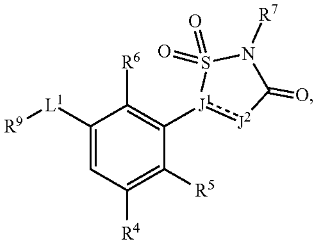

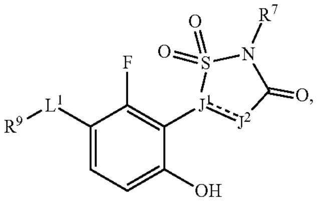

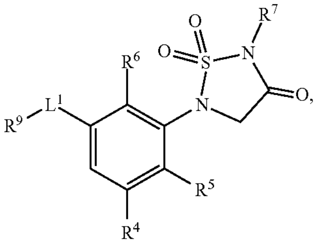

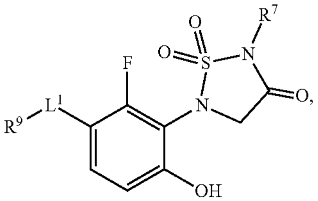

-continued

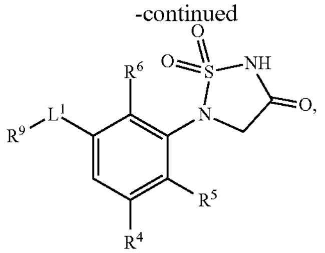

and

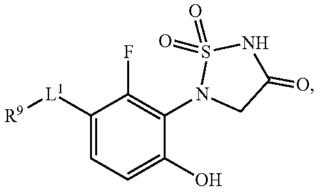

or a pharmaceutically acceptable salt or solvate thereof. Embodiments disclosed herein that refer to a compound of Formula (I) or (I-1) are also intended to apply to a compound of any formula depicted in this paragraph. If any provision of an embodiment that refers to Formula (I) or (I-1) recites a substituent or variable (e.g., $W^1$) not depicted in the compound, then the remainder of said embodiment shall be considered severable and not affected by the missing substituent or variable.

In certain aspects, the present disclosure provides a compound of Formula (II):

(II)

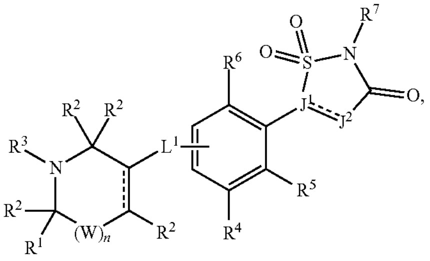

or a pharmaceutically acceptable salt or solvate thereof, wherein:

W is $C(R^2)_2$;

n is 0, 1, or 2;

$J^1$ is N and $J^2$ is $CH_2$; or $J^1$ is C and $J^2$ is CH;

$R^1$ is selected from halogen, —$C_{0-6}$ alkyl-CN, —$C_{0-6}$ alkyl-($C_3$ carbocycle), —$C_{0-6}$ alkyl-($C_{4-5}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, or (1) $R^1$ and $R^2$ attached to the same carbon atom are taken together to form oxo, =$NR^{12}$, or =$C(R^{14})_2$, (2) $R^1$ and $R^2$ attached to the same carbon atom, together with the carbon atom to which they are attached, form $C_{3-12}$ carbocycle or 3- to 12-membered heterocycle, (3) $R^1$ and a vicinal $R^2$, together with the carbon atoms to which they are attached, form $C_{3-12}$ carbocycle or 3- to 12-membered heterocycle, or (4) $R^1$ and $R^3$, together with the atoms to which they are attached, form 3- to 12-membered heterocycle; wherein —$C_{0-6}$ alkyl-($C_3$ carbocycle) is substituted with one, two, or three $R^{20}$, and wherein —$C_{0-6}$ alkyl-CN, —$C_{0-6}$ alkyl-($C_{4-5}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$.

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, optionally wherein one or more of (1) two $R^2$ attached to the same carbon atom are taken together to form oxo, =$NR^{12}$, or =$C(R^{14})_2$, (2) two $R^2$ attached to the same carbon atom, together with the carbon atom to which they are attached, form $C_{3-12}$ carbocycle or 3- to 12-membered heterocycle, and (3) two vicinal $R^2$, together with the carbon atoms to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —$C(O)OR^{12}$, —$C(O)O$—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —$C(O)N(R^{12})C(O)$—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})C(O)$—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})S(O)$—, —$S(O)N(R^{12})$—, —$N(R^{12})S(O)_2N(R^{12})$—, —$N(R^{12})S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)R^{12}$, —$C(O)OR^{12}$, —$P(O)(X—R^{16})(Y—R^{17})$, and —$CH_2P(O)(X—R^{16})(Y—R^{17})$;

X and Y are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —$S(=O)(=NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ═══ independently indicates a single or double bond such that all valences are satisfied.

In certain aspects, the present disclosure provides a compound of Formula (II-a)

(II-a)

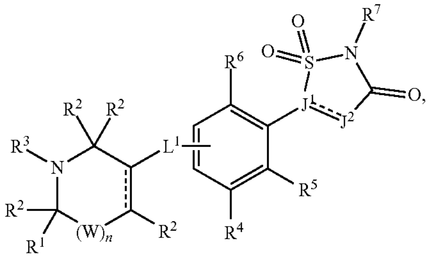

or a pharmaceutically acceptable salt or solvate thereof, wherein:

W is $C(R^2)_2$;

n is 0, 1, or 2;

$J^1$ is N and $J^2$ is $CH_2$; or $J^1$ is C and $J^2$ is CH;

$R^1$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, or (1) $R^1$ and $R^2$ attached to the same carbon atom are taken together to form oxo, =$NR^{12}$, or =$C(R^{14})_2$, (2) $R^1$ and $R^2$ attached to the same carbon atom, together with the carbon atom to which they are attached, form $C_{3-12}$ carbocycle or 3- to 12-membered heterocycle, (3) $R^1$ and a vicinal $R^2$, together with the carbon atoms to which they are attached, form $C_{3-12}$ carbocycle or 3- to 12-membered heterocycle, or (4) $R^1$ and $R^3$, together with the atoms to which they are attached, form 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, optionally wherein one or more of (1) two $R^2$ attached to the same carbon atom are taken together to form oxo, =$NR^{12}$, or =$C(R^{14})_2$, (2) two $R^2$ attached to the same carbon atom, together with the carbon atom to which they are attached, form $C_{3-12}$ carbocycle or 3- to 12-membered heterocycle, and (3) two vicinal $R^2$, together with the carbon atoms to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —$C(O)O$—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —$C(O)N(R^{12})C(O)$—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})C(O)$—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})S(O)$—, —$S(O)N(R^{12})$—, —$N(R^{12})S(O)_2N(R^{12})$—, —$N(R^{12})S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from —$C(O)R^{12}$, —$C(O)OR^{12}$, —$P(O)(X—R^{16})(Y—R^{17})$, and —$CH_2P(O)(X—R^{16})(Y—R^{17})$;

X and Y are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —$S(=O)(=NR^{22})N(R^{22})(R^{23})$, and —$OCH_2C(O)OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —$C(O)OR^{22}$, —$OC(O)N(R^{22})(R^{23})$, —$N(R^{22})C(O)N(R^{22})(R^{23})$, —$N(R^{22})C(O)OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ------ independently indicates a single or double bond such that all valences are satisfied;

wherein:

(1) if n is 0, each $R^2$ is hydrogen, $R^3$ is hydrogen, the left ------ is a double bond, the ------ between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl, ethyl, propyl, isopropyl, butyl, isobutyl, isopentyl, hydroxymethyl, methoxymethyl, methoxy (oxo)methyl, (difluoromethoxy)methyl, 2,2-difluoroethan-1-yl, 2-methoxyethan-1-yl, 2-phenylethan-1-yl, 3,3-difluoropropan-1-yl, but-3-en-1-yl, 3,3-dimethylbutan-1-yl, cyclopropyl, cyclopropylmethyl, 2-cyclopropylethan-1-yl, or 2,2-difluorocyclopropan-1-yl;

(2) if n is 0, three $R^2$ groups are hydrogen and the remaining $R^2$ attached to the same carbon as $R^1$ is methyl, $R^3$ is hydrogen, the left ------ is a double bond, the ------ between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl;

(3) if n is 0, each $R^2$ is hydrogen, $R^3$ is —$C(=NH)NH_2$ or —$C(=NH)NHCN$, the left ------ is a double bond, the ------ between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl;

(4) if n is 0, each $R^2$ is hydrogen, $R^3$ is hydrogen, the left ------ is a double bond, the ------ between $J^1$ and $J^2$ is a single bond, $J^1$ is N, $J^2$ is $CH_2$, $R^4$ is hydrogen, $R^5$ is —$CHF_2$, and $R^6$ is —F, then $R^1$ is not cyclopropylmethyl;

(5) if n is 0, each $R^2$ is hydrogen, $R^3$ is hydrogen, the left ------ is a single bond, the ------ between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl or hydroxymethyl (6) if n is 1, each $R^2$ is hydrogen, $R^3$ is hydrogen, the left ------ is a double bond, the ------ between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl, propyl, or isobutyl; and (7) if n is 1, each $R^2$ is hydrogen, $R^3$ is hydrogen, the left ------ is a double bond, the ------ between $J^1$ and $J^2$ is a single bond, $J^1$ is N, $J^2$ is $CH_2$, $R^4$ is hydrogen, $R^5$ is —$CHF_2$, and $R^6$ is —F, then $R^1$ is not isobutyl.

In certain aspects, the present disclosure provides a compound of Formula (II-1):

(II-1)

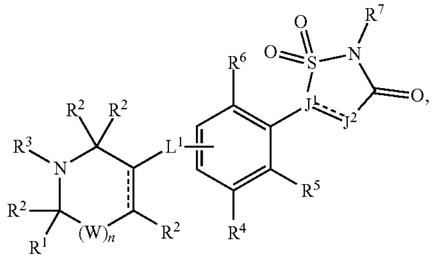

or a pharmaceutically acceptable salt or solvate thereof, wherein:

W is $C(R^2)_2$;

n is 0, 1, or 2;

$J^1$ is N and $J^2$ is $CH_2$; or $J^1$ is C and $J^2$ is CH;

$R^1$ is selected from halogen, —$C_{0-6}$ alkyl-CN, —$C_{0-6}$ alkyl-($C_3$ carbocycle), —$C_{0-6}$ alkyl-($C_{4-5}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, or (1) $R^1$ and $R^2$ attached to the same carbon atom are taken together to form oxo, =$NR^{12}$, or =$C(R^{14})_2$, (2) $R^1$ and $R^2$ attached to the same carbon atom, together with the carbon atom to which they are attached, form $C_{3-12}$ carbocycle or 3- to 12-membered heterocycle, (3) $R^1$ and a vicinal $R^2$, together with the carbon atoms to which they are attached, form $C_{3-12}$ carbocycle or 3- to 12-membered heterocycle, or (4) $R^1$ and $R^3$, together with the atoms to which they are attached, form 3- to 12-membered heterocycle; wherein —$C_{0-6}$ alkyl-($C_3$ carbocycle) is substituted with one, two, or three $R^{20}$; and wherein —$C_{0-6}$ alkyl-CN, —$C_{0-6}$ alkyl-($C_{4-5}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, optionally wherein one or more of (1) two $R^2$ attached to the same carbon atom are taken together to form oxo, =$NR^{12}$, or =$C(R^{14})_2$, (2) two $R^2$ attached to the same carbon atom, together with the carbon atom to which they are attached, form $C_{3-12}$ carbocycle or 3- to 12-membered heterocycle, and (3) two vicinal $R^2$, together with the carbon atoms to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —$C(O)OR^{12}$, —$C(O)O$—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —N($R^{12}$)—, —C($NR^{12}$)—, —N($R^{12}$)C($NR^{12}$)—, —C($NR^{12}$)N($R^{12}$)—, —N($R^{12}$)C($NR^{12}$)N($R^{12}$)—, —C(O)O—, —OC(O)O—, —OC(O)N($R^{12}$)—, —N($R^{12}$)C(O)N($R^{12}$)—, —N($R^{12}$)C(O)O—, —C(O)N($R^{12}$)C(O)—, —C(O)N($R^{12}$)C(O)N($R^{12}$)—, —N($R^{12}$)$S(O)_2$—, —C(O)—, —S(O)—, —OC(O)—, —C(O)N($R^{12}$)—, —C(O)C(O)N($R^{12}$)—, —N($R^{12}$)C(O)—, —$S(O)_2$—, —OS(O)—, —S(O)O—, —$OS(O)_2$—, —$S(O)_2O$—, —S(O)($NR^{12}$)—, —$S(O)_2$N($R^{12}$)—, —S(O)($NR^{12}$)N($R^{12}$)—, —N($R^{12}$)S(O)—, —S(O)N($R^{12}$)—, —N($R^{12}$)$S(O)_2$N($R^{12}$)—, —N($R^{12}$) S(O)N($R^{12}$)—, —P(O)($OR^{12}$)—, and —P(O)($R^{12}$)—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three substituents independently selected from —N($R^{22}$)C(O)CH($R^{20}$)N$(R^{22})_2$, —C(O)CH($R^{20}$)N$(R^{22})_2$, and $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —C(O)$R^{12}$, —C(O)$OR^{12}$, —P(O)(X—$R^{16}$)(Y—$R^{17}$), and —$CH_2$P(O)(X—$R^{16}$)(Y—$R^{17}$);

X and Y are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)$S(O)_2R^{12}$, —N($R^{12}$)$S(O)_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)$OR^{12}$, —C(O)N($R^{12}$)($R^{13}$), —C(O)C(O)N($R^{12}$)($R^{13}$), —N($R^{12}$)C(O)$R^{12}$, —$S(O)_2R^{12}$, —S(O)($NR^{12}$)$R^{12}$, —$S(O)_2$N($R^{12}$)($R^{13}$), —S(O)($NR^{12}$)N($R^{12}$)($R^{13}$), —P(O)$(OR^{12})_2$, —P(O)$(R^{12})_2$, —OP(O)$(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), =$NR^{22}$, =C$(R^{21})_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)$S(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —$S(O)_2R^{22}$, —S(O)($NR^{22}$)$R^{22}$, —$S(O)_2$N($R^{22}$)($R^{23}$)—, —S(=O)(=$NR^{22}$)N($R^{22}$)($R^{23}$), and —$OCH_2$C(O)$OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —N($R^{22}$)($R^{23}$), =$NR^{22}$, =C$(R^{21})_2$, —C(O)$OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)$S(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —$S(O)_2R^{22}$, —S(O)($NR^{22}$)$R^{22}$, —$S(O)_2$N($R^{22}$)($R^{23}$), and —S(=O)(=$NR^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ----- independently indicates a single or double bond such that all valences are satisfied.

In certain aspects, the present disclosure provides a compound of Formula (II-a1)

(II-a1)

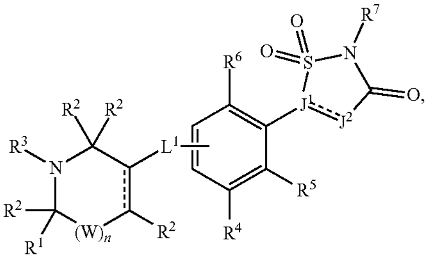

or a pharmaceutically acceptable salt or solvate thereof, wherein:

W is $C(R^2)_2$;

n is 0, 1, or 2;

$J^1$ is N and $J^2$ is $CH_2$; or $J^1$ is C and $J^2$ is CH;

$R^1$ is selected from halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, or (1) $R^1$ and $R^2$ attached to the same carbon atom are taken together to form oxo, =$NR^{12}$, or =$C(R^{14})_2$, (2) $R^1$ and $R^2$ attached to the same carbon atom, together with the carbon atom to which they are attached, form $C_{3-12}$ carbocycle or 3- to 12-membered heterocycle, (3) $R^1$ and a vicinal $R^2$, together with the carbon atoms to which they are attached, form $C_{3-12}$ carbocycle or 3- to 12-membered heterocycle, or (4) $R^1$ and $R^3$, together with the atoms to which they are attached, form 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, optionally wherein one or more of (1) two $R^2$ attached to the same carbon atom are taken together to form oxo, =$NR^{12}$, or =$C(R^{14})_2$, (2) two $R^2$ attached to the same carbon atom, together with the carbon atom to which they are attached, form $C_{3-12}$ carbocycle or 3- to 12-membered heterocycle, and (3) two vicinal $R^2$, together with the carbon atoms to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$C(O)OR^{12}$, —C(O)O—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —$C(O)N(R^{12})C(O)$—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})C(O)$—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})S(O)$—, —$S(O)N(R^{12})$—, —$N(R^{12})S(O)_2N(R^{12})$—, —$N(R^{12})S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three substituents independently selected from —N($R^{22}$)C(O)CH($R^{20}$)N($R^{22}$)$_2$, —C(O)CH($R^{20}$)N($R^{22}$)$_2$, and $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from —C(O)$R^{12}$, —C(O)O$R^{12}$, —P(O)(X—$R^{16}$)(Y—$R^{17}$), and —$CH_2$P(O)(X—$R^{16}$)(Y—$R^{17}$);

X and Y are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —O$R^{12}$, —S$R^{12}$, —N($R^{12}$)($R^{13}$), —C(O)O$R^{12}$, —OC(O)N($R^{12}$)($R^{13}$), —N($R^{12}$)C(O)N($R^{12}$)($R^{13}$), —N($R^{12}$)C(O)O$R^{12}$, —N($R^{12}$)S(O)$_2R^{12}$, —N($R^{12}$)S(O)$_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)O$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)(N$R^{12}$)$R^{12}$, —S(O)$_2$N($R^{12}$)($R^{13}$), —S(O)(N$R^{12}$)N($R^{12}$)($R^{13}$), —P(O)(O$R^{12}$)$_2$, —P(O)($R^{12}$)$_2$, —OP(O)(O$R^{12}$)$_2$, =O, =S, and =N$R^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$)—, —S(=O)(=N$R^{22}$)N($R^{22}$)($R^{23}$), and —O$CH_2$C(O)O$R^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —O$R^{22}$, —S$R^{22}$, —N($R^{22}$)($R^{23}$), =N$R^{22}$, =C($R^{21}$)$_2$, —C(O)O$R^{22}$, —OC(O)N($R^{22}$)($R^{23}$), —N($R^{22}$)C(O)N($R^{22}$)($R^{23}$), —N($R^{22}$)C(O)O$R^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)(N$R^{22}$)$R^{22}$, —S(O)$_2$N($R^{22}$)($R^{23}$), and —S(=O)(=N$R^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each - - - independently indicates a single or double bond such that all valences are satisfied;

wherein:

(1) if n is 0, each $R^2$ is hydrogen, $R^3$ is hydrogen, the left - - - is a double bond, the - - - between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl, ethyl, propyl, isopropyl, butyl, isobutyl, isopentyl, hydroxymethyl, methoxymethyl, methoxy (oxo)methyl, (difluoromethoxy)methyl, 2,2-difluoroethan-1-yl, 2-methoxyethan-1-yl, 2-phenylethan-1-yl, 3,3-difluoropropan-1-yl, but-3-en-1-yl, 3,3-dimethylbutan-1-yl, cyclopropyl, cyclopropylmethyl, 2-cyclopropylethan-1-yl, or 2,2-difluorocyclopropan-1-yl;

(2) if n is 0, three $R^2$ groups are hydrogen and the remaining $R^2$ attached to the same carbon as $R^1$ is methyl, $R^3$ is hydrogen, the left - - - is a double bond, the - - - between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl;

(3) if n is 0, each $R^2$ is hydrogen, $R^3$ is —C(=NH)$NH_2$ or —C(=NH)NHCN, the left - - - is a double bond, the - - - between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl;

(4) if n is 0, each $R^2$ is hydrogen, $R^3$ is hydrogen, the left ------ is a double bond, the ------ between $J^1$ and $J^2$ is a single bond, $J^1$ is N, $J^2$ is $CH_2$, $R^4$ is hydrogen, $R^5$ is —$CHF_2$, and $R^6$ is —F, then $R^1$ is not cyclopropylmethyl;

(5) if n is 0, each $R^2$ is hydrogen, $R^3$ is hydrogen, the left ------ is a single bond, the ------ between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl or hydroxymethyl (6) if n is 1, each $R^2$ is hydrogen, $R^3$ is hydrogen, the left ------ is a double bond, the ------ between $J^1$ and $J^2$ is a single bond, $J^1$ is N, $J^2$ is $CH_2$, $R^4$ is hydrogen, $R^5$ is —OH, and $R^6$ is —F, then $R^1$ is not methyl, propyl, or isobutyl; and (7) if n is 1, each $R^2$ is hydrogen, $R^3$ is hydrogen, the left ------ is a double bond, the ------ between $J^1$ and $J^2$ is a single bond, $J^1$ is N, $J^2$ is $CH_2$, $R^4$ is hydrogen, $R^5$ is —$CHF_2$, and $R^6$ is —F, then $R^1$ is not isobutyl.

In some embodiments, for a compound of Formula (II), (II-1), (II-a), or (II-a1), $R^1$ is selected from halogen, —$C_{0-6}$ alkyl-CN, —$C_{0-6}$ alkyl-($C_3$ carbocycle), —$C_{0-6}$ alkyl-($C_{4-5}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$N(R^{12})(R^{13})$, —$OC(O)R^{12}$, —$C(O)N(R^{12})(R^{13})$, and —$N(R^{12})C(O)R^{12}$, wherein —$C_{0-6}$ alkyl-CN, —$C_{0-6}$ alkyl-($C_3$ carbocycle), —$C_{0-6}$ alkyl-($C_{4-5}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$. In some embodiments, $R^1$ is selected from —$C_{0-6}$ alkyl-CN, —$C_{0-6}$ alkyl-($C_3$ carbocycle), and —$C_{0-6}$ alkyl-($C_{4-5}$ carbocycle), wherein —$C_{0-6}$ alkyl-($C_3$ carbocycle) is substituted with one, two, or three $R^{20}$ and wherein —$C_{0-6}$ alkyl-CN and —$C_{0-6}$ alkyl-($C_{4-5}$ carbocycle) are optionally substituted with one, two, or three $R^{20}$. In some embodiments, $R^1$ is —$C_{0-6}$ alkyl-CN, such as —$CH_2CN$, —$CH_2CH_2CN$, or —$CH_2CH_2CH_2CN$. In some embodiments, $R^1$ is —$C_{0-6}$ alkyl-($C_{4-5}$ carbocycle) optionally substituted with one, two, or three $R^{20}$, such as $R^1$ is cyclobutyl, methylcyclobutan-1-yl, 2-methylcyclobutan-1-yl, 2,2-dimethylcyclobutan-1-yl, cyclobutylmethyl, (1-methylcyclobutyl)methyl, (2-methylcyclobutyl)methyl, (2,2-dimethylcyclobutyl)methyl, cyclobutylethyl, 2-(1-methylcyclobutyl) ethan-1-yl, 2-(2-methylcyclobutyl) ethan-1-yl, 2-(2,2-dimethylcyclobutyl) ethan-1-yl, cyclopentyl, methylcyclopentan-1-yl, 2-methylcyclopentan-1-yl, 2,2-dimethylcyclopentan-1-yl, cyclopentylmethyl, (1-methylcyclopentyl)methyl, (2-methylcyclopentyl)methyl, (2,2-dimethylcyclopentyl)methyl, cyclopentylethyl, 2-(1-methylcyclopentyl) ethan-1-yl, 2-(2-methylcyclopentyl) ethan-1-yl, or 2-(2,2-dimethylcyclopentyl) ethan-1-yl. In some embodiments, $R^1$ is —$C_{0-6}$ alkyl-($C_{4-5}$ carbocycle), such as cyclobutylethyl. In some embodiments, $R^1$ is —$C_{0-6}$ alkyl-($C_3$ carbocycle) substituted with one, two, or three $R^{20}$, such as $R^1$ is methylcyclopropan-1-yl, 2-methylcyclopropan-1-yl, 2,2-dimethylcyclopropan-1-yl, (1-methylcyclopropyl) methyl, (2-methylcyclopropyl)methyl, (2,2-dimethylcyclopropyl)methyl, 2-(1-methylcyclopropyl) ethan-1-yl, 2-(2-methylcyclopropyl) ethan-1-yl, or 2-(2,2-dimethylcyclopropyl) ethan-1-yl. In some embodiments, $R^1$ and $R^2$ attached to the same carbon atom are taken together to form oxo, =$NR^{12}$, or =$C(R^{14})_2$, such as =NH, =NCN, =$CH_2$, =CHF, or =$CF_2$. In some embodiments, $R^1$ and $R^2$ attached to the same carbon atom, together with the carbon atom to which they are attached, form $C_{3-12}$ carbocycle or 3- to 12-membered heterocycle, each of which is optionally substituted with one, two, or three $R^{20}$. In some embodiments, $R^1$ and a vicinal $R^2$, together with the carbon atoms to which they are attached, form $C_{3-12}$ carbocycle or 3- to 12-membered heterocycle, each of which is optionally substituted with one, two, or three $R^{20}$. In some embodiments, $R^1$ and $R^3$, together with the atoms to which they are attached, form 3- to 12-membered heterocycle optionally substituted with one, two, or three $R^{20}$.

In some embodiments, for a compound of Formula (II), (II-1), (II-a), or (II-a1), $R^1$ is selected from

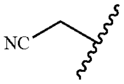, 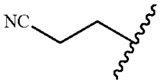, 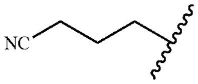,

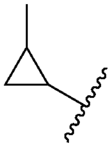, 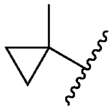, 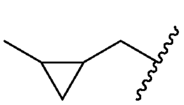,

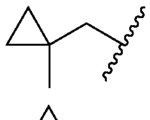, 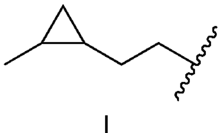,

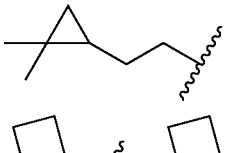, 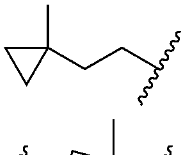,

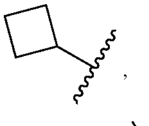, 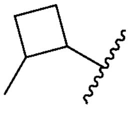, 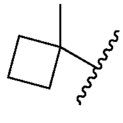,

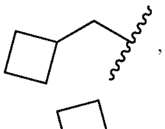, 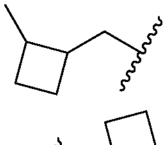, 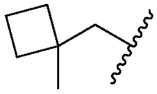,

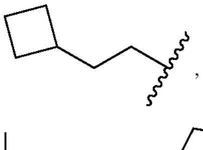, 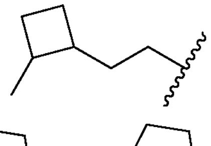,

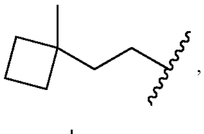, 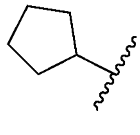, 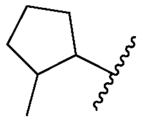,

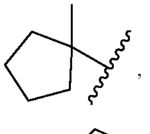, 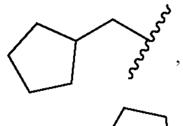, 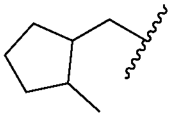,

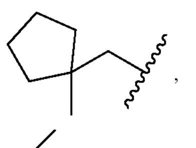, 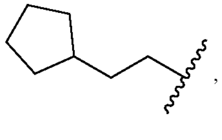,

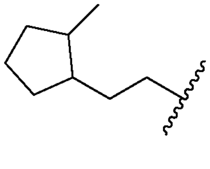, and 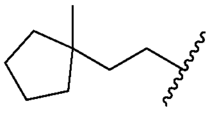.

In some embodiments, $R^1$ is selected from
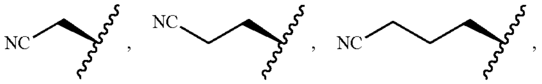
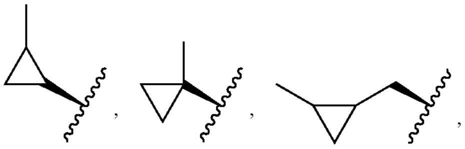
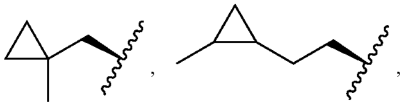
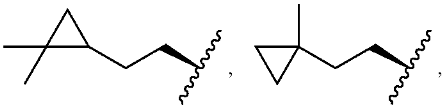
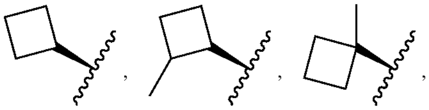
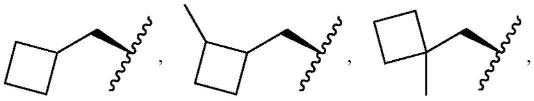
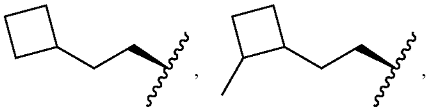
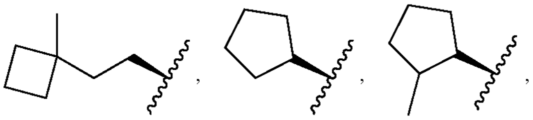
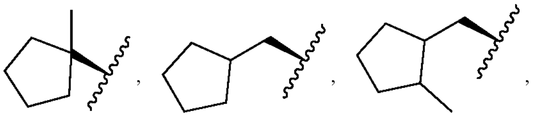
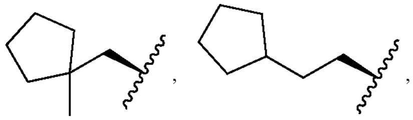
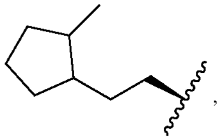
and
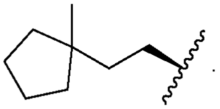
In some embodiments, $R^1$ is selected from
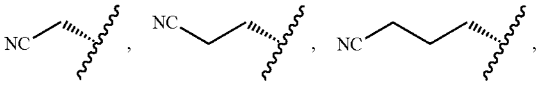
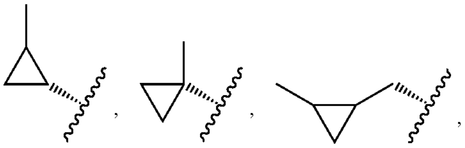
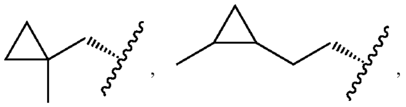
-continued
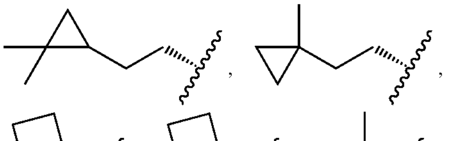
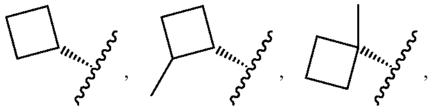
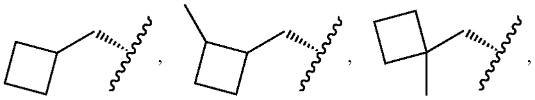
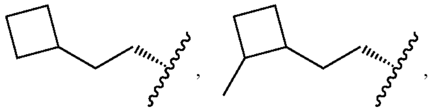
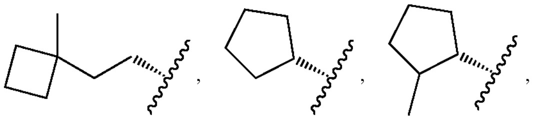
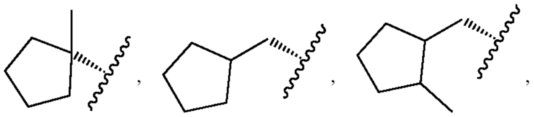
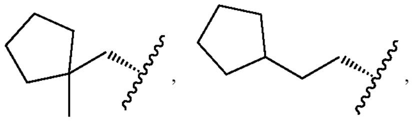
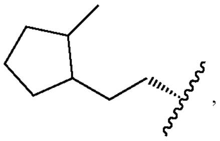
and
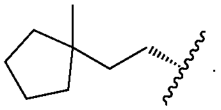
In some embodiments, the compound of Formula (II), (II-1), (II-a), or (II-a1) is a compound selected from:
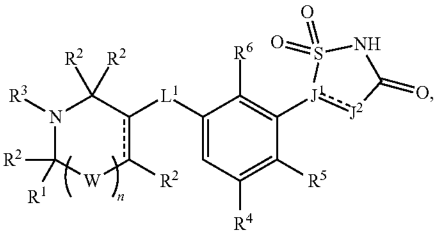
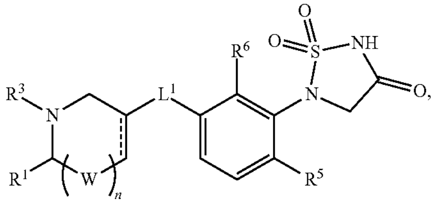
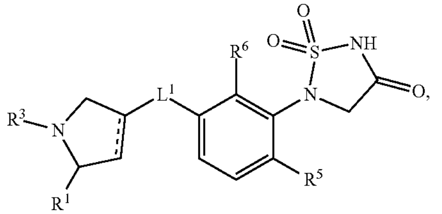

-continued

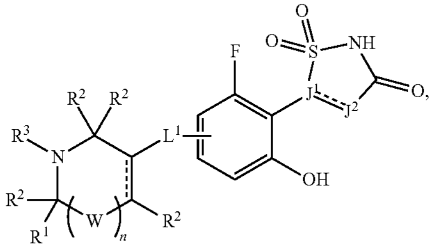

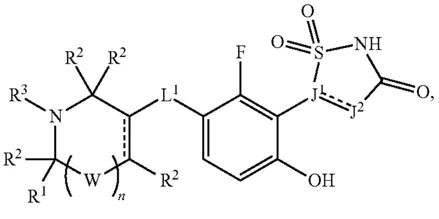

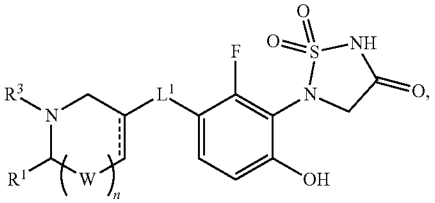

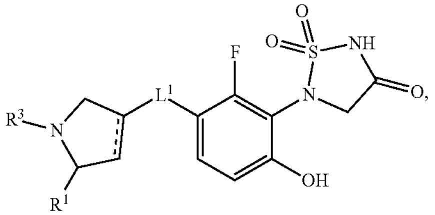

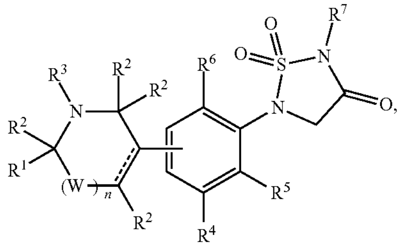

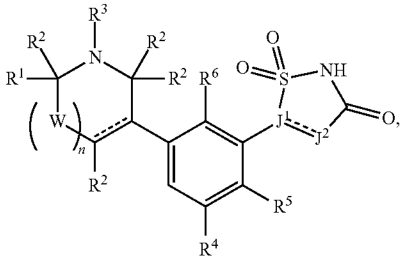

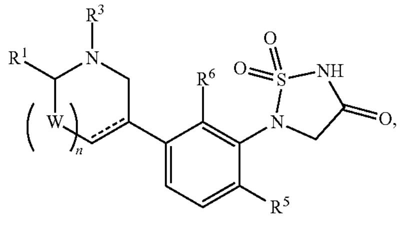

-continued

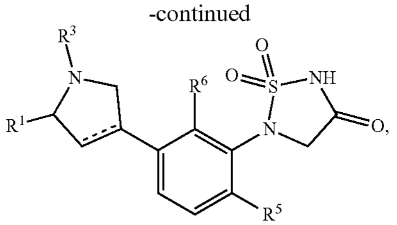

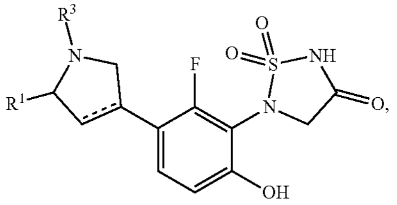

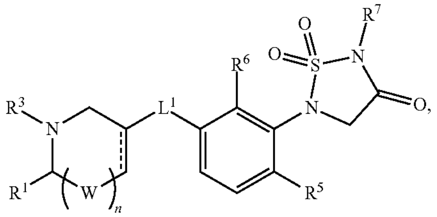

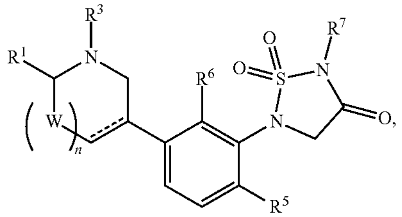

and

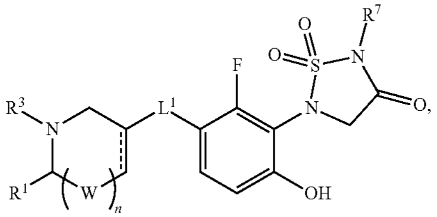

or a pharmaceutically acceptable salt or solvate thereof. Embodiments disclosed herein that refer to a compound of Formula (II), (II-1), (II-a), or (II-a1) are also intended to apply to a compound of any formula depicted in this paragraph. If any provision of an embodiment that refers to Formula (II), (II-1), (II-a), or (II-a1) recites a substituent or variable (e.g., $J^1$) not depicted in the compound, then the remainder of said embodiment shall be considered severable and not affected by the missing substituent or variable.

In certain aspects, the present disclosure provides a compound of Formula (III):

(III)

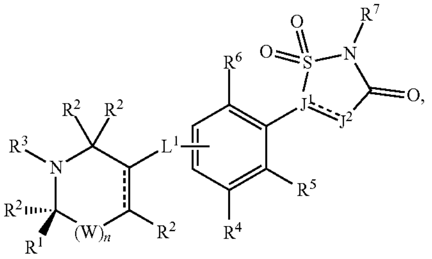

or a pharmaceutically acceptable salt or solvate thereof, wherein:

W is $C(R^2)_2$;

n is 0, 1, or 2;

$J^1$ is N and $J^2$ is $CH_2$; or $J^1$ is C and $J^2$ is CH;

$R^1$ is selected from halogen, —CN, $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, or (1) $R^1$ and $R^2$ attached to the same carbon atom are taken together to form oxo, $=NR^{12}$, or $=C(R^{14})_2$, (2) $R^1$ and $R^2$, together with the atom(s) to which they are attached, form $C_{3-12}$ carbocycle or 3- to 12-membered heterocycle, or (3) $R^1$ and $R^3$, together with the atoms to which they are attached, form 3- to 12-membered heterocycle, wherein $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, optionally wherein one or both of (1) two $R^2$ attached to the same carbon atom are taken together to form oxo, $=NR^{12}$, or $=C(R^{14})_2$ and (2) two $R^2$, together with the atom(s) to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —$C(O)OR^{12}$, —$C(O)O$—($C_{1-6}$ alkyl)-$OR^{15}$, —($C_{1-6}$ alkyl)-$OR^{15}$, —$C(O)R^{12}$, —$C(O)N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —$S(=O)(=NR^{12})N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —$N(R^{12})(R^{13})$, —$C(O)OR^{12}$, —$OC(O)N(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —$C(O)N(R^{12})C(O)$—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})C(O)$—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})S(O)$—, —$S(O)N(R^{12})$—, —$N(R^{12})S(O)_2N(R^{12})$—, —$N(R^{12})$ $S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl- (3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —C(O)$R^{12}$, —C(O)O$R^{12}$, —P(O)(X—$R^{16}$)(Y—$R^{17}$), and —$CH_2$P(O)(X—$R^{16}$)(Y—$R^{17}$);

X and Y are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —O$R^{12}$, —S$R^{12}$, —N($R^{12}$)($R^{13}$), —C(O)O$R^{12}$, —OC(O)N($R^{12}$)($R^{13}$), —N($R^{12}$)C(O)N($R^{12}$)($R^{13}$), —N($R^{12}$)C(O)O$R^{12}$, —N($R^{12}$)S$(O)_2R^{12}$, —N($R^{12}$)S$(O)_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)O$R^{12}$, —C(O)N($R^{12}$)($R^{13}$), —C(O)C(O)N($R^{12}$)($R^{13}$), —N($R^{12}$)C(O)$R^{12}$, —S$(O)_2R^{12}$, —S(O)(N$R^{12}$)$R^{12}$, —S$(O)_2$N($R^{12}$)($R^{13}$), —S(O)(N$R^{12}$)N($R^{12}$)($R^{13}$), —P(O)$(OR^{12})_2$, —P(O)$(R^{12})_2$, —OP(O)$(OR^{12})_2$, =O, =S, and =N$R^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{22}$, —S$R^{22}$, —N($R^{22}$)($R^{23}$), =N$R^{22}$, =C$(R^{21})_2$, —C(O)O$R^{22}$, —OC(O)N($R^{22}$)($R^{23}$), —N($R^{22}$)C(O)N($R^{22}$)($R^{23}$), —N($R^{22}$)C(O) O$R^{22}$, —N($R^{22}$)S$(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S$(O)_2R^{22}$, —S(O)(N$R^{22}$)$R^{22}$, —S$(O)_2$N($R^{22}$)($R^{23}$)—, —S(=O)(=N$R^{22}$)N($R^{22}$)($R^{23}$), and —OC$H_2$C(O) O$R^{22}$, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —O$R^{22}$, —S$R^{22}$, —N($R^{22}$)($R^{23}$), =N$R^{22}$, =C$(R^{21})_2$, —C(O) O$R^{22}$, —OC(O)N($R^{22}$)($R^{23}$), —N($R^{22}$)C(O)N($R^{22}$)($R^{23}$), —N($R^{22}$)C(O) O$R^{22}$, —N($R^{22}$)S$(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S$(O)_2R^{22}$, —S(O)(N$R^{22}$)$R^{22}$, —S$(O)_2$N($R^{22}$)($R^{23}$), and —S(=O)(=N$R^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ------ independently indicates a single or double bond such that all valences are satisfied.

In certain aspects, the present disclosure provides a compound of Formula (IV):

(IV)

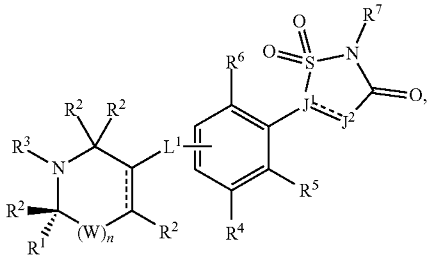

or a pharmaceutically acceptable salt or solvate thereof, wherein:

W is C$(R^2)_2$;

n is 0, 1, or 2;

$J^1$ is N and $J^2$ is $CH_2$; or $J^1$ is C and $J^2$ is CH;

$R^1$ is selected from halogen, —CN, $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —O$R^{12}$, —S$R^{12}$, —N($R^{12}$)($R^{13}$), —C(O) O$R^{12}$, —OC(O)N($R^{12}$)($R^{13}$), —N($R^{12}$)C(O)N($R^{12}$)($R^{13}$), —N($R^{12}$)C(O) O$R^{12}$, —N($R^{12}$)S$(O)_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S$(O)_2R^{12}$, —S(O)(N$R^{12}$)$R^{12}$, —S$(O)_2$N($R^{12}$)($R^{13}$), and —S(O)(N$R^{12}$)N($R^{12}$)($R^{13}$), or (1) $R^1$ and $R^2$ attached to the same carbon atom are taken together to form oxo, =N$R^{12}$, or =C$(R^{14})_2$, (2) $R^1$ and $R^2$, together with the atom(s) to which they are attached, form $C_{3-12}$ carbocycle or 3- to 12-membered heterocycle, or (3) $R^1$ and $R^3$, together with the atoms to which they are attached, form 3- to 12-membered heterocycle, wherein $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —C(O) $OR^{12}$, —OC(O)N$(R^{12})(R^{13})$, —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —C(O)C(O)N$(R^{12})(R^{13})$, —$N(R^{12})C(O)R^{12}$, —$S(O)_2R^{12}$, —S(O)$(NR^{12})R^{12}$, —$S(O)_2N(R^{12})(R^{13})$, and —S(O)$(NR^{12})$N$(R^{12})(R^{13})$, optionally wherein one or both of (1) two $R^2$ attached to the same carbon atom are taken together to form oxo, =$NR^{12}$, or =$C(R^{14})_2$ and (2) two $R^2$, together with the atom(s) to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O) $OR^{12}$, —C(O)O—($C_{1-6}$ alkyl)-$OR^{15}$, —($C_{1-6}$ alkyl)-$OR^{15}$, —$C(O)R^{12}$, —C(O)N$(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(=O)(=$NR^{12}$)$N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ —$N(R^{12})C(O)N(R^{12})(R^{13})$, —$N(R^{12})C(O)OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —C(O)C(O)N$(R^{12})(R^{13})$, —$N(R^{12})C(O)R^{12}$, —$S(O)_2R^{12}$, —S(O)$(NR^{12})R^{12}$, —$S(O)_2N(R^{12})(R^{13})$, and —S(O)$(NR^{12})$N$(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —C(O)N$(R^{12})$C(O)—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})$C(O)—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})$S(O)—, —$S(O)N(R^{12})$—, —$N(R^{12})S(O)_2N(R^{12})$—, —$N(R^{12})$ $S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)R^{12}$, —C(O) $OR^{12}$, —$P(O)(X—R^{16})(Y—R^{17})$, and —$CH_2P(O)(X—R^{16})(Y—R^{17})$;

X and Y are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —C(O) $OR^{12}$, —$OC(O)N(R^{12})(R^{13})$, —$N(R^{12})C(O)N(R^{12})(R^{13})$, —$N(R^{12})$C(O) $OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —S(O)$R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, —$S(O)(NR^{12})N(R^{12})(R^{13})$, —$P(O)(OR^{12})_2$, —P(O)$(R^{12})_2$, —$OP(O)(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O)$OR^{22}$, —OC(O)$N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —S(=O)(=$NR^{22}$)$N(R^{22})(R^{23})$, and —$OCH_2C(O)$ $OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O) $OR^{22}$, —OC(O)$N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —OC(O)$R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —S(=O)(=$NR^{22}$)$N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ------ independently indicates a single or double bond such that all valences are satisfied.

In certain aspects, the present disclosure provides a compound of Formula (III-1):

(III-1)

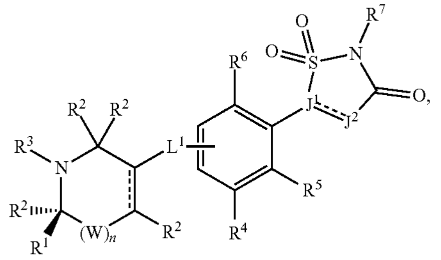

or a pharmaceutically acceptable salt or solvate thereof, wherein:

W is $C(R^2)_2$;

n is 0, 1, or 2;

$J^1$ is N and $J^2$ is $CH_2$; or $J^1$ is C and $J^2$ is CH;

$R^1$ is selected from halogen, —CN, $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —C(O) $OR^{12}$, —OC(O)$N(R^{12})(R^{13})$, —$N(R^{12})C(O)N(R^{12})(R^{13})$, —$N(R^{12})C(O)$ $OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, or (1) $R^1$ and $R^2$ attached to the same carbon atom are taken together to form oxo, =$NR^{12}$, or =$C(R^{14})_2$, (2) $R^1$ and $R^2$, together with the atom(s) to which they are attached, form $C_{3-12}$ carbocycle or 3- to 12-membered heterocycle, or (3) $R^1$ and $R^3$, together with the atoms to which they are attached, form 3- to 12-membered heterocycle, wherein $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —C(O) $OR^{12}$, —OC(O)$N(R^{12})(R^{13})$, —$N(R^{12})C(O)N(R^{12})(R^{13})$, —$N(R^{12})C(O)$ $OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —$C(O)C(O)N(R^{12})(R^{13})$, —$N(R^{12})C(O)R^{12}$, —$S(O)_2R^{12}$, —$S(O)(NR^{12})R^{12}$, —$S(O)_2N(R^{12})(R^{13})$, and —$S(O)(NR^{12})N(R^{12})(R^{13})$, optionally wherein one or both of (1) two $R^2$ attached to the same carbon atom are taken together to form oxo, =$NR^{12}$, or =$C(R^{14})_2$ and (2) two $R^2$, together with the atom(s) to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O) $OR^{12}$, —C(O)O—($C_{1-6}$ alkyl)-$OR^{15}$, —($C_{1-6}$ alkyl)-$OR^{15}$, —C(O)$R^{12}$, —C(O)N($R^{12}$)($R^{13}$), —C(O)C(O)N($R^{12}$)($R^{13}$), —S(O)$_2R^{12}$, —S(O)($NR^{12}$)$R^{12}$, —S(O)$_2$N($R^{12}$)($R^{13}$), and —S(═O)(═$NR^{12}$)N($R^{12}$)($R^{13}$), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ carbocycle, 3- to 10-membered heterocycle, —$OR^{12}$, —$OR^{15}$, —O—($C_{1-6}$ alkyl)-$OR^{15}$, —$SR^{12}$, —N($R^{12}$)($R^{13}$), —C(O) $OR^{12}$, —OC(O)N($R^{12}$)($R^{13}$), —N($R^{12}$)C(O)N($R^{12}$)($R^{13}$), —N($R^{12}$)C(O) $OR^{12}$, —N($R^{12}$)S(O)$_2R^{12}$, —C(O)$R^{12}$, —S(O)$R^{12}$, —OC(O)$R^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), and —S(O)($NR^{12}$)N($R^{12}$)($R^{13}$), wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —N($R^{12}$)—, —C($NR^{12}$)—, —N($R^{12}$)C($NR^{12}$)—, —C($NR^{12}$)N($R^{12}$)—, —N($R^{12}$)C($NR^{12}$)N($R^{12}$)—, —C(O)O—, —OC(O)O—, —OC(O)N($R^{12}$)—, —N($R^{12}$)C(O)N($R^{12}$)—, —N($R^{12}$)C(O)O—, —C(O)N($R^{12}$)C(O)—, —C(O)N($R^{12}$)C(O)N($R^{12}$)—, —N($R^{12}$)S(O)$_2$—, —C(O)—, —S(O)—, —OC(O)—, —C(O)N($R^{12}$)—, —C(O)C(O)N($R^{12}$)—, —N($R^{12}$)C(O)—, —S(O)$_2$—, —OS(O)—, —S(O)O—, —OS(O)$_2$—, —S(O)$_2$O—, —S(O)($NR^{12}$)—, —S(O)$_2$N($R^{12}$)—, —S(O)($NR^{12}$)N($R^{12}$)—, —N($R^{12}$)S(O)—, —S(O)N($R^{12}$)—, —N($R^{12}$)S(O)$_2$N($R^{12}$)—, —N($R^{12}$) S(O)N($R^{12}$)—, —P(O)($OR^{12}$)—, and —P(O)($R^{12}$)—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three substituents independently selected from —N($R^{22}$)C(O)CH($R^{20}$)N($R^{22}$)$_2$, —C(O)CH($R^{20}$)N($R^{22}$)$_2$, and $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —C(O)$R^{12}$, —C(O) $OR^{12}$, —P(O)(X—$R^{16}$)(Y—$R^{17}$), and —$CH_2$P(O)(X—$R^{16}$)(Y—$R^{17}$);

X and Y are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —N($R^{12}$)($R^{13}$), —C(O) $OR^{12}$, —OC(O)N($R^{12}$)($R^{13}$), —N($R^{12}$)C(O)N($R^{12}$)($R^{13}$), —N($R^{12}$)C(O) $OR^{12}$, —N($R^{12}$)S(O)$_2R^{12}$, —N($R^{12}$)S(O)$_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)$OR^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), —P(O)($OR^{12}$)$_2$, —P(O)($R^{12}$)$_2$, —OP(O)($OR^{12}$)$_2$, ═O, ═S, and ═$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), ═$NR^{22}$, ═C($R^{21}$)$_2$, —C(O) $OR^{22}$, —OC(O)N($R^{22}$)($R^{23}$), —N($R^{22}$)C(O)N($R^{22}$)($R^{23}$), —N($R^{22}$)C(O) $OR^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)($NR^{22}$)$R^{22}$, —S(O)$_2$N($R^{22}$)($R^{23}$)—, —S(═O)(═$NR^{22}$)N($R^{22}$)($R^{23}$), and —$OCH_2$C(O) $OR^{22}$, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —OC(O) $R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})$ $(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ------ independently indicates a single or double bond such that all valences are satisfied.

In certain aspects, the present disclosure provides a compound of Formula (IV-1):

(IV-1)

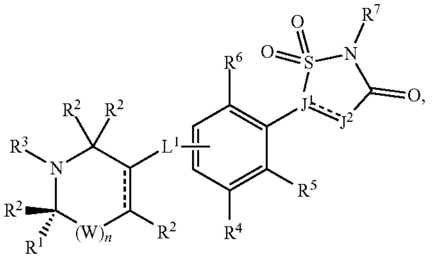

or a pharmaceutically acceptable salt or solvate thereof, wherein:

W is $C(R^2)_2$;

n is 0, 1, or 2;

$J^1$ is N and $J^2$ is $CH_2$; or $J^1$ is C and $J^2$ is CH;

$R^1$ is selected from halogen, —CN, $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —C(O) $OR^{12}$, —OC (O)$N(R^{12})(R^{13})$, —$N(R^{12})C(O)N(R^{12})(R^{13})$, —$N(R^{12})$ C(O) $OR^{12}$, —$N(R^{12})S(O)_2R^{12}$, —$C(O)R^{12}$, —S(O) $R^{12}$, —$OC(O)R^{12}$, —$C(O)N(R^{12})(R^{13})$, —C(O)C(O)N $(R^{12})(R^{13})$, —$N(R^{12})C(O)R^{12}$, —$S(O)_2R^{12}$, —S(O) $(NR^{12})R^{12}$, —$S(O)_2N(R^{12})(R^{13})$, and —$S(O)(NR^{12})N$ $(R^{12})(R^{13})$, or (1) $R^1$ and $R^2$ attached to the same carbon atom are taken together to form oxo, =$NR^{12}$, or =$C(R^{14})_2$, (2) $R^1$ and $R^2$, together with the atom(s) to which they are attached, form $C_{3-12}$ carbocycle or 3- to 12-membered heterocycle, or (3) $R^1$ and $R^3$, together with the atoms to which they are attached, form 3- to 12-membered heterocycle, wherein $C_{2-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^2$ is independently selected at each occurrence from hydrogen, halogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$SR^{12}$, —$N(R^{12})(R^{13})$, —C(O) $OR^{12}$, —OC(O)N $(R^{12})(R^{13})$, —$N(R^{12})C(O)N(R^{12})(R^{13})$, —$N(R^{12})C(O)$ $OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —C(O)C(O)N $(R^{12})(R^{13})$, —$N(R^{12})C(O)R^{12}$, —$S(O)_2R^{12}$, —S(O) $(NR^{12})R^{12}$, —$S(O)_2N(R^{12})(R^{13})$, and —$S(O)(NR^{12})N$ $(R^{12})(R^{13})$, optionally wherein one or both of (1) two $R^2$ attached to the same carbon atom are taken together to form oxo, =$NR^{12}$, or =$C(R^{14})_2$ and (2) two $R^2$, together with the atom(s) to which they are attached, form $C_{3-12}$ carbocycle or 3- to 12-membered heterocycle, wherein $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$;

$R^3$ and $R^7$ are independently selected from hydrogen, —CN, $C_{1-6}$ alkyl, $C_{2-6}$ alkenyl, $C_{2-6}$ alkynyl, 2- to 6-membered heteroalkyl, 3- to 6-membered heteroalkenyl, 3- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), (5-methyl-2-oxo-1,3-dioxol-4-yl)methyl, —C(O) $OR^{12}$, —C(O)O—($C_{1-6}$ alkyl)-$OR^{15}$, —($C_{1-6}$ alkyl)-$OR^{15}$, —$C(O)R^{12}$, —C(O) $N(R^{12})(R^{13})$, —$C(O)C(O)N(R^{12})(R^{13})$, —$S(O)_2R^{12}$, —$S(O)(NR^{12})R^{12}$, —$S(O)_2N(R^{12})(R^{13})$, and —S(=O) $(=NR^{12})N(R^{12})(R^{13})$, wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^4$, $R^5$, and $R^6$ are independently selected from hydrogen, halogen, —CN, $C_{1-6}$ alkyl, $C_{2-6}$ alkenyl, $C_{2-6}$ alkynyl, $C_{3-10}$ —$N(R^{12})C(O)N(R^{12})(R^{13})$, —$N(R^{12})C(O)$ $OR^{12}$, —$N(R^{12})S(O)_2R^{12}$, —$C(O)R^{12}$, —$S(O)R^{12}$, —$OC(O)R^{12}$, —$C(O)N(R^{12})(R^{13})$, —C(O)C(O)N $(R^{12})(R^{13})$, —$N(R^{12})C(O)R^{12}$, —$S(O)_2R^{12}$, —S(O)$(NR^{12})R^{12}$, —$S(O)_2N(R^{12})(R^{13})$, and —$S(O)(NR^{12})N(R^{12})(R^{13})$, wherein $C_{1-6}$ alkyl, $C_{2-6}$ alkenyl, $C_{2-6}$ alkynyl, $C_{3-10}$ carbocycle, and 3- to 10-membered heterocycle are optionally substituted with one, two, or three $R^{20}$;

$L^1$ is absent or selected from $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —S—, —$N(R^{12})$—, —$C(NR^{12})$—, —$N(R^{12})C(NR^{12})$—, —$C(NR^{12})N(R^{12})$—, —$N(R^{12})C(NR^{12})N(R^{12})$—, —C(O)O—, —OC(O)O—, —$OC(O)N(R^{12})$—, —$N(R^{12})C(O)N(R^{12})$—, —$N(R^{12})C(O)O$—, —C(O)$N(R^{12})C(O)$—, —$C(O)N(R^{12})C(O)N(R^{12})$—, —$N(R^{12})S(O)_2$—, —C(O)—, —S(O)—, —OC(O)—, —$C(O)N(R^{12})$—, —$C(O)C(O)N(R^{12})$—, —$N(R^{12})C(O)$—, —$S(O)_2$—, —OS(O)—, —S(O)O—, —$OS(O)_2$—, —$S(O)_2O$—, —$S(O)(NR^{12})$—, —$S(O)_2N(R^{12})$—, —$S(O)(NR^{12})N(R^{12})$—, —$N(R^{12})S(O)$—, —$S(O)N(R^{12})$—, —$N(R^{12})S(O)_2N(R^{12})$—, —$N(R^{12})$ $S(O)N(R^{12})$—, —$P(O)(OR^{12})$—, and —$P(O)(R^{12})$—, wherein $C_{1-6}$ alkylene, $C_{2-6}$ alkenylene, $C_{2-6}$ alkynylene, 2- to 6-membered heteroalkylene, 3- to 6-membered heteroalkenylene, 3- to 6-membered heteroalkynylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three substituents independently selected from —$N(R^{22})C(O)CH(R^{20})N(R^{22})_2$, —$C(O)CH(R^{20})N(R^{22})_2$, and $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{14}$ is independently selected at each occurrence from hydrogen, halogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), or two $R^{14}$ are taken together with the carbon atom to which they are attached to form $C_{3-12}$ carbocycle or 3- to 12-membered heterocycle, wherein $C_{1-6}$ alkyl, $C_{2-6}$ alkenyl, $C_{2-6}$ alkynyl, —$C_{0-6}$ alkyl-($C_{3-12}$ carbocycle), —$C_{0-6}$ alkyl-(3- to 12-membered heterocycle), $C_{3-12}$ carbocycle, and 3- to 12-membered heterocycle are optionally substituted with one, two, or three $R^{20}$;

$R^{15}$ is independently selected at each occurrence from (5-methyl-2-oxo-1,3-dioxol-4-yl)methyl, —$C(O)R^{12}$, —C(O) $OR^{12}$, —$P(O)(X—R^{16})(Y—R^{17})$, and —$CH_2P(O)(X—R^{16})(Y—R^{17})$;

X and Y are independently selected at each occurrence from —O— and —$N(R^{12})$—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —$N(R^{12})(R^{13})$, —C(O) $OR^{12}$, —$OC(O)N(R^{12})(R^{13})$, —$N(R^{12})C(O)N(R^{12})(R^{13})$, —$N(R^{12})C(O)$ $OR^{12}$, —$N(R^{12})S(O)_2R^{12}$, —$N(R^{12})S(O)_2N(R^{12})(R^{13})$, —S—S—$R^{12}$, —S—$C(O)R^{12}$, —$C(O)R^{12}$, —$S(O)R^{12}$, —$OC(O)R^{12}$, —$OC(O)OR^{12}$, —$C(O)N(R^{12})(R^{13})$, —$C(O)C(O)N(R^{12})(R^{13})$, —$N(R^{12})C(O)R^{12}$, —$S(O)_2R^{12}$, —S(O)$(NR^{12})R^{12}$, —$S(O)_2N(R^{12})(R^{13})$, —$S(O)(NR^{12})N(R^{12})(R^{13})$, —$P(O)(OR^{12})_2$, —$P(O)(R^{12})_2$, —$OP(O)(OR^{12})_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —S(=O)(=$NR^{22})N(R^{22})(R^{23})$, and —$OCH_2C(O)$ $OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —OC(O)$R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —S(=O)(=$NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and each ------ independently indicates a single or double bond such that all valences are satisfied.

In some embodiments, the compound of Formula (III) is provided in at least 98% enantiomeric excess. In some embodiments, the compound of Formula (III) is provided in at least 80% enantiomeric excess, such as at least 85%, at least 90%, at least 95%, at least 96%, at least 97%, at least 98%, at least 99%, or at least 99.9% enantiomeric excess. In some embodiments, the compound of Formula (III-1) is provided in at least 98% enantiomeric excess. In some embodiments, the compound of Formula (III-1) is provided in at least 80% enantiomeric excess, such as at least 85%, at least 90%, at least 95%, at least 96%, at least 97%, at least 98%, at least 99%, or at least 99.9% enantiomeric excess. In some embodiments, the compound of Formula (IV) is provided in at least 98% enantiomeric excess. In some embodiments, the compound of Formula (IV) is provided in at least 80% enantiomeric excess, such as at least 85%, at least 90%, at least 95%, at least 96%, at least 97%, at least 98%, at least 99%, or at least 99.9% enantiomeric excess. In some embodiments, the compound of Formula (IV-1) is provided in at least 98% enantiomeric excess. In some embodiments, the compound of Formula (IV-1) is provided in at least 80% enantiomeric excess, such as at least 85%, at least 90%, at least 95%, at least 96%, at least 97%, at least 98%, at least 99%, or at least 99.9% enantiomeric excess.

In some embodiments, for a compound of Formula (III), (III-1), (IV), or (IV-1), $R^1$ is selected from halogen, —CN, $C_{2-6}$ alkyl, $C_{2-6}$ alkenyl, 2- to 6-membered heteroalkyl, 3- to 6-membered heteroalkenyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —$N(R^{12})(R^{13})$, —C(O) $OR^{12}$, —$OC(O)R^{12}$, —$C(O)N(R^{12})(R^{13})$, and —$N(R^{12})C(O)R^{12}$, wherein $C_{2-6}$ alkyl, $C_{2-6}$ alkenyl, 2- to 6-membered heteroalkyl, 3- to 6-membered heteroalkenyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$. In some embodiments, $R^1$ is selected from halogen, —CN, $C_{2-6}$ alkyl, 2- to 6-membered heteroalkyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, and —$N(R^{12})(R^{13})$, wherein $C_{2-6}$ alkyl, 2- to 6-membered heteroalkyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), and -(2- to 6-membered heteroalkyl)-(3- to 12-membered heterocycle) are optionally substituted with one, two, or three $R^{20}$. In some embodiments, $R^1$ is selected from $C_{2-6}$ alkyl and —$C_{0-6}$ alkyl-($C_{3-12}$ carbocycle), each of which is optionally substituted with one, two, or three $R^{20}$. In some embodiments, $R^1$ is selected from $C_{2-6}$ alkyl and —$C_{0-6}$ alkyl-($C_{3-12}$ carbocycle), each of which is optionally substituted with one, two, or three substituents independently selected from —CN and $C_{1-6}$ alkyl.

In some embodiments, for a compound of Formula (III), (III-1), (IV), or (IV-1), $R^1$ is —$C_{2-6}$ alkyl-CN, such as —$CH_2CH_2CN$ or —$CH_2CH_2CH_2CN$. In some embodiments, $R^1$ is —$C_{0-6}$ alkyl-($C_{3-12}$ carbocycle) optionally substituted with one, two, or three $R^{20}$, such as $R^1$ is cyclopropyl, methylcyclopropan-1-yl, 2-methylcyclopropan-1-yl, 2,2-dimethylcyclopropan-1-yl, cyclopropylmethyl, (1-methylcyclopropyl)methyl, (2-methylcyclopropyl)methyl, (2,2-dimethylcyclopropyl)methyl, cyclopropylethyl, 2-(1-methylcyclopropyl) ethan-1-yl, 2-(2-methylcyclopropyl) ethan-1-yl, 2-(2,2-dimethylcyclopropyl) ethan-1-yl, cyclobutyl, methylcyclobutan-1-yl, 2-methylcyclobutan-1-yl, 2,2-dimethylcyclobutan-1-yl, cyclobutylmethyl, (1-methylcyclobutyl)methyl, (2-methylcyclobutyl)methyl, (2,2-dimethylcyclobutyl)methyl, cyclobutylethyl, 2-(1-methylcyclobutyl) ethan-1-yl, 2-(2-methylcyclobutyl) ethan-1-yl, 2-(2,2-dimethylcyclobutyl) ethan-1-yl, cyclopentyl, methylcyclopentan-1-yl, 2-methylcyclopentan-1-yl, 2,2-dimethylcyclopentan-1-yl, cyclopentylmethyl, (1-methylcyclopentyl)methyl, (2-methylcyclopentyl)methyl, (2,2-dimethylcyclopentyl)methyl, cyclopentylethyl, 2-(1-methylcyclopentyl) ethan-1-yl, 2-(2-methylcyclopentyl) ethan-1-yl, or 2-(2,2-dimethylcyclopentyl) ethan-1-yl. In some embodiments, $R^1$ is cyclobutylethyl. In some embodiments, $R^1$ is selected from cyclopropyl, methylcyclopropan-1-yl, 2-methylcyclopropan-1-yl, 2,2-dimethylcyclopropan-1-yl, cyclopropylmethyl, (1-methylcyclopropyl)methyl, (2-methylcyclopropyl)methyl, (2,2-dimethylcyclopropyl)methyl, cyclopropylethyl, 2-(1-methylcyclopropyl) ethan-1-yl, 2-(2-methylcyclopropyl) ethan-1-yl, and 2-(2,2-dimethylcyclopropyl) ethan-1-yl. In some embodiments, $R^1$ is cyclopropylethyl. In some embodiments, $R^1$ is selected from cyclobutyl, methylcyclobutan-1-yl, 2-methylcyclobutan-1-yl, 2,2-dimethylcyclobutan-1-yl, cyclobutylmethyl, (1-methylcyclobutyl)methyl, (2-methylcyclobutyl)methyl, (2,2-dimethylcyclobutyl)methyl, cyclobutylethyl, 2-(1-methylcyclobutyl) ethan-1-yl, 2-(2-methylcyclobutyl) ethan-1-yl, and 2-(2,2-dimethylcyclobutyl) ethan-1-yl. In some embodiments, $R^1$ is selected from cyclopentyl, methylcyclopentan-1-yl, 2-methylcyclopentan-1-yl, 2,2-dimethylcyclopentan-1-yl, cyclopentylmethyl, (1-methylcyclopentyl)methyl, (2-methylcyclopentyl)methyl, (2,2-dimethylcyclopentyl)methyl, cyclopentylethyl, 2-(1-methylcyclopentyl) ethan-1-yl, 2-(2-methylcyclopentyl) ethan-1-yl, and 2-(2,2-dimethylcyclopentyl) ethan-1-yl.

In some embodiments, for a compound of Formula (III), (III-1), (IV), or (IV-1), $R^1$ is selected from halogen, $C_{2-6}$ alkyl, $C_{2-6}$ alkenyl, 2- to 6-membered heteroalkyl, —$C_{0-6}$ alkyl-($C_{3-12}$ carbocycle), and —$C_{0-6}$ alkyl-(3- to 12-membered heterocycle), or $R^1$ and $R^2$ attached to the same carbon atom are taken together to form oxo, =$NR^{12}$, or =$C(R^{14})_2$, or $R^1$ and $R^3$, together with the atoms to which they are attached, form 3- to 12-membered heterocycle, wherein $C_{2-6}$ alkyl, $C_{2-6}$ alkenyl, 2- to 6-membered heteroalkyl, —$C_{0-6}$ alkyl-($C_{3-12}$ carbocycle), —$C_{0-6}$ alkyl-(3- to 12-membered heterocycle), and 3- to 12-membered heterocycle are optionally substituted with one, two, or three $R^{20}$. In some embodiments, $R^1$ is selected from $C_{2-6}$ alkyl and —$C_{0-6}$ alkyl-($C_{3-8}$ carbocycle), each of which is optionally substituted with one, two, or three $R^{20}$. In some embodiments, $R^1$ is selected from $C_{2-6}$ alkyl and —$C_{0-3}$ alkyl-($C_{3-6}$ carbocycle). In some embodiments, $R^1$ is —$CH_2CH_2CH(CH_3)_2$.

In some embodiments, for a compound of Formula (III), (III-1), (IV), or (IV-1), $R^1$ is selected from

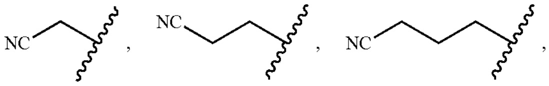,
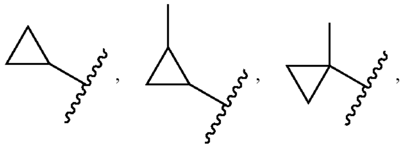,
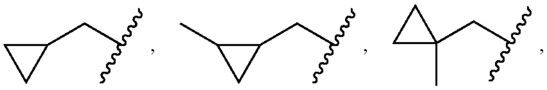,
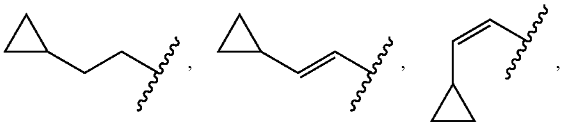,
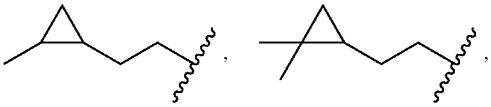,
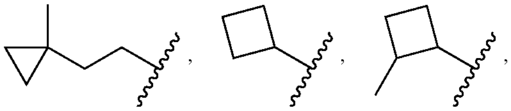,
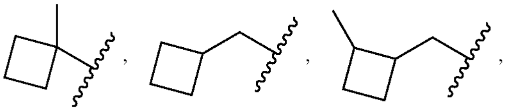,
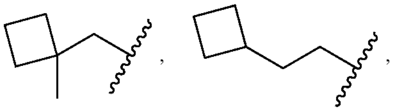,
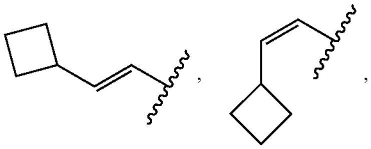,
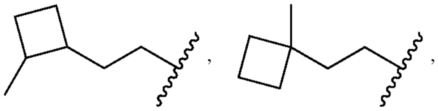,
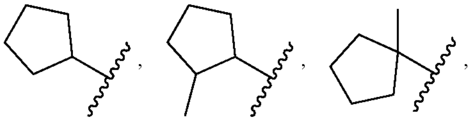,
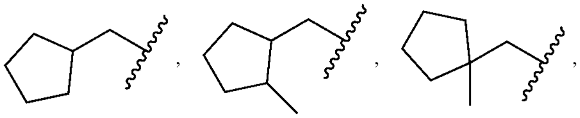,
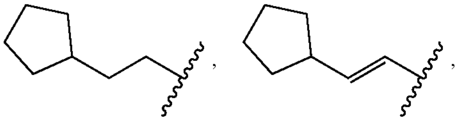,
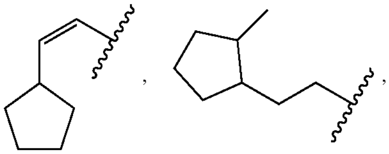, and
-continued
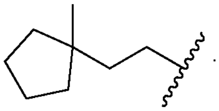.
In some embodiments, $R^1$ is selected from
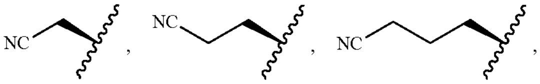,
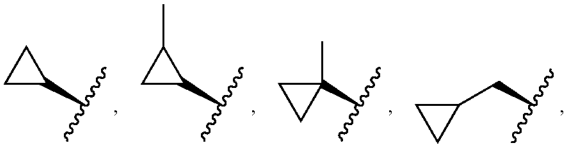,
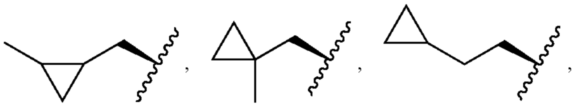,
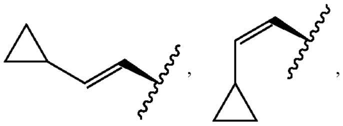,
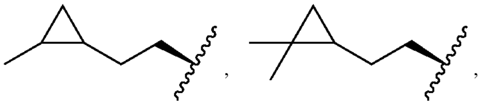,
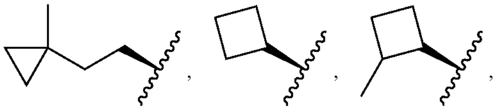,
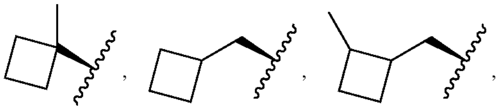,
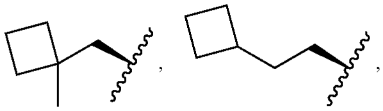,
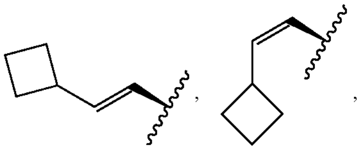,
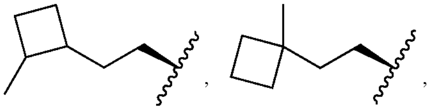,
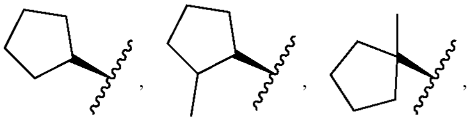,
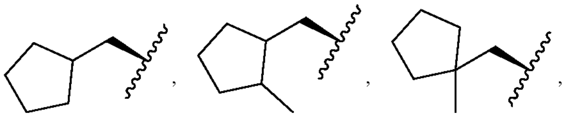, -continued
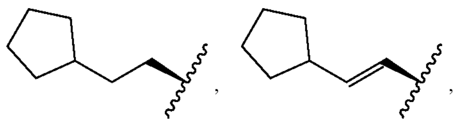
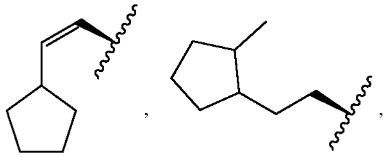
and
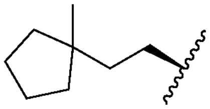
In some embodiments, $R^1$ is selected from
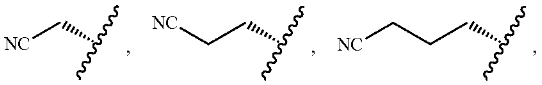
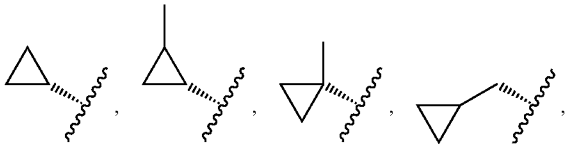
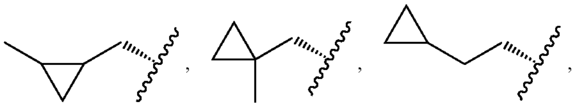
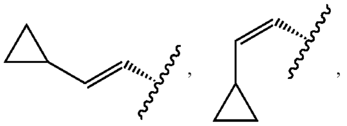
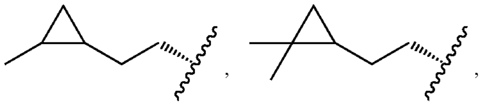
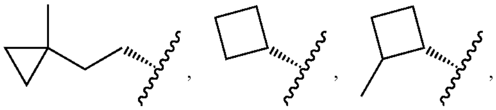
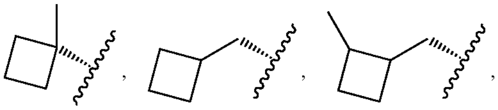
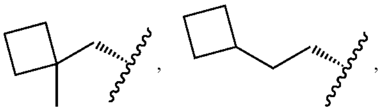
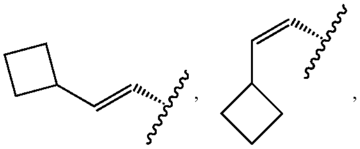
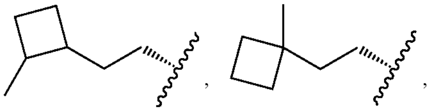
-continued
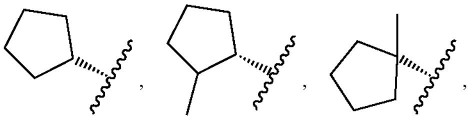
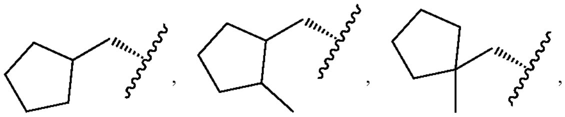
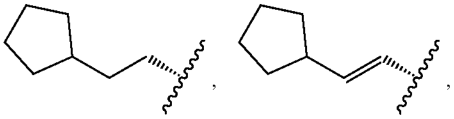
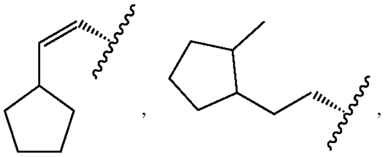
and
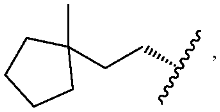
In some embodiments, $R^1$ is
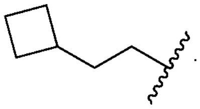 [SMILES: *CCC1CCC1]
In some embodiments, $R^1$ is
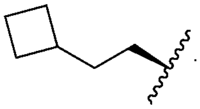
In some embodiments, $R^1$ is
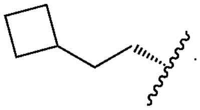
In some embodiments, $R^1$ is
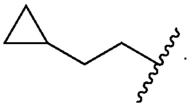 [SMILES: *CCC1CC1]

In some embodiments, $R^1$ is

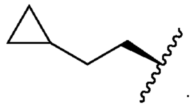

In some embodiments, $R^1$ is

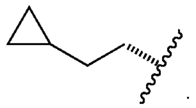

In some embodiments, $R^1$ is

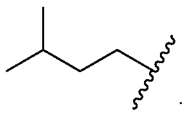 [SMILES: *CCC(C)C]

In some embodiments, $R^1$ is

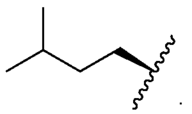

In some embodiments, $R^1$ is

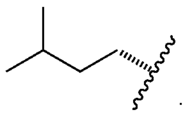

In some embodiments, for a compound of Formula (III), (III-1), (IV), or (IV-1), $R^1$ and $R^2$ attached to the same carbon atom are taken together to form oxo, $=NR^{12}$, or $=C(R^{14})_2$, such as =NH, =NCN, $=CH_2$, =CHF, or $=CF_2$. In some embodiments, $R^1$ and $R^2$, together with the atom(s) to which they are attached, form $C_{3-12}$ carbocycle or 3- to 12-membered heterocycle, each of which is optionally substituted with one, two, or three $R^{20}$. In some embodiments, $R^1$ and a vicinal $R^2$, together with the carbon atoms to which they are attached, form $C_{3-12}$ carbocycle or 3- to 12-membered heterocycle, each of which is optionally substituted with one, two, or three $R^{20}$. In some embodiments, $R^1$ and $R^3$, together with the atoms to which they are attached, form 3- to 12-membered heterocycle optionally substituted with one, two, or three $R^{20}$.

In some embodiments, for a compound of Formula (I), (I-1), (II), (II-1), (II-a), (II-a1), (III), (III-1), (IV), or (IV-1), $R^4$, $R^5$, and $R^6$ are independently selected from hydrogen, halogen, $C_{1-3}$ alkyl, $—OR^{12}$, $—OR^{15}$, and $—O—(C_{1-6}$ alkyl)-$OR^{15}$, wherein $C_{1-3}$ alkyl is optionally substituted with one, two, or three $R^{20}$. In some embodiments, $R^4$, $R^5$, and $R^6$ are independently selected from hydrogen, halogen, $C_{1-6}$ alkyl, $C_{3-6}$ carbocycle, 3- to 6-membered heterocycle, $—OR^{12}$, and $—N(R^{12})(R^{13})$, wherein $C_{1-6}$ alkyl, $C_{3-6}$ carbocycle, and 3- to 6-membered heterocycle are optionally substituted with one, two, or three $R^{20}$. In some embodiments, $R^4$, $R^5$, and $R^6$ are independently selected from hydrogen, halogen, $—OR^{12}$, $—OR^{15}$, and $—O—(C_{1-6}$ alkyl)-$OR^{15}$. In some embodiments, $R^4$, $R^5$, and $R^6$ are independently selected from hydrogen, —Cl, —F, and —OH. In some embodiments, $R^4$, $R^5$, and $R^6$ are independently selected from hydrogen, —F, and —OH.

In some embodiments, for a compound of Formula (I), (I-1), (II), (II-1), (II-a), (II-a1), (III), (III-1), (IV), or (IV-1), $R^4$ is selected from hydrogen, halogen, $C_{1-3}$ alkyl, $—OR^{12}$, $—OR^{15}$, and $—O—(C_{1-6}$ alkyl)-$OR^{15}$, wherein $C_{1-3}$ alkyl is optionally substituted with one, two, or three $R^{20}$. In some embodiments, $R^4$ is selected from hydrogen, halogen, $C_{1-6}$ alkyl, $C_{3-6}$ carbocycle, 3- to 6-membered heterocycle, $—OR^{12}$, and $—N(R^{12})(R^{13})$, wherein $C_{1-6}$ alkyl, $C_{3-6}$ carbocycle, and 3- to 6-membered heterocycle are optionally substituted with one, two, or three $R^{20}$. In some embodiments, $R^4$ is selected from hydrogen, halogen, and —OH. In some embodiments, $R^4$ is hydrogen.

In some embodiments, for a compound of Formula (I), (I-1), (II), (II-1), (II-a), (II-a1), (III), (III-1), (IV), or (IV-1), $R^5$ is selected from hydrogen, halogen, $C_{1-3}$ alkyl, $—OR^{12}$, $—OR^{15}$, and $—O—(C_{1-6}$ alkyl)-$OR^{15}$, wherein $C_{1-3}$ alkyl is optionally substituted with one, two, or three $R^{20}$. In some embodiments, $R^5$ is selected from hydrogen, halogen, $C_{1-6}$ alkyl, $C_{3-6}$ carbocycle, 3- to 6-membered heterocycle, $—OR^{12}$, and $—N(R^{12})(R^{13})$, wherein $C_{1-6}$ alkyl, $C_{3-6}$ carbocycle, and 3- to 6-membered heterocycle are optionally substituted with one, two, or three $R^{20}$. In some embodiments, $R^5$ is selected from halogen, $—OR^{12}$, $—OR^{15}$, $—O—(C_{1-6}$ alkyl)-$OR^{15}$, and $C_{1-6}$ alkyl, wherein $C_{1-6}$ alkyl is optionally substituted with one, two, or three $R^{20}$. In some embodiments, $R^5$ is —OH.

In some embodiments, for a compound of Formula (I), (I-1), (II), (II-1), (II-a), (II-a1), (III), (III-1), (IV), or (IV-1), $R^5$ is selected from $—OR^{15}$, $—O—(C_{1-6}$ alkyl)-$OR^{15}$, and $—OC(O)N(R^{12})(R^{13})$. In some embodiments, $R^5$ is selected from $—OR^{15}$, $—O—(C_{1-6}$ alkyl)-$OR^{15}$, and $—OC(O)N(R^{12})(R^{13})$, and $R^{15}$ is selected from $—C(O)R^{12}$, $—C(O)OR^{12}$, $—P(O)(X—R^{16})(Y—R^{17})$, and $—CH_2P(O)(X—R^{16})(Y—R^{17})$. In some embodiments, $R^5$ is selected from $—OR^{15}$, $—O—(C_{1-6}$ alkyl)-$OR^{15}$, and $—OC(O)N(R^{12})(R^{13})$; $R^{15}$ is selected from $—C(O)R^{12}$, $—C(O)OR^{12}$, $—P(O)(X—R^{16})(Y—R^{17})$, and $—CH_2P(O)(X—R^{16})(Y—R^{17})$; and $R^{12}$ is $C_{1-6}$ alkyl optionally substituted with one, two, or three $R^{20}$. In some embodiments, $R^5$ is selected from $—OR^{15}$, $—O—(C_{1-6}$ alkyl)-$OR^{15}$, and $—OC(O)N(R^{12})(R^{13})$; $R^{15}$ is selected from $—C(O)R^{12}$, $—C(O)OR^{12}$, $—P(O)(X—R^{16})(Y—R^{17})$, and $—CH_2P(O)(X—R^{16})(Y—R^{17})$; and $R^{12}$ is $C_{1-6}$ alkyl. In some embodiments, $R^5$ is selected from $—OP(O)(OH)_2$, $—OCH_2OP(O)(OH)_2$, $—OC(O)N(R^{12})(R^{13})$, $—OCH(R^{20})OC(O)OR^{12}$, $—OC(O)CH(R^{20})NH_2$, $—OCH(R^{20})OC(O)R^{12}$, $—OC(O)R^{12}$, and $—OC(O)OR^{12}$. In some embodiments, $R^5$ is selected from $—OP(O)(OH)_2$, $—OCH_2OP(O)(OH)_2$, $—OC(O)N(R^{12})(R^{13})$, $—OCH(R^{20})OC(O)OR^{12}$, $—OC(O)CH(R^{20})NH_2$, $—OCH(R^{20})OC(O)R^{12}$, $—OC(O)R^{12}$, and $—OC(O)OR^{12}$; $R^{12}$ is $C_{1-6}$ alkyl optionally substituted with one, two, or three $R^{20}$; and $R^{13}$ is selected from hydrogen and $C_{1-6}$ alkyl, wherein $C_{1-6}$ alkyl is optionally substituted with one, two, or three $R^{20}$. In some embodiments, $R^5$ is selected from $—OP(O)(OH)_2$, $—OCH_2OP(O)(OH)_2$, $—OC(O)N(R^{12})(R^{13})$, $—OCH(R^{20})OC(O)OR^{12}$, $—OC(O)CH(R^{20})NH_2$, $—OCH(R^{20})OC(O)R^{12}$, $—OC(O)R^{12}$, and $—OC(O)OR^{12}$; $R^{12}$ is $C_{1-6}$ alkyl; and $R^{13}$ is selected from hydrogen and $C_{1-6}$ alkyl. In some embodiments, $R^5$ is selected from $—OP(O)(OH)_2$, —$OCH_2OP(O)(OH)_2$, —$OC(O)N(R^{12})(R^{13})$, —$OCH_2OC(O)\ OR^{12}$, —$OCH(CH_3)OC(O)OR^{12}$, —$OC(O)CH_2NH_2$, —$OC(O)CH(CH_3)\ NH_2$, —$OCH_2OC(O)R^{12}$, —$OCH(CH_3)OC(O)R^{12}$, —$OC(O)R^{12}$, and —$OC(O)OR^{12}$. In some embodiments, $R^5$ is selected from —$OP(O)(OH)_2$, —$OCH_2OP(O)(OH)_2$, —$OC(O)N(R^{12})(R^{13})$, —$OCH_2OC(O)\ OR^{12}$, —$OCH(CH_3)OC(O)OR^{12}$, —$OC(O)CH_2NH_2$, —$OC(O)CH(CH_3)\ NH_2$, —$OCH_2OC(O)R^{12}$, —$OCH(CH_3)OC(O)R^{12}$, —$OC(O)R^{12}$, and —$OC(O)OR^{12}$; $R^{12}$ is $C_{1-6}$ alkyl optionally substituted with one, two, or three $R^{20}$, and $R^{13}$ is selected from hydrogen and $C_{1-6}$ alkyl, wherein $C_{1-6}$ alkyl is optionally substituted with one, two, or three $R^{20}$. In some embodiments, $R^5$ is selected from —$OP(O)(OH)_2$, —$OCH_2OP(O)(OH)_2$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)\ NH_2$, —$OCH_2OC(O)R^{12}$, —$OCH(CH_3)OC(O)R^{12}$, —$OC(O)R^{12}$, and —$OC(O)OR^{12}$; $R^{12}$ is $C_{1-6}$ alkyl; and $R^{13}$ is selected from hydrogen and $C_{1-6}$ alkyl. In some embodiments, $R^5$ is selected from —$OP(O)(OH)_2$, —$OCH_2OP(O)(OH)_2$, —$OCH_2OC(O)OR^{12}$, —$OCH(CH_3)OC(O)OR^{12}$, —$OCH_2OC(O)R^{12}$, —$OCH(CH_3)OC(O)R^{12}$, —$OC(O)R^{12}$, and —$OC(O)OR^{12}$; and $R^{12}$ is $C_{1-6}$ alkyl. In some embodiments, $R^5$ is selected from —$OC(O)N(CH_3)_2$, —$OC(O)N(CH_3)(CH_2CH_2OCH_3)$, —$OC(O)NHCH_2CH_3$, —OC(O)(pyrrolidine-1-yl), —$OC(O)CH(CH_3)OC(O)CH_3$, —$OC(O)CH(CH_3)OC(O)CH(CH_3)_2$, —$OC(O)CH(CH_3)_2$, methyleneoxy (4-methyl-1,3-dioxol-2-one), —$OCH_2OC(O)CH_2CH_2CH_3$, —$OCH_2OP(O)(OCH_2OC(O)OCH(CH_3)_2)_2$, —$OC(O)CH(NH_2)CH(CH_3)_2$, and —$OCH_2OP(O)(OH)_2$. In some embodiments, $R^5$ is selected from —$OR^{15}$ and —O—($C_{1-6}$ alkyl)-$OR^{15}$. In some embodiments, $R^5$ is selected from —$OR^{15}$ and —O—($C_{1-6}$ alkyl)-$OR^{15}$, wherein $R^{15}$ is selected from —$C(O)R^{12}$, —$P(O)(X—R^{16})(Y—R^{17})$, and —$CH_2P(O)(X—R^{16})(Y—R^{17})$.

In some embodiments, for a compound of Formula (I), (I-1), (II), (II-1), (II-a), (II-a1), (III), (III-1), (IV), or (IV-1), $R^6$ is selected from hydrogen, halogen, $C_{1-3}$ alkyl, —$OR^{12}$, —$OR^{15}$, and —O—($C_{1-6}$ alkyl)-$OR^{15}$, wherein $C_{1-3}$ alkyl is optionally substituted with one, two, or three $R^{20}$. In some embodiments, $R^6$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$. In some embodiments, $R^6$ is selected from halogen, —$OR^{12}$, and $C_{1-6}$ alkyl, wherein $C_{1-6}$ alkyl is optionally substituted with one, two, or three $R^{20}$. In some embodiments, $R^6$ is halogen, such as fluorine or chlorine. In some embodiments, $R^6$ is fluorine. In some embodiments, $R^6$ is chlorine.

In some embodiments, for a compound of Formula (I), (I-1), (II), (II-1), (II-a), (II-a1), (III), (III-1), (IV), or (IV-1), $R^4$ is selected from hydrogen, halogen, and —OH; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, $R^4$ is hydrogen; $R^5$ is selected from —$OR^{15}$ and —O—($C_{1-6}$ alkyl)-$OR^{15}$; and $R^6$ is halogen. In some embodiments, $R^4$ is hydrogen; $R^5$ is selected from —$OR^{15}$ and —O—($C_{1-6}$ alkyl)-$OR^{15}$, and $R^6$ is fluorine. In some embodiments, $R^4$ is hydrogen, $R^5$ is —OH, and $R^6$ is halogen. In some embodiments, $R^4$ is hydrogen, $R^5$ is —OH, and $R^6$ is fluorine.

In some embodiments, for a compound of Formula (I), (I-1), (II), (II-1), (II-a), (II-a1), (III), (III-1), (IV), or (IV-1), $R^7$ is selected from hydrogen, $C_{1-6}$ alkyl, 2- to 6-membered heteroalkyl, (5-methyl-2-oxo-1,3-dioxol-4-yl)methyl, —$C(O)\ OR^{12}$, —C(O)O—($C_{1-6}$ alkyl)-$OR^{15}$, and —($C_{1-6}$ alkyl)-$OR^{15}$, wherein $C_{1-6}$ alkyl and 2- to 6-membered heteroalkyl are optionally substituted with one, two, or three $R^{20}$. In some embodiments, $R^7$ is selected from hydrogen and —($C_{1-6}$ alkyl)-$OR^{15}$. In some embodiments, $R^7$ is hydrogen.

In some embodiments, for a compound of Formula (I), (I-1), (II), (II-1), (II-a), (II-a1), (III), (III-1), (IV), or (IV-1), $R^7$ is —($C_{1-6}$ alkyl)-$OR^{15}$. In some embodiments, $R^7$ is selected from —$CH(R^{20})OC(O)R^{12}$, —$P(O)(X—R^{16})(Y—R^{17})$, and —$CH_2P(O)(X—R^{16})(Y—R^{17})$. In some embodiments, $R^7$ is selected from —$CH(R^{20})OC(O)R^{12}$, —$P(O)(X—R^{16})(Y—R^{17})$, and —$CH_2P(O)(X—R^{16})(Y—R^{17})$; and $R^{12}$ is $C_{1-6}$ alkyl optionally substituted with one, two, or three $R^{20}$. In some embodiments, $R^7$ is selected from —$CH(R^{20})OC(O)R^{12}$, —$P(O)(X—R^{16})(Y—R^{17})$, and —$CH_2P(O)(X—R^{16})(Y—R^{17})$; and $R^{12}$ is $C_{1-6}$ alkyl. In some embodiments, $R^7$ is selected from —$CH_2OC(O)R^{12}$, —$CH(CH_3)OC(O)R^{12}$, —$P(O)(X—R^{16})(Y—R^{17})$, and —$CH_2P(O)(X—R^{16})(Y—R^{17})$. In some embodiments, $R^7$ is selected from —$CH_2OC(O)R^{12}$, —$CH(CH_3)OC(O)R^{12}$, —$P(O)(X—R^{16})(Y—R^{17})$, and —$CH_2P(O)(X—R^{16})(Y—R^{17})$; and $R^{12}$ is $C_{1-6}$ alkyl optionally substituted with one, two, or three $R^{20}$. In some embodiments, $R^7$ is selected from —$CH_2OC(O)R^{12}$, —$CH(CH_3)OC(O)R^{12}$, —$P(O)(X—R^{16})(Y—R^{17})$, and —$CH_2P(O)(X—R^{16})(Y—R^{17})$; and $R^{12}$ is $C_{1-6}$ alkyl. In some embodiments, $R^7$ is selected from —$CH_2OC(O)R^{12}$, —$CH(CH_3)OC(O)R^{12}$, —$P(O)(OH)_2$, and —$CH_2P(O)(OH)_2$. In some embodiments, $R^7$ is selected from —$CH_2OC(O)R^{12}$, —$CH(CH_3)OC(O)R^{12}$, —$P(O)(OH)_2$, and —$CH_2P(O)(OH)_2$; and $R^{12}$ is $C_{1-6}$ alkyl optionally substituted with one, two, or three $R^{20}$. In some embodiments, $R^7$ is selected from —$CH_2OC(O)R^{12}$, —$CH(CH_3)OC(O)R^{12}$, —$P(O)(OH)_2$, and —$CH_2P(O)(OH)_2$; and $R^{12}$ is $C_{1-6}$ alkyl. In some embodiments, $R^7$ is selected from —$CH_2OP(O)(OH)_2$, —$CH(CH_3)OP(O)(OH)_2$, —$CH_2OP(O)(OCH_2OC(O)OCH(CH_3)_2)_2$, —$CH_2OC(O)CH(NH_2)(CH(CH_3)_2)$, —$CH(CH_3)OC(O)CH(NH_2)(CH(CH_3)_2)$, and —$CH_2OC(O)CH(CH_3)_2$.

In some embodiments, for a compound of Formula (I), (I-1), (II), (II-1), (II-a), (II-a1), (III), (III-1), (IV), or (IV-1), $J^1$ ----- $J^2$ is N—$CH_2$. In some embodiments, $J^1$ ----- $J^2$ is C≡CH. In some embodiments, $J^1$ is N and $J^2$ is $CH_2$. In some embodiments, $J^1$ is C and $J^2$ is CH.

In some embodiments, for a compound of Formula (I), (1-1), (II), (II-1), (II-a), (II-a1), (III), (III-1), (IV), or (IV-1), $L^1$ is absent or selected from $C_{1-6}$ alkylene, 2- to 6-membered heteroalkylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, -(2- to 6-membered heteroalkyl)-(3- to 12-membered heterocycle)-, —O—, —$N(R^{12})$—, —C(O)—, —$C(O)N(R^{12})$—, and —$N(R^{12})C(O)$—, wherein $C_{1-6}$ alkylene, 2- to 6-membered heteroalkylene, —$C_{0-6}$ alkyl-($C_{3-12}$ carbocycle)-, -(2- to 6-membered heteroalkyl)-($C_{3-12}$ carbocycle)-, —$C_{0-6}$ alkyl-(3- to 12-membered heterocycle)-, and -(2- to 6-membered heteroalkyl)-(3- to 12-membered heterocycle)- are optionally substituted with one, two, or three $R^{20}$. In some embodiments, $L^1$ is absent or selected from $C_{1-6}$ alkylene, —O—, —S—, —$N(R^{12})$—, —$C(NR^{12})$—, —$N(R^{12})S(O)_2$—, —C(O)—, —$C(O)N(R^{12})$—, —$N(R^{12})C(O)$—, —S(O)—, —$S(O)_2$—, and —$S(O)_2N(R^{12})$—. In some embodiments, $L^1$ is absent or selected from $C_{1-3}$ alkylene, —O—, —$N(R^{12})$—, and —$C(O)N(R^{12})$—. In some embodiments, $L^1$ is absent or selected from $C_{1-3}$ alkylene, —O—, and —$C(O)N(R^{12})$—. In some embodiments, $L^1$ is absent. In some embodiments, $L^1$ is $C_{1-3}$ alkylene optionally substituted with one, two, or three $R^{20}$. In some embodiments, $L^1$ is —O—. In some embodiments, $L^1$ is —C(O)N($R^{12}$)—.

In some embodiments, for a compound of Formula (II), (II-1), (II-a), (II-a1), (III), (III-1), (IV), or (IV-1), W is $C(R^2)_2$, wherein $R^2$ is selected from hydrogen, halogen, $C_{1-3}$ alkyl, $C_{1-3}$ haloalkyl, —OH, —$OCH_3$, —$NH_2$, —$NHCH_3$, and —$N(CH_3)_2$. In some embodiments, W is $CHR^2$. In some embodiments, W is $CH_2$.

In some embodiments, for a compound of Formula (II), (II-1), (II-a), (II-a1), (III), (III-1), (IV), or (IV-1), n is 0 or 1. In some embodiments, n is 1 or 2. In some embodiments, n is 0. In some embodiments, n is 1. In some embodiments, n is 2.

In some embodiments, for a compound of Formula (II), (II-1), (II-a), (II-a1), (III), (III-1), (IV), or (IV-1), $R^2$ is independently selected at each occurrence from hydrogen, halogen, —CN, $C_{1-6}$ alkyl, $C_{2-6}$ alkenyl, 2- to 6-membered heteroalkyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{12}$, —N($R^{12}$)($R^{13}$), —C(O) $OR^{12}$, —C(O)$R^{12}$, —OC(O)$R^{12}$, —C(O)N($R^{12}$)($R^{13}$), and —N($R^{12}$)C(O)$R^{12}$, optionally wherein one or both of (1) two $R^2$ attached to the same carbon atom are taken together to form oxo, =$NR^{12}$, or =$C(R^{14})_2$ and (2) two $R^2$, together with the atom(s) to which they are attached, form $C_{3-12}$ carbocycle or 3- to 12-membered heterocycle, wherein $C_{1-6}$ alkyl, $C_{2-6}$ alkenyl, 2- to 6-membered heteroalkyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one, two, or three $R^{20}$. In some embodiments, $R^2$ is independently selected at each occurrence from hydrogen, halogen, $C_{1-6}$ alkyl, —$OR^{12}$, and —N($R^{12}$)($R^{13}$), wherein one or both of (1) two $R^2$ attached to the same carbon atom are taken together to form oxo, =$NR^{12}$, or =$C(R^{14})_2$ and (2) two $R^2$, together with the atom(s) to which they are attached, form $C_{3-12}$ carbocycle or 3- to 12-membered heterocycle, wherein $C_{1-6}$ alkyl, $C_{3-12}$ carbocycle, and 3- to 12-membered heterocycle are optionally substituted with one, two, or three $R^{20}$. In some embodiments, $R^2$ is independently selected at each occurrence from hydrogen, halogen, $C_{1-6}$ alkyl, —$OR^{12}$, and —N($R^{12}$)($R^{13}$), or two $R^2$ attached to the same carbon atom are taken together to form oxo, =$NR^{12}$, or =$C(R^{14})_2$, wherein $C_{1-6}$ alkyl is optionally substituted with one, two, or three $R^{20}$. In some embodiments, each $R^2$ is hydrogen.

In some embodiments, for a compound of Formula (II), (II-1), (II-a), (II-a1), (III), (III-1), (IV), or (IV-1), $R^3$ is selected from hydrogen, $C_{1-6}$ alkyl, $C_{2-6}$ alkenyl, —$C_{0-6}$ alkyl-($C_{3-12}$ carbocycle), —$C_{0-6}$ alkyl-(3- to 12-membered heterocycle), (5-methyl-2-oxo-1,3-dioxol-4-yl)methyl, —C(O) $OR^{12}$, —C(O)O—($C_{1-6}$ alkyl)-$OR^{15}$, —($C_{1-6}$ alkyl)-$OR^{15}$, —C(O)$R^{12}$, and —C(O)N($R^{12}$)($R^{13}$), wherein $C_{1-6}$ alkyl, $C_{2-6}$ alkenyl, —$C_{0-6}$ alkyl-($C_{3-12}$ carbocycle), and —$C_{0-6}$ alkyl-(3- to 12-membered heterocycle) are optionally substituted with one, two, or three $R^{20}$. In some embodiments, $R^3$ is selected from hydrogen, $C_{1-6}$ alkyl, —$C_{0-6}$ alkyl-(3- to 12-membered heterocycle), —C(O) $OR^{12}$, and —C(O)O—($C_{1-6}$ alkyl)-$OR^{15}$, wherein $C_{1-6}$ alkyl and —$C_{0-6}$ alkyl-(3- to 12-membered heterocycle) are optionally substituted with one, two, or three $R^{20}$. In some embodiments, $R^3$ is hydrogen. In some embodiments, $R^3$ is selected from —$C_2$ alkyl-(5- to 6-membered heterocycle) and —C(O)O—($C_{1-6}$ alkyl)-$OR^{15}$, wherein-$C_2$ alkyl-(5- to 6-membered heterocycle) is substituted with one, two, or three substituents independently selected from $C_{1-3}$ alkyl and oxo. In some embodiments, $R^3$ is (5-methyl-2-oxo-1,3-dioxol-4-yl)methyl.

In some embodiments, for a compound of Formula (II), (II-1), (II-a), (II-a1), (III), (III-1), (IV), or (IV-1), $R^3$ is selected from —C(O) $OR^{12}$, —C(O)O—($C_{1-6}$ alkyl)-$OR^{15}$, —($C_{1-6}$ alkyl)-$OR^{15}$, —P(O)(X—$R^{16}$)(Y—$R^{17}$), and —$CH_2$P(O)(X—$R^{16}$)(Y—$R^{17}$). In some embodiments, $R^3$ is selected from —C(O) $OR^{12}$, —C(O)OCH($R^{20}$)OC(O)$R^{12}$, —CH($R^{20}$)OC(O)$R^{12}$, —P(O)(X—$R^{16}$)(Y—$R^{17}$), and —$CH_2$P(O)(X—$R^{16}$)(Y—$R^{17}$). In some embodiments, $R^3$ is —C(O)OCH($R^{20}$)OC(O)$R^{12}$. In some embodiments, $R^3$ is selected from —C(O) $OR^{12}$, —C(O)OCH($R^{20}$)OC(O)$R^{12}$, —CH($R^{20}$)OC(O)$R^{12}$, —P(O)(X—$R^{16}$)(Y—$R^{17}$), and —$CH_2$P(O)(X—$R^{16}$)(Y—$R^{17}$); and $R^{12}$ is $C_{1-6}$ alkyl optionally substituted with one, two, or three $R^{20}$. In some embodiments, $R^3$ is selected from —C(O) $OR^{12}$, —C(O)OCH($R^{20}$)OC(O)$R^{12}$, —CH($R^{20}$)OC(O)$R^{12}$, —P(O)(X—$R^{16}$)(Y—$R^{17}$), and —$CH_2$P(O)(X—$R^{16}$)(Y—$R^{17}$); and $R^{12}$ is $C_{1-6}$ alkyl. In some embodiments, $R^3$ is selected from —C(O) $OR^{12}$, —C(O)$OCH_2$OC(O)$R^{12}$, —C(O)OCH($CH_3$)OC(O)$R^{12}$, —$CH_2$OC(O)$R^{12}$, —CH($CH_3$)OC(O)$R^{12}$, —P(O)(X—$R^{16}$)(Y—$R^{17}$), and —$CH_2$P(O)(X—$R^{16}$)(Y—$R^{17}$). In some embodiments, $R^3$ is selected from —C(O) $OR^{12}$, —C(O)$OCH_2$OC(O)$R^{12}$, —C(O)OCH($CH_3$)OC(O)$R^{12}$, —$CH_2$OC(O)$R^{12}$, —CH($CH_3$)OC(O)$R^{12}$, —P(O)(X—$R^{16}$)(Y—$R^{17}$), and —$CH_2$P(O)(X—$R^{16}$)(Y—$R^{17}$); and $R^{12}$ is $C_{1-6}$ alkyl optionally substituted with one, two, or three $R^{20}$. In some embodiments, $R^3$ is selected from —C(O) $OR^{12}$, —C(O)$OCH_2$OC(O)$R^{12}$, —C(O)OCH($CH_3$)OC(O)$R^{12}$, —$CH_2$OC(O)$R^{12}$, —CH($CH_3$)OC(O)$R^{12}$, —P(O)(X—$R^{16}$)(Y—$R^{17}$), and —$CH_2$P(O)(X—$R^{16}$)(Y—$R^{17}$); and $R^{12}$ is $C_{1-6}$ alkyl. In some embodiments, $R^3$ is selected from —C(O) $OR^{12}$, —C(O)$OCH_2$OC(O)$R^{12}$, —C(O)OCH($CH_3$)OC(O)$R^{12}$, —$CH_2$OC(O)$R^{12}$, —CH($CH_3$)OC(O)$R^{12}$, —P(O)$(OH)_2$, and —$CH_2$P(O)$(OH)_2$. In some embodiments, $R^3$ is selected from —C(O) $OR^{12}$, —C(O)$OCH_2$OC(O)$R^{12}$, —C(O)OCH($CH_3$)OC(O)$R^{12}$, —$CH_2$OC(O)$R^{12}$, —CH($CH_3$)OC(O)$R^{12}$, —P(O)$(OH)_2$, and —$CH_2$P(O)$(OH)_2$; and $R^{12}$ is $C_{1-6}$ alkyl optionally substituted with one, two, or three $R^{20}$. In some embodiments, $R^3$ is —C(O)OCH($CH_3$)OC(O)$R^{12}$. In some embodiments, $R^3$ is selected from —C(O) $OR^{12}$, —C(O)$OCH_2$OC(O)$R^{12}$, —C(O)OCH($CH_3$)OC(O)$R^{12}$, —$CH_2$OC(O)$R^{12}$, —CH($CH_3$)OC(O)$R^{12}$, —P(O)$(OH)_2$, and —$CH_2$P(O)$(OH)_2$; and $R^{12}$ is $C_{1-6}$ alkyl. In some embodiments, $R^3$ is selected from —C(O)OCH($CH_3$)OC(O)CH$(CH_3)_2$, —C(O)OCH($CH_3$)OC(O)$CH_3$, —C(O)OCH($CH_3$)OC(O)$CH_2CH_2CH_3$, —C(O)OCH$(CH_3)_2$, —C(O)$OCH_2$CH$(CH_3)_2$, —C(O)O$(CH_2)_3CH_3$, ((5-methyl-2-oxo-1,3-dioxol-4-yl) methoxy)(oxo)methyl, (5-methyl-2-oxo-1,3-dioxol-4-yl)methyl, —C(O)OCH($CH_3$)OC(O)CH($NH_2$)(CH$(CH_3)_2$), —C(O)$OCH_2$OC(O)(4-(phosphonooxy)phenyl) methyl, —$CH_2$OP(O)(OH)($OCH_2$OC(O)OCH$(CH_3)_2$), —C(O)OCH($CH_3$)OP(O)$(OH)_2$, and —$CH_2$OP(O)($OH_2$). In some embodiments, $R^3$ is —C(O)OCH($CH_3$)OC(O)CH$(CH_3)_2$. In some embodiments, $R^3$ is —C(O)OCH($CH_3$)OC(O)-cyclopentyl. In some embodiments, $R^3$ is —C(O)OCH($CH_3$)OC(O)$R^{12}$, wherein $R^{12}$ is cyclopentyl. In some embodiments, $R^3$ is selected from —$CH_2$OP(O)$(OH)_2$, —CH($CH_3$)OP(O)$(OH)_2$, —$CH_2$OP(O)($OCH_2$OC(O)OCH$(CH_3)_2)_2$, —$CH_2$OC(O)CH($NH_2$)(CH$(CH_3)_2$), —CH($CH_3$)OC(O)CH($NH_2$)(CH$(CH_3)_2$), and —$CH_2$OC(O)CH$(CH_3)_2$.

In some embodiments, for a compound of Formula (II), (II-1), (II-a), (II-a1), (III), (III-1), (IV), or (IV-1), $R^3$ is selected from —C(O) $OR^{12}$, —C(O)O—($C_{1-6}$ alkyl)-$OR^{15}$, —($C_{1-6}$ alkyl)-$OR^{15}$, —P(O)(X—$R^{16}$)(Y—$R^{17}$), and —$CH_2P(O)(X—R^{16})(Y—R^{17})$, wherein $R^{12}$ is selected from $C_{1-6}$ alkyl, —$C_{0-6}$ alkyl-($C_{3-12}$ carbocycle), and —$C_{0-6}$ alkyl-(3- to 12-membered heterocycle), each of which is optionally substituted with one, two, or three substituents independently selected from —$N(R^{22})C(O)CH(R^{20})N(R^{22})_2$, —$C(O)CH(R^{20})N(R^{22})_2$, and $R^{20}$. In some embodiments, $R^3$ is selected from —C(O) $OR^{12}$, —C(O)$OCH(R^{20})OC(O)R^{12}$, —$CH(R^{20})OC(O)R^{12}$, —$P(O)(X—R^{16})(Y—R^{17})$, and —$CH_2P(O)(X—R^{16})(Y—R^{17})$, wherein $R^{12}$ is selected from $C_{1-6}$ alkyl, —$C_{0-6}$ alkyl-($C_{3-12}$ carbocycle), and —$C_{0-6}$ alkyl-(3- to 12-membered heterocycle), each of which is optionally substituted with one, two, or three substituents independently selected from —$N(R^2)C(O)CH(R^{20})N(R^{22})_2$, —$C(O)CH(R^{20})N(R^{22})_2$, and $R^{20}$. In some embodiments, $R^3$ is selected from —C(O) $OR^{12}$, —$C(O)OCH(R^{20})OC(O)R^{12}$, —$CH(R^{20})OC(O)R^{12}$, —$P(O)(X—R^{16})(Y—R^{17})$, and —$CH_2P(O)(X—R^{16})(Y—R^{17})$; and $R^{12}$ is $C_{1-6}$ alkyl optionally substituted with one, two, or three substituents independently selected from —$N(R^{22})C(O)CH(R^{20})N(R^{22})_2$, —$C(O)CH(R^{20})N(R^{22})_2$, and $R^{20}$. In some embodiments, $R^3$ is selected from —C(O) $OR^{12}$, —$C(O)OCH(R^{20})OC(O)R^{12}$, —$CH(R^{20})OC(O)R^{12}$, —$P(O)(X—R^{16})(Y—R^{17})$, and —$CH_2P(O)(X—R^{16})(Y—R^{17})$; and $R^{12}$ is $C_{1-6}$ alkyl substituted with —$N(R^{22})C(O)CH(R^{20})N(R^{22})_2$. In some embodiments, $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(X—R^{16})(Y—R^{17})$, and —$CH_2P(O)(X—R^{16})(Y—R^{17})$; and $R^{12}$ is $C_{1-6}$ alkyl substituted with —$N(R^{22})C(O)CH(R^{20})N(R^{22})_2$. In some embodiments, $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(X—R^{16})(Y—R^{17})$, and —$CH_2P(O)(X—R^{16})(Y—R^{17})$. In some embodiments, $R^3$ is selected from —$C(O)OCH_2OC(O)R^{12}$ and —$C(O)OCH(CH_3)OC(O)R^{12}$. In some embodiments, $R^3$ is —$C(O)R^{12}$ and $R^{12}$ is $C_{1-6}$ alkyl substituted with —$N(R^{22})C(O)CH(R^{20})N(R^{22})_2$. In some embodiments, $R^3$ is —$C(O)R^{12}$ and $R^{12}$ is $C_{1-6}$ alkyl optionally substituted with —$NHC(O)CH(CH_3)$ $NH_2$, —$NHC(O)CH(CH_3)N(CH_3)_2$, —$NHC(O)CH(CH(CH_3)_2)$ $NH_2$, or —$NHC(O)CH(CH(CH_3)_2)N(CH_3)_2$. In some embodiments, $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(X—R^{16})(Y—R^{17})$, and —$CH_2P(O)(X—R^{16})(Y—R^{17})$; and $R^{12}$ is $C_{1-6}$ alkyl optionally substituted with —$NHC(O)CH(CH_3)$ $NH_2$, —$NHC(O)CH(CH_3)N(CH_3)_2$, —$NHC(O)CH(CH(CH_3)_2)$ $NH_2$, or —$NHC(O)CH(CH(CH_3)_2)N(CH_3)_2$. In some embodiments, $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; and $R^{12}$ is $C_{1-6}$ alkyl substituted with —$N(R^{22})C(O)CH(R^{20})N(R^{22})_2$. In some embodiments, $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; and $R^{12}$ is $C_{1-6}$ alkyl optionally substituted with —$NHC(O)CH(CH_3)$ $NH_2$, —$NHC(O)CH(CH_3)N(CH_3)_2$, —$NHC(O)CH(CH(CH_3)_2)$ $NH_2$, or —$NHC(O)CH(CH(CH_3)_2)N(CH_3)_2$. In some embodiments, $R^3$ is selected from —$C(O)OCH(CH_3)OC(O)CH(CH_3)_2$, —$C(O)OCH(CH_3)OC(O)CH_3$, —$C(O)OCH(CH_3)OC(O)CH_2CH_2CH_3$, —$C(O)OCH(CH_3)_2$, —$C(O)OCH_2CH(CH_3)_2$, —$C(O)O(CH_2)_3CH_3$, ((5-methyl-2-oxo-1,3-dioxol-4-yl) methoxy)(oxo)methyl, (5-methyl-2-oxo-1,3-dioxol-4-yl)methyl, —$C(O)OCH(CH_3)OC(O)CH(NH_2)(CH(CH_3)_2)$, —$C(O)OCH(CH_3)OC(O)CH(CH(CH_3)_2)NHC(O)CH(CH_3)$ $NH_2$, —$C(O)OCH(CH(CH_3)_2)OC(O)CH(CH(CH_3)_2)$ $NHC(O)CH(CH_3)$ $NH_2$, —$C(O)OCH(CH_3)OC(O)CH(CH(CH_3)_2)$ $NHC(O)CH(CH(CH_3)_2)$ $NH_2$, —$C(O)OCH(CH(CH_3)_2)OC(O)CH(CH(CH_3)_2)$ $NHC(O)CH(CH(CH_3)_2)$ $NH_2$, —$C(O)OCH(CH_3)OC(O)CH(CH(CH_3)_2)$ $NHC(O)CH(CH_3)N(CH_3)_2$, —$C(O)OCH(CH(CH_3)_2)OC(O)CH(CH(CH_3)_2)$ $NHC(O)CH(CH_3)N(CH_3)_2$, —$C(O)OCH(CH_3)OC(O)CH(CH(CH_3)_2)$ $NHC(O)CH(CH(CH_3)_2)N(CH_3)_2$, —$C(O)OCH(CH(CH_3)_2)OC(O)CH(CH(CH_3)_2)$ $NHC(O)CH(CH(CH_3)_2)N(CH_3)_2$, —$C(O)OCH_2OC(O)$(4-(phosphonooxy)phenyl)methyl, —$CH_2OP(O)(OH)(OCH_2OC(O)OCH(CH_3)_2)$, —$C(O)OCH(CH_3)OP(O)(OH)_2$, and —$CH_2OP(O)(OH_2)$.

In some embodiments, for a compound of Formula (I), (I-1), (II), (II-1), (II-a), (II-a1), (III), (III-1), (IV), or (IV-1), $R^{15}$ is independently selected at each occurrence from (5-methyl-2-oxo-1,3-dioxol-4-yl)methyl, —$C(O)R^{12}$, —C(O) $OR^{12}$, and —$P(O)(X—R^{16})(Y—R^{17})$. In some embodiments, $R^{15}$ is independently selected at each occurrence from —$C(O)R^{12}$, —C(O) $OR^{12}$, —$P(O)(X—R^{16})(Y—R^{17})$, and —$CH_2P(O)(X—R^{16})(Y—R^{17})$. In some embodiments, $R^{15}$ is independently selected at each occurrence from —$C(O)R^{12}$, —$P(O)(X—R^{16})(Y—R^{17})$, and —$CH_2P(O)(X—R^{16})(Y—R^{17})$. In some embodiments, $R^{15}$ is independently selected at each occurrence from (5-methyl-2-oxo-1,3-dioxol-4-yl)methyl, —$C(O)R^{12}$, —C(O) $OR^{12}$, and —$P(O)(X—R^{16})(Y—R^{17})$, and $R^{12}$ is $C_{1-6}$ alkyl. In some embodiments, $R^{15}$ is independently selected at each occurrence from —$C(O)R^{12}$, —C(O) $OR^{12}$, —$P(O)(X—R^{16})(Y—R^{17})$, and —$CH_2P(O)(X—R^{16})(Y—R^{17})$, and $R^{12}$ is $C_{1-6}$ alkyl In some embodiments, $R^{15}$ is independently selected at each occurrence from —$C(O)R^{12}$, —$P(O)(X—R^{16})(Y—R^{17})$, and —$CH_2P(O)(X—R^{16})(Y—R^{17})$, and $R^{12}$ is $C_{1-6}$ alkyl. In some embodiments, $R^{15}$ is independently selected at each occurrence from —$P(O)(X—R^{16})(Y—R^{17})$ and —$CH_2P(O)(X—R^{16})(Y—R^{17})$. In some embodiments, $R^{15}$ is (5-methyl-2-oxo-1,3-dioxol-4-yl) methyl. In some embodiments, $R^{15}$ is —$C(O)R^{12}$. In some embodiments, $R^{15}$ is —C(O) $OR^{12}$. In some embodiments, $R^{15}$ is —$P(O)(X—R^{16})(Y—R^{17})$. In some embodiments, $R^{15}$ is —$CH_2P(O)(X—R^{16})(Y—R^{17})$. In some embodiments, $R^{15}$ is selected from —$C(O)R^{12}$ and —$P(O)(X—R^{16})(Y—R^{17})$. In some embodiments, $R^{15}$ is —$C(O)R^{12}$, wherein $R^{12}$ is $C_{1-6}$ alkyl optionally substituted with —$NH_2$. In some embodiments, $R^{15}$ is —$C(O)R^{12}$, wherein $R^{12}$ is cyclopentyl. In some embodiments, $R^{12}$ is $C_{1-6}$ alkyl optionally substituted with —$NH_2$. In some embodiments, $R^{15}$ is selected from (5-methyl-2-oxo-1,3-dioxol-4-yl)methyl, —C(O)(pyrrolidine-1-yl), —$C(O)CH(CH_3)_2$, —$C(O)CH_3$, —$C(O)CH_2CH_2CH_3$, —$C(O)CH(NH_2)(CH(CH_3)_2)$, —C(O)(4-(phosphonooxy)phenylmethyl, —$P(O)(OCH_2OC(O)OCH(CH_3)_2)_2$, —$P(O)(OH)(OCH_2OC(O)OCH(CH_3)_2)$, —$P(O)(OH_2)$, and —$CH_2P(O)(OH)_2$. In some embodiments, $R^{15}$ is selected from —$C(O)CH(CH_3)_2$, —$C(O)CH_3$, —$C(O)CH_2CH_2CH_3$, —$C(O)CH(NH_2)(CH(CH_3)_2)$, —C(O)(4-(phosphonooxy)phenyl)methyl, —$P(O)(OH)(OCH_2OC(O)OCH(CH_3)_2)$, and —$P(O)(OH_2)$. In some embodiments, $R^{15}$ is selected from —$P(O)(OH)_2$, —$P(O)(OCH_2OC(O)OCH(CH_3)_2)_2$, —$C(O)CH(NH_2)(CH(CH_3)_2)$, and —$C(O)CH(CH_3)_2$.

In some embodiments, for a compound of Formula (I), (I-1), (II), (II-1), (II-a), (II-a1), (III), (III-1), (IV), or (IV-1), at least one of $R^{16}$ and $R^{17}$ is $C_{1-6}$ alkyl, optionally substituted at each occurrence with one, two, or three substituents independently selected from halogen, —$OR^{12}$, —S—S—$R^{12}$, —S—$C(O)R^{12}$, —$OC(O)R^{12}$, —$OC(O)OR^{12}$, and —$P(O)(OR^{12})_2$. In some embodiments, $R^{16}$ and $R^{17}$ are independently $C_{1-6}$ alkyl optionally substituted at each occurrence with one or more substituents independently selected from halogen, $—OR^{12}$, $—S—S—R^{12}$, $—S—C(O)R^{12}$, $—OC(O)R^{12}$, $—OC(O)OR^{12}$, and $—P(O)(OR^{12})_2$. In some embodiments, $R^{16}$ and $R^{17}$ are independently selected from hydrogen and $C_{1-6}$ alkyl optionally substituted at each occurrence with one or more substituents independently selected from halogen, $—OR^{12}$, $—S—S—R^{12}$, $—S—C(O)R^{12}$, $—OC(O)R^{12}$, $—OC(O)OR^{12}$, and $—P(O)(OR^{12})_2$. In some embodiments, $R^{16}$ and $R^{17}$ are independently selected from hydrogen, $—CH_2OC(O)R^{12}$, and $—CH_2OC(O)OR^{12}$. In some embodiments, $R^{16}$ and $R^{17}$ are independently selected from $—CH_2OC(O)R^{12}$ and $—CH_2OC(O)OR^{12}$. In some embodiments, $R^{16}$ and $R^{17}$ are independently selected from $—CH_2OC(O)C(CH_3)$ 3, $—CH_2OC(O)OCH(CH_3)_2$, $—CH_2OC(O)CH_3$, $—CH_2CH_2—S—S—(CH_2)_2OH$, and $—CH_2CH_2—S—C(O)CH_3$. In some embodiments, $R^{16}$ and $R^{17}$ are independently selected from $C_{1-6}$ alkyl substituted with one or more substituents independently selected from $—OC(O)R^{12}$ and $—OC(O)OR^{12}$, wherein $R^{12}$ is $C_{1-6}$ alkyl. In some embodiments, $R^{16}$ and $R^{17}$ are independently selected from $—CH_2OC(O)C(CH_3)$ 3, $—CH_2OC(O)OCH(CH_3)_2$, and $—CH_2OC(O)CH_3$. In some embodiments, $R^{16}$ and $R^{17}$ are independently selected from $C_{1-6}$ alkyl substituted with one or more substituents independently selected from $—S—S—R^{12}$ and $—S—C(O)R^{12}$. In some embodiments, $R^{16}$ and $R^{17}$ are independently selected from $—CH_2CH_2—S—S—(CH_2)_2OH$ and $—CH_2CH_2—S—C(O)CH_3$.

In some embodiments, for a compound of Formula (I), (I-1), (II), (II-1), (II-a), (II-a1), (III), (III-1), (IV), or (IV-1), $R^{16}$ and $R^{17}$ are independently selected from $C_{3-12}$ carbocycle, such as phenyl, wherein the $C_{3-12}$ carbocycle is optionally substituted with one, two, or three substituents independently selected from halogen, $C_{1-6}$ alkyl, $—OR^{12}$, $—OC(O)R^{12}$, $—C(O)$ $OR^{12}$, and $—C(O)R^{12}$. In some embodiments, $R^{16}$ and $R^{17}$ are independently selected from phenyl, wherein the phenyl is optionally substituted with $—OR^{12}$, such as $—OCH_2CH_3$. In some embodiments, one of $R^{16}$ and $R^{17}$ is selected from $C_{3-12}$ carbocycle, such as phenyl or benzyl, wherein the $C_{3-12}$ carbocycle optionally substituted with one, two, or three substituents independently selected from halogen, $C_{1-6}$ alkyl, $—OR^{12}$, $—OC(O)R^{12}$, $—C(O)$ $OR^{12}$, and $—C(O)R^{12}$, and the other of $R^{16}$ and $R^{17}$ is $C_{1-6}$ alkyl substituted with one, two, or three substituents selected from $—OC(O)R^{12}$, $—C(O)$ $OR^{12}$, and $—OC(O)OR^{12}$, wherein $R^{12}$ is $C_{1-6}$ alkyl. In some embodiments, $R^{16}$ and $R^{17}$ are independently selected from hydrogen and $C_{1-6}$ alkylene-$OR^{30}$, wherein $R^{30}$ is independently selected at each occurrence from $C_{7-20}$ alkyl and $C_{7-20}$ alkenyl. In some embodiments, one of $R^{16}$ and $R^{17}$ is selected from $—C_{1-3}$ alkylene-O—$C_{7-20}$ alkyl and $—C_{1-3}$ alkylene-O—$C_{7-20}$ alkenyl, such as one of $R^{16}$ and $R^{17}$ is selected from hexadecyloxypropyl ($—CH_2(CH_2)_{20}$ $(CH_2)_{15}CH_3$), octadecyloxyethyl ($—CH_2CH_2O(CH_2)_{17}CH_3$), oleyoxyethyl ($—CH_2CH_2O(CH_2)_8CH{=}CH(CH_2)_7CH_3$), and oleyoxypropyl ($—CH_2(CH_2)_2O(CH_2)_8CH{=}CH(CH_2)_7CH_3$), and the other of $R^{16}$ and $R^{17}$ is hydrogen.

In some embodiments, for a compound of Formula (I), (I-1), (II), (II-1), (II-a), (II-a1), (III), (III-1), (IV), or (IV-1), $R^{16}$ is phenyl, optionally substituted with $—OR^{12}$; $R^{17}$ is $C_{1-6}$ alkyl substituted with one, two, or three substituents independently selected from $—OC(O)R^{12}$, $—C(O)$ $OR^{12}$, and $—OC(O)OR^{12}$; and $R^{12}$ is $C_{1-6}$ alkyl. In some embodiments, $R^{16}$ is 3- to 12-membered heterocycle. In some embodiments, $R^{16}$ is 6-membered heterocycle, such as pyridyl. In some embodiments, $R^{16}$ is pyrimidyl. In some embodiments, $R^{16}$ and $R^{17}$ are taken together with the atoms to which they are attached to form 3- to 12-membered heterocycle, optionally substituted with one, two, or three $R^{20}$.

In some embodiments, for a compound of Formula (I), (I-1), (II), (II-1), (II-a), (II-a1), (III), (III-1), (IV), or (IV-1), X and Y are each —O—. In some embodiments, one of X and Y is —O— and the other one of X and Y is $—NR^{12}$, and $R^{16}$ and $R^{17}$ are taken together with the atoms to which they are attached to form 3- to 12-membered heterocycle, such as a 6-membered heterocycle, optionally substituted with one, two, or three $R^{20}$. In some embodiments, at least one of $X—R^{16}$ and $Y—R^{17}$ comprises an amino acid or amino acid ester, such as L-alanine ester, e.g., $—NHCH(CH_3)C(O)OCH(CH_3)_2$ or $—NHCH(CH_3)C(O)OCH_2CH_3$. In some embodiments, at least one of $X—R^{16}$ and $Y—R^{17}$ comprises alanine, serine, phenylalanine, valine, or two or more thereof. In some embodiments, $X—R^{16}$ and $Y—R^{17}$ are each —OH. In some embodiments, $R^{15}$ is $—P(O)(OH)_2$.

In some embodiments, for a compound of Formula (II), (II-1), (II-a), (II-a1), (III), (III-1), (IV), or (IV-1), at least one of $R^3$, $R^5$, and $R^7$ is $—OR^{15}$, $—O—(C_{1-6}$ alkyl)-$OR^{15}$, $—OC(O)N(R^{12})(R^{13})$, $—C(O)$ $OR^{12}$, $—C(O)O—(C_{1-6}$ alkyl)-$OR^{15}$, $—(C_{1-6}$ alkyl)-$OR^{15}$, $—P(O)(X—R^{16})(Y—R^{17})$, or $—CH_2P(O)(X—R^{16})(Y—R^{17})$. In some embodiments, at least one of $R^3$, $R^5$, and $R^7$ is $—OP(O)(X—R^{16})(Y—R^{17})$, $—OCH_2OP(O)(X—R^{16})(Y—R^{17})$, $—OC(O)N(R^{12})(R^{13})$, $—OCH(R^{20})OC(O)OR^{12}$, $—OC(O)CH(R^{20})NH_2$, $—OCH(R^{20})OC(O)R^{12}$, $—OC(O)R^{12}$, $—OC(O)OR^{12}$, $—C(O)$ $OR^{12}$, $—C(O)OCH(R^{20})OC(O)R^{12}$, $—CH(R^{20})OC(O)R^{12}$, $—P(O)(X—R^{16})(Y—R^{17})$, or $—CH_2P(O)(X—R^{16})(Y—R^{17})$. In some embodiments, at least one of $R^3$, $R^5$, and $R^7$ is $—OP(O)(X—R^{16})(Y—R^{17})$, $—OCH_2OP(O)(X—R^{16})(Y—R^{17})$, $—OC(O)N(R^{12})(R^{13})$, $—OCH(R^{20})OC(O)OR^{12}$, $—OC(O)CH(R^{20})$ $NH_2$, $—OCH(R^{20})OC(O)R^{12}$, $—OC(O)R^{12}$, $—OC(O)OR^{12}$, $—C(O)$ $OR^{12}$, $—C(O)OCH(R^{20})OC(O)R^{12}$, $—CH(R^{20})OC(O)R^{12}$, $—P(O)(X—R^{16})(Y—R^{17})$, or $—CH_2P(O)(X—R^{16})(Y—R^{17})$; and $R^{12}$ is $C_{1-6}$ alkyl optionally substituted with one, two, or three $R^{20}$. In some embodiments, at least one of $R^3$, $R^5$, and $R^7$ is $—OP(O)(X—R^{16})(Y—R^{17})$, $—OCH_2OP(O)(X—R^{16})(Y—R^{17})$, $—OC(O)N(R^{12})(R^{13})$, $—OCH(R^{20})OC(O)OR^{12}$, $—OC(O)CH(R^{20})$ $NH_2$, $—OCH(R^{20})OC(O)R^{12}$, $—OC(O)R^{12}$, $—OC(O)OR^{12}$, $—C(O)$ $OR^{12}$, $—C(O)OCH(R^{20})OC(O)R^{12}$, $—CH(R^{20})OC(O)R^{12}$, $—P(O)(X—R^{16})(Y—R^{17})$, or $—CH_2P(O)(X—R^{16})(Y—R^{17})$; and $R^{12}$ is $C_{1-6}$ alkyl. In some embodiments, at least one of $R^3$, $R^5$, and $R^7$ is $—OP(O)(X—R^{16})(Y—R^{17})$, $—OCH_2OP(O)(X—R^{16})(Y—R^{17})$, $—OC(O)N(R^{12})(R^{13})$, $—OCH_2OC(O)$ $OR^{12}$, $—OCH(CH_3)OC(O)OR^{12}$, $—OC(O)CH_2NH_2$, $—OC(O)CH(CH_3)NH_2$, $—OCH_2OC(O)R^{12}$, $—OCH(CH_3)OC(O)R^{12}$, $—OC(O)R^{12}$, $—OC(O)OR^{12}$, $—C(O)$ $OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(X—R^{16})(Y—R^{17})$, or $—CH_2P(O)(X—R^{16})(Y—R^{17})$. In some embodiments, at least one of $R^3$, $R^5$, and $R^7$ is $—OP(O)(X—R^{16})(Y—R^{17})$, $—OCH_2OP(O)(X—R^{16})(Y—R^{17})$, $—OC(O)N(R^{12})(R^{13})$, $—OCH_2OC(O)OR^{12}$, $—OCH(CH_3)OC(O)OR^{12}$, $—OC(O)CH_2NH_2$, $—OC(O)CH(CH_3)$ $NH_2$, $—OCH_2OC(O)R^{12}$, $—OCH(CH_3)OC(O)R^{12}$, $—OC(O)R^{12}$, $—OC(O)OR^{12}$, $—C(O)$ $OR^{12}$, $—C(O)OCH_2OC(O)R^{12}$, $—C(O)OCH(CH_3)OC(O)R^{12}$, $—CH_2OC(O)R^{12}$, $—CH(CH_3)OC(O)R^{12}$, $—P(O)(X—R^{16})(Y—R^{17})$, or $—CH_2P(O)(X—R^{16})(Y—R^{17})$; and $R^{12}$ is $C_{1-6}$ alkyl optionally substituted with one, two, or three $R^{20}$. In some embodiments, at least one of $R^3$, $R^5$, and $R^7$ is $—OP(O)(X—R^{16})(Y—R^{17})$, $—OCH_2OP(O)(X—R^{16})(Y—R^{17})$, $—OC(O)N(R^{12})(R^{13})$, $—OCH_2OC(O)OR^{12}$, $—OCH(CH_3)OC(O)OR^{12}$, $—OC(O)CH_2NH_2$, —OC (O)CH($CH_3$) $NH_2$, —$OCH_2OC(O)R^{12}$, —$OCH(CH_3)OC(O)R^{12}$, —$OC(O)R^{12}$, —$OC(O)OR^{12}$, —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(X—R^{16})(Y—R^{17})$, or —$CH_2P(O)(X—R^{16})(Y—R^{17})$; and $R^{12}$ is $C_{1-6}$ alkyl. In some embodiments, at least one of $R^3$, $R^5$, and $R^7$ is —$OP(O)(OH)_2$, —$OCH_2OP(O)(OH)_2$, —$OC(O)N(R^{12})(R^{13})$, —$OCH_2OC(O)$ $OR^{12}$, —$OCH(CH_3)OC(O)OR^{12}$, —$OC(O)CH_2NH_2$, —$OC(O)CH(CH_3)$ $NH_2$, —$OCH_2OC(O)R^{12}$, —$OCH(CH_3)OC(O)R^{12}$, —$OC(O)R^{12}$, —$OC(O)OR^{12}$, —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, or —$CH_2P(O)(OH)_2$. In some embodiments, at least one of $R^3$, $R^5$, and $R^7$ is —$OP(O)(OH)_2$, —$OCH_2OP(O)(OH)_2$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)$ $NH_2$, —$OCH_2OC(O)R^{12}$, —$OCH(CH_3)OC(O)R^{12}$, —$OC(O)R^{12}$, —$OC(O)OR^{12}$, —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, or —$CH_2P(O)(OH)_2$; and $R^{12}$ is $C_{1-6}$ alkyl optionally substituted with one, two, or three $R^{20}$. In some embodiments, at least one of $R^3$, $R^5$, and $R^7$ is —$OP(O)(OH)_2$, —$OCH_2OP(O)(OH)_2$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)$ $NH_2$, —$OCH_2OC(O)R^{12}$, —$OCH(CH_3)OC(O)R^{12}$, —$OC(O)R^{12}$, —$OC(O)OR^{12}$, —$C(O)OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, or —$CH_2P(O)(OH)_2$; and $R^{12}$ is $C_{1-6}$ alkyl. In some embodiments, at least one of $R^3$, $R^5$, and $R^7$ is —$OC(O)N(CH_3)_2$, —$OC(O)N(CH_3)(CH_2CH_2OCH_3)$, —$OC(O)NHCH_2CH_3$, —OC(O)(pyrrolidine-1-yl), —$OC(O)CH(CH_3)OC(O)CH_3$, —$OC(O)CH(CH_3)OC(O)CH(CH_3)_2$, —$OC(O)CH(CH_3)_2$, methyleneoxy (4-methyl-1,3-dioxol-2-one), —$OCH_2OC(O)CH_2CH_2CH_3$, —$OCH_2OP(O)(OCH_2OC(O)OCH(CH_3)_2)_2$, —$OC(O)CH(NH_2)CH(CH_3)_2$, —$OCH_2OP(O)(OH)_2$, —$C(O)OCH(CH_3)OC(O)CH(CH_3)_2$, —$C(O)OCH(CH_3)OC(O)CH_3$, —$C(O)OCH(CH_3)OC(O)CH_2CH_2CH_3$, —$C(O)OCH(CH_3)_2$, —$C(O)OCH_2CH(CH_3)_2$, —$C(O)O(CH_2)_3CH_3$, ((5-methyl-2-oxo-1,3-dioxol-4-yl) methoxy)(oxo)methyl, (5-methyl-2-oxo-1,3-dioxol-4-yl)methyl, —$C(O)OCH(CH_3)OC(O)CH(NH_2)(CH(CH_3)_2)$, —$C(O)OCH_2OC(O)$(4-(phosphonooxy)phenyl)methyl, —$CH_2OP(O)(OH)(OCH_2OC(O)OCH(CH_3)_2)$, —$C(O)OCH(CH_3)OP(O)(OH)_2$, or —$CH_2OP(O)(OH_2)$. In some embodiments, at least one of $R^3$, $R^5$, and $R^7$ is —$OC(O)N(CH_3)_2$, —$OC(O)N(CH_3)(CH_2CH_2OCH_3)$, —$OC(O)NHCH_2CH_3$, —OC(O)(pyrrolidine-1-yl), —$OC(O)CH(CH_3)OC(O)CH_3$, —$OC(O)CH(CH_3)OC(O)CH(CH_3)_2$, —$OC(O)CH(CH_3)_2$, methyleneoxy (4-methyl-1,3-dioxol-2-one), —$OCH_2OC(O)CH_2CH_2CH_3$, —$OCH_2OP(O)(OCH_2OC(O)OCH(CH_3)_2)_2$, —$OC(O)CH(NH_2)CH(CH_3)_2$, —$OCH_2OP(O)(OH)_2$, —$CH_2OP(O)(OH)_2$, —$CH(CH_3)OP(O)(OH)_2$, —$CH_2OP(O)(OCH_2OC(O)OCH(CH_3)_2)_2$, —$CH_2OC(O)CH(NH_2)(CH(CH_3)_2)$, —$CH(CH_3)OC(O)CH(NH_2)(CH(CH_3)_2)$, or —$CH_2OC(O)CH(CH_3)_2$.

In some embodiments, for a compound of Formula (III) or (III-1),

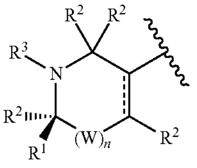

is

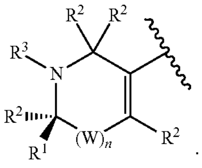

.

In some embodiments, for a compound of Formula (IV) or (IV-1),

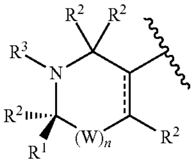

is

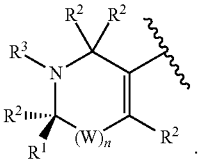

.

In some embodiments, the compound of Formula (III) or (III-1) is a compound selected from:

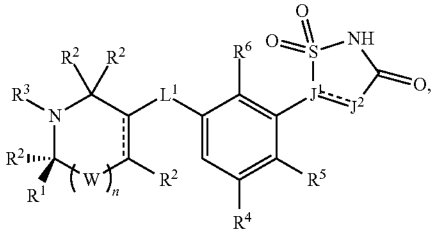

,

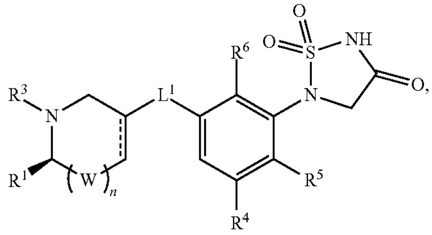

,

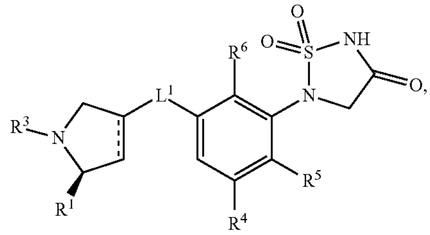

,

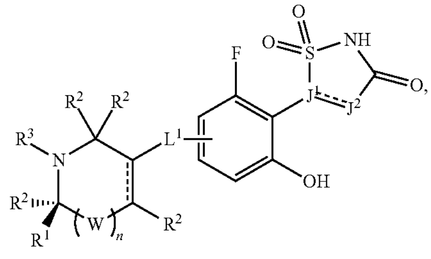

,

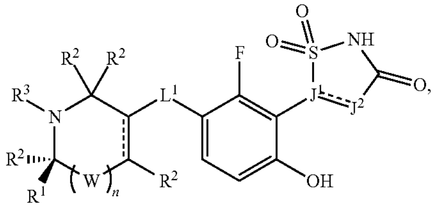

,

-continued
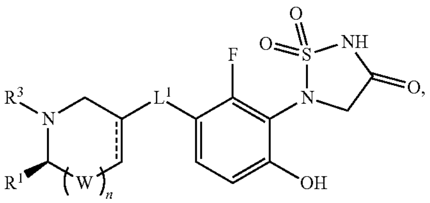
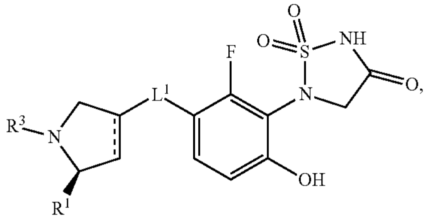
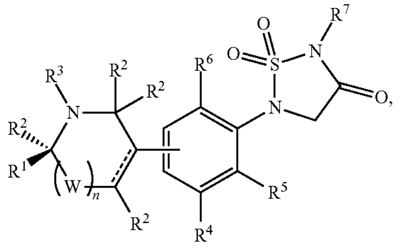
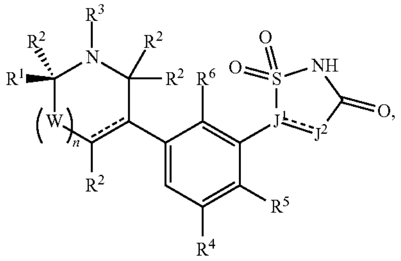
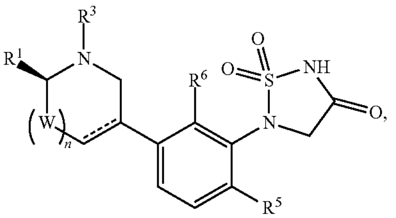
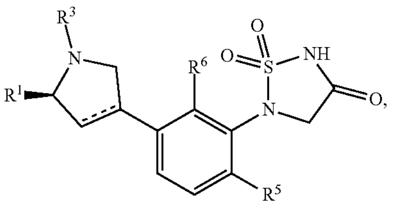
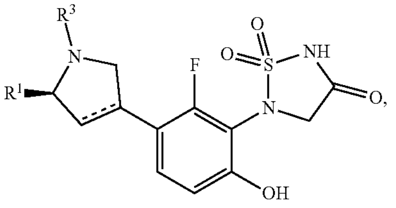
-continued
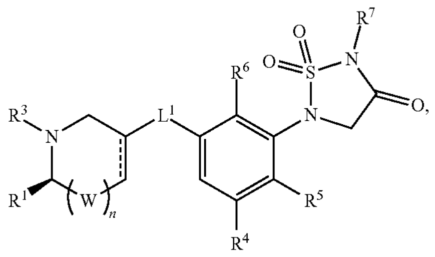
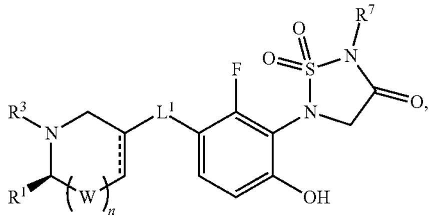
and
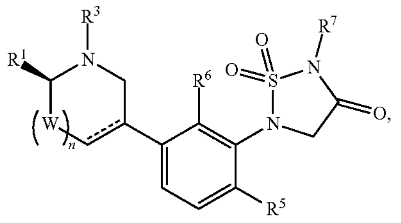
or a pharmaceutically acceptable salt or solvate thereof. In some embodiments, the compound of Formula (III) or (III-1) is a compound selected from:
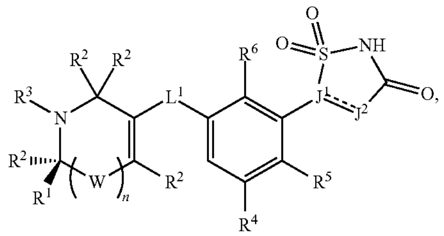
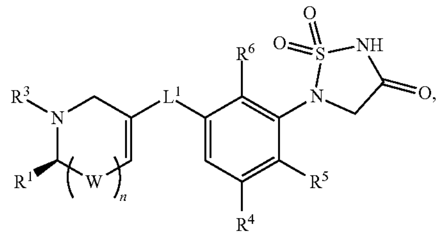
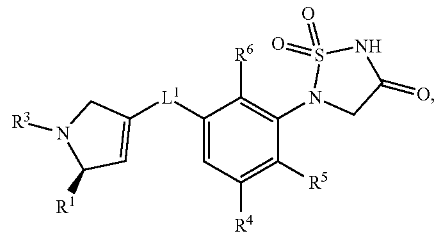

-continued

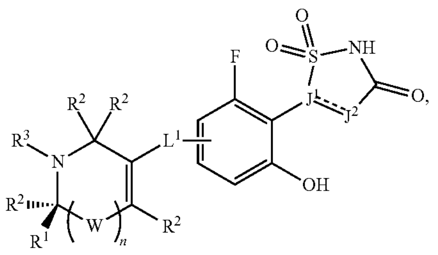

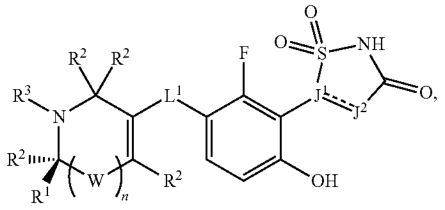

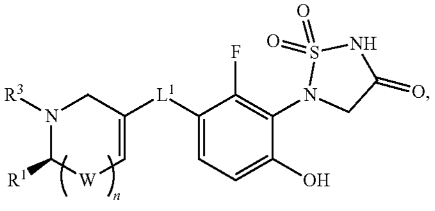

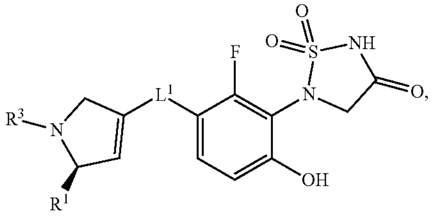

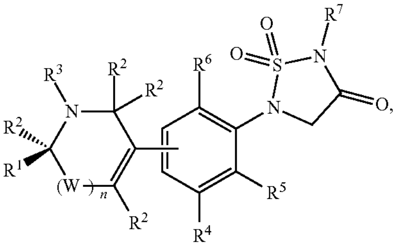

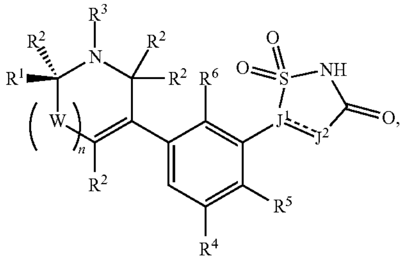

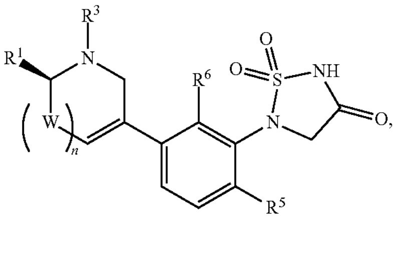

-continued

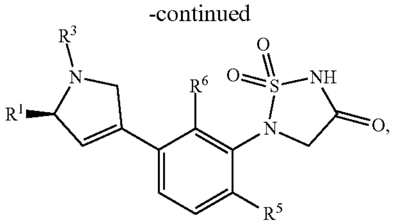

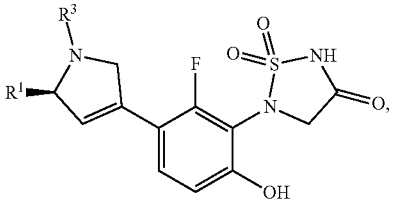

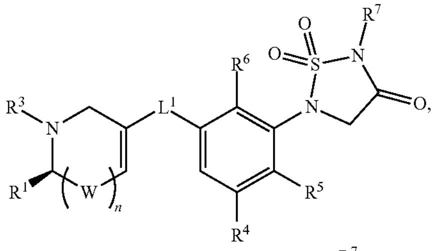

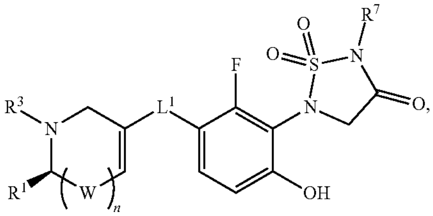

and

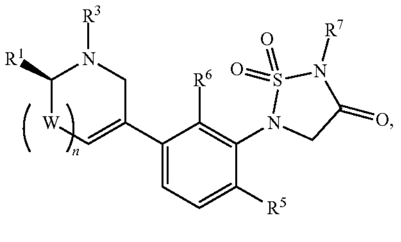

or a pharmaceutically acceptable salt or solvate thereof. Embodiments disclosed herein that refer to a compound of Formula (III) or (III-1) are also intended to apply to a compound of any formula depicted in this paragraph. If any provision of an embodiment that refers to Formula (III) or (III-1) recites a substituent or variable (e.g., $J^1$) not depicted in the compound, then the remainder of said embodiment shall be considered severable and not affected by the missing substituent or variable.

In some embodiments, the compound of Formula (IV) or (IV-1) is a compound selected from:

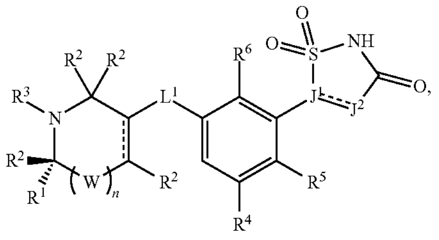

-continued
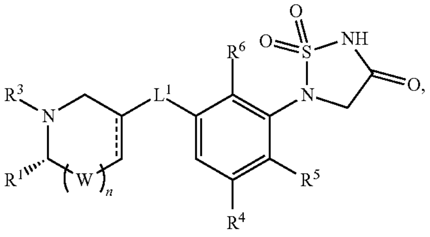
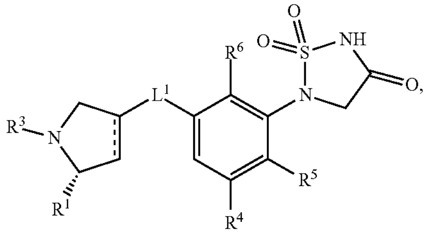
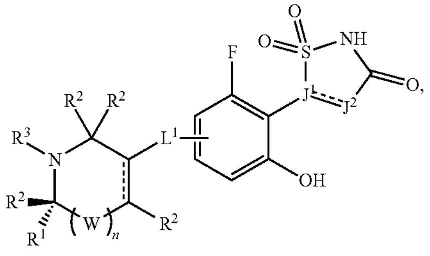
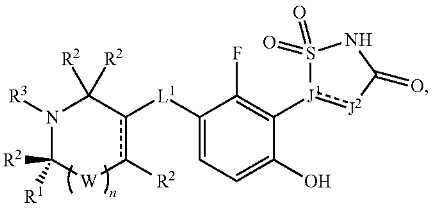
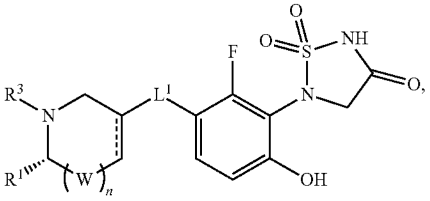
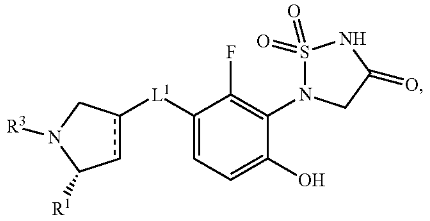
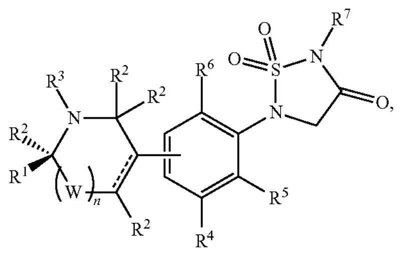
-continued
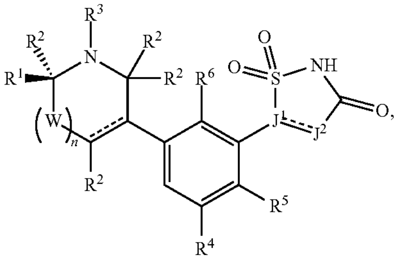
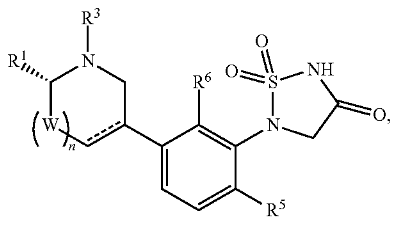
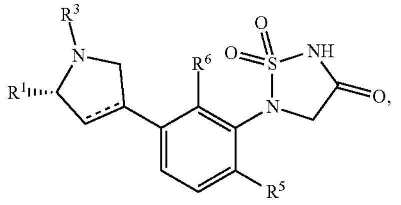
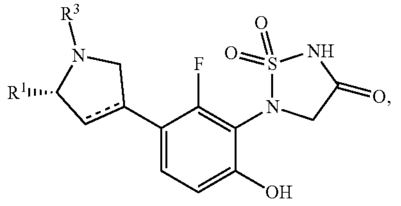
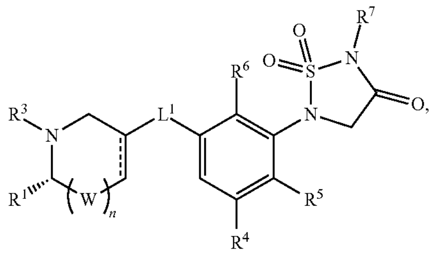
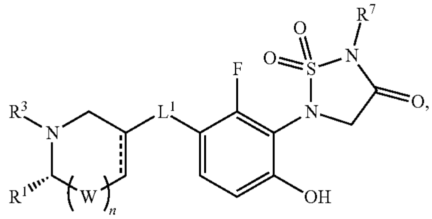
and
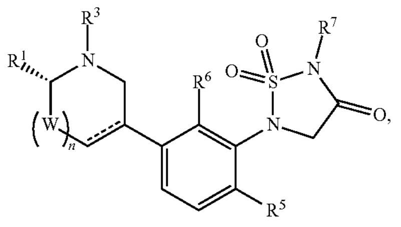
or a pharmaceutically acceptable salt or solvate thereof. In some embodiments, the compound of Formula (IV) or (IV-1) is a compound selected from:

-continued
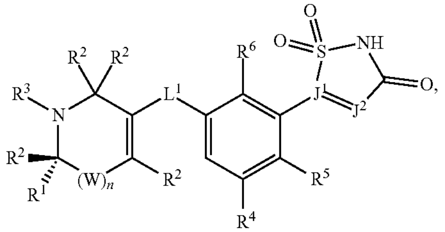
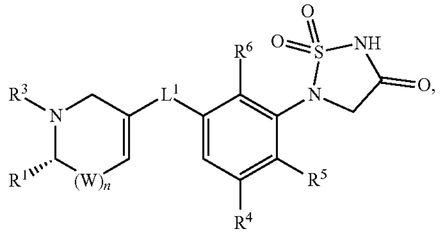
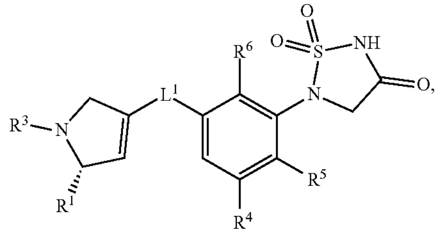
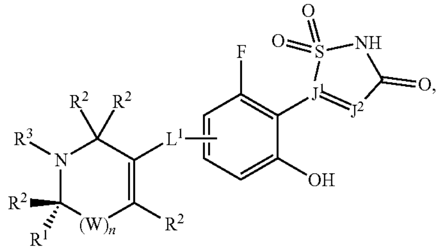
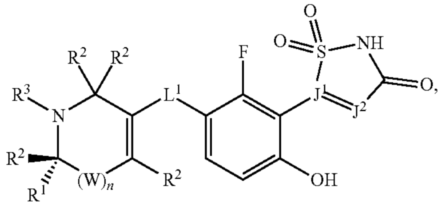
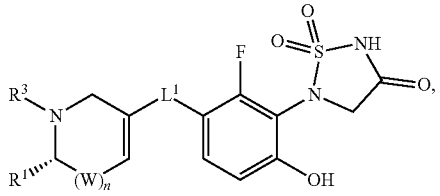
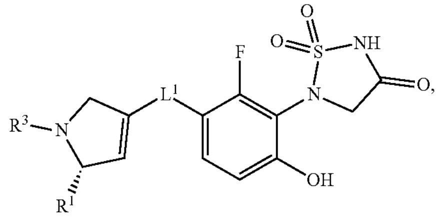
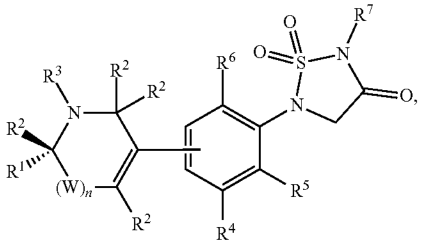
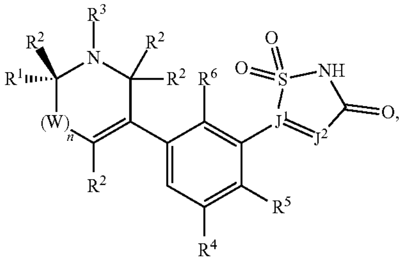
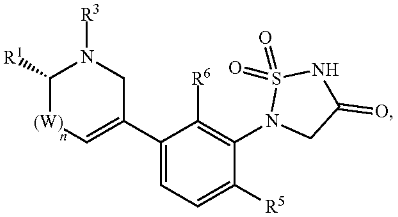
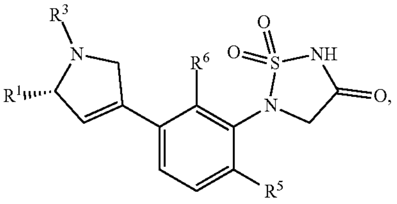
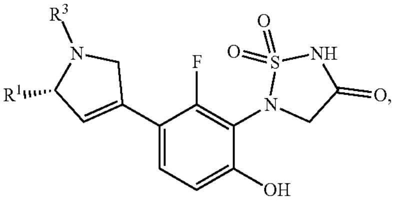
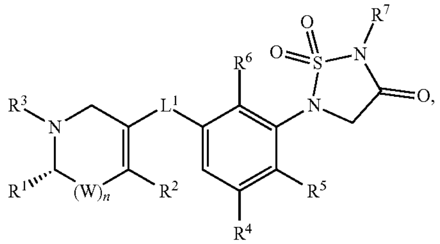
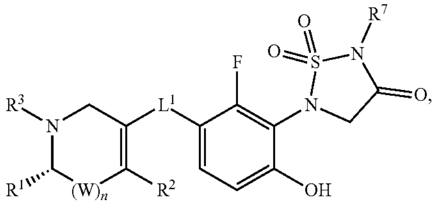
and -continued

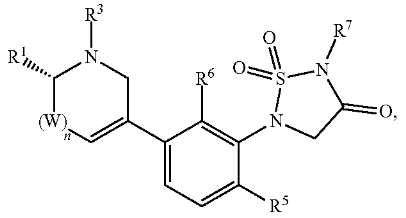

or a pharmaceutically acceptable salt or solvate thereof. Embodiments disclosed herein that refer to a compound of Formula (IV) or (IV-1) are also intended to apply to a compound of any formula depicted in this paragraph. If any provision of an embodiment that refers to Formula (IV) or (IV-1) recites a substituent or variable (e.g., $J^1$) not depicted in the compound, then the remainder of said embodiment shall be considered severable and not affected by the missing substituent or variable.

In some embodiments, a compound disclosed herein, such as a compound of Formula (I), (I-1), (II), (II-1), (II-a), (II-a1), (III), (III-1), (IV), or (IV-1), is prepared using an intermediate selected from

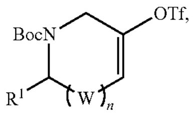 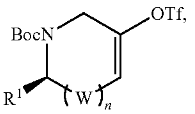

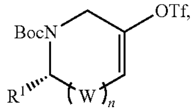 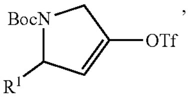 ,

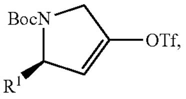 and 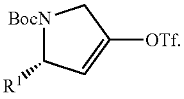

In some embodiments, the intermediate is selected from

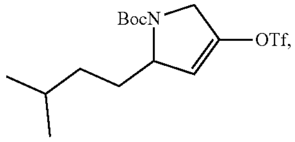 [SMILES: CC(C)CC[C@H]1C=C(OS(=O)(=O)C(F)(F)F)CN1C(=O)OC(C)(C)C]

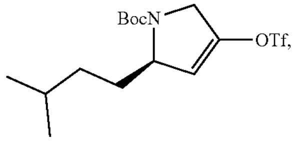

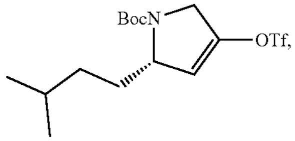

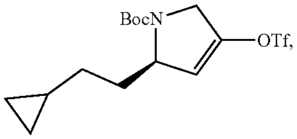

-continued

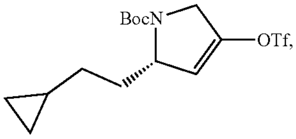

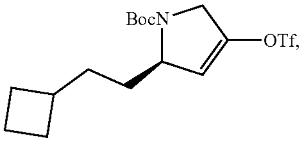 and

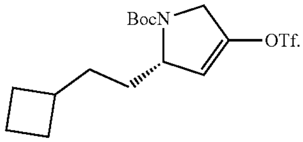

In some embodiments, the intermediate is

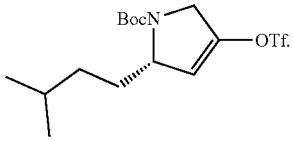

In some embodiments, a compound disclosed herein, such as a compound of Formula (I), (I-1), (II), (II-1), (II-a), (II-a1), (III), (III-1), (IV), or (IV-1), is prepared using an intermediate selected from

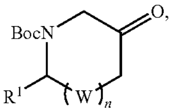 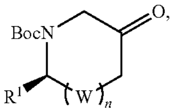 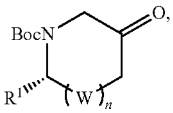

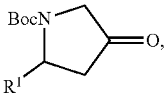 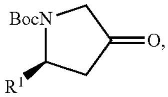 and 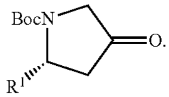

In some embodiments, the intermediate is selected from

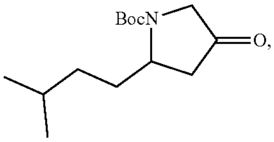 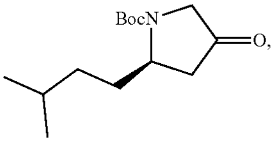

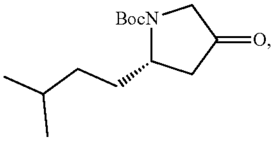 [SMILES: CC(C)CC[C@H]1CC(=O)CN1C(=O)OC(C)(C)C] 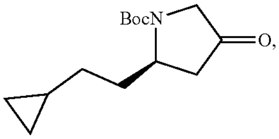

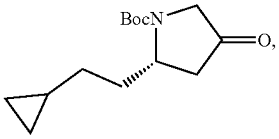

-continued

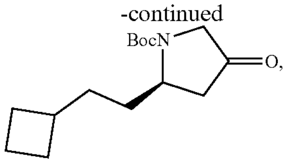

and

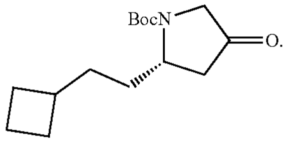

In some embodiments, the intermediate is

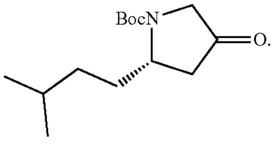

In some embodiments, for a compound of Formula (I), (I-1), (II), (II-1), (II-a), (II-a1), (III), (III-1), (IV), or (IV-1), $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$, $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is halogen. In some embodiments, $R^4$ is hydrogen; $R^5$ is selected from —OH, —$OR^{15}$ and —O—($C_{1-6}$ alkyl)-$OR^{15}$, and $R^6$ is halogen. In some embodiments, $R^4$ is hydrogen; $R^5$ is selected from —OH, —$OR^{15}$ and —O—($C_{1-6}$ alkyl)-$OR^{15}$, and $R^6$ is fluorine. In some embodiments, $R^4$ is hydrogen, $R^5$ is —OH, and $R^6$ is fluorine. In some embodiments, $R^4$ is hydrogen; $R^5$ is selected from —$OR^{15}$ and —O—($C_{1-6}$ alkyl)-$OR^{15}$; and $R^6$ is halogen. In some embodiments, $R^4$ is hydrogen; $R^5$ is selected from —$OR^{15}$ and —O—($C_{1-6}$ alkyl)-$OR^{15}$; and $R^6$ is fluorine.

In some embodiments, for a compound of Formula (I), (I-1), (II), (II-1), (II-a), (II-a1), (III), (III-1), (IV), or (IV-1), $J^1$ is N; $J^2$ is $CH_2$; $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is selected from halogen, —$OR^{12}$, and $C_{1-6}$ alkyl, wherein $C_{1-6}$ alkyl is optionally substituted with one, two, or three $R^{20}$. In some embodiments, $J^1$ is N; $J^2$ is $CH_2$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, $J^1$ is N; $J^2$ is $CH_2$; $R^4$ is hydrogen; $R^5$ is selected from —OH, —$OR^{15}$ and —O—($C_{1-6}$ alkyl)-$OR^{15}$; and $R^6$ is halogen. In some embodiments, $J^1$ is N; $J^2$ is $CH_2$; $R^4$ is hydrogen; $R^5$ is selected from —OH, —$OR^{15}$ and —O—($C_{1-6}$ alkyl)-$OR^{15}$; and $R^6$ is fluorine. In some embodiments, $J^1$ is N; $J^2$ is $CH_2$; $R^4$ is hydrogen, $R^5$ is —OH, and $R^6$ is fluorine. In some embodiments, $J^1$ is N; $J^2$ is $CH_2$; $R^4$ is hydrogen; $R^5$ is selected from —$OR^{15}$ and —O—($C_{1-6}$ alkyl)-$OR^{15}$; and $R^6$ is halogen. In some embodiments, $J^1$ is N; $J^2$ is $CH_2$; $R^4$ is hydrogen; $R^5$ is selected from —$OR^{15}$ and —O—($C_{1-6}$ alkyl)-$OR^{15}$, and $R^6$ is fluorine.

In some embodiments, for a compound of Formula (I), (I-1), (II), (II-1), (II-a), (II-a1), (III), (III-1), (IV), or (IV-1), $J^1$ is N; $J^2$ is $CH_2$; $R^7$ is selected from hydrogen and —($C_{1-6}$ alkyl)-$OR^{15}$; $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $J^1$ is N; $J^2$ is $CH_2$; $R^7$ is selected from hydrogen and —($C_{1-6}$ alkyl)-$OR^{15}$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is halogen. In some embodiments, $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is fluorine. In some embodiments, $J^1$ is N; $J^2$ is $CH_2$; $R^7$ is selected from hydrogen and —($C_{1-6}$ alkyl)-$OR^{15}$; $R^4$ is hydrogen, $R^5$ is —OH, and $R^6$ is fluorine. In some embodiments, $J^1$ is N; $J^2$ is $CH_2$; $R^7$ is hydrogen; $R^4$ is hydrogen, $R^5$ is —OH, and $R^6$ is fluorine. In some embodiments, $J^1$ is N; $J^2$ is $CH_2$; $R^7$ is —($C_{1-6}$ alkyl)-$OR^{15}$; $R^4$ is hydrogen, $R^5$ is —OH, and $R^6$ is fluorine. In some embodiments, $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$, and $R^6$ is halogen. In some embodiments, $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$, and $R^6$ is fluorine.

In some embodiments, for a compound of Formula (I), (I-1), (II), (II-1), (II-a), (II-a1), (III), (III-1), (IV), or (IV-1), $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$, $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is halogen. In some embodiments, $L^1$ is absent; $J^1$ is N; $J^2$ is $CH_2$; $R^7$ is selected from hydrogen and —($C_{1-6}$ alkyl)-$OR^{15}$;

$R^4$ is hydrogen; $R^5$ is selected from —OH, —$OR^{15}$ and —O—($C_{1-6}$ alkyl)-$OR^{15}$, and $R^6$ is halogen. In some embodiments, $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is fluorine. In some embodiments, $L^1$ is absent; $J^1$ is N; $J^2$ is $CH_2$; $R^7$ is selected from hydrogen and —($C_{1-6}$ alkyl)-$OR^{15}$; $R^4$ is hydrogen, $R^5$ is —OH, and $R^6$ is fluorine. In some embodiments, $L^1$ is absent; $J^1$ is N; $J^2$ is $CH_2$; $R^7$ is hydrogen; $R^4$ is hydrogen, $R^5$ is —OH, and $R^6$ is fluorine. In some embodiments, $L^1$ is absent; $J^1$ is N; $J^2$ is $CH_2$; $R^7$ is —($C_{1-6}$ alkyl)-$OR^{15}$; $R^4$ is hydrogen, $R^5$ is —OH, and $R^6$ is fluorine. In some embodiments, $L^1$ is absent; $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$, and $R^6$ is halogen. In some embodiments, $L^1$ is absent; $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$, and $R^6$ is fluorine.

In some embodiments, for a compound of Formula (I), (I-1), (II), (II-1), (II-a), (II-a1), (III), (III-1), (IV), or (IV-1), $L^1$ is absent or selected from $C_{1-6}$ alkylene, —O—, —S—, —N($R^{12}$)—, —C($NR^{12}$)—, —N($R^{12}$)S(O)$_2$—, —C(O)—, —C(O)N($R^{12}$)—, —N($R^{12}$)C(O)—, —S(O)—, —S(O)$_2$—, and —S(O)$_2$N($R^{12}$)—; $J^1$ is N; $J^2$ is $CH_2$; and $R^7$ is selected from hydrogen and —($C_{1-6}$ alkyl)-$OR^{15}$. In some embodiments, $L^1$ is absent or selected from $C_{1-6}$ alkylene, —O—, —S—, —N($R^{12}$)—, —C($NR^{12}$)—, —N($R^{12}$)S(O)$_2$—, —C(O)—, —C(O)N($R^{12}$)—, —N($R^{12}$)C(O)—, —S(O)—, —S(O)$_2$—, and —S(O)$_2$N($R^{12}$)—; $J^1$ is N; $J^2$ is $CH_2$; and $R^7$ is hydrogen. In some embodiments, $L^1$ is absent or selected from $C_{1-6}$ alkylene, —O—, —S—, —N($R^{12}$)—, —C($NR^{12}$)—, —N($R^{12}$)S(O)$_2$—, —C(O)—, —C(O)N($R^{12}$)—, —N($R^{12}$)C(O)—, —S(O)—, —S(O)$_2$—, and —S(O)$_2$N($R^{12}$)—; $J^1$ is N; $J^2$ is $CH_2$; and $R^7$ is —($C_{1-6}$ alkyl)-$OR^{15}$. In some embodiments, $L^1$ is absent or selected from $C_{1-3}$ alkylene, —O—, and —C(O)N($R^{12}$)—; $J^1$ is N; $J^2$ is $CH_2$; and $R^7$ is selected from hydrogen and —($C_{1-6}$ alkyl)-$OR^{15}$. In some embodiments, $L^1$ is absent or selected from $C_{1-3}$ alkylene, —O—, and —C(O)N($R^{12}$)—; $J^1$ is N; $J^2$ is $CH_2$; and $R^7$ is hydrogen. In some embodiments, $L^1$ is absent or selected from $C_{1-3}$ alkylene, —O—, and —C(O)N($R^{12}$)—; $J^1$ is N; $J^2$ is $CH_2$; and $R^7$ is —($C_{1-6}$ alkyl)-$OR^{15}$. In some embodiments, $L^1$ is absent; $J^1$ is N; $J^2$ is $CH_2$; and $R^7$ is selected from hydrogen and —($C_{1-6}$ alkyl)-$OR^{15}$. In some embodiments, $L^1$ is absent; $J^1$ is N; $J^2$ is $CH_2$; and $R^7$ is hydrogen. In some embodiments, $L^1$ is absent; $J^1$ is N; $J^2$ is $CH_2$; and $R^7$ is —($C_{1-6}$ alkyl)-$OR^{15}$.

In some embodiments, for a compound of Formula (I), (I-1), (II), (II-1), (II-a), (II-a1), (III), (III-1), (IV), or (IV-1), $L^1$ is absent or selected from $C_{1-6}$ alkylene, —O—, —S—, —N($R^{12}$)—, —C($NR^{12}$)—, —N($R^{12}$)S(O)$_2$—, —C(O)—, —C(O)N($R^{12}$)—, —N($R^{12}$)C(O)—, —S(O)—, —S(O)$_2$—, and —S(O)$_2$N($R^{12}$)—; $J^1$ is C; $J^2$ is CH; and $R^7$ is selected from hydrogen and —($C_{1-6}$ alkyl)-$OR^{15}$. In some embodiments, $L^1$ is absent or selected from $C_{1-6}$ alkylene, —O—, —S—, —N($R^{12}$)—, —C($NR^{12}$)—, —N($R^{12}$)S(O)$_2$—, —C(O)—, —C(O)N($R^{12}$)—, —N($R^{12}$)C(O)—, —S(O)—, —S(O)$_2$—, and —S(O)$_2$N($R^{12}$)—; $J^1$ is C; $J^2$ is CH; and $R^7$ is hydrogen. In some embodiments, $L^1$ is absent or selected from $C_{1-6}$ alkylene, —O—, —S—, —N($R^{12}$)—, —C($NR^{12}$)—, —N($R^{12}$)S(O)$_2$—, —C(O)—, —C(O)N($R^{12}$)—, —N($R^{12}$)C(O)—, —S(O)—, —S(O)$_2$—, and —S(O)$_2$N($R^{12}$)—; $J^1$ is C; $J^2$ is CH; and $R^7$ is —($C_{1-6}$ alkyl)-$OR^{15}$. In some embodiments, $L^1$ is absent or selected from $C_{1-3}$ alkylene, —O—, and —C(O)N($R^{12}$)—; $J^1$ is C; $J^2$ is CH; and $R^7$ is selected from hydrogen and —($C_{1-6}$ alkyl)-$OR^{15}$. In some embodiments, $L^1$ is absent or selected from $C_{1-3}$ alkylene, —O—, and —C(O)N($R^{12}$)—; $J^1$ is C; $J^2$ is CH; and $R^7$ is hydrogen. In some embodiments, $L^1$ is absent or selected from $C_{1-3}$ alkylene, —O—, and —C(O)N($R^{12}$)—; $J^1$ is C; $J^2$ is CH; and $R^7$ is —($C_{1-6}$ alkyl)-$OR^{15}$. In some embodiments, $L^1$ is absent; $J^1$ is C; $J^2$ is CH; and $R^7$ is selected from hydrogen and —($C_{1-6}$ alkyl)-$OR^{15}$. In some embodiments, $L^1$ is absent; $J^1$ is C; $J^2$ is CH; and $R^7$ is hydrogen. In some embodiments, $L^1$ is absent; $J^1$ is C; $J^2$ is CH; and $R^7$ is —($C_{1-6}$ alkyl)-$OR^{15}$.

In some embodiments, for a compound of Formula (II), (II-1), (II-a), (II-a1), (III), (III-1), (IV), or (IV-1), n is 0 or 1; $R^2$ is independently selected at each occurrence from hydrogen, halogen, $C_{1-6}$ alkyl, —$OR^{12}$, and —N($R^{12}$)($R^{13}$), or two $R^2$ attached to the same carbon atom are taken together to form oxo, =$NR^{12}$, or =C($R^{14}$)$_2$, wherein $C_{1-6}$ alkyl is optionally substituted with one, two, or three $R^{20}$; $R^4$ is selected from hydrogen, halogen, $C_{1-6}$ alkyl, $C_{3-6}$ carbocycle, 3- to 6-membered heterocycle, —$OR^{12}$, and —N($R^{12}$)($R^{13}$), wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is selected from halogen, —$OR^{12}$, and $C_{1-6}$ alkyl, wherein $C_{1-6}$ alkyl is optionally substituted with one, two, or three $R^{20}$. In some embodiments, W is $CH_2$; n is 0 or 1; each $R^2$ is hydrogen; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, $R^4$ is hydrogen; $R^5$ is selected from —OH, —$OR^{15}$ and —O—($C_{1-6}$ alkyl)-$OR^{15}$; and $R^6$ is halogen. In some embodiments, W is $CH_2$; n is 0 or 1; each $R^2$ is hydrogen; $R^4$ is hydrogen; $R^5$ is selected from —OH, —$OR^{15}$ and —O—($C_{1-6}$ alkyl)-$OR^{15}$, and $R^6$ is fluorine. In some embodiments, W is $CH_2$; n is 0 or 1; each $R^2$ is hydrogen; $R^4$ is hydrogen, $R^5$ is —OH, and $R^6$ is fluorine. In some embodiments, W is $CH_2$; n is 0 or 1; each $R^2$ is hydrogen; $R^4$ is hydrogen; $R^5$ is selected from —$OR^{15}$ and —O—($C_{1-6}$ alkyl)-$OR^{15}$; and $R^6$ is halogen. In some embodiments, W is $CH_2$; n is 0 or 1; each $R^2$ is hydrogen; $R^4$ is hydrogen; $R^5$ is selected from —$OR^{15}$ and —O—($C_{1-6}$ alkyl)-$OR^{15}$, and $R^6$ is fluorine.

In some embodiments, for a compound of Formula (II), (II-1), (II-a), (II-a1), (III), (III-1), (IV), or (IV-1), n is 0 or 1; $R^2$ is independently selected at each occurrence from hydrogen, halogen, $C_{1-6}$ alkyl, —$OR^{12}$, and —N($R^{12}$)($R^{13}$), or two $R^2$ attached to the same carbon atom are taken together to form oxo, =$NR^{12}$, or =C($R^{14}$)$_2$, wherein $C_{1-6}$ alkyl is optionally substituted with one, two, or three $R^{20}$; $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$; $R^4$ is selected from hydrogen, halogen, $C_{1-6}$ alkyl, $C_{3-6}$ carbocycle, 3- to 6-membered heterocycle, —$OR^{12}$, and —N($R^{12}$)($R^{13}$), wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, W is $CH_2$; n is 0 or 1; each $R^2$ is hydrogen; $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$, and $R^6$ is halogen. In some embodiments, W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is fluorine. In some embodiments, W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen, $R^5$ is —OH, and $R^6$ is fluorine. In some embodiments, W is $CH_2$; n is 0 or 1; each $R^2$ is hydrogen; $L^1$ is absent; $J^1$ is N; $J^2$ is $CH_2$; $R^7$ is hydrogen; $R^4$ is hydrogen, $R^5$ is —OH, and $R^6$ is fluorine. In some embodiments, $L^1$ is absent; $J^1$ is N; $J^2$ is $CH_2$; $R^7$ is —($C_{1-6}$ alkyl)-$OR^{15}$; $R^4$ is hydrogen, $R^5$ is —OH, and $R^6$ is fluorine. In some embodiments, W is $CH_2$; n is 0 or 1; each $R^2$ is hydrogen; $L^1$ is absent; $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$; and $R^6$ is halogen. In some embodiments, W is $CH_2$; n is 0 or 1; each $R^2$ is hydrogen; $L^1$ is absent; $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$; and $R^6$ is fluorine.

In some embodiments, for a compound of Formula (II), (II-1), (II-a), (II-a1), (III), (III-1), (IV), or (IV-1), $R^1$ is selected from $C_{2-6}$ alkyl and —$C_{0-6}$ alkyl-($C_{3-8}$ carbocycle), each of which is optionally substituted with one, two, or three $R^{20}$, $R^3$ is selected from hydrogen, $C_{1-6}$ alkyl, —$C_{0-6}$ alkyl-(3- to 12-membered heterocycle), —C(O) $OR^{12}$, and —C(O)O—($C_{1-6}$ alkyl)-$OR^{15}$, wherein $C_{1-6}$ alkyl and —$C_{0-6}$ alkyl-(3- to 12-membered heterocycle) are optionally substituted with one, two, or three $R^{20}$; $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^1$ is selected from $C_{2-6}$ alkyl and —$C_{0-3}$ alkyl-($C_{3-6}$ carbocycle); $R^3$ is hydrogen; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is halogen. In some embodiments, $R^1$ is selected from $C_{2-6}$ alkyl and —$C_{0-3}$ alkyl-($C_{3-6}$ carbocycle); $R^3$ is hydrogen; $R^4$ is hydrogen; $R^5$ is selected from —OH, —$OR^{15}$ and —O—($C_{1-6}$ alkyl)-$OR^{15}$; and $R^6$ is halogen. In some embodiments, $R^1$ is selected from $C_{2-6}$ alkyl and —$C_{0-3}$ alkyl-($C_{3-6}$ carbocycle); $R^3$ is hydrogen; $R^4$ is hydrogen; $R^5$ is selected from —OH, —$OR^{15}$ and —O—($C_{1-6}$ alkyl)-$OR^{15}$; and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; $R^4$ is hydrogen; $R^5$ is selected from —$OR^{15}$ and —O—($C_{1-6}$ alkyl)-$OR^{15}$, and $R^6$ is halogen. In some embodiments, $R^1$ is selected from $C_{2-6}$ alkyl and —$C_{0-3}$ alkyl-($C_{3-6}$ carbocycle); $R^3$ is hydrogen; $R^4$ is hydrogen; $R^5$ is selected from —$OR^{15}$ and —O—($C_{1-6}$ alkyl)-$OR^{15}$, and $R^6$ is fluorine.

In some embodiments, for a compound of Formula (II), (II-1), (II-a), (II-a1), (III), (III-1), (IV), or (IV-1), $R^1$ is selected from $C_{2-6}$ alkyl and —$C_{0-6}$ alkyl-($C_{3-8}$ carbocycle), each of which is optionally substituted with one, two, or three $R^{20}$, $R^3$ is selected from hydrogen, $C_{1-6}$ alkyl, —$C_{0-6}$ alkyl-(3- to 12-membered heterocycle), —C(O) $OR^{12}$, and —C(O)O—($C_{1-6}$ alkyl)-$OR^{15}$, wherein $C_{1-6}$ alkyl and —$C_{0-6}$ alkyl-(3- to 12-membered heterocycle) are optionally substituted with one, two, or three $R^{20}$; $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$; $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^1$ is selected from $C_{2-6}$ alkyl and —$C_{0-3}$ alkyl-($C_{3-6}$ carbocycle); $R^3$ is hydrogen; $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is halogen. In some embodiments, $R^1$ is selected from $C_{2-6}$ alkyl and —$C_{0-3}$ alkyl-($C_{3-6}$ carbocycle); $R^3$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is halogen. In some embodiments, $R^1$ is selected from $C_{2-6}$ alkyl and —$C_{0-3}$ alkyl-($C_{3-6}$ carbocycle); $R^3$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; $L^1$ is absent; $J^1$ is N; $J^2$ is $CH_2$; $R^7$ is hydrogen; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; $L^1$ is absent; $J^1$ is N; $J^2$ is $CH_2$; $R^7$ is —($C_{1-6}$ alkyl)-$OR^{15}$; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; $L^1$ is absent; $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$; and $R^6$ is halogen. In some embodiments, $R^1$ is selected from $C_{2-6}$ alkyl and —$C_{0-3}$ alkyl-($C_{3-6}$ carbocycle); $R^3$ is hydrogen; $L^1$ is absent; $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$, and $R^6$ is fluorine.

In some embodiments, for a compound of Formula (II), (II-1), (II-a), (II-a1), (III), (III-1), (IV), or (IV-1), $R^1$ is selected from $C_{2-6}$ alkyl and —$C_{0-6}$ alkyl-($C_{3-8}$ carbocycle), each of which is optionally substituted with one, two, or three $R^{20}$, $R^3$ is selected from hydrogen, $C_{1-6}$ alkyl, —$C_{0-6}$ alkyl-(3- to 12-membered heterocycle), —C(O) $OR^{12}$, and —C(O)O—($C_{1-6}$ alkyl)-$OR^{15}$, wherein $C_{1-6}$ alkyl and —$C_{0-6}$ alkyl-(3- to 12-membered heterocycle) are optionally substituted with one, two, or three $R^{20}$, n is 0 or 1; $R^2$ is independently selected at each occurrence from hydrogen, halogen, $C_{1-6}$ alkyl, —$OR^{12}$, and —$N(R^{12})(R^{13})$, or two $R^2$ attached to the same carbon atom are taken together to form oxo, =$NR^{12}$, or =$C(R^{14})_2$, wherein $C_{1-6}$ alkyl is optionally substituted with one, two, or three $R^{20}$; $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$, $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, $R^1$ is selected from $C_{2-6}$ alkyl and —$C_{0-3}$ alkyl-($C_{3-6}$ carbocycle); $R^3$ is hydrogen; $R^4$ is hydrogen; $R^5$ is selected from —OH, —$OR^{15}$ and —O—($C_{1-6}$ alkyl)-$OR^{15}$; and $R^6$ is halogen. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $R^4$ is hydrogen; $R^5$ is selected from —OH, —$OR^{15}$ and —O—($C_{1-6}$ alkyl)-$OR^{15}$; and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $R^4$ is hydrogen; $R^5$ is selected from —$OR^{15}$ and —O—($C_{1-6}$ alkyl)-$OR^{15}$, and $R^6$ is halogen. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $R^4$ is hydrogen; $R^5$ is selected from —$OR^{15}$ and —O—($C_{1-6}$ alkyl)-$OR^{15}$, and $R^6$ is fluorine.

In some embodiments, for a compound of Formula (II), (II-1), (II-a), (II-a1), (III), (III-1), (IV), or (IV-1), $R^1$ is selected from $C_{2-6}$ alkyl and —$C_{0-6}$ alkyl-($C_{3-8}$ carbocycle), each of which is optionally substituted with one, two, or three $R^{20}$; $R^3$ is selected from hydrogen, $C_{1-6}$ alkyl, —$C_{0-6}$ alkyl-(3- to 12-membered heterocycle), —C(O) $OR^{12}$, and —C(O)O—($C_{1-6}$ alkyl)-$OR^{15}$, wherein $C_{1-6}$ alkyl and —$C_{0-6}$ alkyl-(3- to 12-membered heterocycle) are optionally substituted with one, two, or three $R^{20}$, n is 0 or 1; $R^2$ is independently selected at each occurrence from hydrogen, halogen, $C_{1-6}$ alkyl, —$OR^{12}$, and —$N(R^{12})(R^{13})$, or two $R^2$ attached to the same carbon atom are taken together to form oxo, =$NR^{12}$, or =$C(R^{14})_2$, wherein $C_{1-6}$ alkyl is optionally substituted with one, two, or three $R^{20}$, $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$, $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$, $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is halogen. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is halogen. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $L^1$ is absent; $J^1$ is N; $J^2$ is $CH_2$; $R^7$ is hydrogen; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; $L^1$ is absent; $J^1$ is N; $J^2$ is $CH_2$; $R^7$ is —($C_{1-6}$ alkyl)-$OR^{15}$; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $L^1$ is absent; $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$, and $R^6$ is halogen. In some embodiments, $R^1$ is selected from $C_{2-6}$ alkyl and —$C_{0-3}$ alkyl-($C_{3-6}$ carbocycle); $R^3$ is hydrogen; W is $CH_2$; n is 0 or 1; each $R^2$ is hydrogen; $L^1$ is absent; $J^1$ is N; $J^2$ is $CH_2$; $R^7$ is hydrogen; $R^4$ is hydrogen; $R^5$ is selected from —$OR^{15}$ and —O—($C_{1-6}$ alkyl)-$OR^{15}$; and $R^6$ is fluorine.

In some embodiments, for a compound of Formula (II), (II-1), (II-a), (II-a1), (III), (III-1), (IV), or (IV-1), $R^1$ is selected from $C_{2-6}$ alkyl and —$C_{0-6}$ alkyl-($C_{3-8}$ carbocycle), each of which is optionally substituted with one, two, or three $R^{20}$, $R^3$ is selected from —C(O)$OR^{12}$, —C(O)$OCH_2OC(O)R^{12}$, —C(O)OCH($CH_3$)OC(O)$R^{12}$, —$CH_2OC(O)R^{12}$, —CH($CH_3$)OC(O)$R^{12}$, —P(O)$(OH)_2$, and —$CH_2P(O)(OH)_2$; $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^1$ is selected from $C_{2-6}$ alkyl and —$C_{0-3}$ alkyl-($C_{3-6}$ carbocycle); $R^3$ is selected from —C(O)$OR^{12}$, —C(O)$OCH_2OC(O)R^{12}$, —C(O)OCH($CH_3$)OC(O)$R^{12}$, —$CH_2OC(O)R^{12}$, —CH($CH_3$)OC(O)$R^{12}$, —P(O)$(OH)_2$, and —$CH_2P(O)(OH)_2$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O)$OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $R^4$ is hydrogen; $R^5$ is selected from —OH, —$OR^{15}$ and —O—($C_{1-6}$ alkyl)-$OR^{15}$, and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $R^4$ is hydrogen; $R^5$ is selected from —OH, —$OR^{15}$ and —O—($C_{1-6}$ alkyl)-$OR^{15}$, and $R^6$ is fluorine. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $R^4$ is hydrogen, $R^5$ is —OH, and $R^6$ is fluorine.

In some embodiments, for a compound of Formula (II), (II-1), (II-a), (II-a1), (III), (III-1), (IV), or (IV-1), $R^1$ is selected from $C_{2-6}$ alkyl and —$C_{0-6}$ alkyl-($C_{3-8}$ carbocycle), each of which is optionally substituted with one, two, or three $R^{20}$, $R^3$ is selected from —C(O)$OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$; $R^4$ is selected from hydrogen, halogen, $C_{1-6}$ alkyl, $C_{3-6}$ carbocycle, 3- to 6-membered heterocycle, —$OR^{12}$, and —N($R^{12}$)($R^{13}$), wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^1$ is selected from $C_{2-6}$ alkyl and —$C_{0-3}$ alkyl-($C_{3-6}$ carbocycle); $R^3$ is selected from —C(O)$OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $L^1$ is absent or selected from $C_{1-3}$ alkylene, —O—, and —C(O)N($R^{12}$)—; $J^1$ is N; $J^2$ is $CH_2$; $R^7$ is selected from hydrogen and —($C_{1-6}$ alkyl)-$OR^{15}$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH(CH_3)OC(O)R^{12}$, —$CH_2OC(O)R^{12}$, —$P(O)(OH)_2$, and —$CH_2P(O)(OH)_2$; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$, and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$, and $R^6$ is fluorine. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $L^1$ is absent; $J^1$ is N; $J^2$ is $CH_2$; $R^7$ is selected from hydrogen and —($C_{1-6}$ alkyl)-$OR^{15}$; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $L^1$ is absent; $J^1$ is N; $J^2$ is $CH_2$; $R^7$ is hydrogen; $R^4$ is hydrogen, $R^5$ is —OH, and $R^6$ is fluorine.

In some embodiments, for a compound of Formula (II), (II-1), (II-a), (II-a1), (III), (III-1), (IV), or (IV-1), $R^1$ is selected from $C_{2-6}$ alkyl and —$C_{0-6}$ alkyl-($C_{3-8}$ carbocycle), each of which is optionally substituted with one, two, or three $R^{20}$, $R^3$ is selected from —C(O)$OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; n is 0 or 1; $R^2$ is independently selected at each occurrence from hydrogen, halogen, $C_{1-6}$ alkyl, —$OR^{12}$, and —N($R^{12}$)($R^{13}$), or two $R^2$ attached to the same carbon atom are taken together to form oxo, =N$R^{12}$, or =C($R^{14}$)$_2$, wherein $C_{1-6}$ alkyl is optionally substituted with one, two, or three $R^{20}$; $R^4$ is selected from hydrogen, halogen, $C_{1-6}$ alkyl, $C_{3-6}$ carbocycle, 3- to 6-membered heterocycle, —$OR^{12}$, and —N($R^{12}$)($R^{13}$), wherein $C_{1-6}$ alkyl, $C_{3-6}$ carbocycle, and 3- to 6-membered heterocycle are optionally substituted with one, two, or three $R^{20}$, $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$; and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; $R^4$ is hydrogen; $R^5$ is selected from —OH, —$OR^{15}$ and —O—($C_{1-6}$ alkyl)-$OR^{15}$; and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O)$OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $R^4$ is hydrogen; $R^5$ is selected from —OH, —$OR^{15}$ and —O—($C_{1-6}$ alkyl)-$OR^{15}$; and $R^6$ is fluorine. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$;

n is 0 or 1; each $R^2$ is hydrogen; $R^4$ is hydrogen; $R^5$ is selected from —$OR^{15}$ and —O—($C_{1-6}$ alkyl)-$OR^{15}$; and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $R^4$ is hydrogen; $R^5$ is selected from —$OR^{15}$ and —O—($C_{1-6}$ alkyl)-$OR^{15}$; and $R^6$ is fluorine.

In some embodiments, for a compound of Formula (II), (II-1), (II-a), (II-a1), (III), (III-1), (IV), or (IV-1), $R^1$ is selected from $C_{2-6}$ alkyl and —$C_{0-6}$ alkyl-($C_{3-8}$ carbocycle), each of which is optionally substituted with one, two, or three $R^{20}$, $R^3$ is selected from —$C(O)OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; n is 0 or 1; $R^2$ is independently selected at each occurrence from hydrogen, halogen, $C_{1-6}$ alkyl, —$OR^{12}$, and —$N(R^{12})(R^{13})$, or two $R^2$ attached to the same carbon atom are taken together to form oxo, =$NR^{12}$, or =$C(R^{14})_2$, wherein $C_{1-6}$ alkyl is optionally substituted with one, two, or three $R^{20}$, $L^1$ is absent or selected from $C_{1-3}$ alkylene, —O—, and —$C(O)N(R^{12})$—; $J^1$ is N; $J^2$ is $CH_2$; $R^7$ is selected from hydrogen and —($C_{1-6}$ alkyl)-$OR^{15}$; $R^4$ is selected from hydrogen, halogen, $C_{1-6}$ alkyl, $C_{3-6}$ carbocycle, 3- to 6-membered heterocycle, —$OR^{12}$, and —$N(R^{12})(R^{13})$, wherein $C_{1-6}$ alkyl, $C_{3-6}$ carbocycle, and 3- to 6-membered heterocycle are optionally substituted with one, two, or three $R^{20}$; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is selected from halogen, —$OR^{12}$, and $C_{1-6}$ alkyl, wherein $C_{1-6}$ alkyl is optionally substituted with one, two, or three $R^{20}$. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $L^1$ is absent or selected from $C_{1-3}$ alkylene, —O—, and —$C(O)N(R^{12})$—; $J^1$ is N; $J^2$ is $CH_2$; $R^7$ is selected from hydrogen and —($C_{1-6}$ alkyl)-$OR^{15}$; $R^4$ is hydrogen; $R^5$ is selected from halogen, —$OR^{12}$, —$OR^{15}$, —O—($C_{1-6}$ alkyl)-$OR^{15}$, and $C_{1-6}$ alkyl, wherein $C_{1-6}$ alkyl is optionally substituted with one, two, or three $R^{20}$, and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen; $R^5$ is selected from —OH, —$OR^{15}$ and —O—($C_{1-6}$ alkyl)-$OR^{15}$; and $R^6$ is halogen. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$, $R^4$ is hydrogen; $R^5$ is selected from —OH, —$OR^{15}$ and —O—($C_{1-6}$ alkyl)-$OR^{15}$, and $R^6$ is fluorine. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $L^1$ is absent; $J^1$ is N; $J^2$ is $CH_2$; $R^7$ is selected from hydrogen and —($C_{1-6}$ alkyl)-$OR^{15}$; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is selected from —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$; W is $CH_2$; n is 0 or 1; each $R^2$ is hydrogen; $L^1$ is absent; $J^1$ is N; $J^2$ is $CH_2$; $R^7$ is hydrogen; $R^4$ is hydrogen, $R^5$ is —OH, and $R^6$ is fluorine. In some embodiments, $R^1$ is selected from $C_{2-6}$ alkyl and —$C_{0-3}$ alkyl-($C_{3-6}$ carbocycle); $R^3$ is —$C(O)R^{12}$; $R^{12}$ is $C_{1-6}$ alkyl optionally substituted with —$NHC(O)CH(CH_3)$ $NH_2$, —$NHC(O)CH(CH_3)N(CH_3)_2$, —$NHC(O)CH(CH(CH_3)_2)$ $NH_2$, or —$NHC(O)CH(CH(CH_3)_2)N(CH_3)_2$; W is $CH_2$; n is 0 or 1; each $R^2$ is hydrogen; $L^1$ is absent; $J^1$ is N; $J^2$ is $CH_2$; $R^7$ is hydrogen; $R^4$ is hydrogen, $R^5$ is —OH, and $R^6$ is fluorine.

In certain aspects, the present disclosure provides a compound of the formula:

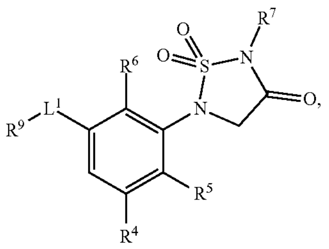

or a pharmaceutically acceptable salt or solvate thereof, wherein:

$L^1$ is absent or selected from $C_{1-6}$ alkylene, —O—, —S—, —$N(R^{12})$—, —$C(NR^{12})$—, —$N(R^{12})S(O)_2$—, —C(O)—, —$C(O)N(R^{12})$—, —$N(R^{12})C(O)$—, —S(O)—, —$S(O)_2$—, and —$S(O)_2N(R^{12})$—; wherein $C_{1-6}$ alkylene is optionally substituted with one, two, or three $R^{20}$;

$R^9$ is selected from $C_{3-12}$ carbocycle and 3- to 12-membered heterocycle, each of which is (i) optionally substituted with one, two, or three $R^{20}$ and (ii) optionally substituted with (5-methyl-2-oxo-1,3-dioxol-4-yl)methyl, —$OP(O)(OH)_2$, —$OCH_2OP(O)(OH)_2$, —$OC(O)N(R^{12})(R^{13})$, —$OCH_2OC(O)$ $OR^{12}$, —$OCH(CH_3)OC(O)OR^{12}$, —$OC(O)CH_2NH_2$, —$OC(O)CH(CH_3)NH_2$, —$OCH_2OC(O)R^{12}$, —$OCH(CH_3)OC(O)R^{12}$, —$OC(O)R^{12}$, —$OC(O)OR^{12}$, —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, or —$CH_2P(O)(OH)_2$;

$R^4$ is hydrogen;

$R^5$ is selected from —OH, —$OP(O)(OH)_2$, —$OCH_2OP(O)(OH)_2$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)$ $NH_2$, —$OCH_2OC(O)R^{12}$, —$OCH(CH_3)OC(O)R^{12}$, —$OC(O)R^{12}$, and —$OC(O)OR^{12}$;

$R^6$ is halogen;

$R^7$ is selected from hydrogen, —$CH_2OC(O)R^{12}$, —$CH(CH_3)OC(O)R^{12}$, —$P(O)(OH)_2$, and —$CH_2P(O)(OH)_2$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —$S(=O)(=NR^{22})N(R^{22})(R^{23})$, and —$OCH_2C(O)$ $OR^{22}$, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —OC(O) $R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ---- indicates a single or double bond such that all valences are satisfied;

wherein at least one of $R^5$, $R^7$, or $R^9$ comprises (5-methyl-2-oxo-1,3-dioxol-4-yl)methyl, —$OP(O)(OH)_2$, —$OCH_2OP(O)(OH)_2$, —$OC(O)N(R^{12})(R^{13})$, —$OCH_2OC(O)$ $OR^{12}$, —$OCH(CH_3)OC(O)OR^{12}$, —$OC(O)CH_2NH_2$, —$OC(O)CH(CH_3)$ $NH_2$, —$OCH_2OC(O)R^{12}$, —$OCH(CH_3)OC(O)R^{12}$, —OC(O)$R^{12}$, —$OC(O)OR^{12}$, —C(O) $OR^{12}$, —C(O)$OCH_2OC(O)R^{12}$, —$C(O)OCH(CH_3)OC(O)R^{12}$, —$CH_2OC(O)R^{12}$, —$CH(CH_3)OC(O)R^{12}$, —P(O)$(OH)_2$, or —$CH_2P(O)(OH)_2$.

In certain aspects, the present disclosure provides a compound of the formula:

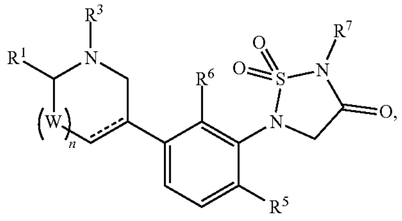

or a pharmaceutically acceptable salt or solvate thereof, wherein:

W is $CH_2$;

n is 0 or 1;

$R^1$ is selected from

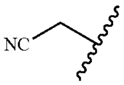, 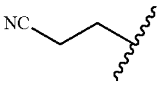, 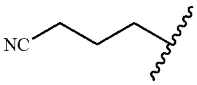,

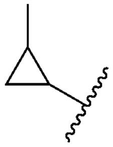, 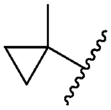, 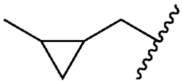,

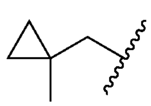, 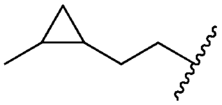,

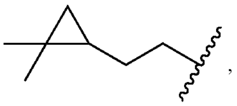, 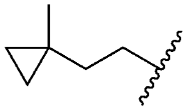,

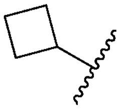, 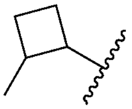, 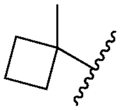,

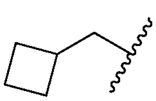, 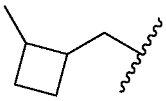, 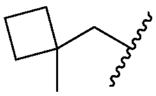,

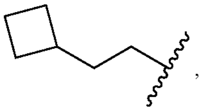, 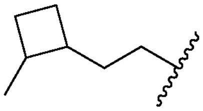,

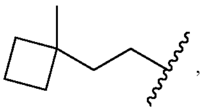, 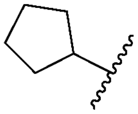, 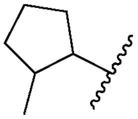,

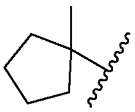, 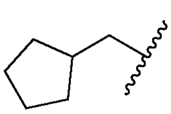, 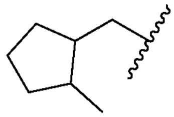,

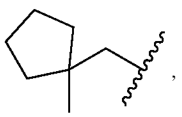, 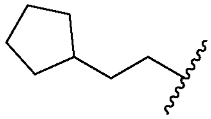,

-continued

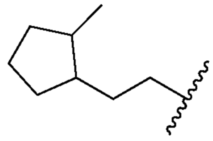, and 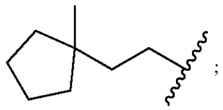;

$R^3$ is hydrogen, —C(O) $OR^{12}$, —$C(O)OCH_2OC(O)R^{12}$, —$C(O)OCH(CH_3)OC(O)R^{12}$, —$CH_2OC(O)R^{12}$, —$CH(CH_3)OC(O)R^{12}$, —$P(O)(OH)_2$, and —$CH_2P(O)(OH)_2$;

$R^5$ is selected from —OH, —$OP(O)(OH)_2$, —$OCH_2OP(O)(OH)_2$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)$ $NH_2$, —$OCH_2OC(O)R^{12}$, —$OCH(CH_3)OC(O)R^{12}$, —$OC(O)R^{12}$, and —$OC(O)OR^{12}$;

$R^6$ is halogen;

$R^7$ is selected from hydrogen, —$CH_2OC(O)R^{12}$, —$CH(CH_3)OC(O)R^{12}$, —$P(O)(OH)_2$, and —$CH_2P(O)(OH)_2$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —$S(=O)(=NR^{22})N(R^{22})(R^{23})$, and —$OCH_2C(O)$ $OR^{22}$, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ------ indicates a single or double bond such that all valences are satisfied.

In some embodiments, for the compound in the preceding paragraph, (i) $R^3$ is not hydrogen; (ii) $R^5$ is not —OH, or (iii) $R^7$ is not hydrogen. In some embodiments, $R^3$ is hydrogen, $R^5$ is —OH, and $R^7$ is hydrogen. In some embodiments, ------ indicates a double bond.

In certain aspects, the present disclosure provides a compound of the formula:

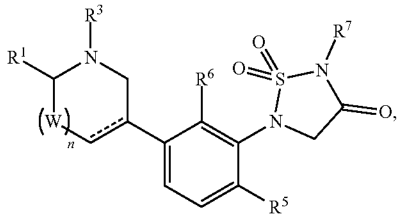

or a pharmaceutically acceptable salt or solvate thereof, wherein:

W is $CH_2$;

n is 0 or 1;

$R^1$ is selected from

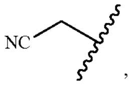, 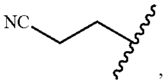, 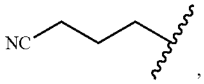,

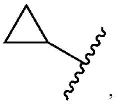, 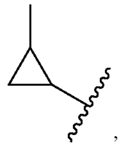, 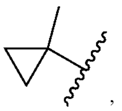, 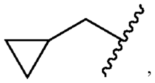,

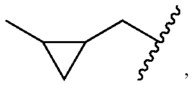, 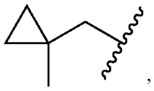, 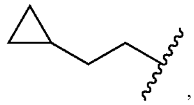,

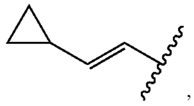, 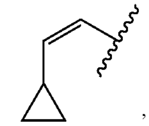,

-continued

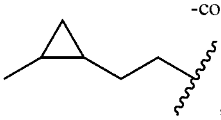,
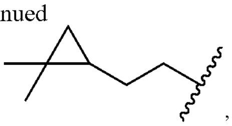,
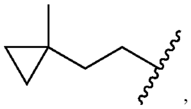,
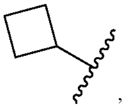,
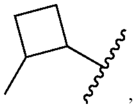,
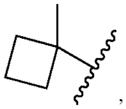,
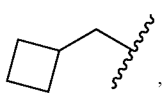,
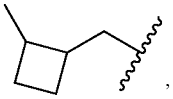,
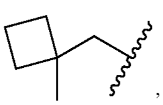,
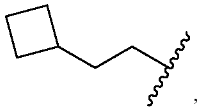,
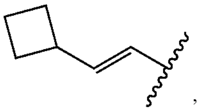,
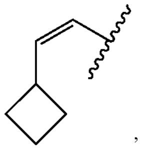,
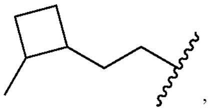,
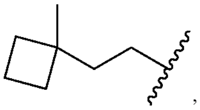,
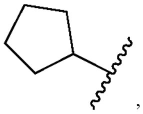,
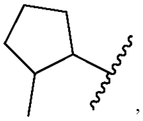,
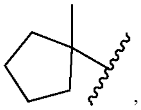,
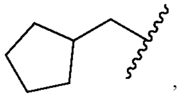,
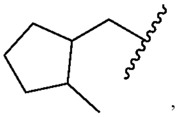,
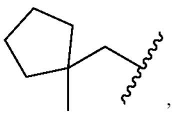,
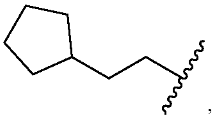,
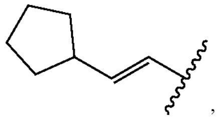,
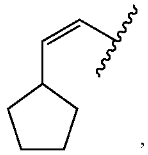,
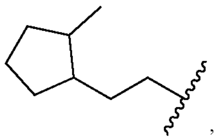, and
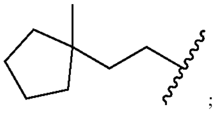;

$R^3$ is hydrogen, —C(O) $OR^{12}$, —C(O)$OCH_2OC(O)R^{12}$, —C(O)OCH($CH_3$)OC(O)$R^{12}$, —$CH_2OC(O)R^{12}$, —CH($CH_3$)OC(O)$R^{12}$, —P(O)$(OH)_2$, and —$CH_2$P(O)$(OH)_2$;

$R^5$ is selected from —OH, —OP(O)$(OH)_2$, —$CH_2$OP(O)$(OH)_2$, —OC(O)N($R^{12}$)($R^{13}$), —$OCH_2OC(O)OR^{12}$, —OCH($CH_3$)OC(O)$OR^{12}$, —OC(O)$CH_2NH_2$, —OC(O)CH($CH_3$) $NH_2$, —$OCH_2OC(O)R^{12}$, —OCH($CH_3$)OC(O)$R^{12}$, —OC(O)$R^{12}$, and —OC(O)$OR^{12}$;

$R^6$ is halogen;

$R^7$ is selected from hydrogen, —$CH_2OC(O)R^{12}$, —CH($CH_3$)OC(O)$R^{12}$, —P(O)$(OH)_2$, and —$CH_2$P(O)$(OH)_2$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), =$NR^{22}$, =C$(R^{21})_2$, —C(O) $OR^{22}$, —OC(O)N($R^{22}$)($R^{23}$), —N($R^{22}$)C(O)N($R^{22}$)($R^{23}$), —N($R^{22}$)C(O) $OR^{22}$, —N($R^{22}$)S$(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S$(O)_2R^{22}$, —S(O)($NR^{22}$)$R^{22}$, —S$(O)_2$N($R^{22}$)($R^{23}$)—, —S(=O)(=$NR^{22}$)N($R^{22}$)($R^{23}$), and —$OCH_2$C(O) $OR^{22}$, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —N($R^{22}$)($R^{23}$), =$NR^{22}$, =C$(R^{21})_2$, —C(O) $OR^{22}$, —OC(O)N($R^{22}$)($R^{23}$), —N($R^{22}$)C(O)N($R^{22}$)($R^{23}$), —N($R^{22}$)C(O) $OR^{22}$, —N($R^{22}$)S$(O)_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S$(O)_2R^{22}$, —S(O)($NR^{22}$)$R^{22}$, —S$(O)_2$N($R^{22}$)($R^{23}$), and —S(=O)(=$NR^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ------ indicates a single or double bond such that all valences are satisfied;

wherein (i) $R^3$ is not hydrogen; (ii) $R^5$ is not —OH, or (iii) $R^7$ is not hydrogen.

In certain aspects, the present disclosure provides a compound of the formula:

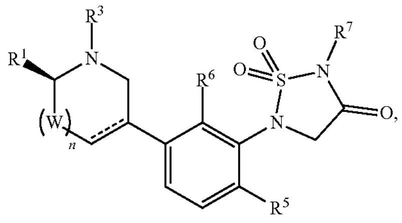

or a pharmaceutically acceptable salt or solvate thereof, wherein:

W is $CH_2$;

n is 0 or 1;

$R^1$ is selected from

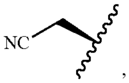, 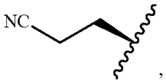, 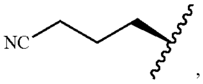,

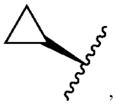, 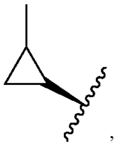, 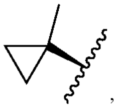, 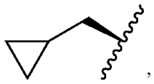,

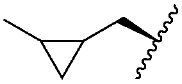, 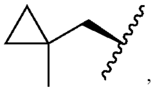, 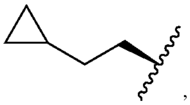,

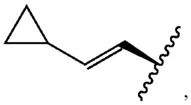, 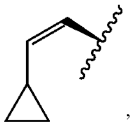,

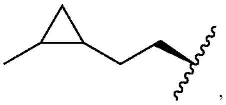, 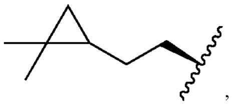,

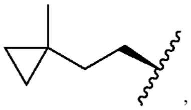, 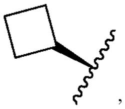, 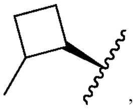,

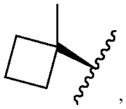, 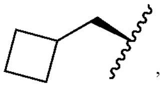, 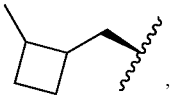,

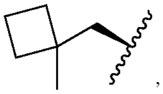, 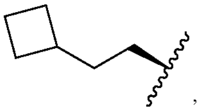,

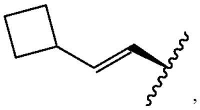, 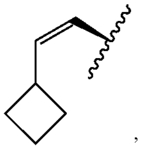,

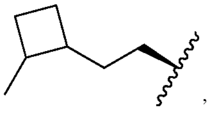, 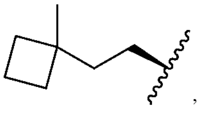,

-continued

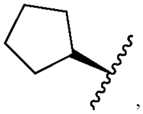, 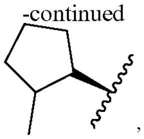, 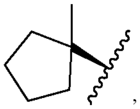,

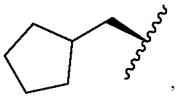, 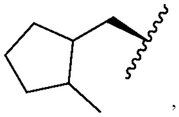, 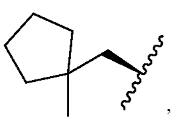,

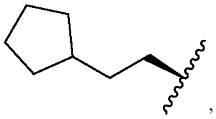, 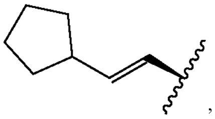,

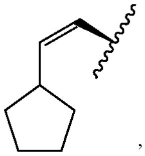, 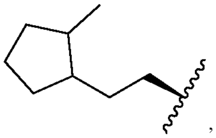, and

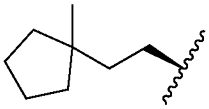;

$R^3$ is selected from hydrogen, —C(O) $OR^{12}$, —C(O)$OCH_2OC(O)R^{12}$, —C(O)$OCH(CH_3)OC(O)R^{12}$, —$CH_2OC(O)R^{12}$, —$CH(CH_3)OC(O)R^{12}$, —P(O)$(OH)_2$, and —$CH_2P(O)(OH)_2$;

$R^5$ is selected from —OH, —$OP(O)(OH)_2$, —$OCH_2OP(O)(OH)_2$, —$OC(O)N(R^{12})(R^{13})$, —$OCH_2OC(O)OR^{12}$, —$OCH(CH_3)OC(O)OR^{12}$, —$OC(O)CH_2NH_2$, —$OC(O)CH(CH_3)$ $NH_2$, —$OCH_2OC(O)R^{12}$, —$OCH(CH_3)OC(O)R^{12}$, —$OC(O)R^{12}$, and —$OC(O)OR^{12}$;

$R^6$ is halogen;

$R^7$ is selected from hydrogen, —$CH_2OC(O)R^{12}$, —$CH(CH_3)OC(O)R^{12}$, —$P(O)(OH)_2$, and —$CH_2P(O)(OH)_2$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O)$OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —$OC(O)R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$—, —$S(=O)(=NR^{22})N(R^{22})(R^{23})$, and —$OCH_2C(O)$ $OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —OC(O) $R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})$ $(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ------ indicates a single or double bond such that all valences are satisfied.

In some embodiments, for the compound in the preceding paragraph, (i) $R^3$ is not hydrogen; (ii) $R^5$ is not —OH, or (iii) $R^7$ is not hydrogen. In some embodiments, $R^3$ is hydrogen, $R^5$ is —OH, and $R^7$ is hydrogen. In some embodiments, ------ indicates a double bond.

In certain aspects, the present disclosure provides a compound of the formula:

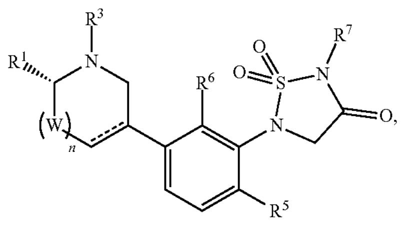

or a pharmaceutically acceptable salt or solvate thereof, wherein:

W is $CH_2$;

n is 0 or 1;

$R^1$ is selected from

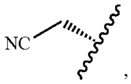 , 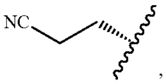 , 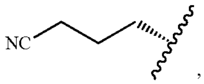 ,

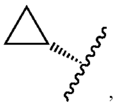 , 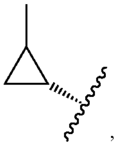 , 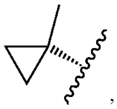 , 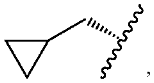 ,

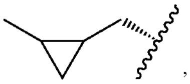 , 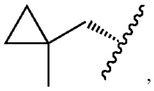 , 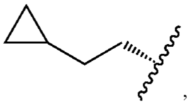 ,

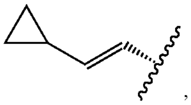 , 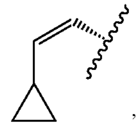 ,

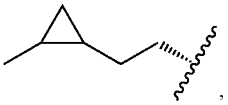 , 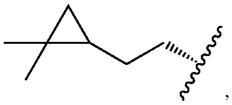 ,

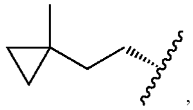 , 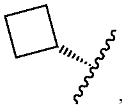 , 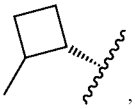 ,

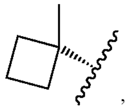 , 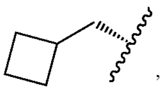 , 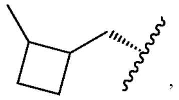 ,

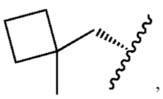 , 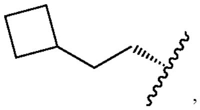 ,

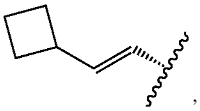 , 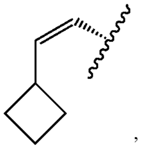 ,

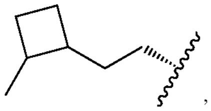 , 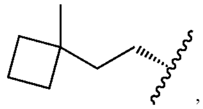 ,

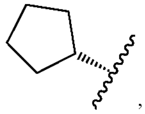 , 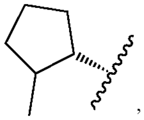 , 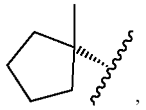 ,

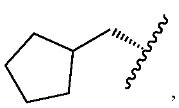 , 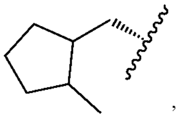 , 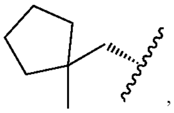 ,

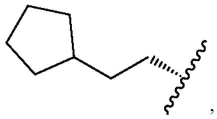 , 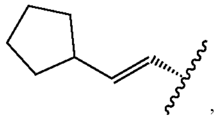 ,

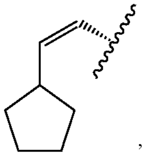 , 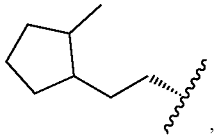 , and

-continued

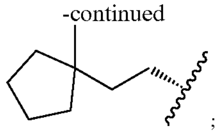

;

$R^3$ is selected from hydrogen, —C(O) $OR^{12}$, —C(O) $OCH_2OC(O)R^{12}$, —$C(O)OCH(CH_3)OC(O)R^{12}$, —$CH_2OC(O)R^{12}$, —$CH(CH_3)OC(O)R^{12}$, —P(O) $(OH)_2$, and —$CH_2P(O)(OH)_2$;

$R^5$ is selected from —OH, —$OP(O)(OH)_2$, —$OCH_2OP$ $(O)(OH)_2$, —$OC(O)N(R^{12})(R^{13})$, —$OCH_2OC(O)$ $OR^{12}$, —$OCH(CH_3)OC(O)OR^{12}$, —$OC(O)CH_2NH_2$, —$OC(O)CH(CH_3)$ $NH_2$, —$OCH_2OC(O)R^{12}$, —OCH $(CH_3)OC(O)R^{12}$, —$OC(O)R^{12}$, and —$OC(O)OR^{12}$;

$R^6$ is halogen;

$R^7$ is selected from hydrogen, —$CH_2OC(O)R^{12}$, —CH $(CH_3)OC(O)R^{12}$, —$P(O)(OH)_2$, and —$CH_2P(O)$ $(OH)_2$;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})$ $(R^{23})$, —$N(R^{22})C(O)$ $OR^{22}$, —$N(R^{22})S(O)_2R^{22}$, —$C(O)R^{22}$, —$S(O)R^{22}$, —$OC(O)R^{22}$, —$C(O)N(R^{22})$ $(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})$ $(R^{23})$—, —$S(=O)(=NR^{22})N(R^{22})(R^{23})$, and —$OCH_2C(O)$ $OR^{22}$, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —OC(O) $R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})$ $(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ------ indicates a single or double bond such that all valences are satisfied.

In some embodiments, for the compound in the preceding paragraph, (i) $R^3$ is not hydrogen; (ii) $R^5$ is not —OH, or (iii) $R^7$ is not hydrogen. In some embodiments, $R^3$ is hydrogen, $R^5$ is —OH, and $R^7$ is hydrogen. In some embodiments, ------ indicates a double bond.

In certain aspects, the present disclosure provides a compound selected from

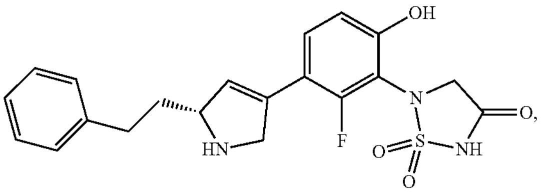

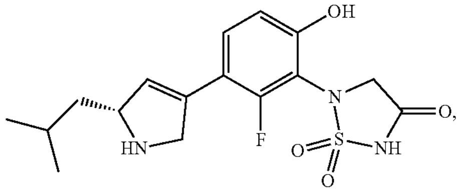

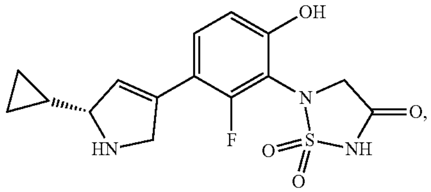

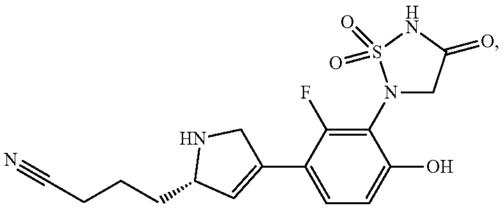

-continued
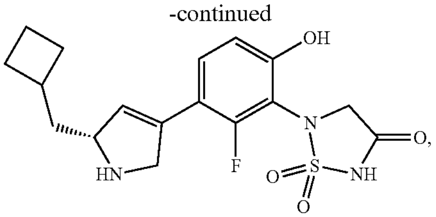
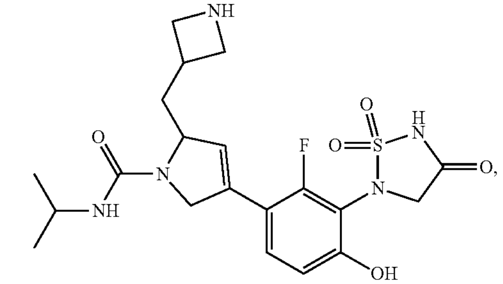
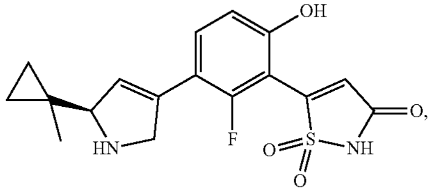
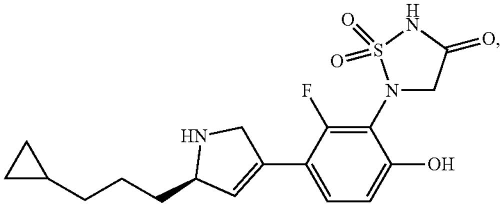
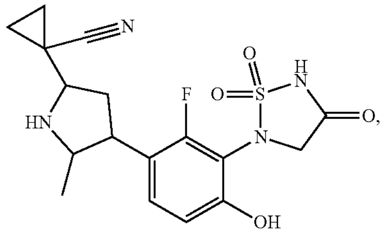
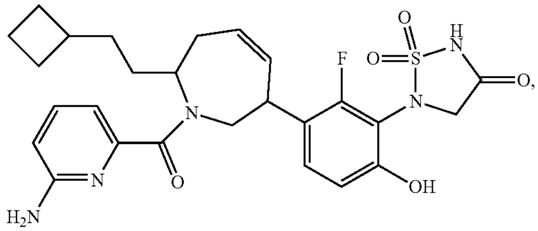
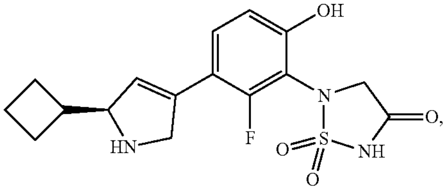
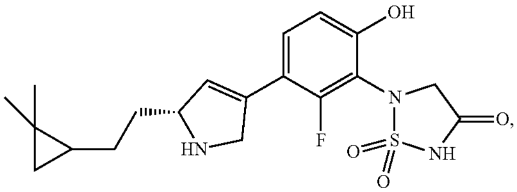
-continued
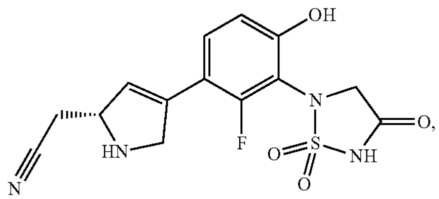
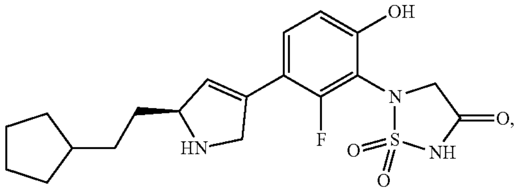
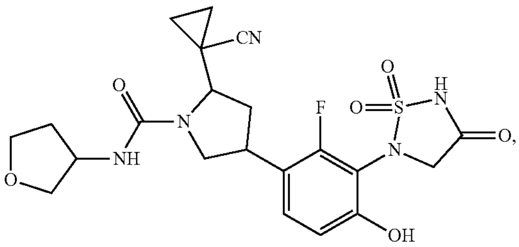
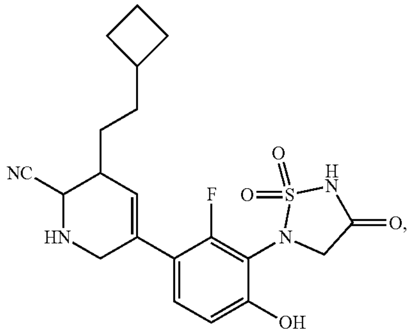
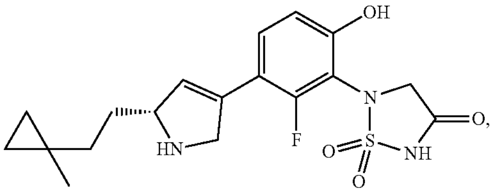
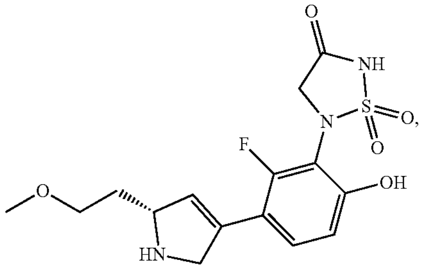
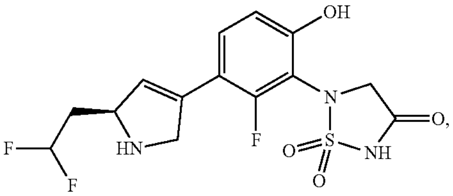

-continued
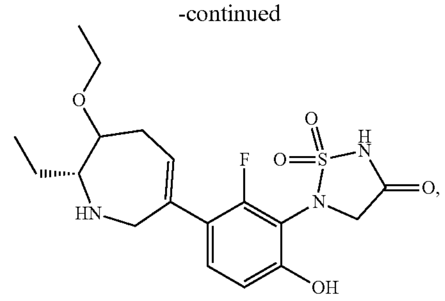
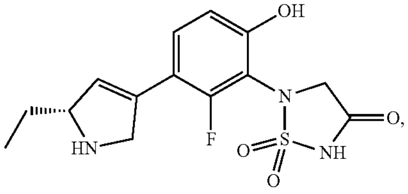
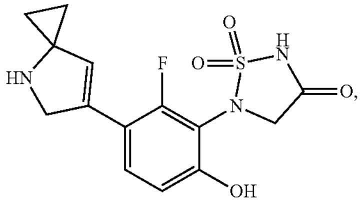
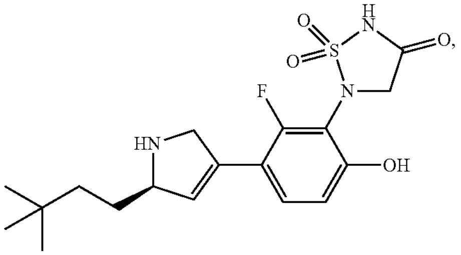
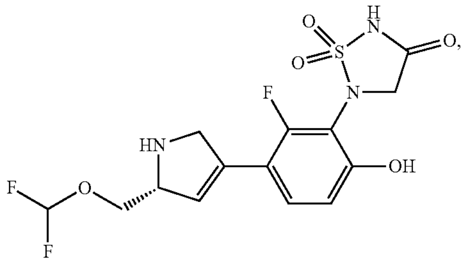
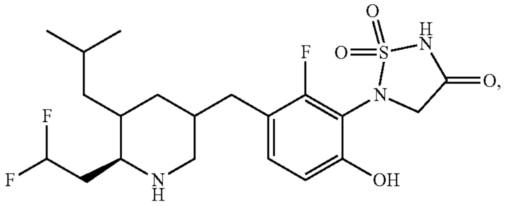
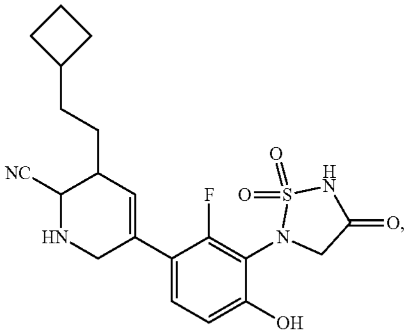
-continued
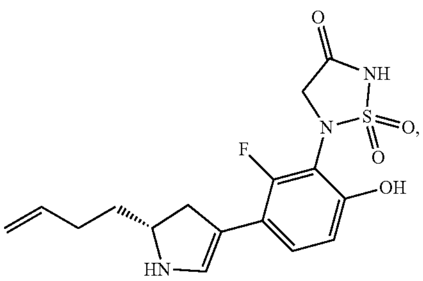
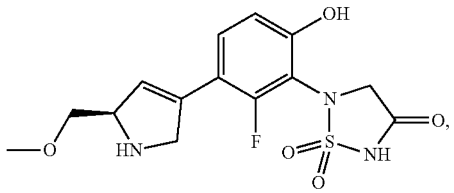
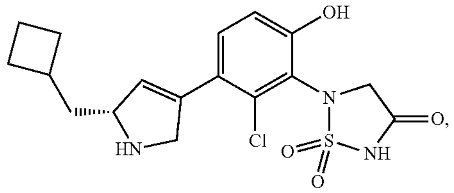
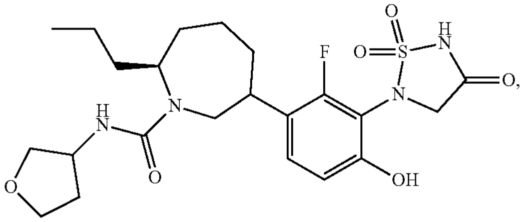
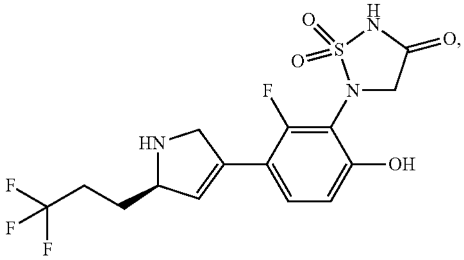
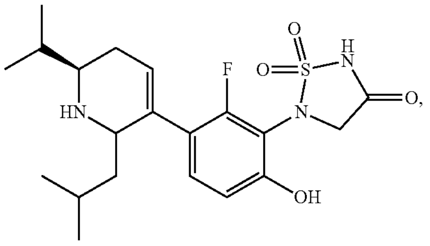
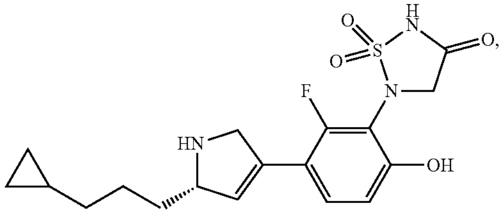

-continued
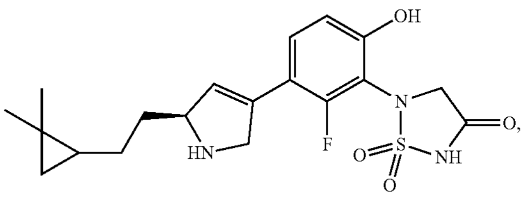
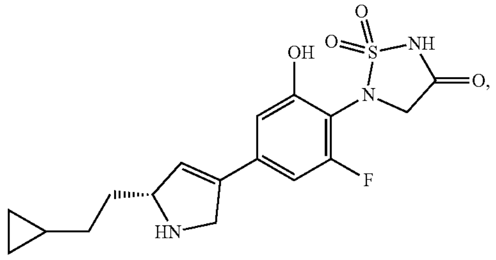
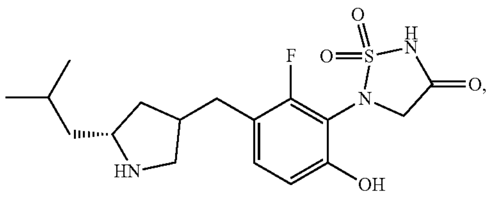
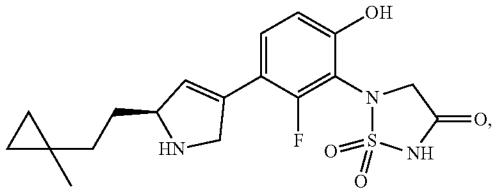
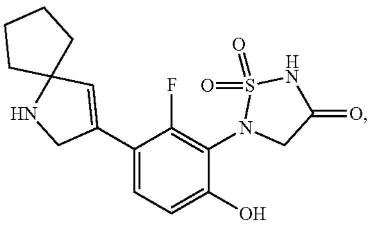
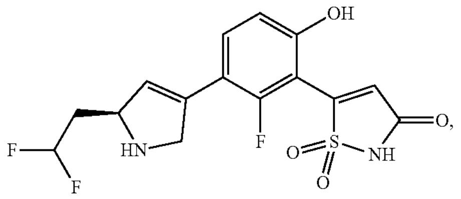
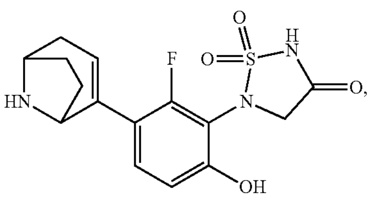
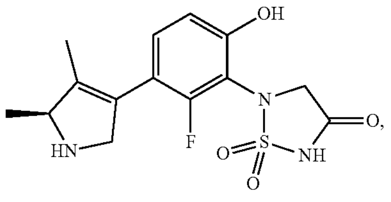
-continued
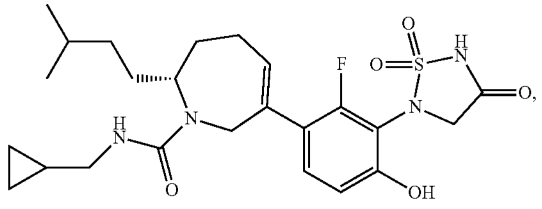
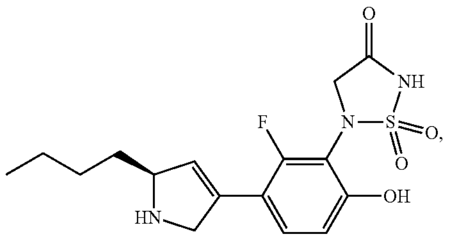
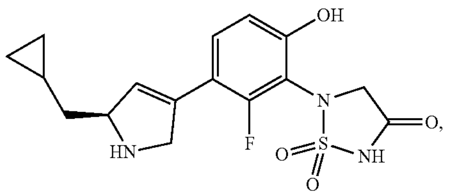
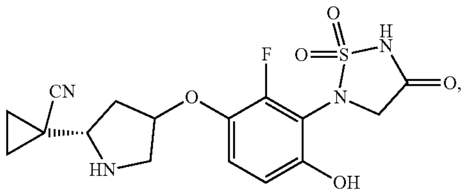
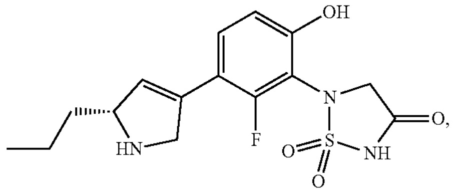
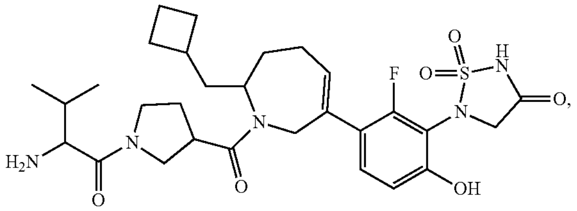
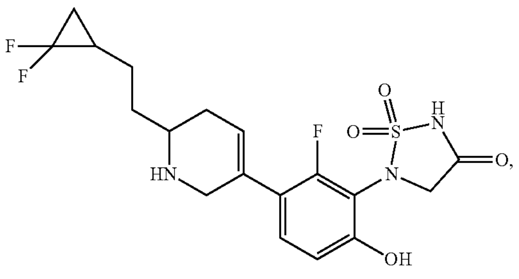

-continued
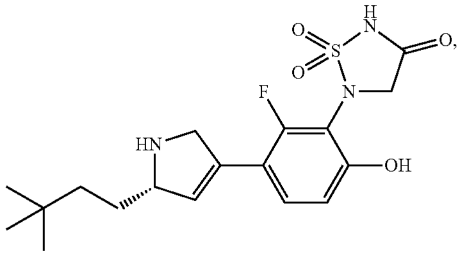
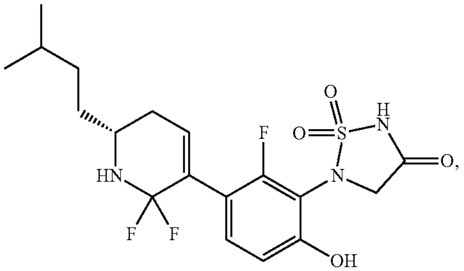
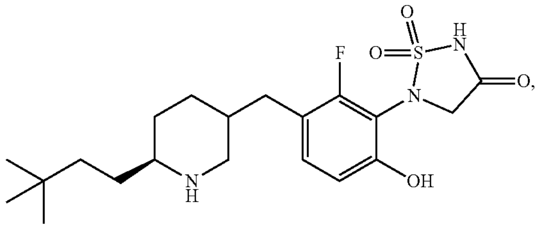
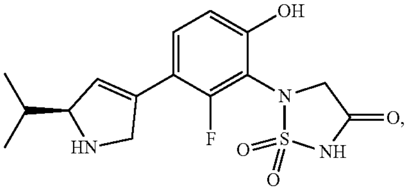
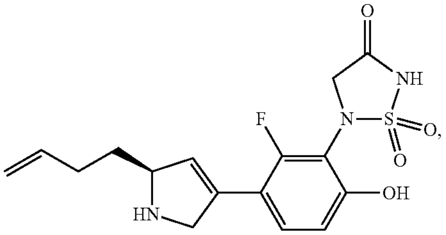
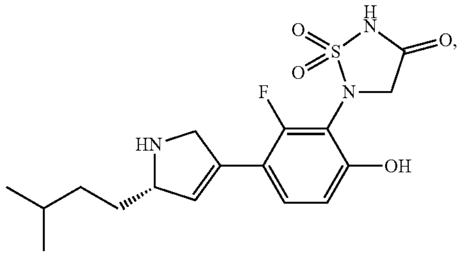
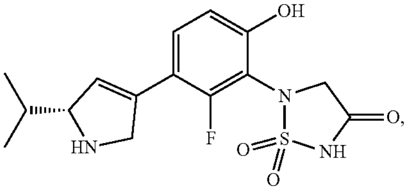
-continued
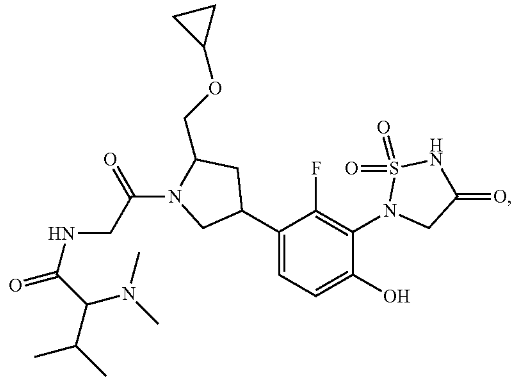
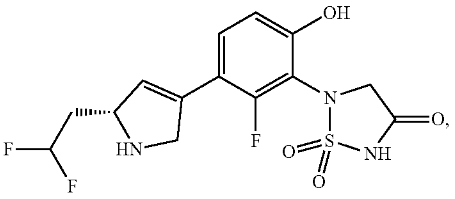
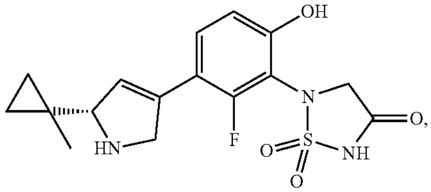
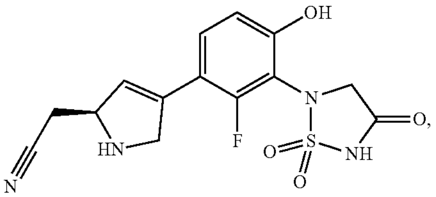
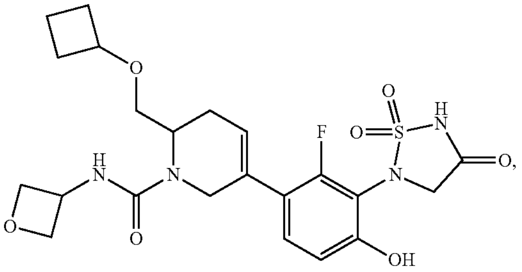
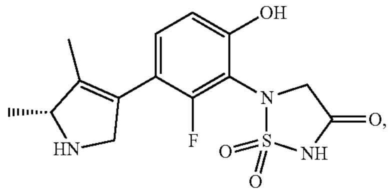
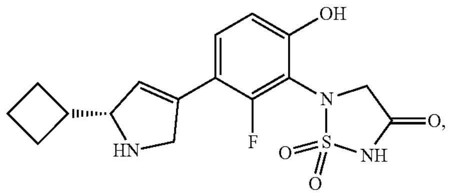

-continued
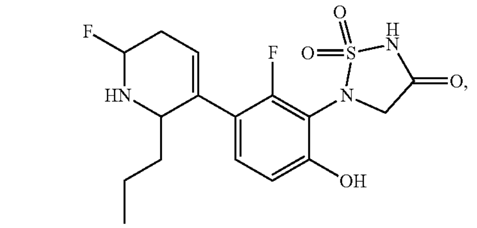
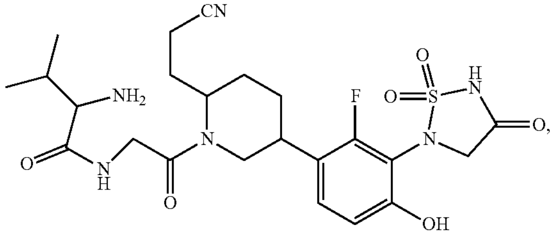
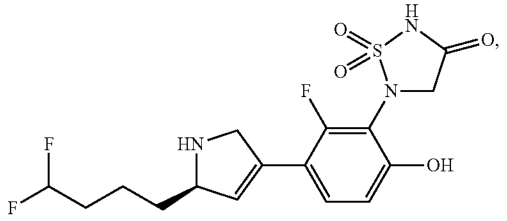
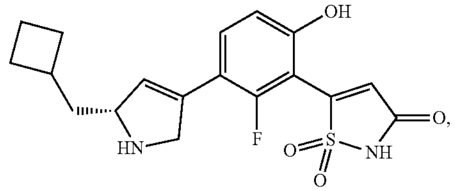
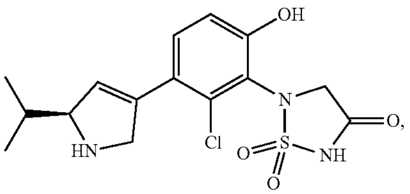
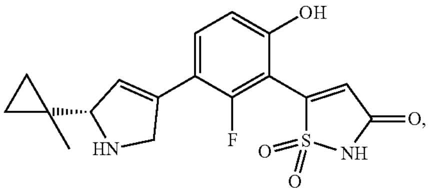
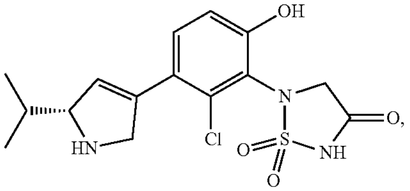
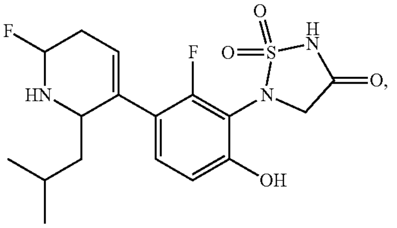
-continued
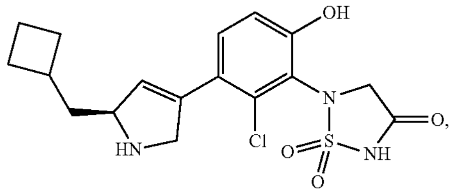
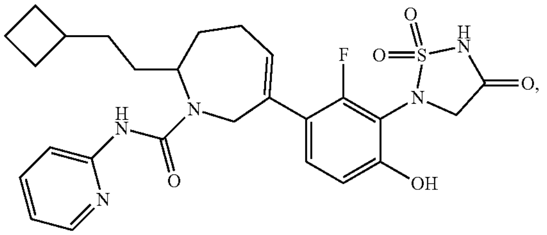
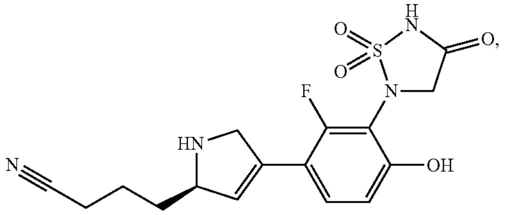
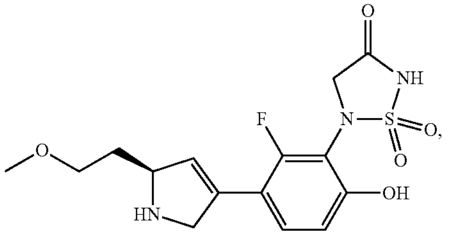
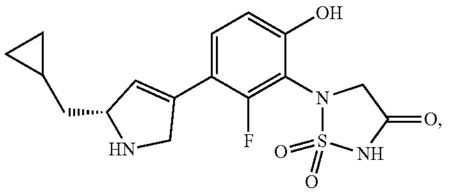
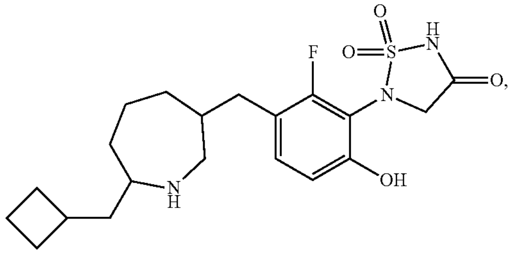
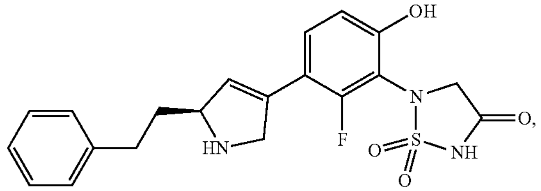
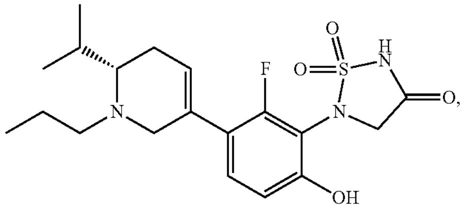

-continued
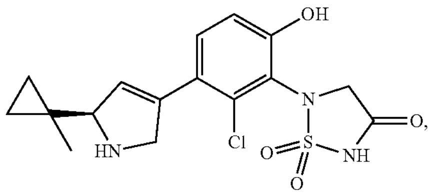
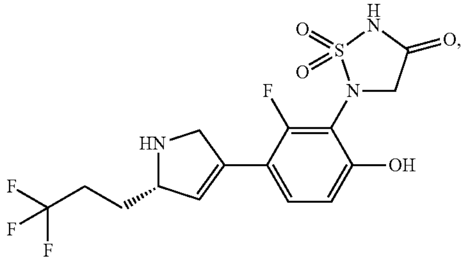
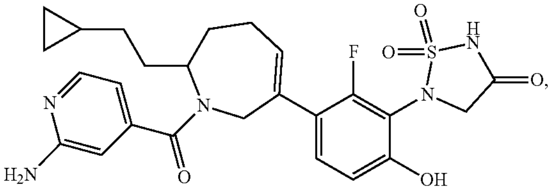
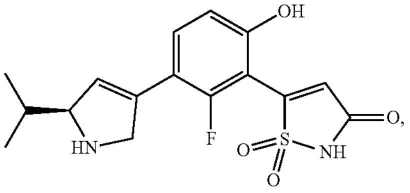
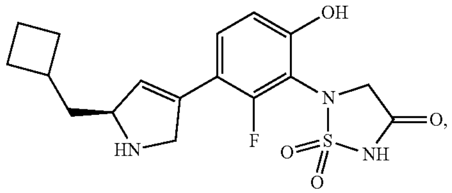
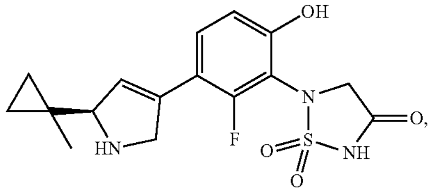
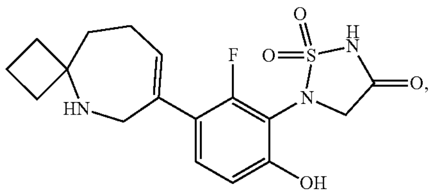
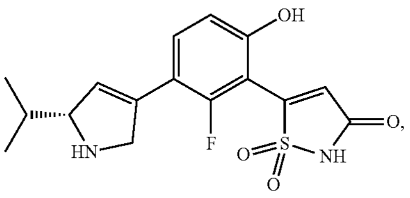
-continued
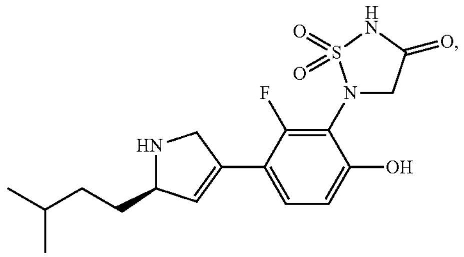
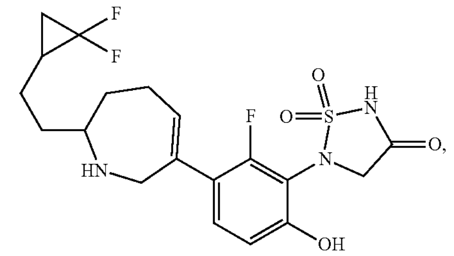
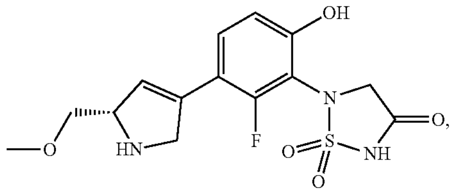
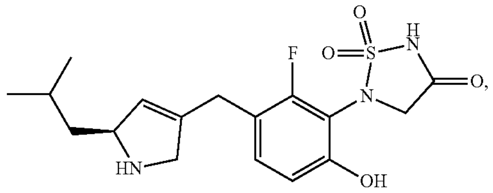
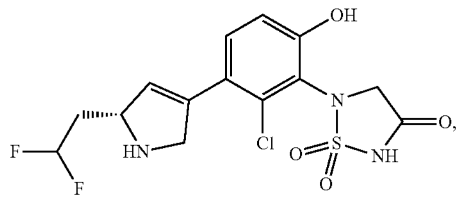
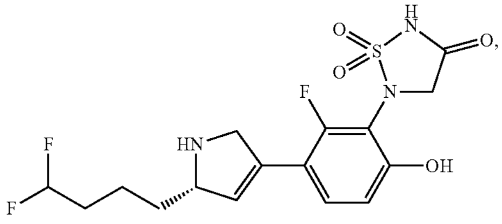
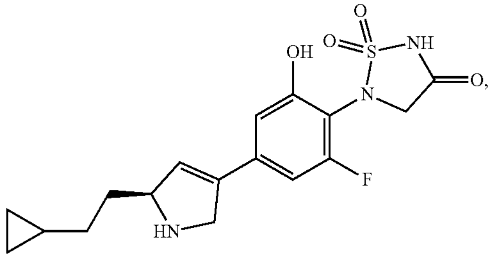

-continued
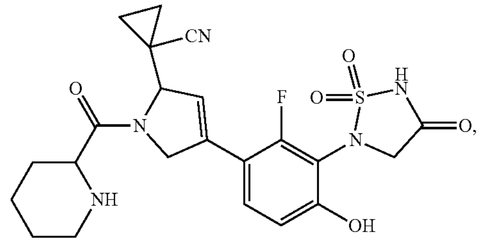
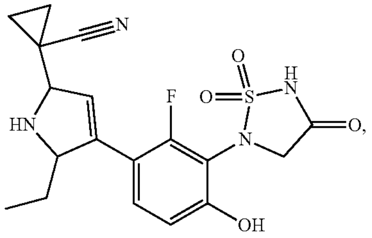
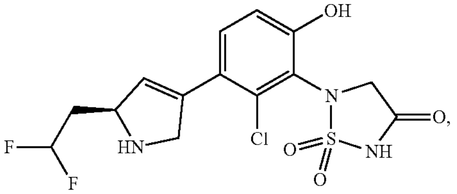
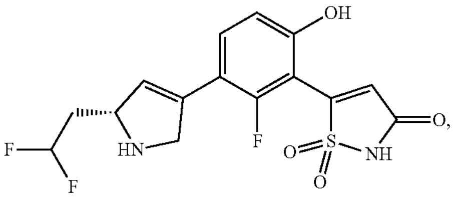
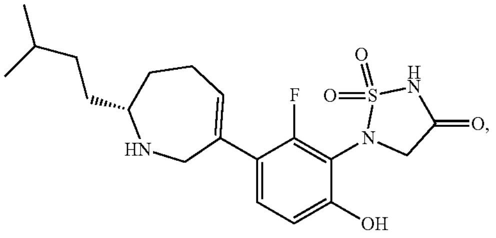
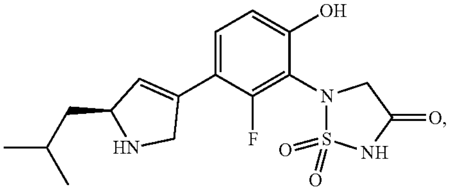
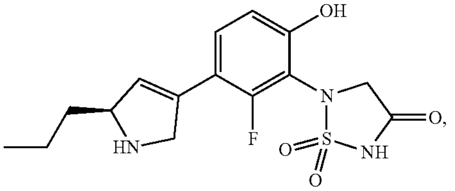
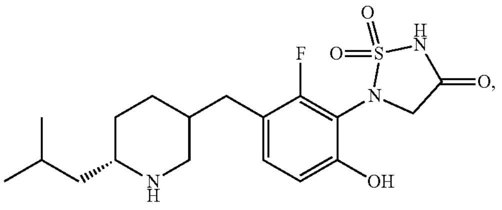
-continued
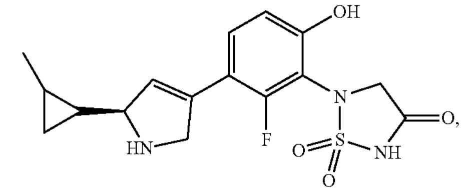
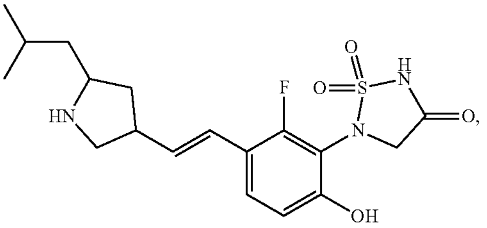
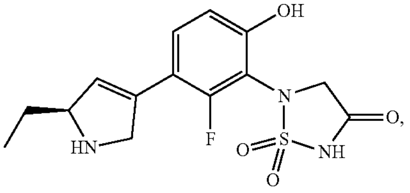
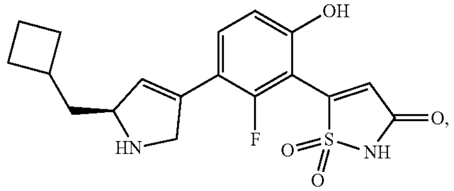
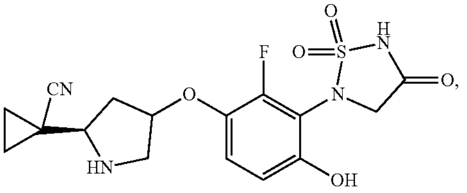
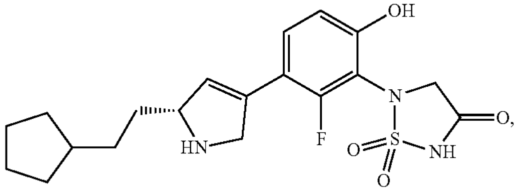
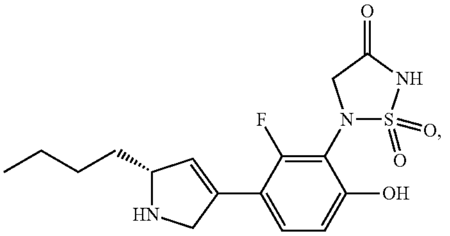
and
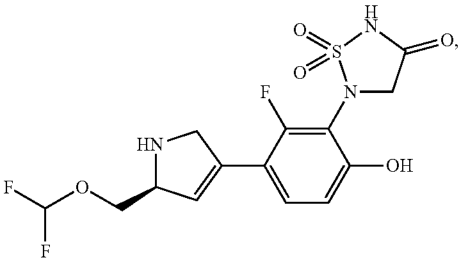
or a pharmaceutically acceptable salt or solvate thereof.

In certain aspects, the present disclosure provides a compound selected from

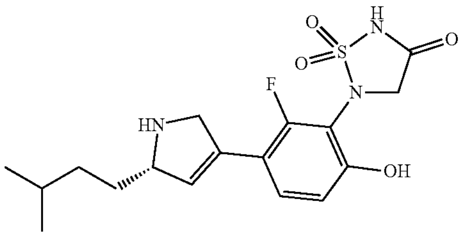

and

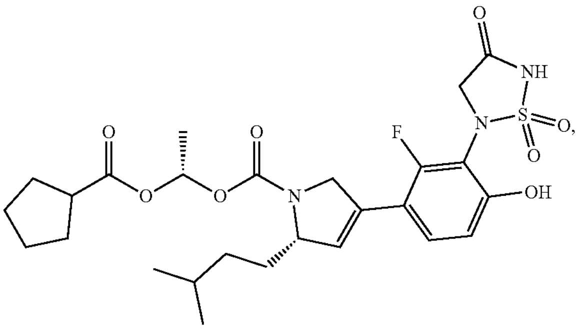

or a pharmaceutically acceptable salt or solvate thereof. In some embodiments, the present disclosure provides a compound selected from

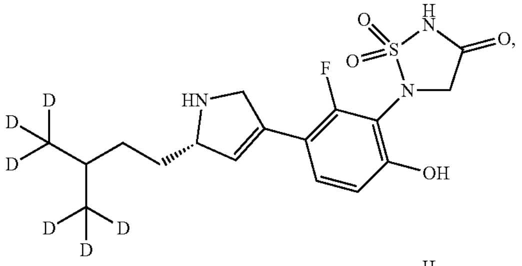

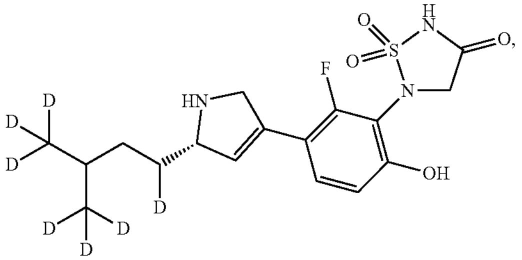

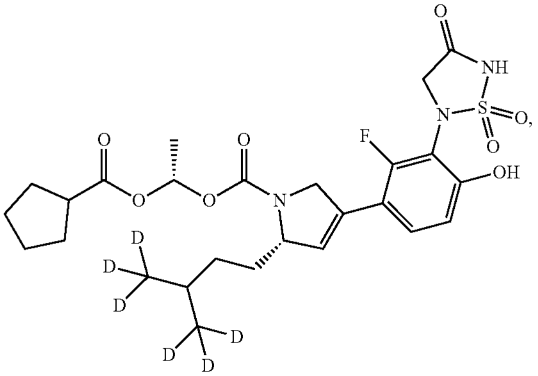

and

-continued

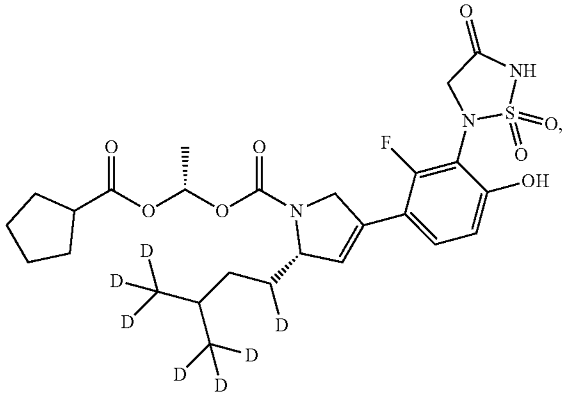

or a pharmaceutically acceptable salt or solvate thereof.

In certain aspects, the present disclosure provides a compound selected from

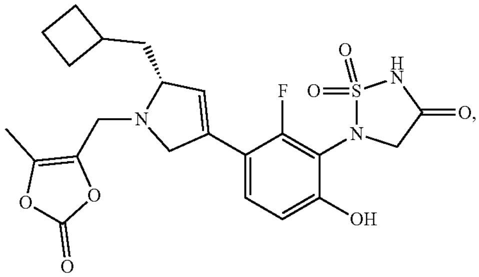

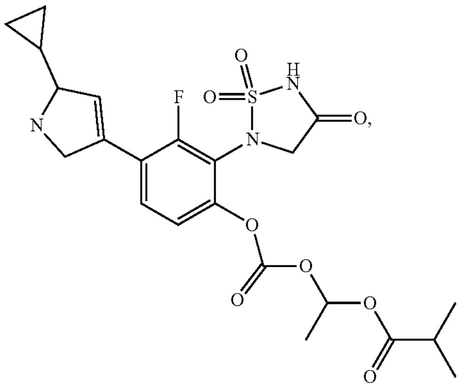

,

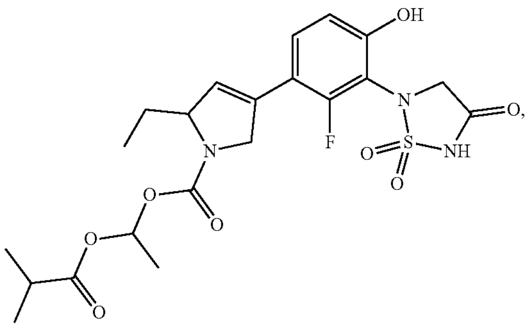

-continued
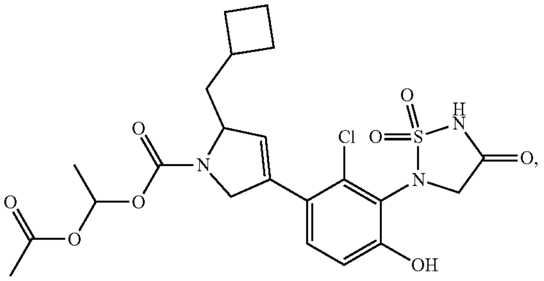
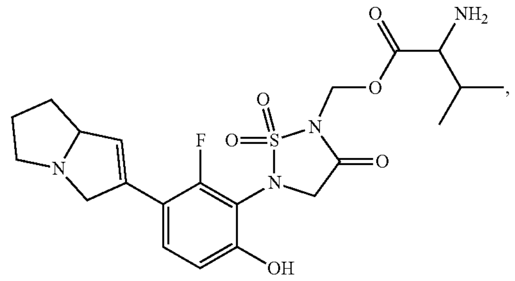
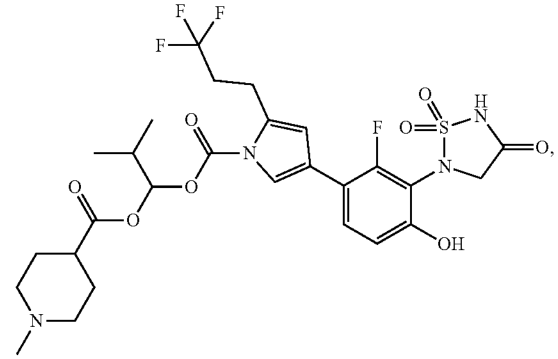
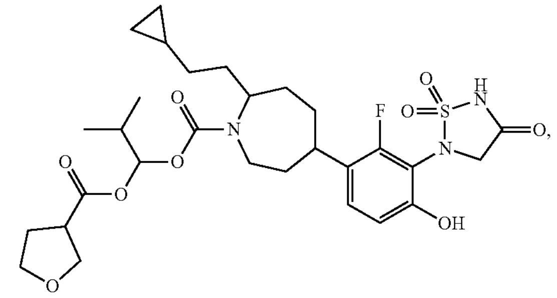
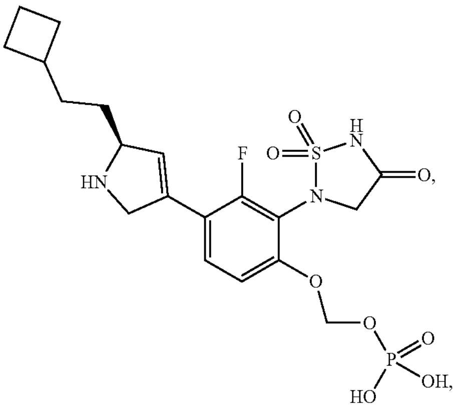
-continued
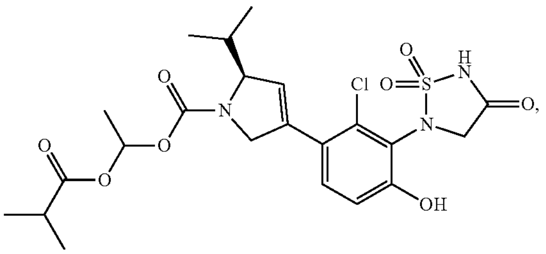
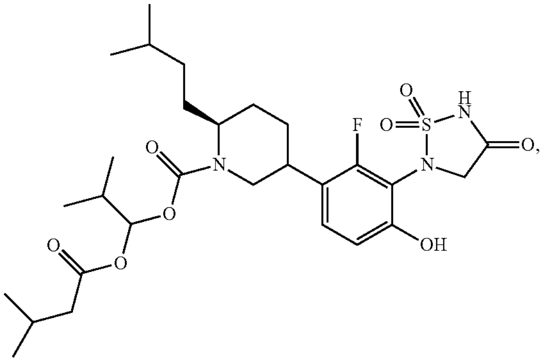
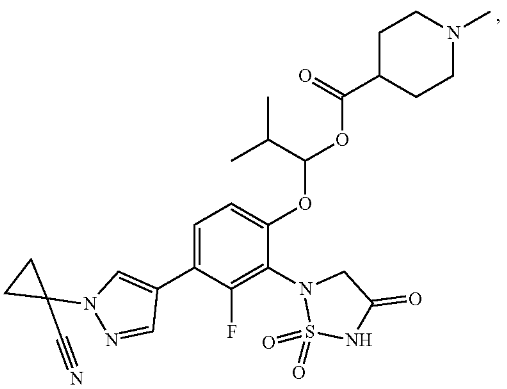
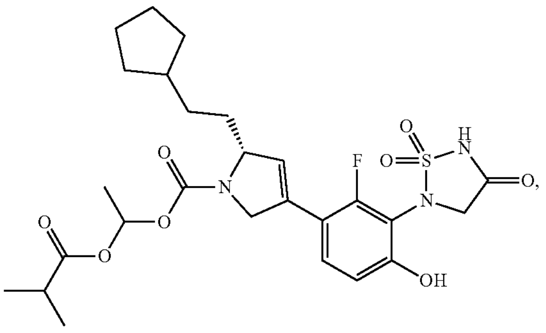
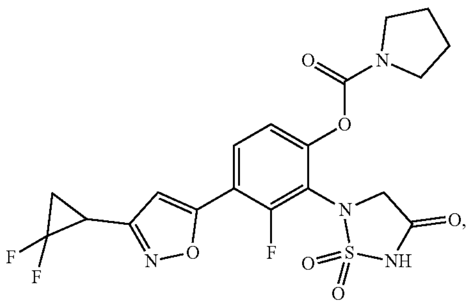

-continued
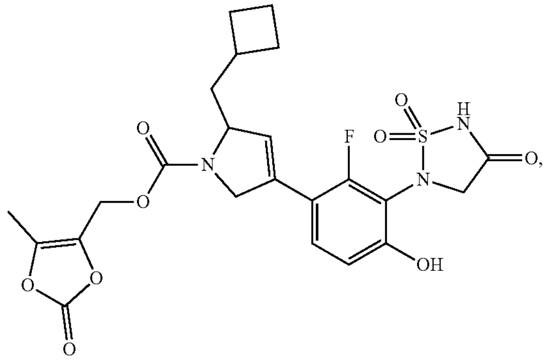
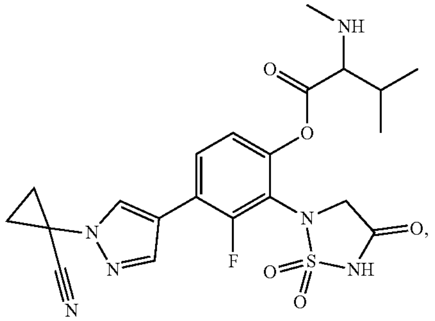
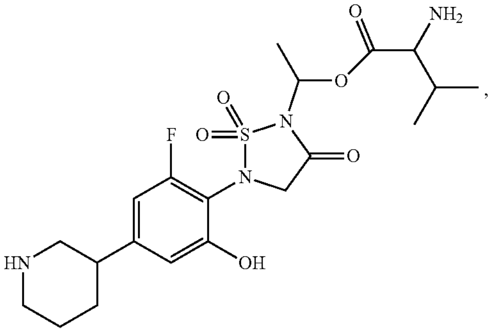
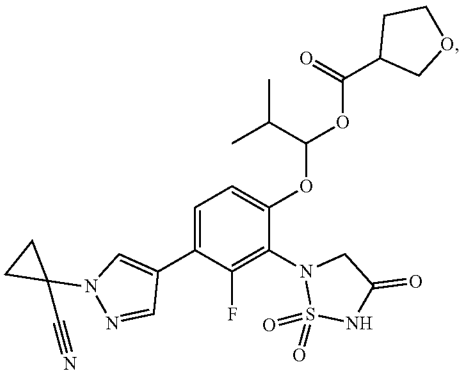
-continued
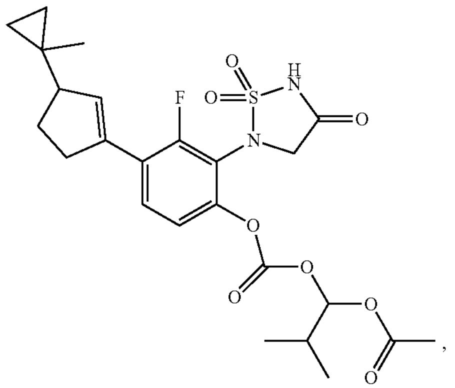
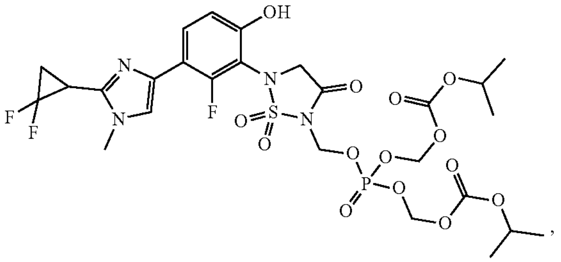
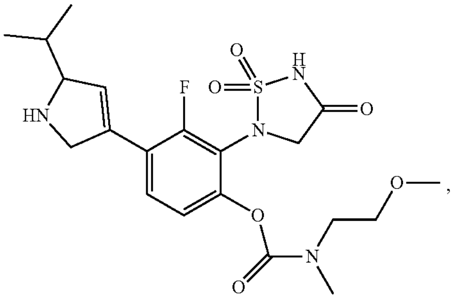
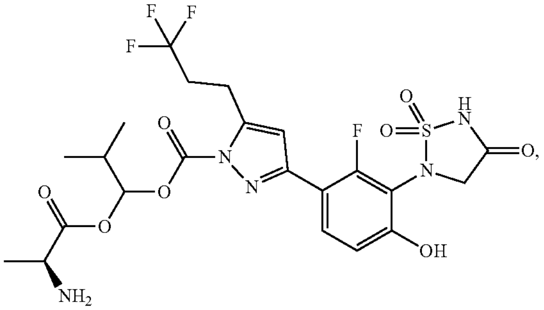
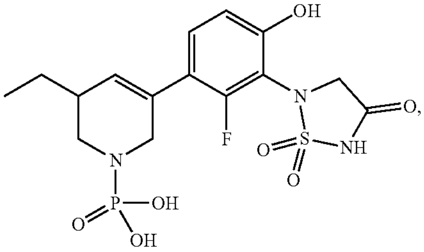

-continued
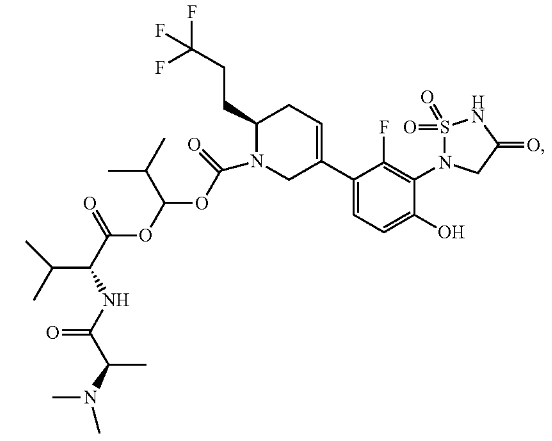
,
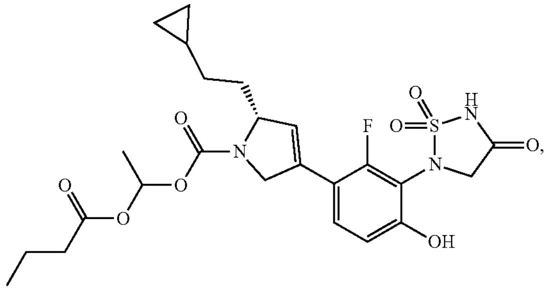
,
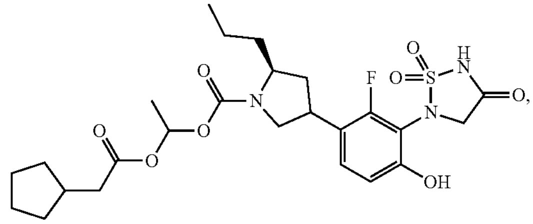
,
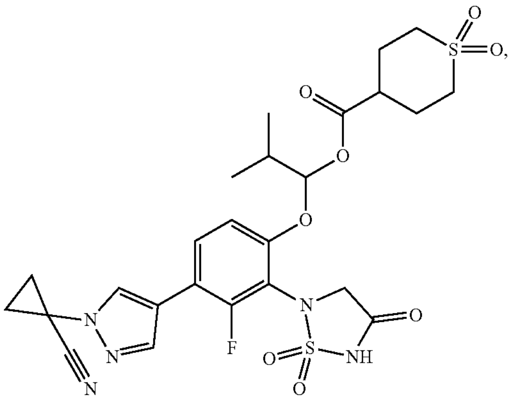
,
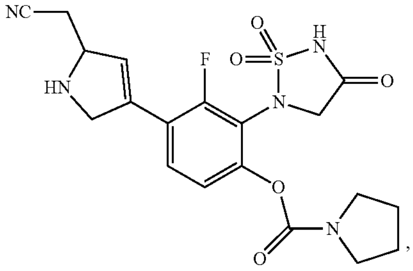
,
-continued
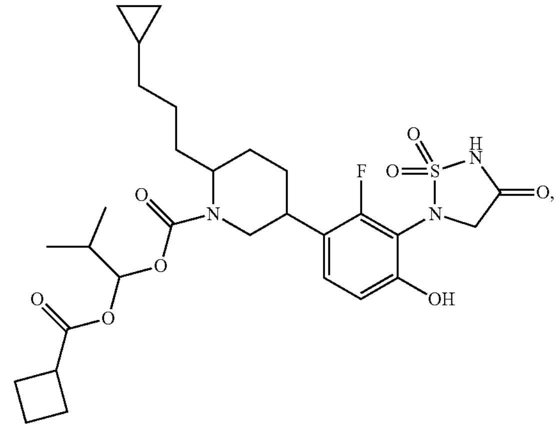
,
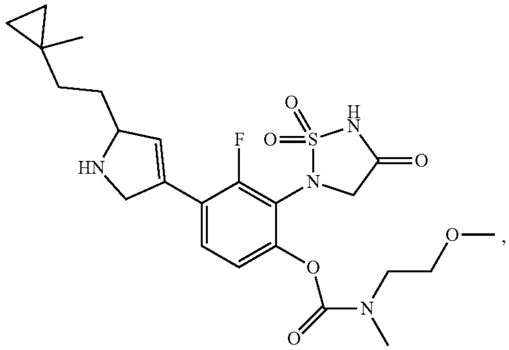
,
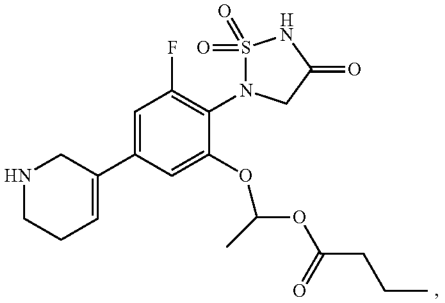
,
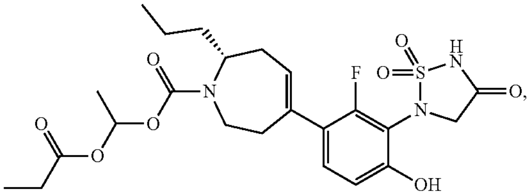
,
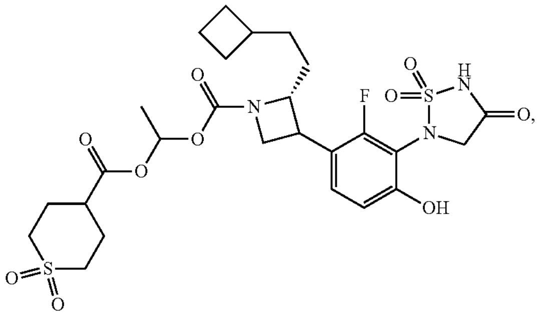
, -continued
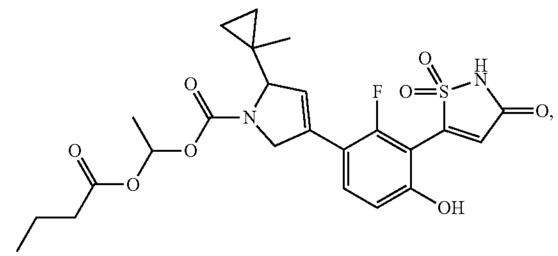
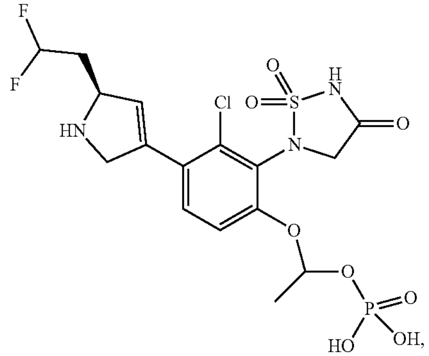
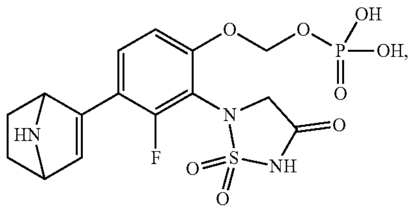
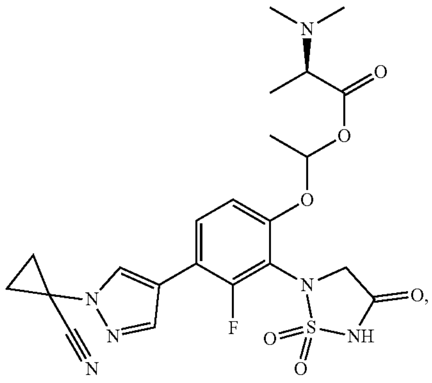
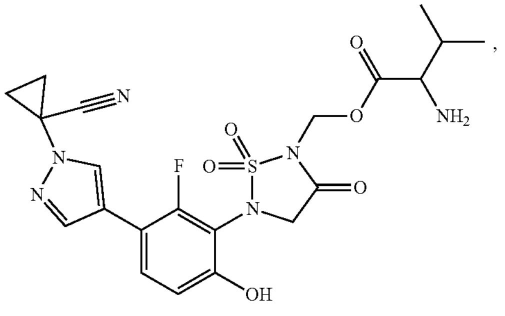
-continued
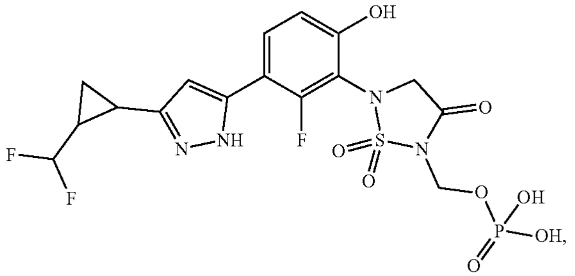
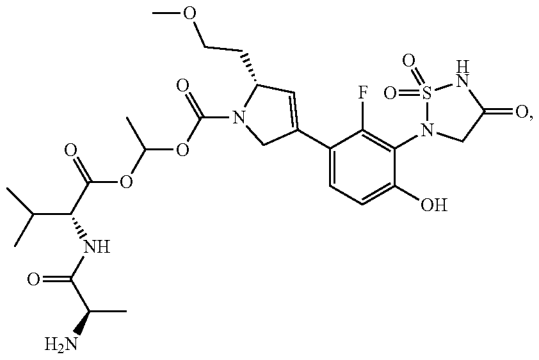
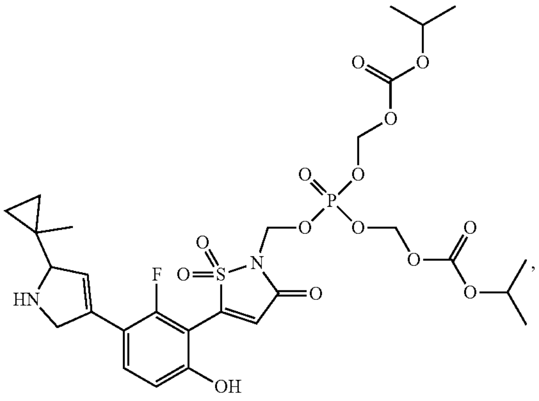
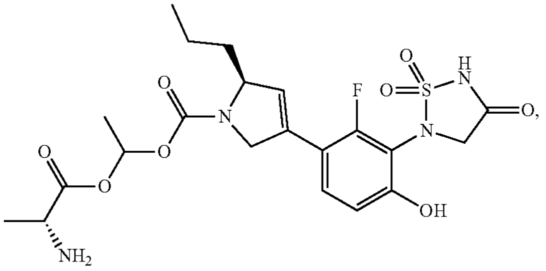
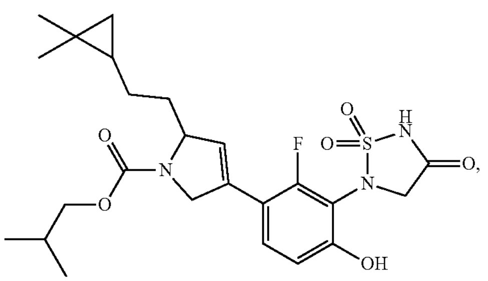

-continued
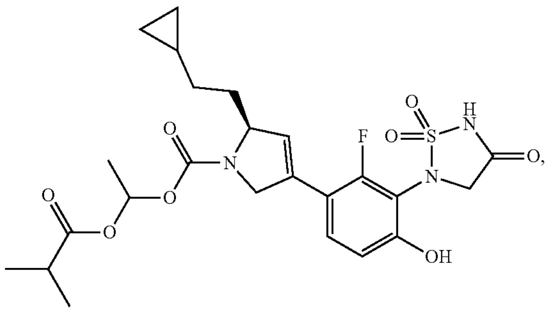
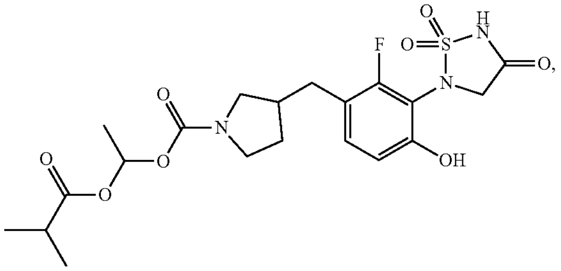
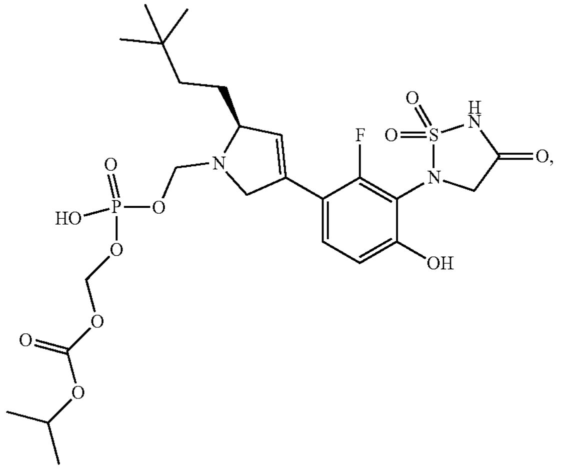
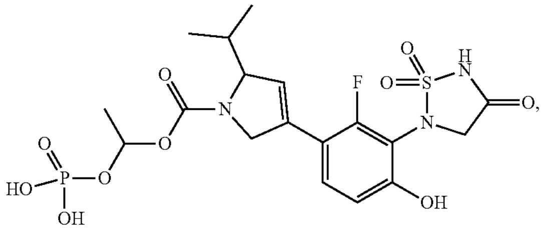
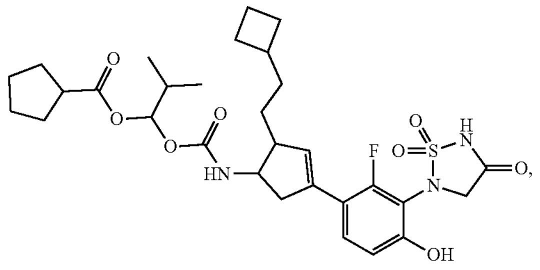
-continued
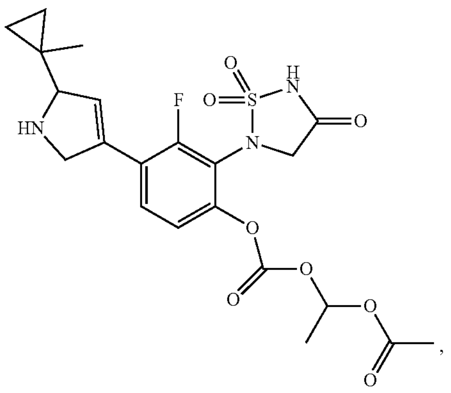
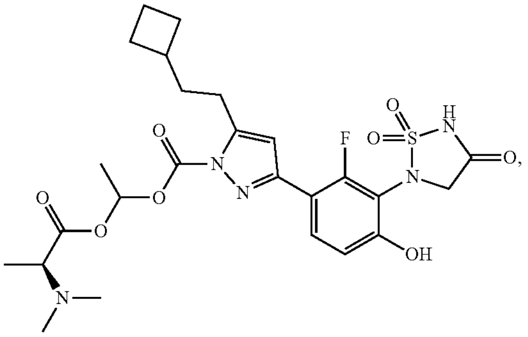
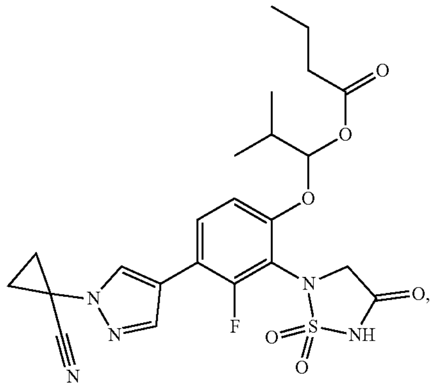
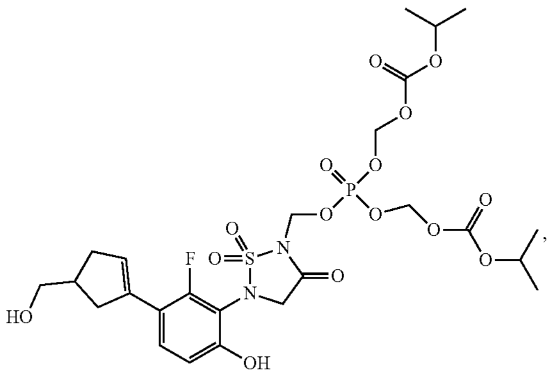

-continued
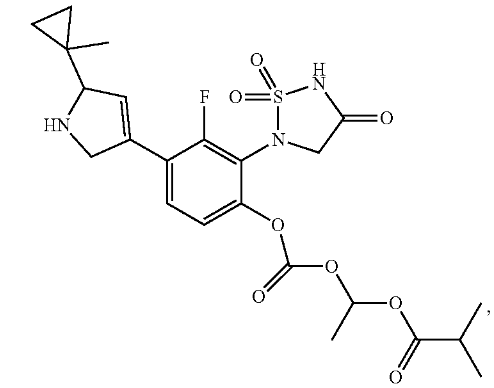
,
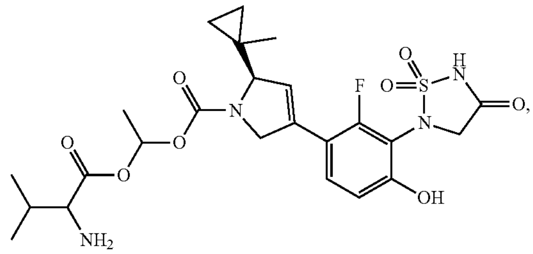
,
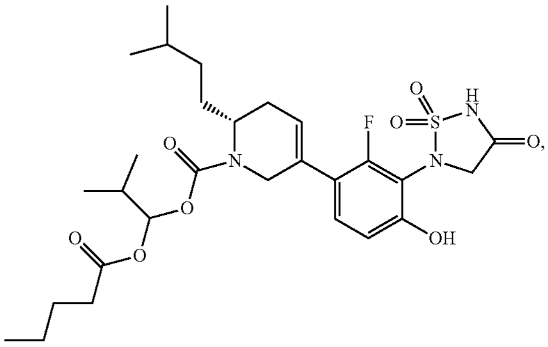
,
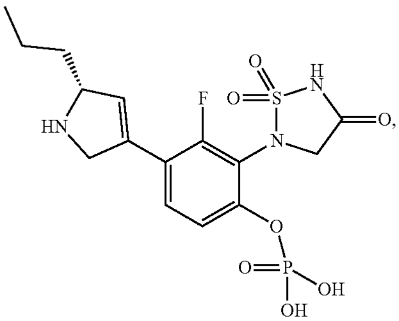
,
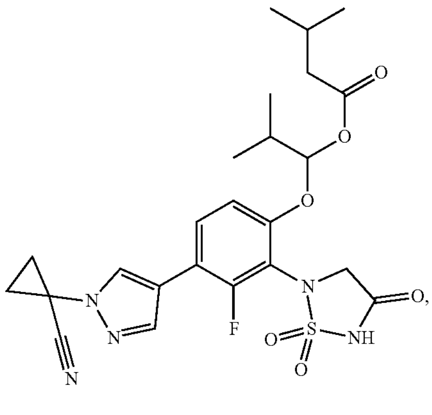
,
-continued
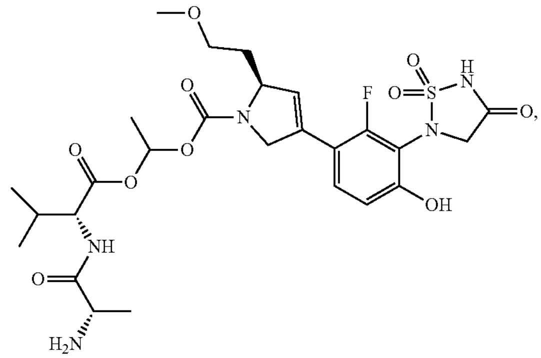
,
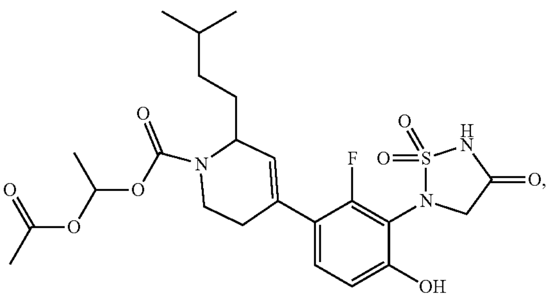
,
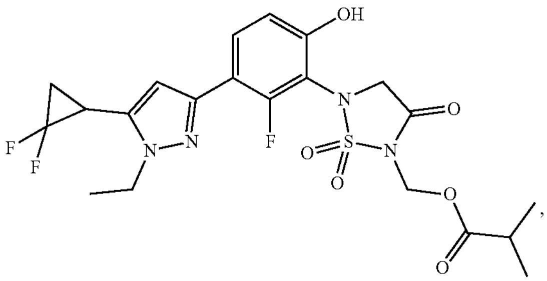
,
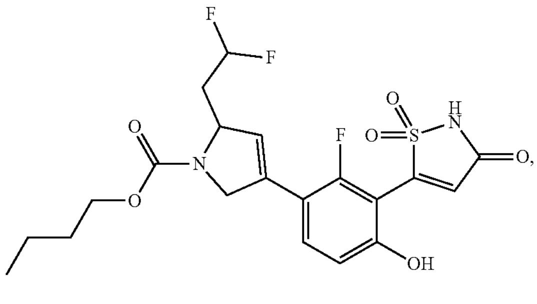
,
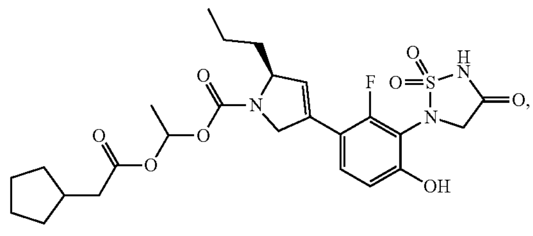
, -continued
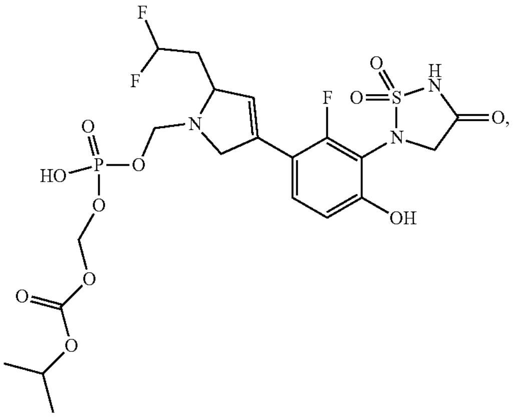
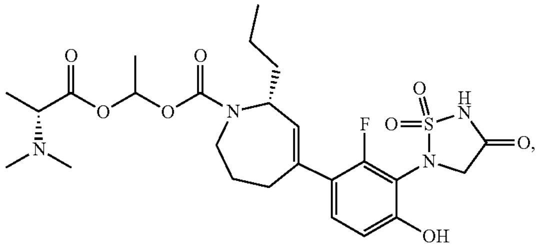
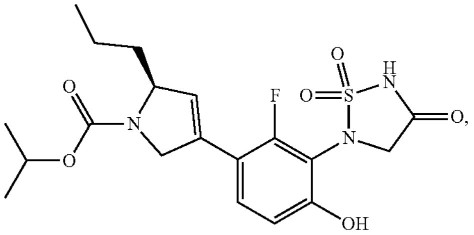
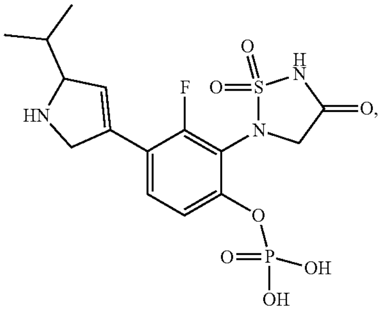
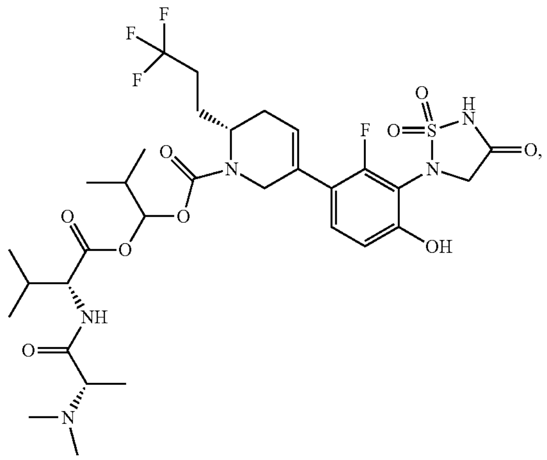
-continued
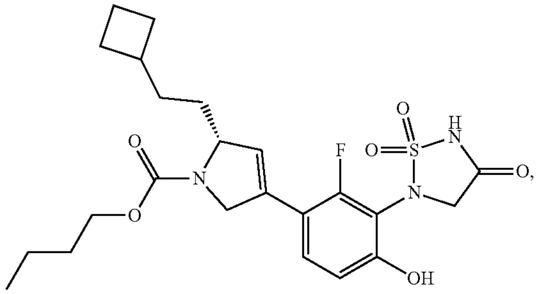
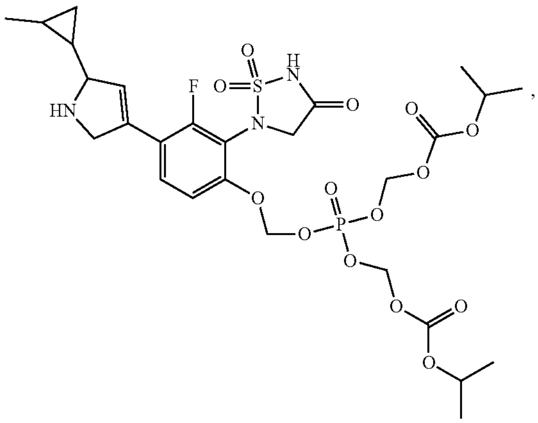
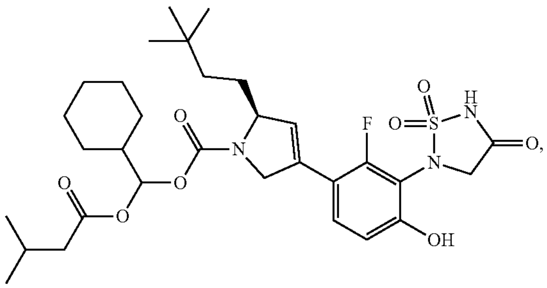
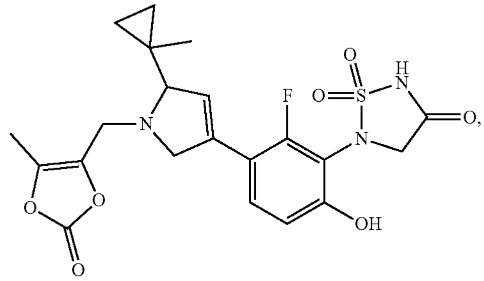
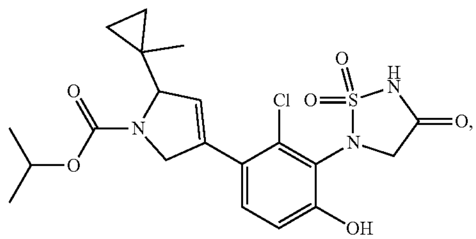

-continued
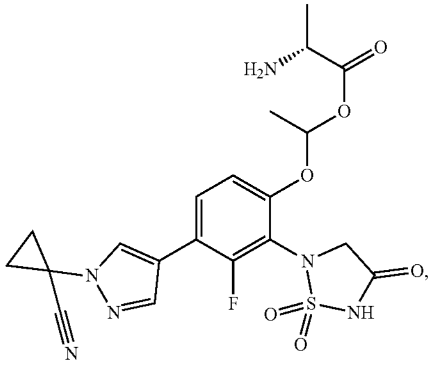
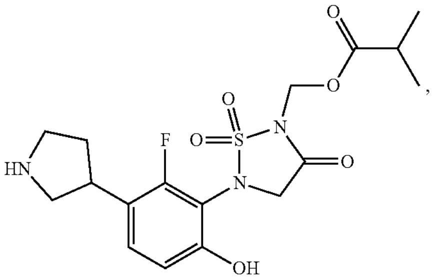
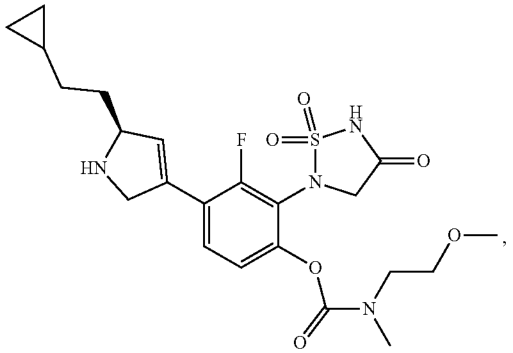
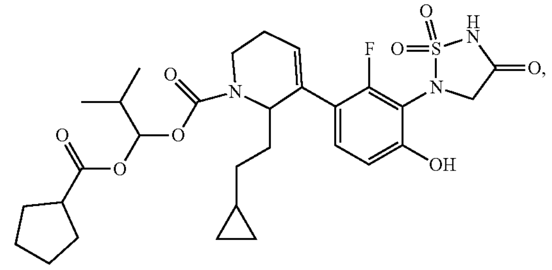
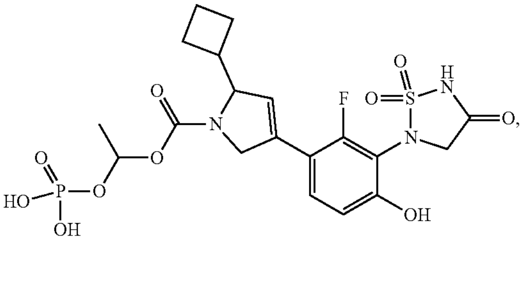
-continued
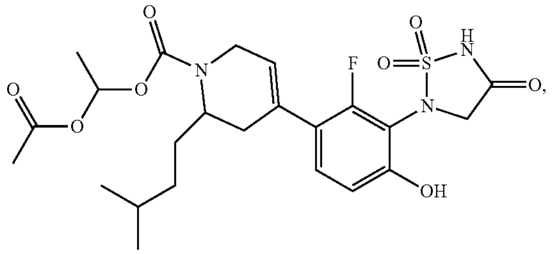
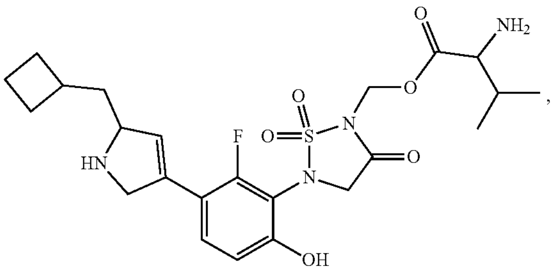
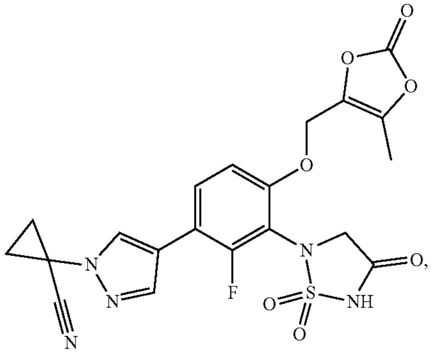
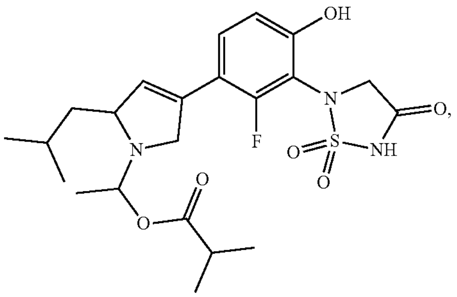
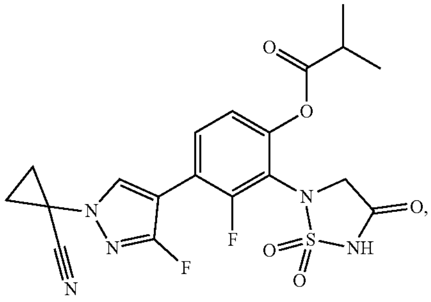

-continued
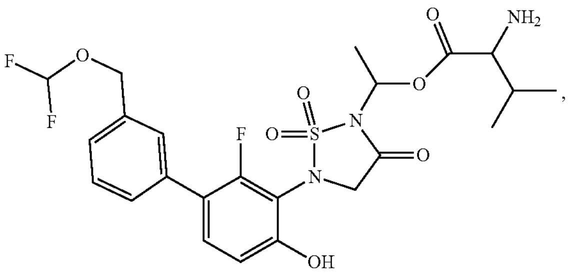
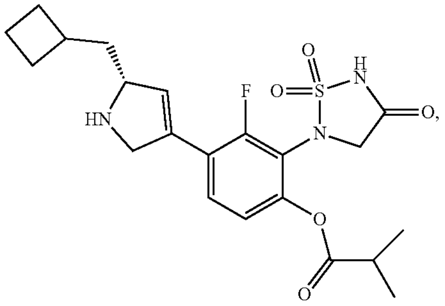
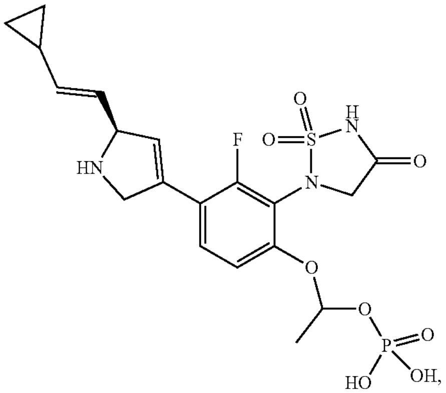
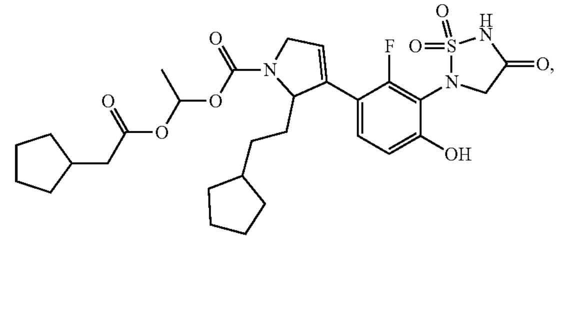
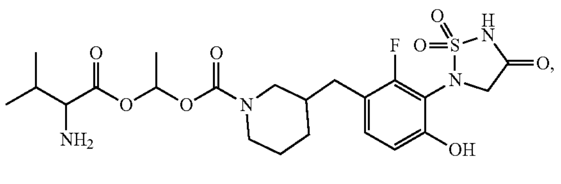
-continued
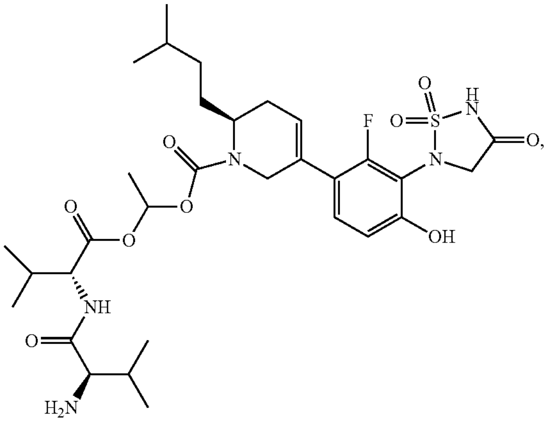
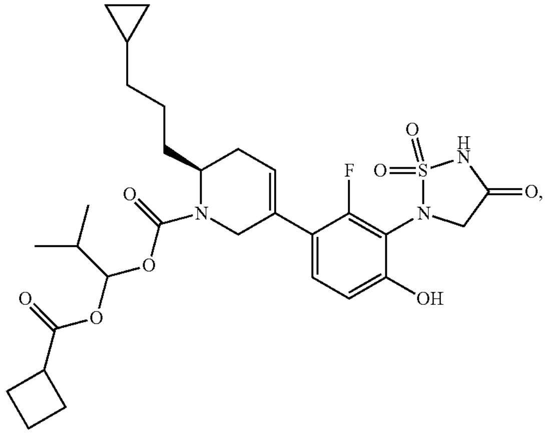
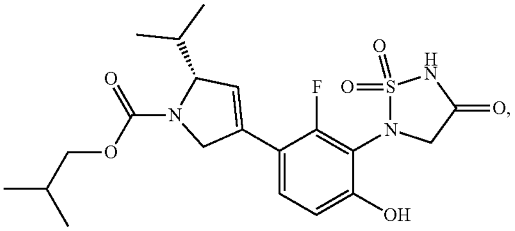
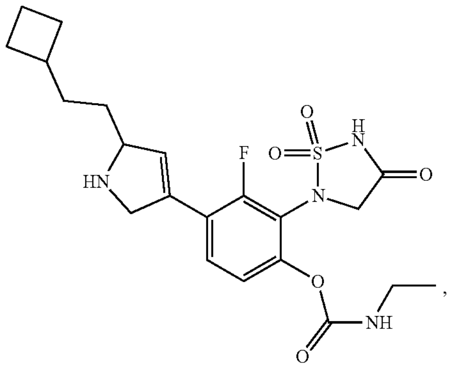
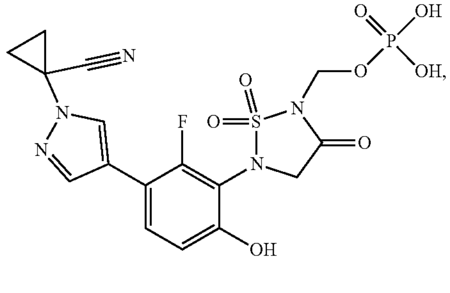

-continued
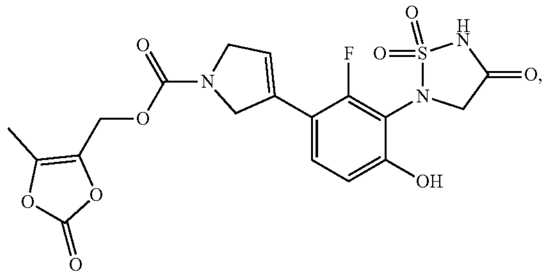
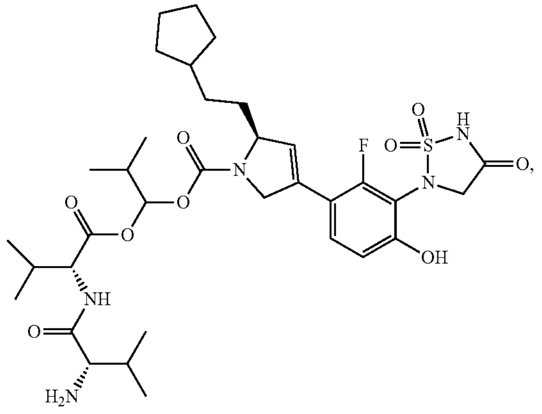
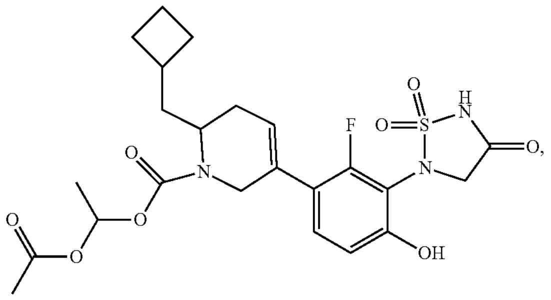
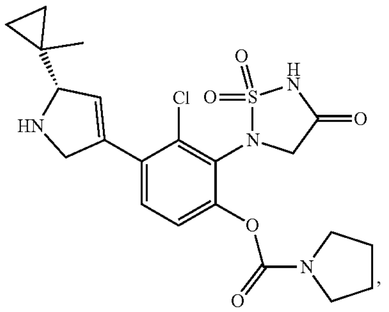
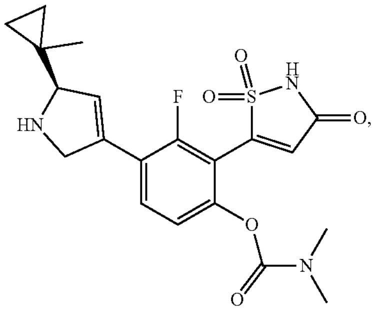
-continued
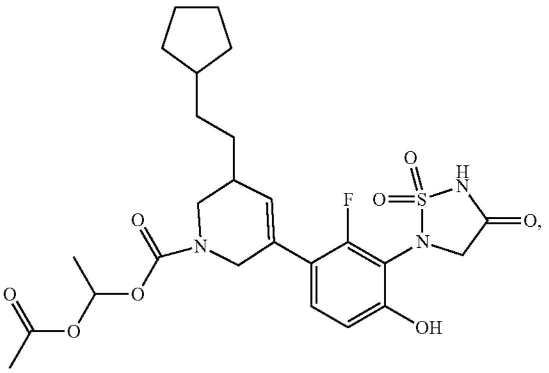
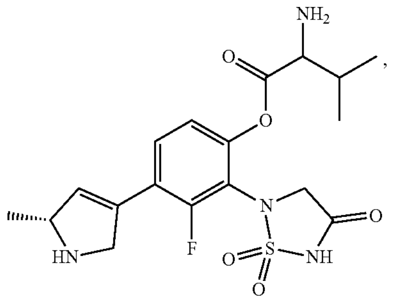
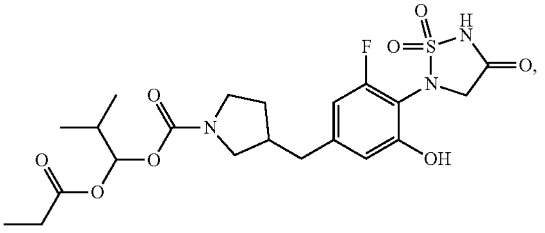
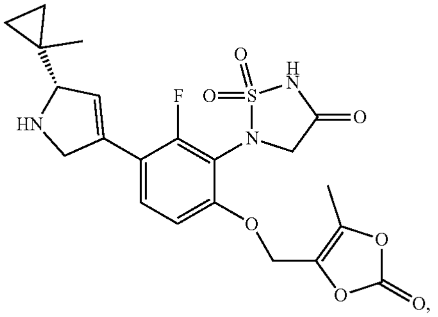
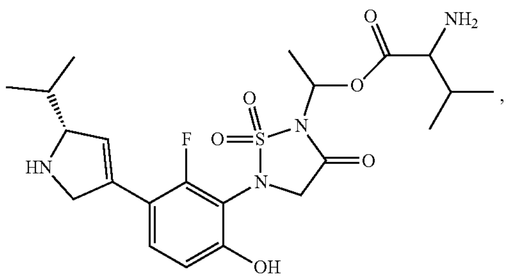

-continued
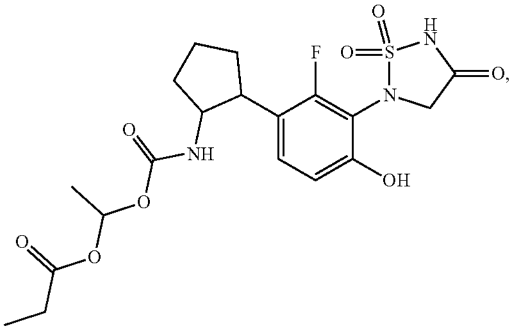
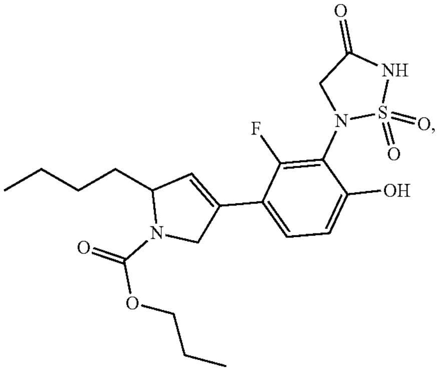
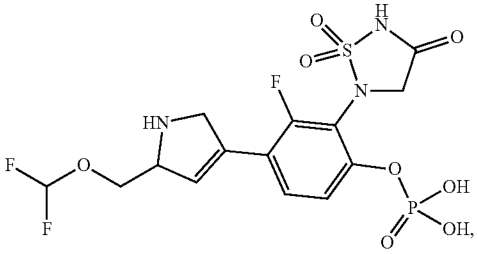
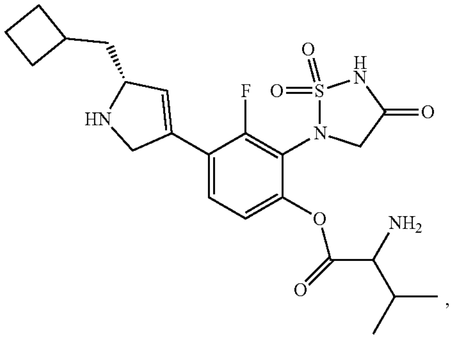
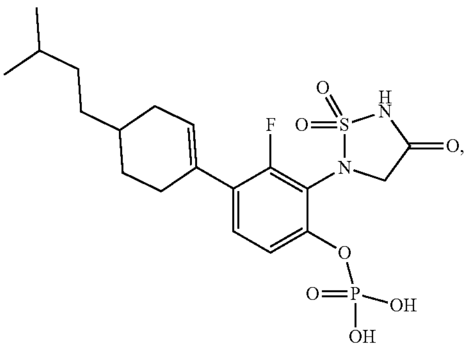
-continued
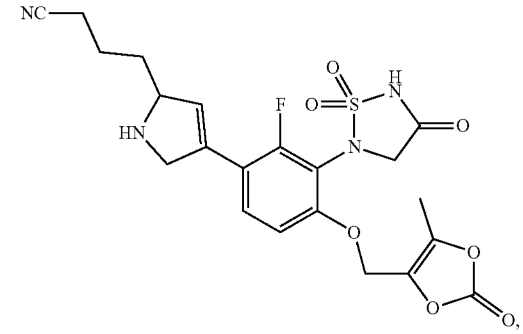
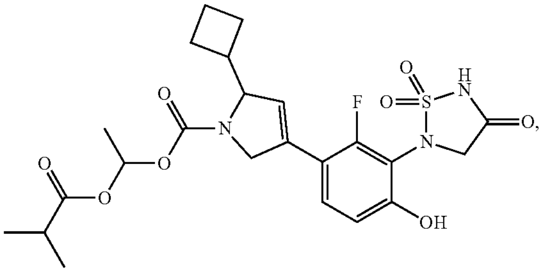
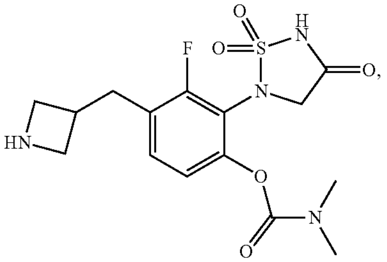
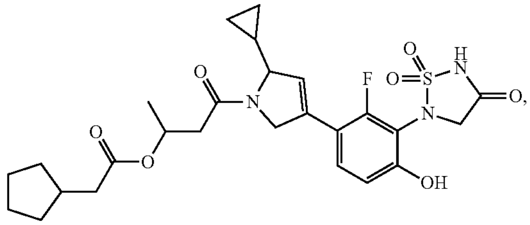
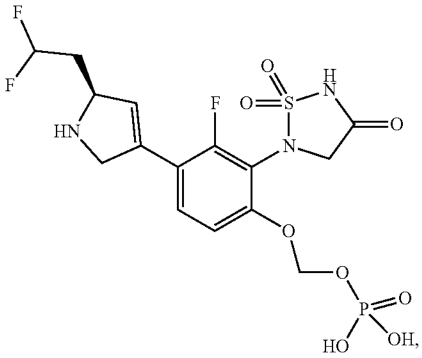

-continued
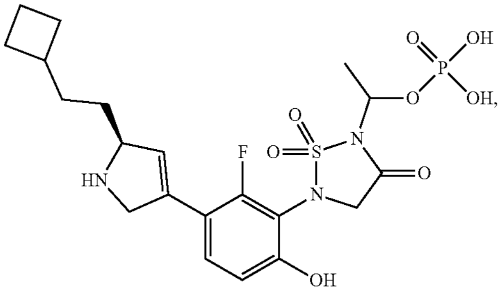
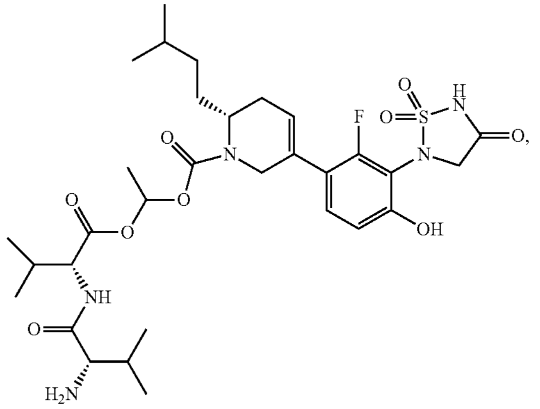
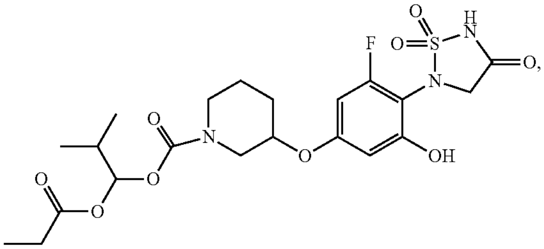
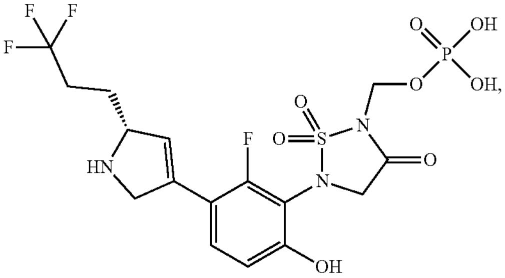
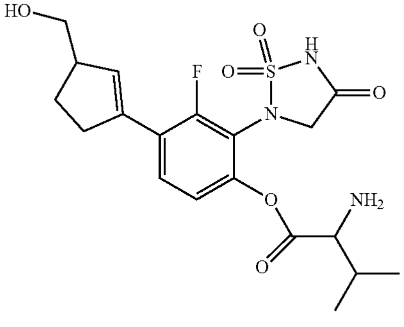
,
-continued
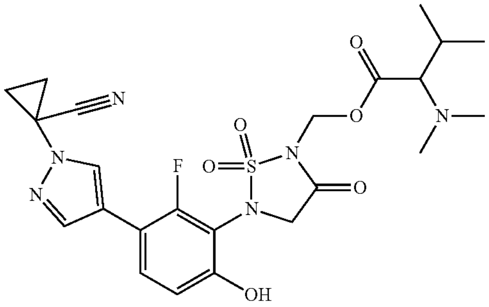
,
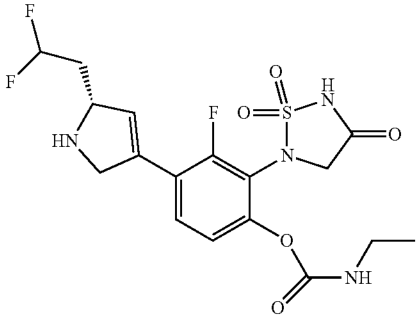
,
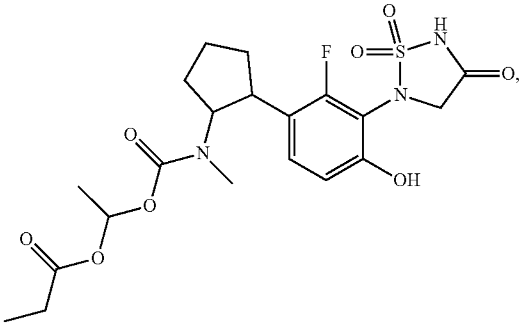
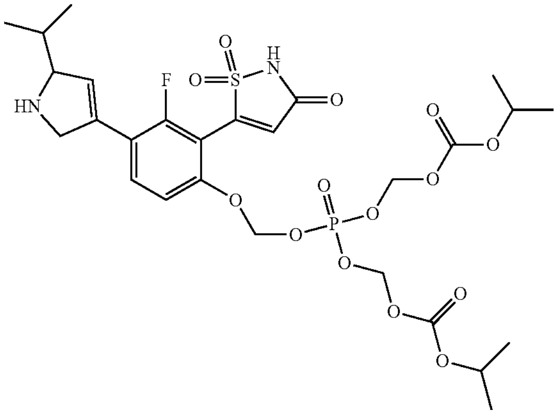
,
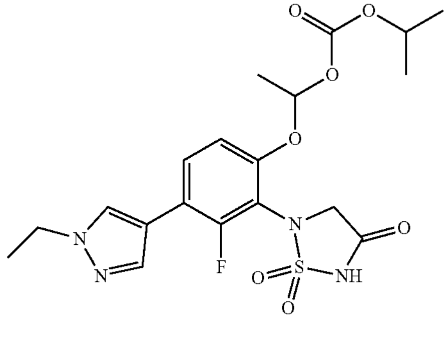
, -continued
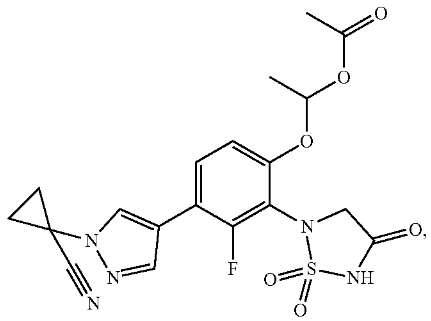
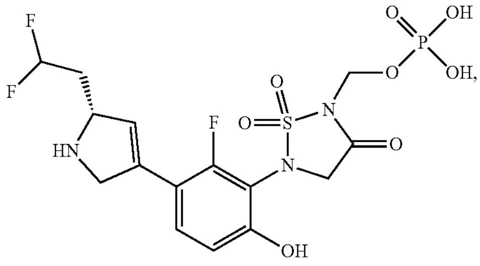
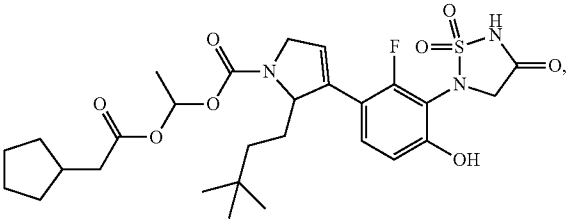
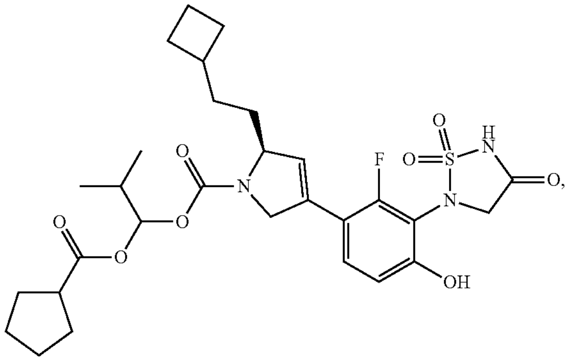
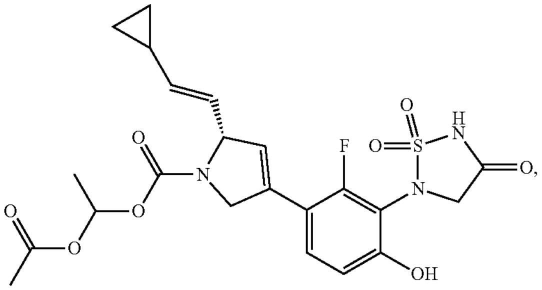
-continued
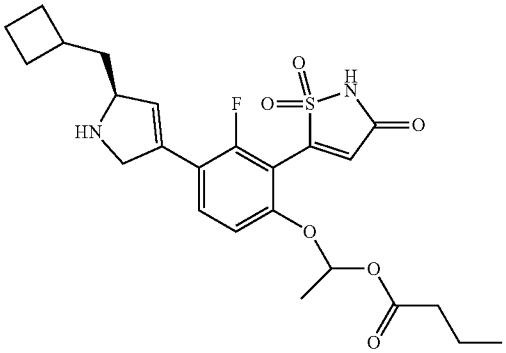
,
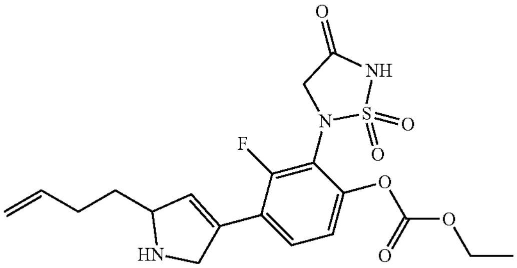
,
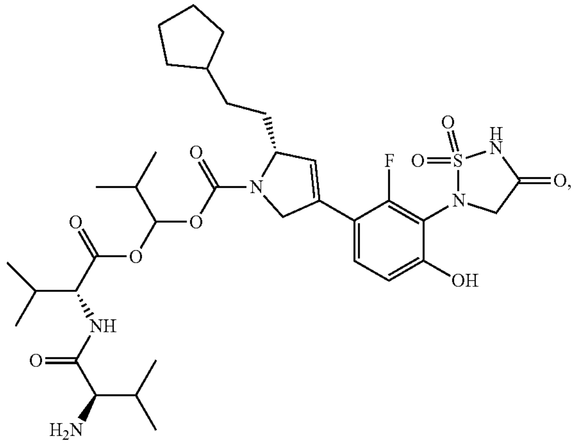
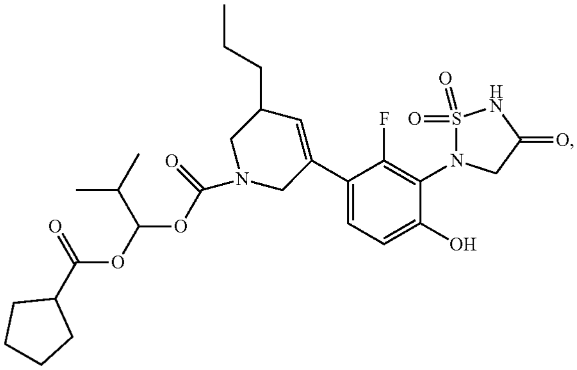

-continued

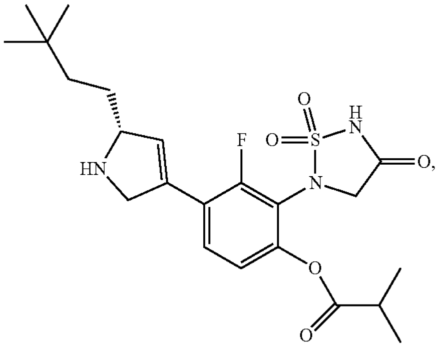

,

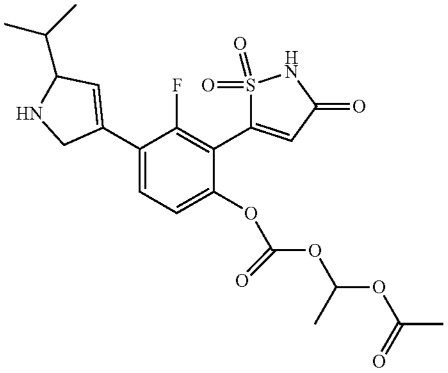

,

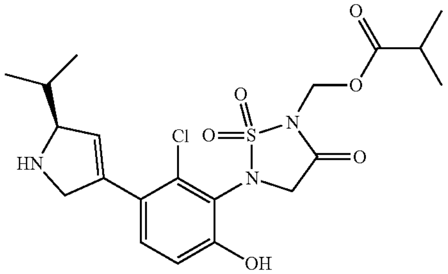

,

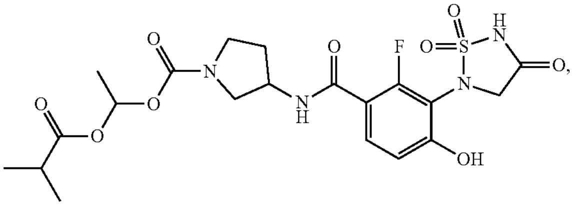

,

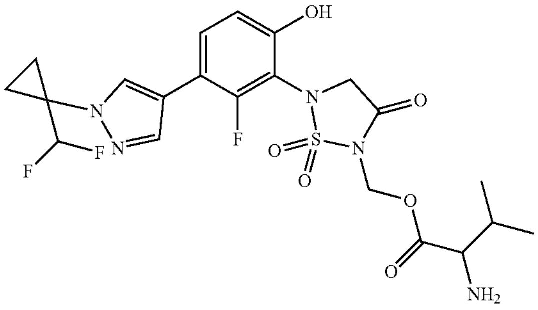

,

-continued

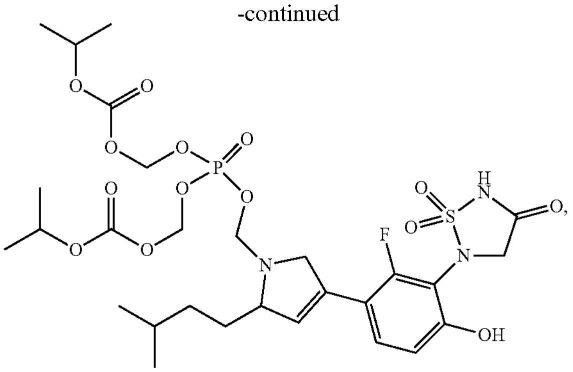

,

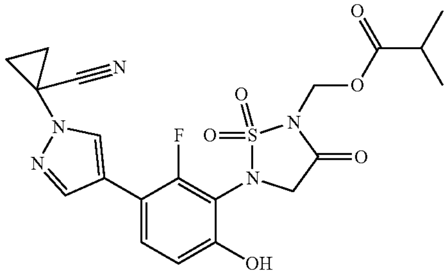

,

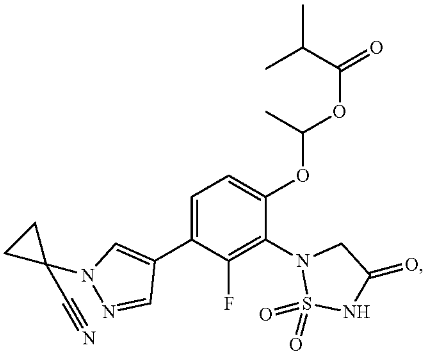

and

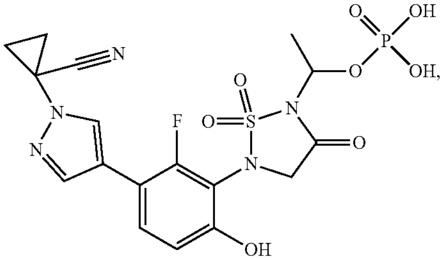

, or a pharmaceutically acceptable salt or solvate thereof.

Small molecule PTPN2 inhibitors suitable for use in the subject methods—including potentiating immunity of a subject—include compounds of Formula (I), encompassing Compound B; Formula (I-1); Formula (II); Formula (II-1); Formula (II-a); Formula (II-a1); Formula (III), encompassing Compound A; Formula (III-1); Formula (IV); and Formula (IV-1). Exemplary small molecule PTPN2 inhibitors include, but are not limited to, compounds selected from Table 1 (including Compound A and Compound B), or a salt or solvate thereof. Also provided herein are derivatives of compounds of Formula (I), (I-1), (II), (II-1), (II-a), (II-a1), (III), (III-1), (IV), or (IV-1), including prodrugs and metabolites thereof, which may exhibit distinct and desirable characteristics relative to the parent compound, such as enhanced in vitro potency, in vivo potency, PK properties, and/or oral bioavailability.

In some embodiments, a compound of Formula (I), (I-1), (II), (II-1), (II-a), (II-a1), (III), (III-1), (IV), or (IV-1) is provided as a substantially pure stereoisomer. In some embodiments, the stereoisomer is provided in at least 80% enantiomeric excess, such as at least 85%, at least 90%, at least 95%, at least 96%, at least 97%, at least 98%, at least 99%, or at least 99.9% enantiomeric excess.

Each enantiomer of a compound disclosed herein may exhibit distinct and desirable characteristics compared to the opposite enantiomer, such as enhanced in vitro potency, in vivo potency, PK properties, and/or oral bioavailability. For example, one enantiomer, such as a compound of Formula (III) or (III-1), may inhibit PTPN2 more potently than the other enantiomer, such as a compound of Formula (IV) or (IV-1), when assessed according to the phosphatase activity assay described in Example 2. In some embodiments, one enantiomer inhibits PTPN2 at least 1.1-fold more potently than the other enantiomer, such as at least 1.2-fold, 1.3-fold, 1.4-fold, 1.5-fold, 2.0-fold, or at least 2.5-fold more potently. One enantiomer, such as a compound of Formula (III) or (III-1), may inhibit PTP1B more potently than the other enantiomer, such as a compound of Formula (IV) or (IV-1), when assessed according to the phosphatase activity assay described in Example 2. In some embodiments, one enantiomer inhibits PTP1B at least 1.1-fold more potently than the other enantiomer, such as at least 1.2-fold, 1.3-fold, 1.4-fold, 1.5-fold, 2.0-fold, or at least 2.5-fold more potently. One enantiomer, such as a compound of Formula (III) or (III-1), may exhibit greater cell potency ($EC_{50}$) than the other enantiomer, such as a compound of Formula (IV) or (IV-1), when assessed in a mouse CD8 pSTAT1, pSTAT5, or CD25 assay. In some embodiments, one enantiomer exhibits a mouse CD8 pSTAT1, pSTAT5, or CD25 $EC_{50}$ at least 1.1-fold lower than the other enantiomer, such as at least 1.2-fold, 1.3-fold, 1.4-fold, 1.5-fold, 2.0-fold, or at least 2.5-fold lower. One enantiomer, such as a compound of Formula (IV) or (IV-1), may exhibit greater oral bioavailability in mice than the other enantiomer, such as a compound of Formula (III) or (III-1). In some embodiments, one enantiomer exhibits an oral bioavailability in mice at least 1.1-fold greater than the other enantiomer, such as at least 1.2-fold, 1.3-fold, 1.4-fold, 1.5-fold, 2.0-fold, or at least 2.5-fold greater. One enantiomer, such as a compound of Formula (III) or (III-1), may inhibit PTPN2 and PTP1B more potently, while the other enantiomer, such as a compound of Formula (IV) or (IV-1), may exhibit greater oral bioavailability. In some embodiments, one enantiomer, such as a compound of Formula (IV) or (IV-1), inhibits PTPN2 and PTP1B more potently, while the other enantiomer, such as a compound of Formula (III) or (III-1), may exhibit greater oral bioavailability.

Similarly, each enantiomer of a compound disclosed herein may exhibit distinct and desirable characteristics compared to a racemic mixture of the compound, such as favorable in vitro potency, in vivo potency, PK properties, and/or oral bioavailability. For example, one enantiomer of a compound, such as a compound of Formula (III), (III-1), (IV), or (IV-1), may inhibit PTPN2 more potently than a racemic mixture of the compound when assessed according to the phosphatase activity assay described in Example 2. In some embodiments, one enantiomer of a compound inhibits PTPN2 at least 1.1-fold more potently than a racemic mixture of the compound, such as at least 1.2-fold, 1.3-fold, 1.4-fold, 1.5-fold, 2.0-fold, or at least 2.5-fold more potently. One enantiomer of a compound, such as a compound of Formula (III), (III-1), (IV), or (IV-1), may inhibit PTP1B more potently than a racemic mixture of the compound when assessed according to the phosphatase activity assay described in Example 2. In some embodiments, one enantiomer of a compound inhibits PTP1B at least 1.1-fold more potently than a racemic mixture of the compound, such as at least 1.2-fold, 1.3-fold, 1.4-fold, 1.5-fold, 2.0-fold, or at least 2.5-fold more potently. One enantiomer of a compound, such as a compound of Formula (III), (III-1), (IV), or (IV-1), may exhibit greater cell potency ($EC_{50}$) than a racemic mixture of the compound when assessed in a mouse CD8 pSTAT1, pSTAT5, or CD25 assay. In some embodiments, one enantiomer of a compound exhibits a mouse CD8 pSTAT1, pSTAT5, or CD25 $EC_{50}$ at least 1.1-fold lower than a racemic mixture of the compound, such as at least 1.2-fold, 1.3-fold, 1.4-fold, 1.5-fold, 2.0-fold, or at least 2.5-fold lower. One enantiomer of a compound, such as a compound of Formula (III), (III-1), (IV), or (IV-1), may exhibit greater oral bioavailability in mice than a racemic mixture of the compound. In some embodiments, one enantiomer of a compound exhibits an oral bioavailability in mice at least 1.1-fold greater than a racemic mixture of the compound, such as at least 1.2-fold, 1.3-fold, 1.4-fold, 1.5-fold, 2.0-fold, or at least 2.5-fold greater.

In some embodiments, a compound of Formula (I), (I-1), (II), (II-1), (II-a), (II-a1), (III), (III-1), (IV), or (IV-1) is a prodrug that is converted under physiological conditions or by solvolysis to a biologically active compound. In some embodiments, the prodrug exhibits increased lipophilicity compared to the active compound. For example, a prodrug described herein may exhibit an increase of at least 5%, 10%, 15%, 20%, 25%, 30%, 35%, 40%, 45%, 50%, 60%, 70%, 80%, 90%, 100%, 125%, 150%, 175%, or at least 200% in lipophilicity relative to the lipophilicity of the active compound. In some embodiments, the prodrug exhibits improved stability (e.g., by reducing gut first-pass metabolism) relative to the active compound. For example, a prodrug described herein may exhibit an increase of at least 5%, 10%, 15%, 20%, 25%, 30%, 35%, 40%, 45%, 50%, 60%, 70%, 80%, 90%, 100%, 125%, 150%, 175%, or at least 200% in stability relative to the stability of the active compound. In some embodiments, the prodrug exhibits increased aqueous solubility relative to the active compound. For example, a prodrug described herein may exhibit an increase of at least 5%, 10%, 15%, 20%, 25%, 30%, 35%, 40%, 45%, 50%, 60%, 70%, 80%, 90%, 100%, 125%, 150%, 175%, or at least 200% in solubility relative to the solubility of the active compound. In some embodiments, an oral dose of the prodrug in a subject (e.g., rat) yields an increased AUC of the active compound relative to an equivalent dose of the active compound. For example, a prodrug described herein may yield an increase of at least 5%, 10%, 15%, 20%, 25%, 30%, 35%, 40%, 45%, 50%, 60%, 70%, 80%, 90%, 100%, 125%, 150%, 175%, or at least 200% in AUC relative to the AUC of the active compound. In some embodiments, the prodrug exhibits an increased oral bioavailability in a subject (e.g., rat) relative to an equivalent dose of the active compound. For example, a prodrug described herein may exhibit an increase of at least 5%, 10%, 15%, 20%, 25%, 30%, 35%, 40%, 45%, 50%, 60%, 70%, 80%, 90%, 100%, 125%, 150%, 175%, or at least 200% in oral bioavailability in a subject (e.g., rat) relative to the oral bioavailability of the active compound. In some embodiments, the increased AUC and increased oral bioavailability observed in rats for the prodrug are maintained across species, such as mice, rats, dogs, monkeys, or humans, in a dose dependent manner.

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases or inorganic or organic acids to form a pharmaceutically acceptable salt. In some embodiments, such salts are prepared in situ during the final isolation and purification of the compounds described herein, or by separately reacting a purified compound in its free form with a suitable acid or base, and isolating the salt thus formed.

In some embodiments, the compounds described herein exist as solvates. In some embodiments are methods of treating diseases by administering such solvates. Further described herein are methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein are conveniently prepared or formed during the processes described herein. By way of example only, hydrates of the compounds described herein are conveniently prepared by recrystallization from an aqueous/organic solvent mixture, using organic solvents including, but not limited to, dioxane, tetrahydrofuran, or MeOH. In addition, the compounds provided herein exist in unsolvated as well as solvated forms. In general, the solvated forms are considered equivalent to the unsolvated forms for the purposes of the compounds and methods provided herein.

In certain aspects, the present disclosure provides a compound of the formula D-$L^{DE}$-E wherein:

D is a monovalent form of a compound described herein;

$L^{DE}$ is a covalent linker bonded to D and E; and

E is a monovalent form of a degradation enhancer.

A "degradation enhancer" is a compound capable of binding a ubiquitin ligase protein (e.g., E3 ubiquitin ligase protein) or a compound capable of binding a protein that is capable of binding to a ubiquitin ligase protein to form a protein complex capable of conjugating a ubiquitin protein to a target protein. In some embodiments, the degradation enhancer is capable of binding to an E3 ubiquitin ligase protein or a protein complex comprising an E3 ubiquitin ligase protein. In some embodiments, the degradation enhancer is capable of binding to an E2 ubiquitin-conjugating enzyme. In some embodiments, the degradation enhancer is capable of binding to a protein complex comprising an E2 ubiquitin-conjugating enzyme and an E3 ubiquitin ligase protein.

In some embodiments, the degradation enhancer is capable of binding a protein selected from E3A, mdm2, APC, EDD1, SOCS/BC-box/eloBC/CUL5/RING, LNXp80, CBX4, CBLL1, HACE1, HECTD1, HECTD2, HECTD3, HECTD4, HECW1, HECW2, HERC1, HERC2, HERC3, HERC4, HER5, HERC6, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE3D, UBE4A, UBE4B, UBOX5, UBR5, VHL (von-Hippel-Lindau ubiquitin ligase), WWP1, WWP2, Parkin, MKRN1, CMA (chaperon-mediated autophage), SCFb-TRCP (Skip-Cullin-F box (Beta-TRCP) ubiquitin complex), b-TRCP (b-transducing repeat-containing protein), cIAP1 (cellular inhibitor of apoptosis protein 1), APC/C (anaphase-promoting complex/cyclosome), CRBN (cereblon), CUL4-RBX1-DDB1-CRBN ($CRL4^{CRBN}$) ubiquitin ligase, XIAP, IAP, KEAP1, DCAF15, RNF114, DCAF16, AhR, SOCS2, KLHL12, UBR2, SPOP, KLHL3, KLHL20, KLHDC2, SPSB1, SPSB2, SPSB4, SOCS6, FBXO4, FBXO31, BTRC, FBW7, CDC20, PML, TRIM21, TRIM24, TRIM33, GID4, avadomide, iberdomide, and CC-885. In some embodiments, the degradation enhancer is capable of binding a protein selected from UBE2A, UBE2B, UBE2C, UBE2D1, UBE2D2, UBE2D3, UBE2DR, UBE2E1, UBE2E2, UBE2E3, UBE2F, UBE2G1, UBE2G2, UBE2H, UBE2I, UBE2J1, UBE2J2, UBE2K, UBE2L3, UBE2L6, UBE2L1, UBE2L2, UBE2L4, UBE2M, UBE2N, UBE20, UBE2Q1, UBE2Q2, UBE2R1, UBE2R2, UBE2S, UBE2T, UBE2U, UBE2V1, UBE2V2, UBE2 W, UBE2Z, ATG3, BIRC6, and UFC1. In some embodiments, the degradation enhancer is a compound described in Ishida and Ciulli, SLAS Discovery 2021, Vol. 25 (4) 484-502, which is incorporated by reference in its entirety for any purpose, for example VH032, VH101, VH298, thalidomide, bestatin, methyl bestatin, nutlin, idasanutlin, bardoxolone, bardoxolone methyl, indisulam (E7070), E7820, chloroquinoxaline sulfonamide (CQS), nimbolide, KB02, ASTX660, lenalidomide, or pomalidomide.

In some embodiments, the degradation enhancer is a compound described in US20180050021, WO2016146985, WO2018189554, WO2018119441, WO2018140809, WO2018119448, WO2018119357, WO2018118598, WO2018102067, WO201898280, WO201889736, WO201881530, WO201871606, WO201864589, WO201852949, WO2017223452, WO2017204445, WO2017197055, WO2017197046, WO2017180417, WO2017176958, WO201711371, WO2018226542, WO2018223909, WO2018189554, WO2016169989, WO2016146985, CN105085620B, CN106543185B, U.S. Pat. Nos. 10,040,804, 9,938,302, 10,144,745, 10,145,848, 9,938,264, 9,632,089, 9,821,068, 9,758,522, 9,500,653, 9,765,019, 8,507,488, 8,299,057, US20180298027, US20180215731, US20170065719, US20170037004, US20160272639, US20150291562, or US20140356322, each of which is incorporated by reference in its entirety for any purpose.

In some embodiments, $L^{DE}$ is -$L^{DE1}$-$L^{DE2}$-$L^{DE3}$-$L^{DE4}$-$L^{DE5}$-;

$L^{DE1}$, $L^{DE2}$, $L^{DE3}$, $L^{DE4}$, and $L^{DE5}$ are independently a bond, —O—, —N($R^{12}$)—, —C(O)—, —N($R^{12}$)C(O)—, —C(O)N($R^{12}$)—, —S—, —S(O)$_2$—, —S(O)—, —S(O)$_2$N($R^{12}$)—, —S(O)N($R^{12}$)—, —N($R^{12}$) S(O)—, —N($R^{12}$)S(O)$_2$—, $C_{1-6}$ alkylene, (—O—$C_{1-6}$ alkyl)$_z$-, (—$C_{1-6}$ alkyl-O)$_z$—, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene, wherein $C_{1-6}$ alkylene, $C_{2-6}$ alkenylene, $C_{2-6}$ alkynylene, $C_{1-6}$ haloalkylene, $C_{3-12}$ cycloalkylene, $C_{1-11}$ heterocycloalkylene, $C_{6-12}$ arylene, or $C_{1-11}$ heteroarylene are optionally substituted with one, two, or three $R^{20}$, and wherein each $C_{1-6}$ alkyl of (—O—$C_{1-6}$ alkyl)$_z$- and (—$C_{1-6}$ alkyl-O)$_z$— is optionally substituted with one, two, or three $R^{20}$, and z is independently an integer from 0 to 10.

In some embodiments, $L^{DE}$ is —(O—$C_2$ alkyl)$_z$- and z is an integer from 1 to 10. In some embodiments, $L^{DE}$ is —($C_2$ alkyl-O—)$_z$— and z is an integer from 1 to 10. In some embodiments, $L^{DE}$ is —$(CH_2)_{zz1}L^{DE2}(CH_2O)_{zz2}$—, wherein $L^{DE}$2 is a bond, a 5- or 6-membered heterocyclene, phenylene, —$C_{2-4}$ alkynylene, —$SO_2$— or —NH—; and zz1 and zz2 are independently an integer from 0 to 10. In some embodiments, $L^{DE}$ is —$(CH_2)_{zz1}(CH_2O)_{zz2}$—, wherein zz1 and zz2 are each independently an integer from 0 to 10. In some embodiments, $L^{DE}$ is a PEG linker (e.g., divalent linker of 1 to 10 ethylene glycol subunits). In some embodiments, E is a monovalent form of a compound selected from

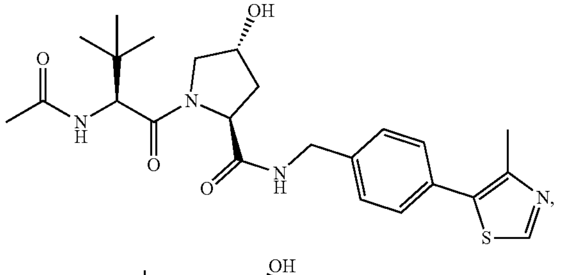
,
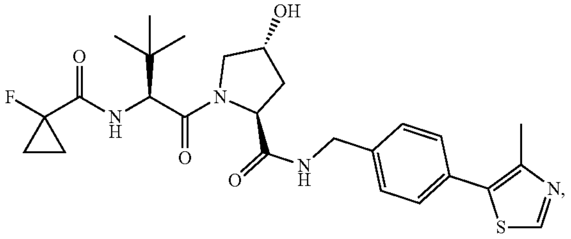
,
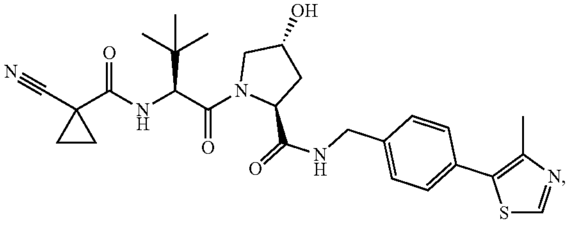
,
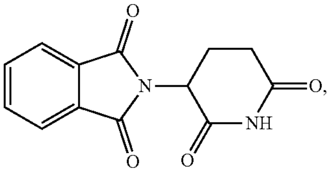
,
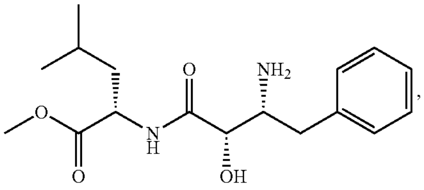
,
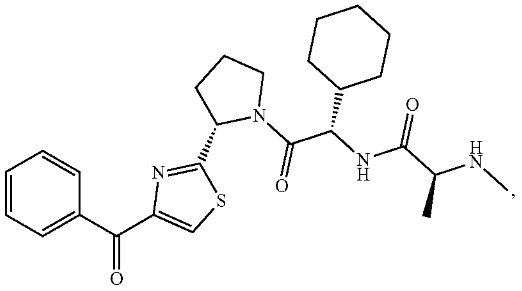
, -continued

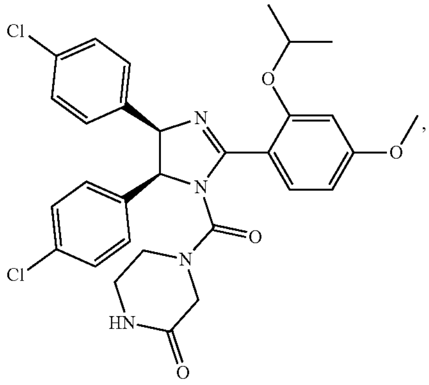
,
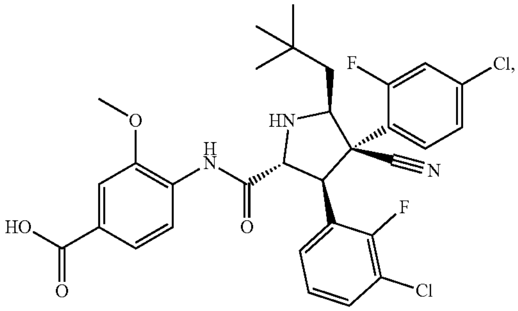
,
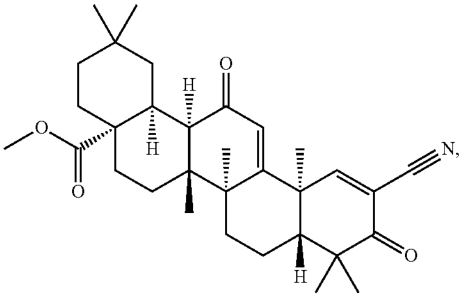
,
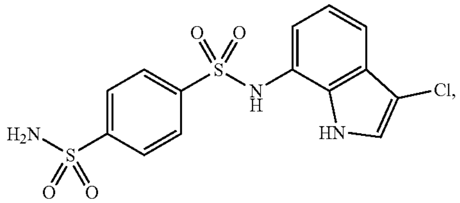
,
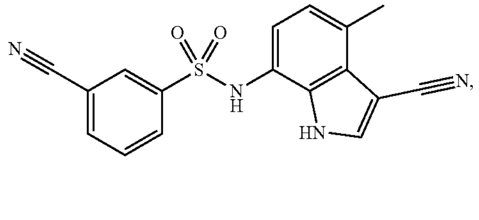
,
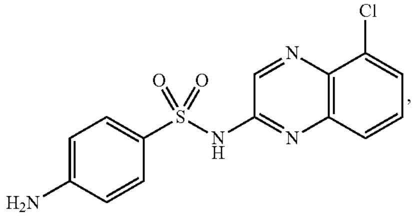
, and -continued
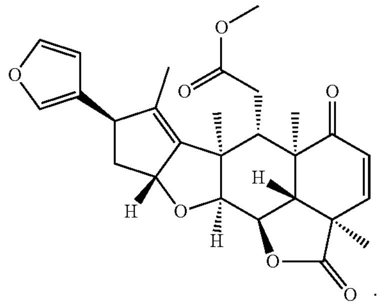
In some embodiments. E is a monovalent form of a compound selected from
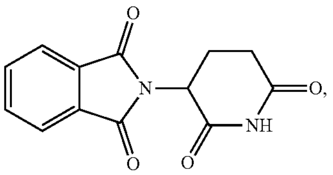
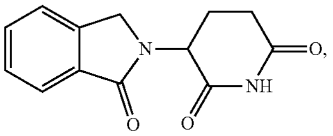
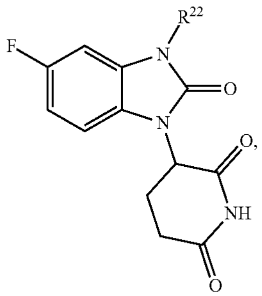
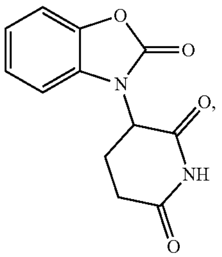
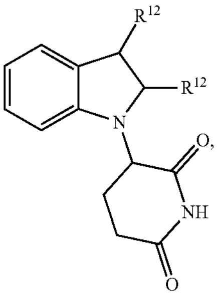
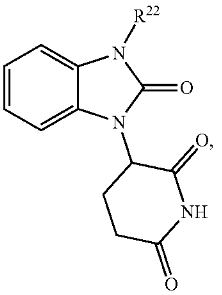
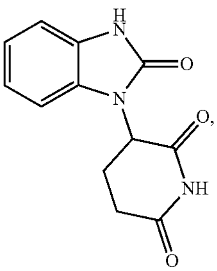
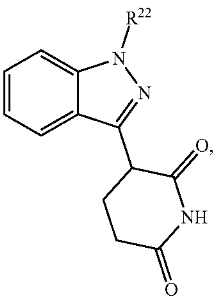
-continued
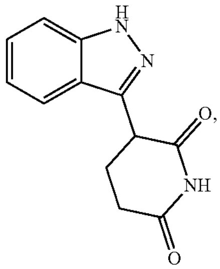
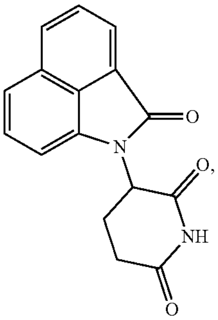
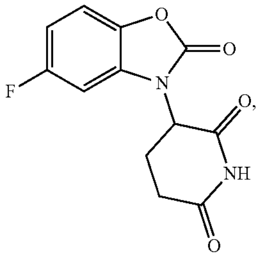
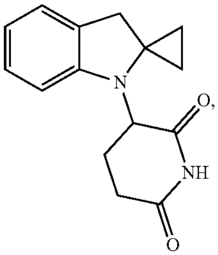
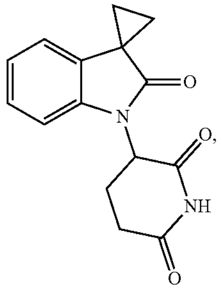
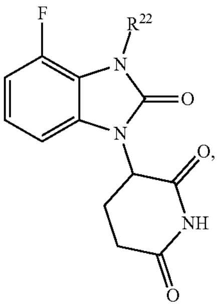
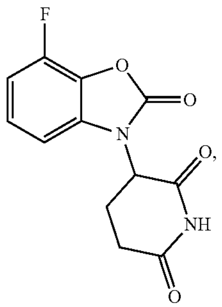
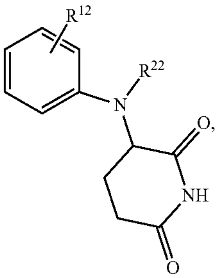
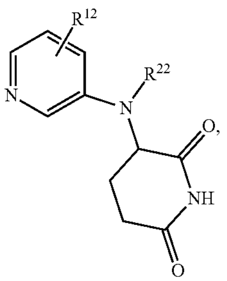
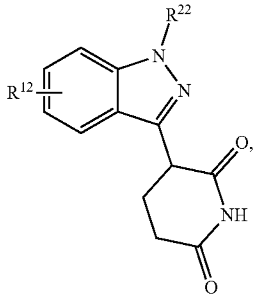

-continued
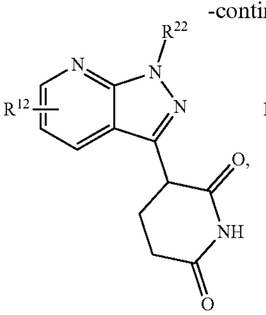
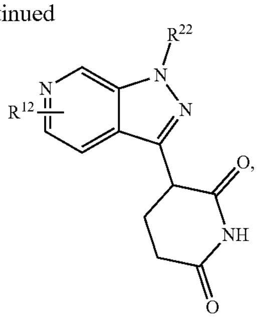
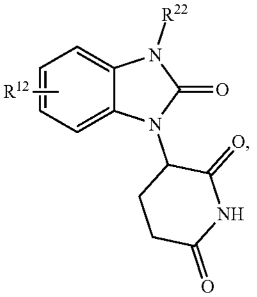
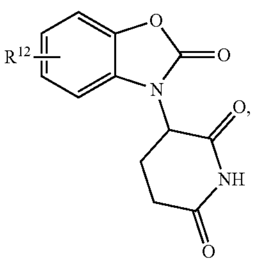
-continued
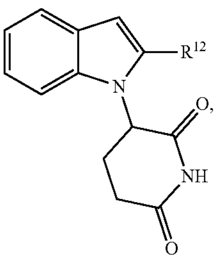
and
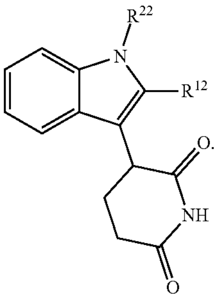
In some embodiments, the compound of formula D-$L^{DE}$-E is selected from:
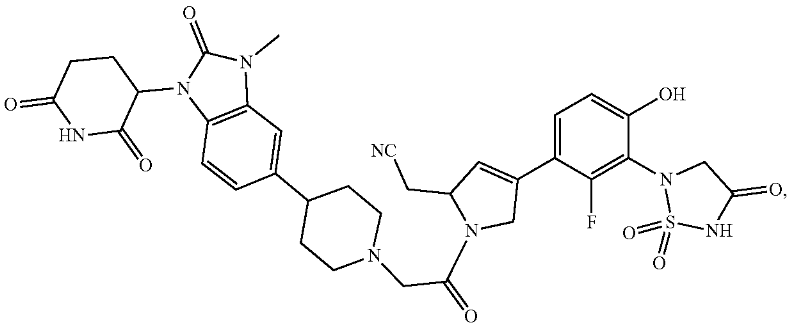
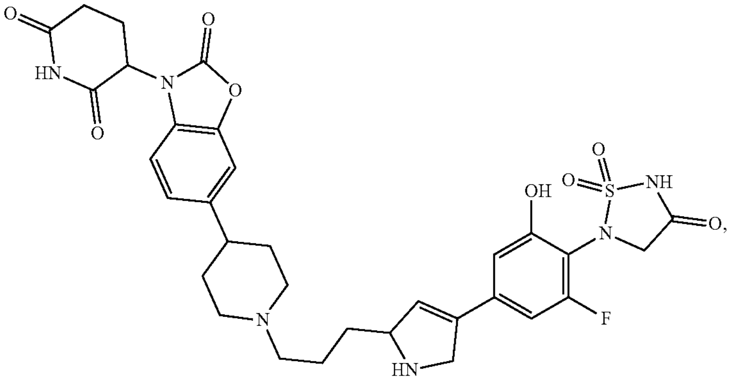
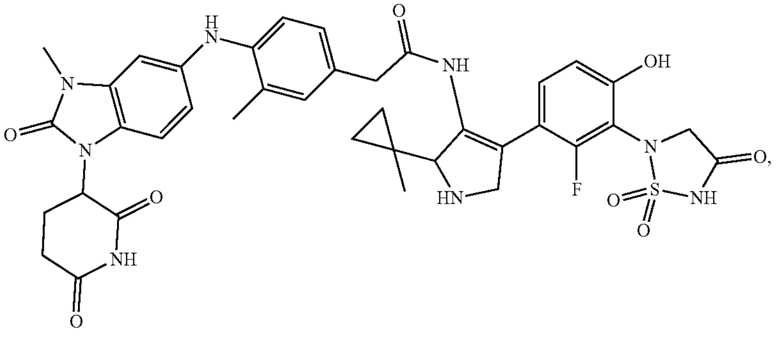

-continued

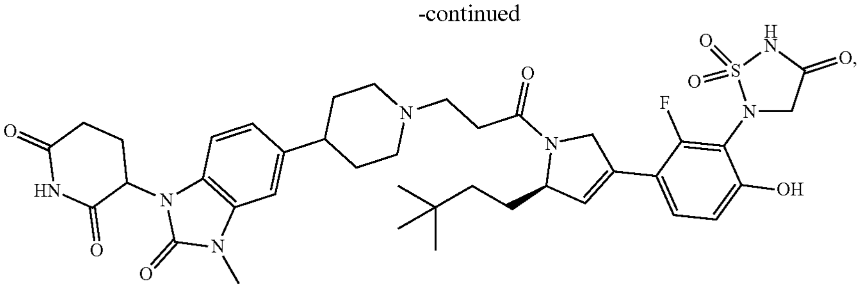

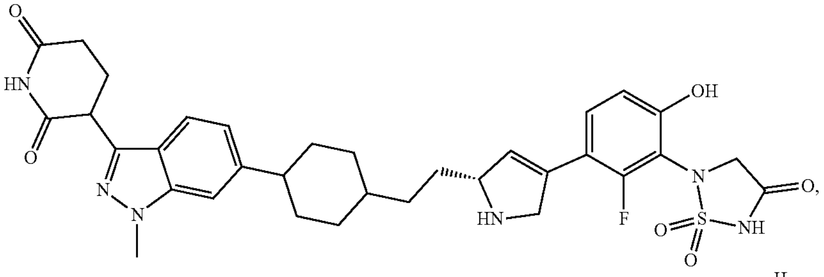

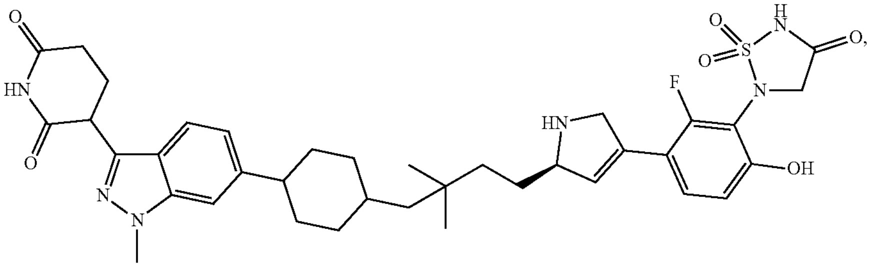

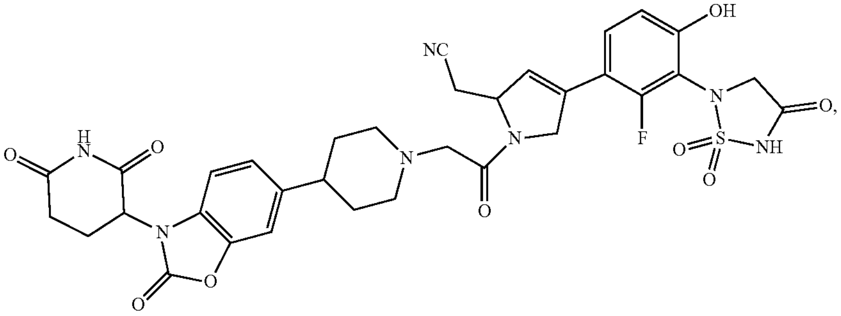

and

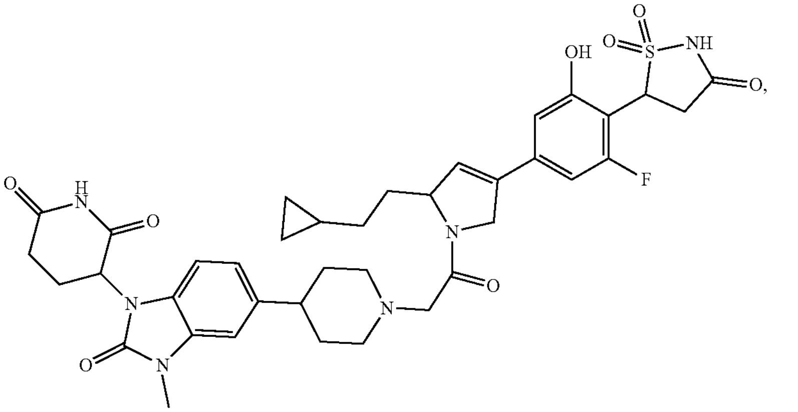

or a pharmaceutically acceptable salt or solvate thereof.

The chemical entities described herein can be synthesized according to one or more illustrative schemes herein and/or techniques known in the art. Materials used herein are either commercially available or prepared by synthetic methods generally known in the art. These schemes are not limited to the compounds listed in the examples or by any particular substituents, which are employed for illustrative purposes. Although various steps are described and depicted in Schemes 1-8, the steps in some cases may be performed in a different order than the order shown in Schemes 1-8. Various modifications to these synthetic reaction schemes may be made and will be suggested to one skilled in the art having referred to the present disclosure. Numberings or R groups in each scheme typically have the same meanings as those defined elsewhere herein unless otherwise indicated.

Unless specified to the contrary, the reactions described herein take place at atmospheric pressure, generally within a temperature range from −10° C. to 200° C. Further, except as otherwise specified, reaction times and conditions are intended to be approximate, e.g., taking place at about atmospheric pressure within a temperature range of about −10° C. to about 110° C. over a period of about 1 to about 24 hours; reactions left to run overnight average a period of about 16 hours.

In general, compounds of the disclosure may be prepared by the following reaction schemes:

Scheme 1

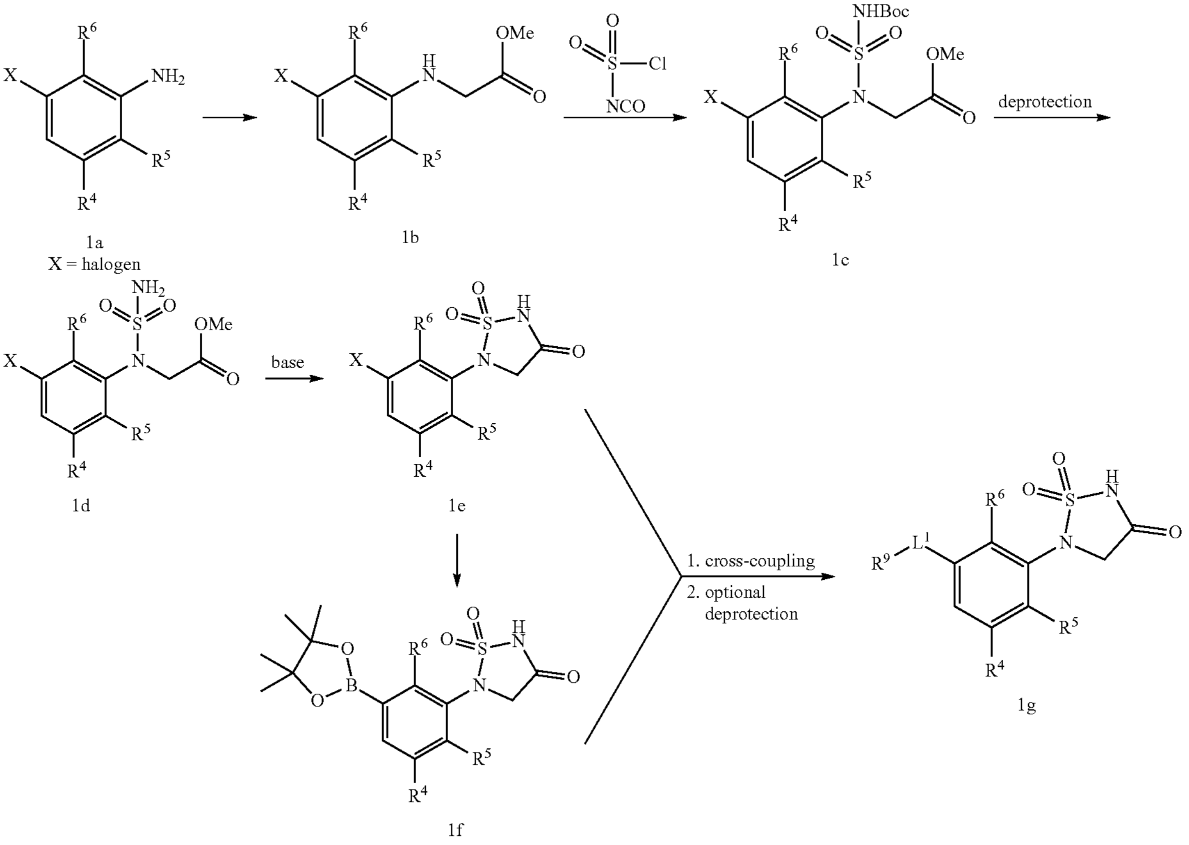

In some embodiments, a compound of Formula 1g may be prepared according to Scheme 1. For example, alkylation of aniline 1a can provide 1b. Addition of sulfurisocyanatidic chloride and a subsequent deprotection step can afford sulfamide 1d, which can undergo a cyclization under basic conditions to give 1e. Halide 1e can either be used directly in a cross coupling reaction—such as a Negishi coupling (e.g., using $R^9L^1ZnBr$), a Kumada coupling (e.g., using $R^9L^1MgCl$), a Stille reaction (e.g., using $R^9L^1SnBu_3$), or a Suzuki reaction (e.g., using $R^9L^1B(OH)_2$)—and optionally one or more protecting group manipulations, to afford a compound of Formula 1g. Alternatively, halide 1e can first be converted to a suitable organoboron derivative followed by an optional deprotection step to afford 1f, then $R^9L^1$ installed via a Suzuki reaction followed by one or more optional protecting group manipulations to provide a compound of Formula 1g.

Scheme 2

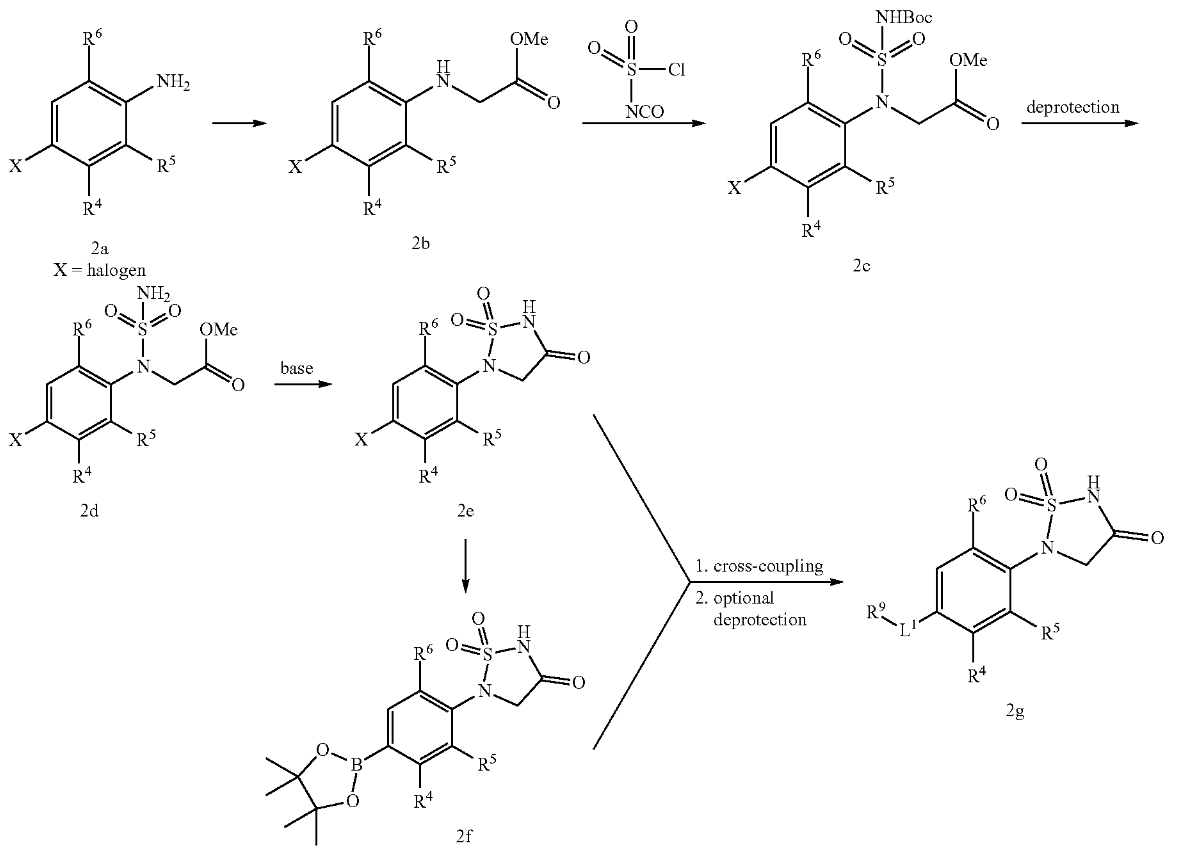

2a
X = halogen
2b
2c
2d
2e
2f
2g

Similarly, a compound of Formula 2g may be prepared according to Scheme 2. For example, alkylation of aniline 2a can provide 2b. Addition of sulfurisocyanatidic chloride and a subsequent deprotection step can afford sulfamide 2d, which can undergo a cyclization under basic conditions to give 2e. Halide 2e can either be used directly in a cross coupling reaction—such as a Negishi coupling (e.g., using $R^9L^1ZnBr$), a Kumada coupling (e.g., using $R^9L^1MgCl$), a Stille reaction (e.g., using $R^9L^1SnBu_3$), or a Suzuki reaction (e.g., using $R^9L^1B(OH)_2$)—and optionally one or more protecting group manipulations, to afford a compound of Formula 2g. Alternatively, halide 2e can first be converted to a suitable organoboron derivative followed by an optional deprotection step to afford 2f, then $R^9L^1$ installed via a Suzuki reaction followed by one or more optional protecting group manipulations to provide a compound of Formula 2g.

Scheme 3

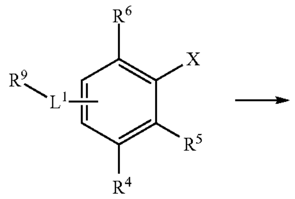

3a
X = halogen

-continued

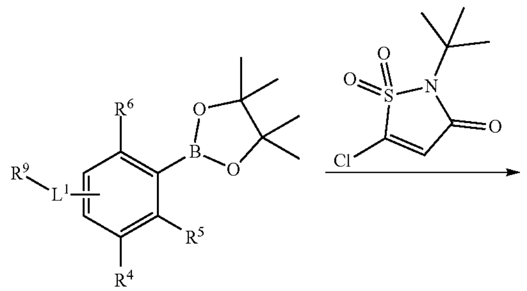

3b

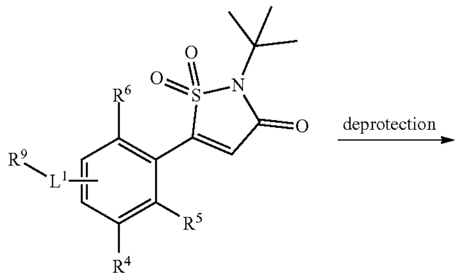

3c

-continued

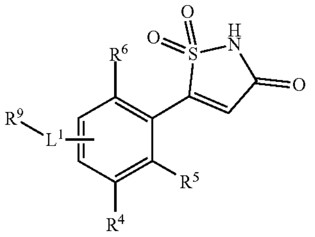

3d

In some embodiments, a compound of Formula 3d may be prepared according to Scheme 3. For example, conversion of aryl halide 3a to dioxoborolane 3b can be followed by a Suzuki reaction with 2-(tert-butyl)-5-chloroisothiazol-3(2H)-one 1,1-dioxide to provide 3c. A deprotection step can reveal a compound of Formula 3d.

Scheme 4

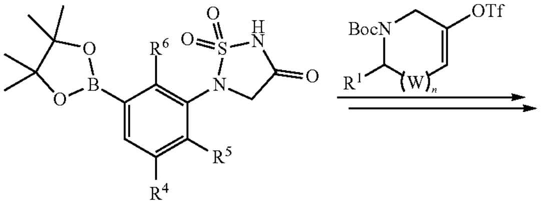

1f

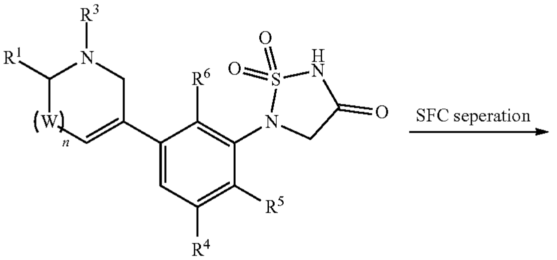

4a

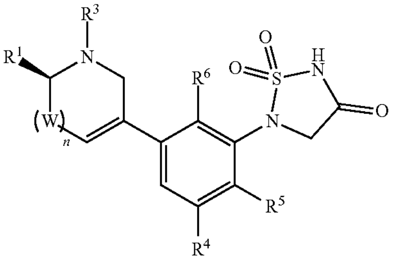

4b

-continued

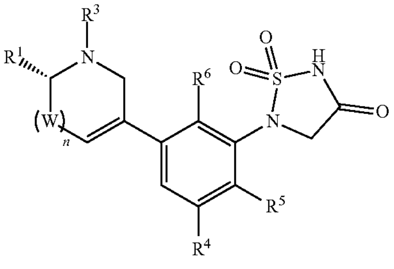

4c

In some embodiments, compounds of Formula 4b and 4c may be prepared according to Scheme 4. For example, a Suzuki reaction with 1f and a suitable triflate can be followed by one or more protecting group manipulations, and optionally one or more coupling reactions, to provide 4a. Chiral separation, such as SFC separation, can be used to separate the two enantiomers (4b and 4c).

Scheme 5

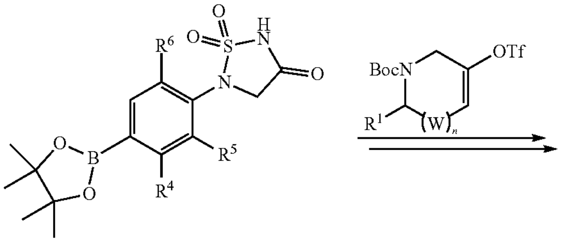

2f

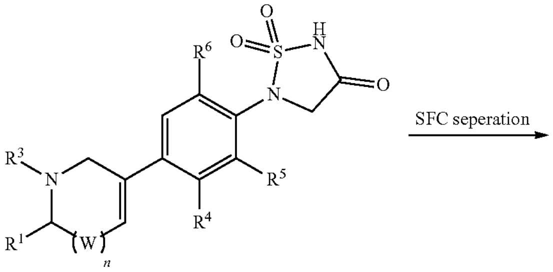

5a

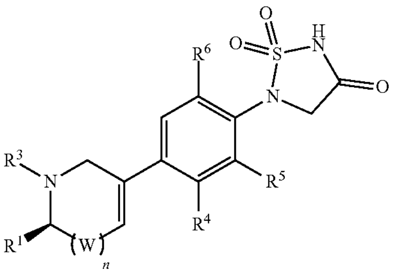

5b

-continued

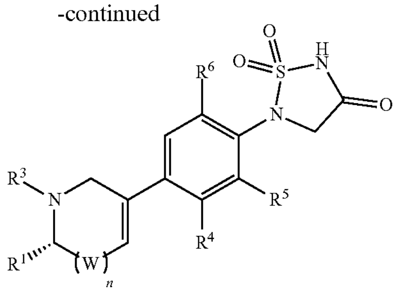

5c

Similarly, compounds of Formula 5b and 5c may be prepared according to Scheme 5. For example, a Suzuki reaction with 2f and a suitable triflate can be followed by one or more protecting group manipulations, and optionally one or more coupling reactions, to provide 5a. Chiral separation, such as SFC separation, can be used to separate the two enantiomers (5b and 5c).

Scheme 6

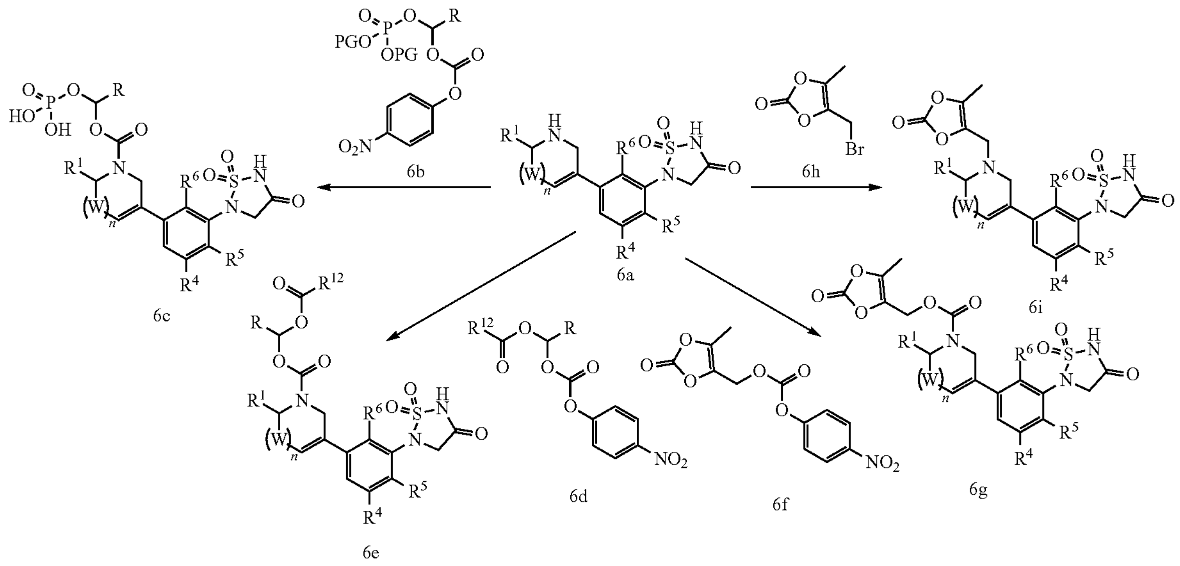

PG = protecting group
R = $C_{1-5}$ alkyl

In some embodiments, compounds of Formula 6c, 6e, 6g, and 6i may be prepared according to Scheme 6. For example, amine 6a can be treated with base and a suitable 4-nitrophenoxycarbonyl derivative, such as 6b, 6d, or 6f, and optionally undergo one or more protecting group manipulations to provide carbamates 6c, 6e, and 6g, respectively. Alternatively, amine 6a can be reacted with alkyl bromide 6h in the presence of a suitable base, optionally followed by one or more protecting group manipulations, to provide a compound of Formula 6i.

Scheme 7

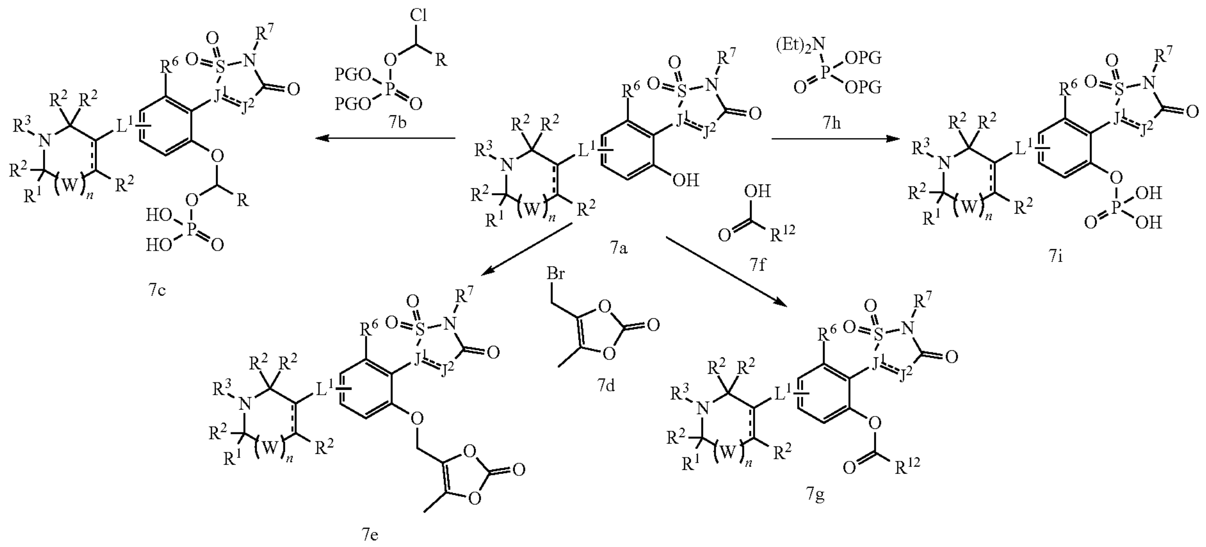

PG = protecting group
R = $C_{1-5}$ alkyl

In some embodiments, compounds of Formula 7c, 7e, 7g, and 7i may be prepared according to Scheme 7. For example, phenol 7a can be treated with base and a suitable alkyl halide, such as 7b or 7d, and optionally undergo one or more protecting group manipulations to provide ethers 7c and 7e, respectively. Alternatively, phenol 7a can undergo an esterification reaction with carboxylic acid 7f, and optionally one or more protecting group manipulations, to afford 7g. Phosphonic acid 7i can be prepared by coupling phenol 7a with 7h, followed by one or more protecting group manipulations.

Scheme 8

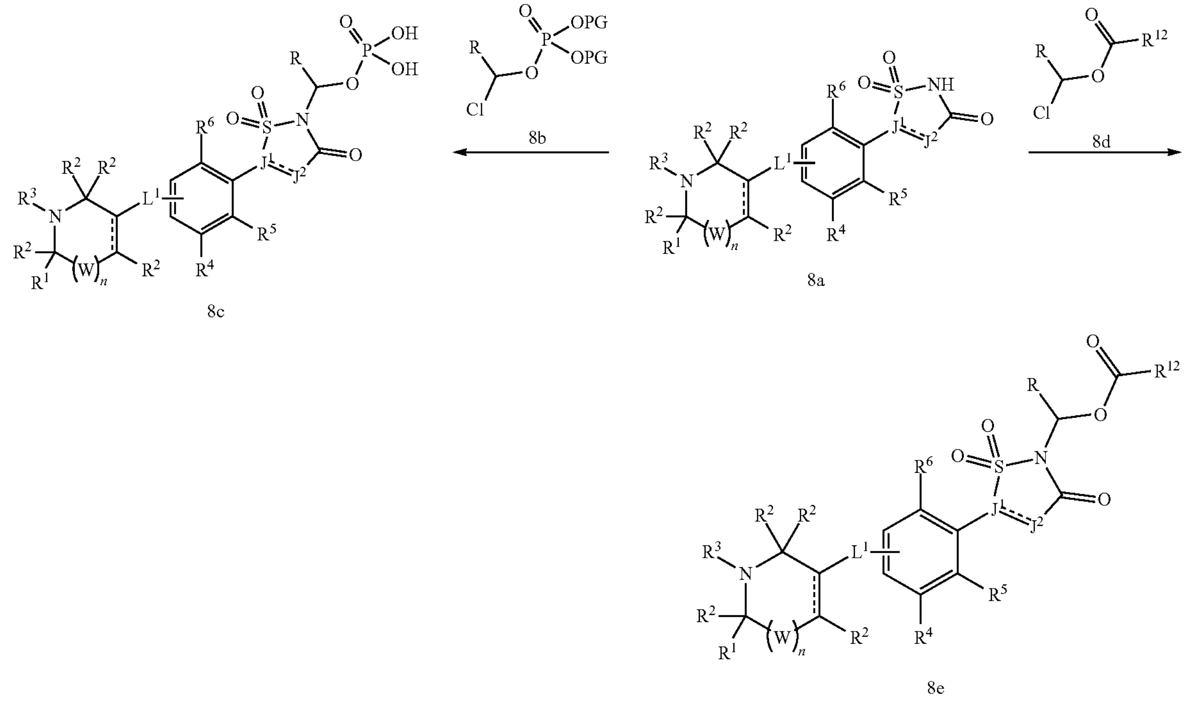

PG = protecting group
R = $C_{1-5}$ alkyl

In some embodiments, compounds of Formula 8c and 8e may be prepared according to Scheme 8. For example, 8a can be treated with base and a suitable alkyl halide, such as 8b or 8d, and optionally undergo one or more protecting group manipulations to provide a compound of Formula 8c or 8e, respectively.

In some embodiments, a compound of the present disclosure, for example, a compound of a formula given in Table 1, was synthesized according to one of the general routes outlined in Schemes 1-8, Examples 1a-1r, or by methods generally known in the art. In some embodiments, exemplary compounds may include, but are not limited to, a compound selected from Table 1, or a salt or solvate thereof.

TABLE 1

| No. | Structure | Chemical Name | [M − H]⁻ |
|---|---|---|---|
| 101 | 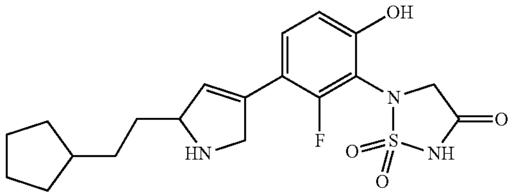 [SMILES: O=C1CN(c2c(O)ccc(C3=CC(CCC4CCCC4)NC3)c2F)S(=O)(=O)N1] | 5-(3-(5-(2-cyclopentylethyl)-2,5-dihydro-1H-pyrrol-3-yl)-2-fluoro-6-hydroxyphenyl)-1,2,5-thiadiazolidin-3-one 1,1-dioxide | 408.3 |
| 102 | 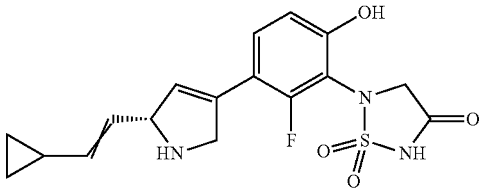 [SMILES: O=C1CN(c2c(O)ccc(C3=C[C@@H](C=CC4CC4)NC3)c2F)S(=O)(=O)N1] | (R,E)-5-(3-(5-(2-cyclopropylvinyl)-2,5-dihydro-1H-pyrrol-3-yl)-2-fluoro-6-hydroxyphenyl)-1,2,5-thiadiazolidin-3-one 1,1-dioxide or (R,Z)-5-(3-(5-(2-cyclopropylvinyl)-2,5-dihydro-1H-pyrrol-3-yl)-2-fluoro-6-hydroxyphenyl)-1,2,5-thiadiazolidin-3-one 1,1-dioxide | 378.0 |
| 103 | 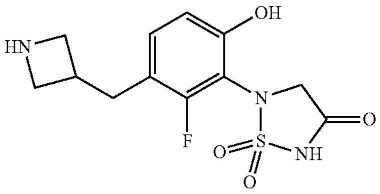 [SMILES: O=C1CN(c2c(O)ccc(CC3CNC3)c2F)S(=O)(=O)N1] | 5-(3-(azetidin-3-ylmethyl)-2-fluoro-6-hydroxyphenyl)-1,2,5-thiadiazolidin-3-one 1,1-dioxide | 314.1 |
| 104 | 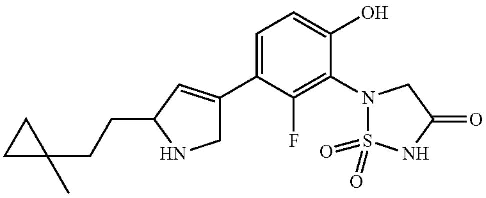 [SMILES: CC1(CCC2C=C(c3ccc(O)c(N4CC(=O)NS4(=O)=O)c3F)CN2)CC1] | 5-(2-fluoro-6-hydroxy-3-(5-(2-(1-methylcyclopropyl)ethyl)-2,5-dihydro-1H-pyrrol-3-yl)phenyl)-1,2,5-thiadiazolidin-3-one 1,1-dioxide | 394.1 |
| 105 | 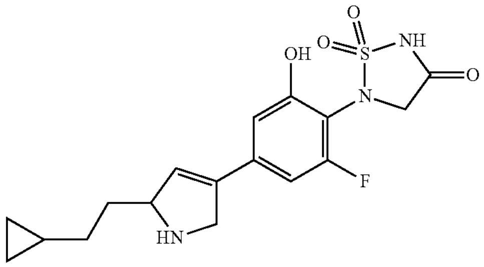 [SMILES: O=C1CN(c2c(O)cc(C3=CC(CCC4CC4)NC3)cc2F)S(=O)(=O)N1] | 5-(4-(5-(2-cyclopropylethyl)-2,5-dihydro-1H-pyrrol-3-yl)-2-fluoro-6-hydroxyphenyl)-1,2,5-thiadiazolidin-3-one 1,1-dioxide | 380.3 |
| 106 | 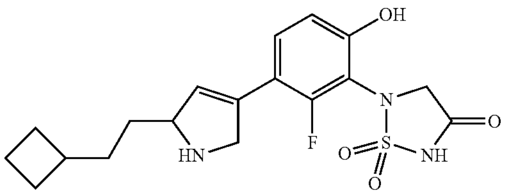 [SMILES: O=C1CN(c2c(O)ccc(C3=CC(CCC4CCC4)NC3)c2F)S(=O)(=O)N1] | 5-(3-(5-(2-cyclobutylethyl)-2,5-dihydro-1H-pyrrol-3-yl)-2-fluoro-6-hydroxyphenyl)-1,2,5-thiadiazolidin-3-one 1,1-dioxide | 394.3 |

TABLE 1-continued

| No. | Structure | Chemical Name | [M − H]⁻ |
|---|---|---|---|
| 107 | 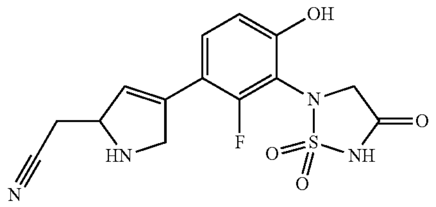 [SMILES: N#CCC1C=C(c2ccc(O)c(N3CC(=O)NS3(=O)=O)c2F)CN1] | 2-(4-(3-(1,1-dioxido-4-oxo-1,2,5-thiadiazolidin-2-yl)-2-fluoro-4-hydroxyphenyl)-2,5-dihydro-1H-pyrrol-2-yl)acetonitrile | 353.1 $[M + H]^+$ |
| 108 | 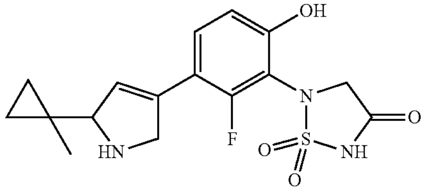 [SMILES: CC1(C2C=C(c3ccc(O)c(N4CC(=O)NS4(=O)=O)c3F)CN2)CC1] | 5-(2-fluoro-6-hydroxy-3-(5-(1-methylcyclopropyl)-2,5-dihydro-1H-pyrrol-3-yl)phenyl)-1,2,5-thiadiazolidin-3-one 1,1-dioxide | 366.1 |
| 109 | 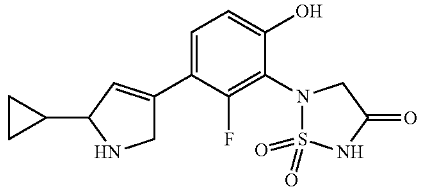 [SMILES: O=C1CN(c2c(O)ccc(C3=CC(C4CC4)NC3)c2F)S(=O)(=O)N1] | 5-(3-(5-cyclopropyl-2,5-dihydro-1H-pyrrol-3-yl)-2-fluoro-6-hydroxyphenyl)-1,2,5-thiadiazolidin-3-one 1,1-dioxide | 354.0 $[M + H]^+$ |
| 110 | 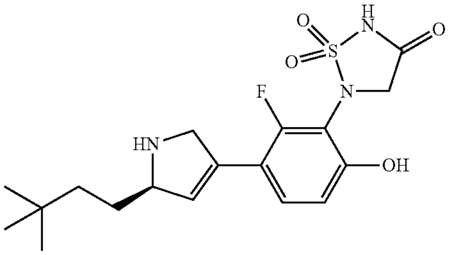 [SMILES: CC(C)(C)CC[C@@H]1C=C(c2ccc(O)c(N3CC(=O)NS3(=O)=O)c2F)CN1] | (R)-5-(3-(5-(3,3-dimethylbutyl)-2,5-dihydro-1H-pyrrol-3-yl)-2-fluoro-6-hydroxyphenyl)-1,2,5-thiadiazolidin-3-one 1,1-dioxide | 398.1 $[M + H]^+$ |
| 111 | 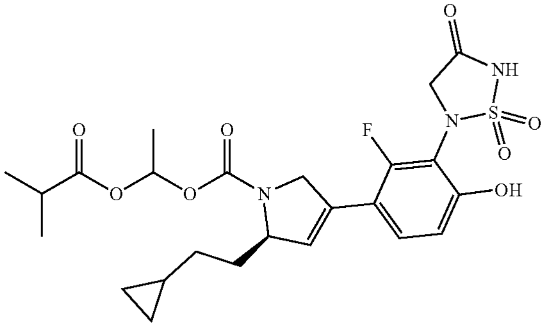 [SMILES: CC(OC(=O)C(C)C)OC(=O)N1CC(c2ccc(O)c(N3CC(=O)NS3(=O)=O)c2F)=C[C@H]1CCC1CC1] | 1-(isobutyryloxy)ethyl (2R)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 538.2 |
| 112 | 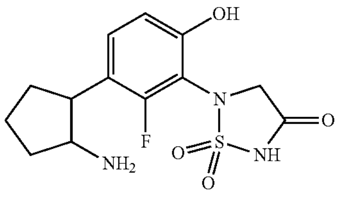 [SMILES: NC1CCCC1c1ccc(O)c(N2CC(=O)NS2(=O)=O)c1F] | 5-(3-(2-aminocyclopentyl)-2-fluoro-6-hydroxyphenyl)-1,2,5-thiadiazolidin-3-one 1,1-dioxide | 329.9 $[M + H]^+$ |

TABLE 1-continued

| No. | Structure | Chemical Name | [M − H]⁻ |
|---|---|---|---|
| 113 | 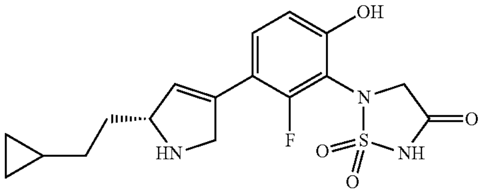 [SMILES: O=C1CN(c2c(O)ccc(C3=C[C@@H](CCC4CC4)NC3)c2F)S(=O)(=O)N1] | (R)-5-(3-(5-(2-cyclopropylethyl)-2,5-dihydro-1H-pyrrol-3-yl)-2-fluoro-6-hydroxyphenyl)-1,2,5-thiadiazolidin-3-one 1,1-dioxide | 382.0 $[M + H]^+$ |
| 114 | 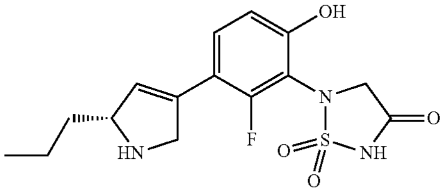 [SMILES: CCC[C@@H]1C=C(c2ccc(O)c(N3CC(=O)NS3(=O)=O)c2F)CN1] | (R)-5-(2-fluoro-6-hydroxy-3-(5-propyl-2,5-dihydro-1H-pyrrol-3-yl)phenyl)-1,2,5-thiadiazolidin-3-one 1,1-dioxide | 356.1 |
| 115 | 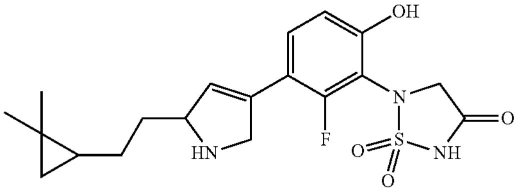 [SMILES: CC1(C)CC1CCC1C=C(c2ccc(O)c(N3CC(=O)NS3(=O)=O)c2F)CN1] | 5-(3-(5-(2-(2,2-dimethylcyclopropyl)ethyl)-2,5-dihydro-1H-pyrrol-3-yl)-2-fluoro-6-hydroxyphenyl)-1,2,5-thiadiazolidin-3-one 1,1-dioxide | 408.1 |
| 116 | 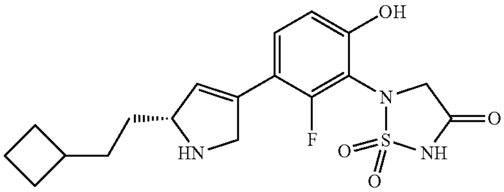 [SMILES: O=C1CN(c2c(O)ccc(C3=C[C@@H](CCC4CCC4)NC3)c2F)S(=O)(=O)N1] | (R)-5-(3-(5-(2-cyclobutylethyl)-2,5-dihydro-1H-pyrrol-3-yl)-2-fluoro-6-hydroxyphenyl)-1,2,5-thiadiazolidin-3-one 1,1-dioxide | 394.1 |
| 117 | 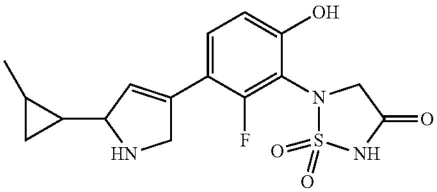 [SMILES: CC1CC1C1C=C(c2ccc(O)c(N3CC(=O)NS3(=O)=O)c2F)CN1] | 5-(2-fluoro-6-hydroxy-3-(5-(2-methylcyclopropyl)-2,5-dihydro-1H-pyrrol-3-yl)phenyl)-1,2,5-thiadiazolidin-3-one 1,1-dioxide | 366.3 |
| 118 | 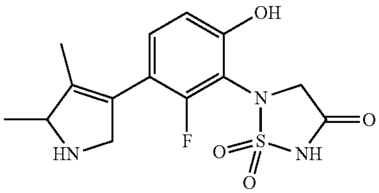 [SMILES: CC1=C(c2ccc(O)c(N3CC(=O)NS3(=O)=O)c2F)CNC1C] | 5-(3-(4,5-dimethyl-2,5-dihydro-1H-pyrrol-3-yl)-2-fluoro-6-hydroxyphenyl)-1,2,5-thiadiazolidin-3-one 1,1-dioxide | 340.0 |
| 119 | 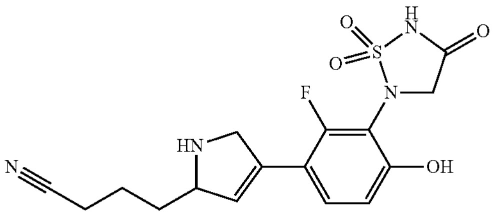 [SMILES: N#CCCCC1C=C(c2ccc(O)c(N3CC(=O)NS3(=O)=O)c2F)CN1] | 4-(4-(3-(1,1-dioxido-4-oxo-1,2,5-thiadiazolidin-2-yl)-2-fluoro-4-hydroxyphenyl)-2,5-dihydro-1H-pyrrol-2-yl)butanenitrile | 379.1 |

TABLE 1-continued

| No. | Structure | Chemical Name | [M − H]⁻ |
|---|---|---|---|
| 120 | 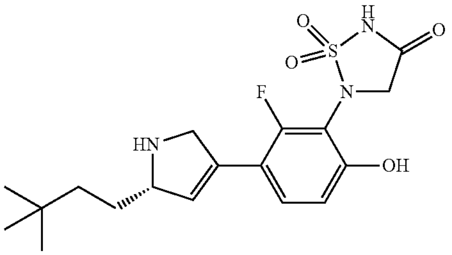 [SMILES: CC(C)(C)CC[C@H]1C=C(c2ccc(O)c(N3CC(=O)NS3(=O)=O)c2F)CN1] | (S)-5-(3-(5-(3,3-dimethylbutyl)-2,5-dihydro-1H-pyrrol-3-yl)-2-fluoro-6-hydroxyphenyl)-1,2,5-thiadiazolidin-3-one 1,1-dioxide | 398.1 $[M + H]^+$ |
| 121 | 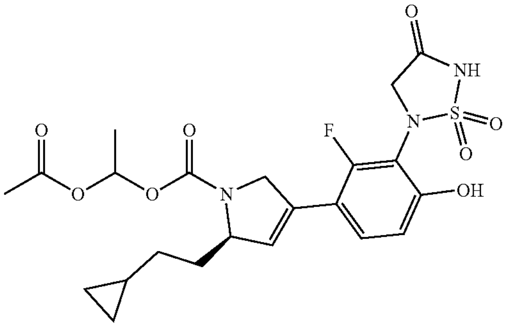 [SMILES: CC(=O)OC(C)OC(=O)N1CC(c2ccc(O)c(N3CC(=O)NS3(=O)=O)c2F)=C[C@H]1CCC1CC1] | 1-acetoxyethyl (2R)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 510.2 |
| 122 | 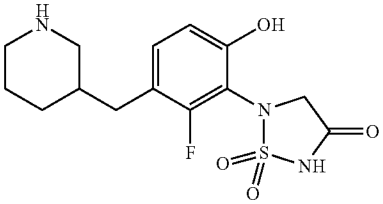 [SMILES: O=C1CN(c2c(O)ccc(CC3CCCNC3)c2F)S(=O)(=O)N1] | 5-(2-fluoro-6-hydroxy-3-(piperidin-3-ylmethyl)phenyl)-1,2,5-thiadiazolidin-3-one 1,1-dioxide | 342.1 |
| 123 | 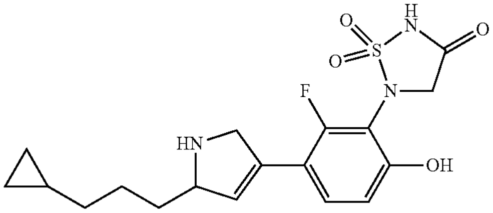 [SMILES: O=C1CN(c2c(O)ccc(C3=CC(CCCC4CC4)NC3)c2F)S(=O)(=O)N1] | 5-(3-(5-(3-cyclopropylpropyl)-2,5-dihydro-1H-pyrrol-3-yl)-2-fluoro-6-hydroxyphenyl)-1,2,5-thiadiazolidin-3-one 1,1-dioxide | 396.1 $[M + H]^+$ |
| 124 | 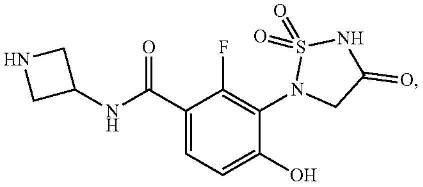 [SMILES: O=C1CN(c2c(O)ccc(C(=O)NC3CNC3)c2F)S(=O)(=O)N1] | N-(azetidin-3-yl)-3-(1,1-dioxido-4-oxo-1,2,5-thiadiazolidin-2-yl)-2-fluoro-4-hydroxybenzamide | 343.1 |
| 125 | 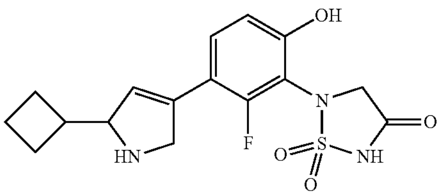 [SMILES: O=C1CN(c2c(O)ccc(C3=CC(C4CCC4)NC3)c2F)S(=O)(=O)N1] | 5-(3-(5-cyclobutyl-2,5-dihydro-1H-pyrrol-3-yl)-2-fluoro-6-hydroxyphenyl)-1,2,5-thiadiazolidin-3-one 1,1-dioxide | 366.1 |

TABLE 1-continued

| No. | Structure | Chemical Name | [M − H]⁻ |
| --- | --- | --- | --- |
| 126 | 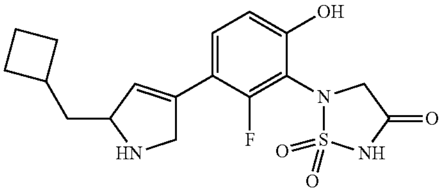 [SMILES: O=C1CN(c2c(O)ccc(C3=CC(CC4CCC4)NC3)c2F)S(=O)(=O)N1] | 5-(3-(5-(cyclobutylmethyl)-2,5-dihydro-1H-pyrrol-3-yl)-2-fluoro-6-hydroxyphenyl)-1,2,5-thiadiazolidin-3-one 1,1-dioxide | 380.2 |
| 127 | 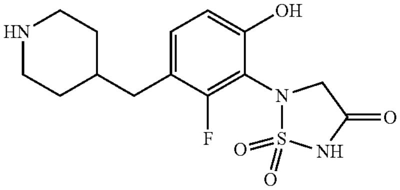 [SMILES: O=C1CN(c2c(O)ccc(CC3CCNCC3)c2F)S(=O)(=O)N1] | 5-(2-fluoro-6-hydroxy-3-(piperidin-4-ylmethyl)phenyl)-1,2,5-thiadiazolidin-3-one 1,1-dioxide | 342.1 |
| 128 | 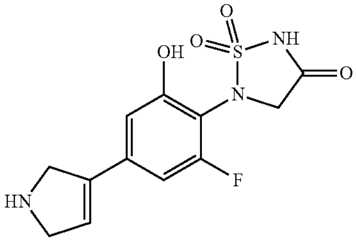 [SMILES: O=C1CN(c2c(O)cc(C3=CCNC3)cc2F)S(=O)(=O)N1] | 5-(4-(2,5-dihydro-1H-pyrrol-3-yl)-2-fluoro-6-hydroxyphenyl)-1,2,5-thiadiazolidin-3-one 1,1-dioxide | 314.0 $[M + H]^+$ |
| 129 | 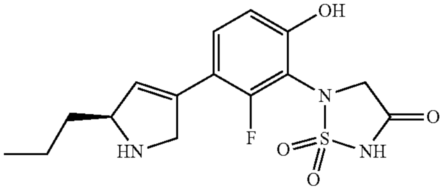 [SMILES: CCC[C@H]1C=C(c2ccc(O)c(N3CC(=O)NS3(=O)=O)c2F)CN1] | (S)-5-(2-fluoro-6-hydroxy-3-(5-propyl-2,5-dihydro-1H-pyrrol-3-yl)phenyl)-1,2,5-thiadiazolidin-3-one 1,1-dioxide | 356.0 |
| 130 | 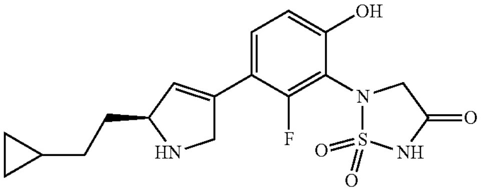 [SMILES: O=C1CN(c2c(O)ccc(C3=C[C@H](CCC4CC4)NC3)c2F)S(=O)(=O)N1] | (S)-5-(3-(5-(2-cyclopropylethyl)-2,5-dihydro-1H-pyrrol-3-yl)-2-fluoro-6-hydroxyphenyl)-1,2,5-thiadiazolidin-3-one 1,1-dioxide | 382.0 $[M + H]^+$ |
| 131 | 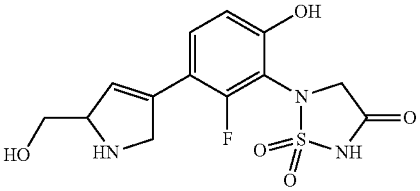 [SMILES: O=C1CN(c2c(O)ccc(C3=CC(CO)NC3)c2F)S(=O)(=O)N1] | 5-(2-fluoro-6-hydroxy-3-(3-(hydroxymethyl)cyclopent-1-en-1-yl)phenyl)-1,2,5-thiadiazolidin-3-one 1,1-dioxide | 341.1 |
| 132 | 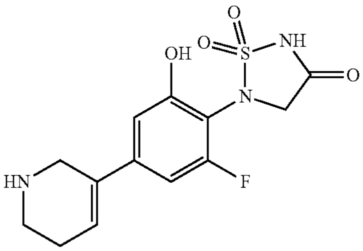 [SMILES: O=C1CN(c2c(O)cc(C3=CCCNC3)cc2F)S(=O)(=O)N1] | 5-(2-fluoro-6-hydroxy-4-(1,2,5,6-tetrahydropyridin-3-yl)phenyl)-1,2,5-thiadiazolidin-3-one 1,1-dioxide | 326.0 |

TABLE 1-continued

| No. | Structure | Chemical Name | [M − H]⁻ |
|---|---|---|---|
| 133 | 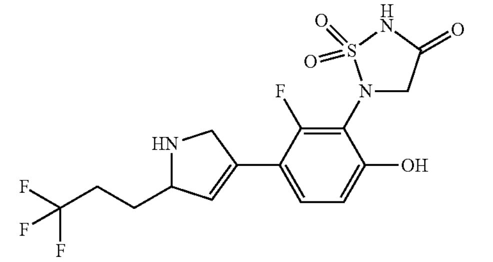 [SMILES: O=C1CN(c2c(O)ccc(C3=CC(CCC(F)(F)F)NC3)c2F)S(=O)(=O)N1] | 5-(2-fluoro-6-hydroxy-3-(5-(3,3,3-trifluoropropyl)-2,5-dihydro-1H-pyrrol-3-yl)phenyl)-1,2,5-thiadiazolidin-3-one 1,1-dioxide | 410.1 [M + H]+ |
| 134 | 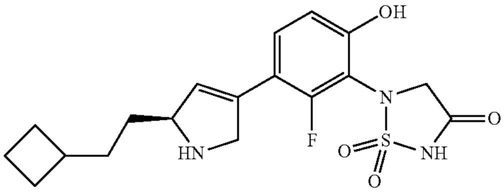 [SMILES: O=C1CN(c2c(O)ccc(C3=C[C@H](CCC4CCC4)NC3)c2F)S(=O)(=O)N1] | (S)-5-(3-(5-(2-cyclobutylethyl)-2,5-dihydro-1H-pyrrol-3-yl)-2-fluoro-6-hydroxyphenyl)-1,2,5-thiadiazolidin-3-one 1,1-dioxide | 394.1 |
| 135 | 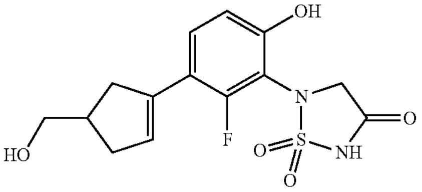 [SMILES: O=C1CN(c2c(O)ccc(C3=CCC(CO)C3)c2F)S(=O)(=O)N1] | 5-(2-fluoro-6-hydroxy-3-(4-(hydroxymethyl)cyclopent-1-en-1-yl)phenyl)-1,2,5-thiadiazolidin-3-one 1,1-dioxide | 341.1 |
| 136 | 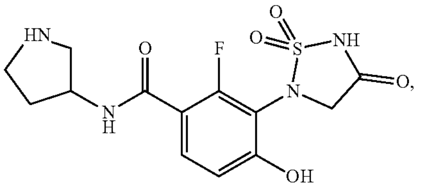 [SMILES: O=C1CN(c2c(O)ccc(C(=O)NC3CCNC3)c2F)S(=O)(=O)N1] | 3-(1,1-dioxido-4-oxo-1,2,5-thiadiazolidin-2-yl)-2-fluoro-4-hydroxy-N-(pyrrolidin-3-yl)benzamide | 357.2 |
| 137 | 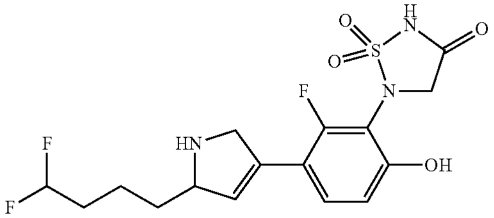 [SMILES: O=C1CN(c2c(O)ccc(C3=CC(CCCC(F)F)NC3)c2F)S(=O)(=O)N1] | 5-(3-(5-(4,4-difluorobutyl)-2,5-dihydro-1H-pyrrol-3-yl)-2-fluoro-6-hydroxyphenyl)-1,2,5-thiadiazolidin-3-one 1,1-dioxide | 406.0 [M + H]+ |
| 138 | 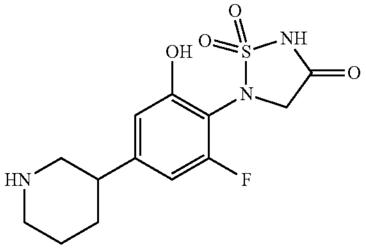 [SMILES: O=C1CN(c2c(O)cc(C3CCCNC3)cc2F)S(=O)(=O)N1] | 5-(2-fluoro-6-hydroxy-4-(piperidin-3-yl)phenyl)-1,2,5-thiadiazolidin-3-one 1,1-dioxide | 328.1 |
| 139 | 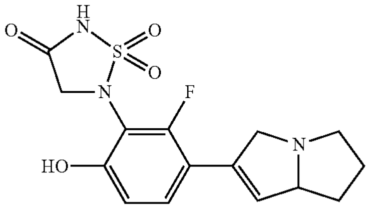 [SMILES: O=C1CN(c2c(O)ccc(C3=CC4CCCN4C3)c2F)S(=O)(=O)N1] | 5-(2-fluoro-6-hydroxy-3-(2,3,5,7a-tetrahydro-1H-pyrrolizin-6-yl)phenyl)-1,2,5-thiadiazolidin-3-one 1,1-dioxide | 352.1 |

TABLE 1-continued

| No. | Structure | Chemical Name | [M − H]⁻ |
| --- | --- | --- | --- |
| 140 | 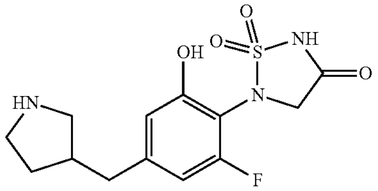 [SMILES: O=C1CN(c2c(O)cc(CC3CCNC3)cc2F)S(=O)(=O)N1] | 5-(2-fluoro-6-hydroxy-4-(pyrrolidin-3-ylmethyl)phenyl)-1,2,5-thiadiazolidin-3-one 1,1-dioxide | 328.1 |
| 141 | 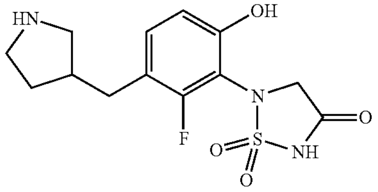 [SMILES: O=C1CN(c2c(O)ccc(CC3CCNC3)c2F)S(=O)(=O)N1] | 5-(2-fluoro-6-hydroxy-3-(pyrrolidin-3-ylmethyl)phenyl)-1,2,5-thiadiazolidin-3-one 1,1-dioxide | 330.2 [M+H]+ |
| 142 | 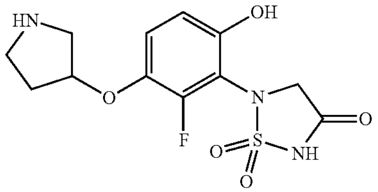 [SMILES: O=C1CN(c2c(O)ccc(OC3CCNC3)c2F)S(=O)(=O)N1] | 5-(2-fluoro-6-hydroxy-3-(pyrrolidin-3-yloxy)phenyl)-1,2,5-thiadiazolidin-3-one 1,1-dioxide | 330.3 |
| 143 | 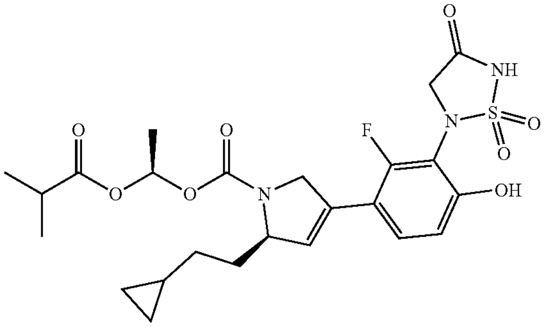 [SMILES: CC(C)C(=O)O[C@@H](C)OC(=O)N1CC(c2ccc(O)c(N3CC(=O)NS3(=O)=O)c2F)=C[C@H]1CCC1CC1] | (R)-1-(isobutyryloxy)ethyl (R)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 538.2 |
| 144 | 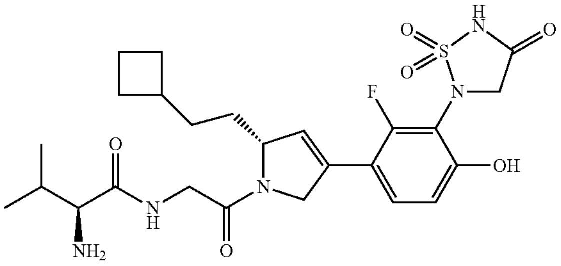 [SMILES: CC(C)[C@H](N)C(=O)NCC(=O)N1CC(c2ccc(O)c(N3CC(=O)NS3(=O)=O)c2F)=C[C@H]1CCC1CCC1] | (S)-2-amino-N-(2-((R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrol-1-yl)-2-oxoethyl)-3-methylbutanamide | 550.2 |
| 145 | 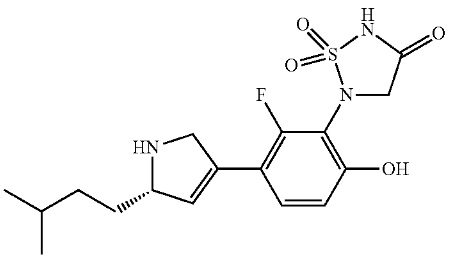 [SMILES: CC(C)CC[C@H]1C=C(c2ccc(O)c(N3CC(=O)NS3(=O)=O)c2F)CN1] | (S)-5-(2-fluoro-6-hydroxy-3-(5-isopentyl-2,5-dihydro-1H-pyrrol-3-yl)phenyl)-1,2,5-thiadiazolidin-3-one 1,1-dioxide | 382.1 |

TABLE 1-continued

| No. | Structure | Chemical Name | [M − H]⁻ |
|---|---|---|---|
| 146 | 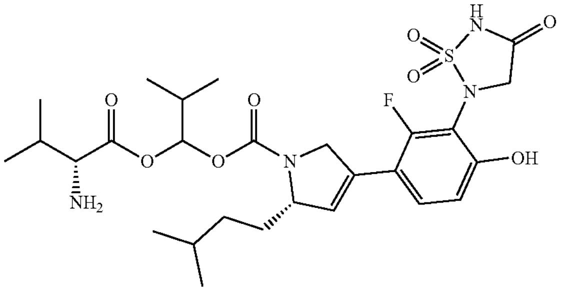 [SMILES: CC(C)CC[C@H]1C=C(c2ccc(O)c(N3CC(=O)NS3(=O)=O)c2F)CN1C(=O)OC(OC(=O)[C@H](N)C(C)C)C(C)C] | 1-((D-valyl)oxy)-2-methylpropyl (2S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate | 597.2 |
| 147 | 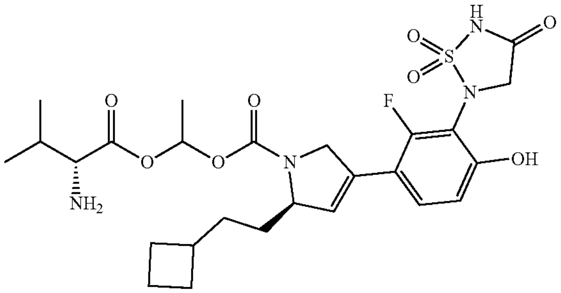 [SMILES: CC(OC(=O)[C@H](N)C(C)C)OC(=O)N1CC(c2ccc(O)c(N3CC(=O)NS3(=O)=O)c2F)=C[C@H]1CCC1CCC1] | 1-((D-valyl)oxy)ethyl (2R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 581.2 |
| 148 | 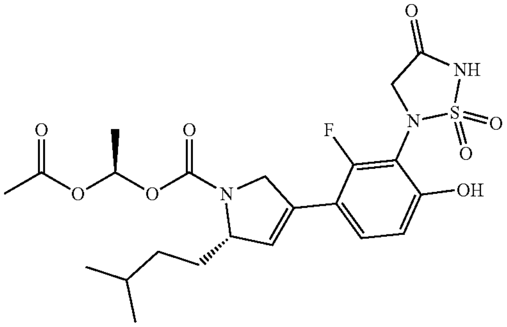 [SMILES: CC(=O)O[C@@H](C)OC(=O)N1CC(c2ccc(O)c(N3CC(=O)NS3(=O)=O)c2F)=C[C@@H]1CCC(C)C] | (R)-1-(isobutyryloxy)ethyl (S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate | 540.2 |
| 149 | 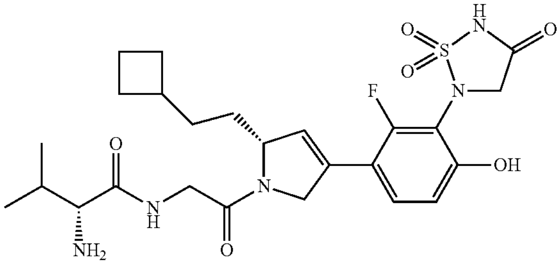 [SMILES: CC(C)[C@@H](N)C(=O)NCC(=O)N1CC(c2ccc(O)c(N3CC(=O)NS3(=O)=O)c2F)=C[C@H]1CCC1CCC1] | (R)-2-amino-N-(2-((R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrol-1-yl)-2-oxoethyl)-3-methylbutanamide | 550.2 |
| 150 | 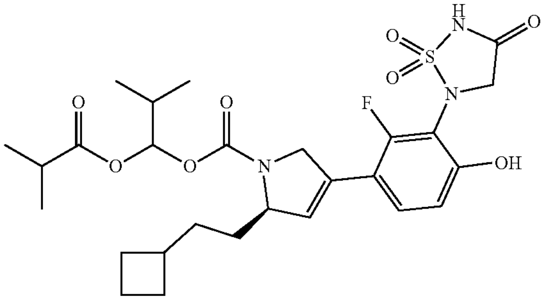 [SMILES: CC(C)C(=O)OC(OC(=O)N1CC(c2ccc(O)c(N3CC(=O)NS3(=O)=O)c2F)=C[C@H]1CCC1CCC1)C(C)C] | 1-(isobutyryloxy)-2-methylpropyl (2R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 580.2 |

TABLE 1-continued

| No. | Structure | Chemical Name | [M − H]⁻ |
|---|---|---|---|
| 151 | 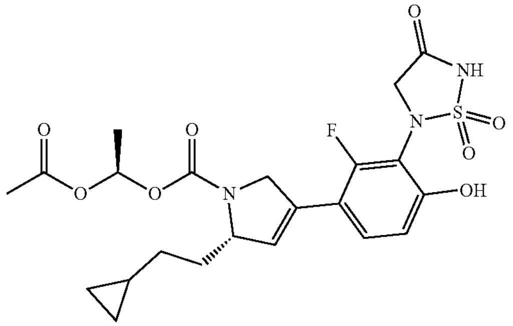 [SMILES: CC(=O)O[C@@H](C)OC(=O)N1CC(c2ccc(O)c(N3CC(=O)NS3(=O)=O)c2F)=C[C@@H]1CCC1CC1] | (R)-1-(isobutyryloxy)ethyl (S)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 538.1 |
| 152 | 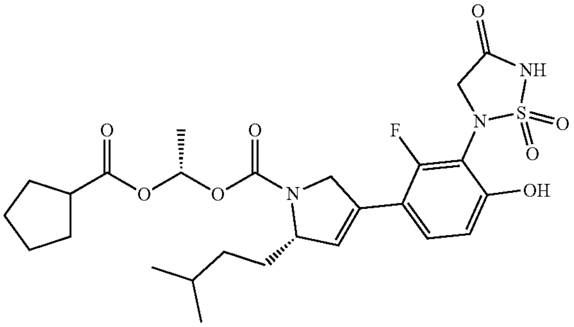 [SMILES: CC(C)CC[C@H]1C=C(c2ccc(O)c(N3CC(=O)NS3(=O)=O)c2F)CN1C(=O)O[C@@H](C)OC(=O)C1CCCC1] | (S)-1-((cyclopentanecarbonyl)oxy)ethyl (S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate | 566.2 |
| 153 | 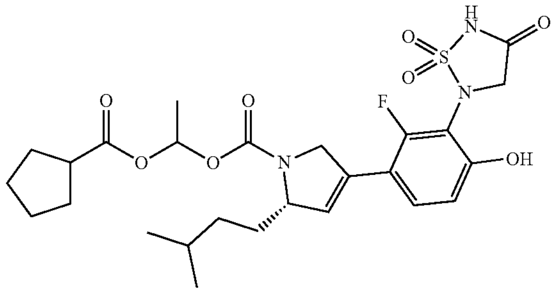 [SMILES: CC(C)CC[C@H]1C=C(c2ccc(O)c(N3CC(=O)NS3(=O)=O)c2F)CN1C(=O)OC(C)OC(=O)C1CCCC1] | 1-((cyclopentanecarbonyl)oxy)ethyl (2S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate | 566.2 |
| 154 | 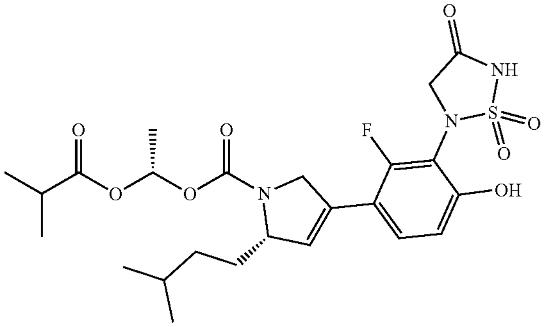 [SMILES: CC(C)CC[C@H]1C=C(c2ccc(O)c(N3CC(=O)NS3(=O)=O)c2F)CN1C(=O)O[C@@H](C)OC(=O)C(C)C] | (S)-1-(isobutyryloxy)ethyl (S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate | 540.2 |

TABLE 1-continued

| No. | Structure | Chemical Name | [M − H]⁻ |
|---|---|---|---|
| 155 | 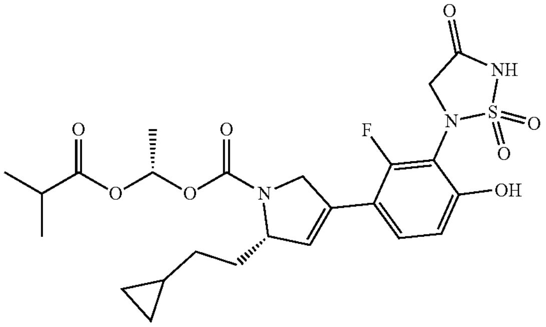 [SMILES: CC(C)C(=O)O[C@H](C)OC(=O)N1CC(c2ccc(O)c(N3CC(=O)NS3(=O)=O)c2F)=C[C@@H]1CCC1CC1] | (S)-1-(isobutyryloxy)ethyl (S)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 538.1 |
| 156 | 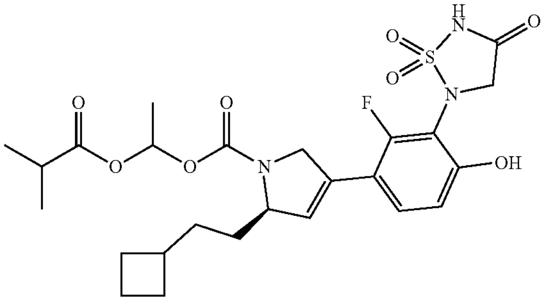 [SMILES: CC(OC(=O)C(C)C)OC(=O)N1CC(c2ccc(O)c(N3CC(=O)NS3(=O)=O)c2F)=C[C@H]1CCC1CCC1] | 1-(isobutyryloxy)ethyl (2R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 552.3 |
| 157 | 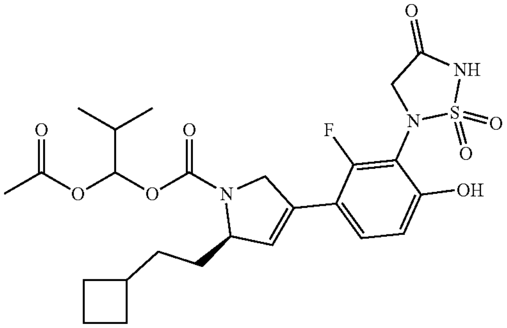 [SMILES: CC(=O)OC(OC(=O)N1CC(c2ccc(O)c(N3CC(=O)NS3(=O)=O)c2F)=C[C@H]1CCC1CCC1)C(C)C] | 1-acetoxy-2-methylpropyl (2R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 552.2 |
| 158 | 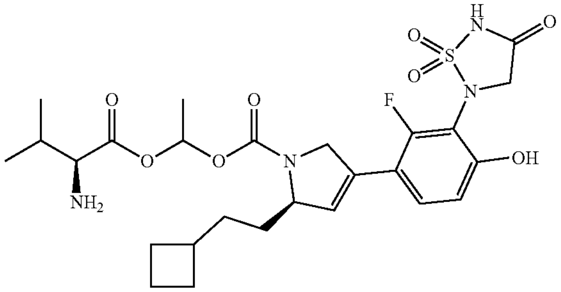 [SMILES: CC(OC(=O)[C@@H](N)C(C)C)OC(=O)N1CC(c2ccc(O)c(N3CC(=O)NS3(=O)=O)c2F)=C[C@H]1CCC1CCC1] | 1-((L-valyl)oxy)ethyl (2R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 581.2 |
| 159 | 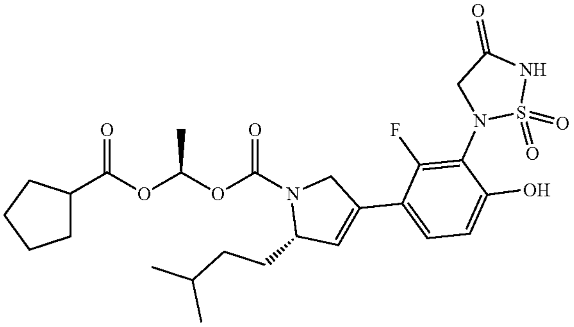 [SMILES: CC(C)CC[C@H]1C=C(c2ccc(O)c(N3CC(=O)NS3(=O)=O)c2F)CN1C(=O)O[C@H](C)OC(=O)C1CCCC1] | (R)-1-((cyclopentanecarbonyl)oxy)ethyl (S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate | 566.2 |

TABLE 1-continued

| No. | Structure | Chemical Name | [M − H]⁻ |
|---|---|---|---|
| 160 | 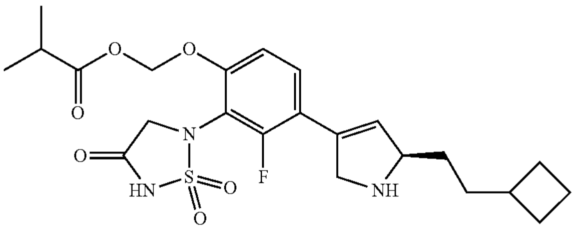 [SMILES: CC(C)C(=O)OCOc1ccc(C2=C[C@@H](CCC3CCC3)NC2)c(F)c1N1CC(=O)NS1(=O)=O] | (R)-(4-(5-(2-cyclobutylethyl)-2,5-dihydro-1H-pyrrol-3-yl)-2-(1,1-dioxido-4-oxo-1,2,5-thiadiazolidin-2-yl)-3-fluorophenoxy)methyl isobutyrate | 494.2 |
| 161 | 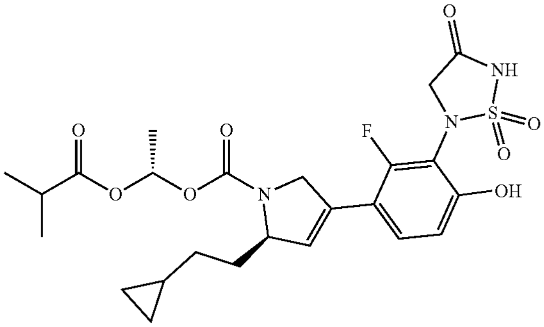 [SMILES: CC(C)C(=O)O[C@H](C)OC(=O)N1CC(c2ccc(O)c(N3CC(=O)NS3(=O)=O)c2F)=C[C@H]1CCC1CC1] | (S)-1-(isobutyryloxy)ethyl (R)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 538.2 |
| 162 | 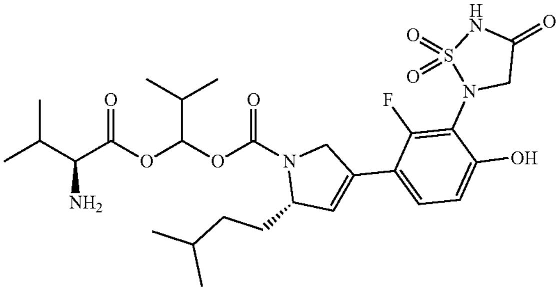 [SMILES: CC(C)CC[C@H]1C=C(c2ccc(O)c(N3CC(=O)NS3(=O)=O)c2F)CN1C(=O)OC(OC(=O)[C@@H](N)C(C)C)C(C)C] | 1-((L-valyl)oxy)-2-methylpropyl (2S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate | 597.2 |
| 163 | 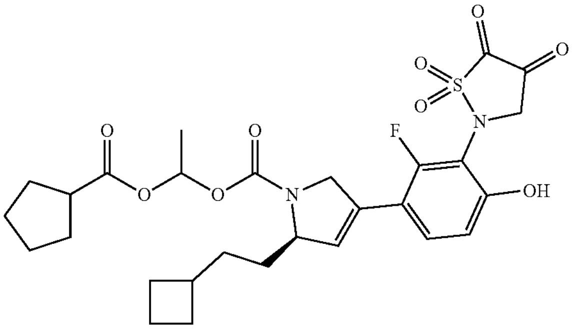 [SMILES: CC(OC(=O)C1CCCC1)OC(=O)N1CC(c2ccc(O)c(N3CC(=O)C(=O)S3(=O)=O)c2F)=C[C@H]1CCC1CCC1] | 1-((cyclopentanecarbonyl)oxy)ethyl (2R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 578.4 |
| 164 | 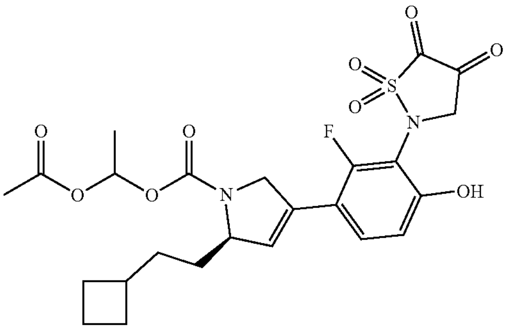 [SMILES: CC(=O)OC(C)OC(=O)N1CC(c2ccc(O)c(N3CC(=O)C(=O)S3(=O)=O)c2F)=C[C@H]1CCC1CCC1] | 1-acetoxyethyl (2R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 524.3 |

TABLE 1-continued

| No. | Structure | Chemical Name | [M − H]⁻ |
|---|---|---|---|
| 165 | 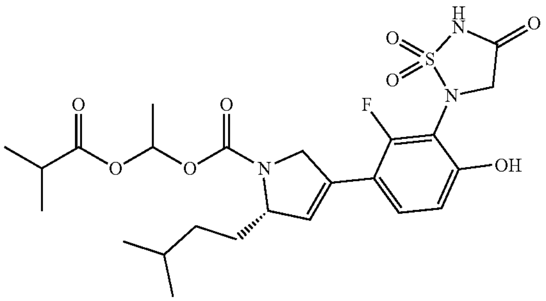 [SMILES: CC(C)CC[C@H]1C=C(c2ccc(O)c(N3CC(=O)NS3(=O)=O)c2F)CN1C(=O)OC(C)OC(=O)C(C)C] | 1-(isobutyryloxy)ethyl (2S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate | 540.2 |
| 166 | 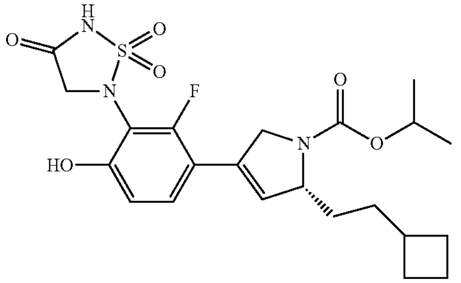 [SMILES: CC(C)OC(=O)N1CC(c2ccc(O)c(N3CC(=O)NS3(=O)=O)c2F)=C[C@H]1CCC1CCC1] | isopropyl (R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate | 480.3 |

Compounds of Table 1 are depicted with flat, wedged, and/or hashed wedged bonds. It is understood that compounds depicted in Table 1 encompass all possible stereoisomers of the compounds of Table 1.

It shall be understood that different aspects of the disclosure can be appreciated individually, collectively, or in combination with each other. Various aspects described herein may be applied to any of the particular applications disclosed herein. The compositions of matter, including compounds of any formulae disclosed in the compound section, of the present disclosure may be utilized in the method section, including methods of use and production disclosed herein, or vice versa.

Methods

Compounds disclosed herein exhibiting anti-PTPN2 activity embody a variety of therapeutic utilities. In an aspect, a PTPN2 inhibitor, such as a compound of Formula (I), (I-1), (II), (II-1), (II-a), (II-a1), (III), (III-1), (IV), or (IV-1), can be administered into a subject in need thereof to treat cancer. In some embodiments, a subject PTPN2 inhibitor is systemically, locally, and/or transiently (including intermittently) administered to the subject in need thereof to treat one or more types of cancer, including solid tumor and liquid tumor. In another aspect, a subject PTPN2 inhibitor is used to potentiate immunity comprising anti-tumor, anti-cancer activity, anti-viral infection activity, and/or anti-bacterial infection activity in a cell or a subject. In practicing any of the subject methods, a PTPN2 inhibitor disclosed herein can be administered as a single agent. In some embodiments, a PTPN2 inhibitor is administered in combination with another agent as a single or unit dose, or as a separate dose. In some embodiments, the other agent can be a cell, including but not limited to a lymphoid cell (e.g., expressing a CAR and/or TCR). In some embodiment, the other agent can be a second agent including without limitation, chemotherapeutic agent, a radioactive agent, a small molecule agent targeting a tumor marker (e.g., an anti-tumor marker inhibitor), an antigen-binding agent specifically binding to a tumor marker, an immune modulator, or any other second agent disclosed herein.

The compounds described herein, or a pharmaceutically acceptable salt or solvate thereof, are PTPN2 inhibitors capable of inhibiting a PTPN2 protein. Compounds, including pharmaceutically acceptable salts or solvates thereof, disclosed herein have a wide range of applications in therapeutics, diagnostics, and other biomedical research. In certain aspects, the present disclosure provides a method of treating cancer in a subject in need thereof, comprising administering to the subject a therapeutically effective amount of a compound described herein, or a pharmaceutically acceptable salt or solvate thereof.

In certain aspects, the present disclosure provides a method of modulating activity of a PTPN2 protein, comprising contacting a PTPN2 protein with an effective amount of a compound described herein, or a pharmaceutically acceptable salt or solvate thereof, thereby modulating the activity of the PTPN2 protein.

In certain aspects, the present disclosure provides a method of inhibiting cell growth, comprising administering an effective amount of a compound described herein, or a pharmaceutically acceptable salt or solvate thereof, to a cell expressing a PTPN2 protein, thereby inhibiting growth of said cells. In some embodiments, the subject method comprises administering an additional agent to said cell.

In certain aspects, the present disclosure provides a method of treating a disease mediated at least in part by a PTPN2 protein in a subject in need thereof, comprising administering to the subject an effective amount of a compound disclosed herein, or a pharmaceutically acceptable salt or solvate thereof. In some embodiments, the disease is cancer, such as a solid tumor or a hematological cancer. In some embodiments, a compound described herein, such as a compound of Formula (I), (I-1), (II), (II-1), (II-a), (II-a1), (III), (III-1), (IV), or (IV-1), is administered for treating a disease condition selected from locally advanced or metastatic, relapsed or refractory head and neck squamous cell carcinoma (HNSCC), relapsed or refractory non-small cell lung cancer (NSCLC), and advanced clear cell renal cell carcinoma (ccRCC). In some embodiments, a compound described herein is administered in combination or conjunction with a PD-1 targeting inhibitor or with a VEGFR tyrosine kinase inhibitor in a subject with locally advanced or metastatic HNSCC, NSCLC, MSI-H tumors refractory to PD-1/PD-L1, or advanced ccRCC. Where desired, any of the treatment methods disclosed herein may further comprise administering an additional agent to the subject, such as a RAS inhibitor, a SHP2 inhibitor, a SOS inhibitor, an EGFR inhibitor, a MEK inhibitor, an ERK inhibitor, a VEGFR inhibitor, a CDK4/6 inhibitor, a BRAF inhibitor, or a combination thereof. In certain aspects, the present disclosure provides a method of treating a PTPN2-mediated cancer in a subject in need thereof, comprising administering to the subject a RAS inhibitor, a SHP2 inhibitor, a SOS inhibitor, an EGFR inhibitor, a MEK inhibitor, an ERK inhibitor, a VEGFR inhibitor, a CDK4/6 inhibitor, a PD-1 inhibitor, a PD-L1 inhibitor, or a BRAF inhibitor and an effective amount of a compound disclosed herein, such as a compound of Formula (I), (I-1), (II), (II-1), (II-a), (II-a1), (III), (III-1), (IV), or (IV-1), or a pharmaceutically acceptable salt or solvate thereof.

In certain aspects, the present disclosure provides a method of inhibiting activity of a PTPN2 protein comprising contacting the PTPN2 protein with a compound disclosed herein, or a pharmaceutically acceptable salt or solvate thereof. In some embodiments, the compound exhibits an $IC_{50}$ against the PTPN2 protein of less than 10 μM, such as less than 5 μM, 1 μM, 500 nM, 100 nM, 50 nM, 10 nM, 5 nM, 1 nM, 500 pM, 50 pM, 10 pM or less.

Not wishing to be bound by any particular theory, a subject PTPN2 inhibitor (e.g., a compound described herein) may be effective in one or more of: stimulating and/or prolonging anti-tumor immunity (e.g., destabilizing Tregs, augmenting CD4+ and CD8+ T cell function, increasing the number of central memory T cells or half-life of such cells), inhibiting proliferation of cancer cells, inhibiting invasion or metastasis of cancer cells, killing cancer cells, increasing the sensitivity of cancer cells to treatment with a second anti-tumor agent, and reducing severity or incidence of symptoms associated with the presence of cancer cells. In some embodiments, said method comprises administering to the cancer cells a therapeutically effective amount of a PTPN2 inhibitor in vivo. In some embodiments, the administration first takes place ex vivo to a population of effector cells, followed by infusing the PTPN2 inhibitor-treated effector cells into the subject as further detailed below.

In some embodiments, the small molecule PTPN2 inhibitor may not affect editing of (i) a gene encoding PTPN2 or (ii) an additional gene operatively linked to PTPN2 (e.g., transcription factor, intron sequence, start codon, etc.). As such, the gene and/or the additional gene may remain the same upon treatment of a cell with a small molecule PTPN2 inhibitor, such as a compound of Formula (I), (I-1), (II), (II-1), (II-a), (II-a1), (III), (III-1), (IV), or (IV-1). In some embodiments, the small molecule PTPN2 inhibitor may be configured to bind at least a portion of PTPN2. The small molecule may exhibit binding specificity to PTPN2 in comparison to one or more other protein tyrosine phosphatases selected from the group consisting of: PTPRA, PTPRB, PTPRC, PTPRD, PTPRE, PTPRF, PTPRG, PTPRH, PTPRJ, PTPRK, PTPRM, PTPRN, PTPRN2, PTPRO, PTPRQ, PTPRR, PTPRS, PTPRT, PTPRU, PTPRV, PTPRZ, PTPN1, PTPN2, PTPN3, PTPN4, PTPN5, PTPN6, PTPN7, PTPN9, PTPN11, PTPN12, PTPN13, PTPN14, PTPN18, PTPN20, PTPN21, PTPN23, DUSP1, DUSP2, DUSP4, DUSP5, DUSP6, DUSP7, DUSP8, DUSP9, DUSP10, DUSP16, MK-STYX, DUSP3, DUSP11, DUSP12, DUSP13Aa, DUSP13Ba, DUSP14, DUSP15, DUSP18, DUSP19, DUSP21, DUSP22, DUSP23, DUSP24, DUSP25, DUSP26, DUSP27b, EPM2A, RNGTT, STYX, SSH1, SSH2, SSH3, PTP4A1, PTP4A2, PTP4A3, CDC14A, CDC14B, CDKN3, PTP9Q22, PTEN, TPIP, TPTE, TNS, TENC1, MTM1, MTMR1, MTMR2, MTMR3, MTMR4, MTMR5, MTMR6, MTMR7, MTMR8, MTMR9, MTMR10, MTMR11, MTMR12, MTMR13, MTMR14, MTMR15, ACP1, CDC25A, CDC25B, CDC25C, EYA1, EYA1, EYA1, and EYA1. In some embodiments, a subject compound, such as a compound of Formula (I), (I-1), (II), (II-1), (II-a), (II-a1), (III), (III-1), (IV), or (IV-1), specifically binds to PTPN2 relative to PTP1B. In some embodiments, a subject compound selectively inhibits PTPN2 relative to PTP1B. In some embodiments, a subject compound, such as a compound of Formula (I), (I-1), (II), (II-1), (II-a), (II-a1), (III), (III-1), (IV), or (IV-1), exhibits the ability to inhibit both PTPN2 and PTP1B. In some embodiments, PTPN2 inhibitors described herein encompass inhibitors of both PTPN2 and PTP1B. In some cases, a subject compound may exhibit a half maximal inhibitory concentration (i.e., $IC_{50}$) of less than or equal to about 10 micromolar (μM), 5 μM, 1 μM, 950 nanomolar (nM), 900 nM, 850 nM, 800 nM, 750 nM, 700 nM, 650 nM, 600 nM, 550 nM, 500 nM, 450 nM, 400 nM, 350 nM, 300 nM, 250 nM, 200 nM, 150 nM, 100 nM, 50 nM, 10 nM, 9 nM, 8 nM, 7 nM, 6 nM, 5 nM, 4 nM, 3 nM, 2 nM, 1 nM, 0.9 nM, 0.8 nM, 0.7 nM, 0.6 nM, 0.5 nM, 0.4 nM, 0.3 nM, 0.2 nM, 0.1 nM, or less for PTPN2. The small molecule PTPN2 inhibitor may exhibit an $IC_{50}$ for PTPN2 that is at least about 0.1-fold, 0.2-fold, 0.3-fold, 0.4-fold, 0.5-fold, 0.6-fold, 0.7-fold, 0.8-fold, 0.9-fold, 1-fold, 2-fold, 3-fold, 4-fold, 5-fold, 6-fold, 7-fold, 8-fold, 9-fold, 10-fold, 11-fold, 12-fold, 13-fold, 14-fold, 15-fold, 16-fold, 17-fold, 18-fold, 19-fold, 20-fold, 30-fold, 40-fold, 50-fold, 60-fold, 70-fold, 80-fold, 90-fold, 100-fold, or more potent than that of one or more other protein tyrosine phosphatases (e.g., $IC_{50}$ concentration is a lower number for PTPN2 than another PTP). In different embodiments, the small molecule PTPN2 inhibitor may be configured to bind at least a portion of one or more substrates of PTPN2 selected from the group consisting of: INSR, EGFR, CSFIR, PDGFR, JAK1, JAK2, JAK3, Src family kinases, STAT1, STAT3, STAT6, FYN, LCK, variations thereof, and combinations thereof.

In some embodiments, a compound of the present disclosure, such as a compound of Formula (I), (I-1), (II), (II-1), (II-a), (II-a1), (III), (III-1), (IV), or (IV-1), may be conjugated to a degradation tag (i.e., degradation enhancer). A degradation tag may be configured to bind a degradation moiety having a capacity to degrade at least a portion of a target moiety that is bound by the degradation tag. For example, the target moiety is PTPN2 or the substrate of PTPN2. A degradation tag may be a biological or chemical compound, such as a simple or complex organic or inorganic molecule, peptide, peptido mimetic, protein (e.g., antibody), liposome, or a polynucleotide (e.g., small interfering RNA, short hairpin RNA, microRNA, antisense, aptamer, ribozyme, triple helix). Alternatively, a degradation tag may be synthetic. In some cases, any one of the methods described herein may utilize a small molecule degradation tag, and non-limiting examples of such small molecule degradation tag may include, but are not limited to, pomalidomide, thalidomide, lenalidomide, VHL-1, adamantane, 1-((4,4,5,5,5-pentafluoropentyl) sulfinyl) nonane, nutlin-3a, RG7112, RG7338, AMG 232, AA-115, bestatin, MV-1, LCL 161, and/or analogs thereof. In some cases, the degradation tag can (i) bind to a degradation moiety such as a ubiquitin ligase (e.g., an E3 ligase such as a cereblon E3 ligase, a VHL E3 ligase, a MDM2 ligase, a TRIM21 ligase, a TRIM24 ligase, and/or a IAP ligase) and/or (ii) serve as a hydrophobic group that leads to protein misfolding of the target moiety, e.g., PTPN2. Misfolding of the target moiety may disrupt activity of the target moiety and/or increase the likelihood of degradation of the target moiety by, e.g., a degradation moiety. In some cases, a small molecule PTPN2 inhibitor, such as a compound of Formula (I), (I-1), (II), (II-1), (II-a), (II-a1), (III), (III-1), (IV), or (IV-1), may be conjugated to the degradation tag via a linker. Examples of such linker may include, but are not limited to, acyclic or cyclic saturated or unsaturated carbon, ethylene glycol, amide, amino, ether, urea, carbamate, aromatic, heteroaromatic, heterocyclic, and/or carbonyl containing groups with different lengths. Exemplary molecules comprising such degradation tag and method of use thereof are provided in U.S. Patent Publication No. 2019/0336503, which is incorporated herein by reference in its entirety.

In some embodiments, a method of the disclosure provides an effective amount of a PTPN2 inhibitor, such as a compound of Formula (I), (I-1), (II), (II-1), (II-a), (II-a1), (III), (III-1), (IV), or (IV-1). An effective dose refers to an amount sufficient to affect the intended application, including treatment of cancer and stimulating or prolonging anti-tumor immunity. Also contemplated in the subject methods is the use of a sub-therapeutic amount of a PTPN2 inhibitor for treating an intended disease condition.

The amount of the PTPN2 inhibitor, such as a compound of Formula (I), (I-1), (II), (II-1), (II-a), (II-a1), (III), (III-1), (IV), or (IV-1), administered may vary depending upon the intended application (in vitro, ex vivo, or in vivo), or the subject and cancer condition being treated, e.g., the weight and age of the subject, the severity of the cancer, the manner of administration and the like. In some cases, a PTPN2 inhibitor may be administered (e.g., systemically administered) to a subject at a dose of at least about 0.1 milligrams per kilogram (mg/kg), 0.2 mg/kg, 0.3 mg/kg, 0.4 mg/kg, 0.5 mg/kg, 0.6 mg/kg, 0.7 mg/kg, 0.8 mg/kg, 0.9 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 25 mg/kg, 30 mg/kg, 35 mg/kg, 40 mg/kg, 45 mg/kg, 50 mg/kg, or more. In some cases, a PTPN2 inhibitor may be administered (e.g., systemically administered) to a subject at a dose of at most about 50 mg/kg, 45 mg/kg, 40 mg/kg, 35 mg/kg, 30 mg/kg, 25 mg/kg, 20 mg/kg, 19 mg/kg, 18 mg/kg, 17 mg/kg, 16 mg/kg, 15 mg/kg, 14 mg/kg, 13 mg/kg, 12 mg/kg, 11 mg/kg, 10 mg/kg, 9 mg/kg, 8 mg/kg, 7 mg/kg, 6 mg/kg, 5 mg/kg, 4 mg/kg, 3 mg/kg, 2 mg/kg, 1 mg/kg, 0.9 mg/kg, 0.8 mg/kg, 0.7 mg/kg, 0.6 mg/kg, 0.5 mg/kg, 0.4 mg/kg, 0.3 mg/kg, 0.2 mg/kg, 0.1 mg/kg, or less.

In some cases, upon administration (e.g., systemic administration), a mean plasma concentration of the PTPN2 inhibitor, such as a compound of Formula (I), (I-1), (II), (II-1), (II-a), (II-a1), (III), (III-1), (IV), or (IV-1), in the subject may be at least about 0.1 microgram per milliliter (μg/ml), 0.2 μg/ml, 0.3 μg/ml, 0.4 μg/ml, 0.5 μg/ml, 0.6 μg/ml, 0.7 μg/ml, 0.8 μg/ml, 0.9 μg/ml, 1 μg/ml, 2 μg/ml, 3 μg/ml, 4 μg/ml, 5 μg/ml, 6 μg/ml, 7 μg/ml, 8 μg/ml, 9 μg/ml, 10 μg/ml, 11 μg/ml, 12 μg/ml, 13 μg/ml, 14 μg/ml, 15 μg/ml, 16 μg/ml, 17 μg/ml, 18 μg/ml, 19 μg/ml, 20 μg/ml, 25 μg/ml, 30 μg/ml, 35 μg/ml, 40 μg/ml, 45 μg/ml, 50 μg/ml, or more. In some cases, upon administration (e.g., systemic administration), a mean plasma concentration of the PTPN2 inhibitor in the subject may be at most about 50 μg/ml, 45 μg/ml, 40 μg/ml, 35 μg/ml, 30 μg/ml, 25 μg/ml, 20 μg/ml, 19 μg/ml, 18 μg/ml, 17 μg/ml, 16 μg/ml, 15 μg/ml, 14 μg/ml, 13 μg/ml, 12 μg/ml, 11 μg/ml, 10 μg/ml, 9 μg/ml, 8 μg/ml, 7 μg/ml, 6 μg/ml, 5 μg/ml, 4 μg/ml, 3 μg/ml, 2 μg/ml, 1 μg/ml, 0.9 μg/ml, 0.8 μg/ml, 0.7 μg/ml, 0.6 μg/ml, 0.5 μg/ml, 0.4 μg/ml, 0.3 μg/ml, 0.2 μg/ml, 0.1 μg/ml, or less.

In some embodiments, a PTPN2 inhibitor, such as a compound of Formula (I), (I-1), (II), (II-1), (II-a), (II-a1), (III), (III-1), (IV), or (IV-1), may be used in combination with another known agent (a second agent) or therapy. Examples of such second agent may be selected from the group consisting of a chemotherapeutic agent, a radioactive agent, a small molecule agent targeting a tumor marker, an antigen-binding agent specifically binding to a tumor marker, and an immune modulator. An immune modulator may be selected from the group consisting of immunostimulatory agents, checkpoint immune blockade agents, and combinations thereof. In some embodiments, the second agent may be a checkpoint inhibitor. In some examples, the second agent may be an inhibitor of PD1, PD-L1, LAG3, CTLA4, CD160, BTLA, LAIR1, TIM3, 2B4, CD93, OX40, Siglec-15, and TIGIT. A PTPN2 inhibitor can be administered as part of a therapeutic regimen that comprises administering one or more second agents (e.g., 1, 2, 3, 4, 5, or more second agents), either simultaneously or sequentially with the PTPN2 inhibitor. When administered sequentially, the PTPN2 inhibitor may be administered before, concurrent with, or after the one or more second agents. When administered simultaneously, the PTPN2 inhibitor and the one or more second agents may be administered by the same route (e.g. injections to the same location; tablets taken orally at the same time), by a different route (e.g. a tablet taken orally while receiving an intravenous infusion), or as part of the same combination (e.g. a solution comprising the PTPN2 inhibitor and one or more second agents). In some examples, a PTPN2 inhibitor can be used in combination with a cell therapy, including a TFP- or CAR-expressing cell (e.g., a TFP- or CAR-expressing stem cell or lymphoid cell) described herein. In other examples, a PTPN2 inhibitor can be used in combination with a non-cell based therapy, such as surgery, chemotherapy, targeted therapy (e.g., using large or small drug molecules targeting a tumor antigen other than PTPN2), radiation, and the like.

In some embodiments, a PTPN2 inhibitor described herein, such as a compound of Formula (I), (I-1), (II), (II-1), (II-a), (II-a1), (III), (III-1), (IV), or (IV-1), is administered to a subject in combination with an indoleamine 2,3-dioxygenase (IDO) inhibitor. IDO is an enzyme that catalyzes the degradation of the amino acid L-tryptophan to kynurenine. Many cancers overexpress IDO, e.g., prostatic, colorectal, pancreatic, cervical, gastric, ovarian, head, and lung cancer. pDCs, macrophages, and dendritic cells (DCs) can express IDO. Without being bound by any particular theory, it has been reported that a decrease in L-tryptophan (e.g., catalyzed by IDO) results in an immunosuppressive milieu by inducing T-cell anergy and apoptosis. It is thought that IDO inhibitor can enhance the efficacy of a CAR-expressing cell by decreasing the suppression or death of a CAR-expressing immune cell. While the clinical trial involving the combination of pembrolizumab (an anti-PD1 antibody) and epacadostat (an IDO inhibitor) did not reach the desired end point, a PTPN2 inhibitor is expected to potentiate the therapeutic effect of IDO inhibitor. Without being bound by a particular theory, PTPN2 inhibitors are expected to destabilize the function of the already activated regulatory T-cells while the IDO inhibitors prevent the activation of new regulatory T-cells. Exemplary inhibitors of IDO that can be used in combination include but are not limited to 1-methyl-tryptophan, indoximod (NewLink Genetics)(see, e.g., Clinical Trial Identifier Nos. NCT01191216; NCT01792050), and INCB024360 (Incyte Corp.)(see, e.g., Clinical Trial Identifier Nos. NCT01604889; NCT01685255).

Additional agents that can be used in combination with a PTPN2 inhibitor, such as a compound of Formula (I), (I-1), (II), (II-1), (II-a), (II-a1), (III), (III-1), (IV), or (IV-1), include the various categories and examples of agents listed in Table 2 below.

TABLE 2

| | |
|---|---|
| Alkylating agents | Examples include, but are not limited to, altretamine (Hexalen ® or hexamethylmelamine or HMM), bendamustine, busulfan (Busulfex ® or Myleran ®), carmustine (BiCNU ® or BCNU ®), chlorambucil, cyclophosphamide (Cytoxan ® or Neosar ®), dacarbazine (DTIC-Dome ®), fotemustine, ifosfamide (Ifex ®), improsulfan, lomustine (CCNU ® or CeeNUR), mechlorethamine or mustine (Mustardgen ®), melphalan (Alkeran ®), nimustine, piposulfan, ranimustine, semustine, streptozocin (Zanosar ®), temozolomide (Temodar ®), thiotepa (Thioplex ®), trofosfamide (Ixoten ®), and uramustine or uracil mustard |
| Anthracyclines | Examples include, but are not limited to, aclarubicin, amrubicin, daunorubicin (Daunomycin ®), daunorubicin (liposomal), doxorubicin (Adriamycin ®), doxorubicin (liposomal), epirubicin, esorubicin, idarubicin, mitoxantrone, pirarubicin, and valrubicin |
| Anti-angiogenic | Examples include, but are not limited to, aflibercept, axitinib (Inlyta ®), bevacizumab (Avastin ®), cabozantinib (Cometriq ®), everolimus (Afinitor ® or Zortress ®), lenalidomide (Revlimid ®), pazopanib (Votrient ®), ponatinib, ramucirumab (Cyramza ®), ranibizumab, regorafenib (Stivarga ®), sorafenib (Nexavar ®), sunitinib (Sutent ®), thalidomide (Synovir ® or Thalomid ®) lapatinib, and vandetanib (Caprelsa ®) |
| Antifolates | Examples include, but are not limited to, aminopterin, edatrexate, folic acid, GW1843, lometrexol, L Y309887, methotrexate, nolatrexed, OSI-7904(L), pemetrexed (Alimta ®), pralatrexate, raltitrexed, trimetrexate, and ZD9331 |
| BCL-2 inhibitors | Examples include, but are not limited to, ABT-199, ABT-263, ABT-737, BH3 mimetics, gossypol, obatoclax (GX15-070), oblimersen (Genasense ®; G3139; Augmerosen ®), and venetoclax |
| Bcr-Abl inhibitors | Examples include, but are not limited to, bafetinib (INNO-406), bosutinib (SKI-606), dasatinib (BMS-354825), imatinib (STI-571), nilotinib (AMN-107), and ponatinib (AP-24534 or Iclusig ®) |
| Biologics | Examples include, but are not limited to, BCG (TheraCys ®), cytokines (such as INF-alfa, Aldesleukin, erythropoietin, GM-CSF, G-CSF), gene therapy (such as CT109 or Kymriah ®), MAbs (such as rituximab, alemtuzumab, ipilimumab, bevacizumab, obinutuzumab, brentuximab), oncolytic viruses (such as T-VEC or Imlygic ®, H101), and treatment vaccines (such as sipuleucel-T or Provenge ®) |
| CDK inhibitors | Examples include, but are not limited to, A-674563, abemaciclib (LY2835219), AT-7519, AZD5438, BMS-265246, BS-181, CYC202 (roscovitine; seliciclib), dinaciclib (SCH-727965), flavopiridol (alvocidib), indirubin, JNJ-7706621, K03861, kenpaullone, LDC000067, LDC4297 (LDC044297), LY2857785, MK-8776 (SCH900776), ML 167, MSC2530818, NU6027, olomoucine, ON123300, P276-00, palbociclib (PD-0332991), PHA-767491, PHA-793887, PHA-848125 (milciclib), purvalanol A, purvalanol B, R547, ribociclib (LEE011), RO-3306, senexin A, SNS-032 (BMS-387032), SU9516, TG003, THZ1, UCN-01 (7-hydroxystaurosporine; KRX-0601), wogonin, and XL413 |
| COX-2 inhibitors | Examples include, but are not limited to, celecoxib (Celebrex ®), etoricoxib, lumiracoxib (Prexige ®), parecoxib (Dynastat ®), rofecoxib, and valdecoxib (Bextra ®) |
| CTLA-4 inhibitors | Examples include, but are not limited to, ipilimumab (MDX-010) and tremelimumab (10D1) |
| DNA methyltransferase inhibitors | Examples include, but are not limited to, 1-hydrazinophthalazine, 5,6-dihydro-5-azacytidine, 5-aza-2'-deoxycytidine, 5-aza-C (5-azacytidine; azacytidine), 5-fluoro-2'-deoxycytidine, arabinosyl-5-azacytidine, decitabine, disulfiram, doxorubicin, EGCG, EGX30P, hydralazine, MG98, nanaomycin A, nanaomycin C, procainamide, procaine, psammaplin A, RG108, SGI-1027, sinefungin, thioguanine, and zebularine |
| ERK inhibitors | Examples include, but are not limited to, AG1478, AG99, andrographolide, apigenin, BAY 43-9006, CAY10561, DEL-22379, ERK inhibitor III, ERK5-IN-1, FR 180204, GDC0994, GDC-0994, GW5074, hypericin, ISIS 5132, KO947, MK-8353 (SCH900353), ML-9, PD169316, PD173074, pluripotin, purvalanol, pyrazolylpyrrole ERK inhibitor, SB203580, SC-1, SCH772984, SL327, SP600125, SU4984, ulixertinib (BVD-523, VRT752271), VX-11e (ERK-11e; TCS ERK 11e), and XMD 8-92 |
| Farnesyltransferase inhibitors | Examples include, but are not limited to, BMS-214662, CP-609754, DK8G557, FTI-277, L744832, L778123, lonafarnib (Sarasar ®; SCH66336), manumycin A, and R115777 (Zarnestra ®; tipifarnib |
| FLT3 inhibitors | Examples include, but are not limited to, crenolanib besylate (CP-868596-26), gilteritinib (ASP2215), lestaurtinib (CEP-701), midostaurin (Rydapt ®, PKC412), pexidartinib (PLX3397), ponatinib (AP24534), quizartinib (AC220), SKLB1028, sorafenib (Nexavar ®), sunitinib (Sutent ®, SU11248), and XL999 |
| HDAC inhibitors | Examples include, but are not limited to, 4SC-202, Abexinostat (PCI-24781), apicidin, AR-42, ATRA, Belinostat (PXD101), BG-45, BRD73954, CAY10603, CG200745, Chidamide, CHR-2845, CHR-3996, Citarinostat (ACY-241), CUDC-101, CUDC-907, curcumin, dacinostat (LAQ824), droxinostat, Entinostat (MS-275), FR901228, Givinostat (ITF2357), HBI-8000, HPOB, ITSA-1, Kevetrin, LAQ824, largazole, LMK-235, M344, MC-1568, m-carboxycinnamic acid bishydroxamide, ME-344, Mocetinostat (MGCD0103), nexturastat A, oxamflatin, Panobinostat (LBH589), pracinostat (SB939), pyroxamide, Quisinostat (JNJ-26481585), Resminostat (4SC-201), RG2833 (RGFP109), RGFP966, ricolinostat (ACY-1215), Romidepsin (FK228; Depsipeptide), Romidepsin (Istodax), santacruzamate A (CAY10683), SB939, SBHA, scriptaid, sulforaphane, tacedinaline (CI994) PCI-34051, |

TABLE 2-continued

| | |
|---|---|
| | tasquinimod, TMP-195, TMP-269, trapoxin A, trichostatin A, tubacin, tubastatin A, Valproic acid (as Mg valproate), and Vorinostat (SAHA |
| Hedgehog signaling inhibitors | Examples include, but are not limited to, AY 9944, BMS-833923 (XL 139), GANT58, GANT61, HPI-4, JK184 , LEQ 506, PF-04449913, SANT-1, SANT-2, sonidegib (LDE-225; Odomzo ®), TAK-441, and vismodegib (IPI-926; Erivedge ®) |
| HIF inhibitors | Examples include, but are not limited to, 2-methoxyestradiol, bortezomib, camptothecin, echinomycin, ENMD-1198, miltefosine, perifosine, romidepsin, and temsirolimus |
| Hormone therapies | Examples include, but are not limited to, 4(5)-imidazoles, 4-hydroxytamoxifen, aminoglutethimide, anastrozole (Arimidex ®), bicalutamide megestrol acetate, diethylstilbestrol, estrace, exemestane (Aromasin ®), fluoxymesterone, flutamide, fulvestrant (Faslodex ®), goserelin (Zoladex ®), keoxifene, letrozole (Femara ®), leuprorelin, LY 117018, medroxyprogesterone acetate, nilutamide, octreotide, onapristone, polyestradiol phosphate, raloxifene, tamoxifen, toremifene, toremifene (Fareston ®), and trioxifene |
| MEK inhibitors | Examples include, but are not limited to, AR-119/RDEA119 (BAY 869766), arctigenin, ARRY-438162, AS-701173, AS-701255, AS703026, AZD6244 (ARRY-142886), AZD8330 (ARRY-704), binimetinib (MEK162), CI-1040 (PD184352), E6201, GDC-0623, GDC-0973 (XL518; cobimetinib), hypothemycin, PD0325901, PD0325901, PD181461, PD98059, pimasertib, refametinib, RO09-2210, RO4927350, RO4987655, RO5068760, RO5126766, selumetinib, TAK-733, trametinib (GSK1120212), U0126, and WX-554 |
| Mitotic inhibitors | Examples include, but are not limited to, colchicine, glaziovianin A, griseofulvin, podophyllotoxin, taxanes, vinblastine, vincristine, vindesine, and vinorelbine |
| mTOR inhibitors - immune enhancing amount which is typically below the therapeutic dose | Examples include, but are not limited to, ABT578, AZD2014, AZD8055, BEZ235, CC-223, everolimus (RAD001), GSK2126458, INK128 (MLN-0128), Ku-0063794 , LY294002, NVP-BEZ235, OSI-027, PI-103, PP242, rapamycin (Sirolimus ®), ridaforolimus (Deforolimus ®; AP-23573), temsirolimus (CCI-779), and XL765 |
| Multi-kinase inhibitors | Examples include, but are not limited to, AT9283, dasatinib, lestaurtinib, midostaurin (Rydapt ®), motesanib, neratinib (HKI-272), nilotinib, pazopanib, regorafenib, sorafenib, sunitinib, vandetanib, and XL 184 |
| Nitrogen mustards | Examples include, but are not limited to, bendamustine, chlorambucil, chlornaphazine, cyclophosphamide, estramustine, ifosfamide, mechlorethamine, mechlorethamine oxide hydrochloride, melphalan, mustine, novembichin, phenesterine, prednimustine, trofosfamide, uracil mustard, and uramustine |
| DNA synthesis inhibitors | Examples include, but are not limited to, 3,4-dihydroxybenzylamine, 5-fluorodeoxyuridine, cladribine, cytarabine, daunorubicin, etoposide, flutarabine, hydroxyurea, idarubicin, methotrexate, mitoxantrone, and pralatrexate |
| PD-1 inhibitors | Examples include, but are not limited to, AMP-224, AMP-514, atezolizumab (RG7446; MPDL3280A), BMS-936559, durvalumab, MAB005, MDX-1106, MEDI4736, MSB0010718C (A09-246-2), nivolumab (BMS936558), pembrolizumab (Lambrolizumab ®; MK-3475; KEYTRUDA ®), and pidilizumab (CT-011)<br>Anti PD-1 antibodies: Examples include, but are not limited to, ABCAM ® (AB137132), AFFYMETRIX EBIOSCIENCE (J105; J116; M1H4), Amplimmune (AMP 514), avelumab (Bavencio ®), and BIOLEGEND ® (EH12.2H7; RMPI-14) |
| RAF inhibitors | Examples include, but are not limited to, AZ 628, CCT196969, CEP-32496, dabrafenib (GSK2118436), encorafenib (LGX818), GDC-0879, GW5074, LY3009120, MLN2480, NVP-BHG712, PLX-4720, PLX-7904, RAF265, RO5126766 (CH5126766), SB590885, sorafenib tosylate, TAK-632, vemurafenib (PLX4032; RG7204), and ZM 336372 |
| RAS inhibitors | Examples include, but are not limited to, deltarasin, lonafarnib, reolysin, salirasib, siG12D LODER, SML-8-73-1, and tipifarnib |
| Others | Examples include, but are not limited to, 5-aminolevulinic acid, afatinib, alectinib, altretamine, anti-CD3 and/or anti-CD33 antibodies (e.g. visilizumab, gemtuzumab, AMG330), antiproliferative antibodies, aprepitant, arsenic trioxide, benzodopa, biological response modifiers, bisphosphonates (such as etridonic, clodronic, tiludronic, pamidronic, alendronic, ibandronic, risedronic, zoledronic acid), bleomycin, blinatumomab (AMG103; Blincyto ®), brigatinib (Alunbrig ®), buserelin, cabazitaxel, carboquone, ceritinib, crizotinib, dactinomycin, degarelix, denosumab, dexamethasone, difluoromethylornithine (DFMO), dronabinol, enasidenib (AG-221), epothilone A or B, eribulin, erlotinib, gefitinib, gonadorelin agonists, granisetron, heparanase inhibitors, histone deacetylase inhibitors, histrelin, ibrutinib, inotuzumab ozogamicin (BesponsaR), ixabepilone, lenvatinib, leuprolide, levoleucovorin, matrix metalloproteinase inhibitors (such as marimastat (BB-2516), prinomastat (AG3340), BMS-279251, BAY 12-9566, TAA211, MMI270B, AAJ996), methionine aminopeptidase inhibitors, meturedopa, mitomycin, mitotane, nabilone, necitumumab, niraparib (Zejula ®), olaparib (AZD-2281; Lynparza ®), osimertinib (Tagrisso ®), palonosetron, panitumumab, pertuzumab, porfimer sodium, revlimid, thalidomide, tipiracil, trabectedin, trastuzumab, triethylenemelamine, triethylenephosphoramide, triethylenethiophosphoramide, trimethylolomelamine, and uredopa |

In embodiments, a compound described herein, such as a compound of Formula (I), (I-1), (II), (II-1), (II-a), (II-a1), (III), (III-1), (IV), or (IV-1), may be administered alone or in combination or in conjunction with another therapy or another agent. By "combination" it is meant to include (a) formulating a subject composition containing a subject compound, such as a compound of Formula (I), (I-1), (II), (II-1), (II-a), (II-a1), (III), (III-1), (IV), or (IV-1), together with another agent, and (b) using the subject composition separate from the other agent as an overall treatment regimen. By "conjunction" it is meant that the other therapy or agent is administered either simultaneously, concurrently or sequentially with a subject composition comprising a compound disclosed herein, with no specific time limits, wherein such conjunctive administration provides a therapeutic effect.

In some embodiment, a subject treatment method (e.g., a method comprising a compound described herein) is combined with surgery, cellular therapy, chemotherapy, radiation, and/or immunosuppressive agents. Additionally, compositions of the present disclosure can be combined with other therapeutic agents, such as other anti-cancer agents, anti-allergic agents, anti-nausea agents (or anti-emetics), pain relievers, cytoprotective agents, immunostimulants, immunomodulatory agents, and combinations thereof.

In an aspect, compositions provided herein can be administered in combination with radiotherapy, such as radiation. Whole body radiation may be administered at 12 Gy. A radiation dose may comprise a cumulative dose of 12 Gy to the whole body, including healthy tissues. A radiation dose may comprise from 5 Gy to 20 Gy. A radiation dose may be 5 Gy, 6 Gy, 7 Gy, 8 Gy, 9 Gy, 10 Gy, 11 Gy, 12, Gy, 13 Gy, 14 Gy, 15 Gy, 16 Gy, 17 Gy, 18 Gy, 19 Gy, or up to 20 Gy. Radiation may be whole body radiation or partial body radiation. In the case that radiation is whole body radiation, it may be uniform or not uniform. For example, when radiation may not be uniform, narrower regions of a body such as the neck may receive a higher dose than broader regions such as the hips.

Where desirable, an immunosuppressive agent can be used in conjunction with a subject treatment method. Exemplary immunosuppressive agents include but are not limited to cyclosporin, azathioprine, methotrexate, mycophenolate, and FK506, antibodies, or other immunoablative agents such as CAMPATH, anti-CD3 antibodies (e.g., muromonab, otelixizumab) or other antibody therapies, cytoxin, fludarabine, cyclosporin, FK506, rapamycin, mycophenolic acid, steroids, FR901228, cytokines, and irradiation, peptide vaccine, and any combination thereof. A method of the present disclosure may comprise administering at least one immunomodulatory agent. In certain embodiments, the at least one immunomodulatory agent is selected from the group consisting of immunostimulatory agents, checkpoint immune blockade agents (e.g., blockade agents or inhibitors of immune checkpoint genes, such as, for example, PD-1, PD-L1, CTLA-4, IDO, TIM3, LAG3, TIGIT, BTLA, VISTA, ICOS, KIRs and CD39), radiation therapy agents, chemotherapy agents, and combinations thereof. In some embodiments, the immunostimulatory agents are selected from the group consisting of IL-12, an agonist costimulatory monoclonal antibody, and combinations thereof. In one embodiment, the immunostimulatory agent is IL-12. In some embodiments, the agonist costimulatory monoclonal antibody is selected from the group consisting of an anti-4-1BB antibody (e.g., urelumab, PF-05082566), an anti-OX40 antibody (pogalizumab, tavolixizumab, PF-04518600), an anti-ICOS antibody (BMS986226, MEDI-570, GSK3359609, JTX-2011), and combinations thereof. In one embodiment, the agonist costimulatory monoclonal antibody is an anti-4-1BB antibody. In some embodiments, the checkpoint immune blockade agents are selected from the group consisting of anti-PD-L1 antibodies (atezolizumab, avelumab, durvalumab, BMS-936559), anti-CTLA-4 antibodies (e.g., tremelimumab, ipilimumab), anti-PD-1 antibodies (e.g., pembrolizumab, nivolumab), anti-LAG3 antibodies (e.g., C9B7 W, 410C9), anti-B7-H3 antibodies (e.g., DS-5573a), anti-TIM3 antibodies (e.g., F38-2E2), and combinations thereof. In one embodiment, the checkpoint immune blockade agent is an anti-PD-L1 antibody. In some cases, a compound of the present disclosure can be administered to a subject in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. In some cases, expanded cells can be administered before or following surgery. Alternatively, compositions comprising a compound described herein can be administered with immunostimulants. Immunostimulants can be vaccines, colony stimulating agents, interferons, interleukins, viruses, antigens, co-stimulatory agents, immunogenicity agents, immunomodulators, or immunotherapeutic agents. An immunostimulant can be a cytokine such as an interleukin. One or more cytokines can be introduced with modified cells provided herein. Cytokines can be utilized to boost function of modified T lymphocytes (including adoptively transferred tumor-specific cytotoxic T lymphocytes) to expand within a tumor microenvironment. In some cases, IL-2 can be used to facilitate expansion of the modified cells described herein. Cytokines such as IL-15 can also be employed. Other relevant cytokines in the field of immunotherapy can also be utilized, such as IL-2, IL-7, IL-12, IL-15, IL-21, or any combination thereof. An interleukin can be IL-2, or aldeskeukin. Aldesleukin can be administered in low dose or high dose. A high dose aldesleukin regimen can involve administering aldesleukin intravenously every 8 hours, as tolerated, for up to about 14 doses at about 0.037 mg/kg (600,000 IU/kg). An immunostimulant (e.g., aldesleukin) can be administered within 24 hours after a cellular administration. An immunostimulant (e.g., aldesleukin) can be administered in as an infusion over about 15 minutes about every 8 hours for up to about 4 days after a cellular infusion. An immunostimulant (e.g., aldesleukin) can be administered at a dose from about 100,000 IU/kg, 200,000 IU/kg, 300,000 IU/kg, 400,000 IU/kg, 500,000 IU/kg, 600,000 IU/kg, 700,000 IU/kg, 800,000 IU/kg, 900,000 IU/kg, or up to about 1,000,000 IU/kg. In some cases, aldesleukin can be administered at a dose from about 100,000 IU/kg to 300,000 IU/kg, from 300,000 IU/kg to 500,000 IU/kg, from 500,000 IU/kg to 700,000 IU/kg, from 700,000 IU/kg to about 1,000,000 IU/kg.

In some other embodiments, any of the compounds herein that is capable of modulating a PTPN2 protein may be administered in combination or in conjunction with one or more pharmacologically active agents including but not limited to: (1) an inhibitor of MEK (e.g., MEK1, MEK2) or of mutants thereof (e.g., trametinib, cobimetinib, binimetinib, selumetinib, refametinib); (2) an inhibitor of epidermal growth factor receptor (EGFR) and/or of mutants thereof (e.g., afatinib, erlotinib, gefitinib, lapatinib, cetuximab panitumumab, osimertinib, olmutinib, EGF-816); (3) an immunotherapeutic agent (e.g., checkpoint immune blockade agents, as disclosed herein); (4) a taxane (e.g., paclitaxel, docetaxel); (5) an anti-metabolite (e.g. antifolates such as methotrexate, raltitrexed, pyrimidine analogues such as 5-fluorouracil (5-FU), ribonucleoside and deoxyribonucleoside analogues, capecitabine and gemcitabine, purine and adenosine analogues such as mercaptopurine, thioguanine, cladribine and pentostatin, cytarabine (ara C), fludarabine); (6) an inhibitor of FGFR1 and/or FGFR2 and/or FGFR3 and/or of mutants thereof (e.g., nintedanib); (7) a mitotic kinase inhibitor (e.g., a CDK4/6 inhibitor, such as, for example, palbociclib, ribociclib, abemaciclib); (8) an anti-angiogenic drug (e.g., an anti-VEGF antibody, such as, for example, bevacizumab); (9) a topoisomerase inhibitor (e.g. epipodophyllotoxins such as for example etoposide and etopophos, teniposide, amsacrin, topotecan, irinotecan, mitoxantrone); (10) a platinum-containing compound (e.g. cisplatin, oxaliplatin, carboplatin); (11) an inhibitor of ALK and/or of mutants thereof (e.g. crizotinib, alectinib, entrectinib, brigatinib); (12) an inhibitor of c-MET and/or of mutants thereof (e.g., K252a, SU11274, PHA665752, PF2341066); (13) an inhibitor of BCR-ABL and/or of mutants thereof (e.g., imatinib, dasatinib, nilotinib); (14) an inhibitor of ErbB2 (Her2) and/or of mutants thereof (e.g., afatinib, lapatinib, trastuzumab, pertuzumab); (15) an inhibitor of AXL and/or of mutants thereof (e.g., R428, amuvatinib, XL-880); (16) an inhibitor of NTRK1 and/or of mutants thereof (e.g., Merestinib); (17) an inhibitor of RET and/or of mutants thereof (e.g., BLU-667, Lenvatinib); (18) an inhibitor of A-Raf and/or B-Raf and/or C-Raf and/or of mutants thereof (RAF-709, LY-3009120); (19) an inhibitor of ERK and/or of mutants thereof (e.g., ulixertinib); (20) an MDM2 inhibitor (e.g., HDM-201, NVP-CGM097, RG-71 12, MK-8242, RG-7388, SAR405838, AMG-232, DS-3032, RG-7775, APG-115); (21) an inhibitor of mTOR (e.g., rapamycin, temsirolimus, everolimus, ridaforolimus); (22) an inhibitor of BET (e.g., I-BET 151, I-BET 762, OTX-015, TEN-010, CPI-203, CPI-0610, olionon, RVX-208, ABBC-744, LY294002, AZD5153, MT-1, MS645); (23) an inhibitor of IGF1/2 and/or of IGF1-R (e.g., xentuzumab, MEDI-573); (24) an inhibitor of CDK9 (e.g., DRB, flavopiridol, CR8, AZD 5438, purvalanol B, AT7519, dinaciclib, SNS-032); (25) an inhibitor of farnesyl transferase (e.g., tipifarnib); (26) an inhibitor of SHIP pathway including SHIP2 inhibitor (e.g., 6-(4-amino-4-methylpiperidin-1-yl)-3-(2,3-dichlorophenyl) pyrazin-2-amine), as well as SHIP1 inhibitors; (27) an inhibitor of SRC (e.g., dasatinib); (28) an inhibitor of JAK (e.g., tofacitinib); (29) a PARP inhibitor (e.g. Olaparib, Rucaparib, Niraparib, Talazoparib), (30) a BTK inhibitor (e.g. Ibrutinib, Acalabrutinib, Zanubrutinib); (31) a ROS1 inhibitor (e.g., entrectinib); (32) an inhibitor of FLT3, HDAC, VEGFR (e.g., bevacizumab (Avastin), sorafenib (Nexavar), sunitinib (Sutent), nilotinib (Tasigna), pazopanib (Votrient), dasatinib (Sprycel)), PDGFR, LCK, Bcr-Abl or AKT; (33) an inhibitor of SHP pathway; (34) an inhibitor of KrasG12C mutant (e.g., including but not limited to AMG510, MRTX849, and any covalent inhibitors binding to the cysteine residue 12 of Kras, the structures of these compounds are publicly known)(e.g., an inhibitor of Ras G12C as described in US20180334454, US20190144444, US20150239900, U.S. Pat. No. 10,246,424, US20180086753, WO2018143315, WO2018206539, WO20191107519, WO2019141250, WO2019150305, U.S. Pat. No. 9,862,701, US20170197945, US20180086753, U.S. Pat. No. 10,144,724, US20190055211, US20190092767, US20180127396, US20180273523, U.S. Pat. No. 10,280,172, US20180319775, US20180273515, US20180282307, US20180282308, WO2019051291, WO2019213526, WO2019213516, WO2019217691, WO2019241157, WO2019217307, WO2020047192, WO2017087528, WO2018218070, WO2018218069, WO2018218071, WO2020027083, WO2020027084, WO2019215203, WO2019155399, WO2020035031, WO2014160200, WO2018195349, WO2018112240, WO2019204442, WO2019204449, WO2019104505, WO2016179558, WO2016176338, or related patents and applications, each of which is incorporated by reference in its entirety); (35) an SHC inhibitor (e.g., PP2, AID371185); (36) a GAB inhibitor (e.g., GAB-0001), (37) a GRB inhibitor; (38) a PI-3 kinase inhibitor (e.g., Idelalisib, Copanlisib, Duvelisib, Alpelisib, Taselisib, Perifosine, Buparlisib, Umbralisib, NVP-BEZ235-AN); (39) a MARPK inhibitor; (40) CDK4/6 (e.g., palbociclib, ribociclib, abemaciclib); (41) a MAPK inhibitor (e.g., VX-745, VX-702, RO-4402257, SCIO-469, BIRB-796, SD-0006, PH-797804, AMG-548, LY2228820, SB-681323, GW-856553, RWJ67657, BCT-197); (42) an inhibitor of SHP pathway including SHP2 inhibitor (e.g., 6-(4-amino-4-methylpiperidin-1-yl)-3-(2,3-dichlorophenyl) pyrazin-2-amine, RMC-4630, ERAS-601,

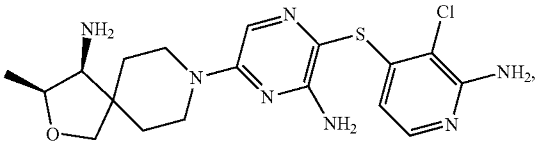

TNO155

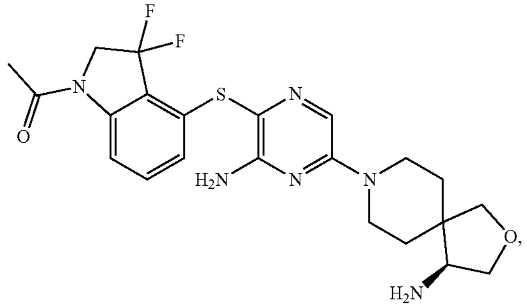

JAB-3068

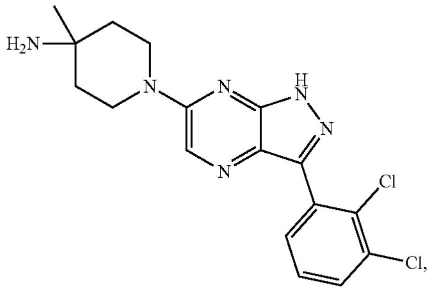

IACS-13909/BBP-398

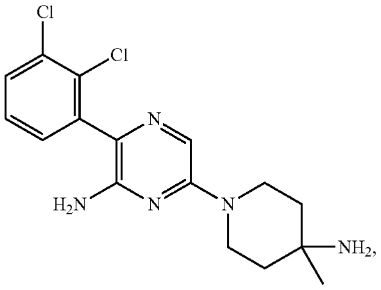

and

SHP099

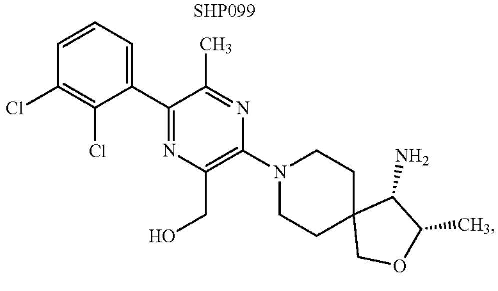

)

RMC-4550 as well as SHP1 inhibitors; or (43) an inhibitor of a Kras mutant (e.g., Kras G12D, including a compound described in WO2021041671, WO2021107160, WO2021091967, WO2021142252, WO2021150613, WO2021211864, WO2021118877, WO2021081212, WO2021108683; KRas G12C, KRas G12D, KRas G12S, KRas G12V, KRas G13D, KRas G13C, or KRas G13V). In some embodiments, any of the compounds herein that is capable of inhibiting a PTPN2 protein may be administered in combination or in conjunction with one or more checkpoint immune blockade agents (e.g., anti-PD-1 and/or anti-PD-L1 antibody, anti-CLTA-4 antibody). In embodiments, a compound described herein may be administered in combination or conjunction with a SOS (e.g., SOS1) inhibitor, including a compound described in WO2021173524, WO2021203768, WO2020180770, WO2020180768, WO2021092115, WO2018172250, WO2019201848, WO2018115380, WO2019122129, or WO2021127429; all of which are herein incorporated by reference for any purpose. In some embodiments, the SOS inhibitor is selected from RMC-5845, BI-1701963,

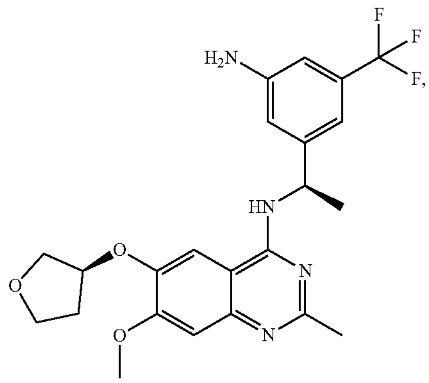

BI-3406

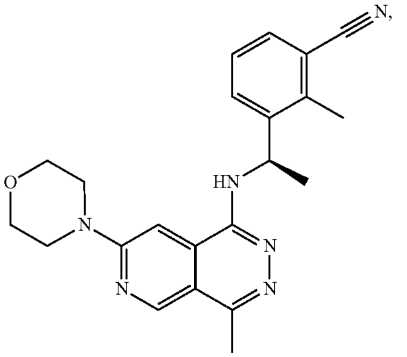

and

MRTX0902

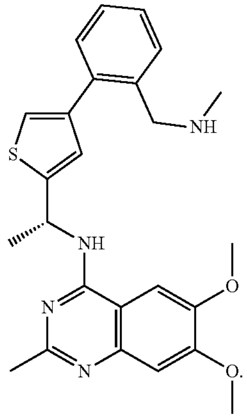

BAY 293

In an aspect, the present disclosure provides a method of potentiating immunity of a subject in need thereof, comprising administering (e.g., systemically or locally administering) a PTPN2 inhibitor, such as a compound of Formula (I), (I-1), (II), (II-1), (II-a), (II-a1), (III), (III-1), (IV), or (IV-1), to the subject, thereby potentiating immunity of the subject. In another aspect, the present disclosure provides a method of potentiating immunity of a subject in need thereof, comprising (e.g., transiently) downregulating expression or activity of PTPN2 in vivo in a cell of the subject, thereby potentiating immunity of the subject. In another aspect, the present disclosure provides a method of potentiating immunity of a subject in need thereof, comprising (a) selecting the subject, wherein a cell of the subject exhibits expression or activity of PTPN2; and (b) downregulating the expression or activity of PTPN2 in a cell of the subject, thereby potentiating immunity of the subject. In another aspect, the present disclosure provides a method of potentiating immunity of a subject in need thereof, comprising (a) administering a lymphoid cell to the subject, wherein the lymphoid cell comprises (i) a chimeric T-cell receptor (TCR) sequence encoding a T-cell receptor fusion protein (TFP) and/or (ii) a chimeric antigen receptor (CAR) sequence encoding a CAR, wherein each of TFP and CAR exhibits specific binding to an antigen; and (b) separately administering a PTPN2 inhibitor, such as a compound of Formula (I), (I-1), (II), (II-1), (II-a), (II-a1), (III), (III-1), (IV), or (IV-1), to the subject, thereby potentiating immunity of the subject. In another aspect, the present disclosure provides a method of potentiating immunity of a cell, comprising (a) contacting the cell with a PTPN2 inhibitor; and (b) introducing to the cell (i) a chimeric T-cell receptor (TCR) sequence encoding a T-cell receptor fusion protein (TFP) and/or (ii) a chimeric antigen receptor (CAR) sequence encoding a CAR, wherein each of TFP and CAR exhibits specific binding to an antigen, thereby potentiating immunity of the cell, wherein (a) is performed prior to or concurrent with (b), thereby potentiating immunity of the cell.

In another aspect, the present disclosure provides a method of increasing efficacy or reducing a side effect of a cell therapy for a subject in need thereof, comprising (a) administering to the subject a cell comprising a chimeric antigen receptor (CAR) sequence encoding a CAR, wherein the CAR comprises an antigen-binding domain and an intracellular signaling domain, wherein the intracellular signaling domain is minimally required for activation of the CAR upon binding to an antigen; and (b) administering a PTNP2 inhibitor, such as a compound of Formula (I), (I-1), (II), (II-1), (II-a), (II-a1), (III), (III-1), (IV), or (IV-1), to said subject prior to, concurrent with, or subsequent to (a). In another aspect, the present disclosure provides a method of increasing efficacy or reducing a side effect of a cell therapy for a subject in need thereof, comprising (a) administering to the subject a sub-therapeutic amount of a cell comprising a chimeric antigen receptor (CAR) sequence encoding a CAR, and (b) administering a PTNP2 inhibitor to said subject prior to, concurrent with, or subsequent to (a).

In another aspect, the present disclosure provides a method of treating cancer in a subject in need thereof, comprising: (a) administering systemically a PTPN2 inhibitor, such as a compound of Formula (I), (I-1), (II), (II-1), (II-a), (II-a1), (III), (III-1), (IV), or (IV-1), to the subject; and (b) administering a second agent or a second therapy concurrently, before, or after step (a), wherein the second agent or the second therapy comprises a lymphoid cell that (1) retains expression or activity of PTPN2 prior to being exposed to the PTPN2 inhibitor, and (2) expresses (i) a chimeric T-cell receptor (TCR) sequence encoding a T-cell receptor fusion protein (TFP) and/or (ii) a chimeric antigen receptor (CAR) sequence encoding a CAR, wherein each of TFP and CAR exhibits specific binding to a tumor antigen. In some embodiments, the second agent or the second therapy comprises a lymphoid cell that (1) retains expression or activity of PTPN2 prior to being exposed to the PTPN2 inhibitor, and (2) expresses a chimeric antigen receptor (CAR) sequence encoding a CAR, wherein each of TFP and CAR exhibits specific binding to a tumor antigen. In some embodiments, the PTPN2 inhibitor is systemically and transiently administered to the subject in need thereof, wherein the second agent or the second therapy comprises a lymphoid cell that (1) retains expression or activity of PTPN2 prior to being exposed to the PTPN2 inhibitor, and (2) comprises a chimeric antigen receptor (CAR) sequence encoding a CAR, wherein the CAR exhibits specific binding to a tumor antigen.

In practicing any of the methods disclosed herein, a PTPN2 inhibitor may be systemically administered to a subject in need thereof. In contrast to conventional teaching that precludes the use of PTPN2 inhibitors for systemic therapy and the promotion of T cell mediated anti-tumor immunity (see, The EMBO Journal, Dec. 5, 2019, 39 (2): e103637), the present disclosure provides, in an aspect, a systemic application of a PTPN2 inhibitor, which mediates regulatable inhibition of PTPN2 signaling. Distinguished from the conventional approach that resorts to cell-specific knock-out of PTPN2 (e.g., utilizing CAR-T cells whose PTPN2 expression is knocked out or knocked down), the present disclosure, in an aspect, demonstrates the utility of direct and systemic use of a PTPN2 inhibitor in potentiating an immune response in a subject. Such approach obviates the needs of separately modifying a therapeutic cell by knocking out its PTPN2 gene expression. In some embodiments, PTPN2 inhibitors exemplified herein potentiate the tumor cell killing activity of CAR- and TFP-expressing immune cells. In some embodiments, such activity is effective and regulatable in that (1) the enhanced tumor cell killing activity of the CAR-T cells persisted for some period of time even after ceasing the application of the PTPN2 inhibitor; and/or (2) the enhanced tumor cell killing activity of the CAR-T cells is attenuated by intermittent or non-continuous application of the inhibitor. The systemic and transient administration of a PTPN2 inhibitor in conjunction with a cell therapy (e.g., CAR- or TFP-expressing lymphoid cells directed to a tumor antigen) can be particularly advantageous in avoiding autoreactivity, cytokine release syndrome, and/or other undesired inflammation associated with constitutive or permanent suppression of PTPN2. In some embodiments, a PTPN2 inhibitor for systemic and transient application is a compound of Formula (I), (I-1), (II), (II-1), (II-a), (II-a1), (III), (III-1), (IV), or (IV-1).

In some embodiments, the PTPN2 inhibitor for systemic and transient application exhibits $IC_{50}$ of less than or equal to 10 μM, 5 μM, 1 μM, 500 nM, 200 nM, 100 nM, 50 nM, 10 nM, 1 nM for PTPN2 as ascertained in a phosphatase activity assay utilizing a PTPN2 substrate including but not limited to DiFMUP, STAT1 and STAT5. In some embodiments, the PTPN2 inhibitor for systemic and transient application exhibits $IC_{50}$ for PTPN2 less than 10 nM, 5 nM, 4 nM, 3 nM, 2 nM, 1 nM, as ascertained in a phosphatase activity assay utilizing DiFMUP as a substrate. In some embodiments, the PTPN2 inhibitor for systemic and transient application exhibits $IC_{50}$ (also can be referred to as $EC_{50}$ as applied to cellular assay) for PTPN2 less than 10 μM, 5 μM, 1 μM, 500 nM, 200 nM, 100 nM, 50 nM, 10 nM, 1 nM as tested in a pSTAT1 assay. In some embodiments, the PTPN2 inhibitor for systemic and transient application exhibits $EC_{50}$ for PTPN2 of less than 15 μM, 10 μM, 5 μM, 1 μM, 500 nM, 200 nM, 100 nM when tested in the CD25 assay disclosed herein. In some embodiments, the PTPN2 inhibitor for systemic and transient application exhibits $IC_{50}$ (also can be referred to as $EC_{50}$ as applied to cellular assay) for PTPN2 less than 10 nM or less than 1 nM as tested in a phosphatase assay utilizing DiFMUP as the substrate, and $EC_{50}$ less than 10 μM or less than 5 μM in a pSTAT1 assay. In some embodiments, the PTPN2 inhibitor for systemic and transient application exhibits $IC_{50}$ (also can be referred to as $EC_{50}$ as applied to cellular assay) for PTPN2 (i) less than 5 nM as tested in a phosphatase assay utilizing DiFMUP as the substrate, (ii) $EC_{50}$ less than 5 μM in a pSTAT1 assay, and (iii) EC 50 less than 1 μM when tested in the CD25 assay disclosed herein.

In practicing any of the methods disclosed herein, a cell or a plurality of such cell may be administered (e.g., systemically administered) to the subject. In some cases, the cell may be a lymphoid cell that optically comprises (i) a chimeric T-cell receptor (TCR) sequence encoding a T-cell receptor fusion protein (TFP) and/or (ii) a chimeric antigen receptor (CAR) sequence encoding a CAR, wherein each of TFP and CAR exhibits specific binding to an antigen. In some cases, the cell may be administered (e.g., systemically administered) to the subject sequentially (e.g., prior to or subsequent to) or concurrent with administering (e.g., systemically administering) a PTPN2 inhibitor to the subject. The cell may have been contacted previously with a PTPN2 inhibitor. Alternatively, the cell may not or need not be contacted with a PTPN2 inhibitor prior to the administration of the cell to the subject.

In some embodiments, (i) the chimeric T-cell receptor sequence and/or (ii) the CAR sequence may be introduced to the cell directly (e.g., via a solution comprising (i) the chimeric T-cell receptor sequence and/or (ii) the CAR sequence), by chemical means (e.g., via one or more carriers such as liposomes for delivery of one or more nucleic acid sequences comprising (i) the chimeric T-cell receptor sequence and/or (ii) the CAR sequence), and/or viral means (e.g., when delivering one or more nucleic acid sequences comprising (i) the chimeric T-cell receptor sequence and/or (ii) the CAR sequence). For the viral means, the one or more nucleic acid sequence may in introduced in a chromosome of the cell, such as a nuclear chromosome and/or a mitochondrial chromosome. In other embodiments, the one or more nucleic acid sequence may not or need not be introduced in the chromosome of the cell, and as such be introduced to the cell as an epichromosomal molecule (e.g., a linear or circular nucleic acid molecule). In some embodiments, the cell may be a lymphoid cell.

Subsequent to the introduction, (i) the chimeric T-cell receptor sequence and/or (ii) the CAR sequence may persist in the cell for at least 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, 3 years, 4 years, 5 years, or more, or any time in between. Subsequent to the introduction, (i) the chimeric T-cell receptor sequence and/or (ii) the CAR sequence may persist in the cell for at most 5 years, 4 years, 3 years, 24 months, 23 months, 22 months, 21 months, 20 months, 19 months, 18 months, 17 months, 16 months, 15 months, 14 months, 13 months, 12 months, 11 months, 10 months, 9 months, 8 months, 7 months, 6 months, 5 months, 4 months, 3 months, 2 months, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days, 2 days, 1 day, or less, or any time in between.

In some embodiments, introducing to the cell (i) the chimeric T-cell receptor sequence and/or (ii) the CAR sequence may be performed sequentially (e.g., prior to or subsequent to) or concurrent with contacting the cell with a PTPN2 inhibitor. When introduced sequentially, introducing (i) the chimeric T-cell receptor sequence and/or (ii) the CAR sequence and contacting with the PTPN2 inhibitor may be performed by the same route (e.g. injections to the same location; tablets taken orally at the same time), or by a different route (e.g. a tablet taken orally while receiving an intravenous infusion). When introduced concurrently, for example, a first composition comprising (i) the chimeric T-cell receptor sequence and/or (ii) the CAR sequence and a second composition comprising the PTPN2 inhibitor may be part of the same composition (e.g., the same condition media or a therapeutic regimen).

Contacting the cell with the PTPN2 inhibitor, whether systemically and/or transiently, as described in the present disclosure, may reduce PTPN2 signaling via reduction of PTPN2 activity or PTPN2 expression in the cell. For example, the cell can be cultured in a suitable medium, to which a PTPN2 inhibitor is introduced for period of time sufficient to affect such reduction (or inhibition). Depending on the choice of the type of PTPN2 inhibitor, the contacting step may be affected by direct physical contact, pressure (e.g. by changing the shape of the cell via squeezing), chemical means (e.g., liposomes for delivery of nucleic acid based PTPN2 inhibitors), or viral means (e.g., when delivering shRNA, siRNA, or CRISPR-based PTPN2 inhibitors). The PTPN2 inhibitor may directly be introduced to a subject lymphoid cell ex vivo or in vitro. In some embodiments, the cell can be in a subject, and the PTPN2 inhibitor may be administered (e.g., systemically administered) to the subject to contact the cell in vivo. Upon such administration, at least a portion of the PTPN2 inhibitor may contact a cell (e.g., a lymphoid cell, a cancer, or tumor cell, etc.) of the subject in vivo. A composition (e.g., a therapeutic regimen) comprising the PTPN2 inhibitor may be administered to a target site comprising the cell (e.g., the cell may be part of the vascular or lymphatic system of the subject, or a localized tissue of interest or tumor). Alternatively or in addition to, the composition comprising the PTPN2 inhibitor may be administered to a different site than the target site. Upon such administration, the PTPN2 inhibitor may be directed to the target site or the cell via diffusion or via a medium such as a bodily fluid (e.g., blood).

When contacting a cell (e.g., a lymphoid cell) with the PTPN2 inhibitor ex vivo, the cell may be treated with a composition (e.g., a solution) comprising the PTPN2 inhibitor for at least 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 12 hours, 16 hours, 20 hours, 24 hours, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 2 months, 3 months, 4 months, 5 months, 6 months, or more, or any time in between. The cell may be treated with the composition comprising the PTPN2 inhibitor for at most 6 months, 5 months, 4 months, 3 months, 2 months, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2 hours, 60 minutes, 50 minutes, 40 minutes, 30 minutes, 20 minutes, 10 minutes, 9 minutes, 8 minutes, 7 minutes, 6 minutes, 5 minutes, 4 minutes, 3 minutes, 2 minutes, 1 minute, or less, or any time in between. During the contacting period, the cell may be subjected to additional PTPN2 inhibitor (e.g., to compensate for a limited half-life of the PTPN2 inhibitor in culture media). Alternatively, during the contacting period, the cell may not be subjected to any additional PTPN2 inhibitor. A process of contacting the cell with the PTPN2 inhibitor (e.g., treating the cell with a composition comprising the PTPN2 inhibitor) may be performed at least 1, 2, 3, 4, 5, or more times. In other embodiments, such process may be performed at most 5, 4, 3, 2, or 1 time.

In some embodiments, the cell as provided herein may retain expression or activity of PTPN2 prior to contacting (e.g., in vivo or ex vivo) the cell with the PTPN2 inhibitor. In some cases, any one of the methods disclosed herein may involve assessing the expression or activity of PTPN2 in the cell prior to contacting the cell with the PTPN2 inhibitor. In some examples, the cell may not exhibit any loss of the expression or activity of PTPN2, as compared to that present in a control sample, derived from e.g., another cell of the same origin of the cell or a progeny of the cell. In other examples, the cell may exhibit an expression or activity level of PTPN2 that is at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more of that present in a control sample, derived from e.g., another cell of the same origin of the cell or a progeny of the cell. In yet some examples, the PTPN2 mRNA level, cDNA level, or PTPN2 polypeptide level expressed in the cell may be at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more of that present in a control sample, derived from e.g., another cell of the same origin of the cell or a progeny of the cell. In other examples, the cell may exhibit an activity level of PTPN2 (e.g., a degree of dephosphorylation of a target substrate) that is at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more of that present in a control sample, derived from e.g., another cell of the same origin of the cell or a progeny of the cell. In other examples, an amount of PTPN2-associated cfDNA or cfRNA level within a source of the cell (e.g., from a plasma of a subject from whom/which the cell was obtained or derived from) may be indicative of an expression level of PTPN2 in the cell. As such, the amount of PTPN2-associated cfDNA or cfRNA level within a source of the cell may be at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more of that present in a control sample, e.g., another healthy subject who does not comprise or is not suspected of having a condition or disease of interest.

For any cell that is administered to a subject in need thereof, either with or without having been treated with a PTPN2 inhibitor as provided in the present disclosure, the cell may be autologous or allogenic to the subject. The cell may have been obtained from the subject and treated ex vivo (e.g., contacting with the PTPN2 inhibitor, engineered to express (i) the TFG and/or (ii) the CAR, etc.) prior to the administration. Alternatively, the cell may be a progeny of a cell obtained from the subject, and the progeny may have been treated ex vivo (e.g., contacting with the PTPN2 inhibitor, engineered to express (i) the TFG and/or (ii) the CAR, etc.) prior to the administration. In a different alternative, the cell may be a progeny of a cell obtained from the subject, and the progeny may be administered to the subject without any engineering or modification thereof. In other embodiments, the cell may be heterologous to the subject. In some examples, the cell may be an allogeneic cell, derived from, e.g., another human subject.

Any one of the subject methods disclosed herein may further comprise administering a PTPN2 inhibitor to the subject sequentially (e.g., prior to or subsequent to) or concurrent with administering a cell (e.g., a lymphoid cell) to the subject. In some embodiments, the cell may have been at least contacted previously with a PTPN2 inhibitor and, optionally, express the TFP and/or the CAR. In other embodiments, the cell may not have been contacted previously with a PTPN2 inhibitor and, optionally, express the TFP and/or the CAR. When introduced sequentially, the PTPN2 inhibitor and the cell may be administered by the same route (e.g. injections to the same location; tablets taken orally at the same time), or separately by a different route (e.g. a tablet taken orally while receiving an intravenous infusion). When introduced concurrently, the PTPN2 inhibitor and the cell may be, e.g., part of the same composition (e.g., the same condition media or a therapeutic regimen).

In some embodiments, a PTPN2 inhibitor is administered into a subject in need thereof systemically and transiently (including intermittently) to potentiate a subject's immunity. In some embodiments, a PTPN2 inhibitor is administered as a single agent. In some embodiments, a PTPN2 inhibitor is administered in combination with another agent as a single or unit dose, or as a separate dose. In some embodiments, the another agent can be a cell, including but not limited to a lymphoid cell (e.g., expressing a CAR and/or TCR).

In some embodiments, separate administrations of a cell (e.g., a lymphoid cell optionally configured to express a TFP and/or a CAR) and a PTPN2 inhibitor to a subject may occur simultaneously, e.g., administering the cell via a first site of the subject's body and administering the PTPN2 inhibitor via a second site of the subject's body at the same time. In other embodiments, separate administrations of the cell and the PTPN2 inhibitor may occur sequentially to a same site or to different sites of the subject's body, e.g., administering the PTPN2 inhibitor subsequent to the cell, or administering the PTPN2 inhibitor prior to the cell. A sequential administration of the cell and the PTPN2 inhibitor may be separated by at least 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 60 minutes, 2 hours, 3 hours, 4 hours, 5 hours, 6 hours, 7 hours, 8 hours, 9 hours, 10 hours, 12 hours, 16 hours, 20 hours, 24 hours, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 2 months, 3 months, 4 months, 5 months, 6 months, or more, or any time in between. A sequential administration of the cell and the PTPN2 inhibitor may be separated by at most 6 months, 5 months, 4 months, 3 months, 2 months, 31 days, 30 days, 29 days, 28 days, 27 days, 26 days, 25 days, 24 days, 23 days, 22 days, 21 days, 20 days, 19 days, 18 days, 17 days, 16 days, 15 days, 14 days, 13 days, 12 days, 11 days, 10 days, 9 days, 8 days, 7 days, 6 days, 5 days, 4 days, 3 days, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2 hours, 60 minutes, 50 minutes, 40 minutes, 30 minutes, 20 minutes, 10 minutes, 9 minutes, 8 minutes, 7 minutes, 6 minutes, 5 minutes, 4 minutes, 3 minutes, 2 minutes, 1 minute, or less, or any time in between.

In practicing any one of the methods disclosed herein, the subject being administered (e.g., systemically administered) with a PTPN2 inhibitor can retain, prior to the administration of the PTPN2 inhibitor, expression or activity of PTPN2 in the subject's cells, such as lymphoid cells (e.g., T cells, NK cells, HKGY cells, and B cells), cancer cells, or tumor cells. For example, the subject retains a PTPN2 expression or activity level in their lymphoid cells, cancer cells, or tumor cells that is at least 10%, 20%, 30%, 40%, 50%, 60%, 70%, 80%, 90%, 95%, 96%, 97%, 98%, 99%, 100% or more of that present in a control sample prior to systemically administering a PTPN2 inhibitor. In some examples, the PTPN2 mRNA level, cDNA level, PTPN2 or PTPN2-associated cfDNA or cfRNA level, expressed in the subject's lymphoid cells, cancer cells, or tumor cells is at least 10%, 20%, 30%, 40%, 50%, 60%, 70%, 80%, 90%, 95%, 96%, 97%, 98%, 99%, 100% or more of that present in a control sample. In some examples, the PTPN2 mRNA level, cDNA level, PTPN2 or PTPN2-associated cfDNA or cfRNA level, expressed in the subject's lymphoid cells is at least 10%, 20%, 30%, 40%, 50%, 60%, 70%, 80%, 90%, 95%, 96%, 97%, 98%, 99%, 100% or more of that present in a control sample. In some examples, the subject's lymphoid cells, cancer cells, or tumor cells carry two copies or least one copy of PTPN2 genomic DNA. In some examples, the PTPN2 polypeptide level expressed in the subject's lymphoid cells is at least 10%, 20%, 30%, 40%, 50%, 60%, 70%, 80%, 90%, 95%, 96%, 97%, 98%, 99%, 100% or more of that present in a control sample. In some examples, the subject's lymphoid cells, cancer cells, or tumor cells exhibit a normal level of expression or activity of PTPN2 as compared to that of a control sample.

The control sample utilized in assessing the PTPN2 expression level can be a biological sample from a subject that does not exhibit a tumor or cancer, or from a subject that has not been diagnosed with a tumor or cancer and that has not been treated with a PTPN2 inhibitor. Such control sample can comprise PTPN2 polynucleotides or PTPN2 polypeptides from any of such subject's tissues or cells, including but not limited to such subject's lymphoid cells.

Subsequent to the administration (e.g., systemic administration) of the PTPN2 inhibitor to the subject, the subject may exhibit a reduced expression or activity level of PTPN2 in a cell of the subject (e.g., a lymphoid cell, a tumor cell, a cancer cell, etc.) as compared to that present in a control sample from the subject prior to the administration of the PTPN2 inhibitor. In some cases, subsequent to a systemic administration of the PTPN2 inhibitor to the subject, the subject may exhibit at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more reduction in the expression or activity level of PTPN2 in a cell of the subject (e.g., a lymphoid cell, a tumor cell, a cancer cell, etc.) as compared to that present in a control sample from the subject prior to the systemic administration of the PTPN2 inhibitor. In some cases, the reduced expression or activity level of PTPN2 may be transient, thus may increase over time to, e.g., a normal level comparable to the control sample. In other cases, the reduced expression or activity level of PTPN2 may be maintained or may even continue to decrease for a period of time.

In practicing any one of the methods disclosed herein, downregulation (e.g., transient downregulation) of PTPN2 expression or activity may be performed in vivo in a cell, such as a lymphoid cell or a diseased cell (e.g., a cancer cell or a tumor cell). In some embodiments, a transient downregulation of expression or activity of a target molecule (e.g., PTPN2) in a cell may involve downregulating the expression or activity of the target molecule for at most about, 6 months, 5 months, 4 months, 3 months, 2 months, 1 month, 21 days, 14 days, 13 days, 12 days, 11 days, 10 days, 9 days, 8 days, 7 days, 6 days, 5 days, 4 days, 3 days, 48 hours, 44 hours, 40 hours, 36 hours, 32 hours, 28 hours, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2 hours, 60 minutes, 55 minutes, 50 minutes, 45 minutes, 40 minutes, 35 minutes, 30 minutes, 25 minutes, 20 minutes, 15 minutes, 10 minutes, 9 minutes, 8 minutes, 7 minutes, 6 minutes, 5 minutes, 4 minutes, 3 minutes, 2 minutes, 1 minute, or a shorter period of time. Subsequent to the transient downregulation, the resulting expression or activity level of the target molecule may be maintained. In other embodiments, subsequent to the transient downregulation, at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more of the downregulated expression or activity level of the target molecule may be regained.

In practicing any one of the methods disclosed herein, a process of downregulating (e.g., transiently downregulating) expression or activity of a target molecule (e.g., PTPN2) may comprise introducing an inhibitor of the target molecule (e.g., a PTPN2 inhibitor). In some embodiments, transiently downregulating expression or activity of PTPN2 in a cell (e.g., a lymphoid cell, a tumor cell, a cancer cell) may comprise introducing a PTPN2 inhibitor to the cell (e.g., treating the cell with a solution comprising a PTPN2 inhibitor) for at most 14 days, 13 days, 12 days, 11 days, 10 days, 9 days, 8 days, 7 days, 6 days, 5 days, 4 days, 3 days, 48 hours, 44 hours, 40 hours, 36 hours, 32 hours, 28 hours, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2 hours, 60 minutes, 55 minutes, 50 minutes, 45 minutes, 40 minutes, 35 minutes, 30 minutes, 25 minutes, 20 minutes, 15 minutes, 10 minutes, 9 minutes, 8 minutes, 7 minutes, 6 minutes, 5 minutes, 4 minutes, 3 minutes, 2 minutes, 1 minute, or a shorter period of time.

In practicing any one of the methods disclosed herein, a cell (e.g., lymphoid cell, a cancer cell, or a tumor cell) of the subject may exhibit expression or activity of PTPN2 (e.g., exhibiting such at a detectable level) before the expression or activity of PTPN2 is downregulated (e.g., transiently downregulated). For example, the cell may exhibit PTPN2 expression or activity level that is at least 10%, 20%, 30%, 40%, 50%, 60%, 70%, 80%, 90%, 95%, 96%, 97%, 98%, 99%, 100% or more of that present in a control sample. In some examples, the PTPN2 mRNA level or cDNA level expressed in the cell is at least 10%, 20%, 30%, 40%, 50%, 60%, 70%, 80%, 90%, 95%, 96%, 97%, 98%, 99%, 100% or more of that present in a control sample. In some examples, the PTPN2 or PTPN2-associated cfDNA or cfRNA level from the cell is at least 10%, 20%, 30%, 40%, 50%, 60%, 70%, 80%, 90%, 95%, 96%, 97%, 98%, 99%, 100% or more of that present in a control sample. In some examples, the cell of interest carries two copies or least one copy of PTPN2 genomic DNA. In some examples, the PTPN2 polypeptide level expressed in the cell is at least 10%, 20%, 30%, 40%, 50%, 60%, 70%, 80%, 90%, 95%, 96%, 97%, 98%, 99%, 100% or more of that present in a control sample. In some examples, the cell exhibits a normal level of expression or activity of PTPN2 as compared to that of a control sample.

The control sample utilized in assessing the PTPN2 expression level in the cell can be a biological sample from a subject that does not exhibit a tumor or cancer, or from a subject that has not been diagnosed with a tumor or cancer and that has not been treated with a PTPN2 inhibitor. Such control sample can comprise PTPN2 polynucleotides or PTPN2 polypeptides from any of such subject's tissues or cells, including but not limited to such subject's blood plasma.

While expression or activity of PTPN2 in the cell is downregulated (e.g., transiently downregulated), the cell may exhibit a reduced expression or activity level of PTPN2 as compared to that present in the cell prior to the downregulation. In some cases, while expression or activity of PTPN2 in the cell is downregulated (e.g., transiently downregulated), the cell may exhibit at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, or more reduction in the expression or activity level of PTPN2 as compared to that present in a control sample from the subject prior to the downregulation.

For any one of the subject methods disclosed herein, a process of transiently downregulating the expression or activity of PTPN2 may be performed once. In other embodiments, a process of transiently downregulating the expression or activity of PTPN2 may be performed two or more times. In some cases, the process of transiently downregulating the expression or activity of PTPN2 may be performed intermittently for at least 2, 3, 4, 5, 6, 7, 8, 9, 10, or more times. In some examples, a first transient downregulation of expression or activity of PTPN2 and a second transient downregulation of expression or activity of PTPN2 may be separated by period of at least 1 minute, 2 minutes, 3 minutes, 4 minutes, 5 minutes, 6 minutes, 7 minutes, 8 minutes, 9 minutes, 10 minutes, 15 minutes, 20 minutes, 25 minutes, 30 minutes, 35 minutes, 40 minutes, 45 minutes, 50 minutes, 55 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 28 hours, 32 hours, 36 hours, 40 hours, 44 hours, 48 hours, 3 days, 4 days, 5 days, 6 days, 7 days, 8 days, 9 days, 10 days, 11 days, 12 days, 13 days, 14 days, or a longer period of time. In other examples, a first transient downregulation of expression or activity of PTPN2 and a second transient downregulation of expression or activity of PTPN2 may be separated by period of at most about, 6 months, 5 months, 4 months, 3 months, 2 months, 1 month, 21 days, 14 days, 13 days, 12 days, 11 days, 10 days, 9 days, 8 days, 7 days, 6 days, 5 days, 4 days, 3 days, 48 hours, 44 hours, 40 hours, 36 hours, 32 hours, 28 hours, 24 hours, 23 hours, 22 hours, 21 hours, 20 hours, 19 hours, 18 hours, 17 hours, 16 hours, 15 hours, 14 hours, 13 hours, 12 hours, 11 hours, 10 hours, 9 hours, 8 hours, 7 hours, 6 hours, 5 hours, 4 hours, 3 hours, 2 hours, 60 minutes, 55 minutes, 50 minutes, 45 minutes, 40 minutes, 35 minutes, 30 minutes, 25 minutes, 20 minutes, 15 minutes, 10 minutes, 9 minutes, 8 minutes, 7 minutes, 6 minutes, 5 minutes, 4 minutes, 3 minutes, 2 minutes, 1 minute, or a shorter period of time.

In some embodiments, transiently downregulating expression or activity of PTPN2 may comprise introducing a PTPN2 inhibitor to a cell (e.g., a lymphoid cell, a cancer cell, or a tumor cell) or a subject comprising the same intermittently for two or more times, as provided in the present disclosure. In some examples, a first intermittent dosing regimen of the PTPN2 inhibitor and a second intermittent dosing regimen of the PTPN2 inhibitor is the same. In yet other examples, a first intermittent dosing regimen of the PTPN2 inhibitor and a second intermittent dosing regimen of the PTPN2 inhibitor are different. The first intermittent dosing regimen of the PTPN2 inhibitor may comprise a PTPN2 inhibitor content that is at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, or more than that in the second intermittent dosing regimen. Alternatively, the second intermittent dosing regimen of the PTPN2 inhibitor may comprise a PTPN2 inhibitor content that is at least 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 100%, 200%, 300%, 400%, 500%, or more than that in the first intermittent dosing regimen. In some examples, the first intermittent dosing regimen and the second intermittent dosing regimen may be administered by the same route (e.g. injections to the same location; tablets taken orally at the same time), or by a different route (e.g. a tablet taken orally while receiving an intravenous infusion).

In practicing any one of the methods disclosed herein, two or more intermittent dosing regimen of a PTPN2 inhibitor may be effective to achieve a therapeutically effective plasma concentration of the PTPN2 inhibitor in a subject for a duration of time that is substantially the same or longer than that achieved by administering an equivalent dose of the PTPN2 inhibitor once daily, thereby potentiating immunity of the subject or a cell of the subject (e.g., a lymphoid cell) without causing a side effect. In some cases, a therapeutically effective plasma concentration of a PTPN2 inhibitor may be at least about 1 nanomolar (nM), 2 nM, 3 nM, 4 nM, 5 nM, 6 nM, 7 nM, 8 nM, 9 nM, 10 nM, 20 nM, 30 nM, 40 nM, 50 nM, 60 nM, 70 nM, 80 nM, 90 nM, 100 nM, 200 nM, 300 nM, 400 nM, 500 nM, 600 nM, 700 nM, 800 nM, 900 nM, 1 micromolar (μM), 2 μM, 3 μM, 4 μM, 5 μM, 6 μM, 7 μM, 8 μM, 9 μM, 10 μM, or more for a duration of time. In some cases, a therapeutically effective plasma concentration of a PTPN2 inhibitor may be at most about 10 μM, 9 μM, 8 μM, 7 μM, 6 μM, 5 μM, 4 μM, 3 μM, 2 μM, 1 μM, 900 nM, 800 nM, 700 nM, 600 nM, 500 nM, 400 nM, 300 nM, 200 nM, 100 nM, 90 nM, 80 nM, 70 nM, 60 nM, 50 nM, 40 nM, 30 nM, 20 nM, 10 nM, 9 nM, 8 nM, 7 nM, 6 nM, 5 nM, 4 nM, 3 nM, 2 nM, 21 nM, or less for a duration of time. Such duration of time may be at least about 0.1 hour, 0.2 hour, 0.3 hour, 0.4 hour, 0.5 hour, 0.6 hour, 0.7 hour, 0.8 hour, 0.9 hour, 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, or longer.

Any one of the subject methods disclosed herein may further comprise administering a lymphoid cell to the subject sequentially (e.g., prior to or subsequent to) or concurrent with administering a PTPN2 inhibitor to the subject. The lymphoid cell may optionally comprise (i) the chimeric T-cell receptor sequence and/or (ii) the CAR sequence. When introduced sequentially, the PTPN2 inhibitor and the lymphoid cell may be administered by the same route (e.g. injections to the same location; tablets taken orally at the same time), or by a different route (e.g. a tablet taken orally while receiving an intravenous infusion). When introduced concurrently, the PTPN2 inhibitor and the cell may be, e.g., part of the same composition (e.g., the same condition media or a therapeutic regimen). As described elsewhere in the present disclosure, the subject being administered a PTPN2 inhibitor can retain, prior to the administration of the PTPN2 inhibitor, expression or activity of PTPN2 in the subject's cells, such as lymphoid cells (e.g., T cells, NK cells, HKGY cells, and B cells), cancer cells, or tumor cells.

In practicing any one of the methods disclosed herein, selecting the subject may be based on one or more thresholds of an expression or activity level of PTPN2 in the subject's cells, such as lymphoid cells including, without limitation, effector cells such as T cells, NK cells, HKGY cells, and B cells, cancer cells, or tumor cells. For example, the subject's lymphoid cells, cancer cells, or tumor cells exhibit a PTPN2 expression or activity level in his or her lymphoid cells, cancer cells, or tumor cells that is at least 30%, 40%, 50%, 60%, 70%, 80%, 90%, 95%, or more of that present in a control sample. In some examples, the PTPN2 mRNA level or cDNA level expressed in the subject's lymphoid cells, cancer cells, or tumor cells is at least 30%, 40%, 50%, 60%, 70%, 80%, 90%, 95%, or more of that present in a control sample. In some examples, the PTPN2 or PTPN2-associated cfDNA or cfRNA level from the subject's lymphoid cells, cancer cells, or tumor cells is at least 30%, 40%, 50%, 60%, 70%, 80%, 90%, 95%, or more of that present in a control sample. In some examples, the subject's lymphoid cells, cancer cells, or tumor cells carry two copies or least one copy of PTPN2 genomic DNA. In some examples, the PTPN2 polypeptide level expressed in the subject's lymphoid cells is at least 30%, 40%, 50%, 60%, 70%, 80%, 90%, 95%, or more of that present in a control sample. In some examples, the subject's lymphoid cells, cancer cells, or tumor cells exhibit a normal level of expression or activity of PTPN2 as compared to that of a control sample. In some cases, selecting the subject that exhibits expression or activity of PTPN2 results in a negative selection against subject that does not express or possess functional PTPN2 as PTPN2-null phenotype, such that the step of downregulating (e.g., transiently downregulating or permanently downregulating) expression or activity of PTPN2 will not be performed.

The control sample utilized in assessing the PTPN2 expression level can be a biological sample from a subject that does not exhibit a tumor or cancer, or from a subject that has not been diagnosed with a tumor or cancer and that has not been treated with a PTPN2 inhibitor. Such control sample can comprise PTPN2 polynucleotides or PTPN2 polypeptides from any of such subject's tissues or cells, including but not limited to such subject's lymphoid cells.

In some embodiments, downregulating (e.g., transiently downregulating or permanently downregulating) expression or activity of PTPN2 in the cell of the subject may be performed in vivo. In some cases, as described elsewhere in the present disclosure, the cell of the subject may be contacted by a PTPN2 inhibitor in vivo by administering the PTPN2 inhibitor to the subject comprising the cell. Administering a PTPN2 inhibitor to a subject disclosed herein can stimulate or prolong anti-tumor or anti-cancer immunity. In other embodiments, downregulating expression or activity of PTPN2 in the cell of the subject may be performed in vivo. In some cases, as described elsewhere in the present disclosure, the cell of the subject may be isolated from the subject and may be contacted by a PTPN2 inhibitor ex vivo, e.g., treated with a composition comprising the PTPN2 inhibitor.

In practicing any one of the methods disclosed herein, administering a cell (e.g., an autologous or allogeneic lymphoid cell that optionally expresses a TFP and/or a CAR) to the subject may be performed sequentially (e.g., prior to or subsequent to) or concurrent with downregulating (e.g., transiently downregulating or permanently downregulating) expression or activity of PTPN2 in the cell. In some embodiments, the downregulating may comprise introducing a PTPN2 inhibitor to the cell, as provided in the present disclosure (e.g., contacting the cell with a PTPN2 inhibitor, or inducing the cell to express a PTPN2 inhibitor). When performed sequentially, a PTPN2 inhibitor and the cell may be introduced to the subject by the same route (e.g. injections to the same location; tablets taken orally at the same time), or by a different route (e.g. a tablet taken orally while receiving an intravenous infusion). When performed concurrently, a PTPN2 inhibitor and the cell may be, e.g., part of the same composition (e.g., the same condition media or a therapeutic regimen).

In some embodiments, a cell (e.g., a lymphoid cell, a cancer or tumor cell, etc.) of the subject may not exhibit a genetic alteration (e.g., mutation) of (i) a first gene encoding PTPN2 or (ii) a second gene operatively linked to PTPN2, wherein the genetic alteration reduces (or substantially inhibits) the expression and/or activity of PTPN2. In some examples, the second gene may be a promoter operatively linked to PTPN2 or an intron operatively linked to a gene product of PTPN2. Genetic alterations can include a mutation in a polynucleotide (e.g., DNA or RNA) encoding PTPN2 gene product. The mutation can affect any portion of the PTPN2 gene. The one or more PTPN2 mutations can include a mutation in the protein. The one or more PTPN2 mutations can be a point mutation, an insertion, a deletion, an amplification, a translocation, an inversion, or loss of heterozygosity. In some embodiments, the mutation is a loss of function. In some embodiments, the loss of function yields a dominant negative mutation. A mutation can be a frameshift mutation. A frameshift mutation can disrupt the reading frame, resulting in a completely different translated protein as compared to the original sequence. The mutation can be a nonsense mutation. The nonsense mutation can result in a premature stop codon, thus encoding a truncated, and possibly nonfunctional protein product. The PTPN2 mutation can be a nonsense mutation, wherein a single nucleotide alteration causes an amino acid substitution in the translated protein. The mutation can cause an alteration in one or more domain of the PTPN2 protein. The mutation can reduce binding efficacy of a PTPN2 protein with a PTPN2 substrate such as INSR, EGFR, CSFIR, PDGFR, JAK1, JAK2, JAK3, Src family kinases, STAT1, STAT3, STAT6, FYN, LCK, variations thereof, or combinations thereof. The mutation can reduce the ability of PTPN2 to dephosphorylate any one of the substrates disclosed herein, or reduce the ability of PTPN2 to interact with its upstream, or a downstream signaling molecules.

A method of potentiating immunity of a subject may comprise administering a lymphoid cell to the subject sequentially (e.g., prior to or subsequent to) and/or concurrent with the downregulation with the PTPN2 inhibitor. In some embodiments, contacting the lymphoid cell with a PTPN2 inhibitor may be performed in vivo, e.g., via administration of the PTPN2 inhibitor to the subject. In some cases, the subject may already comprise the lymphoid cell when the PTPN2 inhibitor is administered to the subject. The lymphoid cell may be an endogenous cell of the subject. Alternatively, the lymphoid cell may be a heterologous lymphoid cell (e.g., an allogeneic cell from a donor or a xenograft cell). In other cases, the subject may not comprise the lymphoid cell when the PTPN2 inhibitor is administered to the subject. Instead, the contact between the PTPN2 inhibitor and the lymphoid cell may occur upon administration of the lymphoid cell to the subject subsequent to the administration of the PTPN2 inhibitor to the subject. In some embodiments, contacting the lymphoid cell with a PTPN2 inhibitor may be performed ex vivo, e.g., in an in vitro culture composition. The lymphoid cell of the subject may be subjected to ex vivo expansion (or cell proliferation) prior to, during, or subsequent to being contacted by the PTPN2 inhibitor. When the resulting lymphoid cell and/or a progeny thereof is administered to the subject, the lymphoid cell and/or the progeny thereof may be washed to be substantially free of the PTPN2 inhibitor. Alternatively, the lymphoid cell and/or the progeny may not or need not be washed to rid of any excess, used, or expressed PTPN2 inhibitor prior to the administration to the subject.

In some embodiments, the method may further comprise introducing to the lymphoid cell (i) a chimeric T-cell receptor sequence encoding a T-cell receptor fusion protein (TFP) and/or (ii) a chimeric antigen receptor (CAR) sequence encoding a CAR, wherein each of TFP and CAR exhibits specific binding to an antigen. In some cases, the contacting of the lymphoid cell by the PTPN2 inhibitor may be performed sequentially (e.g., prior to or subsequent to) or concurrent with the introducing to the lymphoid cell the chimeric T-cell receptor sequence and/or the CAR sequence. In some examples, the lymphoid cell may be contacted with a PTPN2 inhibitor prior to being conditioned to express the TFP and/or the CAR. In other examples, the lymphoid cell may be contacted with a PTPN2 inhibitor while being conditioned to express the TFP and/or the CAR. In different examples, the lymphoid cell may be configured to express the TFP and/or the CAR prior to being contacted with a PTPN2 inhibitor.

In some embodiments, the downregulation of the expression or activity of PTPN2 in the lymphoid cell of the subject may be permanent. In other embodiments, as disclosed herein, the downregulation of the expression or activity of PTPN2 in a cell (e.g., the lymphoid cell of the subject) may comprise transiently downregulating the expression or activity of PTPN2. In some cases, downregulating the expression or activity of PTPN2 in the lymphoid cell performed sequentially (e.g., prior to or subsequent to) or concurrent with the introducing to the lymphoid cell the chimeric T-cell receptor sequence and/or the CAR sequence. In some examples, the expression or activity of PTPN2 in the lymphoid cell may be downregulated (e.g., with a PTPN2 inhibitor) prior to being conditioned to express the TFP and/or the CAR. In other examples, the expression or activity of PTPN2 in the lymphoid cell may be downregulated (e.g., with a PTPN2 inhibitor) while being conditioned to express the TFP and/or the CAR. In different examples, the lymphoid cell may be configured to express the TFP and/or the CAR prior to downregulating the expression or activity of PTPN2 in the lymphoid cell (e.g., with a PTPN2 inhibitor).

In some embodiments, a CAR of the present disclosure contains a minimally required intracellular signaling domain capable of activating a signaling cascade (e.g., an immunoreceptor signaling cascade) of the cell (e.g., in a lymphoid cell) in comparison to a control cell that is (i) without the CAR and/or (ii) in absence of any CAR activation (e.g., in absence of any antigen of the antigen-binding domain of the CAR). A minimally required intracellular signaling domain of the CAR typically consists of a primary signaling domain and lacks a co-stimulatory signaling domain sequence or a functional co-stimulatory signaling domain, and hence exhibiting less potency in activating an immune signaling cascade as compared to one with the co-stimulatory signaling domain. In some examples, the CAR with a minimally required intracellular signaling domain is a first-generation CAR. In some examples, the first-generation CAR contains only a primary signaling domain selected from the group consisting of CD3zeta, CD28, 4-1BB, OX40, DAP10, ICOS, and a variant thereof. In some examples, the CAR with a minimally required intracellular signaling domain is a second-generation CAR. In some examples, the second-generation CAR contains only a primary signaling domain selected from the group consisting of CD3zeta, CD28, 4-1BB, OX40, DAP10, ICOS, and a variant thereof, and a co-stimulatory signaling domain that is a different member from the primary signaling domain. In some examples, a cell comprising the CAR with the minimally required intracellular signaling domain may induce a target activity of the cell of at least about 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, or more than that of a control cell. In some examples, a cell comprising the CAR with the minimally required intracellular signaling domain may induce a target activity of the cell of at most about 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, or 1% or less than that of a control sample comprising a CAR with a more potent intracellular signaling domain. The more potent intracellular signaling domain may comprise a different polypeptide sequence (e.g., a polypeptide fragment derived from a different intracellular protein than the minimally required intracellular signaling domain) or an additional polypeptide sequence (e.g., the minimally required intracellular signaling domain plus one or more additional intracellular signaling domains). The additional polypeptide sequence may comprise at least 1, 2, 3, 4, 5, or more different intracellular signaling domains. Without wishing to be bound by theory, use of a CAR with the minimally required intracellular signaling domain may help to lower toxicity of a cell (e.g., a lymphocyte) expressing the CAR and/or increase persistence of the cell in the body of the subject in need of such cell therapy. In some cases, the use of PTPN2 inhibitor in conjunction with CAR-T therapy obviates the need to use other CAR-T cell proliferation inhibitors to control the toxicities inherent in CAR-T therapy. Non-limiting CAR-T cell proliferation inhibitors are specific protein kinase inhibitors such as INSR, EGFR, CSFIR, PDGFR, JAK1, JAK2, JAK3, Src family kinases, STAT1, STAT3, STAT6, FYN, LCK, variations thereof, or combinations thereof. In some embodiments, the methods disclosed herein obviate the need to utilize Nintedanib, Dasatinib, Saracatinib, Ponatinib, Nilotinib, Danusertib, AT9283, Degrasyn, Bafetinib, KW-2449, NVP-BHG712, DCC-2036, GZD824, GNF-2, PD173955, GNF-5, Bosutinib, Gefitinib, Erlotinib, and/or Sunitinib in conjunction of a CAR-T therapy. Another advantage of using PTPN2 inhibitor in conjunction with CAR-T therapy is that the amount of CAR-T cells required to yield a comparable level of in vivo efficacy is reduced. In some cases, a subtherapeutic amount of CAR-T cells is infused into a subject in need thereof. For example, one, two, or three orders of magnitude less of CAR-T cells are needed for treating a subject in need thereof. Where desired, less than $5\times10^6$, $1\times10^6$, $5\times10^5$, $1\times10^5$, $5\times10^4$, $1\times10^4$ CAR-T cells are needed to yield a comparable level of therapeutic effect as compared to a CAR-T therapy without the use of a PTPN2 inhibitor.

In practicing any one of the methods disclosed herein, examples of the target activity of the cell may include, but are not limited to, cytokine secretion, gene expression, cell proliferation, cytotoxicity against a target cell, cell death, chemotaxis, cellular metabolism, and/or cell exhaustion.

In practicing any one of the methods disclosed herein, a cell to be administered (e.g., systemically administered) may retain expression or activity of PTPN2 prior to administering a PTPN2 inhibitor to the subject. In some examples, a PTPN2 inhibitor may be administered to the subject prior to the administration of the cell, and the cell may be administered and contacted by the PTPN2 inhibitor in vivo to affect downregulation (e.g., transient downregulation) of expression or activity of PTPN2 in the cell in vivo. In other examples, a PTPN2 inhibitor and the cell may be administered at the same time, e.g., in a same composition or in different compositions, and the cell may be contacted by the PTPN2 inhibitor ex vivo and/or in vivo to affect downregulation of expression or activity of PTPN2 in the cell. In different examples, a PTPN2 inhibitor may be administered to the subject subsequent to the administration of the cell to the subject, and the cell may be contacted by the PTPN2 inhibitor in vivo to affect downregulation of expression or activity of PTPN2 in the cell in vivo.

In practicing any of the methods disclosed herein, the PTPN2 inhibitor may be a compound disclosed herein, such as a compound of Formula (I), (I-1), (II), (II-1), (II-a), (II-a1), (III), (III-1), (IV), or (IV-1), or a pharmaceutically acceptable salt or solvate thereof.

In practicing any one of the methods disclosed herein, a therapeutic amount or an effective amount may be an amount of a composition or a pharmaceutical formulation (e.g., a cell, a PTPN2 inhibitor, etc.) that is sufficient to elicit a desired response in the subject upon a treatment or method of the present disclosure. In some embodiments, a sub-therapeutic amount of a composition or a pharmaceutical formulation may be an amount of the composition or pharmaceutical formulation that is a fragment of the therapeutic amount. In some examples, a sub-therapeutic amount of a cell (e.g., a cell expression the CAR) may comprise a cell number that is at most 95%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less than a cell number of a therapeutic amount. For example, one, two, or three orders of magnitude less of CAR-T cells that are normally required absent of the use of PTPN2 inhibitor are contemplated for administering into a subject in need thereof. Where desired, a sub-therapeutic amount of cells such as $5\times10^6$, $1\times10^6$, $5\times10^5$, $1\times10^5$, $5\times10^4$, or $1\times10^4$ CAR-T cells are needed to yield a comparable level of therapeutic effect as compared to a CAR-T therapy without the use of a PTPN2 inhibitor.

In some examples, a sub-therapeutic amount of a drug (e.g., a PTPN2 inhibitor) may comprise a dose of the drug that is at most 95%, 90%, 85%, 80%, 75%, 70%, 65%, 60%, 55%, 50%, 45%, 40%, 35%, 30%, 25%, 20%, 15%, 10%, 9%, 8%, 7%, 6%, 5%, 4%, 3%, 2%, 1%, or less than a dose of the drug of a therapeutic amount. Without wishing to be bound by theory, use of a sub-therapeutic amount (or dose) of a cell expressing the CAR may help to lower toxicity of such cell therapy and/or increase persistence of the cell in the body of the subject in need of such cell therapy.

In practicing any one of the methods disclosed herein, the immunity of a cell or a subject may be anti-tumor, anti-cancer activity, anti-viral infection activity, and/or anti-bacterial infection activity. In some embodiments, examples of a viral infection and bacterial infection may comprise human bacterial, human parasitic protozoan or human viral infections caused by microbial species including *Plasmodium, Pneumocystis*, herpes viruses (CMV, HSV 1, HSV 2, VZV, and the like), retroviruses, adenoviruses, and the like. In some examples, any one of the subject methods of the present disclosure may be used to treat or regulate HIV infections and related conditions such as tuberculosis, malaria, *Pneumocystis* pneumonia, CMV retinitis, AIDS, AIDS-related complex (ARC) and progressive generalized lymphadenopathy (PGL), and AIDS-related neurological conditions such as multiple sclerosis, and tropical spastic paraparesis. Other human retroviral infections that may be treated or regulated by any one of the subject methods of the present disclosure include Human T-cell Lymphotropic virus and HIV-2 infections.

In embodiments, when practicing any one of the methods disclosed herein, the PTPN2 inhibitor does not regulate site-specific recombination of a gene encoding PTPN2. In some examples, the gene encoding PTPN2 or a gene operatively linked to the gene encoding PTPN2 (e.g., a transcription factor, an intron sequence, etc.) may not be flanked by a recombinase site (e.g., Cre recombinase or Flp recombinase substrates). In some examples, the PTPN2 inhibitor may not be an activator of recombination of a recombinase site. In an example, the PTPN2 inhibitor may not be an estrogen antagonist.

In practicing any one of the methods disclosed herein, the PTPN2 expression or activity level can be determined by detecting the PTPN2 polynucleotides or PTPN2 polypeptides present in a cell or tissue. A wide variety of nucleic acid assays are available for detecting and/or quantifying PTPN2 polynucleotides, including PTPN2 DNAs and PTPN2 RNAs. Exemplary nucleic acid assays include but are not limited to genotyping assays and sequencing methods. Sequencing methods can include next-generation sequencing, targeted sequencing, exome sequencing, whole genome sequencing, massively parallel sequencing, and the like.

Additional methods for assessing levels and/or concentration of PTPN2 polynucleotides in a tissue or a cell may include, but are not limited to, microarray hybridization assay, nucleic acid amplification assays including without limitation polymerase chain reaction (PCR), quantitative PCR (qPCR), real-time PCR (RT-PCR), digital PCR, and in situ sequencing (US20190024144, US20140349294, incorporated hereby by reference). Nucleic acid amplification can be linear or non-linear (e.g., exponential). Amplification may comprise directed changes in temperature or may be isothermal. Conditions favorable to the amplification of target sequences by nucleic acid amplification assays are known in the art, can be optimized at a variety of steps in the process, and depend on characteristics of elements in the reaction, such as target type, target concentration, sequence length to be amplified, sequence of the target and/or one or more primers, primer length, primer concentration, polymerase used, reaction volume, ratio of one or more elements to one or more other elements, some or all of which can be altered. In situ hybridization (ISH), RNase protection assay, and the like assays can also be employed for detecting PTPN2 polynucleotides and the expression level.

In some embodiments, the copy number PTPN2 gene is assessed by a method selected from the group consisting of in situ hybridization (ISH), Southern blot, immunohistochemistry (IHC), polymerase chain reaction (PCR), quantitative PCR (qPCR), quantitative real-time PCR (qRT-PCR), comparative genomic hybridization (CGH), microarray-based comparative genomic hybridization, and ligase chain reaction (LCR). In some embodiments, the in situ hybridization is selected from fluorescence in situ hybridization (FISH), chromogenic in situ hybridization (CISH) and silver in situ hybridization (SISH). In some embodiments, the copy number is assessed using a nucleic acid sample from the subject, such as genomic DNA, cDNA, ctDNA, cell-free DNA, RNA or mRNA.

PTPN2 expression and/or activity level can also be assessed by detecting and/or quantifying PTPN2 polypeptide level in a subject's tissue or cell. A variety of techniques are available in the art for protein analysis. They include but are not limited to immunohistochemistry (IHC), radioimmunoassays, ELISA (enzyme linked immunosorbent assays), "sandwich" immunoassays, immunoradiometric assays, in situ immunoassays (using e.g., colloidal gold, enzyme or radioisotope labels), western blot analysis, immunoprecipitation assays, immunofluorescent assays, flow cytometry, confocal microscopy, enzymatic assays, surface plasmon resonance and PAGE-SDS. One or more of these protein assays utilizes antibodies or fragments thereof that exhibits specific binding to PTPN2 polypeptides. A large number of anti-PTPN2 antibodies are available, including those provided by Invitrogen, Santa Cruz Biotechnology, OriGene Technologies, MilliporeSigma, Bio-Rad, Abcam, and Cell Signaling Technology.

In practicing any one of the subject methods as provided herein, the PTPN2 expression or activity, e.g., in a tumor tissue, a cancer cell, or a lymphoid cell, can be determined using any biological sample comprising the target cells (e.g., plasma cells or cells from a tumor site under investigation) or constituents thereof (e.g., constituents such as cfDNA from the plasma or the tumor site). The biological sample may be a solid or liquid biological sample from the subject under investigation or treatment. The biological sample may be a biopsy sample that is fixed, paraffin-embedded, fresh, or frozen. The biological sample may be obtained by any suitable means, including but not limited to needle aspiration, fine needle aspiration, core needle biopsy, vacuum assisted biopsy, large core biopsy, incisional biopsy, excisional biopsy, punch biopsy, shave biopsy, skin biopsy, and venipuncture.

The biological sample can be obtained from, without limitation, skin, heart, lung, kidney, bone marrow, breast, pancreas, liver, muscle, smooth muscle, bladder, gall bladder, colon, intestine, brain, prostate, esophagus, thyroid, serum, saliva, urine, gastric and digestive fluid, tears, stool, semen, vaginal fluid, interstitial fluids derived from tumorous tissue, ocular fluids, sweat, mucus, earwax, oil, glandular secretions, spinal fluid, hair, fingernails, plasma, nasal swab or nasopharyngeal wash, spinal fluid, cerebral spinal fluid, tissue, throat swab, biopsy, placental fluid, amniotic fluid, cord blood, emphatic fluids, cavity fluids, sputum, pus, microbiota, meconium, breast milk, and/or other excretions or body tissues of the subject. In some embodiments, a selection of the biological sample may depend on the condition of the subject to be treated.

In some embodiments, a biological sample comprises cell-free DNA (cfDNA) derived from a whole blood or plasma of the subject. A sample may be analyzed directly for its contents or may be processed to purify one or more of its contents for analysis. Methods of direct analysis of samples are known in the art and include, without limitation, mass spectrometry and histological staining procedures. In some embodiments, one or more components are purified from the sample for the detection of PTPN2 expression level or activity level. In some embodiments, the purified component of the biological sample is protein (e.g. total protein, cytoplasmic protein, or membrane protein). In some embodiments, the purified component of the sample is a nucleic acid, such as DNA (e.g. genomic DNA, cDNA, ctDNA, or cfDNA) or RNA (e.g. total RNA or mRNA).

In some embodiments, as abovementioned, the cell may be contacted by a PTPN2 inhibitor in vivo by administering the PTPN2 inhibitor to the subject comprising the cell. Administering a PTPN2 inhibitor to a subject disclosed herein can stimulate or prolong anti-tumor or anti-cancer immunity. Not wishing to be bound by any particular theory, a PTPN2 inhibitor reduces PTPN2 activity in a cell, leading to an augmented immunoreceptor signaling pathways, which in turn results in the activation of adaptive immunity against tumor or cancer cells.

Stimulation of anti-tumor or anti-cancer immunity can be established by any readout known in the art including without limitation: lymphoid cell proliferation (including proliferation of T cells such as CD4+ and/or CD8+ T cells, and clonal expansion other lymphoid cells), cytokine secretion, activation of effector function of lymphoid cells, reduction in T cell exhaustion, destabilization of regulatory T cells (Tregs) and/or their function, movement and/or trafficking of lymphoid cells, release of other intracellular signaling molecules, and phosphorylation of intracellular signaling molecules.

In some embodiments, anti-tumor immunity encompasses proliferation of the lymphoid cells including clonal expansion of the lymphoid cells that are capable of directly or indirectly mediating anti-tumor activity. Non-limiting examples of anti-tumor lymphoid cells are CD4+ and/or CD8+ T cells, NK cells, tumor infiltrating lymphocytes (TIL), especially those T cells capable of specific binding to one or more tumor antigens. Proliferation of the lymphoid cell can lead to a phenotypic change of the lymphoid cell. Treatment of a PTPN2 inhibitor can stimulate or prolong lymphoid cell proliferation by about 1 fold, about 2 to about 5 fold, about 5 to about 10 fold, about 10 fold to about 50 fold, about 50 fold to about 100 fold or higher. Assessing lymphoid cell proliferation can be performed by a wide variety of assays known in the art, including without limitation, the use of cell staining, microscopy, flow cytometry, cell sorting, and combinations of these. A number of commercial kits for assessing various types of T cell or B cell proliferations are also suitable to assess the effect of PTPN2 inhibitor on T cell or B cell proliferation (e.g., IncuCyte, CellTRrace Cell Proliferation Kits marketed by ThermoFisher). Proliferation can also be determined by phenotypic analysis of the lymphoid cells. For example, clumping of lymphoid cells in culture can signify proliferation of lymphoid cells as compared to comparable lymphoid cells without the treatment with a PTPN2 inhibitor.

In some embodiments, anti-tumor immunity stimulated or prolonged in response to a PTPN2 inhibitor is evidenced by cytokine release from the lymphoid cells. Cytokine release by the lymphoid cell can comprise the release of IFNγ, TNFα, CSF, TGFβ, IL-1, IL-2, IL-4, IL-5, IL-6, IL-13, IL-17, IL-21, IL-22, granzyme, and the like. Lymphoid cells can generate about 1 fold, 2 fold, 3 fold, 4 fold, 5 fold, 6 fold, 7 fold, 8 fold, 9 fold, 10 fold, 50 fold, 100 fold or greater cytokine release in response to a PTPN2 inhibitor treatment as compared to comparable lymphoid cells that are not being exposed to the PTPN2 inhibitor. Cytokine release may be determined and quantified using any immunoassays such as western blot, ELISA, flow cytometry, and the like.

In some embodiments, stimulated or prolonged anti-tumor immunity is evidenced by T cell activation. T cell activation can involve differential expression of antigen specific TCRs, certain cell surface markers and induction of cell proliferation signals. T cell activation may also involve stimulating its effector function including cytolytic activity against tumor or cancer cells, or helper activity including releasing cytokines. In some examples, T cells can be used to kill a tumor or cancer cell in vivo or in vitro in the presence of a PTPN2 inhibitor. Cell killing can be mediated by the release of one or more cytotoxic cytokines, for example IFNγ or granzyme, by the T cells. In some cases, a subject method can stimulate or prolong the (i) release of cytotoxins such as perforin, granzymes, and granulysin and/or (ii) induction of apoptosis via e.g., Fas-Fas ligand interaction between the T cells and a tumor or cancer cell, thereby triggering the destruction of the target cell. Cytotoxicity can be detected by staining, microscopy, flow cytometry, cell sorting, ELISPOT, chromium release cytotoxicity assay, and other cell death assays described in WO2011131472A1, which is incorporated herein by reference.

Cytotoxicity of a lymphoid cell can be greater in response to treating with a PTPN2 inhibitor as compared to a comparable lymphoid cell lacking such treatment. A lymphoid cell treated with a PTPN2 inhibitor can be about 5%, 10%, 15%, 20%, 25%, 30%, 35%, 40%, 45%, 50%, 55%, 60%, 65%, 70%, 75%, 80%, 85%, 90%, 95%, 100%, 500% or more cytotoxic against tumor or cancer cells as compared to a comparable lymphoid cell lacking the treatment. In some embodiments, a change in cytotoxicity can comprise comparing such activity before and after treating the lymphoid cell with a PTPN2 inhibitor.

In some examples, a reduction in expression or activity of such markers including PD1, Foxp3, or FoxO3a is indicative of Treg destabilization, and hence an enhanced anti-tumor immunity. In addition, Treg destabilization, as reflected by a decreased T cell exhaustion, can be demonstrated by an enhanced cytokine release, e.g., release of IL-2, IFNγ, TNF and other chemokines.

Anti-tumor immunity can also be evidenced by movement and/or trafficking of the lymphoid cells in response to a treatment with a PTPN2 inhibitor. In some embodiments, movement can be determined by quantifying localization of the lymphoid cell to a target site such as a tumor tissue. For example, lymphoid cells can be quantified at the target before or after administration of a PTPN2 inhibitor. Quantification can be performed by isolating a lesion and quantifying a number of lymphoid cells, for example tumor infiltrating lymphocytes. Movement and/or trafficking of lymphoid cells in a tumor tissue after administering a PTPN2 inhibitor can be greater than that of a control lacking the administration of a PTPN2 inhibitor. In some embodiments, the number of lymphoid cells accumulated at the tumor tissue of interest can be about 1 fold, 5 fold, 10 fold, 15 fold, 50 fold, 100 fold or greater than that of a control not being treated with a PTPN2 inhibitor. Trafficking can also be determined in vitro utilizing a transwell migration assay. In some embodiments, the number of lymphoid cells administered with a PTPN2 inhibitor exhibits about 1 fold, 5 fold, 10 fold, 15 fold, 50 fold, 100 fold or greater as compared to that of control lymphoid cells not being administered with a PTPN2 inhibitor.

Stimulating and/or prolonging anti-tumor immunity in a subject can also be assessed by one or more (in any combination) of the foregoing results, although alternative or additional results of the referenced tests and/or other tests can evidence such desired outcome. In some embodiments, anti-tumor immunity is considered stimulated if there exists at least about 10%, 20%, 30%, 40%, 50%, 60%, 70%, 75%, 80%, 90%, 95%, 100%, 110%, 120%, 150%, 200%, 300%, 400%, 500%, 600%, 700%, 1000%, 10000% or more improvement, using an appropriate measure (e.g. tumor size reduction, duration of tumor size stability, duration of time free from metastatic events, duration of disease-free survival). Improved immunity may also be expressed as fold improvement, such as at least about 2-fold, 3-fold, 4-fold, 5-fold, 6-fold, 7-fold, 8-fold, 9-fold, 10-fold, 20-fold, 30-fold, 40-fold, 50-fold, 60-fold, 70-fold, 80-fold, 90-fold, 100-fold, 1000-fold, 10000-fold, or more, using an appropriate measure (e.g. tumor size reduction, duration of tumor size stability, duration of time free from metastatic events, duration of disease-free survival).

A number of secondary parameters can be employed to determine stimulated and/or prolonged anti-tumor immunity. Examples of secondary parameters include, but are not limited to, the lack of new tumors, a reduction of circulating tumor antigens or markers (e.g., CEA, PSA, CA-125, or cfDNA, ctDNA), the lack of detectable cancer cell or tumor marker by way of biopsy, surgical downstaging (i.e., conversion of the surgical stage of a tumor from unresectable to resectable), MRI, ultrasound, PET scans and any other detection means, all of which can point to the overall immunity to tumor or cancer in a subject. Examples of tumor markers and tumor-associated antigens that can be evaluated as indicators of improved immunity include, but are not limited to, carcinembryonic antigen (CEA) prostate-specific antigen (PSA), CA-125, CA19-9, ganglioside molecules (e.g., GM2, GD2, and GD3), MART-1, heat shock proteins (e.g., gp96), sialyl Tn (STn), tyrosinase, MUC-1, HER-2/neu, c-erb-B2, KSA, PSMA, p53, RAS, EGF-R, VEGF, MAGE, gp100, Ki-67, STK15, Survivin, Cyclin B1, Stromelysin, Cathepsin L2, 3MYBL2, and any ctDNA known in the art. BMC Med. 16:166, 2018.

In some embodiments, prolonged immunity is evidenced by tumor being stabilized (e.g., one or more tumors do not increase more than 1%, 5%, 10%, 15%, or 20% in size, and/or do not metastasize) as a result of treatment with a PTPN2 inhibitor. In some embodiments, a tumor is stabilized for at least about 1, 2, 3, 4, 5, 6, 7, 8, 9, 10, 11, 12, or more weeks. In some embodiments, a tumor is stabilized for at least about 1, 2, 3, 4, 5, 6, 7, 8, 9, 10, 11, 12, or more months. In some embodiments, a tumor is stabilized for at least about 1, 2, 3, 4, 5, 6, 7, 8, 9, 10, or more years. In some embodiments, the size of a tumor or the number of tumor cells is reduced by at least about 5%, 10%, 15%, 20%, 25, 30%, 35%, 40%, 45%, 50%, 55%, 60%, 65%, 70%, 75%, 80%, 85%, 90%, 95%, or more. In some embodiments, the tumor is completely eliminated, or reduced below a level of detection. In some embodiments, a subject remains tumor free (e.g. in remission) for at least about 1, 2, 3, 4, 5, 6, 7, 8, 9, 10, 11, 12, or more weeks following treatment. In some embodiments, a subject remains tumor free for at least about 1, 2, 3, 4, 5, 6, 7, 8, 9, 10, 11, 12, or more months following treatment. In some embodiments, a subject remains tumor free for at least about 1, 2, 3, 4, 5, 6, 7, 8, 9, 10, or more years after treatment.

The methods disclosed herein can be applied to treat, stimulate and/or or prolong immunity against a wide variety of cancers, including both solid tumor hematological cancers. For example, the subject methods can be applied to: Acute Lymphoblastic Leukemia (ALL), Acute Myeloid Leukemia (AML), Adrenocortical Carcinoma, Childhood Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Appendix Cancer, Astrocytomas, Childhood (Brain Cancer), Atypical Teratoid/Rhabdoid Tumor, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma-see Non-Hodgkin Lymphoma, Carcinoid Tumor (Gastrointestinal), Childhood Carcinoid Tumors, Cardiac (Heart) Tumors, Atypical Teratoid/Rhabdoid Tumor, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma (Mycosis Fungoides and Sézary Syndrome), Ductal Carcinoma In Situ (DCIS), Embryonal Tumors, Endometrial Cancer (Uterine Cancer), Ependymoma, Esophageal Cancer, Esthesioneuroblastoma (Head and Neck Cancer), Ewing Sarcoma (Bone Cancer), Extracranial Germ Cell Tumor, Extragonadal Germ Cell Tumor, Eye Cancer, Childhood Intraocular Melanoma, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Langerhans Cell Hodgkin Lymphoma, Hypopharyngeal Cancer (Head and Neck Cancer), Islet Cell Tumors, Pancreatic Neuroendocrine Tumors, Kaposi Sarcoma (Soft Tissue Sarcoma), Kidney (Renal Cell) Cancer, Laryngeal Cancer (Head and Neck Cancer), Leukemia, Lip and Oral Cavity Cancer (Head and Neck Cancer), Liver Cancer, Lung Cancer (e.g., Non-Small Cell and Small Cell), Lymphoma, Male Breast Cancer, Malignant Fibrous Histiocytoma of Bone and Osteosarcoma, Melanoma, Merkel Cell Carcinoma (Skin Cancer), Mesothelioma, Malignant, Metastatic Cancer, Metastatic Squamous Neck Cancer with Occult Primary (Head and Neck Cancer), Midline Tract Carcinoma, Mouth Cancer (Head and Neck Cancer), Multiple Endocrine Neoplasia, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, CML, Myeloid Leukemia, Acute (AML), Myeloproliferative Neoplasms, Chronic, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Osteosarcoma and Malignant Fibrous Histiocytoma of Bone, Ovarian Cancer, Pancreatic Cancer, Pancreatic Neuroendocrine Tumors (Islet Cell Tumors), Papillomatosis (Childhood Laryngeal), Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Rectal Cancer, Retinoblastoma, Rhabdomyosarcoma, Salivary Gland Cancer (Head and Neck Cancer), Sarcoma, Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Soft Tissue Sarcoma, Uterine Sarcoma, Sezary Syndrome (Lymphoma), Skin Cancer, Childhood Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, T-Cell Lymphoma, Cutaneous, Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter (Kidney (Renal Cell) Cancer), Ureter and Renal Pelvis, Transitional Cell Cancer (Kidney (Renal Cell) Cancer, Urethral Cancer, Uterine Cancer, Endometrial, Uterine Sarcoma, Vaginal Cancer, Vascular Tumors (Soft Tissue Sarcoma), Vulvar Cancer, and Wilms Tumor and Other Childhood Kidney Tumors, and any of the aforementioned cancers exhibiting expression and/or activity of PTPN2 in the cancer cells.

Certain embodiments contemplate a human subject that has been diagnosed with a cancer, such as one in which PTPN2 expression or activity is detectable (e.g., aberrantly low, normal, or high) in the cancer cells or tumor tissue. Certain other embodiments contemplate a non-human subject, for example a non-human primate such as a macaque, chimpanzee, gorilla, vervet, orangutan, baboon or other non-human primate, including such non-human subjects that can be known to the art as preclinical models, the tumor tissue or cancer cells of which exhibit expression and/or activity of PTPN2. Certain other embodiments contemplate a non-human subject that is a mammal, for example, a mouse, rat, rabbit, pig, sheep, horse, bovine, goat, gerbil, hamster, guinea pig or other mammal. There are also contemplated other embodiments in which the subject or biological source can be a non-mammalian vertebrate, for example, another higher vertebrate, or an avian, amphibian or reptilian species, or another subject or biological source. In certain embodiments of the present disclosure, a transgenic animal is utilized. A transgenic animal is a non-human animal in which one or more of the cells of the animal include a nucleic acid that is non-endogenous (i.e., heterologous) and is present as an extrachromosomal element in a portion of its cell or stably integrated into its germ line DNA (i.e., in the genomic sequence of most or all of its cells).

Where desired, the subject can be screened for the presence of expression or activity of PTPN2 in the subject's tumor or cancer cells. The subject can also be screened for the retention of PTPN2 expression and/or activity in one or more types of subject's lymphoid cells. Screening for the presence or the absence of expression or activity of PTPN2 can be carried out by analyzing the PTPN2 polynucleotide or PTPN2 polypeptide with any of the nucleic acid or protein assays disclosed herein. One or more of the screening steps can be performed concurrent with, subsequent to, or more likely, prior to administering a PTPN2 inhibitor to the subject.

In some embodiments, one or more steps in the screening, assessment or reporting of the PTPN2 expression and/or activity level is performed with the aid of a processor, such as with a computer system executing instructions contained in computer-readable media. In one aspect, the disclosure provides a system for assessing the PTPN2 expression or activity level in a subject's tumor tissue, cancer cells, and/or the subject's lymphoid cells. In some embodiments, the system comprises (a) a memory unit configured to store information concerning PTPN2 expression and/or activity level present in a tumor tissue/cancer cell, and/or lymphoid cell from the subject being investigated; and (b) one or more processors alone or in combination programmed to (1) assess the PTPN2 expression or activity in the subject's tumor tissue/cancer cell, and/or the PTPN2 expression or activity level in at least one type of subject's lymphoid cells; and (2) assessing the likelihood of a therapeutic beneficial response to treatment with a PTPN2 inhibitor based on the presence of the PTPN2 expression or activity in the tumor tissue/cancer cells, and/or the PTPN2 expression or activity in the subject's lymphoid cells.

In some embodiments, a processor or computational algorithm may aid in the assessment of a likelihood of a subject exhibiting a therapeutic benefit to treatment with a PTPN2 inhibitor. For example, one or more steps of methods or systems described herein may be implemented in hardware, software, firmware where desirable. When implemented in hardware, some or all of the blocks, operations, techniques, etc. may be implemented in, for example, a custom integrated circuit (IC), an application specific integrated circuit (ASIC), a field programmable logic array (FPGA), a programmable logic array (PLA), etc. A computer system may be involved in one or more of sample collection, sample processing, data analysis, expression profile assessment, calculation of weighted probabilities, calculation of baseline probabilities, comparison of a weighted probability to a reference level and/or control sample, determination of a subject's absolute or increased probability, generating a report, and reporting results to a receiver.

In some embodiments, provided herein is a computer readable medium encoded with computer executable software that includes instructions for a computer to execute functions associated with the identified biomarkers such as PTPN2. Such computer system may include any combination of such codes or computer executable software, depending upon the types of evaluations desired to be completed. The system can have code for calculating a weighted probability of PTPN2 inhibitor responsiveness based on the expression and/or activity level present in a subject's tumor tissue or cancer cells, as well as that present in the subject's lymphoid cells.

In a further embodiment, the present disclosure provides a method of treating a cancer, comprising administering an effective amount of a PTPN2 inhibitor. The PTPN2 inhibitor may be effective in one or more of: stimulating and/or prolonging anti-tumor immunity (e.g., destabilizing Tregs, augmenting CD4+ and CD8+ T cell function), inhibiting proliferation of cancer cells, inhibiting invasion or metastasis of cancer cells, killing cancer cells, increasing the sensitivity of cancer cells to treatment with a second anti-tumor agent, and reducing severity or incidence of symptoms associated with the presence of cancer cells. In some embodiments, said method comprises administering to the cancer cells a therapeutically effective amount of a PTPN2 inhibitor in vivo. In some embodiments, the administration first takes place ex vivo to a population of effector cells, followed by infusing the PTPN2-inhibitor treated effector cells into the subject as further detailed below.

The present disclosure also provides a cell (including a population of cells, such as a population of lymphoid cells) modified to express an exogenous sequence, and wherein expression and/or activity of PTPN2 in said cell has been inhibited (including reduction and elimination). In one aspect, provided in the disclosure is a lymphoid cell in which the expression and/or function of PTPN2 in said cell is inhibited. Such inhibition can be transient or permanent, occurring in vitro, ex vivo, or in vitro. In some cases, as used herein, inhibiting expression and/or function of a target molecule may be referred to downregulation of expression and/or function of the target molecule. A modified lymphoid cell of the present disclosure can be further characterized in that it comprises: (a) a chimeric T-cell receptor sequence encoding a T-cell receptor fusion protein (TFP), and/or (b) a chimeric antigen receptor (CAR) sequence encoding a CAR, wherein each of TFP and CAR exhibits specific binding to an antigen, including but not limited to a tumor or tumor-associated antigen.

Not wishing to be bound by any particular theory, inhibiting PTPN2 expression and/or activity of such lymphoid cell can lead to an augmented immunoreceptor signaling, which in turn results in the activation of an adaptive immunity against tumor or cancer cells. When its PTPN2 expression or activity is inhibited, the modified lymphoid cells can exhibit enhanced cell proliferation (including proliferation of T cells such as CD4+ and/or CD8+ T cells, and clonal expansion other lymphoid cells), enhanced cell activity (including e.g., cytokine secretion, activation of effector function, trafficking to tumor site or cancer cell), or enhanced disability (e.g., reduction in T cell exhaustion, destabilization of regulatory T cells (Tregs) in terms of cell number and cellular function).

In practicing any one of the methods disclosed herein, a subject cell (e.g., a modified cell such as a modified lymphoid cell) may comprise an enhancer moiety capable of enhancing one or more activities of the cell. In some embodiments, an enhancer moiety suitable for incorporating into a subject cell (e.g., a modified lymphoid cell) can be cytokines and growth factors capable of stimulating the growth, clonal expansion, and/or enhancing persistence of the immune cell in vivo. An enhancer may be intracellular, membrane-bound (e.g., a receptor or an adaptor protein of a receptor) or secreted by the cell. Encompassed are enhancer moieties selected from the group consisting of IL-2, IL-3, IL-4, IL-6, IL-7, IL-10, IL-11, IL-12, IL-15, IL-17, IL-18, IL-21, IL-23, PD-1, PD-L1, CD122, CSFIR, CTAL-4, TIM-3, TGFR beta, receptors for the same, functional fragments thereof, functional variants thereof, and combinations thereof. An enhancer moiety may be expressed from an endogenous gene of the cell. Alternatively, or in addition to, an enhancer moiety may be expressed from a heterologous gene introduced to the cell. Such heterologous gene may be chromosomal (e.g., in the nuclear chromosome or mitochondrial chromosome) or epichromosomal. In some examples, a cell (e.g., a modified immune cell configured to express a TFP and/or a CAR) may be engineered such that one or more enhancer moieties are constitutively expressed and/or activated. In other examples, the one or more enhancer moieties may be transiently expressed for a limited time. In different examples, the one or more enhancer moieties may be conditionally expressed under, e.g., activation of a cellular signaling.

In practicing any one of the methods disclosed herein, a subject cell (e.g., a modified cell such as a modified lymphoid cell) may comprise an inducible cell death moiety, which inducible cell death moiety effects cell death (e.g., suicide) of the cell upon contact with a cell death activator. Where desired, an inducible cell death moiety is selected from the group consisting of: caspase-1 ICE, caspase-3 YAMA, inducible Caspase 9 (iCasp9), AP1903, HSV-TK, CD19, RQR8, tBID, CD20, truncated EGFR, Fas, FKBP12, CID-binding domain (CBD), and any combination thereof. Examples of further suicide systems include those described by Jones et al. (Jones B S, Lamb L S, Goldman F and Di Stasi A (2014) Improving the safety of cell therapy products by suicide gene transfer. Front. Pharmacol. 5:254. doi: 10.3389/fphar.2014.00254), which is incorporated herein by reference in its entirety. Where desired, a suitable inducible cell death moiety can be HSV-TK, and the cell death activator is GCV. Where further desired, a suitable inducible cell death moiety can be iCasp9, and the cell death activator is AP1903.

A TFP comprised in the subject lymphoid cell typically comprises a TCR subunit comprising (1) a TCR extracellular domain capable of specific binding to an antigen domain, and (2) an intracellular signaling domain. Upon expression of the TFP, it forms a T cell receptor (TCR) complex. In some embodiments, the TCR extracellular domain comprises (1) an antigen binding domain capable of specific binding to the antigen, and (2) an extracellular domain or portion thereof of a protein including, e.g., the alpha, beta or zeta chain of the T-cell receptor, or CD3 epsilon, CD3 gamma, or CD3 delta, or in alternative embodiments, CD28, CD45, CD4, CD5, CD8, CD9, CD16, CD22, CD33, CD37, CD64, CD80, CD86, CD134, CD137, CD154. In general, the antigen binding domain and the extracellular domain are operatively linked together, e.g., in the same reading frame.

In some embodiments, a subject CAR comprises an antigen-binding domain and an intracellular signaling domain. In some examples, the antigen-binding domain and the intracellular signaling domain of the CAR are linked via a transmembrane domain.

Antigen Binding Domain of TFP or CAR

The antigen binding domain of a TFP or CAR disclosed herein typically comprises an antigen-specific binding element, the choice of which depends upon the type and number of antigens of interest. For example, the antigen binding domain may be chosen to recognize a cell surface marker on a target cell associated with a particular disease state. Non-limiting examples of cell surface markers include those associated with a tumor or cancer, with viral, bacterial and parasitic infections, autoimmune disease, inflammation diseases and metabolic disease. Cell surface markers can include, without limitation, carbohydrates, glycolipids, glycoproteins; CD (cluster of differentiation) antigens present on cells of a hematopoietic lineage (e.g., CD2, CD4, CD8, CD21, etc.), γ-glutamyltranspeptidase, an adhesion protein (e.g., ICAM-1, ICAM-2, ELAM-1, VCAM-1), hormone, growth factor, cytokine, and other ligand receptors, ion channels, and the membrane-bound form of an immunoglobulin u chain.

Of particular interest are biological markers associated with a tumor or cancer or a stage or state of a cancer. A vast variety of disease-related biological markers have been identified, and the corresponding targeting moieties have been generated, including but not limited to cancer antigen- 50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis (a) antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, and NCAM.

In some examples, the antigen binding domain of the subject TCR specifically binds to CD19. A large number of exemplary anti-CD19 antigen binding domains and constructs thereof are described in U.S. Pat. Nos. 8,399,645; 7,446,190; WO2012/079000; WO2014/031687; U.S. Pat. No. 7,446,190; each of which is herein incorporated by reference in its entirety. In some other examples, the antigen binding domain of the subject TCR specifically binds to BCMA. Exemplary anti-BCMA antigen binding domains and constructs thereof are described in e.g., WO2012163805, WO200112812, and WO2003062401, WO2016/014565, WO2014/122144, WO2016/014789, WO2014/089335, WO2014/140248, each of which is hereby incorporated by reference in its entirety. In some other examples, the antigen binding domain of the subject TCR specifically binds to CD123. Exemplary anti-CD123 antigen binding domains and constructs thereof are described in e.g., WO2014/130635, WO2016/028896, WO2008/127735, WO2014/138805, WO2014/138819, WO2013/173820, WO2014/144622, WO2001/66139, WO2010/126066, WO2014/144622, and US2009/0252742, each of which is incorporated herein by reference in its entirety. In yet some other examples, the antigen binding domain of the subject TCR specifically binds to CD38. Exemplary anti-CD38 antigen binding domains are embodied in daratumumab (described in e.g., Groen et al., Blood 116 (21): 1261-1262 (2010); MOR202 (see, e.g., U.S. Pat. No. 8,263,746); or antibodies described in U.S. Pat. No. 8,362,211.

In some other examples, the antigen binding domain of the subject TCR specifically binds to Tn antigen. Exemplary anti-Tn antigen binding domains and constructs thereof are described in e.g., US 2014/0178365, U.S. Pat. No. 8,440, 798, Brooks et al., PNAS 107 (22): 10056-10061 (2010), and Stone et al., OncoImmunology 1 (6): 863-873 (2012). In yet some other examples, the antigen binding domain of the subject TCR specifically binds to CS-1. Exemplary anti-CS-1 antigen binding domains and constructs thereof are described in Elotuzumab (BMS), see e.g., Tai et al., 2008, Blood 112 (4): 1329-37; Tai et al., 2007, Blood. 110 (5): 1656-63. In yet some other examples, the antigen binding domain of the subject TCR specifically binds to mesothelin. Exemplary anti-mesothelin antigen binding domain are described in, e.g., WO2015/090230, WO1997/025068, WO1999/028471, WO2005/014652, WO2006/099141, WO2009/045957, WO2009/068204, WO2013/142034, WO2013/040557, WO2013/063419, each of which is incorporated by reference in its entirety. In yet some other examples, the antigen binding domain of the subject TCR specifically binds to CD22. Exemplary anti-CD22 antigen binding domains are described in Haso et al., Blood, 121 (7): 1165-1174 (2013); Wayne et al., Clin Cancer Res 16 (6): 1894-1903 (2010), each of which is incorporated herein by reference. In yet some other examples, the antigen binding domain of the subject TCR specifically binds to CLL-1. Exemplary anti-CLL-1 antigen binding domains are described in WO2016/014535, incorporated herein by reference.

In yet some other examples, the antigen binding domain of the subject TCR specifically binds to CD33. Exemplary anti-CD33 antigen binding domains are described in WO2016/014576 and WO2016/014576, each of which is incorporated by reference in its entirety. In yet some other examples, the antigen binding domain of the subject TCR specifically binds to GD2. Exemplary anti-GD2 antigen binding domains are described in WO2012033885, WO2013040371, WO2013192294, WO2013061273, WO2013123061, WO2013074916, WO201385552, WO 2011160119, and US20100150910, each of which is incorporated by reference in its entirety. In yet some other examples, the antigen binding domain of the subject TCR specifically binds to PSMA. Exemplary anti-PSMA antigen binding domains are described in US20110268656 (J591 ScFv); WO 2006125481 (mAbs 3/A12, 3/E7 and 3/F11) and single chain antibody fragments (scFv A5 and D7), each of which is incorporated by reference in its entirety. In yet some other examples, the antigen binding domain of the subject TCR specifically binds to FLT3. Exemplary anti-FLT3 antigen binding domains are described in e.g., WO2011076922, U.S. Pat. No. 5,777,084, EP0754230, US20090297529, and several commercial catalog antibodies (R&D, ebiosciences, Abcam), each of which is incorporated by reference in its entirety. In yet some other examples, the antigen binding domain of the subject TCR specifically binds to ROR1. Exemplary anti-ROR1 antigen binding domains are described in WO 2011159847, US20130101607, each of which is incorporated by reference in its entirety. In yet some other examples, the antigen binding domain of the subject TCR specifically binds to TAG72. Exemplary anti-TAG72 antigen binding domains are described in Hombach et al., Gastroenterology 113 (4): 1163-1170 (1997); and Abcam ab691.

In yet some other examples, the antigen binding domain of the subject TCR specifically binds to FAP. Exemplary anti-FAP antigen binding domains are described in US 2009/0304718, incorporated herein by reference. In yet some other examples, the antigen binding domain of the subject TCR specifically binds to CD44v6. Exemplary anti-CD44v6 antigen binding domains are described in Casucci et al., Blood 122 (20): 3461-3472 (2013). In yet some other examples, an antigen binding domain against CEA is an antigen binding portion, e.g., CDRs, of an antibody described in, e.g., Chmielewski et al., Gastoenterology 143 (4): 1095-1107 (2012). In yet some other examples, an antigen binding domain against EPCAM is an antigen binding portion, e.g., CDRS, of an antibody selected from MT110, EpCAM-CD3 bispecific Ab (see, e.g., clinicaltrials.gov/ct2/show/NCT00635596); Edrecolomab; 3622W94; ING-1; and adecatumumab (MT201). In yet some other examples, an antigen binding domain against PRSS21 is an antigen binding portion, e.g., CDRs, of an antibody described in U.S. Pat. No. 8,080,650. In yet some other examples, an antigen binding domain against IL-13Ra2 is an antigen binding portion, e.g., CDRs, of an antibody described in, e.g., WO2008/146911, WO2004087758, several commercial catalog antibodies, and WO2004087758. In yet some other examples, an antigen binding domain against B7H3 is an antigen binding portion, e.g., CDRs, of an antibody MGA271 (Macrogenics). In yet some other examples, an antigen binding domain against KIT is an antigen binding portion, e.g., CDRs, of an antibody described in, e.g., U.S. Pat. No. 7,915,391, US20120288506, and several commercial catalog antibodies. In yet some other examples, an antigen binding domain against CD30 is an antigen binding portion, e.g., CDRs, of an antibody described in, e.g., U.S. Pat. No. 7,090,843 B1, and EP0805871. In yet some other examples, an anti gen binding domain against GD3 is an antigen binding portion, e.g., CDRs, of an antibody described in, e.g., U.S. Pat. Nos. 7,253,263; 8,207,308; US20120276046; EP1013761; WO2005035577; and U.S. Pat. No. 6,437,098. In yet some other examples, an antigen binding domain against CD171 is an antigen binding portion, e.g., CDRs, of an antibody described in, e.g., Hong et al., J Immunother 37 (2): 93-104 (2014). In yet some other examples, an antigen binding domain against IL-11Ra is an antigen binding portion, e.g., CDRs, of an antibody available from Abcam (cat #ab55262) or Novus Biologicals (cat #EPR5446). In another embodiment, an antigen binding domain again IL-11Ra is a peptide, see, e.g., Huang et al., Cancer Res 72 (1): 271-281 (2012). In yet some other examples, an antigen binding domain against PSCA is an antigen binding portion, e.g., CDRs, of an antibody described in, e.g., Morgenroth et al., Prostate 67 (10): 1121-1131 (2007)(scFv 7F5); Nejatollahi et al., J of Oncology 2013 (2013), article ID 839831 (scFv C5-II); and US Pat Publication No. 20090311181. In yet some other examples, an antigen binding domain against VEGFR2 is an antigen binding portion, e.g., CDRs, of an antibody described in, e.g., Chinnasamy et al., J Clin Invest 120 (11): 3953-3968 (2010). In yet some other examples, an antigen binding domain against LewisY is an antigen binding portion, e.g., CDRs, of an antibody described in, e.g., Kelly et al., Cancer Biother Radiopharm 23 (4): 411-423 (2008) (hu3S193 Ab (scFvs)); Dolezal et al., Protein Engineering 16 (1): 47-56 (2003)(NC10 scFv). In yet some other examples, an antigen binding domain against CD24 is an antigen binding portion, e.g., CDRs, of an antibody described in, e.g., Maliar et al., Gastroenterology 143 (5): 1375-1384 (2012). In yet some other examples, an antigen binding domain against CD20 is an antigen binding portion, e.g., CDRs, of the antibody Rituximab, Ofatumumab, Ocrelizumab, Veltuzumab, or GA101. In yet some other examples, an antigen binding domain against PDGFR-beta is an antigen binding portion, e.g., CDRs, of an antibody Abcam ab32570. In yet some other examples, an antigen binding domain against SSEA-4 is an antigen binding portion, e.g., CDRs, of antibody MC813 (Cell Signaling), or other commercially available antibodies. In yet some other examples, an antigen binding domain against Folate receptor alpha is an antigen binding portion, e.g., CDRs, of the antibody IMGN853, or an antibody described in US20120009181; U.S. Pat. No. 4,851,332, LK26: U.S. Pat. No. 5,952,484. In yet some other examples, an antigen binding domain against ERBB2 (Her2/neu) is an antigen binding portion, e.g., CDRs, of the antibody trastuzumab, or pertuzumab. In yet some other examples, an antigen binding domain against MUC1 is an antigen binding portion, e.g., CDRs, of the antibody SAR566658. In yet some other examples, the antigen binding domain against EGFR is antigen binding portion, e.g., CDRs, of the antibody cetuximab, panitumumab, zalutumumab, nimotuzumab, or matuzumab. In one embodiment, the antigen binding domain against EGFRvIII is or may be derived from an antigen binding domain, e.g., CDRs, scFv, or VH and VL, of an antibody, antigen-binding fragment or CAR described in, e.g., PCT publication WO2014/130657 (In one embodiment the CAR is a CAR described in WO2014/130657, the contents of which are incorporated herein in their entirety). In yet some other examples, an antigen binding domain against NCAM is an antigen binding portion, e.g., CDRs, of the antibody clone 2-2B: MAB5324 (EMD Millipore). In yet some other examples, an antigen binding domain against Ephrin B2 is an antigen binding portion, e.g., CDRs, of an antibody described in, e.g., Abengozar et al., Blood 119 (19): 4565-4576 (2012). In yet some other examples, an antigen binding domain against IGF-I receptor is an antigen binding portion, e.g., CDRs, of an antibody described in, e.g., U.S. Pat. No. 8,344,112 B2; EP2322550 A1; WO 2006/138315, or PCT/US2006/022995. In yet some other examples, an antigen binding domain against CAIX is an antigen binding portion, e.g., CDRs, of the antibody clone 303123 (R&D Systems). In yet some other examples, an antigen binding domain against LMP2 is an antigen binding portion, e.g., CDRs, of an antibody described in, e.g., U.S. Pat. No. 7,410,640, or US20050129701. In yet some other examples, an antigen binding domain against gp100 is an antigen binding portion, e.g., CDRs, of the antibody HMB45, NKI-betaB, or an antibody described in WO2013165940, or US20130295007. In yet some other examples, an antigen binding domain against tyrosinase is an antigen binding portion, e.g., CDRs, of an antibody described in, e.g., U.S. Pat. No. 5,843,674; or U.S. Ser. No. 08/504,048. In yet some other examples, an antigen binding domain against EphA2 is an antigen binding portion, e.g., CDRs, of an antibody described in, e.g., Yu et al., Mol Ther 22 (1): 102-111 (2014). In yet some other examples, an antigen binding domain against GD3 is an antigen binding portion, e.g., CDRs, of an antibody described in, e.g., U.S. Pat. Nos. 7,253,263; 8,207,308; US20120276046; EP1013761 A3; 20120276046; WO2005035577; or U.S. Pat. No. 6,437,098. In yet some other examples, an antigen binding domain against fucosyl GM1 is an antigen binding portion, e.g., CDRs, of an antibody described in, e.g., US20100297138; or WO2007/067992. In yet some other examples, an antigen binding domain against sLe is an antigen binding portion, e.g., CDRs, of the antibody G193 (for lewis Y), see Scott A M et al, Cancer Res 60:3254-61 (2000), also as described in Neeson et al, J Immunol May 2013 190 (Meeting Abstract Supplement) 177.10. In yet some other examples, an antigen binding domain against GM3 is an antigen binding portion, e.g., CDRs, of the antibody CA 2523449 (mAb 14F7). In yet some other examples, an antigen binding domain against HMWMAA is an antigen binding portion, e.g., CDRs, of an antibody described in, e.g., Kmiecik et al., Oncoimmunology 3 (1): e27185 (2014)(PMID: 24575382)(mAb9.2.27); U.S. Pat. No. 6,528,481; WO2010033866; or US20140004124. In yet some other examples, an antigen binding domain against o-acetyl-GD2 is an antigen binding portion, e.g., CDRs, of the antibody 8B6. In yet some other examples, an antigen binding domain against TEM1/CD248 is an antigen binding portion, e.g., CDRs, of an antibody described in, e.g., Marty et al., Cancer Lett 235 (2): 298-308 (2006); Zhao et al., J Immunol Methods 363 (2): 221-232 (2011). In yet some other examples, an antigen binding domain against CLDN6 is an antigen binding portion, e.g., CDRs, of the antibody IMAB027 (Ganymed Pharmaceuticals), see e.g., clinicaltrial.gov/show/NCT02054351. In yet some other examples, an antigen binding domain against TSHR is an antigen binding portion, e.g., CDRs, of an antibody described in, e.g., U.S. Pat. Nos. 8,603,466; 8,501,415; or U.S. Pat. No. 8,309,693. In yet some other examples, an antigen binding domain against GPRC5D is an antigen binding portion, e.g., CDRs, of the antibody FAB6300A (R&D Systems); or LS-A4180 (Lifespan Biosciences). In yet some other examples, an antigen binding domain against CD97 is an antigen binding portion, e.g., CDRs, of an antibody described in, e.g., U.S. Pat. No. 6,846,911; de Groot et al., J Immunol 183 (6): 4127-4134 (2009); or an antibody from R&D: MAB3734. In yet some other examples, an antigen binding domain against ALK is an antigen binding portion, e.g., CDRs, of an antibody described in, e.g., Mino-Kenudson et al., Clin Cancer Res 16 (5): 1561-1571 (2010). In yet some other examples, an antigen binding domain against polysialic acid is an antigen binding portion, e.g., CDRs, of an antibody described in, e.g., Nagae et al., J Biol Chem 288 (47): 33784-33796 (2013). In yet some other examples, an antigen binding domain against PLAC1 is an antigen binding portion, e.g., CDRs, of an antibody described in, e.g., Ghods et al., Biotechnol Appl Biochem 2013 doi: 10.1002/bab.1177. In yet some other examples, an antigen binding domain against GloboH is an antigen binding portion of the antibody VK9; or an antibody described in, e.g., Kudryashov V et al, Glycoconj J.15 (3): 243-9 (1998), Lou et al., Proc Natl Acad Sci USA 111 (7): 2482-2487 (2014); MBr1: Bremer E-G et al. J Biol Chem 259:14773-14777 (1984). In yet some other examples, an antigen binding domain against NY-BR-1 is an antigen binding portion, e.g., CDRs of an antibody described in, e.g., Jager et al., Appl Immunohistochem Mol Morphol 15 (1): 77-83 (2007). In yet some other examples, an antigen binding domain against WT-1 is an antigen binding portion, e.g., CDRs, of an antibody described in, e.g., Dao et al., Sci Transl Med 5 (176): 176ra33 (2013); or WO2012/135854. In yet some other examples, an antigen binding domain against MAGE-A1 is an antigen binding portion, e.g., CDRs, of an antibody described in, e.g., Willemsen et al., J Immunol 174 (12): 7853-7858 (2005)(TCR-like scFv). In yet some other examples, an antigen binding domain against sperm protein 17 is an antigen binding portion, e.g., CDRs, of an antibody described in, e.g., Song et al., Target Oncol 2013 Aug. 14 (PMID: 23943313); Song et al., Med Oncol 29 (4): 2923-2931 (2012). In yet some other examples, an antigen binding domain against Tie 2 is an antigen binding portion, e.g., CDRs, of the antibody AB33 (Cell Signaling Technology). In one embodiment, an antigen binding domain against MAD-CT-2 is an antigen binding portion, e.g., CDRs, of an antibody described in, e.g., PMID: 2450952; U.S. Pat. No. 7,635,753. In yet some other examples, an antigen binding domain against Fos-related antigen 1 is an antigen binding portion, e.g., CDRs, of the antibody 12F9 (Novus Biologicals). In yet some other examples, an antigen binding domain against MelanA/MART1 is an antigen binding portion, e.g., CDRs, of an antibody described in, EP2514766 A2; or U.S. Pat. No. 7,749,719. In yet some other examples, an antigen binding domain against sarcoma translocation breakpoints is an antigen binding portion, e.g., CDRs, of an antibody described in, e.g., Luo et al, EMBO Mol. Med. 4 (6): 453-461 (2012). In yet some other examples, an antigen binding domain against TRP-2 is an antigen binding portion, e.g., CDRs, of an antibody described in, e.g., Wang et al, J Exp Med. 184 (6): 2207-16 (1996). In yet some other examples, an antigen binding domain against CYP1B1 is an antigen binding portion, e.g., CDRs, of an antibody described in, e.g., Maecker et al, Blood 102 (9): 3287-3294 (2003). In one embodiment, an antigen binding domain against RAGE-1 is an antigen binding portion, e.g., CDRs, of the antibody MAB5328 (EMD Millipore). In yet some other examples, an antigen binding domain against human telomerase reverse transcriptase is an antigen binding portion, e.g., CDRs, of the antibody cat no: LS-B95-100 (Lifespan Biosciences). In yet some other examples, an antigen binding domain against intestinal carboxyl esterase is an antigen binding portion, e.g., CDRs, of the antibody 4F12: cat no: LS-B6190-50 (Lifespan Biosciences). In yet some other examples, an antigen binding domain against mut hsp70-2 is an antigen binding portion, e.g., CDRs, of the antibody Lifespan Biosciences: monoclonal: cat no: LS-C133261-100 (Lifespan Biosciences). In yet some other examples, an antigen binding domain against CD79a is an antigen binding portion, e.g., CDRs, of the antibody Anti-CD79a antibody [HM47/A9] (ab3121), available from Abcam; antibody CD79A Antibody #3351 available from Cell Signaling Technology; or antibody HPA017748-Anti-CD79A antibody produced in rabbit, available from Sigma Aldrich. In yet some other examples, an antigen binding domain against CD79b is an antigen binding portion, e.g., CDRs, of the antibody polatuzumab vedotin, anti-CD79b described in Dornan et al., "Therapeutic potential of an anti-CD79b antibody-drug conjugate, anti-CD79b-vc-MMAE, for the treatment of non-Hodgkin lymphoma" Blood. 2009 Sep. 24; 114 (13): 2721-9. doi: 10.1182/blood-2009-02-205500. Epub 2009 Jul. 24, or the bispecific antibody Anti-CD79b/CD3 described in "4507 Pre-Clinical Characterization of T Cell-Dependent Bispecific Antibody Anti-CD79b/CD3 As a Potential Therapy for B Cell Malignancies" Abstracts of 56th ASH Annual Meeting and Exposition, San Francisco, Calif. Dec. 6-9, 2014. In yet some other examples, an antigen binding domain against CD72 is an antigen binding portion, e.g., CDRs, of the antibody J3-109 described in Leuk Lymphoma. 1995 June; 18 (1-2): 119-22; Cancer Res Mar. 15, 2009 69; 2358. In yet some other examples, an antigen binding domain against LAIR1 is an antigen binding portion, e.g., CDRs, of the antibody ANT-301 LAIR1 antibody, available from ProSpec; or anti-human CD305 (LAIR1) Antibody, available from BioLegend.

In yet some other examples, an antigen binding domain against FCAR is an antigen binding portion, e.g., CDRs, of the antibody CD89/FCAR Antibody (Catalog #10414-H08H), available from Sino Biological Inc. In yet some other examples, an antigen binding domain against LILRA2 is an antigen binding portion, e.g., CDRs, of the antibody LILRA2 monoclonal antibody (M17), clone 3C7, available from Abnova, or Mouse Anti-LILRA2 antibody, Monoclonal (2D7), available from Lifespan Biosciences. In yet some other examples, an antigen binding domain against CD300LF is an antigen binding portion, e.g., CDRs, of the antibody Mouse Anti-CMRF35-like molecule 1 antibody, Monoclonal [UP-D2], available from BioLegend, or Rat Anti-CMRF35-like molecule 1 antibody, Monoclonal [234903], available from R&D Systems. In yet some other examples, an antigen binding domain against CLEC12A is an antigen binding portion, e.g., CDRs, of the antibody Bispecific T cell Engager (BiTE) scFv-antibody and ADC described in Noordhuis et al., "Targeting of CLEC12A In Acute Myeloid Leukemia by Antibody-Drug-Conjugates and Bispecific CLL-1.times.CD3 BiTE Antibody" 53$^{rd}$ ASH Annual Meeting and Exposition, Dec. 10-13, 2011, and MCLA-117 (Merus). In yet some other examples, an antigen binding domain against BST2 (also called CD317) is an antigen binding portion, e.g., CDRs, of the antibody Mouse Anti-CD317 antibody, Monoclonal [3H4], available from Antibodies-Online or Mouse Anti-CD317 antibody, Monoclonal [696739], available from R&D Systems. In yet some other examples, an antigen binding domain against EMR2 (also called CD312) is an antigen binding portion, e.g., CDRs, of the antibody Mouse Anti-CD312 antibody, Monoclonal [LS-B8033] available from Lifespan Biosciences, or Mouse Anti-CD312 antibody, Monoclonal [494025] available from R&D Systems. In yet some other examples, an antigen binding domain against LY75 is an antigen binding portion, e.g., CDRs, of the antibody Mouse Anti-Lymphocyte antigen 75 antibody, Monoclonal [HD30] available from EMD Millipore or Mouse Anti-Lymphocyte antigen 75 antibody, Monoclonal [A15797] available from Life Technologies. In still yet some other examples, an antigen binding domain against GPC3 is an antigen binding portion, e.g., CDRs, of the antibody hGC33 described in Anticancer Drugs. 2010 November; 21 (10): 907-916, or MDX-1414, HN3, or YP7, all three of which are described in FEBS Lett. 2014 Jan. 21; 588 (2): 377-82. In still yet some other examples, an antigen binding domain against FCRL5 is an antigen binding portion, e.g., CDRs, of the anti-FcRL5 antibody described in Mol Cancer Ther. 2012 October; 11 (10): 2222-32. In still yet some other examples, an antigen binding domain against IGLL1 is an antigen binding portion, e.g., CDRs, of the antibody Mouse Anti-Immunoglobulin lambda-like polypeptide 1 antibody, Monoclonal [AT1G4] available from Lifespan Biosciences, Mouse Anti-Immunoglobulin lambda-like polypeptide 1 antibody, Monoclonal [HSL 11] available from BioLegendSad.

In still yet some other examples, the antigen binding domain comprises one, two three (e.g., all three) heavy chain CDRs, HC CDR1, HC CDR2 and HC CDR3, from an antibody listed above, and/or one, two, three (e.g., all three) light chain CDRs, LC CDR1, LC CDR2 and LC CDR3, from an antibody listed above. In one embodiment, the antigen binding domain comprises a heavy chain variable region and/or a variable light chain region of an antibody listed above.

The antigen binding domain can be any domain that binds to the antigen including but not limited to a monoclonal antibody, a polyclonal antibody, a recombinant antibody, a human antibody, a humanized antibody, and a functional fragment thereof, including a Fab, a Fab', a F(ab') 2, an Fv, a single chain antibody (e.g., scFv), a minibody, a diabody, a single-domain antibody ("sdAb" or "nanobodies" or "camelids"), or an Fc binding domain. In some instances, it may be beneficial for the antigen binding domain to be derived from the same species in which the CAR will ultimately be used in. For example, for use in humans, it may be beneficial for the antigen binding domain of the CAR to comprise human or humanized residues for the antigen binding domain of an antibody or antibody fragment. In some instances, the antigen binding domain are "cross-species" in that it binds to the counterpart antigen in a non-human primate, such as Callithrix jacchus, Saguinus oedipus or Saimiri sciureus, in order to facilitate a testing of immunogenicity of the antigen binding domain in these animals.

Cytoplastic Domain of TFP or CAR

The cytoplasmic domain of the TFP or CAR can include an intracellular signaling domain. An intracellular signaling domain is generally responsible for activation of at least one of the normal effector functions of the immune cell in which the CAR has been introduced. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in some cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal. Examples of intracellular signaling domains for use in the TFP or CAR of the disclosure include the cytoplasmic sequences of the T cell receptor (TCR) and co-receptors that act in concert to initiate signal transduction following antigen receptor engagement, as well as any derivative or variant of these sequences and any recombinant sequence that has the same functional capability.

It is known that signals generated through the TCR alone are insufficient for full activation of the T cell and that a secondary and/or costimulatory signal is also required. Thus, T cell activation can be said to be mediated by two distinct classes of cytoplasmic signaling sequences: those that initiate antigen-dependent primary activation through the TCR (primary intracellular signaling domains) and those that act in an antigen-independent manner to provide a secondary or costimulatory signal (secondary cytoplasmic domain, e.g., a costimulatory domain).

A primary signaling domain regulates primary activation of the TCR complex either in a stimulatory way, or in an inhibitory way. Primary intracellular signaling domains that act in a stimulatory manner may contain signaling motifs which are known as immunoreceptor tyrosine-based activation motifs or ITAMs. Examples of ITAM containing primary intracellular signaling domains that are of particular use in the disclosure include those of CD3 zeta, common FcR gamma (FCER1G), Fc gamma RIIa, FcR beta (Fc Epsilon R1b), CD3 gamma, CD3 delta, CD3 epsilon, CD79a, CD79b, DAP10, and DAP12. In one embodiment, a CAR of the disclosure comprises an intracellular signaling domain, e.g., a primary signaling domain of CD3-zeta.

In one embodiment, a primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

The intracellular signaling domain of the TFP or CAR can comprise the CD3-zeta signaling domain by itself or it can be combined with any other desired intracellular signaling domain(s) useful in the context of a CAR of the disclosure. For example, the intracellular signaling domain of the CAR can comprise a CD3 zeta chain portion and a costimulatory signaling domain. The costimulatory signaling domain refers to a portion of the CAR comprising the intracellular domain of a costimulatory molecule. A costimulatory molecule is a cell surface molecule other than an antigen receptor or its ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like. For example, CD27 costimulation has been demonstrated to enhance expansion, effector function, and survival of human CART cells in vitro and augments human T cell persistence and antitumor activity in vivo (Song et al. Blood. 2012; 119 (3): 696-706). Further examples of such costimulatory molecules include CDS, ICAM-1, GITR, BAFFR, HVEM (LIGHTR), SLAMF7, NKp80 (KLRF1), NKp44, NKp30, NKp46, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAMI (CD226), SLAMF4 (CD244, 2B4), CD84, CD96 (Tactile), NKG2D, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

The intracellular signaling sequences within the cytoplasmic portion of the TFP or CAR of the disclosure may be linked to each other in a random or specified order. Optionally, a short oligo- or polypeptide linker, for example, between 2 and 10 amino acids (e.g., 2, 3, 4, 5, 6, 7, 8, 9, or 10 amino acids) in length may form the linkage between intracellular signaling sequence. In one embodiment, a glycine-serine doublet can be used as a suitable linker. In one embodiment, a single amino acid, e.g., an alanine, a glycine, can be used as a suitable linker.

In one aspect, the intracellular signaling domain is designed to comprise two or more, e.g., 2, 3, 4, 5, or more, costimulatory signaling domains. In an embodiment, the two or more, e.g., 2, 3, 4, 5, or more, costimulatory signaling domains, are separated by a linker molecule, e.g., a linker molecule described herein. In one embodiment, the intracellular signaling domain comprises two costimulatory signaling domains. In some embodiments, the linker molecule is a glycine residue. In some embodiments, the linker is an alanine residue. In one aspect, the intracellular signaling domain is designed to comprise the signaling domain of CD3-zeta and the signaling domain of CD28. In one aspect, the intracellular signaling domain is designed to comprise the signaling domain of CD3-zeta and the signaling domain of 4-1BB.

Transmembrane Domain of TFP or CAR

The extracellular region of TFP or CAR comprising an antigen binding domain can be linked to the intracellular region, for example by a transmembrane domain. A transmembrane domain can include one or more additional amino acids adjacent to the transmembrane region, e.g., one or more amino acid associated with the extracellular region of the protein from which the transmembrane was derived (e.g., 1, 2, 3, 4, 5, 6, 7, 8, 9, 10 or up to 15 amino acids of the extracellular region) and/or one or more additional amino acids associated with the intracellular region of the protein from which the transmembrane protein is derived (e.g., 1, 2, 3, 4, 5, 6, 7, 8, 9, 10 or up to 15 amino acids of the intracellular region). In one aspect, the transmembrane domain is one that is associated with one of the other domains of the TFP or CAR used. In some instances, the transmembrane domain can be selected or modified by amino acid substitution to avoid binding of such domains to the transmembrane domains of the same or different surface membrane proteins, e.g., to minimize interactions with other members of the receptor complex. In one aspect, the transmembrane domain is capable of homodimerization with another TFP on the TFP-T-cell surface (or another CAR on the CAR-T cell surface). In a different aspect the amino acid sequence of the transmembrane domain may be modified or substituted so as to minimize interactions with the binding domains of the native binding partner present in the same TFP or CAR.

The transmembrane domain may be derived either from a natural or from a recombinant source. Where the source is natural, the domain may be derived from any membrane-bound or transmembrane protein. In one aspect the transmembrane domain is capable of signaling to the intracellular domain(s) whenever the TFP or CAR has bound to a target. A transmembrane domain of particular use in this disclosure may include at least the transmembrane region(s) of e.g., the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154. Where desired, a hinge sequence or linker can be utilized to connect the extracellular domain to the transmembrane domain. Nonlimiting examples of hinge sequences are hinge sequences derived from a human immunoglobulin (Ig) hinge, e.g., an IgG4 hinge, or a CD8a hinge. A variety of linkers, such as oligo- or polypeptide linkers, are available in the art for linking various domains together. They may vary in length from about 2 to 50 amino acids and vary in amino acid composition. A commonly utilized linker is one enriched in glycine, e.g., amino acid sequence of GGGGSGGGGS, or variations thereof.

In some embodiments, the TFP- or the CAR-expressing cell described herein can further comprise multiple types of TFPs or CARs capable of binding to different antigens, or different epitopes on the same antigen. For instance, a TFP- or CAR-expressing cell of the present disclosure can comprise a second TFP or CAR that includes a different antigen binding domain, e.g., to the same target (CD19 or BCMA) or a different target (e.g., CD123). In one embodiment, when the TFP-expressing cell comprises two or more different TFPs or CARs, the antigen binding domains of the different TFPs or CARs can be such that the antigen binding domains do not interact with one another. For example, a cell expressing a first and second TFP can have an antigen binding domain of the first TFP, e.g., as a fragment, e.g., a scFv, that does not form an association with the antigen binding domain of the second TFP, e.g., the antigen binding domain of the second TFP is a $V_{HH}$. Similarly, a cell expressing a first and second CAR can have an antigen binding domain of the first CAR, e.g., as a fragment, e.g., a scFv, that does not form an association with the antigen binding domain of the second CAR, e.g., the antigen binding domain of the second CAR is a $V_{HH}$.

In some other embodiments, the TFP- or CAR-expressing cell described herein can further express another agent, e.g., an agent which enhances the activity of a TFP- or CAR-expressing cell. For example, in one embodiment, the agent can be an agent which inhibits an inhibitory molecule. Inhibitory molecules, e.g., PD1, can, in some embodiments, decrease the ability of a TFP- or CAR-expressing cell to mount an immune effector response. Examples of inhibitory molecules include PD1, PD-L1, CTLA4, TIM3, LAG3, VISTA, BTLA, TIGIT, LAIR1, CD160, 2B4 and TGFR beta. In one embodiment, the agent which inhibits an inhibitory molecule comprises a first polypeptide, e.g., an inhibitory molecule, associated with a second polypeptide that provides a positive signal to the cell, e.g., an intracellular signaling domain described herein. In one embodiment, the agent comprises a first polypeptide, e.g., of an inhibitory molecule such as PD1, LAG3, CTLA4, CD160, BTLA, LAIR1, TIM3, 2B4, CD93, OX40, Siglec-15, and TIGIT, or a fragment of any of these (e.g., at least a portion of an extracellular domain of any of these), and a second polypeptide which is an intracellular signaling domain described herein (e.g., comprising a costimulatory domain (e.g., 4-1BB, CD27 or CD28, e.g., as described herein) and/or a primary signaling domain (e.g., a CD3 zeta signaling domain described herein). In one embodiment, the agent comprises a first polypeptide of PD1 or a fragment thereof (e.g., at least a portion of an extracellular domain of PD1), and a second polypeptide of an intracellular signaling domain described herein (e.g., a CD28 signaling domain described herein and/or a CD3 zeta signaling domain described herein). PD1 is an inhibitory member of the CD28 family of receptors that also includes CD28, CTLA-4, ICOS, and BTLA. PD-1 is expressed on activated B cells, T-cells and myeloid cells (Agata et al. 1996 Int. Immunol 8:765-75). Two ligands for PD1, PD-L1 and PD-L2 have been shown to downregulate T-cell activation upon binding to PD1 (Freeman et al. 2000 J Exp Med 192:1027-34; Latchman et al. 2001 Nat Immunol 2:261-8; Carter et al. 2002 Eur J Immunol 32:634-43). Immune suppression can be reversed by inhibiting the local interaction of PD1 with PD-L1.

In one embodiment, the agent comprises the extracellular domain (ECD) of an inhibitory molecule, e.g., Programmed Death 1 (PD1) can be fused to a transmembrane domain and optionally an intracellular signaling domain such as 41BB and CD3 zeta (also referred to herein as a PD1 TFP). In one embodiment, the PD1 TFP, when used in combinations with an anti-CD19 TFP described herein, improves the persistence of the T-cell. In one embodiment, the TFP or CAR comprises the extracellular domain of PD1. Alternatively, provided are TFPs or CARs containing an antibody or antibody fragment such as a scFv that specifically binds to the Programmed Death-Ligand 1 (PD-L1) or Programmed Death-Ligand 2 (PD-L2).

In some embodiments, the present disclosure provides a population or a mixture of populations of TFP- or CAR-expressing cells, in which PTPN2 expression or activity is downregulated (e.g., inhibited). In some examples, the population of TFP-expressing T-cells comprises a mixture of cells expressing different TFPs. The population of TFP-T-cells can include a first cell expressing a TFP having an anti-CD19 or anti-BCMA binding domain described herein, and a second cell expressing a TFP having a different anti-CD19 or anti-BCMA binding domain, e.g., an anti-CD19 or anti-BCMA binding domain described herein that differs from the anti-CD19 binding domain in the TFP expressed by the first cell. As another example, the population of TFP-expressing cells can include a first cell expressing a TFP that includes an anti-CD19 or anti-BCMA binding domain, e.g., as described herein, and a second cell expressing a TFP that includes an antigen binding domain to a target other than CD19 or BCMA (e.g., another tumor-associated antigen). The same approach may apply to a mixture of CAR-expressing cells, individual cells may target the same or different antigens.

Encompassed herein are also additional TFP or CAR configurations known in the art, including Split CARs, RCARs, as well as other TFP and CAR combinations described in WO2016187349, U.S. Pat. No. 9,856,497, WO2017123556, all of which are incorporated herein by reference in their entirety.

Further contemplated are allogeneic CAR-expressing cells in which expression or activity of PTPN2 is inhibited. For example, the cell can be an allogeneic T cell, e.g., an allogeneic T cell lacking expression of a functional T cell receptor (TCR) and/or human leukocyte antigen (HLA), e.g., HLA class I and/or HLA class II. In particular, a T cell lacking a functional TCR can be, e.g., engineered such that it does not express any functional TCR on its surface, or engineered such that it does not express one or more subunits that comprise a functional TCR, or engineered such that it produces very little functional TCR on its surface. Alternatively, the T cell can express a substantially impaired TCR, e.g., by expression of mutated or truncated forms of one or more of the subunits of the TCR. The term "substantially impaired TCR" means that this TCR will not substantially elicit an adverse immune reaction in a host.

Allogeneic T cells that lack expression of a functional TCR and/or HLA can be obtained by any suitable means, including a knock out or knock down of one or more subunit of TCR or HLA. For example, the T cell can include a knock down of TCR and/or HLA using siRNA, shRNA, a CRISPR system, transcription activator like effector nuclease (TALEN), or zinc finger endonuclease (ZFN).

In some embodiments, an allogeneic cell can be a cell which does not express or expresses at low levels an inhibitory molecule, e.g. by any method described herein. For example, the cell can be a cell that does not express or expresses at low levels an inhibitory molecule, e.g., that can decrease the ability of a TFP- or CAR-expressing cell to mount an immune effector response. Examples of inhibitory molecules include PD1, PD-L1, CTLA4, TIM3, CEACAM (e.g., CEACAM-1, CEACAM-3 and/or CEACAM-5), LAGS, VISTA, BTLA, TIGIT, LAIR1, CD160, 2B4 and TGF beta.

The nucleic acid sequences coding for a desired TFP or CAR can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned. Where desired, the TFP- and CAR-expressing cells of the present disclosure are generated using lentiviral viral vectors.

Conventional viral and non-viral based gene transfer methods can be used to introduce TFP- or CAR-encoding sequences to a cell of interest, e.g., a lymphoid cell as disclosed herein. Such methods can be used to introduce the TFP- or CAR-encoding sequences to cells in culture, which in turn is administered into a subject. Non-viral vector delivery systems can include DNA plasmids, RNA (e.g. a transcript of a vector described herein), naked nucleic acid, and nucleic acid complexed with a delivery vehicle, such as a liposome. Viral vector delivery systems can include DNA and RNA viruses, which can have either episomal or integrated genomes after delivery to the cell.

Viral based systems can include retroviral, lentivirus, adenoviral, adeno-associated and herpes simplex virus vectors for gene transfer. Integration in the host genome can occur with the retrovirus, lentivirus, and adeno-associated virus gene transfer methods, which can result in long term expression of the inserted sequence. High transduction efficiencies can be observed in many different cell types and target tissues.

A subject lymphoid cell in which its PTPN2 expression and/or activity is downregulated (e.g., inhibited) finds an array of utility in treating a range of diseases associated with the antigen to which the TFP or CAR binds. For instance, PTPN2 downregulation (e.g., inhibition) enhances lymphoid cell expansion, effector function, and survival of human TFP- or CAR-expressing T cells in vitro, and human T cell persistence and antitumor activity in vivo.

In one aspect, the present disclosure provides a method of augmenting activity of an effector cell (e.g., T cells, NK cells, KHYG cells). The method typically comprises: contacting said effector cell with an effective amount of a PTPN2 inhibitor, such as a compound of Formula (I), (I-1), (II), (II-1), (II-a), (II-a1), (III), (III-1), (IV), or (IV-1), such that PTPN2 expression and activity is downregulated (e.g., inhibited) in said effector cell. Augmentation of effector activity can be evidenced by the cytolytic activity against a target cell such as a tumor or cancer cell, or helper activity including the release of cytokines. Assessing augmented effector function can be carried out using any methods known in the art or disclosed here. In some instances, cytotoxicity of an effector cell expressing TFP or CAR as disclosed herein can be greater in response to PTPN2-inhibitor treatment as compared to a control lymphoid cell lacking such treatment. A TFP- or CAR-expressing effector cell treated with a PTPN2 inhibitor can be about 5%, 10%, 15%, 20%, 25%, 30%, 35%, 40%, 45%, 50%, 55%, 60%, 65%, 70%, 75%, 80%, 85%, 90%, 95%, 100%, 500% or more cytotoxic against tumor or cancer cells as compared to an effector cell lacking the treatment. In some embodiments, a change in cytotoxicity can comprise comparing such activity before and after treating the effector cell with a PTPN2 inhibitor. In some other instances, release of cytotoxic cytokines of an effector cell expressing TFP or CAR as disclosed herein can be greater in response to treating with a PTPN2 inhibitor as compared to a control lymphoid cell lacking such treatment. Exemplary cytokines include IFNγ, TNFα, CSF, TGFβ, IL-1, IL-2, IL-4, IL-5, IL-6, IL-13, IL-17, IL-21, IL-22, granzyme, and the like. A TFP- or CAR-expressing effector cell can generate about 1 fold, 2 fold, 3 fold, 4 fold, 5 fold, 6 fold, 7 fold, 8 fold, 9 fold, 10 fold, 50 fold, 100 fold or greater release of cytotoxic cytokines in response to a PTPN2 inhibitor treatment as compared to a control lymphoid cell that is not being exposed to the PTPN2 inhibitor.

In another aspect, the present disclosure provides a method of treating cancer in a subject in need thereof, comprising: administering to the subject an effective amount of lymphoid cells, wherein an individual lymphoid cell comprises (a) a chimeric T-cell receptor sequence encoding a T-cell receptor fusion protein (TFP), and/or (b) a chimeric antigen receptor (CAR) sequence encoding a CAR, wherein each of TFP and CAR, when present, exhibits specific binding to an antigen, and wherein expression and/or function of PTPN2 in said cell is downregulated (e.g., inhibited). In some embodiments of the disclosure, downregulation of PTPN2 expression and/or activity can be affected by one or more types of PTPN2 inhibitor disclosed herein. Where desired, downregulation of expression or activity of PTPN2 takes place transiently by contacting the cells with a small molecule PTPN2 inhibitor, such as a compound of Formula (I), (I-1), (II), (II-1), (II-a), (II-a1), (III), (III-1), (IV), or (IV-1), or a nucleic acid based PTPN2 inhibitor (e.g., siRNA or shRNA) that asserts such downregulation transiently without being integrated into the cell's genome. Alternatively, PTPN2 downregulation can occur permanently by contacting the cell with a PTPN2 inhibitor that disrupts the expression of the PTPN2 gene permanently by cleaving such gene with a CRISPR-based PTPN2 inhibitor.

In some examples, the practice of the subject method involves downregulating PTPN2 expression and/or activity in the lymphoid cells, ex vivo, prior to administering an effective amount of PTPN2-treated lymphoid cells (e.g., effector cells) to the subject. The ex vivo inhibition can be carried out prior to, concurrent with, or after the introduction of the nucleic acid encoding the TFP or CAR into the lymphoid cell. Such ex vivo treatment may facilitate the expansion and proliferation of the effector cells to yield to a cell count reaching a desired effective amount to be administered to a subject. Such ex vivo treatment may also prolong the survival effector cell persistence and antitumor activity in vivo. For instances, an effector cell of the present disclosure when infused into a subject is capable of killing tumor or cancer cells in the subject. Unlike antibody therapies, TFP-modified or CAR-modified immune effector cells (e.g., T cells, NK cells, KHYG cells) are able to replicate in vivo resulting in long-term persistence that can lead to sustained tumor control. In various aspects, the immune effector cells (e.g., T cells, NK cells, KHYG cells) administered to the subject, or their progeny, persist in the subject for at least four months, five months, six months, seven months, eight months, nine months, ten months, eleven months, twelve months, thirteen months, fourteen month, fifteen months, sixteen months, seventeen months, eighteen months, nineteen months, twenty months, twenty-one months, twenty-two months, twenty-three months, two years, three years, four years, or five years after administration of the T cell or NK cell or KHYG cells to the subject.

Accordingly, the present disclosure also provides a method of increasing the therapeutic efficacy of a TFP- or CAR-expressing cell directed to a tumor or tumor associated antigen. In some embodiments, administering a PTPN2 inhibitor occurs ex vivo. In other embodiments, administering a PTPN2 inhibitor occurs in vivo prior to, concurrent with, or after the cells have been administered to a subject, where the cell may have or may not have previously been exposed to the PTPN2 inhibitor ex vivo.

In one aspect, a fully-human TFP- or CAR-modified immune effector cells (e.g., T cells, NK cells, KHGY cells) of the disclosure may be a type of vaccine for ex vivo immunization and/or in vivo therapy in a mammal including a human.

The subject methods utilizing a TFP- or CAR-expressing lymphoid cells (including e.g., effector cells) that target one or more tumor antigens can be applied to treat solid tumor and hematological cancers. For example, the subject methods can be used to treat: Acute Lymphoblastic Leukemia (ALL), Acute Myeloid Leukemia (AML), Adrenocortical Carcinoma, Childhood Adrenocortical Carcinoma, AIDS-Related Cancers, Kaposi Sarcoma (Soft Tissue Sarcoma), AIDS-Related Lymphoma (Lymphoma), Primary CNS Lymphoma (Lymphoma), Anal Cancer, Appendix Cancer, Astrocytomas, Childhood (Brain Cancer), Atypical Teratoid/Rhabdoid Tumor, Basal Cell Carcinoma of the Skin, Bile Duct Cancer, Bladder Cancer, Bone Cancer (includes Ewing Sarcoma and Osteosarcoma and Malignant Fibrous Histiocytoma), Brain Tumors, Breast Cancer, Bronchial Tumors, Burkitt Lymphoma-see Non-Hodgkin Lymphoma, Carcinoid Tumor (Gastrointestinal), Childhood Carcinoid Tumors, Cardiac (Heart) Tumors, Atypical Teratoid/Rhabdoid Tumor, Embryonal Tumors, Germ Cell Tumor, Primary CNS Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colorectal Cancer, Craniopharyngioma, Cutaneous T-Cell Lymphoma (Mycosis Fungoides and Sézary Syndrome), Ductal Carcinoma In Situ (DCIS), Embryonal Tumors, Endometrial Cancer (Uterine Cancer), Ependymoma, Esophageal Cancer, Esthesioneuroblastoma (Head and Neck Cancer), Ewing Sarcoma (Bone Cancer), Extracranial Germ Cell Tumor, Extragonadal Germ Cell Tumor, Eye Cancer, Childhood Intraocular Melanoma, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Extragonadal Germ Cell Tumors, Ovarian Germ Cell Tumors, Testicular Cancer, Gestational Trophoblastic Disease, Hairy Cell Leukemia, Head and Neck Cancer, Heart Tumors, Hepatocellular (Liver) Cancer, Histiocytosis, Langerhans Cell Hodgkin Lymphoma, Hypopharyngeal Cancer (Head and Neck Cancer), Islet Cell Tumors, Pancreatic Neuroendocrine Tumors, Kaposi Sarcoma (Soft Tissue Sarcoma), Kidney (Renal Cell) Cancer, Laryngeal Cancer (Head and Neck Cancer), Leukemia, Lip and Oral Cavity Cancer (Head and Neck Cancer), Liver Cancer, Lung Cancer (e.g., Non-Small Cell and Small Cell), Lymphoma, Male Breast Cancer, Malignant Fibrous Histiocytoma of Bone and Osteosarcoma, Melanoma, Merkel Cell Carcinoma (Skin Cancer), Mesothelioma, Malignant, Metastatic Cancer, Metastatic Squamous Neck Cancer with Occult Primary (Head and Neck Cancer), Midline Tract Carcinoma, Mouth Cancer (Head and Neck Cancer), Multiple Endocrine Neoplasia, Multiple Myeloma/Plasma Cell Neoplasms, Mycosis Fungoides (Lymphoma), Myelodysplastic Syndromes, Myelodysplastic/Myeloproliferative Neoplasms, Myelogenous Leukemia, CML, Myeloid Leukemia, Acute (AML), Myeloproliferative Neoplasms, Chronic, Nasal Cavity and Paranasal Sinus Cancer (Head and Neck Cancer), Nasopharyngeal Cancer (Head and Neck Cancer), Neuroblastoma, Non-Hodgkin Lymphoma, Non-Small Cell Lung Cancer, Oral Cancer, Lip and Oral Cavity Cancer and Oropharyngeal Cancer (Head and Neck Cancer), Osteosarcoma and Malignant Fibrous Histiocytoma of Bone, Ovarian Cancer, Pancreatic Cancer, Pancreatic Neuroendocrine Tumors (Islet Cell Tumors), Papillomatosis (Childhood Laryngeal), Paraganglioma, Paranasal Sinus and Nasal Cavity Cancer (Head and Neck Cancer), Parathyroid Cancer, Penile Cancer, Pharyngeal Cancer (Head and Neck Cancer), Pheochromocytoma, Pituitary Tumor, Plasma Cell Neoplasm/Multiple Myeloma, Pleuropulmonary Blastoma, Pregnancy and Breast Cancer, Primary Central Nervous System (CNS) Lymphoma, Primary Peritoneal Cancer, Rectal Cancer, Retinoblastoma, Rhabdomyosarcoma, Salivary Gland Cancer (Head and Neck Cancer), Sarcoma, Childhood Rhabdomyosarcoma (Soft Tissue Sarcoma), Childhood Vascular Tumors (Soft Tissue Sarcoma), Ewing Sarcoma (Bone Cancer), Kaposi Sarcoma (Soft Tissue Sarcoma), Osteosarcoma (Bone Cancer), Soft Tissue Sarcoma, Uterine Sarcoma, Sézary Syndrome (Lymphoma), Skin Cancer, Childhood Skin Cancer, Small Cell Lung Cancer, Small Intestine Cancer, Soft Tissue Sarcoma, Squamous Cell Carcinoma of the Skin, Squamous Neck Cancer with Occult Primary, Metastatic (Head and Neck Cancer), Stomach (Gastric) Cancer, T-Cell Lymphoma, Cutaneous, Testicular Cancer, Throat Cancer (Head and Neck Cancer), Nasopharyngeal Cancer, Oropharyngeal Cancer, Hypopharyngeal Cancer, Thymoma and Thymic Carcinoma, Thyroid Cancer, Transitional Cell Cancer of the Renal Pelvis and Ureter (Kidney (Renal Cell) Cancer), Ureter and Renal Pelvis, Transitional Cell Cancer (Kidney (Renal Cell) Cancer, Urethral Cancer, Uterine Cancer, Endometrial, Uterine Sarcoma, Vaginal Cancer, Vascular Tumors (Soft Tissue Sarcoma), Vulvar Cancer, and Wilms Tumor and Other Childhood Kidney Tumors, and any of the aforementioned cancers exhibiting expression and/or activity of PTPN2 in the cancer cells.

The present disclosure also provides pharmaceutical compositions comprising a TFP- or CAR-expressing cell, e.g., a plurality of TFP-expressing cells, as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are in one aspect formulated for intravenous administration.

Pharmaceutical compositions of the present disclosure may be administered in a manner appropriate to the disease to be treated (or prevented). The quantity of administration will be determined by such factors as the condition of the subject, and the type and severity of the subject's disease, although appropriate dosages may be determined by clinical trials.

In one embodiment, the pharmaceutical composition is substantially free of, e.g., there are no detectable levels of a contaminant, e.g., selected from the group consisting of endotoxin, *Mycoplasma*, replication competent lentivirus (RCL), p24, VSV-G nucleic acid, HIV gag, residual anti-CD3/anti-CD28 coated beads, mouse antibodies, pooled human serum, bovine serum albumin, bovine serum, culture media components, vector packaging cell or plasmid components, a bacterium and a fungus. In one embodiment, the bacterium is at least one selected from the group consisting of *Alcaligenes faecalis, Candida albicans, Escherichia coli, Haemophilus influenza, Neisseria meningitides, Pseudomonas aeruginosa, Staphylococcus aureus, Streptococcus pneumonia*, and *Streptococcus pyogenes* group A.

The precise effective amount of the compositions of the present disclosure to be administered can be determined by a physician with consideration of individual differences in age, weight, tumor size, extent of infection or metastasis, and condition of the subject. It can generally be stated that a pharmaceutical composition comprising the T-cells described herein may be administered at a dosage of $10^4$ to $10^9$ cells/kg body weight, in some instances $10^5$ to $10^6$ cells/kg body weight, including all integer values within those ranges. T-cell compositions may also be administered multiple times at these dosages. The cells can be administered by using infusion techniques that are commonly known in immunotherapy (see, e.g., Rosenberg et al., New Eng. J. of Med. 319:1676, 1988).

In some examples, it may be desired to administer activated T-cells to a subject and then subsequently redraw blood (or have an apheresis performed), activate T-cells therefrom according to the present disclosure, and reinfuse the patient with these activated and expanded T-cells. This process can be carried out multiple times every few weeks. In certain aspects, T-cells can be activated from blood draws of from 10 cc to 400 cc. In certain aspects, T-cells are activated from blood draws of 20 cc, 30 cc, 40 cc, 50 cc, 60 cc, 70 cc, 80 cc, 90 cc, or 100 cc. In some embodiments, the T-cell compositions of the present disclosure are administered by i.v. injection. The compositions of T-cells may be injected directly into a tumor, lymph node, or site of infection.

In some examples, a subject may undergo leukapheresis, wherein leukocytes are collected, enriched, or depleted ex vivo to select and/or isolate the cells of interest, e.g., T-cells. These T-cell isolates may be expanded by methods known in the art and treated such that one or more TFP constructs of the disclosure may be introduced, thereby creating a TFP-expressing or CAR-expressing T-cell of the disclosure.

Pharmaceutical Compositions and Methods of Administration

In an aspect is provided a pharmaceutical composition comprising a compound described herein, or a pharmaceutically acceptable salt or solvate thereof, and a pharmaceutically acceptable excipient.

In some embodiments, a compound described herein, or a pharmaceutically acceptable salt or solvate thereof, is administered to a subject in a biologically compatible form suitable for administration to treat or prevent diseases, disorders, or conditions. Administration of a compound described herein can be in any pharmacological form including a therapeutically effective amount of a compound described herein, or a pharmaceutically acceptable salt or solvate thereof, alone or in combination with a pharmaceutically acceptable carrier.

In some embodiments, a compound described herein is administered as a pure chemical. In some embodiments, the compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in Remington: The Science and Practice of Pharmacy (Gennaro, $21^{st}$ Ed. Mack Pub. Co., Easton, PA (2005)).

Accordingly, provided herein is a pharmaceutical composition comprising at least one compound described herein, or a pharmaceutically acceptable salt, together with one or more pharmaceutically acceptable excipients. The excipient (s)(or carrier(s)) is acceptable or suitable if the excipient is compatible with the other ingredients of the composition and not deleterious to the recipient (i.e., the subject) of the composition.

In some embodiments of the methods described herein, a compound described herein is administered either alone or in combination with pharmaceutically acceptable carriers, excipients or diluents, in a pharmaceutical composition. Administration of a compound or composition described herein can be affected by any method that enables delivery of the compound to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, a compound described herein can be administered locally to the area in need of treatment, by, for example, local infusion during surgery, topical application such as creams or ointments, injection, catheter, or implant. The administration can also be by direct injection at the site of a diseased tissue or organ. In some embodiments, a compound described herein, or a pharmaceutically acceptable salt or solvate thereof, is administered orally.

In some embodiments of the methods described herein, a pharmaceutical composition suitable for oral administration is presented as a discrete unit such as a capsule, cachet or tablet, each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary, or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments of the methods described herein, pharmaceutical compositions are formulated for parenteral administration by injection, e.g., by bolus injection or continuous infusion. Formulations for injection may be presented in unit dosage form, e.g., in ampoules or in multidose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compound which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long-acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

EXAMPLES

The following examples are provided for illustrative purposes only and not to limit the scope of the claims provided herein. Unless noted otherwise, all materials, such as reagents, starting materials and solvents, were purchased from commercial suppliers, such as Sigma-Aldrich, VWR, and the like, and were used without further purification. Reactions were run under nitrogen atmosphere, unless noted otherwise. The progress of reactions was monitored by thin layer chromatography (TLC), analytical high performance liquid chromatography (anal. HPLC), and mass spectrometry, the details of which may be provided in specific examples.

Reactions were worked up as described specifically in each preparation; commonly, reaction mixtures were purified by extraction and other purification methods such as temperature- and solvent-dependent crystallization, and precipitation. In addition, reaction mixtures were routinely purified by preparative HPLC, for example, using Microsorb C18 or Microsorb BDS column packings and conventional eluents. Progress of reactions was typically monitored by liquid chromatography mass spectrometry (LCMS). Characterization of isomers was typically done by Nuclear Overhauser effect spectroscopy (NOE). Characterization of reaction products was routinely carried out by mass spectrometry and/or 1H-NMR spectroscopy. For NMR measurement, samples were dissolved in deuterated solvent ($CD_3OD$, $CDCl_3$, or DMSO-$d_6$).

Example 1a: Synthesis of 5-(2-fluoro-6-hydroxy-3-(4,4,5,5-tetramethyl-1,3,2-dioxaborolan-2-yl)phenyl)-1,2,5-thiadiazolidin-3-one 1,1-dioxide (1-12)

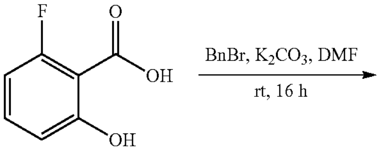

1-1

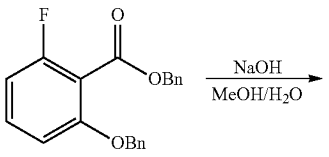

1-2

-continued

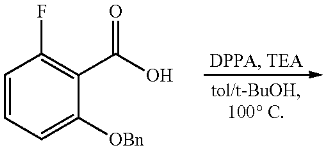

1-3

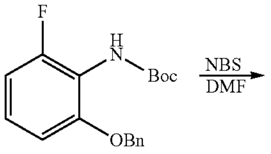

1-4

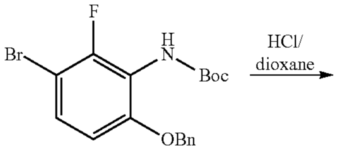

1-5

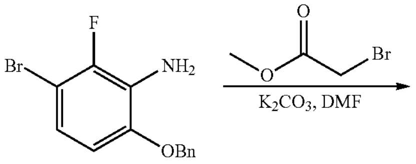

1-6

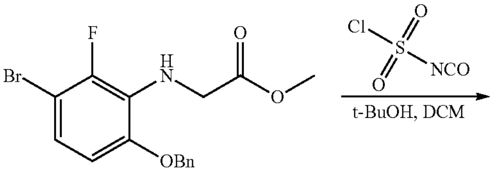

1-7

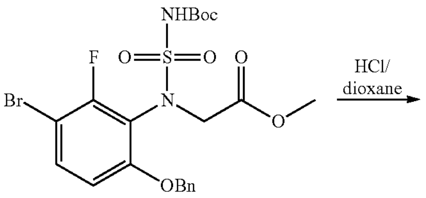

1-8

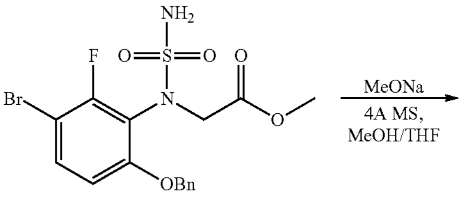

1-9

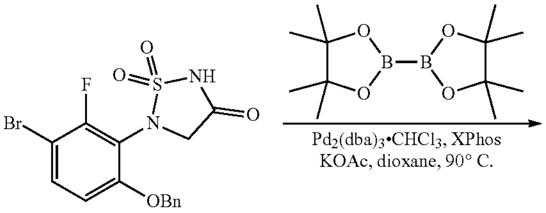

1-10

-continued

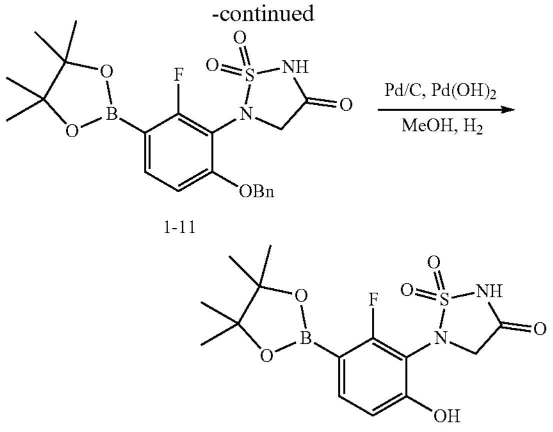

1-11

1-12

Step A: To a mixture of 1-1 (110 g, 705.1 mmol, 1 eq) in DMF (1.1 L) were added BnBr (241.1 g, 1410.2 mmol, 2.0 eq) and $K_2CO_3$ (292.3 g, 2115.3 mmol, 3.0 eq). The reaction was stirred at rt for 16 h, then extracted with 3×1 L of EA, washed with brine, dried over $Na_2SO_4$, and concentrated under vacuum to give 1-2 (220 g, crude). LC-MS m/z: 337.0 $[M+H]^+$.

Step B: To a mixture of 1-2 (220 g, crude, 1 eq) in MeOH (2.2 L) were added NaOH (107 g, 2682.9 mmol, 3.0 eq) and $H_2O$ (440 ml). The reaction was stirred at 50° C. for 18 h, then extracted with 3×1 L of EA. The aqueous phase was adjusted to pH=5-6 with HCl and was extracted with 3×1 L of EA, washed with water, dried over $Na_2SO_4$, and concentrated under vacuum. The residue was purified by flash column chromatography on silica gel (PE/EA=10:1) to give 1-3 (120 g, 74.5% yield). LC-MS m/z: 247.0 $[M+H]^+$.

Step C: To a mixture of 1-3 (120 g, 487 mmol, 1.0 eq.) in toluene (480 mL) were added t-BuOH (480 mL), TEA (98.53 g, 976 mmol, 2.0 eq) and DPPA (201.0 g, 730.5 mmol, 1.5 eq). The reaction was stirred at 100° C. for 18 h. The reaction mixture was cooled, poured into water (1 L) and extracted with ethyl acetate (1 L×3), dried over anhydrous $Na_2SO_4$, filtered and concentrated under vacuum. The residue was purified by flash column chromatography on silica gel (PE/EA=3:1) to afford 1-4 (117.5 g, 75.9% yield). LC-MS m/z: 318.0 $[M+H]^+$.

Step D: To a mixture of 1-4 (117.5 g, 370 mmol, 1 eq) in DMF (1.1 L) was added NBS (72.5 g, 407 mmol, 1.1 eq). The reaction was stirred at rt for 16 h, then extracted with 3×1 L of EA, washed with brine, dried over $Na_2SO_4$, and concentrated under vacuum to give 1-5 (150 g, crude). LC-MS m/z: 397.0 $[M+H]^+$.

Step E: A mixture of 1-5 (150 g, crude, 1.0 eq.) in dioxane/HCl (1 L) was stirred at rt for 16 h. The reaction mixture was adjusted to pH=8-10 with 4 M NaOH solution, then extracted with ethyl acetate (1 L×3), dried over anhydrous $Na_2SO_4$, filtered, and concentrated under vacuum. The residue was purified by flash column chromatography on silica gel (PE/EA=10:1) to afford 1-6 (65 g, 57.9% yield). LC-MS m/z: 297.0 $[M+H]^+$.

Step F: To a mixture of 1-6 (65 g, 219.6 mmol, 1.0 eq.) in DMF (600 mL) were added methyl 2-bromoacetate (50.4 g, 329.4 mmol, 1.5 eq) and $K_2CO_3$ (121.4 g, 878.4 mmol, 4.0 eq). The reaction was stirred at 60° C. for 16 h. The reaction mixture was cooled, poured into water (1 L) and extracted with petroleum ether/ethyl acetate (3/1, 1 L×3), dried over anhydrous $Na_2SO_4$, filtered and concentrated under vacuum. The residue was purified by flash column chromatography on silica gel (PE/EA=10:1) to afford 1-7 (36 g, 44.5% yield). LC-MS m/z: 369.0 $[M+H]^+$.

Step G: To a mixture of sulfurisocyanatidic chloride (137 g, 978 mmol, 10 eq.) in DCM (500 mL) was added t-BuOH (72 g, 978 mmol, 10 eq.) at 0° C. under $N_2$. The reaction was stirred at rt for 1 h, then 1-7 (36 g, 97.8 mmol, 1.0 eq.) and TEA (197 g, 1956 mmol, 20 eq.) in DCM (100 mL) were added at 0° C. under $N_2$. The reaction was stirred at rt for 16 h. The reaction mixture was extracted with 3×1 L of DCM, dried over anhydrous $Na_2SO_4$, filtered, and concentrated under vacuum to afford 1-8 (70 g, crude). LC-MS m/z: 546.0 $[M-H]^-$.

Step H: A mixture of 1-8 (70 g crude, 128 mmol, 1.0 eq.) in dioxane/HCl (500 mL) was stirred at rt for 2 h. The reaction mixture was adjusted to pH=8-10 with sat. $NaHCO_3$ solution and extracted with 3×500 mL of EA, dried over anhydrous $Na_2SO_4$, and concentrated under vacuum. The residue was purified by flash column chromatography on silica gel (PE/EA=3:1) to afford 1-9 (24 g, 41.9% yield). LC-MS m/z: 446.0 $[M-H]^-$.

Step I: To a mixture of 1-9 (24 g, 31.3 mmol, 1.0 eq.) in THF (96 mL) and MeOH (48 mL) were added MeONa (48 mL) and 4A molecular sieves (50 g) under $N_2$. The reaction was stirred at rt for 1 h, then concentrated under vacuum. The residue was purified by flash column chromatography on silica gel (MeOH/EA=1:5) to afford 1-10 (15 g, 67.3% yield). LC-MS m/z: 414.0 $[M-H]^-$.

Step J: To a mixture of 1-10 (15 g, 36.1 mmol, 1.0 eq.) in 1,4-dioxane (150 mL) were added KOAc (10.63 g, 108.4 mmol, 3.0 eq), 4,4,4',4',5,5,5',5'-octamethyl-2,2'-bi (1,3,2-dioxaborolane)(22.93 g, 90.3 mmol, 2.5 eq), Xphos (3.4 g, 7.2 mmol, 0.2 eq) and $Pd_2(dba)_3 \cdot CHCl_3$ (3.7 g, 3.6 mmol, 0.1 eq) under $N_2$. The reaction was stirred at 90° C. for 16 h, then concentrated under vacuum. The residue was purified by flash column chromatography on silica gel (MeOH/EA=1:5) to afford 1-11 (10 g, 60.0% yield). LC-MS m/z: 461.1 $[M-H]^-$; $^1H$ NMR (400 MHZ, $CD_3OD$): δ 7.65 (dd, J=8.5, 6.6 Hz, 0.5H), 7.50 (d, J=7.3 Hz, 2H), 7.39-7.24 (m, 3.5H), 6.95 (t, J=7.7 Hz, 1H), 5.22-5.17 (m, 2H), 4.30 (dd, J=5.7, 3.2 Hz, 2H), 1.20 (s, 12H).

Step K: To a solution of 1-11 (5.0 g, 10.82 mmol) in MeOH (50 mL) were added $Pd(OH)_2/C$ (500 mg) and Pd/C (500 mg), then the mixture was stirred at 25° C. for 2 h under $H_2$ atmosphere (30 psi). The mixture was filtered and the filter cake was rinsed with MeOH (50 mL). The combined filtrates were concentrated under reduced pressure to give 1-12 (4.1 g, 96% yield). LC-MS m/z: 371.1 $[M-H]^-$.

Example 1b: Synthesis of 5-(2-fluoro-6-hydroxy-4-(pyrrolidin-3-ylmethyl)phenyl)-1,2,5-thiadiazolidin-3-one 1,1-dioxide (140)

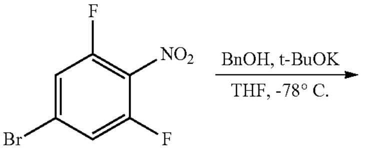

2-1

-continued

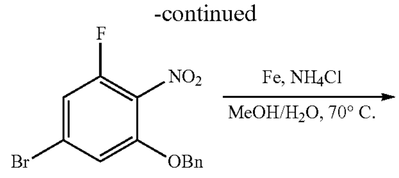

2-2

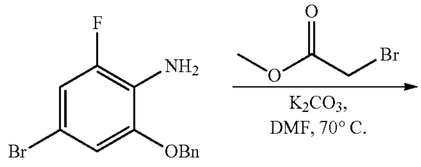

2-3

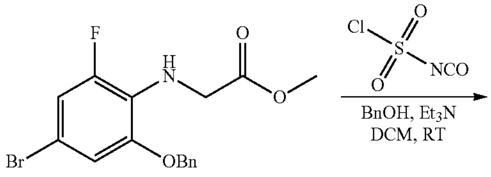

2-4

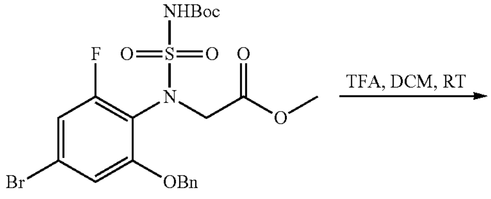

2-5

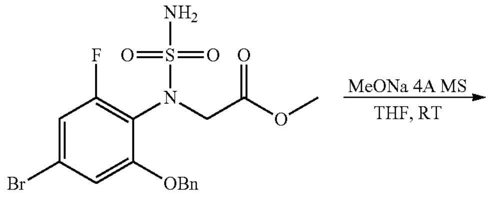

2-6

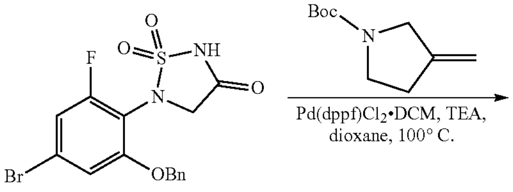

2-7

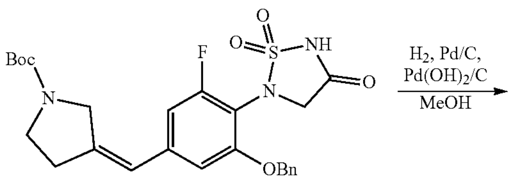

2-8

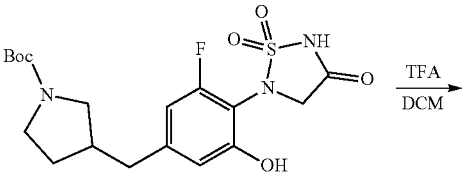

2-9

-continued

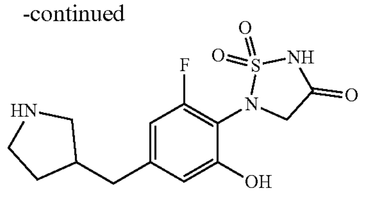

140

Step A: To a solution of 2-1 (20.0 g, 84.38 mmol, 1.0 eq.) and BnOH (9.1 g, 84.38 mmol, 1.0 eq.) in THF (200 mL) was added t-BuOK (84.38 mL, 84.38 mmol, 1.0 eq.) slowly at −78° C. under $N_2$. The reaction mixture was stirred at −78° C. under $N_2$ for 15 min, then quenched with saturated aqueous $NH_4Cl$ solution and extracted with EA. The organic layer was dried over anhydrous $Na_2SO_4$, filtered, and concentrated in vacuo to obtain 2-2 (13.0 g, 47.4% yield), which was used in the next step without further purification.

Step B: To a solution of 2-2 (13.0 g, 39.88 mmol, 1.0 eq.) in MeOH (100 mL) were added Fe (4.5 g, 79.76 mmol, 2.0 eq.) and saturated aqueous $NH_4Cl$ solution (20 mL). The reaction mixture was stirred at 70° C. overnight under $N_2$, then concentrated in vacuo and diluted with EA (200 mL). The mixture was filtered, and the filter cake was rinsed with EA (100 mL). The filtrate was washed with water (300 mL×2) and brine (300 mL), dried over anhydrous $Na_2SO_4$, filtered, and concentrated under reduced pressure to obtain 2-3 (12 g, crude) which was used in the next step without further purification. LC-MS m/z: 296.1 $[M+H]^+$.

Step C: To a solution of 2-3 (12.0 g, 40.67 mmol, 1.0 eq.) in DMF (120 mL) were added methyl 2-bromoacetate (9.33 g, 61.01 mmol, 1.5 eq.) and $K_2CO_3$ (9.33 g, 122.02 mmol, 3.0 eq.). The reaction mixture was stirred at 60° C. overnight under $N_2$. The reaction mixture was filtered, the filtrate was adjusted to pH=5~6 with saturated aqueous $NH_4Cl$ solution. The mixture was extracted with EA (200 mL) and the organic layer was dried over anhydrous $Na_2SO_4$, filtered, and concentrated under reduced pressure. The residue was purified by flash column chromatography on silica gel eluting with PE/EA (1/0-5/1) to give 2-4 (6.5 g, 43.5% yield). LC-MS m/z: 368.0 $[M+H]^+$.

Step D: To a solution of chlorosulfonyl isocyanate (17.3 g, 122.6 mmol, 10.0 eq.) in DCM (30 mL) was added t-BuOH (9.1 g, 122.6 mmol, 10.0 eq.) in DCM (10 mL) dropwise at 0° C. The resulting mixture was stirred at rt for 30 min under $N_2$. A solution of 2-4 (4.5 g, 12.26 mmol, 1 eq.) and $Et_3N$ (24.7 g, 245.2 mmol, 20.0 eq.) in DCM (20 mL) was added dropwise to the mixture at 0° C. and the resulting mixture was stirred at rt overnight. The reaction mixture was diluted with EA (250 mL) and washed with $H_2O$ (300 mL×2) and brine (300 mL). The organic layer was dried over anhydrous $Na_2SO_4$, filtered, and concentrated under reduced pressure to give 2-5 (5.0 g, 74.7% yield), which was used in the next step without further purification. LC-MS m/z: 547.0 $[M+H]^+$.

Step E: To a solution of 2-5 (5.0 g, 9.16 mmol, 1.0 eq.) in DCM (50 mL) was added TFA (10 mL). The mixture was stirred at rt for 3 h, then the pH was adjusted to 8~9 with saturated aqueous $NaHCO_3$ solution and the mixture extracted with EA (150 mL×2). The combined organic layers were dried over anhydrous $Na_2SO_4$, filtered, and concentrated under reduced pressure to give 2-6 (3.2 g, 78.3% yield). LC-MS m/z: 447.0 $[M+H]^+$.

Step F: To a mixture of 2-6 (3.2 g, 7.17 mmol, 1.0 eq.) and 4A molecular sieves (5 g) in THF (50 mL) was added sodium methoxide (4 mL, 21.52 mmol, 3.0 eq., 5.4 M) dropwise under $N_2$. The reaction mixture was stirred at room temperature under $N_2$ for 16 h, then concentrated under reduced pressure. The residue was purified by flash column chromatography on silica gel eluting with ethyl acetate/MeOH (1/0-2/1) to obtain 2-7 (1.36 g, 45.8% yield). LC-MS m/z: 413.0 $[M-H]^-$.

Step G: A sealed tube was charged with a mixture of 2-7 (80 mg, 0.19 mmol, 1.0 eq.), tert-butyl 3-methylenepyrrolidine-1-carboxylate (176 mg, 0.96 mmol, 5 eq.), TEA (97 mg, 0.96 mmol, 5 eq.) and $Pd(dppf)Cl_2$.DCM (16 mg, 0.019 mmol, 0.1 eq.) in dioxane (2 mL) and the resulting mixture was stirred at 100° C. under Ar for 3 h. The reaction mixture was purified by flash column chromatography on silica gel eluting with methanol/ethyl acetate (0-100%) to give crude 2-8 (97 mg, 97.4% yield). LC-MS m/z: 516.3 $[M-H]^-$.

Step H: To a mixture of 2-8 (134 mg, 0.26 mmol, 1.0 eq.) in MeOH (5 mL) was added $Pd(OH)_2/C$ (60 mg). The reaction mixture was stirred at RT for 16 h under hydrogen (30 psi), then filtered to remove the catalyst. The filtrate was concentrated under reduced pressure to give 2-9 (136 mg, crude), which was used in the next step without further purification. LC-MS m/z: 518.4 $[M-H]^-$.

Step I: To a mixture of 2-9 (68 mg, 0.16 mmol, 1.0 eq.) in DCM (1.5 mL) was added TFA (0.75 mL). After addition, the mixture was stirred at room temperature for 1 h. The mixture was quenched with MeOH carefully at −78° C., adjusted to pH=8-9 with $NH_3 \cdot H_2O$ (28% aq), and concentrated under reduced pressure. The residue was purified by prep-HPLC to afford 140 (2.84 mg, 6.6%-yield). LC-MS m/z: 328.3 $[M-H]^-$; $^1H$ NMR (400 MHZ, $CD_3OD$): δ 6.64-6.57 (m, 2H), 4.18 (s, 2H), 3.38-3.30 (m, 2H), 3.23-3.16 (m, 1H), 2.89-2.80 (m, 1H), 2.88-2.81 (m, 2H), 2.59-2.53 (m, 1H), 2.17-2.06 (m, 1H), 1.74-1.62 (m, 1H).

Example 1c: Synthesis of 5-(2-fluoro-6-hydroxy-3-(5-(1-methylcyclopropyl)-2,5-dihydro-1H-pyrrol-3-yl)phenyl)-1,2,5-thiadiazolidin-3-one 1,1-dioxide (108)

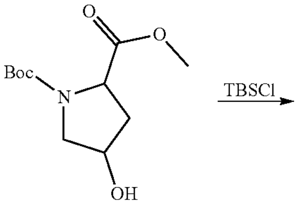

3-1

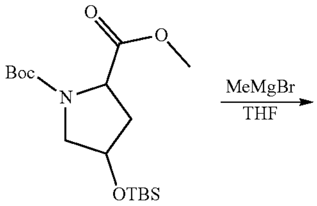

3-2

-continued

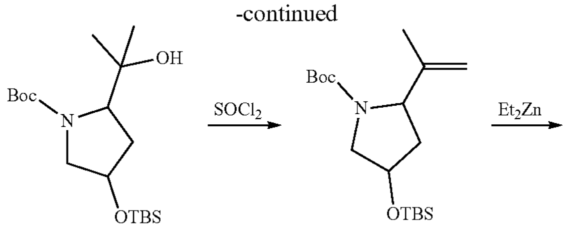

3-3

3-4

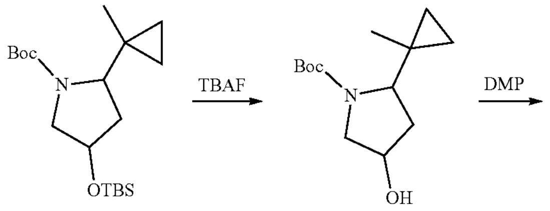

3-5

3-6

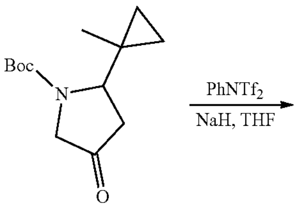

3-7

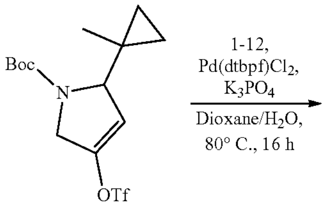

3-8

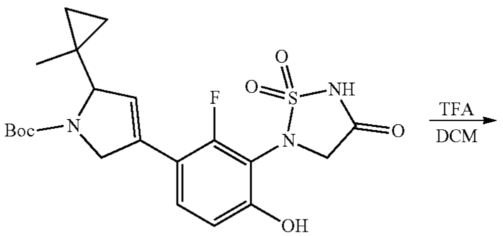

3-9

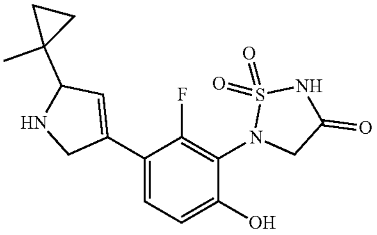

108

Step A: A mixture of 3-1 (10 g, 40.82 mmol, 1.0 eq.), imidazole (8.33 g, 122.41 mmol, 3 eq) and TBSCl (9.3 g, 61.23 mmol, 1.5 eq) in DCM (100 mL) was stirred at room temperature for 12 h. The mixture was quenched with aqueous $NH_4Cl$ solution (80 mL) and extracted with DCM (50 mL). The organic layer was dried over anhydrous $Na_2SO_4$, filtered, and concentrated under reduced pressure.

The residue was purified by flash column chromatography on silica gel eluting with PE/EA=3/1 to obtain 3-2 (12 g, 82% yield). LC-MS m/z: 360.2 $[M+H]^+$.

Step B: To a mixture of 3-2 (1 g, 2.8 mmol, 1.0 eq.) in THF (10 mL) was added MeMgBr (2.1 mL, 6.3 mmol, 2.25 eq., 3 M) dropwise at 0° C. under argon. The reaction mixture was stirred at RT under argon for 2 h, then quenched with aqueous $NH_4Cl$ solution (30 mL) and extracted with EtOAc (30 mL). The organic layer was washed with brine (30 mL), dried over anhydrous $Na_2SO_4$, filtered, and concentrated under reduced pressure. The residue was purified by flash column chromatography on silica gel eluting with PE/EA=3/1 to obtain 3-3 (300 mg, 30% yield). $^1H$ NMR (400 MHZ, $CDCl_3$): δ 5.77 (s, 1H), 4.18 (s, 1H), 4.01 (t, J=8.3 Hz, 1H), 3.68-3.55 (m, 1H), 3.18-3.05 (m, 1H), 1.96-1.84 (m, 1H), 1.62-1.53 (m, 1H), 1.41 (m, 9H), 1.07 (m, 3H), 1.00 (s, 3H), 0.81 (s, 9H), 0.00 (s, 6H).

Step C: To a mixture of 3-3 (95 mg, 0.27 mmol, 1.0 eq.) in toluene (10 mL) were added $SOCl_2$ (48 mg, 0.40 mmol, 1.5 eq.) and TEA (101 mg, 67 mmol, 3.0 eq.). The reaction mixture was stirred at RT under argon for 16 h. The mixture was concentrated under reduced pressure. The residue was purified by flash column chromatography on silica gel eluting with PE/EA=5/1 to obtain 3-4 (45 mg, 65% yield). $^1H$ NMR (400 MHZ, $CDCl_3$): δ 4.80-4.60 (m, 2H), 4.39-4.14 (m, 2H), 3.48-3.28 (m, 2H), 1.99-1.89 (m, 1H), 1.81-1.69 (m, 1H), 1.59 (s, 3H), 1.45-1.28 (m, 9H), 0.82 (s, 9H), −0.00 (s, 6H).

Step D: To a mixture of $ZnEt_2$ (0.5 mL, 1 mmol, 2 M) in DCE (2 mL) at −20° C. was added $CH_2I_2$ (508 mg, 2.20 mmol) under $N_2$. The reaction mixture was stirred at −20° C. for 10 min under $N_2$. A solution of 3-4 (100 mg, 0.29 mmol, 1.0 eq.) in DCE (1 mL) was added to the mixture at −20° C. The mixture was stirred at room temperature under $N_2$ for 4 h, then quenched with aqueous $NH_4Cl$ solution (20 mL) and extracted with EtOAc (20 mL). The organic layer was washed with brine (20 mL), dried over anhydrous $Na_2SO_4$, filtered, and concentrated under reduced pressure to give 3-5 (120 mg, crude), which was used in the next step without further purification. $^1H$ NMR (400 MHZ, $CDCl_3$): δ 4.31-4.25 (m, 1H), 3.70-3.30 (m, 2H), 3.26-3.19 (m, 1H), 1.96-1.86 (m, 2H), 1.42 (s, 9H), 0.89 (s, 3H), 0.81 (s, 9H), 0.59-0.49 (m, 1H), 0.41-0.12 (m, 3H), −0.00 (d, J=1.2 Hz, 6H).

Step E: To a mixture of 3-5 (2.1 g, 5.91 mmol, 1.0 eq.) in THF (20 mL) was added TBAF (5 mL, 5 mmol, 1 M in THF) dropwise. The mixture was stirred at room temperature for 3 h. The reaction mixture was poured into water (50 mL) and extracted with ethyl acetate (50 mL×2). The combined organic layers were washed with water (100 mL), dried over anhydrous $Na_2SO_4$, filtered, and concentrated under reduced pressure to obtain 3-6 (2 g, crude), which was used in the next step without further purification. $^1H$ NMR (400 MHZ, $CDCl_3$): δ 4.36-4.27 (m, 1H), 3.68-3.36 (m, 2H), 3.27 (dd, J=12.2, 4.0 Hz, 1H), 2.01-1.94 (m, 2H), 1.40 (s, 9H), 0.86 (s, 3H), 0.58-0.49 (m, 1H), 0.35-0.27 (m, 1H), 0.25-0.12 (m, 2H).

Step F: To a solution of 3-6 (2 g, 8.3 mmol) in DCM (20 mL) was added Dess-Martin reagent (4.57 mg, 10.78 mmol). The mixture was stirred at room temperature for 2 h, then quenched with aq. $NaHCO_3$ solution (50 mL) and extracted with DCM (3×50 mL). The combined organic layers were washed with aq. $NaHCO_3$ solution (2×100 mL), dried over anhydrous $Na_2SO_4$, filtered, and concentrated under reduced pressure. The residue was purified by flash column chromatography on silica gel eluting with PE/EA=4/1 to give 3-7 (680 mg, 34% yield). $^1H$ NMR (400 MHZ, $CDCl_3$): δ 3.96-3.72 (m, 2H), 3.59-3.51 (m, 1H), 2.73-2.62 (m, 1H), 2.41-2.32 (m, 1H), 1.40 (s, 9H), 0.87 (s, 3H), 0.70-0.55 (m, 1H), 0.35-0.12 (m, 3H). Alternatively, 3-7 can be prepared in an enantioselective process and/or using one or more chiral building blocks to provide a single enantiomer (for example, according to the general procedure in Example 11), or the two enantiomers can be separated using chiral SFC.

Step G: To a solution of 3-7 (480 mg, 2.0 mmol, 1.0 eq.) in THF (8 mL) at 0° C. was added NaH (201 mg, 5.02 mmol, 2.5 eq, 60% in mineral oil) under $N_2$. The mixture was stirred at 0° C. for 30 min under $N_2$. $PhNTf_2$ (1.43 g, 4.02 mmol, 2.0 eq) was added to the mixture and the resulting mixture was stirred at room temperature for 3 h. The mixture was quenched with aq. $NH_4Cl$ solution (20 mL) and extracted with EA (2×20 mL). The combined organic layers were dried over anhydrous $Na_2SO_4$, filtered, and concentrated under reduced pressure to give 3-8 (600 mg, crude), which was used in the next step without further purification.

Step H: To a solution of 3-8 (200 mg, 0.53 mmol, 1.0 eq.), 1-12 (200 mg, 0.53 mmol, 1.0 eq.) and $K_3PO_4$ (342 mg, 1.61 mmol, 3.0 eq.) in dioxane (4 mL) and $H_2O$ (1 mL) was added $PdCl_2$ (dtbpf)(35 mg, 0.054 mmol, 0.1 eq.). The mixture was stirred at 90° C. under argon for 16 h. The reaction mixture was cooled and concentrated in vacuo. The residue was purified by flash column chromatography on silica gel eluting with PE in EtOAc (0-30%) to obtain 3-9 (180 mg, 72% yield). LC-MS m/z: 466.2 $[M-H]^-$.

Step I: To a solution of 3-9 (200 mg, 0.28 mmol, 1.0 eq.) in anhydrous DCM (2 mL) was added TFA (1 mL) dropwise at 0° C. After addition, the mixture was stirred at room temperature for 2 h. The reaction mixture was adjusted to pH=8-9 with $NH_3{\cdot}H_2O$ at 0° C., then concentrated under reduced pressure. The residue was purified by prep-HPLC to obtain 108 (20.5 mg, 10% yield). LC-MS m/z: 366.1 $[M-H]^-$; $^1H$ NMR (400 MHZ, DMSO-$d_6$): δ 7.31 (t, J=8.5 Hz, 2H), 6.74 (d, J=8.6 Hz, 1H), 6.12 (s, 1H), 4.32 (s, 2H), 4.17-4.13 (m, 1H), 3.98 (s, 2H), 1.08 (s, 3H), 0.70-0.60 (m, 2H), 0.54-0.44 (m, 2H).

Example 1d: Synthesis of (R)-5-(3-(5-(3,3-dimethylbutyl)-2,5-dihydro-1H-pyrrol-3-yl)-2-fluoro-6-hydroxyphenyl)-1,2,5-thiadiazolidin-3-one 1,1-dioxide (110) and(S)-5-(3-(5-(3,3-dimethylbutyl)-2,5-dihydro-1H-pyrrol-3-yl)-2-fluoro-6-hydroxyphenyl)-1,2,5-thiadiazolidin-3-one 1,1-dioxide (120)

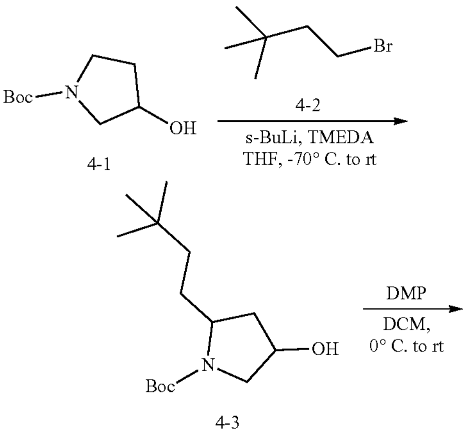

-continued

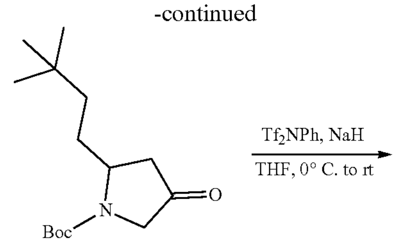

4-4

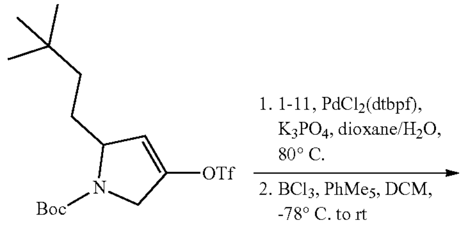

4-5

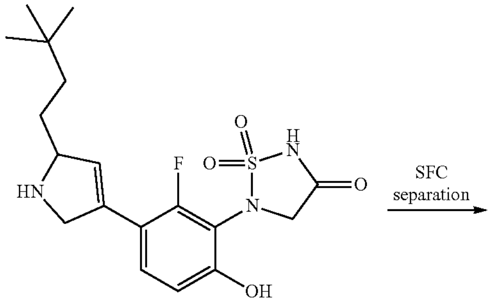

4-6

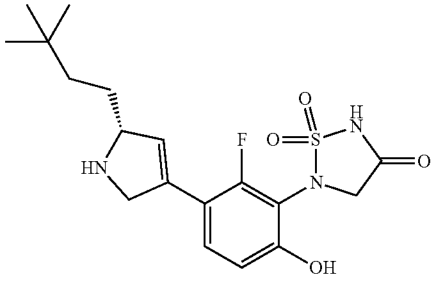

110

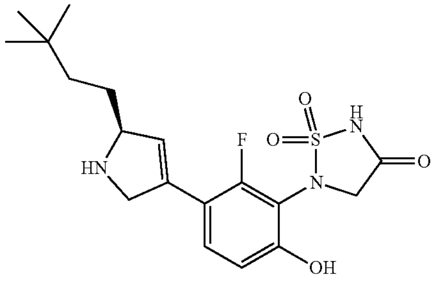

120

Step A: To a solution of 4-1 (3.00 g, 16.04 mmol, 1.0 eq) in THF (80 mL) at −70° C. was added TMEDA (3.70 g, 32.08 mmol, 2.0 eq) under argon. The mixture was stirred at −70° C. for 10 min, then s-BuLi (1.3 M in hexane, 49.4 mL, 64.16 mmol, 4.0 eq) was added dropwise at −70° C.~−65° C. under argon. After stirring at −70° C.~−65° C. for 2 h, a solution of 4-2 (5.80 g, 35.29 mmol, 2.2 eq) in THF (20 mL) was added dropwise. The mixture was allowed to warm to room temperature and stirred at RT for 15 h. This mixture was quenched with aq. $NH_4Cl$ solution (150 mL) and extracted with EtOAc (100 mL×3). The combined organic layers were washed with brine (150 mL), dried over anhydrous $Na_2SO_4$, and concentrated in vacuo. The residue was purified by flash column chromatography on silica gel eluting with EtOAc in petroleum ether (0-30%) to obtain 4-3 (1.63 g, 37% yield). LC-MS m/z: 257.3 $[M+H]^+$.

Step B: To a solution of 4-3 (600 mg, 2.21 mmol, 1.0 eq) in DCM (15 mL) at 0° C. was added DMP (1.40 g, 3.32 mmol, 1.5 eq) and the resulting mixture was stirred at RT for 2 h. The reaction mixture was treated with aq. $NaHCO_3$ solution (100 mL) and extracted with DCM (40 mL×3). The combined organic layers were washed with brine (80 mL), dried over anhydrous $Na_2SO_4$, filtered, and concentrated in vacuo. The residue was purified by flash column chromatography on silica gel eluting with EtOAc in petroleum ether (0-20%) to obtain 4-4 (250 mg, 42% yield). LC-MS m/z: 255.2 $[M+H+CH_3CN-56]^+$. Alternatively, 4-4 can be prepared in an enantioselective process and/or using one or more chiral building blocks to provide a single enantiomer (for example, according to the general procedure in Example 11), or the two enantiomers can be separated using chiral SFC.

Step C: To a solution of 4-4 (250 mg, 0.93 mmol, 1.0 eq) in THF (5 mL) at 0° C. was added NaH (60% w/w, 76 mg, 2.79 mmol, 3.0 eq) in portions. The mixture was stirred at 0° C. for 1 h, then $Tf_2NPh$ (498 mg, 1.40 mmol, 1.5 eq) was added. The mixture was stirred at RT for 2 h, then quenched with water (40 mL) and extracted with EtOAc (20 mL×3). The combined organic layers were washed with brine (40 mL), dried over anhydrous $Na_2SO_4$, and concentrated in vacuo to obtain 4-5 (400 mg, crude), which was used directly in the next step without further purification.

Step D: To a mixture of 4-5 (200 mg, 0.49 mmol, 1.0 eq), 1-11 (230 mg, 0.49 mmol, 1.0 eq) and $K_3PO_4$ (311 mg, 1.47 mmol, 3 eq) in dioxane/$H_2O$ (8 mL/1 mL) was added $PdCl_2$ (dtbpf)(32 mg, 0.05 mmol, 0.1 eq). The mixture was stirred at 80° C. under argon for 16 h. The reaction mixture was concentrated in vacuo and the residue was purified by flash column chromatography on silica gel eluting with MeOH in EtOAc (0-30%) to obtain tert-butyl 4-(4-(benzyloxy)-3-(1,1-dioxido-4-oxo-1,2,5-thiadiazolidin-2-yl)-2-fluorophenyl)-2-(3,3-dimethylbutyl)-2,5-dihydro-1H-pyrrole-1-carboxylate (260 mg, 90% yield). LC-MS m/z: 586.6 $[M-H]^-$.

Step E: To a mixture of tert-butyl 4-(4-(benzyloxy)-3-(1,1-dioxido-4-oxo-1,2,5-thiadiazolidin-2-yl)-2-fluorophenyl)-2-(3,3-dimethylbutyl)-2,5-dihydro-1H-pyrrole-1-carboxylate (260 mg, 0.44 mmol, 1.0 eq) and $PhMe_5$ (197 mg, 1.33 mmol, 3.0 eq) in DCM (12 mL) at −70° C. was added $BCl_3$ (1 M in DCM, 6 mL, 6 mmol, 13.6 eq) dropwise under argon. After addition, the mixture was stirred at RT for 2 h, then concentrated in vacuo at RT. The residue was diluted with DCM (5 mL) and cooled to −70° C., then quenched carefully with methanol (15 mL), adjusted to pH 8 with $NH_3$/MeOH (7 M) and concentrated in vacuo. The residue was purified by prep-HPLC ($CH_3CN/H_2O$+0.1% $NH_4HCO_3$) to obtain 4-6 (6.5 mg, 3.7% yield). LC-MS m/z: 396.3 $[M-H]^-$; $^1H$ NMR (400 MHZ, DMSO-$d_6$): δ 7.25 (t, J=8.4 Hz, 1H), 6.72 (d, J=8.4 Hz, 1H), 6.25 (s, 1H), 4.40 (t, J=7.2 Hz, 1H), 4.28 (d, J=7.2 Hz, 2H), 3.97 (s, 2H), 1.73-1.66 (m, 2H), 1.30 (dd, J=12.0, 5.2 Hz, 2H), 0.89 (s, 9H).

Step F: Compound 4-6 was separated by chiral SFC (flow rate: 1.5 mL/min, 40% MeOH with 0.1% DEA and 60% $CO_2$, DAICELCHIRALPAK® IC column) to give two enantiomers, which were further purified separately by reverse phase C18 column chromatography eluting with $H_2O$:MeCN=0~22% with formic acid to give 110 and 120. 110: LC-MS m/z: 398.1 $[M+H]^+$; $^1H$ NMR (400 MHZ, DMSO-$d_6$): δ 7.26 (t, J=8.6 Hz, 1H), 6.73 (d, J=8.6 Hz, 1H), 6.25 (s, 1H), 4.47-4.39 (m, 1H), 4.37-4.25 (m, 2H), 3.98 (s, 2H), 1.76-1.67 (m, 2H), 1.34-1.27 (m, 2H), 0.90 (s, 9H). 120: LC-MS m/z: 398.1 $[M+H]^+$; $^1H$ NMR (400 MHZ, DMSO-$d_6$): δ 7.26 (t, J=8.7 Hz, 1H), 6.73 (d, J=8.6 Hz, 1H), 6.26 (s, 1H), 4.44-4.38 (m, 1H), 4.34-4.24 (m, 2H), 3.98 (s, 2H), 1.74-1.66 (m, 2H), 1.35-1.27 (m, 2H), 0.90 (s, 9H).

Example 1e: Synthesis of 5-(2-fluoro-6-hydroxy-3-(2,3,5,7a-tetrahydro-1H-pyrrolizin-6-yl)phenyl)-1,2,5-thiadiazolidin-3-one 1,1-dioxide (139)

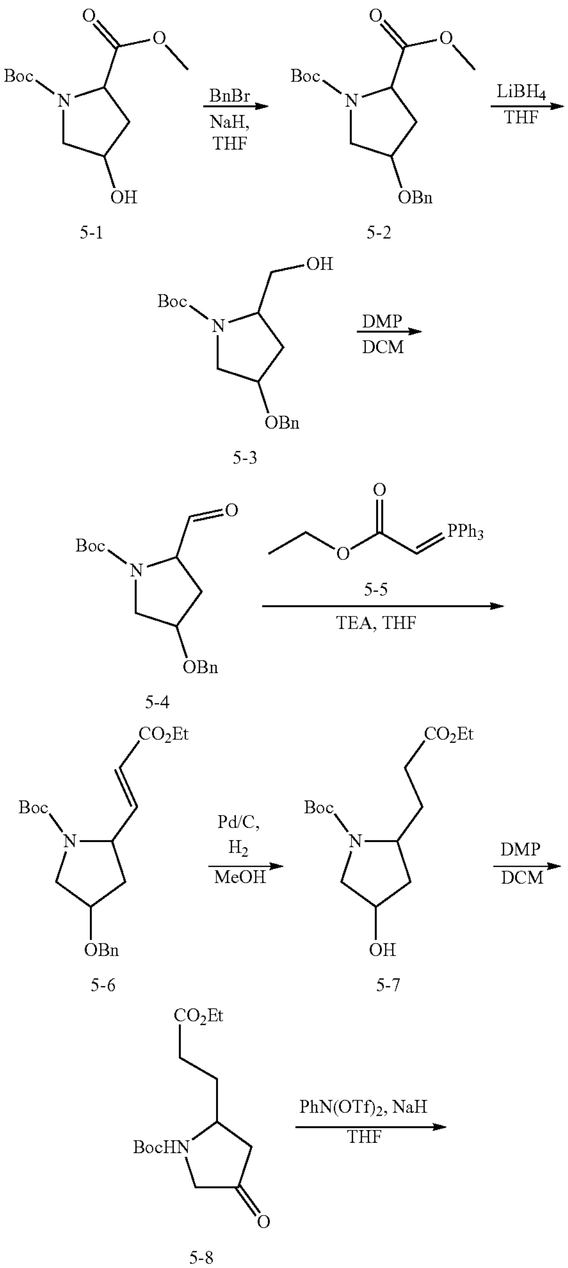

5-1 5-2 5-3 5-4 5-6 5-7 5-8

-continued

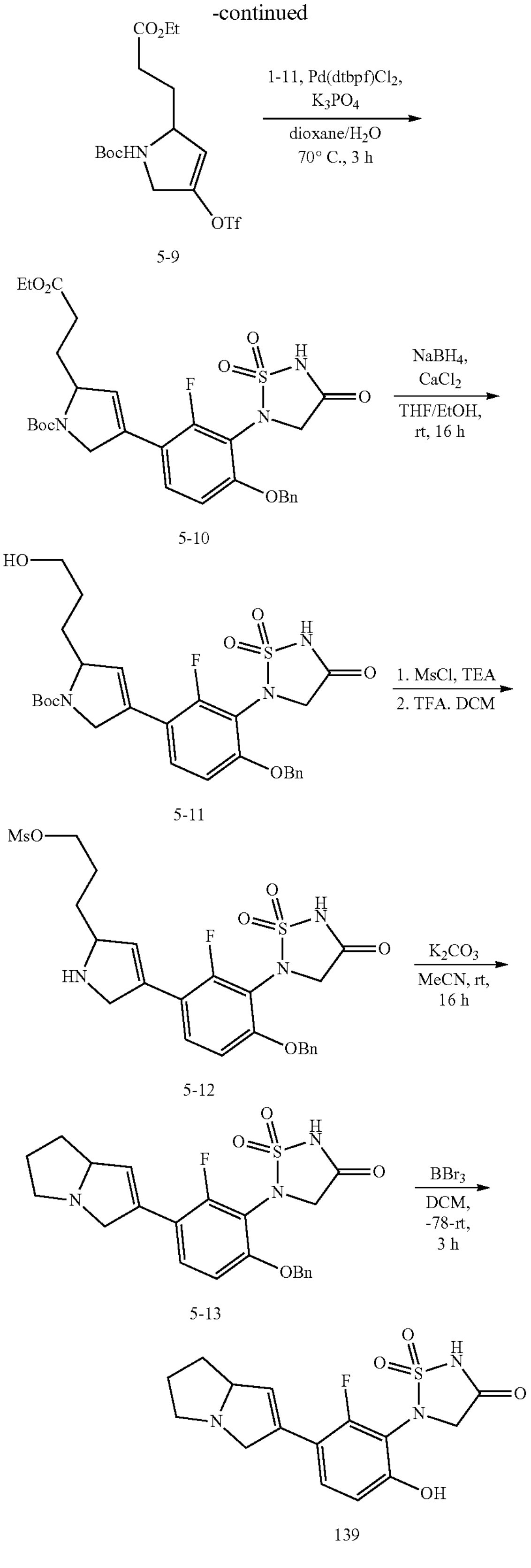

5-9 5-10 5-11 5-12 5-13 139

Step A: To a solution of 5-1 (25 g, 102 mmol) in THF (250 mL) was added NaH (5.3 g, 132.6 mmol, 60% in mineral oil) at 0° C. under nitrogen and the resulting mixture was stirred at 0° C. for 1 h under nitrogen. BnBr (19 g, 8112.2 mmol) was added to the mixture at 0° C., then the mixture stirred at 25° C. for 12 h. The mixture was quenched with aqueous $NH_4Cl$ solution (100 mL) and extracted with EA (100 mL×3). The combined organic layers were dried over anhydrous $Na_2SO_4$, filtered, and concentrated under reduced pressure. The residue was purified by flash column chromatography on silica gel eluting with PE:EA=3/1 to give 5-2 (24.5 g, 71.5% yield). LC-MS m/z: 336.2 $[M+H]^+$.

Step B: To a solution of 5-2 (24.5 g, 73.1 mmol) in THF (250 mL) was added $LiBH_4$ (2.4 g, 109.7 mmol) at 0° C. under nitrogen, then the mixture was stirred at 25° C. for 12 h. The mixture was quenched with aqueous $NH_4Cl$ solution (100 mL) and extracted with EA (100 mL×3). The combined organic layers were dried over anhydrous $Na_2SO_4$, filtered, and concentrated under reduced pressure to give 5-3 (22 g, crude), which was used in the next step without further purification. LC-MS m/z: 308.2 $[M+H]^+$.

Step C: To a solution of 5-3 (22 g, 71.6 mmol) in DCM (220 mL) was added DMP (45 g, 107 mmol) at 0° C., and the mixture was stirred at 25° C. for 3 h. The reaction was quenched with aqueous $NaHCO_3$ solution (100 mL) and filtered. The filtrate was extracted with DCM (100 mL×3), then the combined organic layers were dried over anhydrous $Na_2SO_4$, filtered, and concentrated under reduced pressure. The residue was purified by flash column chromatography on silica gel eluting with PE:EA=3/1 to give 5-4 (16 g, 72% yield). LC-MS m/z: 206.2 $[M+H-100]^+$.

Step D: To a mixture of 5-4 (5 g, 16.39 mmol, 1 eq) and TEA (8.29 g, 81.97 mmol, 5 eq) in THF (40 mL) was added 5-5 (8.57 g, 24.59 mmol, 1.5 eq) at 0° C., and the resulting mixture was stirred 25° C. for 16 h under nitrogen. The mixture was quenched with $H_2O$ (50 mL) and extracted with EA (50 mL×3). The combined organic layers were dried over anhydrous $Na_2SO_4$, filtered, and concentrated under reduced pressure. The residue was purified by flash column chromatography on silica gel eluting with PE:EA=0-30% to give 5-6 (4.36 g, 70.9% yield). LC-MS m/z: 276.2 $[M+H-100]^+$.

Step E: To a solution of 5-6 (4.36 g, 11.63 mmol, 1 eq) in MeOH (20 mL) was added dry Pd/C (300 mg). The mixture was stirred at 40° C. for 48 h under $H_2$ (30 psi), then filtered and the filter cake washed with MeOH (30 mL). The filtrate was concentrated under reduced pressure to obtain crude 5-7 (3 g), which was used in the next step without further purification. LC-MS m/z: 288.2 $[M+H]^+$.

Step F: To a solution of 5-7 (3 g, 10.45 mmol, 1 eq) in DCM (40 mL) was added Dess-Martin reagent (13.3 g, 31.36 mmol, 3 eq) at 0° C., then the mixture was stirred 25° C. for 16 h. The reaction was quenched with aqueous $NaHCO_3$ solution (50 mL) and filtered. The filtrate was extracted with DCM (50 mL×3). The combined organic layers were dried over anhydrous $Na_2SO_4$, filtered, and concentrated under reduced pressure. The residue was purified by flash column chromatography on silica gel eluting with PE:EA=0-30% to give 5-8 (1.98 g, 66.5% yield). LC-MS m/z: 186.1 $[M+H-100]^+$. Alternatively, 5-8 can be prepared in an enantioselective process and/or using one or more chiral building blocks to provide a single enantiomer (for example, according to the general procedure in Example 11), or the two enantiomers can be separated using chiral SFC.

Step G: To a solution of 5-8 (1.98 g, 6.39 mmol, 1 eq) in THF (40 mL) was added NaH (556 mg, 13.9 mmol, 2 eq, 60% in mineral oil) at 0° C. under nitrogen. The reaction mixture was stirred at 0° C. for 1 h, then $PhN(OTf)_2$ (3.73 g, 10.43 mmol, 1.5 eq) was added at 0° C. The mixture was stirred 25° C. for 2 h under nitrogen, then quenched with aqueous $NH_4Cl$ solution (50 mL) and extracted with EA (50 mL×3). The combined organic layers were dried over anhydrous $Na_2SO_4$, filtered, and concentrated under reduced pressure to obtain 5-9 (5 g, crude), which was used in the next step without further purification. LC-MS m/z: 418.1 $[M+H]^+$.

Step H: To a mixture of 5-9 (1.0 g, 2.4 mmol, 1.0 eq.), 1-11 (550 mg, 1.2 mmol, 0.5 eq.) and $K_3PO_4$ (1.5 g, 7.2 mmol, 3.0 eq.) in dioxane (20 mL) and water (3 mL) was added Pd(dtbpf) $Cl_2$ (155 mg, 0.24 mmol, 0.1 eq.) under nitrogen. The reaction mixture was stirred at 70° C. under nitrogen for 3 h, then filtered and concentrated under reduced pressure. The residue was purified by flash column chromatography on silica gel eluting with ethyl acetate/MeOH (1/0-5/1) to obtain 5-10 (300 mg, 21% yield). LC-MS m/z: 602.2 $[M-H]^-$.

Step I: To a mixture of 5-10 (300 mg, 0.5 mmol, 1.0 eq.) and $CaCl_2$ (555 mg, 5.0 mmol, 10.0 eq.) in THF (3 mL) and EtOH (3 mL) was added $NaBH_4$ (152 mg, 4.0 mmol, 8.0 eq.) at 0° C. under nitrogen. The reaction mixture was stirred at RT under nitrogen for 16 h. The reaction mixture was diluted with EtOAc (10 mL) and washed with $H_2O$ (2×10 mL), dried over anhydrous $Na_2SO_4$, filtered, and concentrated under reduced pressure. The residue was purified by flash column chromatography on silica gel eluting with ethyl acetate/MeOH (1/0-4/1) to obtain 5-11 (150 mg, 54% yield). LC-MS m/z: 560.2 $[M-H]^-$.

Step J: To a mixture of 5-11 (150 mg, 0.27 mmol, 1.0 eq.) and TEA (135 mg, 1.34 mmol, 5.0 eq.) in DCM (3 mL) was added MsCl (77 mg, 0.4 mmol, 1.5 eq.) at 0° C. under nitrogen. The reaction mixture was stirred at RT under nitrogen for 2 h, then diluted with DCM (10 mL), washed with $H_2O$ (2×10 mL), dried over anhydrous $Na_2SO_4$, filtered, and concentrated under reduced pressure. The residue was purified by flash column chromatography on silica gel eluting with ethyl acetate/MeOH (1/0-6/1) to obtain tert-butyl 4-(4-(benzyloxy)-3-(1,1-dioxido-4-oxo-1,2,5-thiadiazolidin-2-yl)-2-fluorophenyl)-2-(3-((methylsulfonyl)oxy) propyl)-2,5-dihydro-1H-pyrrole-1-carboxylate (150 mg, 87.8% yield). LC-MS m/z: 638.3 $[M-H]^-$.

Step K: To a solution of tert-butyl 4-(4-(benzyloxy)-3-(1,1-dioxido-4-oxo-1,2,5-thiadiazolidin-2-yl)-2-fluorophenyl)-2-(3-((methylsulfonyl)oxy) propyl)-2,5-dihydro-1H-pyrrole-1-carboxylate (50 mg, 0.08 mmol, 1.0 eq.) in DCM (2 mL) was added TFA (0.5 mL). The mixture was stirred at rt for 1 h, then concentrated under reduced pressure to give 5-12 (45 mg, crude), which was used in the next step without further purification. LC-MS m/z: 538.0 $[M-H]^-$.

Step L: A mixture of 5-12 (45 mg, 0.08 mmol, 1.0 eq.) and $K_2CO_3$ (69 mg, 0.5 mmol, 6.0 eq.) in MeCN (2 mL) was stirred at RT under nitrogen for 16 h. The reaction mixture was filtered and concentrated under reduced pressure to obtain 5-13 (30 mg, 81.1% yield), which was used in the next step without further purification. LC-MS m/z: 444.0 $[M+H]^+$.

Step M: To a mixture of 5-13 (45 mg, 0.1 mmol, 1.0 eq.) in DCM (2 mL) was added $BBr_3$ (0.5 mL) at −78° C. After addition, the mixture was stirred at RT for 3 h under nitrogen, then quenched by dropwise addition of $NH_3$:$H_2O$ at −78° C. to pH~8. The reaction mixture was filtered and concentrated. The residue was purified by prep-HPLC (TFA) to obtain 139 (1.3 mg, 4% yield). LC-MS m/z: 354.0 $[M+H]^+$; $^1H$ NMR (400 MHZ, DMSO-$d_6$): δ 10.54 (s, 1H), 9.96 (s, 1H), 7.21 (t, J=8.4 Hz, 1H), 6.73 (d, J=9.2 Hz, 1H), 6.16 (s, 1H), 5.12-4.99 (m, 1H), 4.74-4.61 (m, 1H), 4.42-

4.32 (m, 1H), 3.96 (s, 2H), 3.66-3.49 (m, 1H), 3.44-3.36 (m, 1H), 2.25-2.19 (m, 1H), 2.06-1.85 (m, 3H).
Example 1f: Synthesis of(S)-1-(isobutyryloxy)ethyl (R)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate (161) and (R)-1-(isobutyryloxy)ethyl (R)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate (143)
4-1
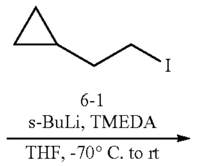
6-1
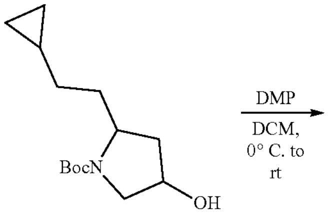
6-2
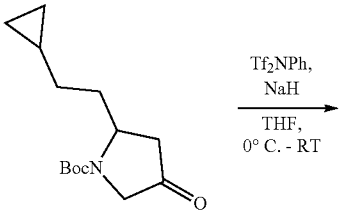
6-3
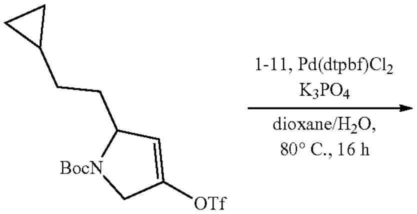
6-4
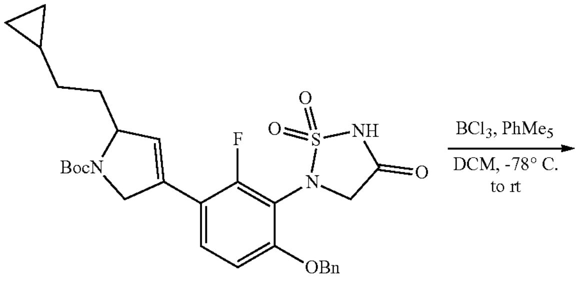
6-5
-continued
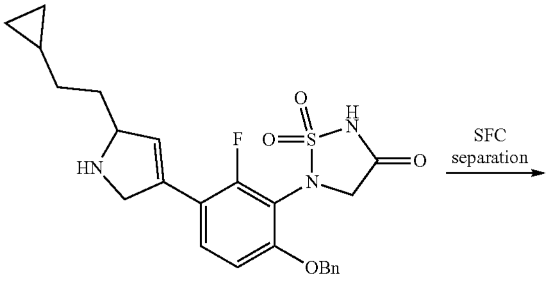
6-6
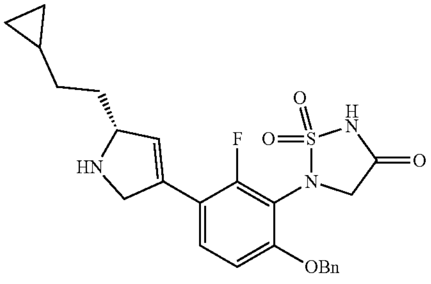
113
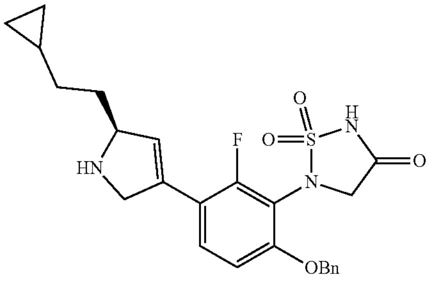
130
113
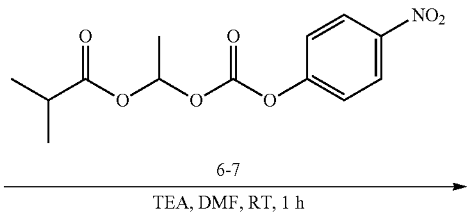
6-7
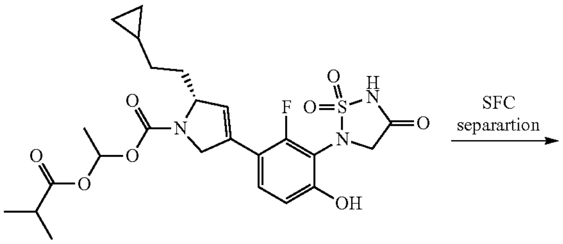
111

-continued

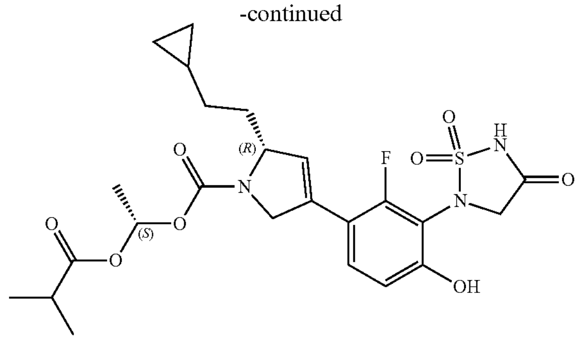

161

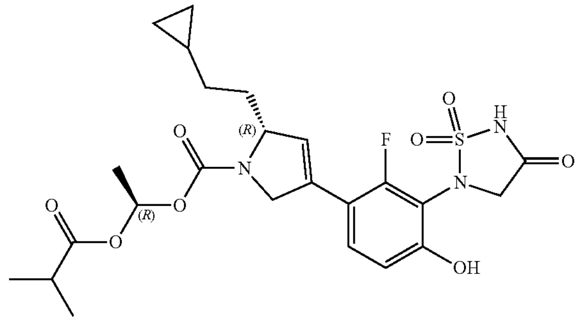

143

Step A: To a solution of 4-1 (600 mg, 3.2 mmol, 1.0 eq) in THF (8 mL) at −78° C. was added TMEDA (930 mg, 80.2 mmol, 2.5 eq), then sec-BuLi (10 mL, 128.4 mmol, 4 eq, 1.3 M) was added dropwise over 10 min under nitrogen. After stirring for 2.5 h at −78° C. under $N_2$, a solution of 6-1 (1.38 g, 7.1 mmol, 2.2 eq) in THF (2 mL) was added and the mixture stirred an additional 30 minutes at −78° C. The mixture was allowed to warm to 25° C. and stirred overnight, then quenched with aqueous $NH_4Cl$ solution (20 mL) and extracted with EtOAc (20 mL×3). The combined organic layers were dried over $Na_2SO_4$, filtered, and concentrated under vacuum. The residue was purified by flash column chromatography on silica gel eluting with PE/EtOAc=0-30% to give 6-2 (250 mg, 31% yield). LC-MS m/z: 256.3 $[M+H]^+$.

Step B: To a solution of 6-2 (250 mg, 0.1 mmol, 1.0 eq) in DCM (5 mL) was added Dess-Martin reagent (848 mg, 0.2 mmol, 2.0 eq). The mixture was stirred at 25° C. for 2 h, then quenched with aqueous $NaHCO_3$ solution (10 mL) and extracted with DCM (10 mL×2). The combined organic layers were dried over $Na_2SO_4$, filtered, and concentrated under vacuum. The residue was purified by flash column chromatography on silica gel eluting with PE/EtOAc=0-15% to give 6-3 (180 mg, 73% yield). LC-MS m/z: 239.2 $[M+H-56+CH_3CN]^+$. Alternatively, 6-3 can be prepared in an enantioselective process and/or using one or more chiral building blocks to provide a single enantiomer (for example, according to the general procedure in Example 11), or the two enantiomers can be separated using chiral SFC.

Step C: To a solution of 6-3 (180 mg, 0.71 mmol, 1.0 eq) in THF (4 mL) at 0° C. was added NaH (57 mg, 1.42 mmol, 2.0 eq, 60% wt) and the resulting mixture was stirred for 1 h at 25° C. under nitrogen. The mixture was cooled to 0° C., then a solution of $Tf_2NPh$ (381 mg, 1.07 mmol, 1.5 eq) in THF (1 mL) was added and the resulting mixture was allowed to warm to 25° C. and stirred for 2 h. The reaction was quenched with ice-water (8 mL) and extracted with EtOAc (8 mL×3). The combined organic layers were dried over $Na_2SO_4$, filtered, and concentrated under vacuum to give 6-4 (110 mg, crude), which was used in the next step without further purification.

Step D: To a mixture of 6-4 (110 mg, 0.29 mmol, 1.0 eq), 1-11 (79 mg, 0.17 mmol, 0.6 eq.) and $K_3PO_4$ (180 mg, 0.85 mmol, 3 eq.) in dioxane (5 mL) and $H_2O$ (1 mL) was added Pd(dtbpf) $Cl_2$ (20 mg, 0.029 mmol, 0.1 eq.) under nitrogen. The reaction mixture was stirred at 70° C. under nitrogen for 2 h, then concentrated under reduced pressure. The residue was purified by flash column chromatography on silica gel eluting with EA/MeOH (1/0-4/1) to give 6-5 (80 mg, 34% purity). LC-MS m/z: 570.2 $[M-H]^-$.

Step E: To a solution of 6-5 (80 mg, 0.14 mmol, 1.0 eq) and $PhMe_5$ (62 mg, 0.42 mmol, 3.0 eq) in DCM (2 mL) was added $BCl_3$ (0.5 mL). The mixture was stirred at 25° C. for 2 h, then quenched by addition of $NH_3$:$H_2O$ dropwise at −78° C. to pH~8. The mixture was filtered and concentrated, and the residue was purified by prep-HPLC to give 6-6 (2.13 mg). LC-MS m/z: 380.3 $[M-H]^-$.

Step F: Compound 6-6 was separated by chiral SFC (C6 IC column) following the general procedure in Example 1d (Step F) to give two enantiomers, 113 and 130. 113: LC-MS m/z: 380.2 $[M-H]^-$; $^1H$ NMR (400 MHZ, DMSO-$d_6$): δ 10.1-8.80 (br, 3H), 7.26 (t, J=8.6 Hz, 1H), 6.72 (d, J=8.6 Hz, 1H), 6.24 (s, 1H), 4.54-4.47 (m, 1H), 4.36-4.24 (m, 2H), 3.97 (s, 2H), 1.87-1.77 (m, 2H), 1.38-1.27 (m, 2H), 0.78-0.65 (m, 1H), 0.46-0.38 (m, 2H), 0.11-0.04 (m, 2H). 130: LC-MS m/z: 380.2 $[M-H]^-$; $^1H$ NMR (400 MHz, DMSO-$d_6$): δ 10.4-8.70 (m, 3H), 7.26 (t, J=8.6 Hz, 1H), 6.72 (d, J=8.6 Hz, 1H), 6.24 (s, 1H), 4.54-4.45 (m, 1H), 4.35-4.23 (m, 2H), 3.97 (s, 2H), 1.87-1.77 (m, 2H), 1.36-1.28 (m, 2H), 0.77-0.67 (m, 1H), 0.46-0.38 (m, 2H), 0.11-0.04 (m, 2H).

Step G: To a solution of 113 (50 mg, 0.13 mmol) and 6-7 (39.0 mg, 0.13 mmol) in DMF (2 mL) was added TEA (40.0 mg, 0.39 mmol). The mixture was stirred at RT for 1 h, then purified by prep-HPLC to obtain 111 (54.6 mg). LC-MS m/z: 538.2 $[M-H]^-$; $^1H$ NMR (400 MHZ, DMSO-$d_6$): δ 9.78 (s, 1H), 7.25-7.15 (m, 1H), 6.75-6.66 (m, 2H), 6.21-6.11 (m, 1H), 4.73-4.61 (m, 1H), 4.54-4.28 (m, 2H), 3.97 (s, 2H), 2.60-2.51 (m, 1H), 1.97-1.69 (m, 2H), 1.46 (t, J=4.8 Hz, 3H), 1.23-1.05 (m, 8H), 0.70-0.58 (m, 1H), 0.42-0.32 (m, 2H), 0.01-0.06 (m, 2H).

Step H: Compound 111 (200 mg) was separated by SFC separation to give two diastereomers, which were further purified by prep-HPLC to obtain 161 (30.8 mg) and 143 (37.6 mg). 161: LC-MS m/z: 538.2 $[M-H]^-$; $^1H$ NMR (400 MHZ, DMSO-$d_6$): δ 9.83 (s, 1H), 7.28-7.15 (m, 1H), 6.76-6.65 (m, 2H), 6.24-6.10 (m, 1H), 4.74-4.61 (m, 1H), 4.48-4.28 (m, 2H), 3.98 (s, 2H), 2.60-2.54 (m, 1H), 1.96-1.69 (m, 2H), 1.46 (t, J=4.8 Hz, 3H), 1.22-1.04 (m, 8H), 0.70-0.58 (m, 1H), 0.42-0.31 (m, 2H), 0.02-0.06 (m, 2H). 143: LC-MS m/z: 538.2 $[M-H]^-$; $^1H$ NMR (400 MHZ, DMSO-$d_6$): δ 9.82 (s, 1H), 7.27-7.15 (m, 1H), 6.75-6.66 (m, 2H), 6.20-6.13 (m, 1H), 4.72-4.61 (m, 1H), 4.54-4.29 (m, 2H), 3.98 (s, 2H), 2.59-2.53 (m, 1H), 1.92-1.74 (m, 2H), 1.50-1.43 (m, 3H), 1.22-1.04 (m, 8H), 0.71-0.58 (m, 1H), 0.41-0.32 (m, 2H), 0.02-0.05 (m, 2H).

Example 1g: Synthesis of 3-(1,1-dioxido-4-oxo-1,2,5-thiadiazolidin-2-yl)-2-fluoro-4-hydroxy-N-(pyrrolidin-3-yl)benzamide (136)

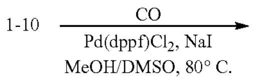

-continued

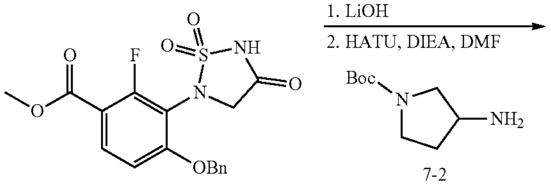

7-1

7-2

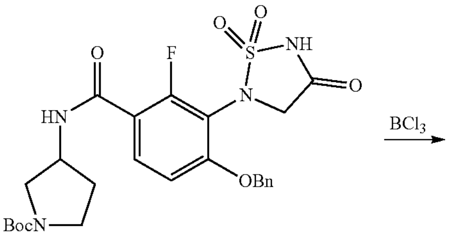

7-3

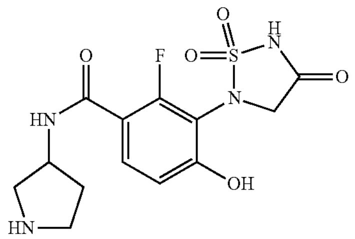

136

Step A: To a mixture of 1-10 (100 mg, 0.24 mmol, 1.0 eq) in MeOH (2 mL) and DMSO (2 ml) were added NaI (35 mg, 0.24 mmol, 1.0 eq), TEA (73 mg, 0.72 mmol, 3.0 eq) and $Pd(dppf)Cl_2$ (17.6 mg, 0.024 mmol, 0.1 eq). The reaction mixture was stirred at 80° C. for 16 h under CO (50 psi), then concentrated under vacuum. The residue was purified by flash column chromatography on silica gel eluting with MeOH/EA=1:5 to obtain 7-1 (60 mg, 63.2% yield). LC-MS m/z: 393.2 $[M-H]^-$.

Step B: To a mixture of 7-1 (60 mg, 0.15 mmol, 1.0 eq) in MeOH (6 mL) and $H_2O$ (1.5 ml) was added $LiOH{\cdot}H_2O$ (10 mg, 0.30 mmol, 2.0 eq). The reaction mixture was stirred at rt for 72 h, then concentrated under vacuum. The residue was purified by flash column chromatography on silica gel eluting with MeOH/EA=1:5 to obtain 4-(benzyloxy)-3-(1,1-dioxido-4-oxo-1,2,5-thiadiazolidin-2-yl)-2-fluorobenzoic acid (50 mg, 86.4% yield). LC-MS m/z: 379.2 $[M-H]^-$.

Step C: To a mixture of 4-(benzyloxy)-3-(1,1-dioxido-4-oxo-1,2,5-thiadiazolidin-2-yl)-2-fluorobenzoic acid (50 mg, 0.13 mmol, 1.0 eq) in DMF (1 mL) were added 7-2 (36 mg, 0.19 mmol, 1.5 eq), DIEA (249 mg, 0.65 mmol, 5.0 eq) and HATU (22 mg, 0.17 mmol, 1.3 eq). The reaction mixture was stirred at 80° C. for 16 h, then concentrated under vacuum. The residue was purified by flash column chromatography on silica gel eluting with MeOH/EA=1:5 to obtain 7-3 (50 mg, 69.3% yield). LC-MS m/z: 547.4 $[M-H]^-$.

Step D: To a mixture of 7-3 (100 mg, 0.18 mmol, 1.0 eq) in DCM (3 mL) were added $PhMe_5$ (80 mg, 0.54 mmol, 3.0 eq) and $BCl_3$ (0.5 ml) at −78° C. under nitrogen. The reaction mixture was stirred at rt for 3 h, then quenched with MeOH (12 mL) at −70° C. and adjusted to pH=8-9 with $NH_3{\cdot}H_2O$. The mixture was concentrated under reduced pressure. The residue was purified by prep-HPLC ($CH_3CN/H_2O$+0.1% $NH_4HCO_3$) to obtain 136 (31 mg, 47% yield). LC-MS m/z: 357.2 $[M-H]^-$; $^1H$ NMR (400 MHZ, $CD_3OD$): δ 7.63 (t, J=8.5 Hz, 1H), 6.81 (d, J=8.8 Hz, 1H), 4.62-4.54 (m, 2H), 4.28 (s, 2H), 3.58-3.49 (m, 2H), 2.44-2.33 (m, 1H), 2.20-2.10 (m, 1H).

Example 1h: Synthesis of 5-(2-fluoro-6-hydroxy-3-(pyrrolidin-3-yloxy)phenyl)-1,2,5-thiadiazolidin-3-one 1,1-dioxide (142)

1-10

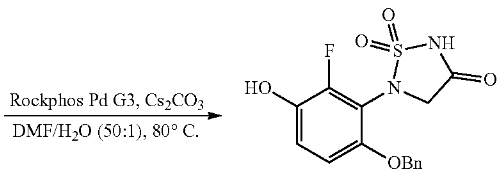

8-1

4-1

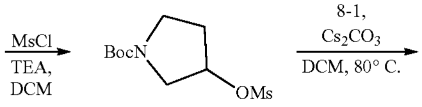

8-2

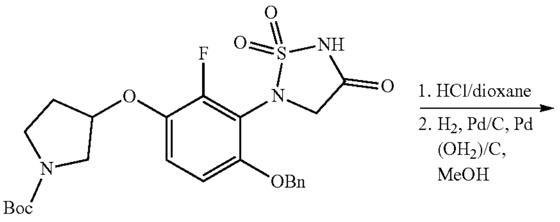

8-3

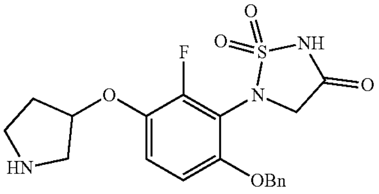

142

Step A: To a solution of 1-10 (250 mg, 0.60 mmol, 1.0 eq) in $DMF/H_2O$ (50:1, 3.06 mL) were added Rockphos Pd G3 (151 mg, 0.180 mmol, 0.3 eq) and $Cs_2CO_3$ (588 mg, 1.806 mmol, 3.0 eq). The mixture was stirred at 80° C. under argon for 12 h, then concentrated to dryness and the residue was purified by flash column chromatography on silica gel eluting with MeOH in EtOAc (0-25%) to obtain 8-1 (146 mg, 69% yield). LC-MS m/z: 351.0 $[M-H]^-$.

Step B: To a solution of 4-1 (1.00 g, 5.24 mmol, 1.0 eq) and TEA (1.06 g, 10.48 mmol, 2.0 eq) in DCM (10 mL) at 0° C. was added MsCl (919 mg, 8.02 mmol, 1.5 eq) in DCM (5 mL) dropwise. After addition, the mixture was stirred at room temperature for 3 h. The mixture was partitioned between DCM (40 mLx3) and $H_2O$ (80 mL). The separated organic layers were washed with brine (60 mL), dried over anhydrous $Na_2SO_4$, filtered, and concentrated under reduced pressure to obtain 8-2 (1.52 g, crude), which was used directly in the next step without further purification.

Step C: To a solution of 8-2 (180 mg, 0.68 mmol, 1.0 eq) and 8-1 (359 mg, 1.02 mmol, 1.5 eq) in DMF (6 mL) was added $Cs_2CO_3$ (553 mg, 1.70 mmol, 2.5 eq). The mixture was stirred at 80° C. under argon in a sealed tube for 12 h. The reaction mixture was concentrated to dryness and the residue was purified by flash column chromatography on silica gel eluting with MeOH in EtOAc (0-50%) to obtain 8-3 (200 mg, 57% yield). LC-MS m/z: 520.3 $[M-H]^-$.

Step D: To a solution of 8-3 (200 mg, 0.38 mmol) in DCM (3 mL) was added HCl/dioxane (4 M, 2 mL). The mixture was stirred at room temperature for 1 h, then concentrated to dryness to obtain 5-(6-(benzyloxy)-2-fluoro-3-(pyrrolidin-3-yloxy)phenyl)-1,2,5-thiadiazolidin-3-one 1,1-dioxide (210 mg, crude), which was used directly in the next step. LC-MS m/z: 420.2 $[M-H]^-$.

Step E: To a solution of 5-(6-(benzyloxy)-2-fluoro-3-(pyrrolidin-3-yloxy)phenyl)-1,2,5-thiadiazolidin-3-one 1,1-dioxide (210 mg, 0.49 mmol) in MeOH (5 mL) were added Pd/C (50 mg, 10% w/w) and $Pd(OH)_2$/C (50 mg, 20% w/w). The mixture was stirred at room temperature under $H_2$ atmosphere for 1 h. The reaction mixture was filtered, and the filtrate was concentrated to dryness. The residue was purified by prep-HPLC ($CH_3CN/H_2O$+0.1% $NH_4HCO_3$) to obtain 142 (13.3 mg, 8.5% yield). LC-MS m/z: 330.3 $[M-H]^-$; $^1$H NMR (400 MHZ, $CD_3OD$): δ 7.08 (t, J=8.9 Hz, 1H), 6.69 (dd, J=9.0, 1.8 Hz, 1H), 4.28 (s, 2H), 3.56 (s, 1H), 3.52-3.47 (m, 2H), 3.45-3.37 (m, 2H), 2.36-2.30 (m, 1H), 2.21-2.15 (m, 1H).

Example 1i: Synthesis of 5-(2-fluoro-6-hydroxy-3-(piperidin-3-ylmethyl)phenyl)-1,2,5-thiadiazolidin-3-one 1,1-dioxide (122)

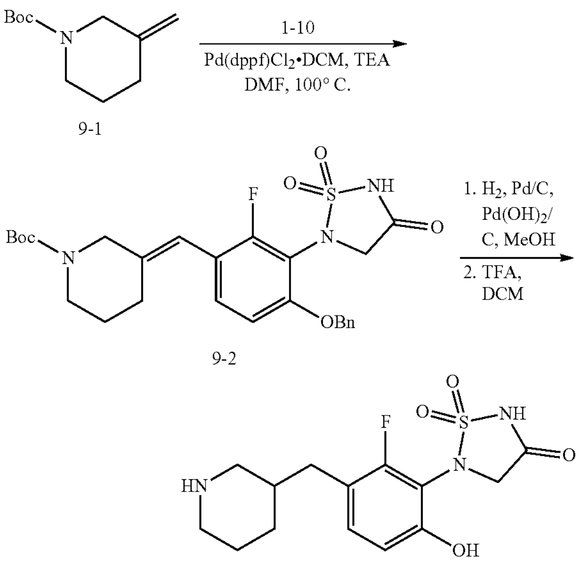

9-1

9-2

122

Step A: To a mixture of 9-1 (250 mg, 0.60 mmol, 1.0 eq), 1-10 (357 mg, 1.81 mmol, 3 eq), and TEA (303 mg, 3.00 mmol, 5 eq) in DMF (3 mL) was added $Pd(dppf)Cl_2$.DCM (51 mg, 0.06 mmol, 0.1 eq). The mixture was stirred at 100° C. under argon for 3 h, then concentrated in vacuo and the resulting residue purified by flash column chromatography on silica gel eluting with MeOH in EtOAc (0-30%) to obtain 9-2 (260 mg, 82% yield). LC-MS m/z: 530.3 $[M-H]^-$.

To a solution of 9-2 (260 mg, 0.49 mmol) in MeOH (2 mL) were added Pd/C (10% w/w, 80 mg) and $Pd(OH)_2$/C (20% w/w, 80 mg), and the mixture was stirred at RT under $H_2$ (30 psi) atmosphere for 12 h. The reaction mixture was filtered, and the filtrate was concentrated in vacuo to obtain tert-butyl 3-(3-(1,1-dioxido-4-oxo-1,2,5-thiadiazolidin-2-yl)-2-fluoro-4-hydroxybenzyl) piperidine-1-carboxylate (200 mg, crude), which was used directly in the next step. LC-MS m/z: 442.2 $[M-H]^-$.

To a solution of tert-butyl 3-(3-(1,1-dioxido-4-oxo-1,2,5-thiadiazolidin-2-yl)-2-fluoro-4-hydroxybenzyl) piperidine-1-carboxylate (200 mg, 0.45 mmol) in DCM (2 mL) was added TFA (1 mL). The mixture was stirred at RT for 1 h, then concentrated in vacuo and diluted with DCM (5 mL). The mixture was adjusted to pH 8 with $NH_3$/MeOH (7 M) and concentrated to dryness. The residue was purified by prep-HPLC ($CH_3CN/H_2O$+0.1% $NH_4HCO_3$) to obtain 122 (7.8 mg, 5% yield). LC-MS m/z: 342.0 $[M-H]^-$; 1H NMR (400 MHZ, $CD_3OD$): δ 7.07 (t, J=7.7 Hz, 1H), 6.71 (d, J=8.6 Hz, 1H), 4.27 (s, 2H), 3.26-3.18 (m, 1H), 2.91-2.82 (m, 1H), 2.78-2.46 (m, 3H), 2.14-1.85 (m, 3H), 1.79-1.64 (m, 1H), 1.45-1.13 (m, 2H).

Example 1j: Synthesis of (R)-5-(3-(5-(2-cyclobutylethyl)-2,5-dihydro-1H-pyrrol-3-yl)-2-fluoro-6-hydroxyphenyl)-1,2,5-thiadiazolidin-3-one 1,1-dioxide (116) and(S)-5-(3-(5-(2-cyclobutylethyl)-2,5-dihydro-1H-pyrrol-3-yl)-2-fluoro-6-hydroxyphenyl)-1,2,5-thiadiazolidin-3-one 1,1-dioxide (134)

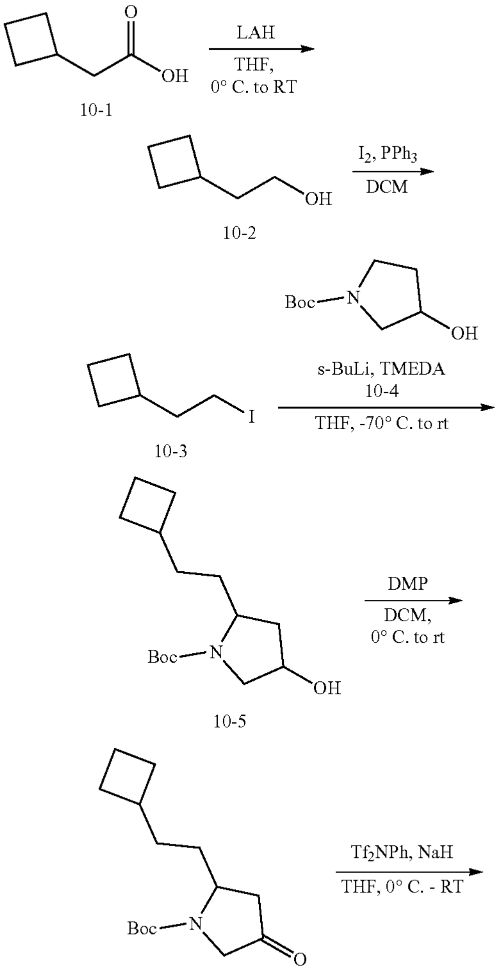

10-1

10-2

10-3

10-5

10-6

-continued

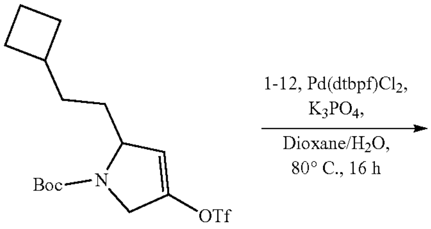

10-7

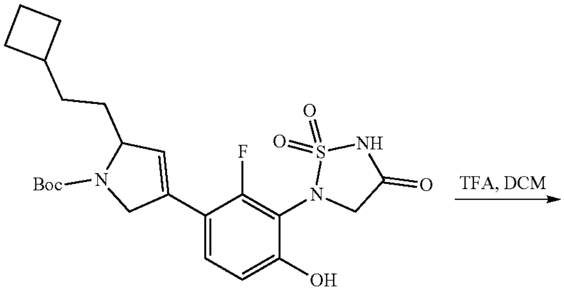

10-8

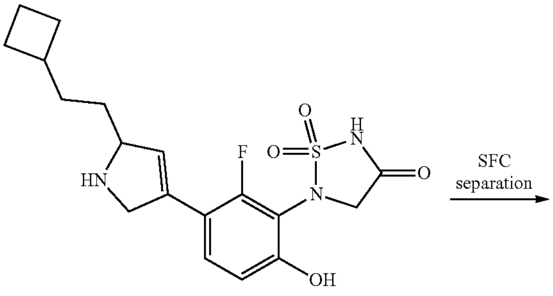

106

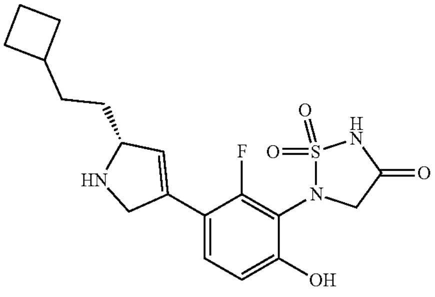

116

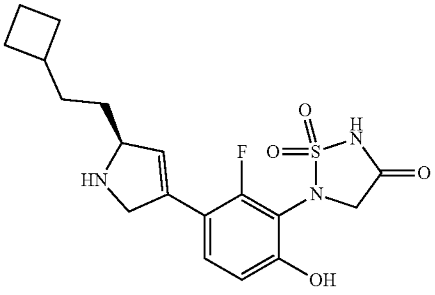

134

Step A: $LiAlH_4$ (5.32 g, 140 mmol) was added in portions to a mixture of 10-1 (8 g, 70 mmol) in THF (100 mL) at 0° C., then the mixture was stirred at 0° C.-RT for 2 h. The reaction mixture was quenched with $Na_2SO_4 \cdot 10H_2O$, filtered, and the filtrate concentrated under reduced pressure to give 10-2 (6.9 g), which was used directly in the next step.

Step B: To a solution of 10-2 (6.9 g, 6.9 mmol) in DCM (70 mL) at 0° C. were added $PPh_3$ (2.35 g, 8.97 mmol) and imidazole (704 mg, 10.35 mmol) and the resulting solution was stirred for 5 min. Then, $I_2$ (2.1 g, 8.28 mmol) was added in portions at 0° C. The mixture was stirred at 25° C. for 12 h, then diluted with $H_2O$ (80 mL). The organic layer was washed with each of 10% HCl (aq)(40 mL) and saturated $NaHCO_3$(aq)(40 mL), then dried over $Na_2SO_4$, filtered, and concentrated in vacuo. Petroleum ether (80 mL) was added to the solid. The solid was then filtered and the filter cake was washed with petroleum ether (30 mL). The filtrate was combined and concentrated at 25° C. under vacuum and the residue was purified by column chromatography on silica gel eluting with PE to give 10-3 (12 g).

Step C: To a cooled (−70° C.) solution of 10-4 (2.2 g, 12 mmol) in THF (30 mL) was added TMEDA (3.50 g, 29 mmol). The mixture was stirred at −70° C. for 10 min, then s-BuLi (1.3 M in hexane, 27.7 mL, 36 mmol) was added dropwise at −70° C. After stirring at −70° C. for 3 h, a solution of 10-3 (5 g, 24 mmol) in THF (20 mL) was added dropwise. The mixture was allowed to warm to room temperature (RT) and stirred for 15 h, then quenched with aq. $NH_4Cl$ (sat. 150 mL) and extracted with EtOAc (100 mLx3). The combined organic layer was washed with brine (150 mL), dried over anhydrous $Na_2SO_4$, and concentrated in vacuo. The residue was purified by silica gel column chromatography eluting with EA in PE (0-25%) to obtain 10-5 (700 mg). LC-MS m/z: 170.1 $[M+H-56]^+$.

Step D: To a cooled (0° C.) solution of 10-5 (700 mg, 2.6 mmol) in DCM (20 mL) was added DMP (2.2 g, 5.2 mmol). The mixture was stirred at RT for 16 h, then treated with aqueous $NaHCO_3$ (sat. 100 mL) and extracted with DCM (40 mLx3). The combined organic layer was washed with brine (80 mL), dried over anhydrous $Na_2SO_4$, filtered, and concentrated in vacuo. The residue was purified by silica gel column chromatography eluting with EA in PE (0-20%) to obtain 10-6 (500 mg). LC-MS m/z: 253.2 $[M+H+CH_3CN-56]^+$. Alternatively, 10-6 can be prepared in an enantioselective process and/or using one or more chiral building blocks to provide a single enantiomer (for example, according to the general procedure in Example 11), or the two enantiomers can be separated using chiral SFC.

Step E: To a cooled (0° C.) solution of 10-6 (500 mg, 1.87 mmol) in THF (50 mL) was added NaH (60% w/w, 150 mg, 3.74 mmol) in portions. The mixture was stirred at 0° C. for 1 h, then $Tf_2NPh$ (1 g, 2.81 mmol) was added. The resulting mixture was stirred at RT for 2 h, then quenched with water (40 mL) and extracted with EA (30 mLx3). The combined organic layer was washed with brine (40 mL), dried over anhydrous $Na_2SO_4$, and concentrated in vacuo to obtain 10-7 (500 mg, crude), which was used directly in the next step.

Step F: To a mixture of 10-7 (500 mg, 1.25 mmol), 1-12 (466 mg, 1.25 mmol) and $K_3PO_4$ (795 mg, 3.75 mmol) in dioxane/$H_2O$ (10 mL/2 mL) was added $PdCl_2$ (dtbpf)(82 mg, 0.125 mmol). The mixture was stirred at 80° C. for 16 h, then concentrated in vacuo and the residue was purified by silica gel column chromatography eluting with MeOH in EA (0-30%) to obtain 10-8 (300 mg). LC-MS m/z: 494.0 [M−H].

Step G: To a mixture of 10-8 (300 mg, 0.606 mmol) in DCM (20 mL) was added TFA (3 mL, 6 mmol) at 0° C. After addition, the mixture was stirred at 0° C.-RT for 2 h, then concentrated in vacuo. The residue was purified by prep-HPLC to obtain 106 (30.41 mg). LC-MS m/z: 394.3

[M−H]$^-$; $^1$H NMR (400 MHZ, DMSO-$d_6$): δ 9.95 (s, 1H), 9.45 (s, 1H), 8.88 (s, 1H), 7.26 (t, J=8.5 Hz, 1H), 6.73 (d, J=8.7 Hz, 1H), 6.24 (s, 1H), 4.51-4.41 (m, 1H), 4.36-4.25 (m, 2H), 3.97 (s, 2H), 2.31-2.22 (m, 1H), 2.07-1.97 (m, 2H), 1.88-1.75 (m, 2H), 1.68-1.57 (m, 4H), 1.53-1.44 (m, 2H).

Step H: Compound 106 was separated by chiral SFC (DAICEL CHIRALPAK® IC column) following the general procedure in Example 1d (Step F) to give two enantiomers, 116 and 134. 116: LC-MS m/z: 394.1 [M−H]$^-$; $^1$H NMR (400 MHZ, DMSO-$d_6$): δ 9.46 (br s, 2H), 7.25 (t, J=8.6 Hz, 1H), 6.72 (d, J=8.5 Hz, 1H), 6.23 (s, 1H), 4.47-4.36 (m, 1H), 4.33-4.21 (m, 2H), 3.97 (s, 2H), 2.31-2.22 (m, 1H), 2.06-1.97 (m, 2H), 1.88-1.73 (m, 2H), 1.68-1.56 (m, 4H), 1.53-1.44 (m, 2H). 134: LC-MS m/z: 394.1 [M−H]$^-$; $^1$H NMR (400 MHZ, DMSO-$d_6$): δ 9.95 (br s, 1H), 9.10 (br s, 1H), 7.26 (t, J=8.6 Hz, 1H), 6.73 (d, J=8.1 Hz, 1H), 6.24 (s, 1H), 4.50-4.40 (m, 1H), 4.36-4.24 (m, 2H), 3.97 (s, 2H), 2.30-2.22 (m, 1H), 2.06-1.97 (m, 2H), 1.87-1.75 (m, 2H), 1.66-1.57 (m, 4H), 1.53-1.45 (m, 2H).

Example 1k: Synthesis of 1-(isobutyryloxy)ethyl (2S)-2-(2-cyclopropylethyl)-4-(3-(1,1-dioxido-4-oxo-1,2,5-thiadiazolidin-2-yl)-2-fluoro-4-hydroxyphenyl)-2,5-dihydro-1H-pyrrole-1-carboxylate (167)

130

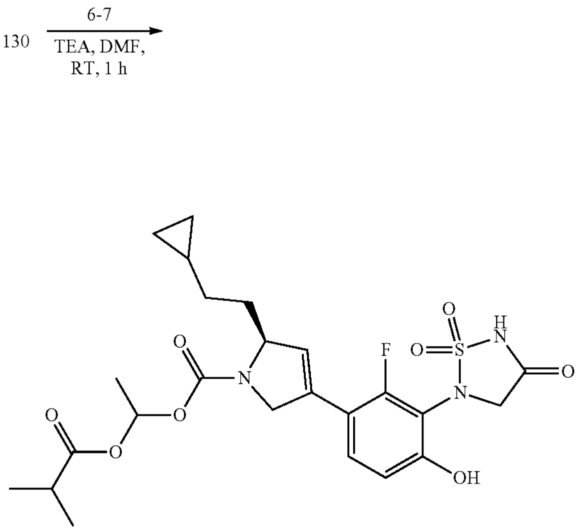

167

To a solution of 130 (0.1 g, 0.26 mmol) and 6-7 (78.0 mg, 0.26 mmol) in DMF (3 mL) was added TEA (80.0 mg, 0.79 mmol). The mixture was stirred at RT for 1 h, then purified by prep-HPLC to obtain 167 (80.0 mg). LC-MS m/z: 538.2 [M−H]$^-$; 1H NMR (400 MHZ, DMSO-$d_6$): δ 9.80 (s, 1H), 7.24-7.15 (m, 1H), 7.08 (s, 1H), 6.95 (s, 1H), 6.78-6.62 (m, 2H), 6.24-6.06 (m, 1H), 4.73-4.60 (m, 1H), 4.57-4.26 (m, 2H), 3.97 (s, 2H), 2.59-2.52 (m, 1H), 1.94-1.67 (m, 2H), 1.46 (t, J=4.8 Hz, 3H), 1.22-1.02 (m, 8H), 0.72-0.56 (m, 1H), 0.42-0.31 (m, 2H), 0.02-0.05 (m, 2H).

Example 11: Synthesis of 1-(isobutyryloxy)ethyl (2S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate (165)

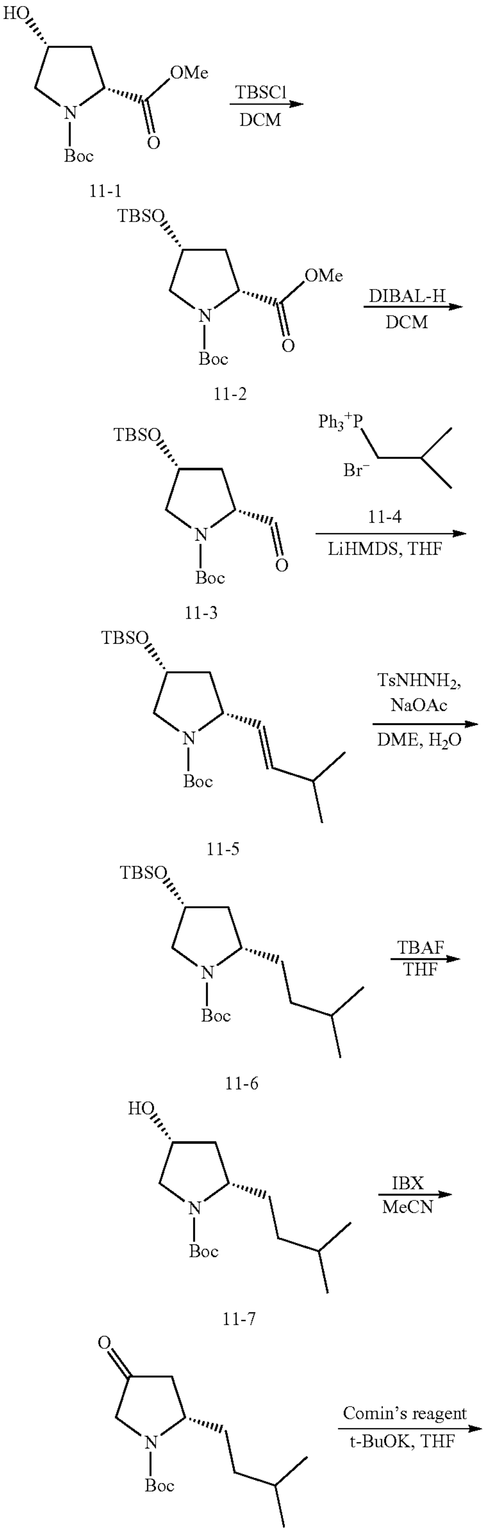

11-1

11-2

11-3

11-5

11-6

11-7

11-8

-continued

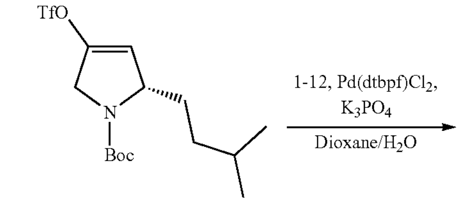

11-9

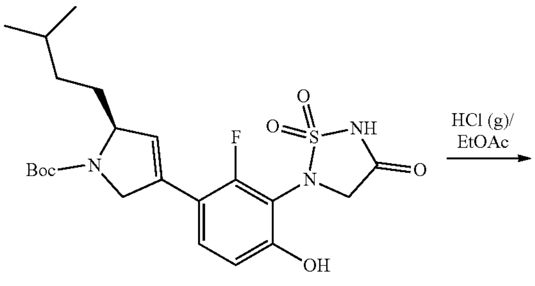

11-10

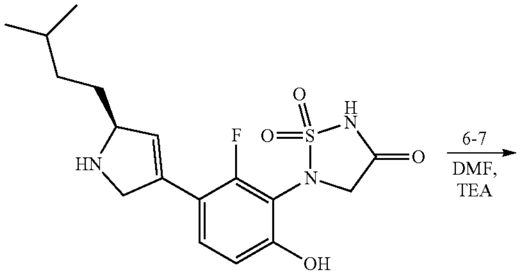

145

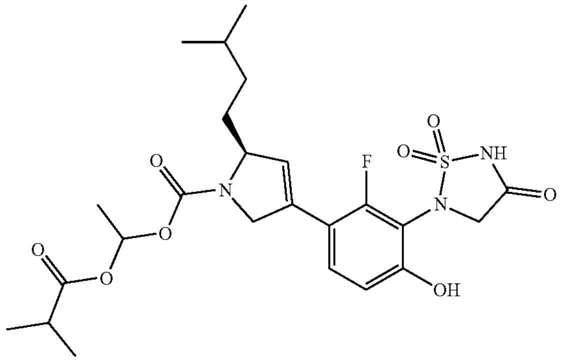

165

Step A: To a solution of 11-1 (150 g, 0.61 mol) in DCM (900 mL) were added imidazole (124.6 g, 1.83 mol) and TBSCl (110.3 g, 0.73 mol) at 0~5° C. The mixture was warmed to 20~25° C. and stirred for 2 h, then poured into water (900 mL) and separated. The organic layer was adjusted to pH=3~4 with 0.5 M HCl, washed with saturated $NaHCO_3$ solution (900 mL) and brine (750 mL), then concentrated to afford 11-2 (205 g). $^1$H NMR (400 MHZ, $CDCl_3$): δ 4.31-4.28 (m, 2H), 3.70 (s, 3H), 3.65~3.61 (m, 1H), 3.35-3.25 (m, 1H), 2.31-2.25 (m, 1H), 2.11-2.07 (m, 1H), 1.47 (s, 3H), 1.41 (s, 6H), 0.88 (s, 9H), 0.045 (s, 6H).

Step B: To a solution of 11-2 (205 g, 0.57 mol) in DCM (1025 mL) was added DIBAL-H (1.03 L, 1.03 mol, 1 mol/L) dropwise at −70° C. After addition, the mixture was stirred at −70° C. for 1 h, then quenched with AcOH (68.5 g, 1.14 mol) at −70° C. The resulting clear colorless solution was poured into saturated aqueous potassium sodium tartrate (820 mL) and filtered. The organic layer was dried over $Na_2SO_4$, filtered, and concentrated under reduced pressure to give 11-3 (140 g). $^1$H NMR (400 MHZ, $CDCl_3$): δ 9.60-9.56 (m, 1H), 4.37-4.07 (m, 2H), 3.50-3.41 (m, 2H), 2.23-2.19 (m, 2H), 1.64-1.42 (m, 9H), 0.92-0.85 (m, 9H), 0.10-0.043 (m, 6H).

Step C: To a solution of 11-4 (18.2 g, 45.5 mmol) in THF (50 mL) was added LiHMDS (45.5 mL, 45.5 mmol, 1 M) at 0° C. The mixture was stirred at 20° C. for 1 h, then 11-3 (10.0 g, 30.3 mmol) in THF (10 mL) was added to the mixture dropwise at 0° C. The reaction mixture was warmed to 20° C. and stirred for 2 h. The reaction was quenched by addition of saturated $NH_4Cl$ solution (100 mL) and extracted with n-heptane (60 mL). The organic layer was dried over $Na_2SO_4$, filtered, and concentrated under reduced pressure to give a crude product. The crude product was triturated with n-heptane (20 mL) at 25° C. for 1 h, then filtered and the filtrate concentrated under reduced pressure. The resulting residue was purified by column chromatography on silica gel eluting with petroleum ether/ethyl acetate (100:1~30:1) to give 11-5 (6.50 g). $^1$H NMR (400 MHZ, $CDCl_3$): δ 5.44-5.40 (m, 1H), 5.13-5.12 (mi, 1H), 4.54-4.50 (m, 1H), 4.34-4.29 (m, 1H), 3.67-3.61 (m, 1H), 3.26-3.24 (m, 1H), 2.63-2.53 (m, 1H), 2.26-2.23 (m, 1H), 1.69-1.64 (m, 1H), 1.44 (s, 9H), 0.98-0.88 (m, 15H), 0.066-0.056 (m, 6H).

Step D: To a solution of 11-5 (6.50 g, 17.6 mmol) in DME (39 mL) and $H_2O$ (26 mL) was added NaOAc (10.1 g, 123.2 mmol) in one portion. The mixture was heated to 80° C., then $TsNHNH_2$ (22.9 g, 123.2 mmol) was added at 80~90° C. The resulting mixture was stirred at 80~90° C. for 3 h, then poured into water (40 mL) and extracted with n-heptane (40 mL). The organic layer was washed with brine (20 mL) and concentrated under reduced pressure. The residue was purified by column chromatography on silica gel eluting with petroleum ether/ethyl acetate (100:1~30:1) to give 11-6 (4.30 g). $^1$H NMR (400 MHZ, $CDCl_3$): δ 4.32-4.27 (m, 1H), 3.75-3.58 (m, 2H), 3.16-3.13 (m, 1H), 2.15-2.10 (m, 1H), 2.00-1.80 (m, 1H), 1.70-1.47 (m, 3H), 1.44 (s, 9H), 1.20-1.05 (m, 2H), 0.92-0.88 (m, 15H), 0.08 (s, 6H).

Step E: To a solution of 11-6 (4.30 g, 11.6 mmol) in THF (17 mL) was added TBAF (11.6 mL, 1 mol/L) dropwise at 0~5° C. The mixture was warmed to 20~30° C. and stirred for 1 h, then poured into water (26 mL) and diluted with EtOAc (15 mL). The mixture was stirred for 5 min, then the organic phase was separated. The aqueous layer was extracted with EtOAc (15 mL) twice. The combined organic phase was washed with brine (15 mL), dried over $Na_2SO_4$, filtered, and concentrated under reduced pressure. The residue was purified by column chromatography on silica gel eluting with petroleum ether/ethyl acetate (30:1~1:1) to give 11-7 (1.90 g). $^1$H NMR (400 MHZ, $CDCl_3$): δ 4.40-4.35 (m, 1H), 3.75-3.65 (m, 2H), 3.25-3.21 (m, 1H), 2.20-2.15 (m, 1H), 2.16-2.14 (m, 1H), 1.85-1.75 (m, 1H), 1.75-1.70 (m, 1H), 1.57-1.52 (m, 2H), 1.50 (s, 9H), 1.16-1.15 (m, 2H), 0.88 (d, J=6.4 Hz, 6H).

Step F: To a solution of 11-7 (1.90 g, 7.38 mmol) in MeCN (19 mL) was added IBX (5.17 g, 18.5 mmol) at 20° C. The reaction mixture was stirred at 80° C. for 3 h, then diluted with MTBE (19 mL), filtered and concentrated in vacuo. The residue was purified by column chromatography on silica gel eluting with petroleum ether/ethyl acetate (100:1~10:1) to give 11-8 (1.20 g). $^1$H NMR (400 MHZ, $CDCl_3$): δ 4.30-4.25 (m, 1H), 3.96-3.91 (m, 1H), 3.62-3.57 (m, 1H), 2.77-2.72 (m, 1H), 2.29-2.25 (m, 1H), 1.70-1.60 (m, 3H), 1.51 (s, 9H), 1.30-1.20 (m, 2H), 0.88 (d. J=6.4 Hz, 6H).

Step G: To a solution of 11-8 (1.20 g, 4.7 mmol) in THF (12 mL) at −25° C., was added t-BuOK (1.05 g, 9.4 mmol) in portions. After stirring for 30 min at −25° C., a solution of Comin's reagent (3.69 g, 9.4 mmol) in THF (6 mL) was added dropwise at −25° C. The mixture was stirred an additional 3 h at −25° C., then poured into water (15 mL) and extracted with n-heptane (15 mL) twice. The combined organic phase was washed with 10% sodium hydroxide solution (15 mL), washed with water (15 mL) twice, dried over anhydrous $Na_2SO_4$, filtered, and concentrated in vacuo. The resulting residue was purified by column chromatography ($SiO_2$, petroleum ether/ethyl acetate=100/1 to 30/1) to give 11-9 (0.45 g). $^1$H NMR (400 MHZ, $CDCl_3$): δ 5.71-5.66 (m, 1H), 4.64-4.56 (m, 1H), 4.35-4.24 (m, 1H), 4.17-4.13 (m, 1H), 1.73-1.51 (m, 3H), 1.50 (s, 9H), 1.30-1.15 (m, 2H), 0.87 (d, J=6.4 Hz, 6H).

Step H: A mixture of 11-9 (4.65 g, 12 mmol), 1-12 (4.47 g, 12 mmol), $K_3PO_4$ (7.64 g, 36 mmol), Pd(dtbpf) $Cl_2$ (0.23 g, wt % 5%) in dioxane (28 mL) and $H_2O$ (11.6 mL) was degassed and purged 3 times with $N_2$. The resulting mixture was stirred for 5 h, then diluted with EtOAc (15 mL), filtrated through Celite, and adjusted to pH=2~3 with citric acid (10% wt %) solution. The mixture was extracted with EtOAc (15 mL) and the combined organic layer was washed with brine (15 mL), dried over anhydrous $Na_2SO_4$, filtered, and concentrated in vacuo. The residue was purified by prep-HPLC to give 11-10 (3.50 g). $^1$H NMR (400 MHZ, $CDCl_3$): δ 10.19 (s, 1H), 7.23-7.18 (s, 1H), 6.72 (d, J=8.8 Hz, 1H), 6.17-6.14 (m, 1H), 4.60-4.55 (m, 1H), 4.45-4.41 (m, 1H), 4.31- 4.03 (m, 4H), 1.70-1.60 (m, 2H), 1.59-1.51 (m, 1H), 1.50 (s, 9H), 1.13-1.11 (m, 2H), 0.86 (d, J=6.0 Hz, 6H).

Step I: A solution of 11-10 (2.50 g, 5.17 mmol) in HCl (g)/EtOAc (4 M, 17.5 mL) was stirred at 20~30° C. for 2 h. The reaction mixture was cooled to −10° C., then filtered and the filter cake rinsed with EtOAc (5 mL) twice. The filter cake was ground and dissolved in deionized water (50 mL). With stirring at 25° C., the pH of the solution was adjusted to 8 with ammonium bicarbonate, then stirred at 25° C. for 0.5 h. The mixture was filtered to give a filter cake, then ground and lyophilized with deionized water to give 145 (1.30 g). LC-MS m/z: 384.1 $[M+1]^+$; $^1$H NMR (400 MHZ, $CDCl_3$): δ 9.99-9.91 (m, 1H), 9.29-9.06 (m, 2H), 7.26 (t, J=8.4 Hz, 1H), 6.72 (d. J=8.8 Hz, 1H), 6.24 (s, 1H), 4.50-4.40 (m, 1H), 4.36-4.27 (m, 2H), 3.95 (s, 2H), 1.76-1.71 (m, 2H), 1.59-1.55 (m, 1H), 1.32-1.28 (m, 2H), 0.89 (d, J=6.0 Hz, 6H).

Step J: To a solution of 145 (30 mg, 0.078 mmol) and 6-7 (23 mg, 0.077 mmol) in DMF (2 mL) was added TEA (8 mg, 0.079 mmol). The mixture was stirred at rt for 0.5 h, then purified by prep-HPLC to obtain 165 (29.3 mg). LC-MS m/z: 540.2 $[M-H]^-$; 1H NMR (400 MHZ, DMSO-$d_6$): δ 9.82 (s, 1H), 7.26-7.14 (m, 1H), 6.76-6.66 (m, 2H), 6.23-6.11 (m, 1H), 4.71-4.58 (m, 1H), 4.54- 4.30 (m, 2H), 3.98 (s, 2H), 2.57-2.51 (m, 1H), 1.87-1.59 (m, 2H), 1.55-1.43 (m, 4H), 1.18-1.05 (m, 8H), 0.88-0.81 (m, 6H).

Example 1m: Synthesis of (R)-1-(isobutyryloxy)ethyl(S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate (148) and(S)-1-(isobutyryloxy)ethyl(S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate (154)

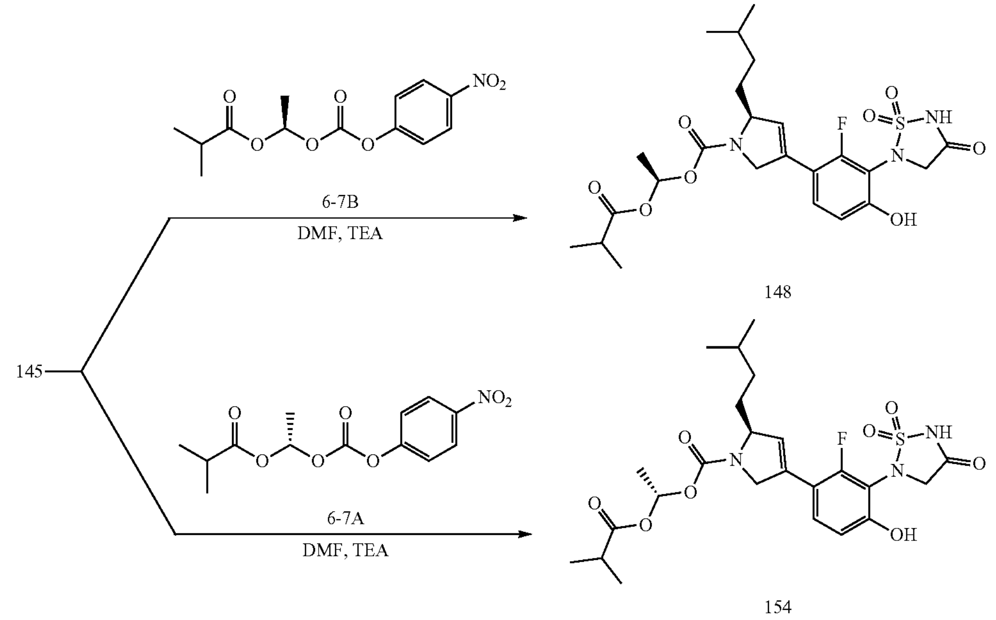

Step A1: To a solution of 145 (30 mg, 0.078 mmol) and 6-7B (23 mg, 0.077 mmol) in DMF (2 mL) was added TEA (8 mg, 0.079 mmol). The mixture was stirred at rt for 0.5 h, then purified by prep-HPLC to obtain 148 (32.5 mg). LC-MS m/z: 540.2 $[M-H]^-$; $^1$H NMR (400 MHZ, DMSO-$d_6$): δ 9.82 (s, 1H), 7.26-7.14 (m, 1H), 6.76-6.66 (m, 2H), 6.23-6.11 (m, 1H), 4.72-4.59 (m, 1H), 4.50-4.30 (m, 2H), 3.98 (s, 2H), 2.57-2.51 (m, 1H), 1.88-1.58 (m, 2H), 1.54-1.43 (m, 4H), 1.18-1.05 (m, 8H), 0.88-0.81 (m, 6H).

Step A2: To a solution of 145 (30 mg, 0.078 mmol) and 6-7A (23 mg, 0.077 mmol) in DMF (2 mL) was added TEA (8 mg, 0.079 mmol). The mixture was stirred at rt for 0.5 h, then purified by prep-HPLC to obtain 154 (31.6 mg). LC-MS m/z: 540.2 $[M-H]^-$; $^1H$ NMR (400 MHZ, DMSO-$d_6$): δ 9.85 (s, 1H), 7.24-7.16 (m, 1H), 6.76-6.67 (m, 2H), 6.20-6.13 (m, 1H), 4.68-4.58 (m, 1H), 4.55-4.29 (m, 2H), 3.99 (s, 2H), 2.57-2.51 (m, 1H), 1.83-1.59 (m, 2H), 1.57-1.41 (m, 4H), 1.19-1.05 (m, 8H), 0.880.79 (m, 6H).

Example 1n: Synthesis of 1-((cyclopentanecarbonyl)oxy)ethyl (2S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate (153)

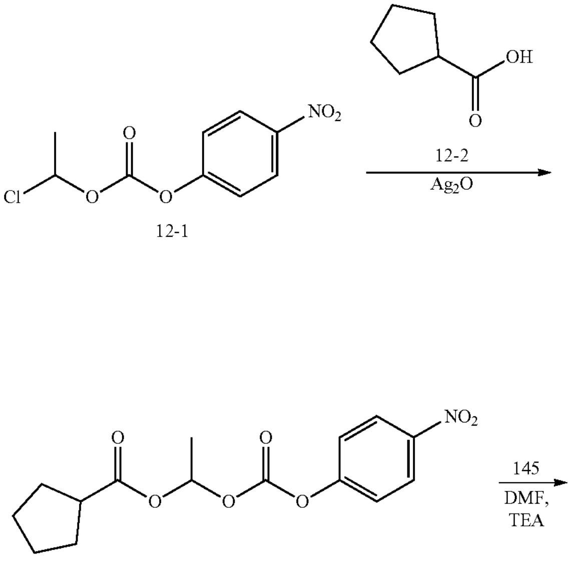

-continued

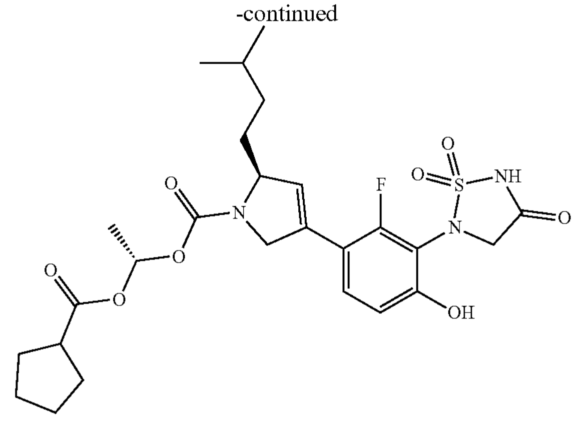

153

Step A: To a mixture of 12-1 (0.5 g, 2.03 mmol) and 12-2 (5 mL) was added $Ag_2O$ (0.47 g, 2.03 mmol). The mixture was stirred at 100° C. for 2 h, then diluted with water (20 mL) and extracted with EA (3×20 mL). The combined organic layer was dried over $Na_2SO_4$, filtered, and concentrated under reduced pressure to afford 12-3 (500 mg), which was used directly in the next step. $^1H$ NMR (400 MHZ, $CDCl_3$): δ 8.28 (d, J=9.2 Hz, 2H), 7.40 (d, J=9.3 Hz, 2H), 6.84 (q, J=5.4 Hz, 1H), 2.88-2.73 (m, 1H), 1.97-1.61 (m, 11H).

Step B: To a solution of 145 (30 mg, 0.078 mmol) and 12-3 (25 mg, 0.077 mmol) in DMF (2 mL) was added TEA (8 mg, 0.079 mmol). The mixture was stirred at rt for 0.5 h, then purified by prep-HPLC to obtain 153 (23.8 mg). LC-MS m/z: 566.2 $[M-H]^-$; $^1H$ NMR (400 MHZ, DMSO-$d_6$): δ 9.86 (s, 1H), 7.25-7.16 (m, 1H), 6.75-6.67 (m, 2H), 6.22-6.11 (m, 1H), 4.69-4.58 (m, 1H), 4.55-4.29 (m, 2H), 4.00 (s, 2H), 2.80-2.71 (m, 1H), 1.86-1.63 (m, 6H), 1.62-1.48 (m, 5H), 1.47-1.42 (m, 3H), 1.19-1.05 (m, 2H), 0.88-0.81 (m, 6H).

Example 10: Synthesis of (R)-1-((cyclopentanecarbonyl)oxy)ethyl(S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate (159) and(S)-1-((cyclopentanecarbonyl)oxy)ethyl (S)-4-(3-(1,1-dioxido-4-oxo-1,2,5-thiadiazolidin-2-yl)-2-fluoro-4-hydroxyphenyl)-2-isopentyl-2,5-dihydro-1H-pyrrole-1-carboxylate (152)

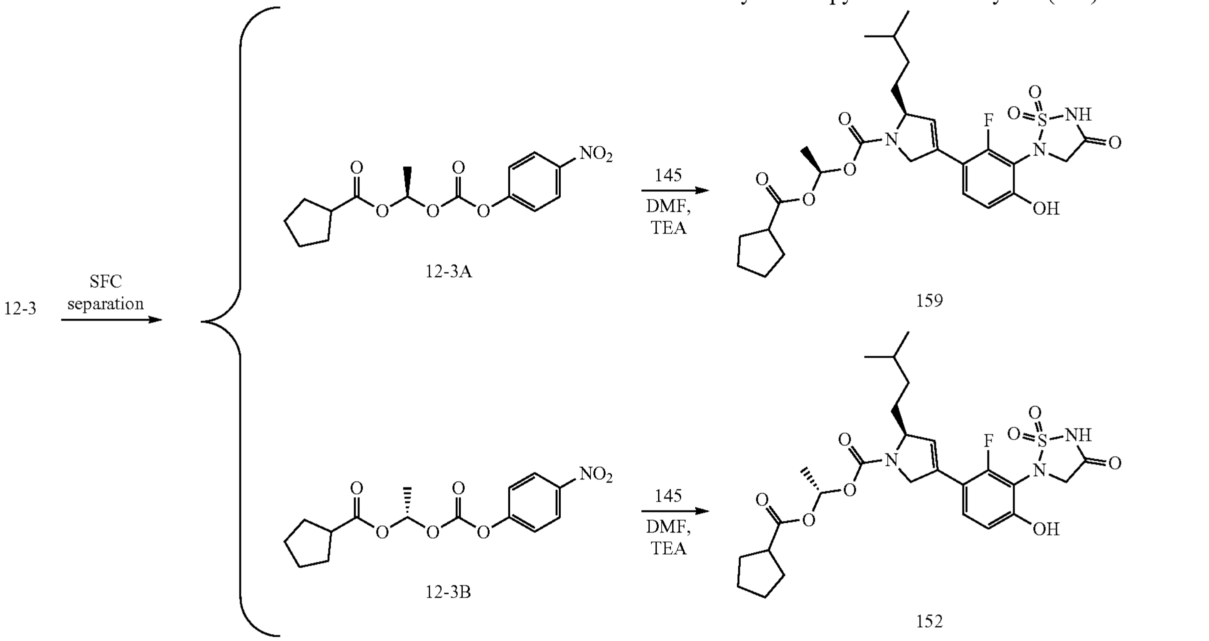 [SMILES: C[C@@H](OC(=O)Oc1ccc([N+](=O)[O-])cc1)OC(=O)C1CCCC1 ; CC(C)CC[C@H]1C=C(c2ccc(O)c(N3CC(=O)NS3(=O)=O)c2F)CN1C(=O)O[C@H](C)OC(=O)C1CCCC1 ; C[C@H](OC(=O)Oc1ccc([N+](=O)[O-])cc1)OC(=O)C1CCCC1 ; CC(C)CC[C@H]1C=C(c2ccc(O)c(N3CC(=O)NS3(=O)=O)c2F)CN1C(=O)O[C@@H](C)OC(=O)C1CCCC1]

Step A: Compound 12-3 (300 mg, 0.93 mmol) was separated by SFC to obtain 12-3A (80 mg) and 12-3B (80 mg).

Step B1: To a solution of 145 (10 mg, 0.026 mmol) and 12-3A (8 mg, 0.026 mmol) in DMF (1.5 mL) was added TEA (3 mg, 0.026 mmol). The mixture was stirred for 0.5 h, then purified by prep-HPLC to obtain 159 (3.0 mg). LC-MS m/z: 566.2 $[M-H]^-$; 1H NMR (400 MHZ, DMSO-$d_6$): δ 9.84 (d, J=3.6 Hz, 1H), 7.23-7.16 (m, 1H), 6.75-6.67 (m, 2H), 6.22-6.12 (m, 1H), 4.69-4.59 (m, 1H), 4.49-4.30 (m, 2H), 3.99 (s, 2H), 2.80-2.71 (m, 1H), 1.86-1.65 (m, 5H), 1.65-1.50 (m, 5H), 1.50-1.42 (m, 4H), 1.18-1.05 (m, 2H), 0.88-0.82 (m, 6H).

Step B2: To a solution of 145 (10 mg, 0.026 mmol) and 12-3B (8 mg, 0.026 mmol) in DMF (1.5 mL) was added TEA (3 mg, 0.026 mmol). The mixture was stirred for 0.5 h, then purified by prep-HPLC to obtain 152 (3.8 mg). LC-MS m/z: 566.2 $[M-H]^-$; 1H NMR (400 MHZ, DMSO-$d_6$): δ 9.86 (s, 1H), 7.25-7.16 (m, 1H), 6.75-6.67 (m, 2H), 6.19-6.14 (m, 1H), 4.67-4.57 (m, 1H), 4.54- 4.29 (m, 2H), 4.00 (s, 2H), 2.81-2.72 (m, 1H), 1.87-1.66 (m, 6H), 1.65-1.48 (m, 5H), 1.47-1.43 (m, 3H), 1.18-1.06 (m, 2H), 0.88-0.82 (m, 6H).

Example 1p: Synthesis of(S)-2-amino-N-(2-((R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrol-1-yl)-2-oxoethyl)-3-methylbutanamide (144)

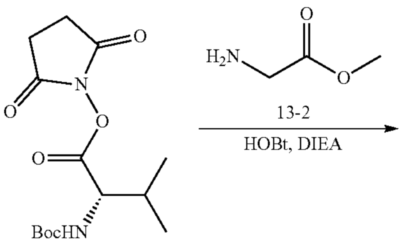

13-1

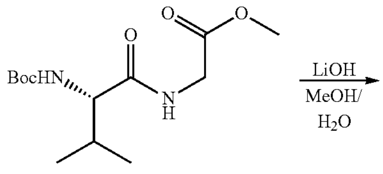

13-3

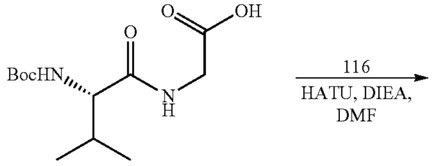

13-4

-continued

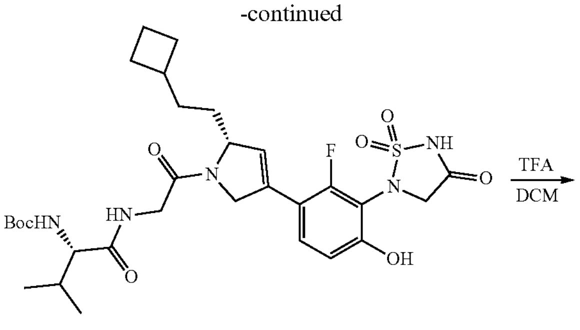

13-5

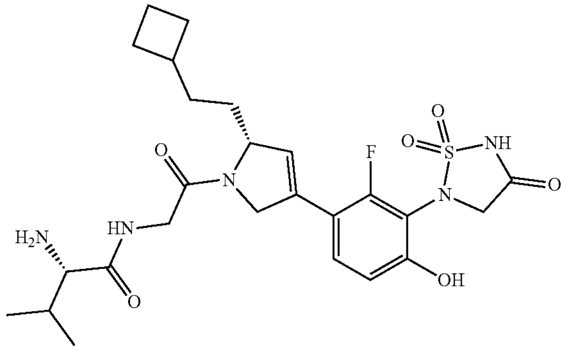

144

Step A: To a mixture of 13-1 (0.5 g, 1.59 mmol) in DMF (5 mL) were added DIEA (0.62 g, 4.78 mmol), HOBt (0.26 g, 1.91 mmol) and 13-2 (0.22 g, 1.75 mmol). The mixture was stirred for 12 h, then diluted with water (30 mL) and extracted with EA (3×30 mL). The combined organic layer was dried over $Na_2SO_4$, filtered, and concentrated under reduced pressure to afford 13-3 (410 mg), which was used directly in the next step. LC-MS m/z: 311.2 $[M+Na]^-$.

Step B: To a mixture of 13-3 (410 mg, 1.42 mmol) in MeOH (5 mL) and $H_2O$ (5 mL) was added NaOH (28.5 mg, 7.12 mmol). The mixture was stirred for 3 h, then diluted with water (30 mL) and washed with EA (30 mL). The aqueous layer was adjusted to pH=5 with 1M HCl and extracted with EA (50 mL×3). The combined organic layer was dried over $Na_2SO_4$, filtered, and concentrated under reduced pressure to afford 13-4 (260 mg), which was used directly in the next step. LC-MS m/z: 297.1 $[M+Na]^-$.

Step C: To a mixture of 116 (30 mg, 0.06 mmol) and 13-4 (25.0 mg, 0.09 mmol) in DMF (2 mL) were added HATU (46.0 mg, 0.12 mmol) and DIEA (23.0 mg, 0.18 mmol). The mixture was stirred for 16 h, then purified by prep-HPLC to obtain 13-5 (15 mg). LC-MS m/z: 650.3 $[M-H]^-$.

Step D: To a solution of 13-5 (15 mg, 0.023 mmol) in DCM (1 mL) was added TFA (0.3 mL). The mixture was stirred for 1 h, then concentrated under reduced pressure. The residue was dissolved in MeOH (0.5 mL) and purified by prep-HPLC to obtain 144 (3.1 mg). LC-MS m/z: 550.2 $[M-H]^-$; $^1H$ NMR (400 MHZ, DMSO-$d_6$): δ 9.82 (d, J=10.8 Hz, 1H), 8.59 (s, 1H), 8.07 (s, 3H), 7.25 (t, J=8.8 Hz, 1H), 6.72 (d, J=8.8 Hz, 1H), 6.21 (s, 1H), 4.82-4.58 (m, 2H), 4.25-4.05 (m, 1H), 4.08-3.95 (m, 3H), 3.79-3.65 (m, 1H), 2.24-2.05 (m, 2H), 2.02-1.90 (m, 2H), 1.85-1.65 (m, 3H), 1.63-1.48 (m, 3H), 1.36-1.28 (m, 3H), 1.03-0.89 (m, 6H).

Example 1q: Synthesis of (R)-2-amino-N-(2-((R)-2-(2-cyclobutylethyl)-4-(3-(1,1-dioxido-4-oxo-1,2,5-thiadiazolidin-2-yl)-2-fluoro-4-hydroxyphenyl)-2,5-dihydro-1H-pyrrol-1-yl)-2-oxoethyl)-3-methylbutanamide (149)

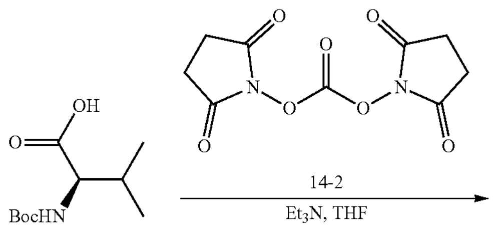

14-1

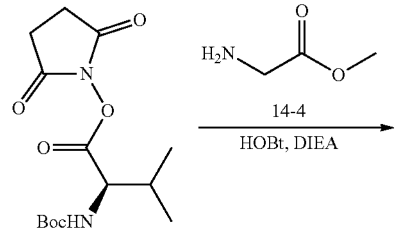

14-3

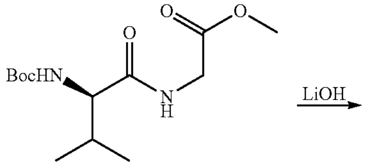

14-5

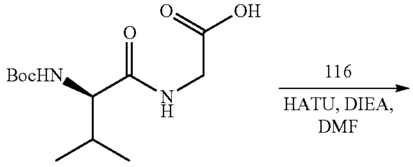

14-6

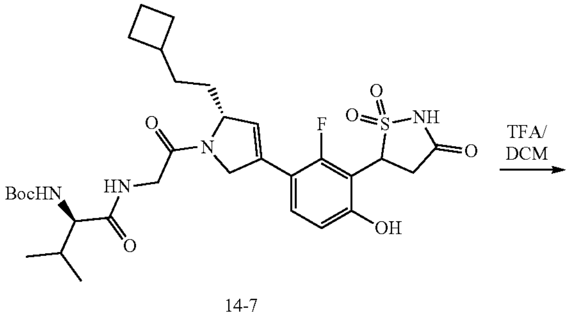

14-7

-continued

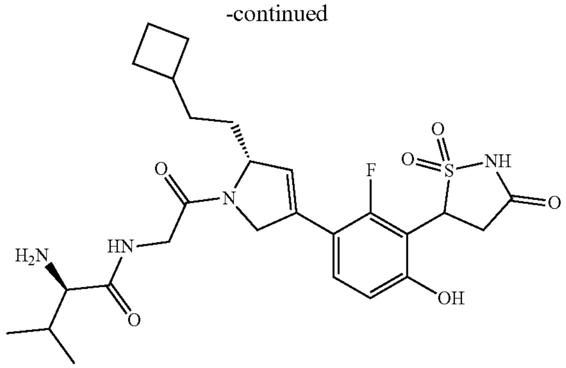

149

Step A: To a mixture of 14-1 (0.5 g, 2.30 mmol) in THF (5 mL) were added TEA (0.58 g, 2.77 mmol) and 14-2 (0.71 g, 2.77 mmol). The mixture was stirred for 16 h, then diluted with water (20 mL) and extracted with EA (3x20 mL). The combined organic layer was dried over $Na_2SO_4$, filtered, and concentrated under reduced pressure to afford 14-3 (500 mg), which was used directly in the next step. $^1H$ NMR (400 MHZ, $CDCl_3$): δ 4.52 (dd, J=9.0, 4.8 Hz, 1H), 2.77 (s, 4H), 2.23 (dd, J=12.2, 6.2 Hz, 1H), 1.39 (s, 9H), 0.98 (dd, J=13.6, 6.8 Hz, 6H).

Step B: To a mixture of 14-3 (0.3 g, 0.96 mmol) in DMF (5 mL) were added DIEA (0.37 g, 2.87 mmol), HOBt (0.16 g, 1.15 mmol) and 14-4 (0.094 g, 1.06 mmol). The mixture was stirred for 12 h, then diluted with water (20 mL) and extracted with EA (3x20 mL). The combined organic layer was dried over $Na_2SO_4$, filtered, and concentrated under reduced pressure to afford 14-5 (100 mg), which was used directly in the next step. LC-MS m/z: 311.2 $[M+Na]^+$.

Step C: To a mixture of 14-5 (100 mg, 0.35 mmol) in MeOH (5 mL) and $H_2O$ (5 mL) was added LiOH (17 mg, 0.71 mmol). The mixture was stirred for 1 h, then diluted with water and washed with EA (20 mL). The aqueous layer was adjusted to pH=5 with 1M HCl and extracted with EA (20 mLx3). The combined organic layer was dried over $Na_2SO_4$, filtered, and concentrated under reduced pressure to afford 14-6 (80 mg), which was used directly in the next step. LC-MS m/z: 297.3 $[M+Na]^+$.

Step D: To a mixture of compound 116 (30 mg, 0.076 mmol) and 14-6 (80.0 mg, 0.29 mmol) in DMF (2 mL) were added HATU (58.0 mg, 0.15 mmol) and DIEA (29.0 mg, 0.23 mmol). The mixture was stirred at for 16 h, then purified by prep-HPLC to obtain 14-7 (20 mg). LC-MS m/z: 650.3 $[M-H]^-$.

Step E: To a solution of 14-7 (20 mg, 0.03 mmol) in DCM (1.5 mL) was added TFA (0.5 mL). The mixture was stirred for 1 h, then concentrated under reduced pressure. The residue was dissolved in MeOH (0.5 mL) and purified by prep-HPLC to obtain compound 149 (4.45 mg). LC-MS m/z: 550.2 $[M-H]^-$; $^1H$ NMR (400 MHZ, DMSO-$d_6$): δ 8.60 (d, J=30.8 Hz, 1H), 7.24 (t, J=8.6 Hz, 1H), 6.71 (d, J=9.0 Hz, 1H), 6.21 (s, 1H), 4.95-4.55 (m, 3H), 4.14-4.015 (m, 2H), 3.98 (s, 2H), 3.72-3.61 (m, 1H), 2.25-2.14 (m, 1H), 2.12-2.04 (m, 1H), 2.01-1.90 (m, 2H), 1.82-1.65 (m, 3H), 1.62-1.48 (m, 3H), 1.37-1.26 (m, 2H), 1.01-0.93 (m, 6H).

Example 1r: Synthesis of (R)-(4-(5-(2-cyclobutylethyl)-2,5-dihydro-1H-pyrrol-3-yl)-2-(1,1-dioxido-4-oxo-1,2,5-thiadiazolidin-2-yl)-3-fluorophenoxy) methyl isobutyrate (160)

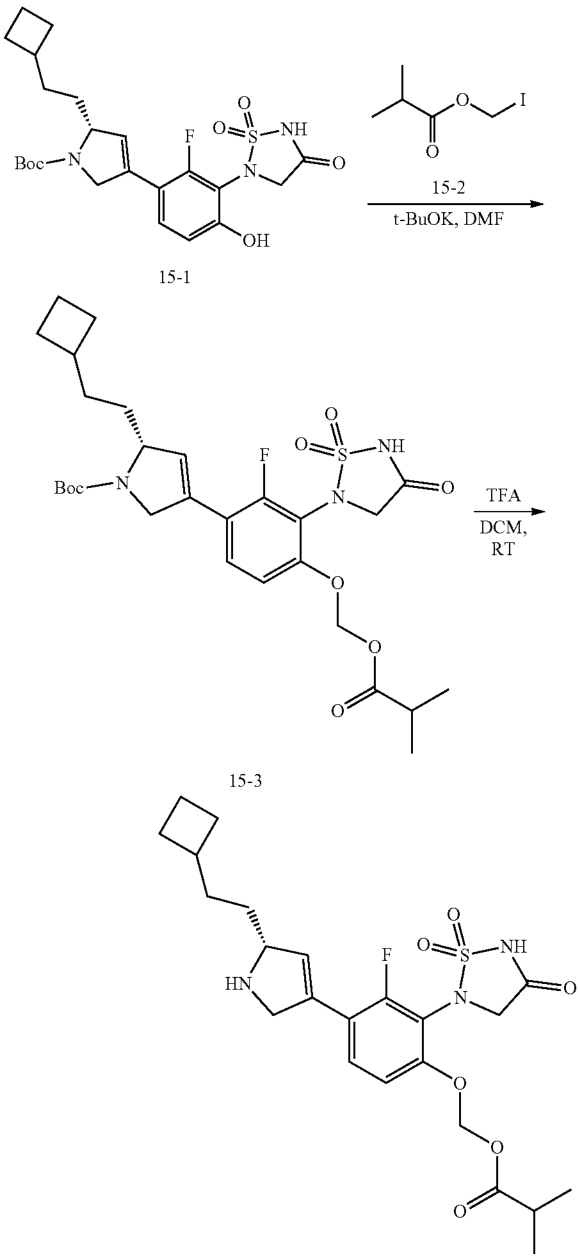

15-1

15-3

160

Step A: To a mixture of 15-1 (50 mg, 0.1 mmol) in DMF (2 mL) was added t-BuOK (33.6 mg, 0.3 mmol) at 0° C. The mixture was stirred at 25° C. for 0.5 h, then 15-2 (68 mg, 0.3 mmol) in DMF (0.5 mL) was added to the mixture. The reaction mixture was stirred at 50° C. for 16 h, then purified by prep-HPLC to obtain 15-3 (10 mg). LC-MS m/z: 594.2 $[M-H]^-$.

Step B: To a solution of 15-3 (10 mg, 0.017 mmol) in DCM (1 mL) was added TFA (0.3 mL). The mixture was stirred for 1 h, then concentrated under reduced pressure.

The residue was dissolved in MeOH (0.5 mL) and purified by pre-HPLC to obtain 160 (1.32 mg). LC-MS m/z: 494.2 $[M-H]^-$; $^1H$ NMR (400 MHZ, DMSO-$d_6$): δ 8.37 (s, 3H), 7.27 (t, J=8.4 Hz, 1H), 7.02 (t, J=10.4 Hz, 1H), 6.26 (s, 1H), 5.80-5.74 (m, 2H), 4.10-3.98 (m, 3H), 3.92 (s, 2H), 2.62-2.57 (m, 1H), 2.26-2.20 (m, 1H), 2.02-1.97 (m, 2H), 1.81-1.76 (m, 2H), 1.60-1.53 (m, 2H), 1.47-1.32 (m, 4H), 1.08 (d, J=7.2 Hz, 6H).

Example 2: Phosphatase Activity Assay

Assessing Selectivity and Potency of a Small Molecule PTPN2 Inhibitor

The selectivity and potency of a small molecule PTPN2 inhibitor as provided herein against one or more protein tyrosine phosphatase (PTP) enzymes, and specifically against PTPN2, is assessed in various ways. The one or more PTP enzymes comprise *Mycobacterium* protein tyrosine phosphatase A (mPTPA), *Mycobacterium* protein tyrosine phosphatase B (mPTPB), PTPN1 (i.e., PTP1B), PTPN2 (i.e., TC-PTP), PTPN22 (i.e., LYP), SHP-1, SHP-2, FAP-1, Meg2, HePTP, Laforin, VHX, VHR, LMWPTP, Cdc14A, LAR, CD45, PTPRG, a fragment thereof, a variant thereof, and a combination thereof. Selectivity and potency of a small molecule PTPN2 inhibitor is evaluated using a PTP activity inhibition assay. The assay is performed using a buffer comprising 50 mM HEPES buffer pH 7.5, 150 mM NaCl, 0.5 mM EDTA, 1 mM DTT, 0.001% Tween-20.

The assay is performed using a phosphated substrate, e.g., 10 mM 6,8-Difluoro-4-Methylumbelliferyl Phosphate (DIFMUP) that is stored at −20° C. Alternatively or in addition to, the assay is performed using other phosphated substrate (e.g., fluorescein diphosphate). Each PTP enzyme is diluted in the assay buffer The assay can be carried out at room temperature in multiplate format, e.g., using 384 well plates. A small molecule PTPN2 inhibitor dissolved in DMSO at one of 10 concentrations from a serial dilution or DMSO alone for control is added to each well. A mixture of the assay buffer comprising PTP enzyme (e.g., 0.025 ng/ul PTPN2) is added to each well and mixed for approximately 2 minutes. The reaction is initiated by adding DiFMUP diluted in the assay buffer to a final concentration of approximately 45 μM DiFMUP in PTPN2 assay. For each PTP enzyme, DiFMUP is added at the Km (Michaelis constant) of the enzyme that had been independently determined. The phosphatase activity of the PTP enzyme is assessed by monitoring appearance of a fluorescent product (6,8-difluoro-7-hydroxyl-4-coumarin (DiFMU) from DiFMUP) continuously for about 15 to 30 minutes, using the INFINITE M1000Pro plate reader (Tecan) with excitation at 360 nm and emission at 450 nm (cutoff filter at 435 nm) for DiFMU. Each assay is performed at least in duplicate. The rate (e.g., the initial rate) of DiFMU formation is plotted against the concentration of the small molecule PTPN2 inhibitor, and the data is fitted (e.g., using a 4-parameter equation) to determine the inflection point of the fit as the $IC_{50}$ of the small molecule PTPN2 inhibitor for a specific enzyme. Utilizing this assay, the ability of the compounds in Table 1 to inhibit PTPN2 and PTP1B has been assessed. Table 3 summarizes the $IC_{50}$ values.

TABLE 3

| | ≤1 μM | >1 μM |
|---|---|---|
| PTPN2 $IC_{50}$ | 101, 102, 103, 104, 105, 106, 107, 108, 109, 110, 111, 113, 114, 115, 116, 117, 119, 120, 121, 122, 123, 125, 126, 127, 128, 129, 130, 131, 132, 133, 134, 135, 137, 138, 139, 140, 141, 143, 144, 145, 146, 147, 148, 149, 150, 151, 154, 155, 156, 157, 158, 160, 161, 162, 163, 164, 165, 166 | 112, 118, 124, 136, 142, 152, 153, 159 |
| PTP1B $IC_{50}$ | 101, 102, 103, 104, 105, 106, 107, 109, 110, 111, 113, 114, 115, 116, 117, 119, 120, 121, 122, 123, 125, 126, 127, 128, 129, 130, 131, 132, 133, 134, 135, 137, 138, 139, 140, 141, 142, 143, 144, 145, 146, 147, 148, 149, 150, 151, 152, 154, 155, 156, 157, 158, 159, 160, 161, 162, 163, 164, 165, 166 | 108, 112, 118, 124, 136, 153 |

Example 3: Cytokine Release Assay

Responder isolated T or NK cells or PBMCs including modified T cells (e.g., non-modified T cells, or TFP- or CAR-expressing T cells) are activated with CD3/CD28 beads (CD3/CD28 CTS Dynabeads) or K562 tumor cells (Stimulator) in the presence of a small molecule PTPN2 inhibitor for 12-24 hours (optionally longer). The activated responder cells are induced to release cytokine by co-culturing at a desired Responder:Stimulator cell ratio, e.g., 10:1, 5:1, or 1:1. Co-culture supernatant is harvested after approximately 20 hrs. These supernatants are then used to measure the released cytokines such as IL-2 and IFN-g by ELISA or LEGENDplex immunoassays (BioLegend) according to the manufacturer's protocol. This assay is to demonstrate that inhibiting PTPN2 by a small molecule PTPN2 inhibitor causes an increase in cytokine release (e.g., IL-2 or IFN-g) by T cells in response to the antigen to which the responder cell binds.

Example 4: Cell Proliferation Assay

Immune cells (e.g., PBMCs, non-modified T cells, OT-1 transgenic T cells, or TFP- or CAR-expressing T cells) are activated with CD3/CD28 beads (e.g., CD3/CD28 CTS Dynabeads), ovalbumin antigen (SIINFEKL, OVA peptide), MHC-deficient tumor cells (e.g., K562 cells), or cells expressing CAR-reactive antigens (e.g., HER2 or CD19) in the presence of a small molecule PTPN2 inhibitor for 12-24 hours (optionally longer). The activated immune cells (CAR-expressing T cells) may also be induced to proliferate by co-culturing with a target tumor cell line (e.g., K562, OVCAR3, or Raji) that may comprise the target tumor antigen to which the TFP or CAR binds. Typically, the target cells are irradiated, washed and counted. Proliferation of the effector immune cells are evaluated, typically 3 to 10 days post stimulation. The number of cells per mL and the viability of cells are measured by Cellometer and by flow cytometry (Cytek Aurora). This example is to demonstrate that PTPN2 inhibition by a small molecule PTPN2 inhibitor yields an increase in effector cell number and viability relative to effector cells not treated with a small molecule PTPN2 inhibitor.

Example 5: Cytotoxicity Assay

Effector immune cells (e.g., non-modified T or NK cells, or TFP- or CAR-expressing T cells) are activated with CD3/CD28 beads (CD3/CD28 CTS Dynabeads) or appropriate target tumor cells (e.g., K562) in the presence of a PTPN2 inhibitor, such as a compound of Formula (I), for 12-24 hours (optionally longer). Target cells (e.g., cancer or tumor cells) are distinguished from responder immune cells by expression of a fluorescent tag (e.g., RFP or GFP). Co-culturing is performed at a desired Effector:Target cell ratio, e.g., 10:1, 5:1, or 1:1. At the end of the co-culture period (e.g., 24 hours), the number of target cells and the viability of the target cells are assessed by measuring the abundance of cells containing the fluorescent tag by flow cytometry (Cytek Aurora). This example is to demonstrate that PTPN2 inhibition by a PTPN2 inhibitor yields an increase in cytotoxicity of effector cells against target cells relative to effector cells not treated with a PTPN2 inhibitor.

Example 6: CAR-T Killing Assay

The ability of PTPN2 inhibitors to potentiate tumor cell killing using CAR-Ts that express a tumor antigen (e.g., HER2) is demonstrated as follows. HER-2 specific CAR-T cells (CAR-Ts) are generated by transducing primary human CD3+ T cells (Discovery Life Sciences) with a lentivirus expressing a chimeric antigen receptor specific to human HER2, as well as GFP or RFP (Creative Bio). Prior to transduction, T cells are stimulated overnight with anti-CD3 and anti-CD28 antibodies coated onto magnetic beads (Invitrogen) at a 1:1 bead-to-cell ratio. Four days after transduction, the beads are removed and the following day CAR-Ts were sorted based on GFP or RFP expression and expanded in IL-2, hIL7, and hIL15. Thereupon, CAR-Ts are co-cultured with a fluorescent-labeled HER-2 positive tumor line (e.g., OVCAR-3) or a HER-2 negative line (e.g., HEK293T) for 18-24 h at a 1:1 effector:target cell ratio.

CAR-Ts are pretreated with 0.1% DMSO (vehicle control) or a PTPN2 inhibitor during co-culture with cell lines at indicated concentrations. Tumor killing is assessed by comparing DMSO-treated CAR-Ts to PTPN2 inhibitor-treated CAR-Ts using flow cytometry. Percent killing is assessed by calculating the number of viable cells at a given time point as compared to untreated tumor cells, tumor cells treated with PTPN2 inhibitor, and tumor cells cultured with DMSO treated CAR-T cells as a control.

Example 7: CAR-T Adoptive Cell Transfer Xenograft Tumor Assay

For in vivo studies with CAR-Ts, nude mice are implanted with OVCAR xenografts. After reaching a suitable size of 50-100 $mm^3$, approximately $10^6$ CAR-Ts transiently treated (e.g., for 1 hr and then washing away) with or without PTPN2 inhibitor are transferred i.v. into tumor bearing mice. Tumor volume and CAR-T cell count are measured at multiple time points and compared to control groups treated with DMSO (e.g., for 1 hr and then washing away). It is expected that mice administered with CAR-Ts that are treated with PTPN2 inhibitor exhibit lower tumor volume, higher frequency of CAR-Ts in the blood, and/or greater infiltration and/or activation of CAR-Ts into tumors, smaller tumor volume and/or higher CAR-T cell counts.

Example 8: Mouse Adoptive Cell Transfer Syngeneic Tumor Assay

Thy 1.1 congenic C57BL/6 mice are implanted with approximately $5\times10^5$ of OVA expressing syngeneic tumor cells (B16-OVA, EL4 OVA, or YUMM1.1) formulated with 50% Matrigel (50% PBS). Prior to the implantation, the B16-OVA, EL4 OVA, or YUMM1.1 tumor cell lines are transduced with a lentivirus encoding an OVA-GFP fusion protein. After sorting for GFP expression, the B16-OVA, EL4 OVA, or YUMM1.1 cells are shown to grow in untreated C57BL/6 mice. After growing to a volume of ~50-100 $mm^3$, tumor bearing mice would receive i.v. transfer of approximately $1\times10^6$ OT-1 transgenic T cells that will undergo the following treatments. First, primary OT-1 splenocytes are treated with 10 nm of SIINFEKL peptide or anti-CD3/anti-CD28 coated beads. After 2 days, the cells are washed and transferred into culture medium with IL-2, IL-7 and IL-15 (all at 5 ng/ml) for another 3 days. In other experiments, naïve OT-1 CD8 T cells are isolated for transfer. Prior to the transfer, the OT-1 cells are treated with DMSO (vehicle control) or a PTPN2 inhibitor for a certain time period and washed in PBS prior to adoptive transfer into tumor-bearing animals.

The test groups are separated as follows: Tumor alone, Tumor+DMSO treated OT-1s, Tumor+PTPN2 inhibitor treated OT-1s. Each group may include 8 mice. To assess in vivo efficacy, tumor volume is measured 3×/week using calipers at various time points post OT-1 injection. Furthermore, at day 7, the first group of mice are sacrificed to compare immune activation and infiltration in both secondary lymphoid tissue and in tumors, staining for markers including but not limited to CD4, CD8, CD25, CD69, CD44, CD62L, TCF1, TOX, TIM3, PD1. The abundance and activation state of immune cells are quantified using flow cytometry. The results are expected to demonstrate that a transient treatment with PTPN2 is effective to potentiate anti-tumor killing as evidenced by (a) a decrease in tumor volume, and/or (b) an increase in the abundance of activated T cells in spleen, lymph nodes and/or in tumor.

Example 9: Mobility Shift Assay Used to Determine Potency of PTPN2 Inhibitors

Compound activity can be determined using PTPN2 in an in vitro enzymatic reaction. The enzymatic assay used to determine activity can be a mobility shift assay using a LabChip EZ Reader by Caliper Life Sciences. The enzymatic reaction is carried out in assay buffer (50 mM HEPES pH 7.5, 1 mM EGTA, 10 mM EDTA, 0.01% Tween® 20, and 2 mM DTT). The compounds are dispensed on a white 384 well ProxiPlate™ (PerkinElmer Catalog #6008289) plate using the Labcyte Echo at varying concentrations (12 point, 1:3 dilution). The enzyme (at 0.5 nM) is incubated with compound for 10 minutes at room temperature. Then the substrate (phosphorylated insulin receptor probe sequence is added at 2 μM to the plates and incubated for another 10 minutes at room temperature. Finally, a quench solution (water and 4-bromo-3-(2-oxo-2-propoxyethoxy)-5-(3-{[1-(phenylmethanesulfonyl) piperidin-4-yl]amino}phenyl)thiophene-2-carboxylic acid) is added to the plates, which are then run on the EZ Reader (excitation 488 nm, emission 530 nm) to measure % conversion (the amount of phosphorylated substrate which is de-phosphorylated by PTPN2). Each plate has a 100% control (inhibitor: 4-bromo-3-(2-oxo-2-propoxyethoxy)-5-(3-{[1-(phenylmethanesulfonyl) piperidin-4-yl]amino}phenyl)thiophene-2-carboxylic acid) and 0% control (DMSO), which are used to calculate % inhibition. The % inhibition is then used to calculate the $IC_{50}$ values.

Example 10: Mobility Shift Assay (MSA) to Determine Potency of PTPN1 (Also Known as PTP1B) Inhibitors Compound activity can be determined using full-length PTPN1 protein in an in vitro enzymatic reaction. The enzymatic assay to determine activity can be a mobility shift assay using a LabChip EZ Reader by Caliper Life Sciences. The enzymatic reaction is carried out in assay buffer (50 mM HEPES pH 7.5, 1 mM EGTA, 10 mM EDTA, 0.01% Tween® 20, and 2 mM DTT). The compounds are dispensed on a white 384 well ProxiPlate™ (PerkinElmer Cat #6008289) plate using a Labcyte Echo® liquid handler at varying concentrations (12 point, 1:3 dilution). The enzyme (at 0.5 nM) is incubated with compound for 10 minutes at room temperature. Then the substrate (phosphorylated insulin 30 receptor probe sequence is added at 2 μM to the plates and incubated for another 10 minutes at room temperature. Finally, a quench solution (water and 4-bromo-3-(2-oxo-2-propoxyethoxy)-5-(3-{[1-(phenylmethanesulfonyl) piperidin-4-yl]amino}phenyl)thiophene-2-carboxylic acid) is added to the plates, which are then run on the EZ Reader (excitation 488 nm, emission 530 nm) to measure % conversion (the amount of phosphorylated substrate which is de-phosphorylated by PTPN1). Each plate has a 100% control (inhibitor: 4-bromo-3-(2-oxo-2-propoxyethoxy)-5-(3-{[1-(phenylmethanesulfonyl) piperidin-4-yl]amino}phenyl)thiophene-2-carboxylic acid) and 0% control (DMSO), which are used to calculate % inhibition. The % inhibition is then used to calculate the $IC_{50}$ values.

Example 11: B16F10 IFNγ-Induced MHC Upregulation and Cellular Growth Inhibition

B16F10 mouse melanoma cells (ATCC Cat #CRL-6475, Manassas, VA) are seeded at a density of 500 cells per well in a 384-well clear bottom plate in 25 μL total volume of DMEM+10% FBS. Cells are allowed to adhere overnight at 37° C.+5% $CO_2$. On the following day, compounds are added to cells in a dilution range from 100 μM to 0.001 μM with a final DMSO concentration of 0.1% in the presence or absence of recombinant mouse IFNγ (0.5 ng/ml). After 3 days of treatment, cell growth is assessed by a CellTiter-Glo luminescent cell viability assay as per the manufacturer's recommended protocol. The percent growth inhibition is calculated relative to the "DMSO/with IFNγ" control. At these same time points, MHC upregulation is assessed by flow cytometry by staining cells with anti-mouse MHC antibodies (anti-mouse H-2Kd clone SF1-1.1 or H2Kb/H-2 Db clone 28-8-6, BioLegend) according to the manufacturer's recommended protocol. Cells treated with a compound inhibiting PTPN2 are expected to exhibit an increase in surface levels of MHC in an IFNγ-mediated manner.

Example 12: Mouse T Cell Activation and Signaling Assay by Flow Cytometry

Pan T cells are isolated from C57BL6 splenocytes. Isolated T cells (50,000 cells/well in a 96 well flat-bottom plate) are cultured in RPMI 1640 supplemented with 10% FBS, 50 nM 2-mercatoethanol, 100 U/mL penicillin, and 100 μg/mL streptomycin, and incubated with the indicated concentration of compound or DMSO in duplicates. After 1 hour, mouse T cell activator CD3/CD28 Dynabeads are added at a 1:5 beads to cells ratio to stimulate the T cells for 2 or 3 days as described below. Alternatively, plate-bound anti-CD3 (1 to 5 μg/mL) and soluble anti-CD28 are used. After 2 days of stimulation, activation status and levels of phosphorylated STAT1 or STAT5 are assessed by flow cytometry. The expression levels of CD25, CD69, and PD1 indicate the activation status of cells on a per cell basis and is evaluated by the mean fluorescence intensities (MFI) of CD25 and CD69. For signaling, the cells are fixed in fixation buffer and subsequently permeabilized with ice cold methanol or Perm Buffer III (BD Biosciences or BioLegend) and stained with fluor-conjugated anti-phospho-STAT1 or -STAT5 antibodies (Cell Signaling Technology). The median fluorescence intensity of phosphorylated STATs indicate the activation status of immune cells.

Example 13: In Vivo Efficacy of Compounds in Mouse Syngeneic Tumor Models

Tumor Cell Inoculation and Treatments

Cells are grown to passage 3 in vitro. A total of $1\times10^5$ viable MC-38, B16F10, CT26.WT, or EMT-6 cells are inoculated subcutaneously into the right flank of female C57Bl/6 mice (5-6 weeks old) or BALB/C mice on Day 0. The injection volume is 0.1 mL and is composed of a 1:1 mixture of PBS and Matrigel® (Corning, NY, USA). Tumors are size matched, randomized, and treatments are initiated on a daily or twice daily schedule.

Tumor volume is calculated three times weekly. Measurements of the length (L) and width (W) of the tumor are taken via electronic caliper and the volume is calculated according to the following equation: $V=L\times W^2/2$. Mice are euthanized when tumor volume is ≤2000 $mm^3$ or skin ulcerations occur. Following the overall procedure described in this example, treatment of mice bearing MC-38 tumors with a PTPN2 inhibitor of the present disclosure (Compound A) for 21 days elicited complete tumor remission in every animal in the treatment group (n=8). FIG. 1 depicts the results of treating mice bearing MC-38 tumors with a PTPN2 inhibitor of the present disclosure (Compound B), demonstrating a complete remission of the MC-38 tumors in every animal in each treatment group (n=10) at both once and twice daily dosing schedules.

Tumor Rechallenge

Figure 2:
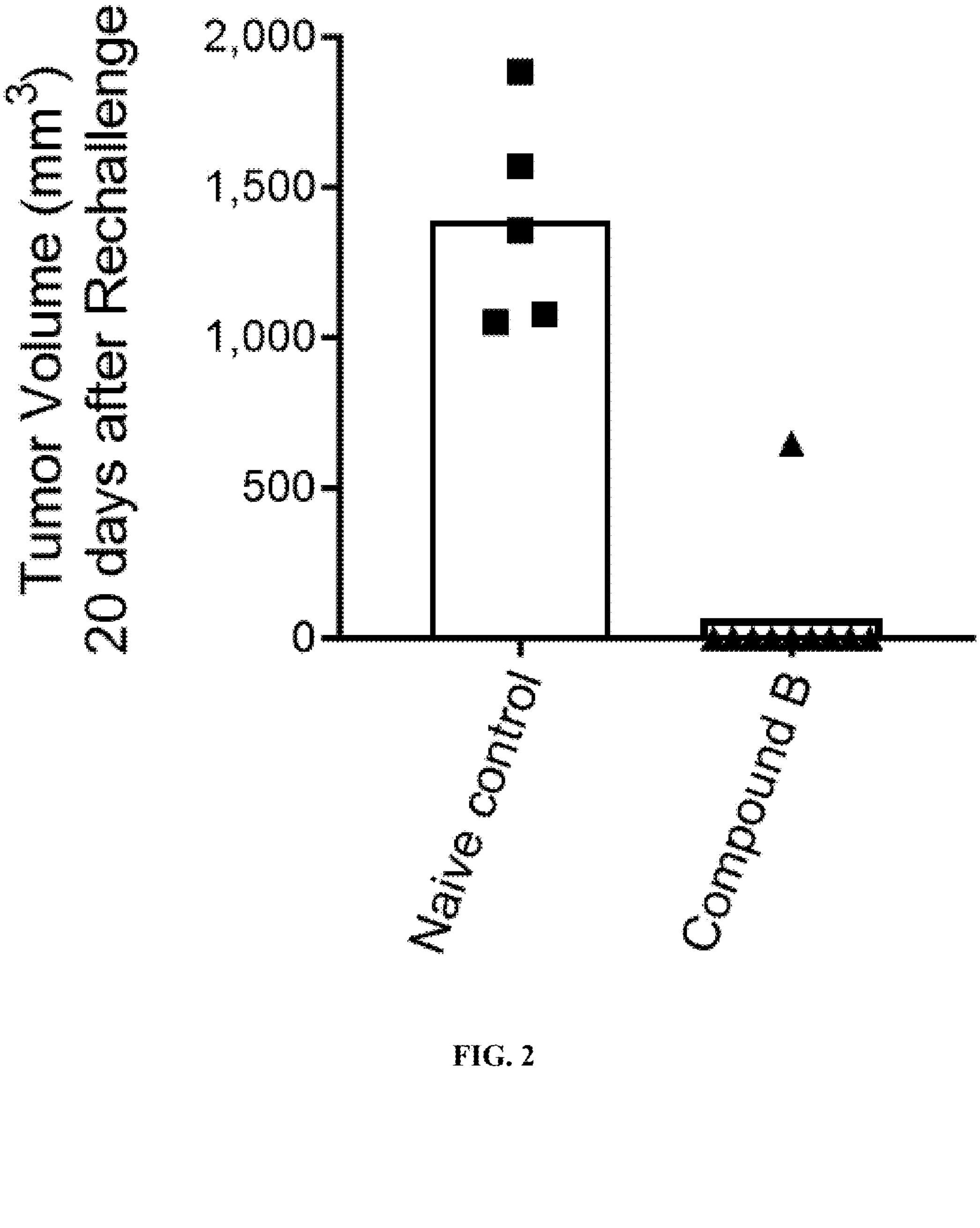
FIG. 2 shows results of a study in which mice cured of MC38 tumors by a PTPN2 inhibitor of the present disclosure (e.g., Compound B) were rechallenged with MC38 cells 30 days following the last dose of the PTPN2 inhibitor without any further treatment. Naïve mice challenged with MC38 cells were used as a control.

Animals that cleared the original MC-38 tumors following treatment with a PTPN2 inhibitor of the present disclosure (Compound B) are rechallenged roughly 30 days after the end of the treatment period with the same amount of MC-38 cells as in the original implant as stated above, but on the contralateral flank of the animal. A control group of naïve mice are implanted with the same amount of MC-38 cells in the right flank. As shown in FIG. 2, all animals in the naïve group established tumors (n=5), while 90% of the rechallenged animals remained tumor free 20-days after implantation, demonstrating that anti-tumor immunological memory of animals treated with a PTPN2 inhibitor disclosed herein persists even after the treatment regimen has been completed.

Analysis of Tumor Infiltrating T Cells

Tumor-bearing mice are sacrificed, and tumors are excised and processed for single cell isolation with a gentleMACS Octo dissociator (Miltenyi) and processed for flow cytometry staining. For assessing T cell activation and immunophenotype of infiltrating immune cells, samples are surface stained with fluorophore-conjugated antibodies to CD62L, CD44, CD25, PD1, TIM3, CD45, CD8, and CD69, including a viability dye (Zombie NIR). Treatment of MC-38-tumor bearing mice with a PTPN2 inhibitor of the present disclosure (Compound A) yielded an increase in CD8+ T cell infiltration in tumors by approximately 2-fold compared to that in vehicle treated mice.

Analysis of Tumor Specific Biomarkers

Tumor-bearing mice are sacrificed, and tumors are excised and snap frozen in liquid nitrogen. Frozen tumor fragments are pulverized and macerated in cell signaling technology cell lysis buffer with Halt protease and phosphatase inhibitor cocktail (Thermo Fisher) and processed for western blotting. Phospho-STAT1 (Y701)(CST), MHC1 H-2Kb expression (clone Y-3), PD-L1, and actin (CST) are assessed by western blotting using standard procedures. Dose dependent increases in pSTAT1 and MHC-1 (H-2Kb) expression in tumors were observed following treatment with Compound B.

pSTAT5 Flow Cytometry Assay in Mouse Whole Blood

Whole blood is drawn into EDTA powder coated tubes by cardiac puncture from mice on day 7 of dosing with indicated compound. 100 μL of whole blood are stimulated with 100 ng/ml murine IL-2 for 20 minutes at 37° C., 5% $CO_2$. After stimulation, 1.8 mL of prewarmed BD Phosflow Lyse/Fix Buffer is added for 20 minutes at 37° C. Cells are washed twice in FACS buffer (Dulbecco's PBS with 0.2% BSA) and incubated for 30 minutes on ice in cold Perm Buffer III. Cells are washed with FACS buffer and resuspended in 50 μL of FACS buffer with antibodies and stained for 3 hours at room temperature with gentle shaking. The antibodies added are a combination of the following: anti-CD3-AF647, clone 145-2C11; anti-CD4-FITC, clone GK1.5; anti-pSTAT5 (pY694)-PE, clone 47; anti-CD45-BUV395, clone 30-F11. After staining, cells are washed twice with FACS buffer, and the samples are acquired on a BD LSRFortessa™ X20 flow cytometers (BD Biosciences, San Jose, CA) and analyzed with FLowJo V10 software (FlowJo, Ashland, OR). The mean fluorescence intensity (MFI) of pSTAT5 as a measure of the amount of phosphorylated STAT5 in the CD3+ T cell population is reported as fold-change of compound treated over vehicle treated animal groups.

Granzyme B Staining of CD8 T Cells Flow Cytometry Assay in Mouse Spleen

Mice are sacrificed on day 7 of dosing with compound and spleens are excised. Spleens are dissociated, red blood cells lysed, and single cell suspensions are prepared. Splenocytes are stained with Zombie UV™ Fixable Viability kit diluted in Dulbecco's PBS for 10 minutes at room temperature to exclude dead cells followed by staining for surface markers for 45 minutes on ice using the following flow cytometry antibodies diluted in autoMACS® Running Buffer (Miltenyi Biotec, Bergisch Gladbach, Germany): Brilliant Violet 510-labeled anti-CD45, Brilliant Ultraviolet 395-labeled anti-CD3, Brilliant Violet 786-labeled anti-CD4, APC/Cy7-labeled anti-CD8. Cells are washed twice with autoMACS® Running Buffer, permeabilized with Fixation/Permeabilization buffer (FoxP3/Transcription Factor Staining Buffer Set) and stained intracellularly with PE-labeled anti-Granzyme B antibody diluted in Permeabilization buffer (FoxP3/Transcription Factor Staining Buffer Set) for 1 hour on ice. After staining, cells are washed twice with autoMACS® Running Buffer, and the samples are acquired on a BD LSR- Fortessa™ X20 flow cytometers (BD Biosciences, San Jose, CA) and analyzed with FLowJo V10 software (FlowJo, Ashland, OR).

Cytokine Measurement in Mouse Plasma

Whole blood is drawn into sodium heparin by cardiac puncture from mice on day 7 of dosing with compound and plasma is prepared by centrifugation. Cytokines in plasma are measured using the Th1/Th2 Cytokine & Chemokine 20-Plex Mouse ProcartaPlex™ Panel 1 (Invitrogen, Carlsbad, CA). IP10 levels are expressed as fold-changes over the vehicle control animal group.

Example 14: Mouse Primary Splenocyte p-STAT1 Assay

Spleens are isolated from C57/B16 mice (4-6 wk old; Charles Rivers) and single cells are isolated by mechanical disruption. Red cells are lysed with ACK buffer and splenocytes are seeded into U-bottom 96 well plates at 250,000 cells/well with culture media (RPMI 1640 supplemented with 10% FBS, 50 nM 2-mercaptoethanol, 100 U/mL penicillin, and 100 μg/mL streptomycin). Serial dilutions of compounds of the present disclosure in DMSO are acoustically dispensed (Echo) and splenocytes are activated with mouse IFNa1 (10 ng/ml; Peprotech) for 5 hrs. Next, splenocytes are fixed with 2% PFA for 20 mins and resuspended in FACS buffer for surface staining of anti-CD8, followed by permeabilization with BD Phosflow Perm Buffer III and staining with anti p-STAT1-BV421 conjugated antibody. Median fluorescent intensity of p-STAT1 is reported in CD8+ T cells by flow cytometry (Cytek Aurora). One or more compounds of the present disclosure, including Compound A and Compound B, increased pSTAT1 at an $EC_{50}$ of less than 4 μM, such as less than 3 μM, less than 2.5 μM, less than 2 μM, less than 1.5 μM, less than 1 μM, less than 0.75 μM, less than 0.5 μM, or less than 0.25 μM.

Example 15: Mouse Primary Splenocyte p-STAT5 Assay

Spleens are isolated from C57/B16 mice (4-6 wk old; Charles Rivers) and single cells are isolated by mechanical disruption. Red cells are lysed with ACK buffer and $CD_3$+ T cells are purified with a pan-CD3 T cell isolation kit (Biolegend) and seeded into U-bottom 96 well plates at 50,000 cells/well in with culture media (RPMI 1640 supplemented with 10% FBS, 50 nM 2-mercaptoethanol, 100 U/mL penicillin, and 100 μg/mL streptomycin). Serial dilutions of compounds of the present disclosure in DMSO are acoustically dispensed (Echo). T cells are treated for 30 minutes, then transferred to an anti-CD3 coated plate (5 μg/mL) with soluble anti-CD28 (Biolegend, 10 μg/mL). Cells are activated for about 48 hrs and subsequently processed for flow cytometry. Cells are fixed with 2% PFA for 20 mins and resuspended in FACS buffer for surface staining of anti-CD8, anti-CD25, and anti-CD69 followed by permeabilization with BD Phosflow Perm Buffer III and staining with anti p-STAT5-PE conjugated antibody. Median fluorescent intensity of p-STAT5 is reported in CD8+ T cells by flow cytometry (Cytek Aurora). One or more compounds of the present disclosure, including Compound A and Compound B, increased pSTAT5 at an $EC_{50}$ of less than 4 μM, such as less than 3 μM, less than 2.5 μM, less than 2 μM, less than 1.5 μM, less than 1 μM, less than 0.75 μM, less than 0.5 μM, less than 0.25 μM, less than 0.1 μM, less than 0.075 μM, or less than 0.050 μM.

Example 16: Rat Intravenous (i.v.) Clearance, Volume of Distribution, and Oral Bioavailability For rat (Sprague-Dawley) PK studies, animal weights are approximately 180 to 300 g, and animals are allowed to acclimate to their new environment for at least 3 days prior to the initiation of any studies. One set of animals is dosed intravenous (IV) with test compound, 2 mg/kg in 20% HP-beta-CD or 20% Captisol, pH adjusted to above 4 with 1N HCl or NaOH. The IV dosing solution concentration is 0.4 mg/mL test compound. Time of blood sampling is 0.083, 0.25, 0.5, 1, 2, 4, 8 and 24 hours following IV dosing. Another set of animals is dosed oral (po) with test compound, 10, 30, 100 and 300 mg/kg in 20% HP-beta-CD or 20% Captisol, pH adjusted to above 3 by 1 N HCl or NaOH. The oral dosing volume is 10 mL/kg test compound. Time of blood sampling is 0.25, 0.5, 1, 2, 4, 6, 8 and 24 following oral (po) dosing.

The blood samples (0.2 mL/sample) are placed into tubes containing K2EDTA as the anticoagulant and kept on ice before centrifugation at approximately 6800 g for 6 minutes at 28° C. to separate plasma from blood cells. The obtained plasma samples are stored frozen at approximately −70° C. The determination of a test article (TA) concentration in SD rat plasma is performed by non-validated LC-MS/MS bioanalytical methods. The standard and quality control samples are processed in the same manner and at the same time as the analytical PK samples containing K2EDTA as the anticoagulant. The prodrug and active drug in calibration standards, QCs, and PK samples are extracted from plasma via protein precipitation by quenching certain amounts of plasma samples with 300 or 400 μL methanol containing the specific internal standard. Following thorough mixing and centrifugation, the supernatant is obtained for LC-MS/MS analysis.

Quantification is performed by a linear regression of peak area ratios (TA/IS) to a calibration curve constructed with calibration standards in the designated concentration range of TA in plasma. Calibration standards are acceptable if the back-calculated standard concentrations do not differ by more than ±20% from the nominal values. Pharmacokinetic parameters are calculated using individual rat plasma concentration with FDA-certified pharmacokinetic program Phoenix WinNonlin 7.0 (Pharsight, Mountain View, CA). All concentrations reported as non-zero values are used for calculation of mean concentration. The maximum plasma concentration ($C_{max}$) and time to maximum plasma concentration ($t_{max}$) are the observed values. The slope $\lambda_z$ of the elimination phase is derived by linear regression using at least three concentrations of the terminal elimination phase. The terminal elimination half-life ($t_{1/2}$) is calculated using the relationship, $t_{1/2}=0.693/\lambda_z$. Area under the plasma concentration versus time profile from time zero to infinity ($AUC_\infty$) and time zero to the time of last quantifiable plasma sample ($AUC_{last}$) are calculated using non-compartmental analysis (NCA) by the linear-trapezoidal linear-interpolation method. The total body clearance (CL) is calculated from the dose divided by the $AUC_\infty$. The mean residence time ($MRT_{last}$) is calculated using the area under the first statistical moment of the plasma concentration vs. time curve ($AUMC_{last}$) divided by the $AUC_{last}$. The volume of distribution at steady state ($V_{ss}$) is calculated by the product of CL and the mean residence time ($MRT_{last}$).

Percentage rat bioavailability is calculated based on equation 1.

$$\% \ F\,(\text{rat}) = \frac{AUC_{po} * \text{Dose}_{IV}}{AUC_{IV} * \text{Dose}_{po}} \quad \text{Equation 1}$$

where F is bioavailability, $AUC_{po}$ is area under curve of oral drug, $AUC_{IV}$ is area under curve of intravenous drug, $Dose_{IV}$ is the intravenous dose and $Dose_{po}$ is the oral dose.

A PTPN2 inhibitor of the present disclosure (Compound B) was found to exhibit an oral bioavailability of at least 1%, such as at least 2%, at least 3%, at least 4%, at least 5%, at least 6%, at least 7%, at least 8%, or even more at one or more of the tested doses of 10, 30, 100, or 300 mg/kg in rats. Exposure was found to increase proportionally across the same dosing range, exhibiting an AUC last of at least 200 ng*h/mL, such as at least 300, at least 400, at least 500, at least 750, at least 1000, at least 1500, at least 2000, at least 3000, at least 4000, or at least 5000 ng*h/mL at one or more of the tested doses.

Example 17: Mouse Plasma Stability

A stock solution of a compound of the present disclosure is prepared at a concentration of 10 mM in DMSO (Fisher Scientific). For this assay, 0.5 mM working solution is prepared by diluting 5 μL of stock solution with 95 μL of DMSO. Plasma stability of the test compound is assayed at 37° C. using pooled plasma of human and several animal species. An aliquot of 5 μL of 500 μM test compound (in 100% DMSO, v/v) is mixed with 495 μL plasma (the final concentration of the test compound is 5 μM), then 50 μL of each mixture is dispensed to the 96 well tubes and incubated at 37° C. After 0-, 1-, 2- and 4-hours incubation in a shaking incubator, the reactions are terminated by adding 100 μL of acetonitrile (ice-cold) containing 50 nM Verapamil as an internal standard. All incubations are conducted in duplicate. Plates are vortexed vigorously using a Fisher Scientific microplate vortex mixer. Samples are then centrifuged at 4000 rpm for 10 minutes (4° C.). Supernatants (30 μL) are transferred into clean, 96-deep well plates. To each well is added 170 μL of ultrapure water (Milli-Q, Millipore Corporation) with 0.1% (v/v) formic acid (Fisher Chemical), mixed thoroughly and subjected to LC/MS/MS analysis in MRM positive ionization mode.

All samples are analyzed by a mass spectrometer (Sciex Qtrap 5500/6500) coupled with a Shimadzu HPLC system. The HPLC system consists of a Shimadzu series degasser, binary quaternary gradient pumps, column heater coupled to an autosampler, and a Luna Omega 5 μm C18 100 Å, LC Column 50×2.1 mm HPLC column, eluting with a mobile phase gradient consisting of Solution A (0.1% formic acid water) and Solution B (0.1% formic acid acetonitrile). The column temperature is maintained at 40° C. All the analytes are detected with positive-mode or negative-mode electrospray ionization (ES+ or ES−).

The relative concentration of a test compound is assessed by comparison of the analyte/IS peak area ratio. The data are plotted by percentage of the peak area ratio at each time point to the value at time zero (%) remaining.

One or more prodrug of the present disclosure was found to release the corresponding active compound following 1-, 2-, or 4-hours incubation in plasma. For example, less than 25%, such as less than 20%, less than 15%, less than 10%, or less than 5% of the prodrug was remaining in the sample following 1-, 2- or 4-hours incubation in plasma. Utilizing this assay, the ability of certain prodrugs in Table 1 to release the corresponding active compound following incubation in mouse plasma has been assessed. Table 4 summarizes the percent of prodrug remaining following 4-hours incubation in mouse plasma.

TABLE 4

| | ≤25% | 25 to 90% |
|---|---|---|
| Compound Remaining at 4 h (%) | 111, 121, 143, 147, 150, 152, 154, 155, 156, 157, 160, 161, 163, 164 | 146, 148, 149, 151, 153, 158, 159, 162, 165, 166 |

Example 18: Kinetic Solubility

Aqueous kinetic solubility can be defined as the concentration at which a compound precipitates upon addition of a DMSO solution into an aqueous buffer. A stock solution of a compound of the present disclosure (10 mM in DMSO) is diluted with DMSO or KPBS buffer to 100 μM concentration. Next, 5 μL of 10 mM stock solution is pipetted into 495 μL DMSO or KPBS. The final working concentration is 100 μM (DMSO, 1%).

The above solution is then sealed with sealing tape and shaken at 150 RPM for 24 hours at room temperature. After incubation, the solution is centrifuged for 10 minutes at 4000 rpm at room temperature and the supernatant is collected. Supernatant (10 μL) is mixed with 90 μL of stop solution (ice cold acetonitrile) containing an internal standard, then vortexed for approximately 2 min and centrifuged for 10 minutes at 4000 rpm at 4° C. Supernatant (50 μL) is then transferred into a clean, deep 96-well plate followed by addition of 50 μL of water containing 0.1% formic acid. After vortex mixing, the samples are analyzed by LC-MS/MS.

All samples are analyzed using an Agilent Technologies 6430 Triple Quad LC/MS system. The HPLC system consists of an Agilent 1290 Infinity Liquid Chromatograph coupled to an autosampler (Agilent 1290 Infinity LC Injector HTC), and a Phenomenex Gemini-NX, C18, 3.0 μm or Phenomenex Lunar, C8, 5.0 μM HPLC column (Phenomenex, Torrance, CA), eluting with a mobile phase gradient consisting of Solution A (0.1% formic acid water) and Solution B (0.1% formic acid acetonitrile). The column temperature is maintained at 40° C. All analytes are detected with positive-mode or negative-mode electrospray ionization (ES+ or ES−).

The peak area ratio of test compound in KPBS=Peak Area of test compound/Peak Area of internal standard in KPBS. The peak area ratio of test compound in DMSO=Peak Area of test compound/Peak Area of internal standard in DMSO. The kinetic solubility of the test compound=(the peak area ratio of KPBS/the peak area ratio of DMSO)*100 (μM).

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the invention. It is intended that the following claims define the scope of the invention and that methods and structures within the scope of these claims and their equivalents be covered thereby.

What is claimed is:

1. A compound having the formula:

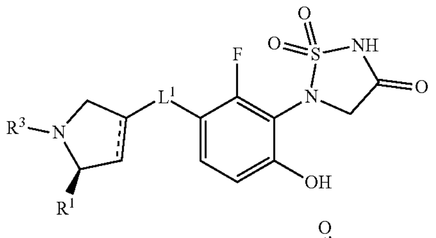

or

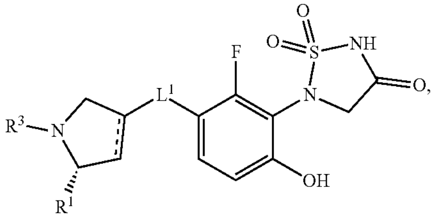

or a pharmaceutically acceptable salt or solvate thereof, wherein:

$R^1$ is selected from $C_{2-6}$ alkyl and —$C_{0-6}$ alkyl-($C_{3-8}$ carbocycle), each of which is optionally substituted with one, two, or three $R^{20}$;

$R^3$ is selected from —$C_2$ alkyl-(5- to 6-membered heterocycle) and —C(O)O—($C_{1-6}$ alkyl)-$OR^{15}$, wherein-$C_2$ alkyl-(5- to 6-membered heterocycle) is substituted with one, two, or three substituents independently selected from $C_{1-3}$ alkyl and oxo;

$L^1$ is absent;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{15}$ is selected at each occurrence from —C(O)$R^{12}$ and —P(O)(X—$R^{16}$)(Y—$R^{17}$);

X and Y are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —N($R^{12}$)($R^{13}$), —C(O)$OR^{12}$, —OC(O)N($R^{12}$)($R^{13}$), —N($R^{12}$)C(O)N($R^{12}$)($R^{13}$), —N($R^{12}$)C(O)$OR^{12}$, —N($R^{12}$)S(O)$_2R^{12}$, —N($R^{12}$)S(O)$_2$N($R^{12}$)($R^{13}$), —S—S—$R^{12}$, —S—C(O)$R^{12}$, —C(O)$R^{12}$, —S(O)$R^{12}$, —OC(O)$R^{12}$, —OC(O)$OR^{12}$, —C(O)N($R^{12}$)($R^{13}$), —C(O)C(O)N($R^{12}$)($R^{13}$), —N($R^{12}$)C(O)$R^{12}$, —S(O)$_2R^{12}$, —S(O)($NR^{12}$)$R^{12}$, —S(O)$_2$N($R^{12}$)($R^{13}$), —S(O)($NR^{12}$)N($R^{12}$)($R^{13}$), —P(O)($OR^{12}$)$_2$, —P(O)($R^{12}$)$_2$, —OP(O)($OR^{12}$)$_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), =$NR^{22}$, =C($R^{21}$)$_2$, —C(O)$OR^{22}$, —OC(O)N($R^{22}$)($R^{23}$), —N($R^{22}$)C(O)N($R^{22}$)($R^{23}$), —N($R^{22}$)C(O) $OR^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)($NR^{22}$)$R^{22}$, —S(O)$_2$N($R^{22}$)($R^{23}$)—, —S(=O)(=$NR^{22}$)N($R^{22}$)($R^{23}$), and —$OCH_2$C(O) $OR^{22}$; wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —N($R^{22}$)($R^{23}$), =$NR^{22}$, =C($R^{21}$)$_2$, —C(O) $OR^{22}$, —OC(O)N($R^{22}$)($R^{23}$), —N($R^{22}$)C(O)N($R^{22}$)($R^{23}$), —N($R^{22}$)C(O)$OR^{22}$, —N($R^{22}$)S(O)$_2R^{22}$, —C(O)$R^{22}$, —S(O)$R^{22}$, —OC(O)$R^{22}$, —C(O)N($R^{22}$)($R^{23}$), —C(O)C(O)N($R^{22}$)($R^{23}$), —N($R^{22}$)C(O)$R^{22}$, —S(O)$_2R^{22}$, —S(O)($NR^{22}$)$R^{22}$, —S(O)$_2$N($R^{22}$)($R^{23}$), and —S(=O)(=$NR^{22}$)N($R^{22}$)($R^{23}$);

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ------ indicates a single or double bond such that all valences are satisfied.

2. The compound, salt, or solvate of claim 1, wherein the compound is provided in at least 98% enantiomeric excess.

3. The compound, salt, or solvate of claim 1, wherein $R^1$ is selected from $C_{2-6}$ alkyl and —$C_{0-3}$ alkyl-($C_{3-6}$ carbocycle).

4. The compound, salt, or solvate of claim 1, wherein $R^3$ is —C(O)O—($C_{1-6}$ alkyl)-$OR^{15}$.
5. The compound, salt, or solvate of claim 4, wherein $R^{15}$ is —C(O)$R^{12}$.
6. The compound, salt, or solvate of claim 1, wherein the compound is selected from:
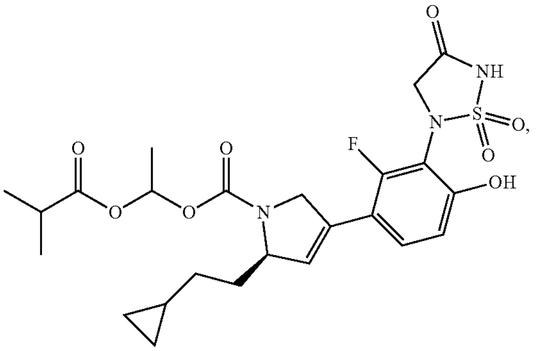
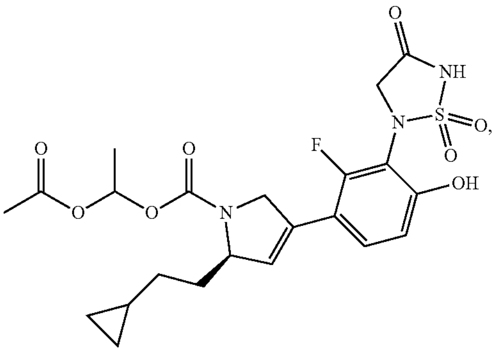
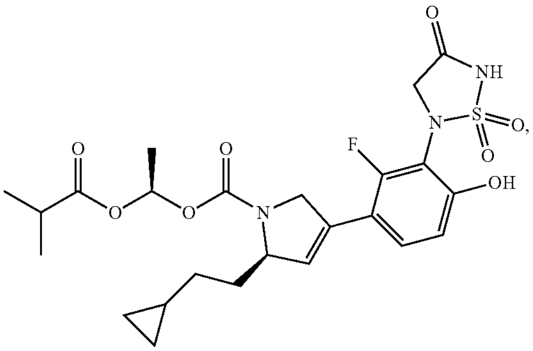
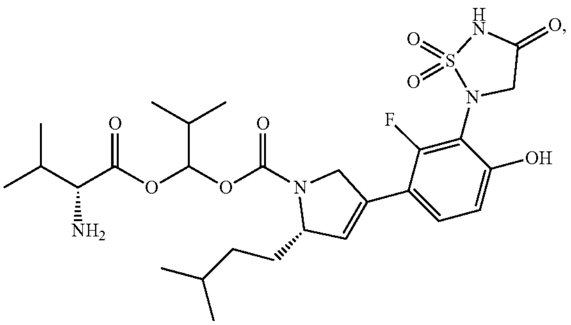
-continued
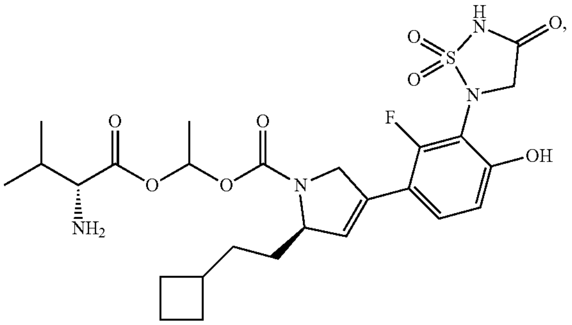
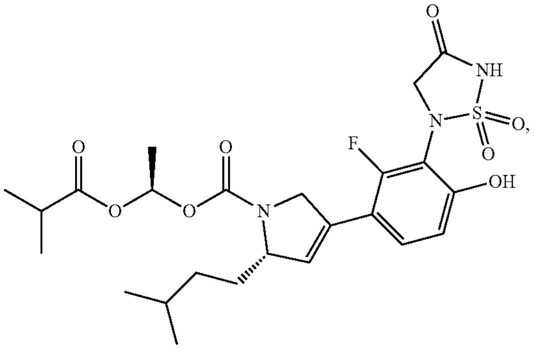
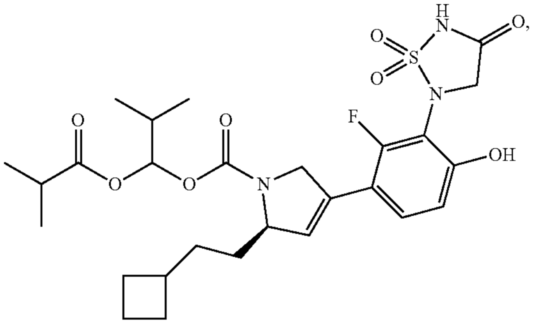
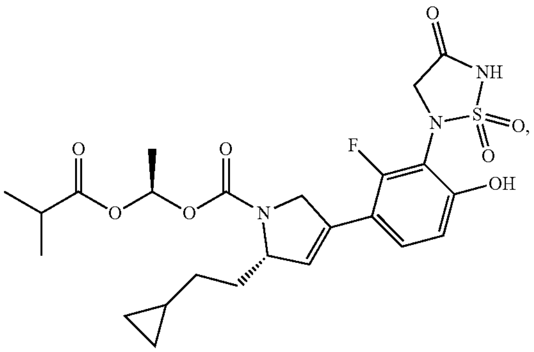
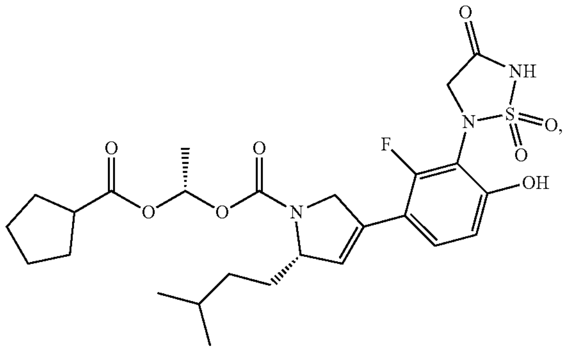

-continued
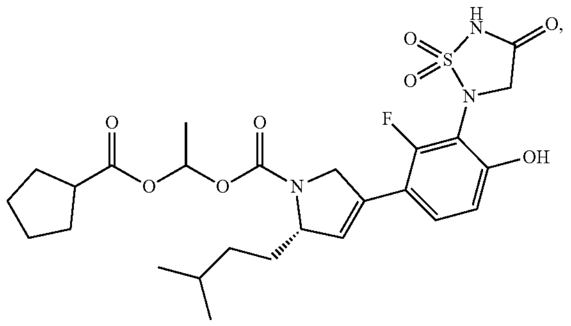
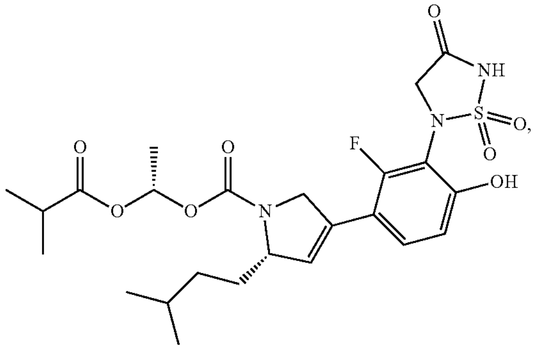
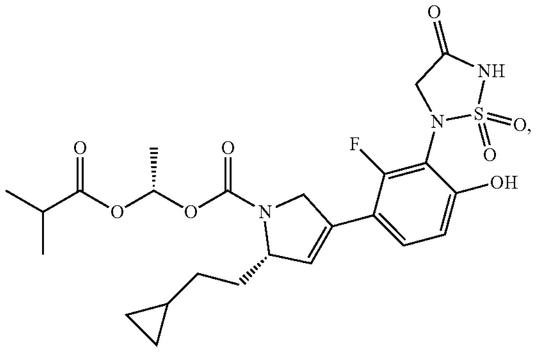
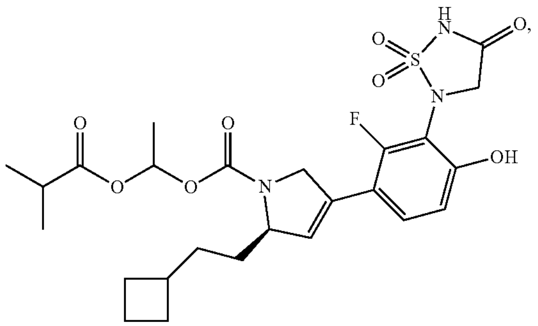
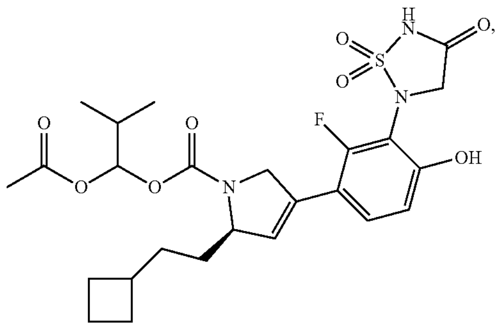
-continued
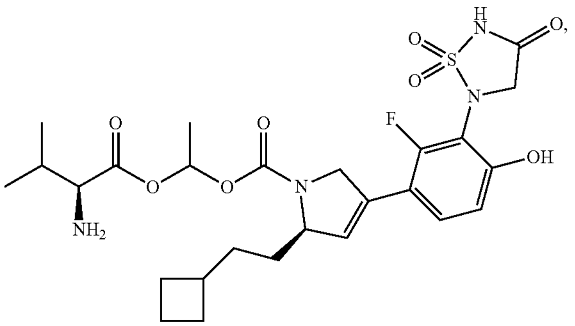
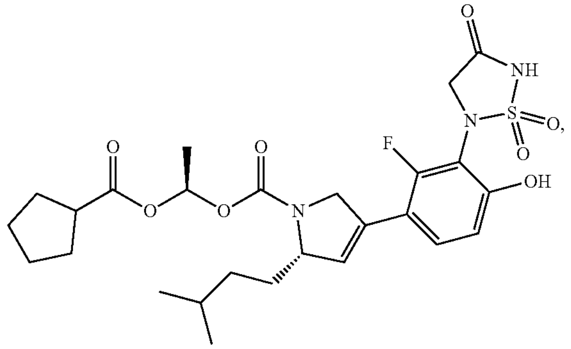
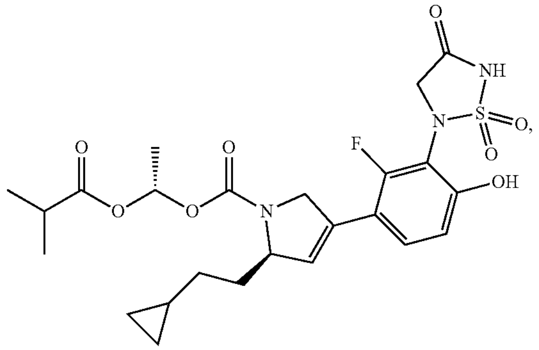
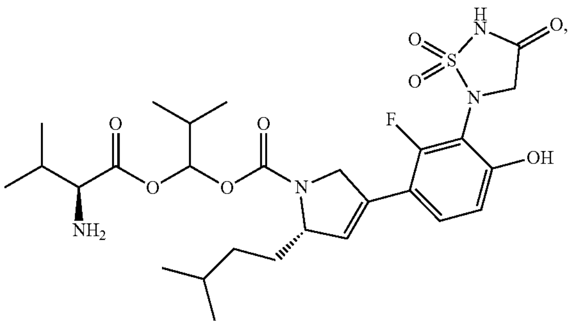
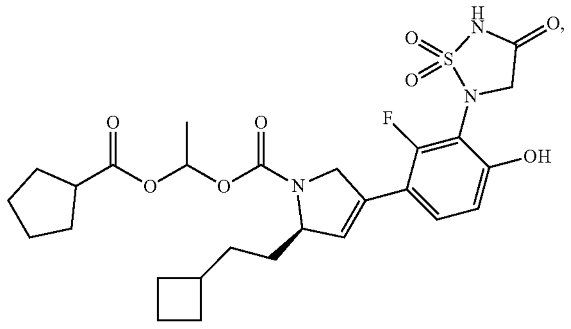

-continued

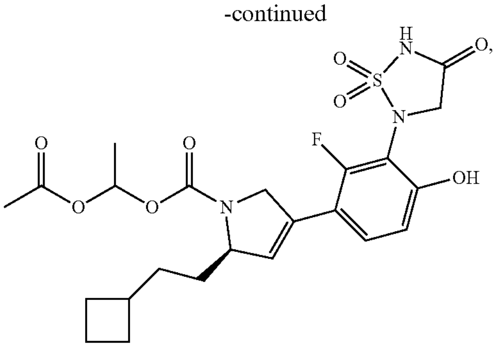

and

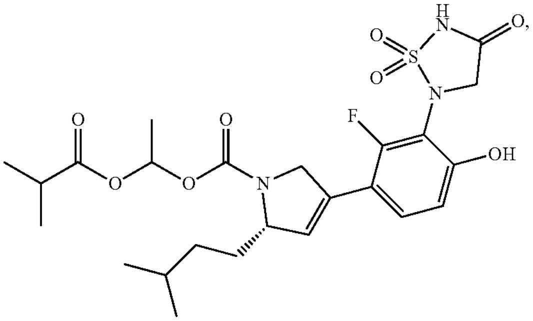

or a pharmaceutically acceptable salt or solvate thereof.

7. The compound, salt, or solvate of claim 1, wherein the compound is

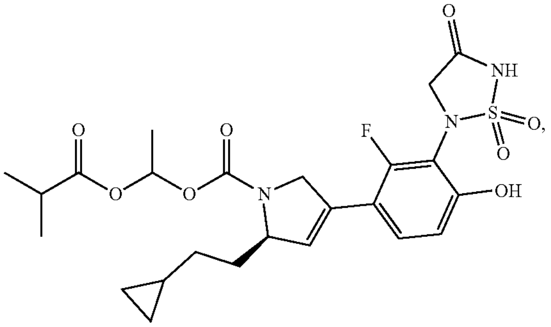 [SMILES: CC(OC(=O)C(C)C)OC(=O)N1CC(c2ccc(O)c(N3CC(=O)NS3(=O)=O)c2F)=C[C@H]1CCC1CC1]

or a pharmaceutically acceptable salt or solvate thereof.

8. The compound, salt, or solvate of claim 1, wherein the compound is

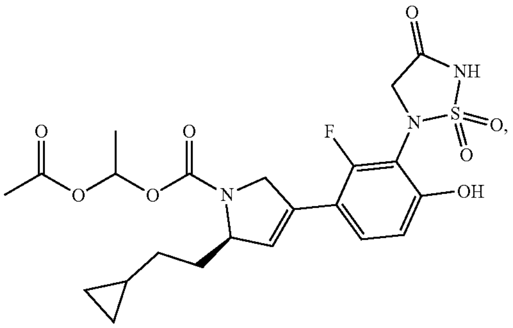 [SMILES: CC(=O)OC(C)OC(=O)N1CC(c2ccc(O)c(N3CC(=O)NS3(=O)=O)c2F)=C[C@H]1CCC1CC1]

or a pharmaceutically acceptable salt or solvate thereof.

9. The compound, salt, or solvate of claim 1, wherein the compound is

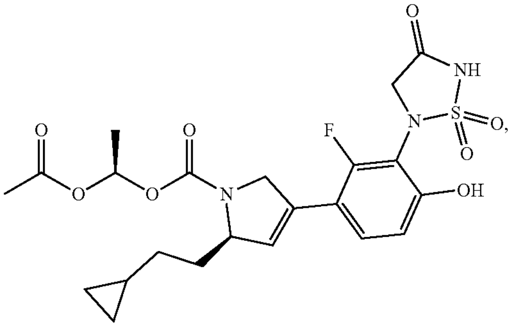 [SMILES: CC(=O)O[C@@H](C)OC(=O)N1CC(c2ccc(O)c(N3CC(=O)NS3(=O)=O)c2F)=C[C@H]1CCC1CC1]

or a pharmaceutically acceptable salt or solvate thereof.

10. The compound, salt, or solvate of claim 1, wherein the compound is

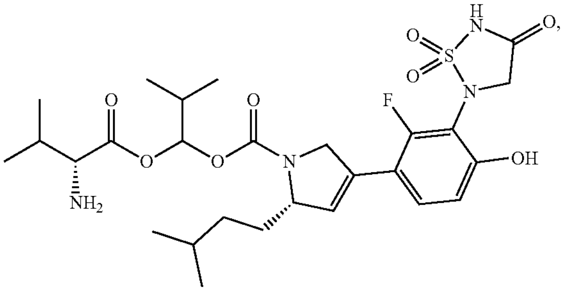 [SMILES: CC(C)CC[C@H]1C=C(c2ccc(O)c(N3CC(=O)NS3(=O)=O)c2F)CN1C(=O)OC(OC(=O)[C@H](N)C(C)C)C(C)C]

or a pharmaceutically acceptable salt or solvate thereof.

11. The compound, salt, or solvate of claim 1, wherein the compound is

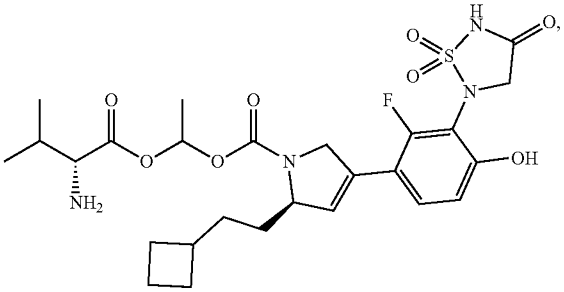 [SMILES: CC(OC(=O)[C@H](N)C(C)C)OC(=O)N1CC(c2ccc(O)c(N3CC(=O)NS3(=O)=O)c2F)=C[C@H]1CCC1CCC1]

or a pharmaceutically acceptable salt or solvate thereof.

12. The compound, salt, or solvate of claim 1, wherein the compound is

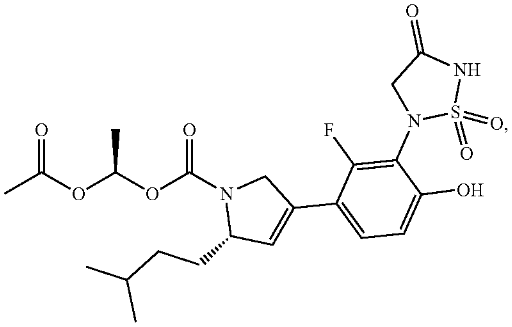 [SMILES: CC(=O)O[C@@H](C)OC(=O)N1CC(c2ccc(O)c(N3CC(=O)NS3(=O)=O)c2F)=C[C@@H]1CCC(C)C]

or a pharmaceutically acceptable salt or solvate thereof.

13. The compound, salt, or solvate of claim 1, wherein the compound is

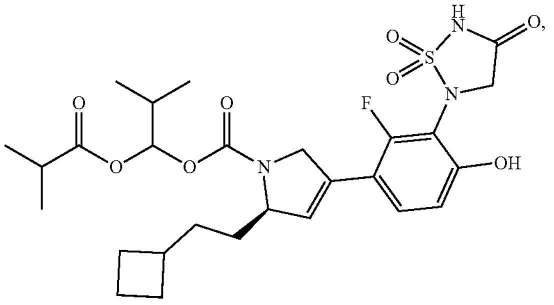 [SMILES: CC(C)C(=O)OC(OC(=O)N1CC(c2ccc(O)c(N3CC(=O)NS3(=O)=O)c2F)=C[C@H]1CCC1CCC1)C(C)C]

or a pharmaceutically acceptable salt or solvate thereof.

14. The compound, salt, or solvate of claim 1, wherein the compound is

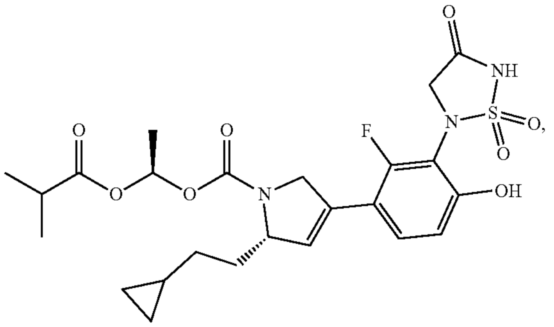 [SMILES: CC(C)C(=O)O[C@@H](C)OC(=O)N1CC(c2ccc(O)c(N3CC(=O)NS3(=O)=O)c2F)=C[C@@H]1CCC1CC1]

or a pharmaceutically acceptable salt or solvate thereof.

15. The compound, salt, or solvate of claim 1, wherein the compound is

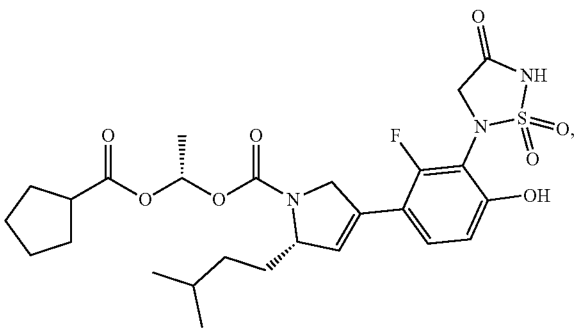 [SMILES: CC(C)CC[C@H]1C=C(c2ccc(O)c(N3CC(=O)NS3(=O)=O)c2F)CN1C(=O)O[C@@H](C)OC(=O)C1CCCC1]

or a pharmaceutically acceptable salt or solvate thereof.

16. The compound, salt, or solvate of claim 1, wherein the compound is

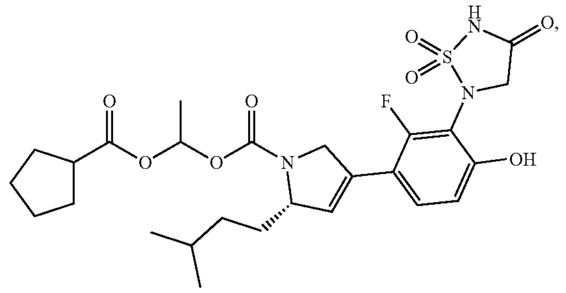 [SMILES: CC(C)CC[C@H]1C=C(c2ccc(O)c(N3CC(=O)NS3(=O)=O)c2F)CN1C(=O)OC(C)OC(=O)C1CCCC1]

or a pharmaceutically acceptable salt or solvate thereof.

17. The compound, salt, or solvate of claim 1, wherein the compound is

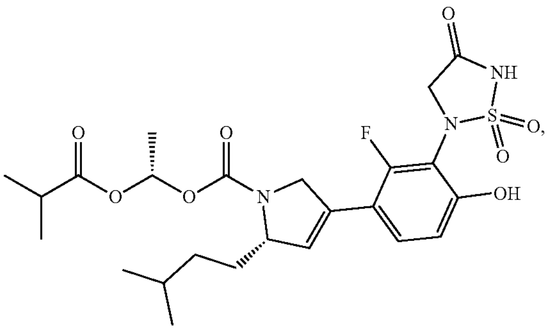 [SMILES: CC(C)CC[C@H]1C=C(c2ccc(O)c(N3CC(=O)NS3(=O)=O)c2F)CN1C(=O)O[C@@H](C)OC(=O)C(C)C]

or a pharmaceutically acceptable salt or solvate thereof.

18. The compound, salt, or solvate of claim 1, wherein the compound is

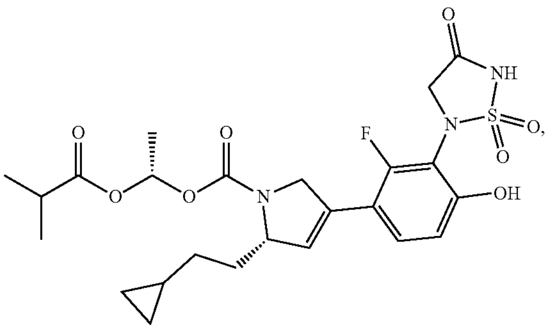 [SMILES: CC(C)C(=O)O[C@H](C)OC(=O)N1CC(c2ccc(O)c(N3CC(=O)NS3(=O)=O)c2F)=C[C@@H]1CCC1CC1]

or a pharmaceutically acceptable salt or solvate thereof.

19. The compound, salt, or solvate of claim 1, wherein the compound is

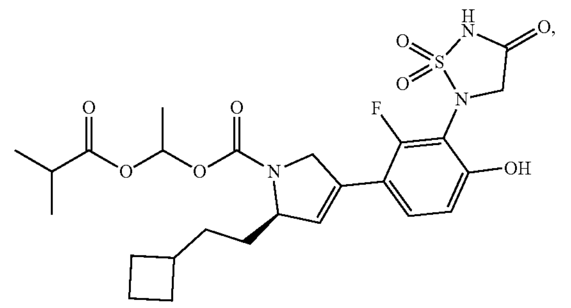 [SMILES: CC(OC(=O)C(C)C)OC(=O)N1CC(c2ccc(O)c(N3CC(=O)NS3(=O)=O)c2F)=C[C@H]1CCC1CCC1]

or a pharmaceutically acceptable salt or solvate thereof.

20. The compound, salt, or solvate of claim 1, wherein the compound is

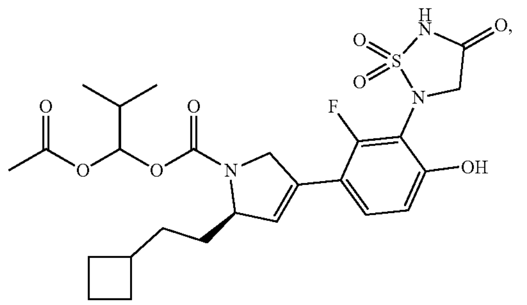 [SMILES: CC(=O)OC(OC(=O)N1CC(c2ccc(O)c(N3CC(=O)NS3(=O)=O)c2F)=C[C@H]1CCC1CCC1)C(C)C]

or a pharmaceutically acceptable salt or solvate thereof.

21. The compound, salt, or solvate of claim 1, wherein the compound is

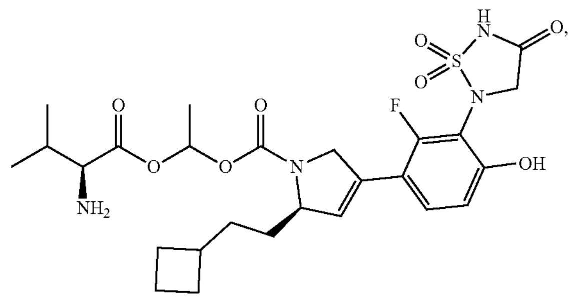 [SMILES: CC(OC(=O)[C@@H](N)C(C)C)OC(=O)N1CC(c2ccc(O)c(N3CC(=O)NS3(=O)=O)c2F)=C[C@H]1CCC1CCC1]

or a pharmaceutically acceptable salt or solvate thereof.

22. The compound, salt, or solvate of claim 1, wherein the compound is

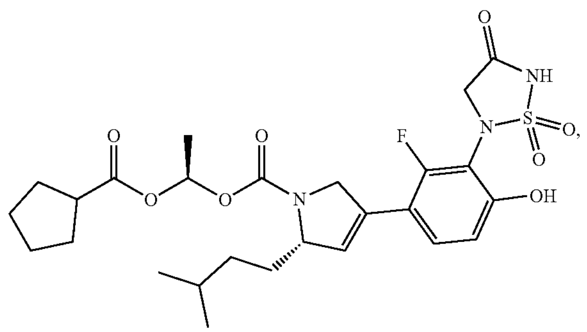 [SMILES: CC(C)CC[C@H]1C=C(c2ccc(O)c(N3CC(=O)NS3(=O)=O)c2F)CN1C(=O)O[C@H](C)OC(=O)C1CCCC1]

or a pharmaceutically acceptable salt or solvate thereof.

23. The compound, salt, or solvate of claim 1, wherein the compound is

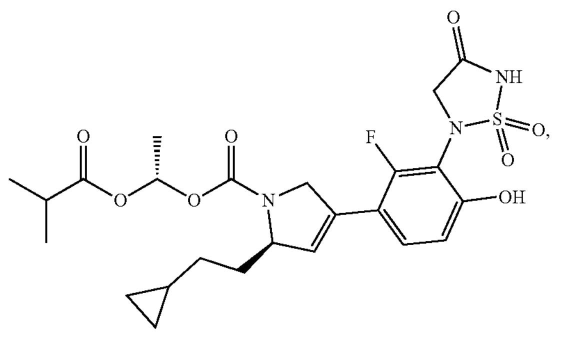 [SMILES: CC(C)C(=O)O[C@H](C)OC(=O)N1CC(c2ccc(O)c(N3CC(=O)NS3(=O)=O)c2F)=C[C@H]1CCC1CC1]

or a pharmaceutically acceptable salt or solvate thereof.

24. The compound, salt, or solvate of claim 1, wherein the compound is

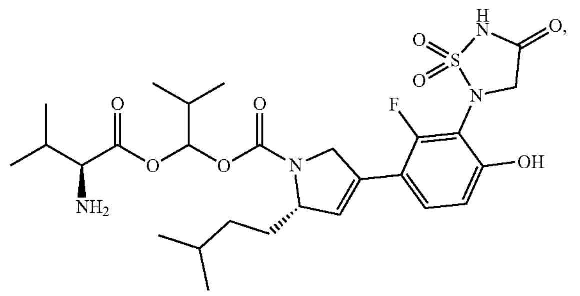 [SMILES: CC(C)CC[C@H]1C=C(c2ccc(O)c(N3CC(=O)NS3(=O)=O)c2F)CN1C(=O)OC(OC(=O)[C@@H](N)C(C)C)C(C)C]

or a pharmaceutically acceptable salt or solvate thereof.

25. The compound, salt, or solvate of claim 1, wherein the compound is

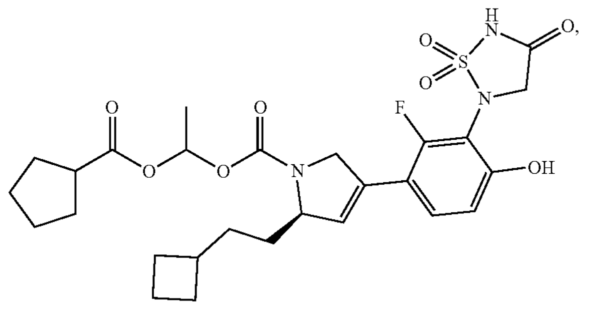 [SMILES: CC(OC(=O)C1CCCC1)OC(=O)N1CC(c2ccc(O)c(N3CC(=O)NS3(=O)=O)c2F)=C[C@H]1CCC1CCC1]

or a pharmaceutically acceptable salt or solvate thereof.

26. The compound, salt, or solvate of claim 1, wherein the compound is

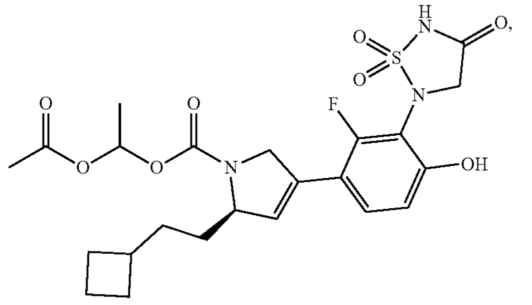 [SMILES: CC(=O)OC(C)OC(=O)N1CC(c2ccc(O)c(N3CC(=O)NS3(=O)=O)c2F)=C[C@H]1CCC1CCC1]

or a pharmaceutically acceptable salt or solvate thereof.

27. The compound, salt, or solvate of claim 1, wherein the compound is

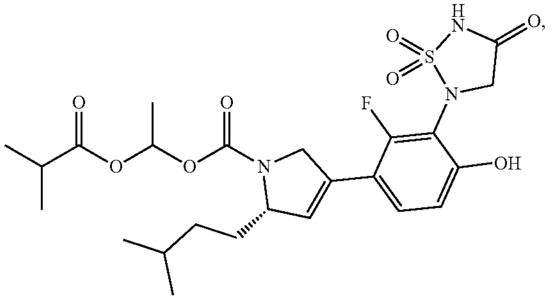 [SMILES: CC(C)CC[C@H]1C=C(c2ccc(O)c(N3CC(=O)NS3(=O)=O)c2F)CN1C(=O)OC(C)OC(=O)C(C)C]

or a pharmaceutically acceptable salt or solvate thereof.

28. A pharmaceutical composition comprising a compound of claim 1, or a pharmaceutically acceptable salt or solvate thereof, and a pharmaceutically acceptable excipient.

29. A pharmaceutical composition comprising a compound of claim 15, or a pharmaceutically acceptable salt or solvate thereof, and a pharmaceutically acceptable excipient.

30. A method of potentiating immunity of a subject in need thereof, comprising downregulating expression or activity of PTPN2 and/or PTP1B in a cell of the subject with a compound having the formula

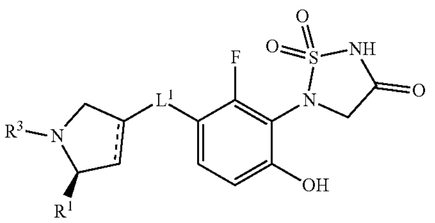

or

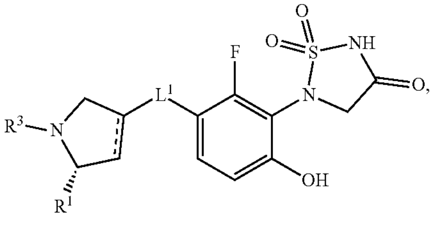

or a pharmaceutically acceptable salt or solvate thereof, wherein:

$R^1$ is selected from $C_{2-6}$ alkyl and —$C_{0-6}$ alkyl-($C_{3-8}$ carbocycle), each of which is optionally substituted with one, two, or three $R^{20}$;

$R^3$ is selected from —$C_2$ alkyl-(5- to 6-membered heterocycle) and —C(O)O—($C_{1-6}$ alkyl)-$OR^{15}$, wherein-$C_2$ alkyl-(5- to 6-membered heterocycle) is substituted with one, two, or three substituents independently selected from $C_{1-3}$ alkyl and oxo;

$L^1$ is absent;

$R^{12}$ is independently selected at each occurrence from hydrogen, $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle), wherein $C_{1-6}$ alkyl, $C_{2-6}$ alkenyl, $C_{2-6}$ alkynyl, —$C_{0-6}$ alkyl-($C_{3-12}$ carbocycle), and —$C_{0-6}$ alkyl-(3- to 12-membered heterocycle) are optionally substituted with one, two, or three $R^{20}$;

$R^{13}$ is independently selected at each occurrence from hydrogen, $C_{1-6}$ alkyl, and $C_{1-6}$ haloalkyl; or $R^{12}$ and $R^{13}$ attached to the same nitrogen atom form 3- to 10-membered heterocycle optionally substituted with one, two, or three $R^{20}$;

$R^{15}$ is selected at each occurrence from —$C(O)R^{12}$ and —P(O)(X—$R^{16}$)(Y—$R^{17}$);

X and Y are independently selected at each occurrence from —O— and —N($R^{12}$)—;

$R^{16}$ and $R^{17}$ are independently selected at each occurrence from hydrogen, $C_{1-6}$ alkyl, and phenyl, wherein $C_{1-6}$ alkyl and phenyl are optionally substituted with one, two, or three substituents independently selected from halogen, —$NO_2$, —CN, $C_{3-12}$ carbocycle, 3- to 12-membered heterocycle, —$OR^{12}$, —$SR^{12}$, —N($R^{12}$)($R^{13}$), —C(O) $OR^{12}$, —OC(O)N($R^{12}$)($R^{13}$), —N($R^{12}$)C(O)N($R^{12}$)($R^{13}$), —N($R^{12}$)C(O) $OR^{12}$, —N($R^{12}$)$S(O)_2R^{12}$, —N($R^{12}$)$S(O)_2$N($R^{12}$)($R^{13}$), —S—S—$R^{12}$, —S—$C(O)R^{12}$, —$C(O)R^{12}$, —S(O)$R^{12}$, —$OC(O)R^{12}$, —$OC(O)OR^{12}$, —C(O)N($R^{12}$)($R^{13}$), —C(O)C(O)N($R^{12}$)($R^{13}$), —N($R^{12}$)$C(O)R^{12}$, —$S(O)_2R^{12}$, —S(O)($NR^{12}$)$R^{12}$, —$S(O)_2$N($R^{12}$)($R^{13}$), —S(O)($NR^{12}$)N($R^{12}$)($R^{13}$), —P(O)($OR^{12}$)$_2$, —P(O)($R^{12}$)$_2$, —OP(O)($OR^{12}$)$_2$, =O, =S, and =$NR^{12}$; or $R^{16}$ and $R^{17}$ are taken together with the atoms to which they are attached to form 3- to 12-membered heterocycle optionally substituted with one, two, or three $R^{20}$;

$R^{20}$ is independently selected at each occurrence from halogen, oxo, —CN, $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), —$OR^{22}$, —$SR^{22}$, —N($R^{22}$)($R^{23}$), =$NR^{22}$, =C($R^{21}$)$_2$, —C(O) $OR^{22}$, —OC(O)N($R^{22}$)($R^{23}$), —N($R^{22}$)C(O)N($R^{22}$)($R^{23}$), —N($R^{22}$)C(O) $OR^{22}$, —N($R^{22}$)$S(O)_2R^{22}$, —$C(O)R^{22}$, —S(O)$R^{22}$, —$OC(O)R^{22}$, —C(O)N($R^{22}$)($R^{23}$), —C(O)C(O)N($R^{22}$)($R^{23}$), —N($R^{22}$)$C(O)R^{22}$, —$S(O)_2R^{22}$, —S(O)($NR^{22}$)$R^{22}$, —$S(O)_2$N($R^{22}$)($R^{23}$)—, —S(=O)(=$NR^{22}$)N($R^{22}$)($R^{23}$), and —$OCH_2C(O)$ $OR^{22}$, wherein two $R^{20}$ attached to the same or adjacent atoms optionally join to form $C_{3-12}$ carbocycle or 3- to 12-membered heterocycle; wherein $C_{1-6}$ alkyl, $C_{2-6}$ alkenyl, $C_{2-6}$ alkynyl, 2- to 6-membered heteroalkyl, 2- to 6-membered heteroalkenyl, 2- to 6-membered heteroalkynyl, —$C_{0-6}$ alkyl-($C_{3-12}$ carbocycle), -(2- to 6-membered heteroalkyl)-($C_{3-12}$ carbocycle), —$C_{0-6}$ alkyl-(3- to 12-membered heterocycle), -(2- to 6-membered heteroalkyl)-(3- to 12-membered heterocycle), $C_{3-12}$ carbocycle, and 3- to 12-membered heterocycle are optionally substituted with one or more substituents independently selected from halogen, oxo, —CN, $C_{1-6}$ alkyl, $C_{1-6}$ haloalkyl, $C_{1-6}$ alkoxy, $C_{1-6}$ haloalkoxy, —$OR^{22}$, —$SR^{22}$, —$N(R^{22})(R^{23})$, =$NR^{22}$, =$C(R^{21})_2$, —C(O) $OR^{22}$, —$OC(O)N(R^{22})(R^{23})$, —$N(R^{22})C(O)N(R^{22})(R^{23})$, —$N(R^{22})C(O)$ $OR^{22}$, —$N(R^{22})S(O)_2R^{22}$, —$C(O)R^{22}$, —$S(O)R^{22}$, —OC(O) $R^{22}$, —$C(O)N(R^{22})(R^{23})$, —$C(O)C(O)N(R^{22})(R^{23})$, —$N(R^{22})C(O)R^{22}$, —$S(O)_2R^{22}$, —$S(O)(NR^{22})R^{22}$, —$S(O)_2N(R^{22})(R^{23})$, and —$S(=O)(=NR^{22})N(R^{22})(R^{23})$;

$R^{21}$ is independently selected at each occurrence from hydrogen, halogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle), or two $R^{21}$ are taken together with the carbon atom to which they are attached to form $C_{3-12}$ carbocycle or 3- to 12-membered heterocycle, each of which is optionally substituted with one, two, or three substituents independently selected from halogen, $C_{1-3}$ alkyl, $C_{1-3}$ haloalkyl, and —OH;

$R^{22}$ is independently selected at each occurrence from hydrogen, $C_{1-6}$ alkyl, $C_{1-6}$ haloalkyl, —$C_{0-6}$ alkyl-($C_{3-12}$ carbocycle), and —$C_{0-6}$ alkyl-(3- to 12-membered heterocycle);

$R^{23}$ is independently selected at each occurrence from hydrogen and $C_{1-6}$ alkyl; or $R^{22}$ and $R^{23}$ attached to the same nitrogen atom form 3- to 10 membered heterocycle; and ------ indicates a single or double bond such that all valences are satisfied.

* * * * *